(12) United States Patent
Murata et al.

(10) Patent No.: US 9,567,304 B2
(45) Date of Patent: Feb. 14, 2017

(54) QUINAZOLINEDIONE DERIVATIVE

(71) Applicant: Chugai Seiyaku Kabushiki Kaisha, Tokyo (JP)

(72) Inventors: Takeshi Murata, Kanagawa (JP); Hatsuo Kawada, Shizuoka (JP); Satoshi Niizuma, Kanagawa (JP); Sousuke Hara, Kanagawa (JP); Kihito Hada, Kanagawa (JP); Hideaki Shimada, Shizuoka (JP); Hiroshi Tanaka, Kanagawa (JP); Toshiyuki Mio, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/396,498

(22) PCT Filed: Apr. 24, 2013

(86) PCT No.: PCT/JP2013/062006
§ 371 (c)(1),
(2) Date: Oct. 23, 2014

(87) PCT Pub. No.: WO2013/161853
PCT Pub. Date: Oct. 31, 2013

(65) Prior Publication Data
US 2015/0141400 A1    May 21, 2015

(30) Foreign Application Priority Data

Apr. 24, 2012 (JP) ................................. 2012-098954

(51) Int. Cl.
| | | |
|---|---|---|
| *C07D 239/96* | (2006.01) | |
| *C07D 401/06* | (2006.01) | |
| *C07D 403/06* | (2006.01) | |
| *C07D 405/04* | (2006.01) | |
| *C07D 405/12* | (2006.01) | |
| *C07D 487/04* | (2006.01) | |
| *C07D 401/14* | (2006.01) | |

(52) U.S. Cl.
CPC .......... *C07D 239/96* (2013.01); *C07D 401/06* (2013.01); *C07D 401/14* (2013.01); *C07D 403/06* (2013.01); *C07D 405/04* (2013.01); *C07D 405/12* (2013.01); *C07D 487/04* (2013.01)

(58) Field of Classification Search
CPC ............................ C07D 239/96; C07D 405/04
See application file for complete search history.

(56) References Cited

U.S. PATENT DOCUMENTS

| | | | |
|---|---|---|---|
| 4,943,583 A | 7/1990 | Lüthy | |
| 4,968,805 A | 11/1990 | Okada et al. | |
| 9,090,568 B2 | 7/2015 | Liu et al. | |
| 9,102,631 B2 | 8/2015 | Cai et al. | |
| 9,290,460 B2 | 3/2016 | Cai et al. | |
| 2005/0009894 A1 | 1/2005 | Babin et al. | |
| 2006/0106062 A1 | 5/2006 | Kuang et al. | |
| 2009/0099184 A1 | 4/2009 | Delombaert et al. | |
| 2010/0298298 A1 | 11/2010 | Clauss et al. | |
| 2011/0124670 A1 | 5/2011 | Buchdunger et al. | |
| 2012/0094997 A1 | 4/2012 | England et al. | |
| 2015/0152047 A1 | 6/2015 | Murata et al. | |

FOREIGN PATENT DOCUMENTS

| | | |
|---|---|---|
| CA | 2 093 203 C | 10/1993 |
| CN | 101842368 A | 9/2010 |
| CN | 102036990 A | 4/2011 |
| CN | 102099039 A | 6/2011 |
| EP | 0 329 020 A1 | 8/1989 |
| EP | 0 564 409 A1 | 10/1993 |
| EP | 1 702 917 A1 | 9/2006 |
| JP | H05-255268 A | 10/1993 |
| JP | H07-133266 A | 5/1995 |
| JP | 2009-528992 A | 8/2009 |
| JP | 2010-523674 A | 7/2010 |
| JP | 2010-540602 A | 12/2010 |
| JP | 2011-515397 A | 5/2011 |
| JP | 2011-528015 A | 11/2011 |
| JP | 2012-505881 A | 3/2012 |
| WO | WO 03/053958 A1 | 7/2003 |
| WO | WO 2004/005281 A1 | 1/2004 |
| WO | WO 2004/085388 A2 | 10/2004 |

(Continued)

OTHER PUBLICATIONS

Pinedo et al. (2000).*
McMahon et al. (2000).*
Deng, X., et al., "Discovery of 3,5-Diamino-1,2,4-triazole Ureas as Potent Anaplastic Lymphoma Kinase Inhibitors," *ACS Med. Chem. Lett. 2*:379-384, American Chemical Society, United States (2011).
Zubarev, A.A., et al., "3-Cyanopyridine-2(1H)-thiones and 3-cyano-2- (methylthio)pyridines in the synthesis of substituted 3-(aminomethyl)pyridines," *Russian Chemical Bulletin* 52(4):978-983, Springer, Germany (2003).
International Search Report for International Application No. PCT/JP2013/062003, Japanese Patent Office, Japan, mailed Jul. 23, 2013 (Not a Corresponding Application).

(Continued)

*Primary Examiner* — Paul V Ward
(74) *Attorney, Agent, or Firm* — Sterne, Kessler, Goldstein & Fox P.L.L.C.

(57) ABSTRACT

The present invention relates to quinazolinedione derivatives represented by formula (I) or pharmaceutically acceptable salts thereof.

(I)

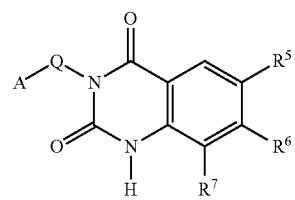

10 Claims, 2 Drawing Sheets

(56) References Cited

FOREIGN PATENT DOCUMENTS

| WO | WO 2005/063709 A1 | 7/2005 |
|---|---|---|
| WO | WO 2007/098352 A2 | 8/2007 |
| WO | WO 2008/127615 A1 | 10/2008 |
| WO | WO 2009/117097 A1 | 9/2009 |
| WO | WO 2010/007034 A1 | 1/2010 |
| WO | WO 2010/056230 A1 | 5/2010 |
| WO | WO 2011/050120 A1 | 4/2011 |
| WO | WO 2011/062927 A1 | 5/2011 |
| WO | WO 2012/061926 A1 | 5/2012 |

OTHER PUBLICATIONS

Co-pending Application, U.S. Appl. No. 14/396,678, inventors Murata, T., et al., Int'l Filing Date Apr. 24, 2013 (Not Yet Published).

Avivi-Green, C., et al., "Discoidin Domain Receptor 1-deficient Mice Are Resistant to Bleomycin-induced Lung Fibrosis," *Am. J. Respir. Crit. Care Med. 174*:420-427, American Thoracic Society, United States (2006).

Barker, K.T., et al., "Expression patterns of the novel receptor-like tyrosine kinase, DDR, in human breast tumours," *Oncogene 10*:569-575, Stockton Press, United States (1995).

Day, E., et al., "Inhibition of collagen-induced discoidin domain receptor 1 and 2 activation by imatinib, nilotinib and dasatinib," *European Journal of Pharmacology 599*:44-53, Elsevier B.V., Netherlands (2008).

Franco, C., et al., "Discoidin Domain Receptor 1 (Ddr 1) Deletion Decreases Atherosclerosis by Accelerating Matrix Accumulation and Reducing Inflammation in Low-Density Lipoprotein Receptor-Deficient Mice," *Circ. Res. 102*:1202-1211, American Heart Association, United States (2008).

Gu, T-L., et al., "Survey of Tyrosine Kinase Signaling Reveals ROS Kinase Fusions in Human Cholangiocarcinoma," *PLoS One* 6(1):e15640, Public Library of Science, United States (2011).

Guerrot, D., et al., "Discoidin Domain Receptor 1 Is a Major Mediator of Inflammation and Fibrosis in Obstructive Nephropathy," *The American Journal of Pathology* 179(1):83-91, Elsevier Inc., United States (2011).

Kamohara, H., et al., "Discoidin domain receptor 1 isoform-a (DDR1a) promotes migration of leukocytes in three-dimensional collagen lattices," *The FASEB Journal 15*:2724-2726, Federation of American Societies for Experimental Biology, United States (2001).

Kim, H-G., et al., "DDR1 Receptor Tyrosine Kinase Promotes Prosurvival Pathway through Notch1 Activation," *The Journal of Biological Chemistry* 286(20):17672-17681, The American Society for Biochemistry and Molecular Biology, Inc., United States (2011).

Rikova, K.., et al., "Global Survey of Phosphotyrosine Signaling Identifies Oncogenic Kinases in Lung Cancer," *Cell 131*:1190-1203, Elsevier Inc., United States (2007).

Rix, U., et al., "Chemical proteomic profiles of the BCR-ABL inhibitors imatinib, nilotinib, and dasatinib reveal novel kinase and nonkinase targets," *Blood* 110(12):4055-4063, The American Society of Hematology, United States (2007).

Rix, U., et al., "A comprehensive target selectivity survey of the BCR-ABL kinase inhibitor INNO-406 by kinase profiling and chemical proteomics in chronic myeloid leukemia cells," *Leukemia 24*:44-50, Macmillan Publishers Limited, United Kingdom (2010).

Song, S., et al., "Discoidin Domain Receptor 1 Isoform Expression and Potential Functions in Cirrhotic Human Liver," *The American Journal of Pathology* 178(3):1134-1144, Elsevier Inc., United States (2011).

Sun, X., et al., "LCB 03-0110, a Novel Pan-Discoidin Domain Receptor/c-Src Family Tyrosine Kinase Inhibitor, Suppresses Scar Formation by Inhibiting Fibroblast and Macrophage Activation," *The Journal of Pharmacology and Experimental Therapeutics* 340(3):510-519, American Society for Pharmacology and Experimental Therapeutics, United States (2012).

Valencia, K., et al., "Inhibition of Collagen Receptor Discoidin Domain Receptor-1 (DDR1) Reduces Cell Survival, Homing, and Colonization in Lung Cancer Bone Metastasis," *Clinical Cancer Research* 18(4):969-980, American Association for Cancer Research, United States (2012).

Valiathan, R.R., et al., "Discoidin domain receptor tyrosine kinases: new players in cancer progression," *Cancer Metastasis Rev. 31*:295-321, Springer Science, Germany (2012).

Vogel, W., et al., "The Discoidin Domain Receptor Tyrosine Kinases Are Activated by Collagen," *Molecular Cell 1*:13-23, Cell Press, United States (1997).

Vogel, W., "Discoidin domain receptors: structural relations and functional implications," *The FASEB Journal 13*:S77-S82, Federation of American Societies for Experimental Biology, United States (1999).

Yamanaka, R., et al., "Identification of expressed genes characterizing long-term survival in malignant glioma patients," *Oncogene 25*:5994-6002, Nature Publishing Group, United Kingdom (2006).

Yang, S.H., et al., "Discoidin domain receptor 1 is associated with poor prognosis of non-small cell lung carcinomas," *Oncology Reports 24*:311-319, Spandidos Publications, Greece (2010).

International Search Report for International Application No. PCT/JP2013/062006, Japanese Patent Office, Japan, mailed May 28, 2013.

Unverified English language machine translation of JP H05-255268.

McMahon, G., "VEGF Receptor Signaling in Tumor Angiogenesis," *The Oncologist* 5(Suppl. 1):3-10, AlphaMed Press, United States (2000).

Pinedo, H.M. and Slamon, D.J., "Translational Research: The Role of VEGF in Tumor Angiogenesis," *The Oncologist* 5 (Suppl. 1):1-2, AlphaMed Press, United States (2000).

Gao, M., et al., "Discovery and Optimization of 3-(2-(Pyrazolo[1,5-a]pyrmidin-6-yl)-ethynyl)benzamides as Novel Selective and Orally Bioavaliable Discoidin Domain Receptor 1 (DDR1) Inhibitors," *Journal of Medicinal Chemistry* 56:3281-3295, American Chemical Society, United States (2013).

Kim, H.-G., et al., "Discovery of a Potent and Selective DDR1 Receptor Tyrosine Kinase Inhibitor," *ACS Chemical Biology* 8:2145-2150, American Chemical Society, United States (2013).

Unverified English language machine translation of JP H07-133266.

U.S. Appl. No. 15/030,804, inventors Murata, T., et al., 371(c) date of Apr. 20, 2016 (Not Yet Published).

Borza, C.M. and Pozzi, A., "Discoidin domain receptors in disease," *Matrix Biology* 34:185-192, Elsevier B.V., Netherlands (2014).

Matsuo, Y. and Maruyama, M., "The chemistry of four-membered aromatics," *Chemical Communications* 48:9334-9342, The Royal Society of Chemistry, England (2012).

\* cited by examiner

QUINAZOLINEDIONE DERIVATIVE

TECHNICAL FIELD

The present invention relates to quinazolinedione derivatives or salts thereof, or solvates thereof. More specifically, the present invention relates to quinazolinedione derivatives, and provides pharmaceuticals, pharmaceutical compositions, and DDR1 inhibitors comprising the compounds, as well as pharmaceuticals comprising the above-mentioned compounds for treatment of diseases including cancer, cancer metastasis and invasion, fibrosis, and inflammation. The present invention also relates to methods for treating the above-mentioned diseases comprising administering effective doses of the compounds or salts thereof, or solvates thereof, and to use of the quinazolinedione derivatives for the manufacture of the above-mentioned pharmaceutical compositions.

BACKGROUND ART

Discoidin Domain Receptor 1 (DDR1) is a receptor tyrosine kinase, and it is known that DDR1 is activated by collagen as a ligand to transduce signals into cells, and to promote invasion/metastasis or survival of the cells (Non-Patent Document 1, Non-Patent Document 2, and Non-Patent Document 3). DDR1 is considered to be an important factor that links extracellular matrix with malignant transformation of cancer, because high expression and activation of DDR1 is observed in various types of cancers.

For example, it is known that clinically DDR1 is highly expressed in non-small-cell lung cancer, glioma, breast cancer, and the like (Non-Patent Document 4, Non-Patent Document 5, Non-Patent Document 6, and Non-Patent Document 7), and it is reported that high expression correlates with poor prognosis in non-small-cell lung cancer and glioma. Further, in non-small-cell lung cancer and bile duct cancer, enhancement of DDR1 phosphorylation is observed, and its activation is strongly suggested (Non-Patent Document 8, and Non-Patent Document 9).

Studies using RNA interference reveal that DDR1 plays an important role in bone metastasis of lung cancer cells (Non-Patent Document 5), and contributes to tumorigenicity of colon cancer or breast cancer cells as well as their survival in the presence of DNA-damaging agents (Non-Patent Document 10). Accordingly, compounds having a DDR1 inhibitory effect are extremely useful for cancer treatment.

It is also reported that the DDR1 ligand, collagen, is abundantly present in fibrous tissues, and functions mediated through DDR1 activation are involved in various types of fibrosis. For example, DDR1 expression is enhanced in the liver of hepatic cirrhosis patients (Non-Patent Document 11). It is reported that in DDR1 knockout mice, fibril formation in the kidney induced by unilateral ureteral ligation is suppressed (Non-Patent Document 12), and fibril formation in a pulmonary fibrosis model induced by bleomycin is reduced (Non-Patent Document 13). As it is clear from above, DDR1 inhibition is extremely useful for the prevention and treatment of organ fibrosis. DDR1 also enhances lymphocyte migration, and migration and inflammatory functions of macrophages (Non-Patent Document 14, and Non-Patent Document 15). For example, in DDR1 knockout mice, accumulation of macrophages is suppressed in an arteriosclerosis model (Non-Patent Document 15). It is reported that lymphocytes and macrophages also accumulate and are activated in inflammatory diseases such as rheumatoid arthritis, Crohn's disease, ulcerative colitis, and multiple sclerosis. Accordingly, DDR1 inhibition is also extremely useful for the prevention and treatment of these diseases which originate from inflammation.

Examples of DDR1 inhibitory substances include multi-kinase inhibitors which have DDR1 inhibitory effect as one of their effects. Reported examples include Gleevec which has a 3-pyridylpyrimidine structure and serves as an inhibitor for bcr-abl, c-kit, CSFIR, PDGFRα, and the like (Patent Document 1, Non-Patent Document 16, and Non-Patent Document 17), and Tasigna which has a 3-pyridylpyrimidine structure and serves as an inhibitor for bcr-abl, c-kit, PDGFRα, Lck, Lyn, and the like (Patent Document 2, Non-Patent Document 16, and Non-Patent Document 17). Other reported examples include Sprycel which has a 2-methylpyrimidine structure and serves as an inhibitor for the Src family and the like (Patent Document 3, Non-Patent Document 16, and Non-Patent Document 17), INNO-406 which has a bipyrimidin-2-ylamino structure and serves as an inhibitor for bcr-abl, PDGFRα, Lyn, ZAK, and the like (Patent Document 4, and Non-Patent Document 18), and LCB03-0110 which has a thieno[3,2-b]pyridine structure and serves as an inhibitor for the Src family and the like (Non-Patent Document 19).

However, compounds that selectively inhibit DDR1 are not yet known.

PRIOR ART DOCUMENTS

Patent Documents

[Patent Document 1] European Patent Application Publication No. 0564409
[Patent Document 2] International Publication No. WO 2004/005281
[Patent Document 3] International Publication No. WO 2004/085388
[Patent Document 4] International Publication No. WO 2005/063709

Non-Patent Documents

[Non-Patent Document 1] FASEB J, 13, S77-S82, 1999
[Non-Patent Document 2] Mol Cell, 1, 13-23, 1997
[Non-Patent Document 3] Cancer Metastasis Rev, electronic edition, Feb. 26, 2012
[Non-Patent Document 4] Oncol Rep, 24, 311-319, 2010
[Non-Patent Document 5] Clin Cancer Res, 18, 969-980, 2012
[Non-Patent Document 6] Oncogene, 25, 5994-6002, 2006
[Non-Patent Document 7] Oncogene, 10, 569-575, 1995
[Non-Patent Document 8] Cell, 131, 1190-1203, 2007
[Non-Patent Document 9] PloS One, 6, e15640, 2011
[Non-Patent Document 10] J Biol Chem, 286, 17672-17681, 2011
[Non-Patent Document 11] Am J Pathol, 178, 1134-44, 2011
[Non-Patent Document 12] Am J Pathol, 179, 83-91, 2011
[Non-Patent Document 13] Am J Respir Crit Care Med, 174, 420-427, 2006
[Non-Patent Document 14] FASEB J, 15, 2724-2726, 2001
[Non-Patent Document 15] Circ Res, 102, 1202-1211, 2008
[Non-Patent Document 16] Blood, 110, 4055-4063, 2007
[Non-Patent Document 17] European Journal of Pharmacology 599, 44-53, 2008
[Non-Patent Document 18] Leukemia, 22, 44-50, 2010
[Non-Patent Document 19] THE JOURNAL OF PHARMACOLOGY AND EXPERIMENTAL THERAPEUTICS 340, 510-519, 2012

SUMMARY OF THE INVENTION

Problems to be Solved by the Invention

An objective of the present invention is to provide low-molecular-weight compounds that can selectively inhibit Discoidin Domain Receptor 1 (DDR1) and to provide drugs effective for diseases associated with abnormalities of DDR1, such as cancer, cancer metastasis and invasion, fibrosis, and inflammation.

Means for Solving the Problems

Specifically, the present invention includes:

[1] a compound represented by general formula (I) below, a pharmaceutically acceptable salt thereof, or a solvate thereof:

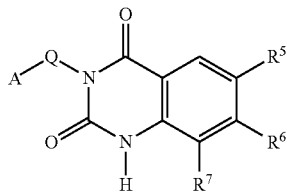
(I)

wherein
A represents formula (1) or (2) below:

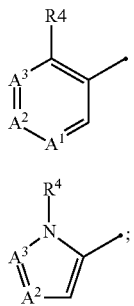

Q represents $CH_2$ or NH;
$A^1$ represents N or $CR^1$;
$R^1$ represents a hydrogen atom, $C_{1-3}$ alkyl group, $C_{1-3}$ alkoxy group, halogen atom, or cyano group, wherein the $C_{1-3}$ alkyl group or $C_{1-3}$ alkoxy group may be substituted with 1 to 5 halogen atoms,
wherein when $A^2$ and/or $A^3$ is N, $R^1$ may be an hydrogen atom;
$A^2$ represents N or $CR^2$;
$R^2$ represents a hydrogen atom, $C_{1-3}$ alkyl group, $C_{1-3}$ alkoxy group, or halogen atom;
$A^3$ represents N or $CR^3$;
$R^3$ represents a hydrogen atom, $C_{1-6}$ alkyl group, $C_{1-6}$ alkoxy group, or halogen atom;
$R^4$ represents a $C_{1-6}$ alkylsulfonyl group, $C_{1-6}$ alkylsulfanyl group, $C_{1-6}$ alkylsulfinyl group, $C_{3-8}$ cycloalkylsulfonyl group, $C_{3-8}$ cycloalkylsulfanyl group, $C_{3-8}$ cycloalkylsulfinyl group, $C_{6-10}$ arylsulfonyl group, $C_{6-10}$ arylsulfanyl group, or $C_{6-10}$ arylsulfinyl group;
$R^5$ represents a halogen atom, $C_{1-6}$ alkyl group, $C_{1-6}$ alkoxy group, $C_{2-6}$ alkenyl group, cyano group, nitro group, $C_{3-8}$ cycloalkyl group, 4- to 10-membered aromatic ring, 4- to 10-membered aromatic heterocycle, 3- to 12-membered heterocycle, or $C_{1-6}$ alkylsulfanyl group, wherein the $C_{1-6}$ alkyl group, $C_{1-6}$ alkoxy group, $C_{2-6}$ alkenyl group, or $C_{1-6}$ alkylsulfanyl group may be substituted with 1 to 5 halogen atoms;
$R^6$ represents a hydrogen atom, a $C_{1-6}$ alkyl group, $C_{2-6}$ alkenyl group, halogen atom, formyl group, [1,3]dioxolane, or a group represented by formula (i) below, wherein the $C_{1-6}$ alkyl group or $C_{2-6}$ alkenyl group may be substituted with 1 to 5 amino, hydroxyl, and/or $OSO_2CH_3$ groups, ●—X—Y—Z    (i)

wherein in formula (i),
X represents $—(CH_2)_n—$, —NH—, or —O—;
Y represents a 4- to 10-membered aromatic ring, 3- to 12-membered heterocycle, or 4- to 10-membered aromatic heterocycle, wherein the 4- to 10-membered aromatic ring, 3- to 12-membered heterocycle, and 4- to 10-membered aromatic heterocycle may be substituted with 1 to 5 halogen atoms and/or $C_{1-3}$ alkyl groups;
Z represents a hydrogen atom, a $C_{1-6}$ alkyl group, a $C_{2-6}$ alkynyl group, a $C_{3-8}$ cycloalkyl group, $—(CH_2)_m NRaRb$, $—NHCO(CH_2)_m Rc$, $—(CH_2)_m NHCORc$, $—NH(CH_2)_m CORc$, $—(CH_2)_m N(CH_3)CORc$, $—(CH_2)_m ORd$, $—(CH_2)_m CORe$, $—(CH_2)_m COORe$, $—(CH_2)_m NHSO_2 Rf$, $—(CH_2)_m SO_2 Rf$, $—(CH_2)_m CONRgRh$, a 4- to 10-membered aromatic ring, 4- to 10-membered aromatic heterocycle, or a 3- to 12-membered heterocycle, wherein the $C_{1-6}$ alkyl group may be substituted with 1 to 5 halogen atoms, hydroxyl groups, and/or cyano groups; and the 3- to 12-membered heterocycle and 4- to 10-membered aromatic heterocycle may be substituted with 1 to 5 halogen atoms, $C_{1-3}$ alkyl groups, and/or oxo groups;
n represents 0, 1, 2, or 3;
m represents 0, 1, 2, or 3;
Ra and Rb are identical or different, each representing a hydrogen atom, $C_{1-6}$ alkyl group, $C_{2-6}$ alkynyl group, 3- to 12-membered heterocycle, 4- to 10-membered aromatic heterocycle, or $—SO_2CH_3$, wherein the $C_{1-6}$ alkyl group may be substituted with 1 to 5 halogen atoms, amino groups, mono-$C_{1-6}$ alkylamino groups, di-$C_{1-6}$ alkylamino groups, hydroxyl groups, and/or cyano groups;
Rc represents a $C_{1-6}$ alkyl group, $C_{1-6}$ alkoxy group, $C_{3-8}$ cycloalkyl group, amino group, or 3- to 12-membered heterocycle, wherein the C-s alkyl group may be substituted with 1 to 3 amino groups, mono-$C_{1-6}$ alkylamino groups, di-$C_{1-6}$ alkylamino groups, and/or 3- to 12-membered heterocycles;
Rd represents a hydrogen atom, $C_{1-6}$ alkyl group, or $C_{2-6}$ alkynyl group, wherein the $C_{1-6}$ alkyl group may be substituted with 1 to 5 $C_{1-6}$ alkoxy groups and/or amino groups;
Re represents a hydrogen atom or $C_{1-6}$ alkyl group, wherein the $C_{1-6}$ alkyl group may be substituted with an amino group;
Rf represents a $C_{1-6}$ alkyl group, an amino group, a mono-$C_{1-6}$ alkylamino group, or a di-$C_{1-6}$ alkylamino group; and
Rg and Rh are identical or different, each representing a hydrogen atom, $C_{1-6}$ alkyl group, or 3-to 12-membered heterocycle, wherein the $C_{1-6}$ alkyl group may be substituted with 1 to 3 amino groups, mono-$C_{1-6}$ alkylamino groups, and/or di-$C_{1-6}$ alkylamino groups; and
$R^7$ represents a hydrogen atom, halogen atom, $C_{1-6}$ alkyl group, $C_{2-6}$ alkenyl group, $C_{1-6}$ alkoxy group, cyano group, or a group represented by formula (ii) below, wherein the $C_{1-6}$ alkyl group may be substituted with 1 to 5 halogen atoms:

wherein $X^2$ represents —$(CH_2)_p$—;
$Y^2$ represents a 3- to 12-membered heterocycle or 4- to 10-membered aromatic heterocycle;
$Z^2$ represents a hydrogen atom, $C_{1-6}$ alkyl group, $C_{2-6}$ alkenyl group, $C_{1-6}$ alkoxy group, $C_{3-7}$ cycloalkyl group, cyano group, or COORi;
p represents 0, 1, or 2; and
Ri represents a $C_{1-6}$ alkyl group;

[2] the compound, pharmaceutically acceptable salt thereof, or solvate thereof according to [1], wherein A is formula (1) below:

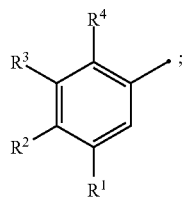

[3] the compound, pharmaceutically acceptable salt thereof, or solvate thereof according to [1] or [2], wherein Q is $CH_2$;

[4] the compound, pharmaceutically acceptable salt thereof, or solvate thereof according to any one of [1] to [3], wherein $R^2$ is a hydrogen atom or $C_{1-3}$ alkyl group;

[5] the compound, pharmaceutically acceptable salt thereof, or solvate thereof according to any one of [1] to [4], wherein $R^3$ is a hydrogen atom, $C_{1-6}$ alkyl group, or halogen atom;

[6] the compound, pharmaceutically acceptable salt thereof, or solvate thereof according to any one of [1] to [5], wherein $R^4$ is a $C_{1-6}$ alkylsulfonyl group or $C_{1-6}$ alkylsulfanyl group;

[7] the compound, pharmaceutically acceptable salt thereof, or solvate thereof according to any one of [1] to [6], wherein $R^5$ represents a halogen atom, $C_{1-3}$ alkyl group, or $C_{1-3}$ alkoxy group, wherein the $C_{1-3}$ alkyl group or $C_{1-3}$ alkoxy group may be substituted with 1 to 5 halogen atoms;

[8] the compound, pharmaceutically acceptable salt thereof, or solvate thereof according to any one of [1] to [7], wherein
$R^6$ represents a hydrogen atom or a group represented by formula (i) below:

wherein X represents $CH_2$;
Y represents piperazine, pyrrolidine, piperidine, morpholine, 3,3-dimethylpiperazine, (R) or (S)-hexahydro-pyrrolo[1,2-a]pyrazine, 3-oxopiperazine, azetidine, pyridine, or 2-oxo-imidazolidine; Z represents a hydrogen atom, a $C_{1-3}$ alkyl group, a $C_{4-6}$ cycloalkyl group, —$(CH_2)_m$NRaRb, —NHCO$(CH_2)_m$Rc, —$(CH_2)_m$NHCORc, —NH$(CH_2)_m$CORc, —$(CH_2)_m$N$(CH_3)$CORc, ORd, —CORe, —COORe, —NHSO$_2$Rf, —SO$_2$Rf, —$(CH_2)_m$CONRgRh, or piperazine, pyrrolidine, piperidine, tetrahydropyran, morpholine, or oxetane, wherein the piperazine, pyrrolidine, piperidine, tetrahydropyran, morpholine, or oxetane may be substituted with 1 to 5 halogen atoms, $C_{1-3}$ alkyl groups, and/or oxo groups;

m represents 0 or 1;
Ra and Rb are identical or different, each representing a hydrogen atom, a $C_{1-3}$ alkyl group, —SO$_2$CH$_3$, prop-2-ynyl, or oxetane, wherein the $C_{1-3}$ alkyl group may be substituted with 1 to 5 halogen atoms;
Rc represents a $C_{1-3}$ alkyl group, a $C_{1-4}$ alkoxy group, a $C_{4-6}$ cycloalkyl group, or an amino group, wherein the $C_{1-3}$ alkyl group may be substituted with 1 to 2 amino, mono-$C_{1-2}$ alkylamino, and/or di-$C_{1-2}$ alkylamino groups;
Rd represents a hydrogen atom, $C_{1-2}$ alkyl group, or $C_{2-3}$ alkenyl group, wherein the $C_{1-2}$ alkyl group may be substituted with 1 to 2 $C_{1-2}$ alkoxy groups;
Re represents a hydrogen atom or $C_{1-4}$ alkyl group, wherein the $C_{1-4}$ alkyl group may be substituted with an amino group;
Rf represents a $C_{1-3}$ alkyl group, an amino group, a mono-$C_{1-3}$ alkylamino group, or a di-$C_{1-3}$ alkylamino group; and
Rg and Rh are identical or different, each representing a hydrogen atom or $C_{1-3}$ alkyl group;

[9] the compound, pharmaceutically acceptable salt thereof, or solvate thereof according to any one of [1] to [8], wherein
$R^7$ represents a $C_{1-6}$ alkyl group, $C_{2-6}$ alkenyl group, $C_1$-6 alkoxy group, cyano group or a group represented by formula (ii) below, wherein the $C_{1-6}$ alkyl group may be substituted with 1 to 5 halogen atoms:

wherein $X^2$ represents —$CH_2$—;
$Y^2$ represents piperazine;
$Z^2$ represents a hydrogen atom, a methyl group, or COORi; and
Ri represents a $C_{1-6}$ alkyl group;

[10] a pharmaceutical comprising the compound, pharmaceutically acceptable salt thereof, or solvate thereof according to any one of [1] to [9] as an active ingredient;

[11] the pharmaceutical according to [10], wherein the pharmaceutical is used for prevention or treatment of cancer and/or for prevention or treatment of cancer invasion/metastasis;

[12] the pharmaceutical according to [10], wherein the pharmaceutical is used for prevention or treatment of fibrosis and/or inflammation;

[13] a method for treating cancer and/or cancer invasion/metastasis, comprising administering a pharmaceutically effective amount of a composition comprising the compound, pharmaceutically acceptable salt thereof, or solvate thereof according to any one of [1] to [9] to a patient in need thereof;

[14] a method for treating fibrosis and/or inflammation, comprising administering a pharmaceutically effective amount of a composition comprising the compound, pharmaceutically acceptable salt thereof, or solvate thereof according to any one of [1] to [9] to a patient in need thereof;

[15] use of the compound, pharmaceutically acceptable salt thereof, or solvate thereof according to any one of [1] to [9] for the manufacture of an agent for treating cancer and/or cancer invasion/metastasis;

[16] use of the compound, pharmaceutically acceptable salt thereof, or solvate thereof according to any one of [1] to [9] for the manufacture of an agent for treating fibrosis and/or inflammation;

[17] the compound, pharmaceutically acceptable salt thereof, or solvate thereof according to any one of [1] to [9] for use in treating cancer and/or cancer invasion/metastasis; and

[18] the compound, pharmaceutically acceptable salt thereof, or solvate thereof according to any one of [1] to [9] for use in treating fibrosis and/or inflammation.

Effects of the Invention

The compounds according to the present invention or pharmaceutically acceptable salts thereof, or solvates thereof have an effect of selectively inhibiting Discoidin Domain Receptor 1 (DDR1). The compounds of the present application can have a medicinal effect for diseases associated with abnormalities of DDR1, such as cancer, cancer metastasis and invasion, fibrosis, and inflammation; and can prevent and/or treat diseases for which previous therapeutic agents are not sufficiently effective.

MODE FOR CARRYING OUT THE INVENTION

Figure 1:
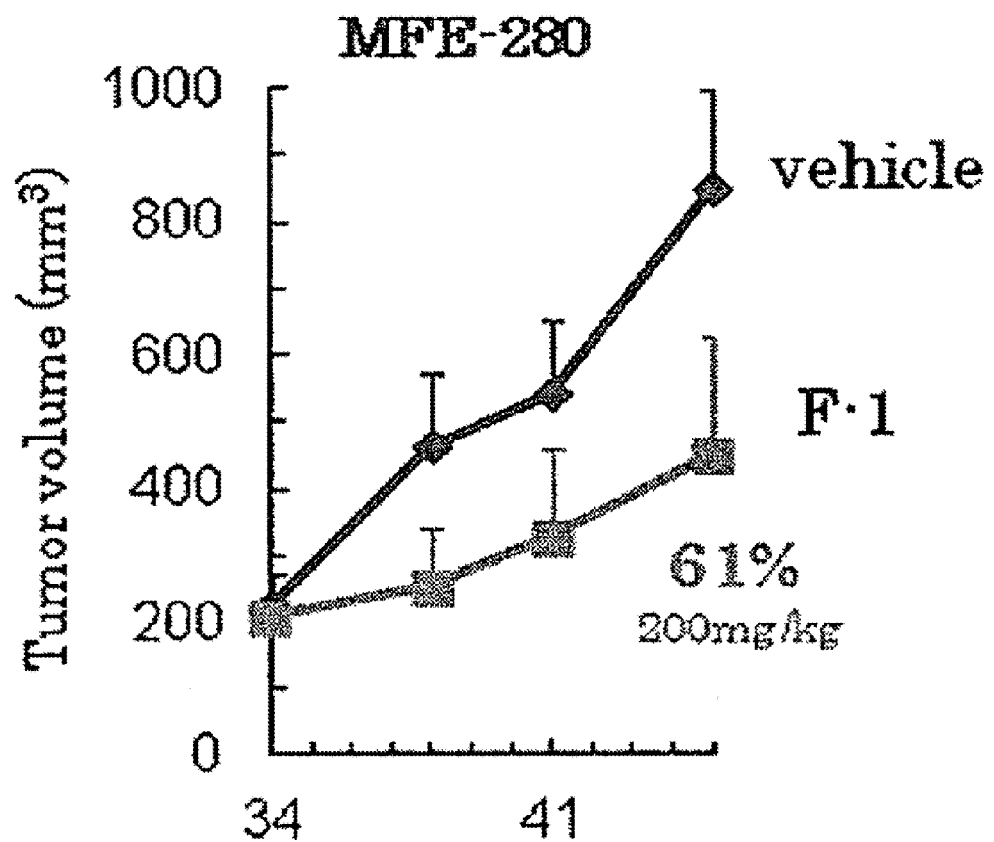
FIG. 1 is a graph showing an antitumor effect of Compound F-1.

The present invention relates to quinazolinedione derivatives and uses thereof. The present inventors have synthesized compounds represented by formula (I) above or pharmaceutically acceptable salts thereof for the first time, and discovered that the compounds or salts thereof have a DDR1 inhibitory effect.

Herein, "alkyl" refers to a monovalent group derived by removing any one hydrogen atom from an aliphatic hydrocarbon, and covers a subset of hydrocarbyl or hydrocarbon group structures that include hydrogen and carbon atoms, but do not contain a heteroatom or an unsaturated carbon-carbon bond in the backbone. Examples of the alkyl group include those of linear or branched structures. The alkyl group is preferably an alkyl group having 1 to 6 carbon atoms ($C_{1-6}$; "$C_{p-q}$" hereinafter means that the group has p to q carbon atoms), such as a $C_{1-5}$ alkyl group, $C_{1-4}$ alkyl group, or $C_{1-3}$ alkyl group.

Specific examples of the alkyl include a methyl group, an ethyl group, an n-propyl group, an isopropyl group, an n-butyl group, an isobutyl group, an s-butyl group, a t-butyl group, a pentyl group, an isopentyl group, a 2,3-dimethylpropyl group, a 3,3-dimethylbutyl group, and a hexyl group.

Herein, "alkenyl" refers to a monovalent hydrocarbon group having at least one double bond (two adjacent SP2 carbon atoms), and includes linear or branched ones. Depending on the configuration of the double bond and the substituent (if present), the geometry of the double bond can be an entgegen (E) or zuzammen (Z) configuration, or a cis or trans configuration. Preferred examples of the alkenyl group include $C_{2-6}$ alkenyl groups.

Specific examples of the alkenyl include a vinyl group, an allyl group, a 1-propenyl group, a 2-propenyl group, a 1-butenyl group, a 2-butenyl group (including cis and trans), a 3-butenyl group, a pentenyl group, and a hexenyl group.

Herein, "alkynyl" refers to a monovalent hydrocarbon group having at least one triple bond (two adjacent SP carbon atoms), and includes linear or branched ones. Preferred examples include $C_{2-6}$ alkynyl groups.

Specific examples of the alkynyl include an ethynyl group, a 1-propynyl group, a propargyl group, a 3-butynyl group, a pentynyl group, and a hexynyl group.

The alkenyl or alkynyl can have one or more double bonds or triple bonds, respectively.

Herein, "cycloalkyl" refers to a saturated or partially saturated cyclic, monovalent aliphatic hydrocarbon group, and includes single rings, bicyclo rings, and spiro rings. Preferred examples of the cycloalkyl include $C_{3-7}$ cycloalkyl groups. Specific examples of the cycloalkyl group include a cyclopropyl group, cyclobutyl group, cyclopentyl group, cyclohexyl group, and cycloheptyl group.

Herein, "aryl" refers to a monovalent aromatic hydrocarbon ring. Preferred examples include $C_{6-10}$ aryl. Specific examples of the aryl include a phenyl group and naphthyl group (e.g., a 1-naphthyl group or 2-naphthyl group).

Herein, "halogen atom" refers to a fluorine atom, a chlorine atom, a bromine atom, or an iodine atom.

Herein, "alkoxy" refers to an oxy group to which the above-defined "alkyl" is bonded. Preferred examples include $C_{1-6}$ alkoxy groups, $C_{1-4}$ alkoxy groups, and $C_{1-3}$ alkoxy groups. Specific examples of the alkoxy include a methoxy group, an ethoxy group, a 1-propoxy group, a 2-propoxy group, an n-butoxy group, an i-butoxy group, a sec-butoxy group, and a tert-butoxy group.

Herein, "aromatic ring" refers to an aromatic monovalent or divalent hydrocarbon ring. The aromatic ring may be a single ring or a fused ring. The number of the ring-forming atoms is preferably 4 to 10 (4- to 10-membered aromatic ring).

Specific examples of the aromatic ring include benzene and naphthalene.

Herein, "heterocycle" refers to a non-aromatic monovalent or divalent heterocycle containing preferably 1 to 5 heteroatoms in the ring-forming atoms. The heterocycle may have a double and/or triple bond in the ring, and a carbon atom in the ring oxidized to form carbonyl; and it may be a single ring, fused ring, or spiro ring. The number of ring-forming atoms is preferably 3 to 12 (3- to 12-membered heterocycle), more preferably 4 to 7 (4- to 7-membered heterocycle), and even more preferably 5 to 6 (5- to 6-membered heterocycle).

Specific examples of the heterocycle include piperazine, pyrrolidine, piperidine, morpholine, (R)-hexahydropyrrolo[1,2-a]pyrazine, (S)-hexahydropyrrolo[1,2-a]pyrazine, 3-oxopiperazine, 2-oxopyrrolidine, azetidine, 2-oxoimidazolidine, oxetane, dihydrofuran, tetrahydrofuran, dihydropyran, tetrahydropyran, tetrahydropyridine, thiomorpholine, pyrazolidine, imidazoline, oxazolidine, isoxazolidine, thiazolidine, imidazolidine, isothiazolidine, thiadiazolidine, oxazolidone, benzodioxane, benzoxazoline, and dioxolane.

Herein, "aromatic heterocycle" refers to an aromatic monovalent or divalent heterocycle containing preferably 1 to 5 heteroatoms in the ring-forming atoms. The aromatic heterocycle may be partially saturated, and may be a single ring, fused ring (such as a bicyclic aromatic heterocycle in which a monocyclic aromatic heterocycle is fused with a benzene ring or another monocyclic aromatic heterocycle), or spiro ring. The number of ring-forming atoms is preferably 4 to 10 (4- to 10-membered aromatic heterocycle).

Specific examples of the aromatic heterocycle include furan, thiophene, pyrrole, imidazole, pyrazole, thiazole, isothiazole, oxazole, isoxazole, oxadiazole, thiadiazole, triazole, tetrazole, pyridine, pyrimidine, pyridazine, pyrazine, triazine, benzofuran, benzothiophene, benzothiadiazole, benzothiazole, benzoxazole, benzoxadiazole, benzimidazole, indole, isoindole, indazole, quinoline, isoquinoline, cinnoline, quinazoline, quinoxaline, indolizine, and imidazopyridine.

Herein, "heteroatom" refers to a nitrogen atom (N), an oxygen atom (O), or a sulfur atom (S).

Herein, "monoalkylamino" refers to an amino group to which one of the above-defined "alkyl" groups is bonded. Preferred examples of the monoalkylamino include mono-$C_{1-6}$ alkylamino.

Herein, "dialkylamino" refers to an amino group to which two of the above-defined "alkyl" groups are bonded, where the alkyl groups may be identical or different. Preferred examples of the dialkylamino include di-$C_{1-6}$ alkylamino.

Herein, "alkylsulfonyl" refers to a sulfonyl group to which the above-defined "alkyl" is bonded (i.e., alkyl-$SO_2$—). Preferred examples of the alkylsulfonyl include $C_{1-6}$ alkylsulfonyl and $C_{1-3}$ alkylsulfonyl, specifically methylsulfonyl, ethylsulfonyl, n-propylsulfonyl, and i-propylsulfonyl.

Herein, "alkylsulfanyl" refers to a sulfanyl group to which the above-defined "alkyl" is bonded (i.e., alkyl-S—). Preferred examples of the alkylsulfanyl include $C_{1-6}$ alkylsulfanyl and $C_{1-3}$ alkylsulfanyl, specifically methylsulfanyl, ethylsulfanyl, n-propylsulfanyl, and i-propylsulfanyl.

Herein, "alkylsulfinyl" refers to a sulfinyl group to which the above-defined "alkyl" is bonded (i.e., alkyl-SO—). Preferred examples of the alkylsulfinyl include $C_{1-6}$ alkylsulfinyl and $C_{1-3}$ alkylsulfinyl, specifically methylsulfinyl, ethylsulfinyl, n-propylsulfinyl, and i-propylsulfinyl.

Herein, "arylsulfonyl" refers to a sulfonyl group to which the above-defined "aryl" is bounded (i.e., aryl-$SO_2$—). Preferred examples of the arylsulfonyl include $C_{6-10}$ arylsulfonyl, specifically, phenylsulfonyl, 1-naphthylsulfonyl, and 2-naphthylsulfonyl.

Herein, "arylsulfanyl" refers to a sulfanyl group to which the above-defined "aryl" is bounded (i.e., aryl-S—). Preferred examples of the arylsulfanyl include $C_{6-10}$ arylsulfanyl, specifically, phenylsulfanyl, 1-naphthylsulfanyl, and 2-naphthylsulfanyl.

Herein, "arylsulfinyl" refers to a sulfinyl group to which the above-defined "aryl" is bounded (i.e., aryl-SO—). Preferred examples of the arylsulfinyl include $C_{6-10}$ arylsulfinyl, specifically, phenylsulfinyl, 1-naphthylsulfinyl, and 2-naphthylsulfinyl.

Herein, "cycloalkylsulfonyl" refers to a sulfonyl group to which the above-defined "cycloalkyl" is bounded (i.e., cycloalkyl-$SO_2$—). Preferred examples of the cycloalkylsulfonyl include $C_{3-8}$ cycloalkylsulfonyl, specifically, cyclopentylsulfonyl, cyclohexylsulfonyl, and cycloheptylsulfonyl.

Herein, "cycloalkylsulfanyl" refers to a sulfanyl group to which the above-defined "cycloalkyl" is bounded (i.e., cycloalkyl-S—). Preferred examples of the cycloalkylsulfanyl include $C_{3-8}$ cycloalkylsulfanyl, specifically, cyclopentylsulfanyl, cyclohexylsulfanyl, cycloheptylsulfanyl.

Herein, "cycloalkylsulfinyl" refers to a sulfinyl group to which the above-defined "cycloalkyl" is bounded (i.e., cycloalkyl-SO—). Preferred examples of the cycloalkylsulfinyl include $C_{3-8}$ cycloalkylsulfinyl, specifically, cyclopentylsulfinyl, cyclohexylsulfinyl, cycloheptylsulfinyl.

The compounds according to the present invention, whether free forms or pharmacologically acceptable salts, are included in the present invention. Examples of such "salts" include inorganic acid salts, organic acid salts, inorganic base salts, organic base salts, and acidic or basic amino acid salts.

Preferred examples of the inorganic acid salts include hydrochlorides, hydrobromides, sulfates, nitrates, and phosphates. Preferred examples of the organic acid salts include acetates, succinates, fumarates, maleates, tartrates, citrates, lactates, malates, stearates, benzoates, methanesulfonates, and p-toluenesulfonates.

Preferred examples of the inorganic base salts include alkali metal salts such as sodium salts and potassium salts, alkaline earth metal salts such as calcium salts and magnesium salts, aluminum salts, and ammonium salts. Preferred examples of the organic base salts include diethylamine salts, diethanolamine salts, meglumine salts, and N,N-dibenzylethylenediamine salts.

Preferred examples of the acidic amino acid salts include aspartates and glutamates. Preferred examples of the basic amino acid salts include arginine salts, lysine salts, and ornithine salts.

The compounds of the present invention may absorb moisture, contain adsorbed water, or form hydrates when left in the air. Such hydrates are also included in the salts of the present invention.

Further, the compounds according to the present invention may absorb certain other solvents to form solvates. Such solvates are also included in the salts of the present invention.

The present invention includes all isomers (such as geometric isomers, optical isomers, stereoisomers, and tautomers) that arise structurally from the compounds of the present invention, as well as mixtures of these isomers.

The compounds according to the present invention may exhibit crystalline polymorphism, and all polymorphs of the compounds are included in the present invention.

The compounds according to the present invention include prodrugs thereof. The prodrugs are derivatives of the compounds of the present invention which have chemically or metabolically decomposable groups, and are converted back to the original compounds after administration in vivo to exhibit their original efficacy; and they include non-covalently bonded complexes and salts.

The compounds according to the present invention include those in which one or more atoms in the molecule are substituted with isotopes. In the present invention, the isotope refers to an atom having the same atomic number (proton number) but a different mass number (sum of the number of protons and neutrons). Examples of atoms contained in the compounds of the present invention to be substituted with isotopes include a hydrogen atom, a carbon atom, a nitrogen atom, an oxygen atom, a phosphorus atom, a sulfur atom, a fluorine atom, and a chlorine atom. Examples of the isotopes include $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$. In particular, radioisotopes that decay by emitting radioactivity such as $^3H$ and $^{14}C$ are useful in tests of body tissue distribution for pharmaceuticals or compounds. Stable isotopes do not decay, and are almost equally abundant. They do not emit radioactivity, and thus can be used safely. Isotopically-substituted forms of the compounds of the present invention can be obtained according to conventional methods by substituting a reagent containing a corresponding isotope for the reagent used for synthesis.

The compounds represented by formula (I) above according to the present invention are preferably as follows.

The above A is preferably formula (1) below.

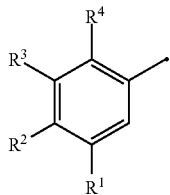

The above Q is preferably $CH_2$.

The above $A^1$ is preferably $CR^1$.

The above $R^1$ is preferably a chlorine atom, a bromine atom, a fluorine atom, a methyl group, or a cyano group, and more preferably a chlorine atom.

The above $A^2$ is preferably $CR^2$.

The above $R^2$ is preferably a hydrogen atom or $C_{1-3}$ alkyl group, and more preferably a hydrogen atom.

The above $A^3$ is preferably $CR^3$.

The above $R^3$ is preferably a hydrogen atom, $C_{1-3}$ alkyl group, or halogen atom, more preferably a chlorine atom, hydrogen atom, or methyl group, and more preferably a hydrogen atom.

The above $R^4$ is preferably a $C_{2-4}$ alkylsulfonyl group, $C_{2-4}$ alkylsulfanyl group, or $C_{2-4}$ alkylsulfinyl group, more preferably a $C_{2-4}$ alkylsulfonyl group, and still more preferably an ethylsulfonyl group.

Preferably, the above $R^5$ represents a halogen atom, $C_{1-3}$ alkyl group, or $C_{1-3}$ alkoxy group, where the $C_{1-3}$ alkyl group or $C_{1-3}$ alkoxy group may be substituted with 1 to 5 halogen atoms. More preferably, the above $R^5$ represents a halogen atom, $C_{1-2}$ alkyl group, or $C_{1-2}$ alkoxy group, where the $C_{1-2}$ alkyl group or $C_{1-2}$ alkoxy group may be substituted with 1 to 3 halogen atoms. The above $R^5$ is more preferably a trifluoromethyl group, trifluoromethoxy group, methyl group, ethyl group, chlorine atom, or bromine atom, and particularly preferably a trifluoromethyl group.

Preferably, the above $R^6$ represents a hydrogen atom or a group represented by formula (i) below.

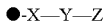-X—Y—Z    (i)

The above X is preferably —(CH$_2$)n-, where n represents 1 or 2, and n is preferably 1.

The above Y preferably represents a 5- to 6-membered heterocycle, where the 5- to 6-membered heterocycle may be substituted with 1 to 5 halogen atoms and/or $C_{1-3}$ alkyl groups. The above Y is more preferably piperazine, pyrrolidine, piperidine, morpholine, 3,3-dimethylpiperazine, (R) or (S)-hexahydro-pyrrolo[1,2-a]pyrazin-2-yl, 3-oxopiperazin-1-yl, azetidin-3-yl, or 2-oxo-imidazolidin-1-yl.

The above Z preferably represents a hydrogen atom, a $C_{1-3}$ alkyl group, a $C_{4-6}$ cycloalkyl group, —(CH$_2$)$_m$—NRaRb, —NHCO(CH$_2$)$_m$Rc, —(CH$_2$)$_m$NHCORc, —NH(CH$_2$)$_m$CORc, —(CH$_2$)$_m$N(CH$_3$)CORc, —ORd, —CORe, —COORe, —NHSO$_2$Rf, —SO$_2$Rf, —(CH$_2$)$_m$CONRgRh, or a 5-to 6-membered heterocycle, where the $C_{1-3}$ alkyl group may be substituted with 1 to 5 halogen atoms, hydroxyl groups, and/or cyano groups; the 5- to 6-membered heterocycle may be substituted with 1 to 5 halogen atoms, $C_{1-3}$ alkyl groups, and/or oxo groups; and m represents 0 or 1. The above Z is more preferably a hydrogen atom, —(CH$_2$)$_m$—NRaRb, —NHCO(CH$_2$)$_m$Rc, —(CH$_2$)$_m$NHCORc, —CORe, or a 4- to 6-membered heterocycle, where m represents 0 or 1.

Preferably, the above Ra and Rb are identical or different, each representing a hydrogen atom, a $C_{1-3}$ alkyl group, —SO$_2$CH$_3$, a prop-2-ynyl group, or an oxetan-3-yl group, where the $C_{1-3}$ alkyl group may be substituted with 1 to 5 halogen atoms. More preferably, the above Ra and Rb are identical or different, each representing a hydrogen atom, a $C_{1-3}$ alkyl group, or —SO$_2$CH$_3$.

Preferably, the above Rc represents a $C_{1-4}$ alkyl group, a $C_{1-4}$ alkoxy group, a $C_{4-6}$ cycloalkyl group, or an amino group, where the $C_{1-4}$ alkyl group may be substituted with 1 to 3 groups independently selected from amino, mono-$C_{14}$ alkylamino, and di-$C_{1-4}$ alkylamino groups. More preferably, the above Rc represents a $C_{1-2}$ alkyl group, a $C_{1-2}$ alkoxy group, or an amino group, where the $C_{1-2}$ alkyl group may be substituted with 1 to 2 groups independently selected from amino, mono-$C_{1-2}$ alkylamino, and di-$C_{1-2}$ alkylamino groups.

The above Rd preferably represents a hydrogen atom, $C_{1-3}$ alkyl group, or $C_{2-3}$ alkenyl group, where the $C_{1-3}$ alkyl group may be substituted with 1 to 2 $C_{1-2}$ alkoxy groups. The above Rd is more preferably a hydrogen atom or methyl group.

Preferably, the above Re represents a hydrogen atom or $C_{1-4}$ alkyl group, where the $C_{1-4}$ alkyl group may be substituted with 1 to 3 amino groups. More preferably, the above Re represents a $C_{1-2}$ alkyl group, where the $C_{1-2}$ alkyl group may be substituted with 1 to 2 amino groups.

The above Rf is preferably a $C_{1-3}$ alkyl group, an amino group, a mono-$C_{1-3}$ alkylamino group, or a di-$C_{1-3}$ alkylamino group, and more preferably a methyl group, an amino group, a monomethylamino group, or a dimethylamino group.

Preferably, the above Rg and Rh are identical or different, and each is a hydrogen atom or $C_{1-3}$ alkyl group.

The above $R^7$ is preferably a hydrogen atom, a halogen atom, a cyano group, a methyl group, an ethyl group, a vinyl group, or a group represented by formula (ii) below.

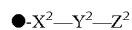-X$^2$—Y$^2$—Z$^2$    (ii)

The above $X^2$ is preferably a single bond or —(CH$_2$)p-, where p represents 0 or 1, and p is preferably 1.

The above $Y^2$ is preferably a 5- to 6-membered heterocycle, and more preferably piperazine.

The above $Z^2$ is preferably a hydrogen atom, a methyl group, or —COORi.

The above Ri is preferably a $C_{1-4}$ alkyl group.

Such compounds represented by formula (I) or pharmaceutically acceptable salts thereof according to the present invention are useful as compounds having an effect of selectively inhibiting Discoidin Domain Receptor 1 (DDR1), and are useful for prevention and/or treatment of cancer, prevention and/or treatment of cancer invasion and metastasis, and prevention and/or treatment of fibrosis and inflammation.

Examples of the cancer include leukemia (such as acute myeloid leukemia, chronic myeloid leukemia, acute lymphocytic leukemia, and chronic lymphocytic leukemia), malignant lymphoma (such as Hodgkin's lymphoma and non-Hodgkin's lymphoma), brain tumor, neuroblastoma, glioma, thyroid cancer, myelodysplastic syndrome, head and neck cancer, esophageal cancer, gastric cancer, colon cancer, colorectal cancer, breast cancer, ovarian cancer, lung cancer, pancreatic cancer, liver cancer, gallbladder cancer, skin cancer, malignant melanoma, renal cancer, renal pelvic and ureteral cancer, bladder cancer, uterine cancer, testicular cancer, and prostatic cancer. Preferred examples include non-small-cell lung cancer, pancreatic cancer, endometrial cancer, brain tumor, bile duct cancer, colon cancer, breast cancer, ovarian cancer, and prostatic cancer.

Examples of the fibrosis and inflammation include hepatic fibrosis, renal fibrosis, pulmonary fibrosis, scleroderma/systemic sclerosis, myelofibrosis, endomyocardial fibrosis, hepatitis (nonalcoholic steatohepatitis, alcoholic hepatitis, drug-induced hepatitis, autoimmune hepatitis, and primary biliary cirrhosis), diabetic nephropathy, membranoproliferative glomerulonephritis, focal glomerulosclerosis, IgA nephropathy, membranous nephropathy, light chain deposition disease, lupus nephritis, cryoglobulinemic nephritis, HIV-associated nephritis, purpura nephritis, membranoproliferative nephritis, endocapillary proliferative nephritis, mesangial proliferative nephritis, crescentic nephritis, interstitial nephritis, hypertensive nephrosclerosis, anti-GBM nephritis (Goodpasture syndrome), HCV, HBV-associated nephropathy, ANCA nephritis, Alport's syndrome, chronic pancreatitis, rheumatoid arthritis, atherosclerosis, Crohn's disease, ulcerative colitis, and multiple sclerosis.

The compounds or salts thereof according to the present invention can be formulated by conventional methods into tablets, powders, fine granules, granules, coated tablets, capsules, syrups, troches, inhalations, suppositories, injections, ointments, ophthalmic ointments, ophthalmic preparations, nasal preparations, ear preparations, cataplasms, lotions, and the like. Commonly used excipients, binding agents, lubricants, colorants, corrigents; and as necessary, stabilizers, emulsifiers, absorption promoters, surfactants, pH adjusters, preservatives, antioxidants, and the like can be used for formulation. They are blended with ingredients commonly used as raw materials in pharmaceutical preparations, and formulated by conventional methods.

For example, oral preparations are manufactured by adding to the compound or a pharmacologically acceptable salt thereof according to the present invention, an excipient, and as necessary, a binding agent, disintegrant, lubricant, colorant, corrigent, and the like, and then formulating them into powder, fine granules, granules, tablets, coated tablets, capsules, and the like by a conventional method.

Examples of these ingredients include animal and vegetable oils such as soybean oil, beef tallow, and synthetic glyceride; hydrocarbons such as liquid paraffin, squalane, and solid paraffin; ester oils such as octyldodecyl myristate and isopropyl myristate; higher alcohols such as cetostearyl alcohol and behenyl alcohol; silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil, and polyoxyethylene-polyoxypropylene block copolymer; water-soluble polymers such as hydroxyethylcellulose, polyacrylic acid, carboxyvinyl polymer, polyethylene glycol, polyvinylpyrrolidone, and methylcellulose; lower alcohols such as ethanol and isopropanol; polyhydric alcohols such as glycerol, propylene glycol, dipropylene glycol, and sorbitol; sugars such as glucose and sucrose; inorganic powders such as silicic anhydride, magnesium aluminum silicate, and aluminum silicate; and purified water.

Examples of the excipients include lactose, corn starch, white soft sugar, glucose, mannitol, sorbitol, microcrystalline cellulose, and silicon dioxide.

Examples of the binding agents include polyvinyl alcohol, polyvinyl ether, methylcellulose, ethylcellulose, acacia, tragacanth, gelatin, shellac, hydroxypropylmethylcellulose, hydroxypropylcellulose, polyvinylpyrrolidone, polypropylene glycol-polyoxyethylene block polymer, and meglumine.

Examples of the disintegrants include starch, agar, gelatin powder, microcrystalline cellulose, calcium carbonate, sodium bicarbonate, calcium citrate, dextrin, pectin, and carboxymethylcellulose calcium.

Examples of the lubricants include magnesium stearate, talc, polyethylene glycol, silica, and hydrogenated vegetable oil.

Colorants used are approved for addition into pharmaceuticals. Corrigents used are cocoa powder, peppermint camphor, empasm, mentha oil, borneol, powdered cinnamon bark, and the like.

By all means, these tablets and granules may be sugar-coated or appropriately coated with something else as necessary. Liquid preparations such as syrups and injectable preparations are manufactured by adding a pH adjuster, solubilizer, tonicity adjusting agent, or such, and as necessary, a solubilizing agent, stabilizer, or such to the compound or a pharmacologically acceptable salt thereof according to the present invention, followed by formulation using a conventional method.

The method of manufacturing external preparations is not limited, and they can be manufactured by conventional methods. Specifically, various raw materials commonly used for pharmaceuticals, quasi drugs, cosmetics, and such can be used as base materials for formulation. Specific examples of the base materials used include raw materials such as animal and vegetable oils, mineral oils, ester oils, waxes, higher alcohols, fatty acids, silicone oil, surfactants, phospholipids, alcohols, polyhydric alcohols, water-soluble polymers, clay minerals, and purified water. Further, pH adjusters, antioxidants, chelators, preservatives and fungicides, colorants, flavoring ingredients, and the like may be added as necessary. The base materials for external preparations according to the present invention are not limited to these materials.

Ingredients such as ingredients having a differentiation-inducing effect, blood flow promoters, bactericides, anti-inflammatory agents, cell activators, vitamins, amino acids, humectants, and keratolytic agents may also be blended as necessary. The aforementioned base materials are added in an amount to yield a concentration commonly set for the manufacture of external preparations.

The mode of administering the compounds or salts thereof, or solvates of the compounds or salts according to the present invention is not particularly limited, and they may be orally or parenterally administered by methods commonly used. For example, they can be administered after they are formulated into preparations such as tablets, powders, granules, capsules, syrups, troches, inhalations, suppositories, injections, ointments, ophthalmic ointments, ophthalmic preparations, nasal preparations, ear preparations, cataplasms, or lotions.

The dosage of the medicine according to the present invention can be appropriately selected depending on the symptom severity, age, sex, body weight, mode of administration, type of salt, specific type of the disease, and such.

Although the dosage varies significantly according to the type of the disease, symptom severity, patient's age, sex, and drug sensitivity, and such, the dosage is usually about 0.03 to 1000 mg, preferably 0.1 to 500 mg, and more preferably 0.1 to 100 mg per day for adults, and is administered in one to several doses a day. For injections, the dosage is usually about 1 µg/kg to 3000 µg/kg, preferably about 3 µg/kg to 1000 µg/kg.

In the manufacturing of the compounds according to the present invention, raw material compounds and various reagents may form salts, hydrates, or solvates; and all vary depending on the starting material, solvent used, and such, and there is no particular limitation as long as they do not inhibit the reaction.

The solvent used also varies depending on the starting material, reagent, and such, and is not particularly limited as long as it does not inhibit the reaction and dissolves the starting material to a certain extent.

Various isomers (e.g., geometric isomers, optical isomers based on asymmetric carbons, rotamers, stereoisomers, and tautomers) can be purified and isolated using common separation means, e.g., recrystallization, diastereomeric salt methods, enzymatic resolution methods, and various chromatography methods (e.g., thin-layer chromatography, column chromatography, high performance liquid chromatography, and gas chromatography).

When the compounds of the present invention are obtained as free forms, they can be converted into salts or solvates of the compounds by conventional methods. When the compounds of the present invention are obtained as salts or solvates of the compounds, they can also be converted into free forms of the compounds by conventional methods.

The compounds according to the present invention can be isolated and purified by applying common chemical operations such as extraction, concentration, evaporation, crystallization, filtration, recrystallization, and various chromatographic methods.

All prior art documents cited herein are incorporated by reference.

General production methods for the compounds of the present invention and examples thereof will be shown below.

Compounds of the present invention can be synthesized by various methods, some of which will be described with reference to the following schemes. The schemes are illustrative, and the present invention is not limited to only the chemical reactions and conditions explicitly indicated. Although some substituents may be excluded in the following schemes for the sake of clarity, such exclusion is not intended to limit the disclosure of the schemes. Representative compounds of the present invention can be synthesized using appropriate intermediates, known compounds, and reagents.

Abbreviations generally used in the General production methods and Examples below, and the names of reagents and solvents corresponding to the chemical formulas will be described below.

AcOH Acetic acid
AD mix Asymmetric Dihydroxylation Mix
AIBN Azobisisobutyronitrile
Boc t-butoxycarbonyl
Boc$_2$O Di-t-butyl dicarbonate
BOP Benzotriazol-1-yloxy-trisdimetylaminophosphonium salts and derivatives thereof
BuPAd2 Butyldi-1-adamantylphosphine
9-BBN 9-borabicyclo[3.3.1]nonane
CPME Cyclopentyl methyl ether
CDI 1,1'-Carbonylbis-1H-imidazole
DBU 1,8-Diazabicyclo[5.4.0]-7-undecene
DCC N,N'-Dicylohexylcarbodiimide
DCM Dichloromethane
DIPEA N,N-Diisopropylethylamine
DMF Dimethylformamide
DMA Dimethylacetamide
DMAP N,N-Dimethyl-4-aminopyridine
DMSO Dimethyl sulfoxide
DMT-MM 4-(4,6-Dimethoxy-1,3,5-triazin-2-yl)-4-methyl-morpholinium Chloride
DPPA diphenylphosphorylazide
dppf 1,1'-Bis(diphenylphosphino)ferrocene
EtOH Ethanol
2-PrOH 2-Propanol
EtOAc Ethyl acetate
HATU O-(7-Azabenzotriazol-1-yl)-N,N,N',N'-tetramethyluronium hexafluorophosphate
HBTU O-(Benzotriazol-1-yl)-N,N,N',N'-tetramethyluronium hexafluorophosphate
HOBT 1-Hydroxybenzotriazole
LDA lithium diisopropylamide
LiHMDS Lithium bis(trimethylsilyl)amide(=Lithium hexamethyl disilazide)
m-CPBA m-Chloroperbenzoic acid
n-BuLi n-Butyllithium
NMP N-Methylpyrrolidone
NBS N-Bromosuccinimide
NCS N-Chlorosuccinimide
MeOH Methanol
PTSA p-Toluenesulfonic acid
RuPhos 2-Dicyclohexylphosphino-2',6'-di-i-propoxy-1,1'-biphenyl
TBME t-Butyl methyl ether
TBAF Tetrabutylammonium fluoride
TBSCl t-Butyldimethylsilyl chloride
TEA Triethylamine
TFA Trifluoroacetic acid
THF Tetrahydrofuran
WSCDI 1-Ethyl-3-(3-dimethylaminopropyl)carbodiimide hydrochloride
X-Phos 2',4',6'-Triisopropyl-2-(dicyclohexylphosphino)biphenyl Production Method I The method is a method for forming a backbone of formula (I), where Q is CH$_2$; A$^1$, A$^2$ and A$^3$ are CR$^1$, CR$^2$, and CR$^3$, respectively; and R$^6$ and R$^7$ are H or halogen.

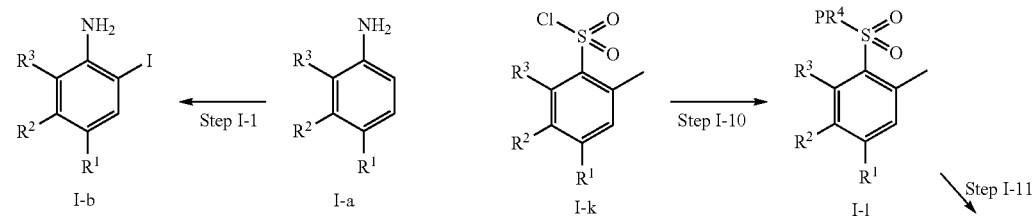

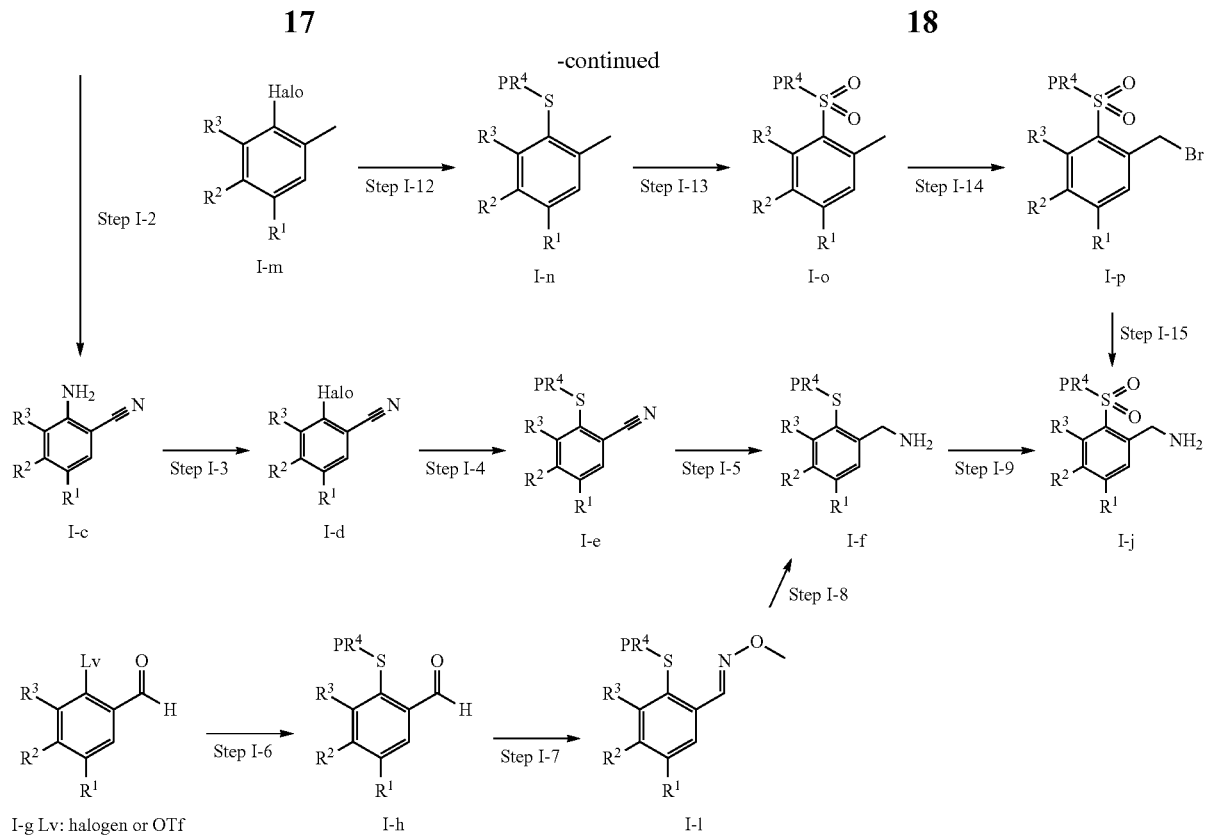

Step I-1

The step is halogenation (iodination) of an aniline derivative I-a by electrophilic substitution reaction. This step can be performed by reacting the aniline derivative I-a with iodine ($I_2$) in the presence of sodium hydrogen carbonate. This step can be performed using, for example, the method of Org. Synth., Coll. Vol. 2, p. 347 (1943); Vol. 11, p. 62 (1931). Examples of the solvent include alcohols, water, and mixed solvents thereof. An aqueous ethanol solution is preferred.

Step I-2

The step is cyanation of an iodoaniline derivative I-b by nucleophilic substitution reaction. This step can be performed by reacting the iodoaniline derivative I-b with a transition-metal cyanide by heating. This step can be performed using, for example, the method of J. Org. Chem., 26, 2522 (1961). The transition-metal cyanide is preferably copper(I) cyanide. Examples of the solvent include aromatic amines such as pyridine and quinoline; and polar aprotic solvents such as DMF, NMP, and HMPA. DMF is preferred. The heating condition is preferably 150° C. or higher or heating under reflux.

Step I-3

The step is iodination of a cyanoaniline derivative I-c. This step can be performed by converting the cyanoaniline derivative I-c to a diazonium salt using a nitrite under acidic conditions (Griess reaction), and then reacting it with a metal iodide without isolation (Sandmeyer reaction). The nitrite used for the conversion to a diazonium salt is preferably sodium nitrite. Examples of the acid include sulfuric acid, hydrochloric acid, methanesulfonic acid, and TFA. TFA or sulfuric acid is preferred. Examples of the solvent here include polar solvents such as trifluoroethanol, DMF, and acetonitrile. Trifluoroethanol is preferred. Examples of the metal iodide include potassium iodide, sodium iodide, and lithium iodide. Potassium iodide is preferred.

Step I-4

The step is sulfanylation of a halobenzonitrile derivative I-d by producing a carbon-sulfur bond. This step can be performed by reacting the halobenzonitrile derivative I-d with an alkylthiol or arylthiol reagent which corresponds to $PR^4$ in the presence of a base. Examples of the thiol reagent include acyclic alkylthiols such as methanethiol, ethanethiol, n-propylthiol, and i-propylthiol; cyclic alkylthiols such as cyclopentylthiol; and arylthiols such as phenylthiol. Examples of the base include inorganic bases such as potassium carbonate, sodium carbonate, cesium carbonate, calcium carbonate, and sodium hydride; and organic bases such as t-BuOK, LDA, LiHMDS, N,N-dimethyl-4-aminopyridine, and DBU. Potassium carbonate and sodium carbonate are preferred. Examples of the solvent include DMF, DMA, DMSO, dichloromethane, THF, acetonitrile, and mixtures thereof. DMF is preferred. This step can also be performed by reacting the halobenzonitrile derivative I-d with a metal alkyl/aryl thiolate which corresponds to $PR^4$ under heating in a polar solvent such as DMF as in the method described in WO 2009/131245. Further, this step can be performed by an alternative method of reacting the halobenzonitrile derivative I-d with an acyclic alkylthiol which corresponds to $PR^4$ by heating in a polar solvent such as 1,4-dioxane in the presence of a Pd catalyst, a Pd catalyst ligand, and a base as in the method described in WO 2006/038741. Here, the Pd catalyst is preferably $Pd_2(dba)_3$, the Pd catalyst ligand is preferably Xantphos, the base is preferably N,N-diisobutylethylamine, and the solvent is preferably 1,4-dioxane.

Step I-5

The step is reduction of an alkylsulfanylbenzonitrile derivative I-e. This step can be performed by reducing the nitrile group of the alkylsulfanylbenzonitrile derivative I-e by reaction with a reducing agent. Examples of the reducing agent include metal-reducing agents such as lithium aluminum hydride, diisobutylaluminum hydride, Selectride, Super-Hydride, and sodium borohydride-nickel chloride; and boron reducing agents such as borane-THF complex and borane-dimethyl sulfide complex. Lithium aluminum hydride and borane-THF complex are preferred. Examples of the solvent include THF, dimethyl ether, and dimethoxyethane. THF is preferred.

Step I-6

The step is sulfanylation of an aldehyde I-g by producing a carbon-sulfur bond. This step can be performed by reacting the aldehyde I-g with a metal alkyl/aryl thiolate which corresponds to $PR^4$ under heating by referring to, for example, the method described in WO 2009/131245. Examples of the metal alkyl/aryl thiolate include sodium ethanethiolate, sodium methanethiolate, and potassium ethanethiolate. Examples of the solvent include DMF, DMA, DMSO, dichloromethane, THF, acetonitrile, and mixtures thereof. DMF is preferred. The heating is preferably performed at 50° C. to 90° C. This step can also be performed by reacting the aldehyde I-g with an alkyl- or arylthiol reagent which corresponds to $PR^4$ in the presence of a base as in the method described in Step I-4. Further, this step can be performed by an alternative method of reacting the aldehyde I-d with an acyclic alkylthiol which corresponds to $PR^4$ by heating in a polar solvent such as 1,4-dioxane in the presence of a Pd catalyst, a Pd catalyst ligand, and a base as in the method described in WO 2006/038741.

Step I-7

The step is oximation of an alkylsulfanylbenzaldehyde derivative I-h. This step can be performed by reacting the aldehyde I-h with O-methylhydroxylamine hydrochloride in the presence of a base. Examples of the base include pyridine, triethylamine, N,N-diisobutylethylamine, and N,N-dimethyl-4-aminopyridine. Pyridine is preferred. Examples of the solvent used for the reaction include dichloromethane, THF, acetonitrile, and CPME. The solvent need not be used when pyridine is used as a base.

Step I-8

The step is reduction of an O-methyl oxime derivative I-i. This step can be performed by reducing the O-methyl oxime derivative I-i with a boron reagent under heating and then treating with an acid. Examples of the boron reagent include boron reducing agents such as borane-THF complex, borane-dimethyl sulfide complex, thexylborane, and 9-BBN. Borane-THF complex is preferred. Examples of the acid include hydrochloric acid solutions. An aqueous hydrochloric acid solution is preferred. Examples of the solvent include aprotic solvents. THF is preferred. The heating can be performed at 50° C. to 90° C.

Step I-9

The step is conversion of a sulfanylbenzylamine derivative I-f to a sulfoxide in three steps. This step can be performed by protecting the free primary amine of the sulfanylbenzylamine derivative I-f with a Boc group or the like, converting the derivative to a sulfoxide by oxidation with a peracid such as mCPBA, tBuOOH, $H_2O_2$, oxone, or potassium permanganate, and deprotecting the Boc group or such by treatment with hydrochloric acid, with reference to the method described in WO 2009/131245. The protecting group is preferably a Boc group, and the oxidizing agent is preferably two or more equivalents of mCPBA. The resulting sulfonylbenzylamine derivative I-j may be isolated as a hydrochloride.

Step I-10

The step is alkylation of a sulfonyl chloride derivative I-k. This step can be performed by converting the sulfonyl chloride derivative I-k to a sulfinate using a reducing agent under heating in situ, and then alkylating the sulfinate by treatment with an alkylating agent. The step can be performed by the method of Bioorg. Med. Chem. 13 (2005) 397-416, for example. The reducing agent for a sulfinate is preferably sodium sulfite. Examples of the alkylating agent include alkyl halides and 2-halocarboxylic acids. Alkyl iodides such as ethyl iodide are preferred.

Step I-11

The step is bromination of a sulfonyltoluene derivative I-1 (Wohl-Ziegler reaction). This step can be performed by reacting the sulfonyltoluene derivative I-1 with a brominating agent by heating in the presence of a catalytic amount of a radical initiator. Examples of the brominating agent include NBS and N-bromoimide. NBS is preferred. Examples of the radical initiator include benzoyl peroxide and AIBN. Benzoyl peroxide is preferred. Examples of the solvent include carbon tetrachloride, benzene, cyclohexane, and acetonitrile. Acetonitrile and carbon tetrachloride are preferred. The heating temperature is preferably 80° C. or higher.

Step I-12

The step is a step of sulfanylating a halobenzene derivative I-m by producing a carbon-sulfur bond. This step can be performed by reacting the halobenzene derivative I-m with an alkylthiol or arylthiol reagent which corresponds to $PR^4$ in the presence of a base. Examples of the thiol reagent include acyclic alkylthiols such as methanethiol, ethanethiol, n-propylthiol, and i-propylthiol; cyclic alkylthiols such as cyclopentylthiol; and arylthiols such as phenylthiol. Examples of the base include inorganic bases such as potassium carbonate, sodium carbonate, cesium carbonate, calcium carbonate, and sodium hydride; and organic bases such as t-BuOK, LDA, LiHMDS, N,N-dimethyl-4-aminopyridine, and DBU. Potassium carbonate and sodium carbonate are preferred. Examples of the solvent include DMF, DMA, DMSO, dichloromethane, THF, acetonitrile, and mixtures thereof. DMF is preferred.

Step I-13

The step is oxidation of a sulfanyltoluene derivative I-n to a sulfoxide. This step can be performed by reacting the sulfanyltoluene derivative I-n with an oxidizing agent. Examples of the oxidizing agent include peracids such as mCPBA, tBuOOH, $H_2O_2$, oxone, and potassium permanganate. It is preferably two or more equivalents of mCPBA. Examples of the solvent include aprotic solvents. Dichloromethane and ethyl acetate are preferred.

Step I-14

The step is bromination of a sulfonyltoluene derivative I-o (Wohl-Ziegler reaction). This step can be performed by reacting the sulfonyltoluene derivative I-o with a brominating agent by heating in the presence of a catalytic amount of a radical initiator. The conditions to be selected in this step such as the reaction reagent and solvent are the same as those in Step I-11.

Step I-15

The step is amination of a benzyl bromide derivative I-p. This step can be performed by reacting the benzyl bromide derivative I-p with an aminating agent. Examples of the aminating agent include aqueous ammonia, liquid ammonia, and ammonia gas. Aqueous ammonia is preferred. Examples of the solvent include protic alcohol solvents, water, THF, and mixed solvents thereof. Ethanol is preferred. The resulting sulfonylbenzylamine derivative I-j may be isolated as a hydrochloride.

Step I-16

The step is amidation of the sulfanylbenzylamine derivative I-f. This step can be performed by reacting the sulfanylbenzylamine derivative I-f with a corresponding carboxylic acid in the presence of a condensing agent and a base. A condensing additive may be added as necessary. Examples of the condensing agent include WSCDI, HBTU, HATU, BOP, DCC, DPPA, and DMT-MM. WSCDI, HBTU, and HATU are preferred. Examples of the base include tertiary amines. N,N-Diisobutylethylamine is preferred. Examples of the condensing additive under the above preferred conditions include HOBT and HOOBT. HOBT is preferred. Examples of the solvent include aprotic solvents. Dichloromethane, THF, DMF, and such are preferred.

Step I-17

This step is cyclization of a 2-aminobenzamide derivative I-q (to a quinazolinedione). This step can be performed by reacting the 2-aminobenzamide derivative I-q with a carbonylating agent in the presence of a base. Examples of the carbonylating agent include carbonyldiimidazole, triphosgene, phosgene, thiophosgene, phenyl chloroformate, alkyl chloroformates, urea, and carbon monoxide. Carbonyldiimidazole and triphosgene are preferred. The base is preferably DBU, pyridine, or triethylamine. Examples of the solvent include ether solvents, aprotic polar solvents, and halomethane solvents. THF, dichloromethane, and DMF are preferred.

Step I-18

The step is oxidation of a sulfanylquinazolinedione derivative I-r to a sulfoxide. This step can be performed by reacting the sulfanylquinazolinedione derivative I-r with an oxidizing agent. The conditions to be selected in this step such as the reaction reagent and solvent are the same as those in Step I-13.

Step I-19

The step is oxidation of the sulfanylbenzamide derivative I-q to a sulfoxide. This step can be performed by reacting the sulfanylbenzamide derivative I-q with an oxidizing agent. The conditions to be selected in this step such as the reaction reagent and solvent are the same as those in Step I-13.

Step I-20

The step is amidation of a sulfonylbenzylamine derivative I-j. This step can be performed by reacting the sulfonylbenzylamine derivative I-j with a corresponding carboxylic acid in the presence of a condensing agent and a base. A condensing additive may be added as necessary. The conditions to be selected in this step such as the reaction reagent and solvent are the same as those in Step I-16.

Step I-21

This step is cyclization of a 2-aminobenzamide derivative I-t (to a quinazolinedione). This step can be performed by reacting the 2-aminobenzamide derivative I-t with a carbonylating agent in the presence of a base. The conditions to be selected in this step such as the reaction reagent and solvent are the same as those in Step I-17.

Step I-22

The step is sulfinylation of the sulfanyl derivative I-r. This step can be performed by reacting the sulfanyl derivative I-r with an oxidizing agent. The resulting sulfanyl derivative I-u is a racemate. Examples of the oxidizing agent include peracids such as mCPBA, tBuOOH, $H_2O_2$, oxone, and potassium permanganate. mCPBA is preferred. The amount of the reagent is preferably 0.9 to 1.0 equivalent. Examples of the solvent include aprotic solvents. Dichloromethane and ethyl acetate are preferred.

Production Method II

The method is a method for forming a backbone of formula (I), where Q represents $CH_2$; $A^1$, $A^2$, and $A^3$ are $CR^1$, $CR^2$, and $CR^3$, respectively; $R^4$ represents a sulfonyl group; $R^6$ represents $X^1Y^1Z^1$; and $R^7$ represents H.

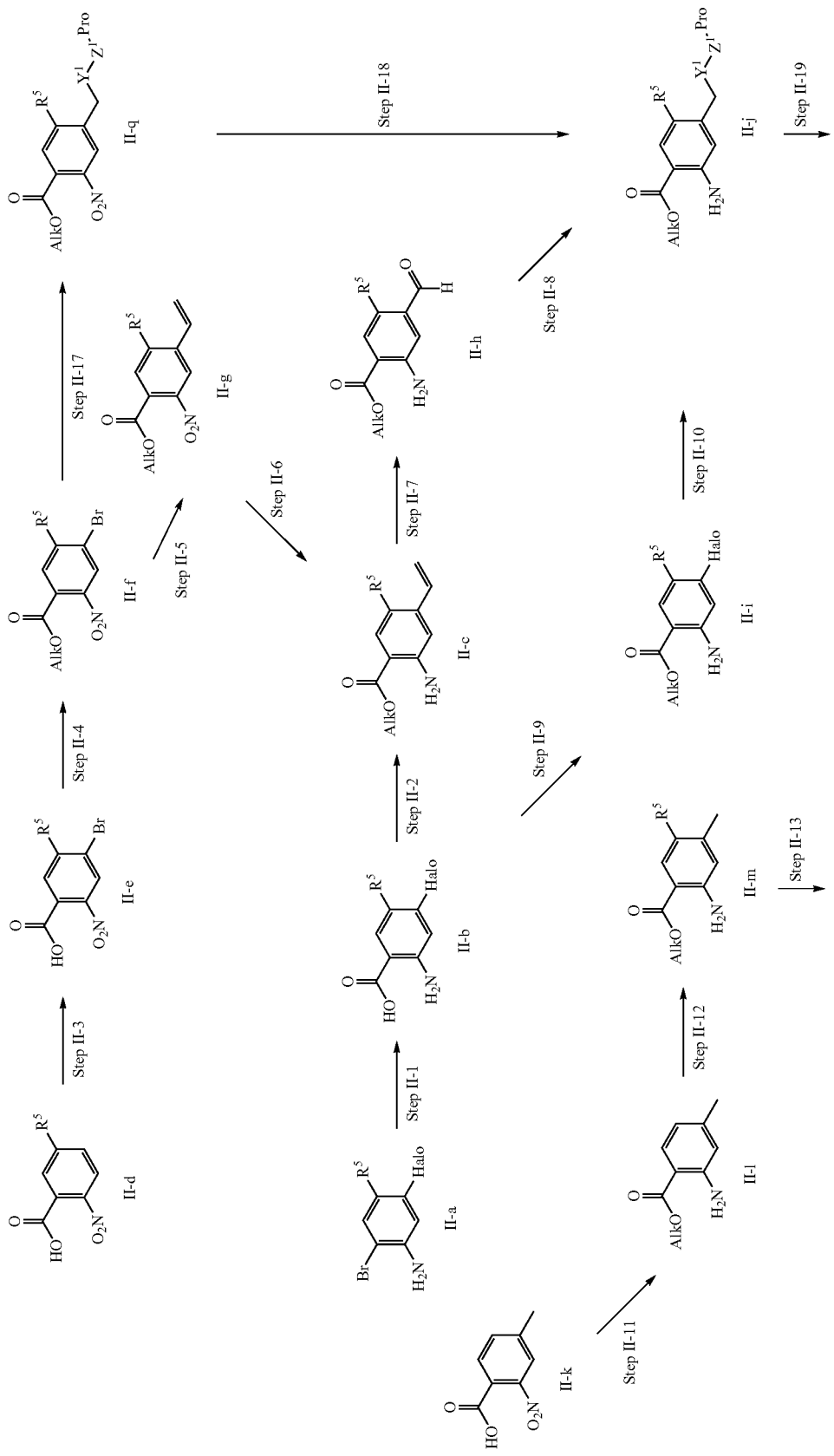

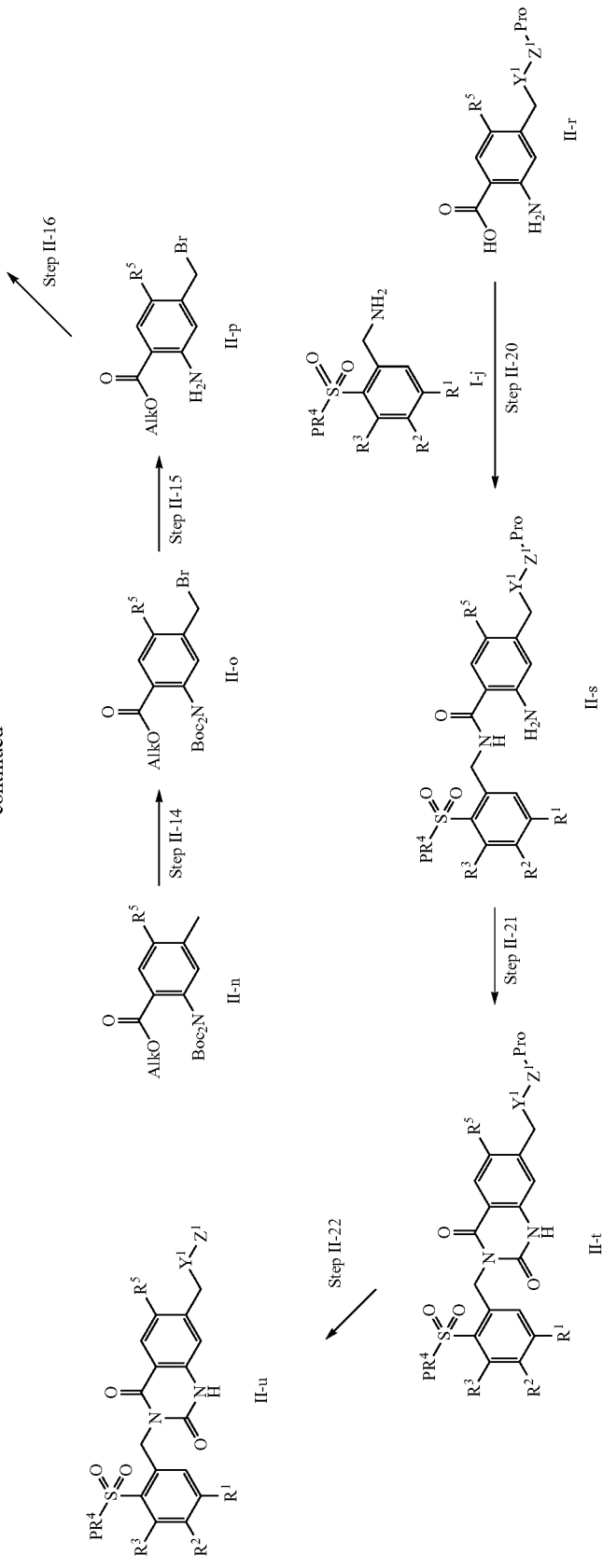

Step II-1

The step is conversion of a bromoaniline derivative II-a to a benzoic acid derivative II-b in three steps. This step can be performed by protecting the amino group of the bromoaniline derivative II-a with a diBoc group under basic conditions, and isolating and purifying the protected derivative; subsequently transferring the t-butoxycarbonyl group by treatment with n-butyllithium at −78° C.; and further deprotecting both the t-Bu group of the ester and the Boc group of the amine protecting group under acidic conditions. The step is performed by referring to the method of SYNLETT 20 (2005) 3107-3108. Under the diBoc protection conditions, a catalytic amount of 4-dimethylaminopyridine is preferably used, and the solvent can be an aprotic solvent such as a halomethane or ether solvent, and is preferably THF. In the t-butoxycarbonyl transfer, the solvent can be a strongly basic and stable aprotic solvent, and is preferably THF. In the deprotection of the t-Bu and Boc groups, the acid can be hydrochloric acid, sulfuric acid, TFA, or the like, and is preferably TFA; and the solvent is preferably dichloromethane.

Step II-2

The step is conversion of the benzoic acid derivative II-b to a vinylbenzoate derivative II-c in two steps. This step can be performed by carrying out esterification of the carboxylic acid of the benzoic acid derivative II-b using an alkylating agent under basic conditions, isolation and purification, and subsequent vinylation using a Pd catalyst under heating conditions. Examples of the alkylating agent in the esterification include alkyl halides. Alkyl iodides are preferred. Examples of the base include inorganic bases such as potassium carbonate, sodium carbonate, cesium carbonate, calcium carbonate, and sodium hydride; and organic bases such as t-BuOK, LDA, LiHMDS, N,N-dimethyl-4-aminopyridine, and DBU. Potassium carbonate and sodium carbonate are preferred. Examples of the solvent include aprotic polar solvents and ether solvents. DMF is preferred. Examples of the Pd catalyst in the vinylation include zerovalent Pd complexes represented by tetrakis(triphenylphosphine) palladium. Palladium acetate using BuPAd2 as a ligand is preferred. Examples of the vinylating agent include potassium vinyltrifluoroborate, vinylboronic acid, and vinylboronates. Potassium vinyltrifluoroborate is preferred. The solvent is preferably a mixed solvent of toluene and water.

Step II-3

The step is halogenation of a nitrobenzoic acid derivative II-d. This step can be performed by reacting the nitrobenzoic acid derivative II-d with a halogenating agent under heating. An acid or a catalytic amount of a radical initiator can be added when the reaction proceeds slowly. Examples of the halogenating agent include N-halosuccinimides, sulfuryl halides, as well as chlorine, bromine, and iodine under acidic conditions or in the presence of reduced iron powder. NBS which is an N-halosuccinimide is preferred. The solvent is preferably concentrated sulfuric acid.

Step II-4

The step is esterification of a nitrobenzoic acid derivative II-e. This step can be performed by reacting the nitrobenzoic acid derivative II-e with an alkylating agent in the presence of a base. Examples of the alkylating agent include alkyl halides. Alkyl iodides such as ethyl iodide are preferred. Examples of the base include inorganic bases such as potassium carbonate, sodium carbonate, cesium carbonate, calcium carbonate, and sodium hydride; and organic bases such as t-BuOK, LDA, LiHMDS, N,N-dimethyl-4-aminopyridine, and DBU. Potassium carbonate and sodium carbonate are preferred. Examples of the solvent include aprotic polar solvents. DMF is preferred.

Step II-5

The step is vinylation of a halobenzoate derivative II-f by producing a C—C bond. This step can be performed by carrying out a heating reaction of the halobenzoate derivative II-f using a Pd catalyst in the presence of a base and a vinylating agent. Examples of the Pd catalyst include zerovalent Pd complexes represented by tetrakis(triphenylphosphine) palladium. Palladium acetate using BuPAd2 as a ligand is preferred. Examples of the vinylating agent include potassium vinyltrifluoroborate, vinylboronic acid, and vinylboronates. Potassium vinyltrifluoroborate is preferred. Examples of the base include inorganic bases such as potassium carbonate, sodium carbonate, cesium carbonate, calcium carbonate, and sodium hydride; and organic bases such as t-BuOK, t-BuONa, LDA, LiHMDS, and DBU. Potassium carbonate is preferred. The solvent is preferably a mixed solvent of toluene and water.

Step II-6

The step is amination (reduction) of a nitrobenzoate derivative II-g. This step can be performed by reacting the nitrobenzoate derivative II-g with a metal reducing agent under acidic conditions. Examples of the reducing agent include iron powder, zinc powder, and tin reagents. Zinc powder is preferred. Examples of the acid to be added include ammonium chloride, acetic acid, and hydrochloric acid. Ammonium chloride is preferred. Examples of the solvent include protic alcohol solvents, water, and mixed solvents thereof. A mixed solvent of 2-propanol and water is preferred.

Step II-7

The step is conversion of the vinylaniline derivative II-c to a benzaldehyde derivative II-h in two steps. This step can be performed by carrying out dihydroxylation of the vinylaniline derivative II-c using an osmium reagent, isolation and purification, and subsequent glycol cleavage. The step can be performed by referring to, for example, the method described in WO 2010/065760. In the dihydroxylation, the osmium reagent can be osmium tetroxide, AD-mix, or the like, and is preferably AD-mix-α or AD-mix-β. The solvent can be a mixed solvent of a water-soluble solvent and water, and is preferably a mixed solvent of t-BuOH and water. In the glycol cleavage, the oxidizing agent can be sodium metaperiodate, lead tetraacetate, or the like, and is preferably sodium metaperiodate. The solvent can be a mixed solvent of an organic solvent and water, an acetic acid solution, or the like, and is preferably a mixed solvent of TBME and water.

Step II-8

This step is production of a C—N bond from the benzaldehyde derivative II-h by reductive amination. This step can be performed by reacting the benzaldehyde derivative II-h with a primary or secondary amine which corresponds to Y1-Z1-Pro in the presence of a reducing agent. Examples of the reducing agent include sodium triacetoxyborohydride, sodium cyanoborohydride, and 2-picoline-borane. Sodium triacetoxyborohydride is preferred. Examples of the solvent include halomethane solvents and ether solvents. Chloroform, dichloromethane, and THF are preferred.

Step II-9

The step is esterification of the benzoic acid derivative II-b. This step can be performed by reacting the benzoic acid derivative II-b with an alkylating agent in the presence of a base. The conditions to be selected in this step such as the reaction reagent and solvent are the same as those in Step II-4.

Step II-10

The step is production of a C—C bond from a halobenzoate derivative II-i by Suzuki-Molander coupling reaction. This step can be performed by reacting the halobenzoate derivative II-i with a Molander reagent (potassium trifluoroborate derivative) which corresponds to CH2-Y1-Z1-Pro by heating in the presence of a palladium reagent and a base. Here, a reagent for palladium ligands is added as necessary. The step can be performed using the method of Acc. Chem. Res. 2007, 40, 275-286, for example. Typical examples of the Pd reagent include palladium acetate, tetrakis(triphenylphosphine) palladium, and a 1,1'-bis(diphenylphosphino)ferrocene-palladium(II) dichloride-dichloromethane complex. Palladium acetate is preferred. Examples of the reagent for palladium ligands include X-Phos, S-Phos, Ru-Phos, nBuPAd$_2$, triphenylphosphine, and tricyclohexylphosphine. X-Phos, S-Phos, and Ru-Phos are preferred. Examples of the base include inorganic bases such as potassium carbonate, sodium carbonate, cesium carbonate, and tripotassium phosphate; and organic amines such as triethylamine, t-butylamine, N,N-diisobutylethylamine, and pyridine. Potassium carbonate and cesium carbonate are preferred. Examples of the solvent include alcohols, toluene, THF, and mixed solvents of these solvents and water. A mixed solvent of THF and water, toluene, and a mixed solvent of toluene and water are preferred.

Step II-11

The step is conversion of a nitrobenzoic acid derivative II-k to an aminobenzoate II-l in two steps. This step can be performed by reacting the nitrobenzoic acid derivative II-k with an alkylating agent in the presence of a base, isolating and purifying the nitrobenzoate derivative, and subsequently reducing the nitro group using a reducing agent. Examples of the alkylating agent in the alkylation include alkyl halides. Alkyl iodides such as ethyl iodide are preferred. Examples of the base include inorganic bases such as potassium carbonate, sodium carbonate, cesium carbonate, calcium carbonate, and sodium hydride; and organic bases such as t-BuOK, LDA, LiHMDS, N,N-dimethyl-4-aminopyridine, and DBU. Potassium carbonate and sodium carbonate are preferred. Examples of the solvent include aprotic polar solvents. DMF is preferred. Examples of the reducing agent in the reduction of the nitro group include catalytic hydrogenation reducing agents such as palladium catalysts such as palladium on carbon, nickel catalysts such as Raney Ni, and platinum catalysts such as Adam's catalyst; hydride reducing agents such as lithium aluminum hydride; and metal powders. Palladium catalysts such as palladium on carbon are preferred. Examples of the solvent include alcohols, ethyl acetate, halomethane solvents, aromatic solvents, and water. Methanol is preferred.

Step II-12

The step is halogenation of the aminobenzoate derivative II-l. This step can be performed by reacting the aminobenzoate derivative II-l with a halogenating agent under heating. An acid or a catalytic amount of a radical initiator can be added when the reaction proceeds slowly. Examples of the halogenating agent include N-halosuccinimides, sulfuryl halides, and chlorine, bromine, and iodine under acidic conditions or in the presence of reduced iron powder. NBS or NCS which is an N-halosuccinimide is preferred. The solvent is preferably DMF.

Step II-13

The step is protection of the amino group of an aminobenzoate derivative II-m with a diBoc group. This step can be performed by reacting the aminobenzoate derivative II-m with di-tert-butyl dicarbonate in the presence of a base. Examples of the base include triethylamine, pyridine, N,N-diisobutylmethylamine, DBU, and sodium hydride. Triethylamine is preferred. 4-DMAP is preferably added when the reaction is slow. Examples of the solvent include halomethane solvents, ether solvents, and aprotic polar solvents. Acetonitrile and dichloromethane are preferred.

Step II-14

The step is bromination of a toluene derivative II-n (Wohl-Ziegler reaction). This step can be performed by reacting the toluene derivative II-n with a brominating agent under heating in the presence of a catalytic amount of a radical initiator. The conditions to be selected in this step such as the reaction reagent and solvent are the same as those in Step I-11.

Step II-15

The step is deprotection of the diBoc group of a diBoc amine derivative II-o. This step can be performed by reacting the diBoc amine derivative II-o under strongly acidic conditions. Examples of the acid include TFA, hydrochloric acid, sulfuric acid, mesylic acid, and Lewis acids. TFA and hydrochloric acid are preferred. Examples of the solvent include dichloromethane, ethyl acetate, 1,4-dioxane, acetonitrile, water, and mixed solvents thereof. Dichloromethane, ethyl acetate, and 1,4-dioxane are preferred.

Step II-16

This step is production of a C—N bond from a benzyl bromide derivative II-p by substitution reaction. This step can be performed by reacting the benzyl bromide derivative II-p with a primary or secondary amine which corresponds to Y1-Z1-Pro. A base is preferably added when the reaction is slow. Examples of the base include inorganic bases such as potassium carbonate, sodium carbonate, cesium carbonate, calcium carbonate, and sodium hydride; and organic bases such as pyridine, triethylamine, N,N-diisobutylethylamine, N,N-dimethyl-4-aminopyridine, t-BuOK, LDA, LiHMDS, N,N-dimethyl-4-aminopyridine, and DBU. Triethylamine and potassium carbonate are preferred. Examples of the solvent include halomethane solvents, ether solvents, and aprotic polar solvents. Dichloromethane, THF, and DMF are preferred.

Step II-17

The step is production of a C—C bond from the halobenzoate derivative II-f by Suzuki-Molander coupling reaction. This step can be performed by reacting the halobenzoate derivative II-f with a Molander reagent (potassium trifluoroborate derivative) which corresponds to CH2-Y1-Z1-Pro by heating in the presence of a palladium reagent and a base. Here, a reagent for palladium ligands is added as necessary. The step can be performed using the method of Acc. Chem. Res. 2007, 40, 275-286, for example. The conditions to be selected in this step such as the reaction reagent and solvent are the same as those in Step II-10.

Step II-18

The step is amination (reduction) of a nitrobenzoate derivative II-q. This step can be performed by reacting the nitrobenzoate derivative II-q with a metal reducing agent under acidic conditions. The conditions to be selected in this step such as the reaction reagent and solvent are the same as those in Step II-6.

Step II-19

The step is saponification (hydrolysis) of a benzoate derivative II-j. This step can be performed by reacting the benzoate derivative II-j with an inorganic base. Examples of the inorganic base include sodium hydroxide, lithium hydroxide, potassium hydroxide, calcium hydroxide, and barium hydroxide. Sodium hydroxide and potassium hydroxide are preferred. Examples of the solvent include alcohols, water, and mixed solvents thereof. An aqueous ethanol solution and an aqueous methanol solution are preferred. Heating can be performed at 40° C. to 60° C. when the reaction is slow.

Step II-20

The step is condensation (amidation) of a benzoic acid derivative II-r. This step can be performed by reacting the benzoic acid derivative II-r with a corresponding benzylamine derivative I-j in the presence of a condensing agent and a base. A condensing additive may be added as necessary. The conditions to be selected in this step such as the reaction reagent and solvent are the same as those in Step I-16.

Step II-21

This step is cyclization of a 2-aminobenzamide derivative II-s (to a quinazolinedione). This step can be performed by reacting the 2-aminobenzamide derivative II-s with a carbonylating agent in the presence of a base. The conditions to be selected in this step such as the reaction reagent and solvent are the same as those in Step I-17.

Step II-22

This step is deprotection of the amine protecting group of a protected aminosulfonylquinazolinedione derivative II-t. Here, the protecting group mainly refers to a Boc group. This step can be performed by reacting the protected aminosulfonylquinazolinedione derivative II-t under strongly acidic conditions. Examples of the acid include TFA, hydrochloric acid, sulfuric acid, mesylic acid, and Lewis acids. TFA and hydrochloric acid are preferred. Examples of the solvent include dichloromethane, ethyl acetate, 1,4-dioxane, acetonitrile, water, and mixed solvents thereof. Dichloromethane, ethyl acetate, and 1,4-dioxane are preferred.

Production Method III

The method is a method for forming a backbone of formula (I), where Q represents $CH_2$; $A^1$, $A^2$, and $A^3$ are $CR^1$, $CR^2$, and $CR^3$, respectively; $R^4$ represents a sulfonyl group; $R^6$ represents $X^1Y^1Z^1$; and $R^7$ represents halogen.

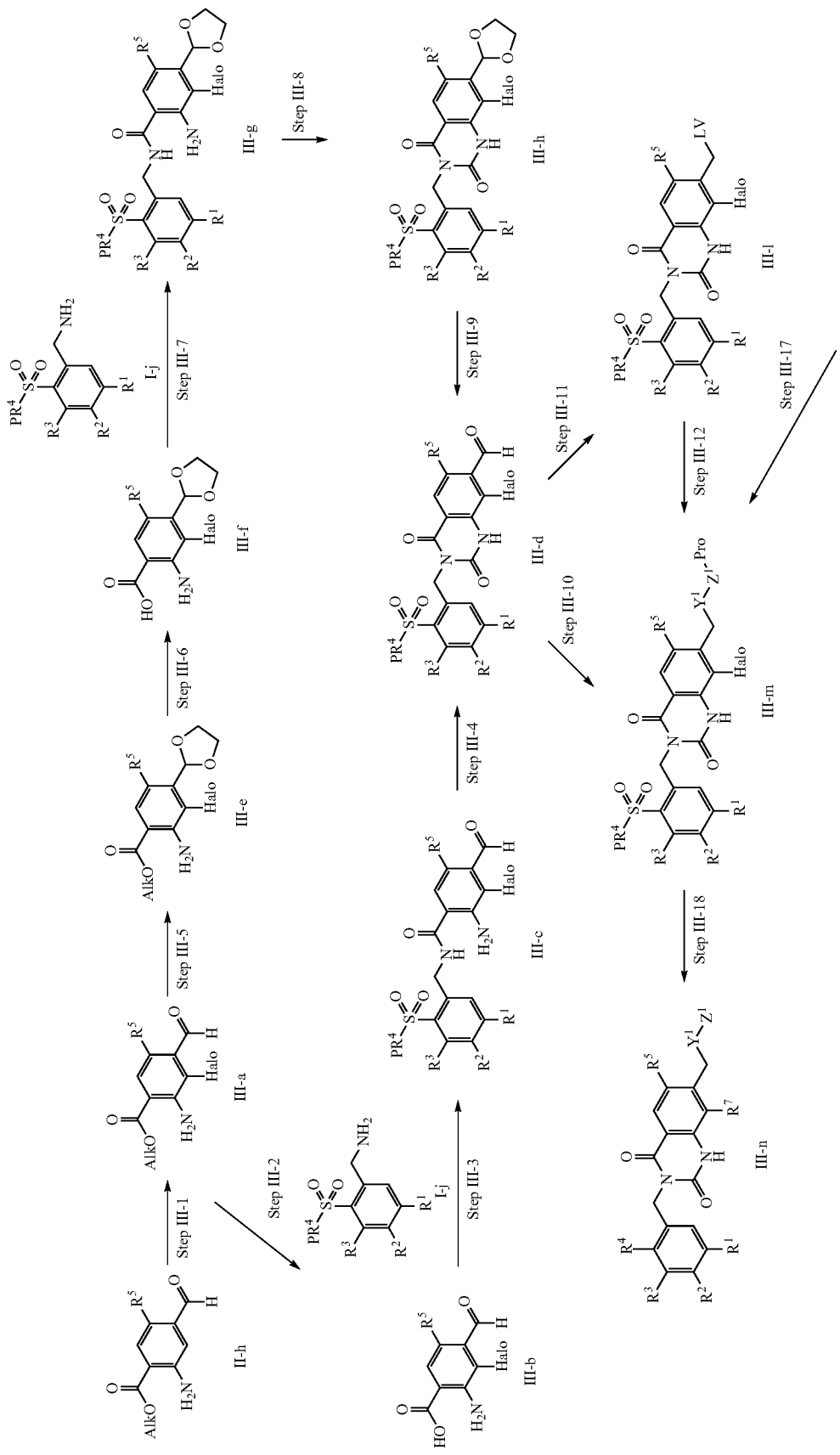

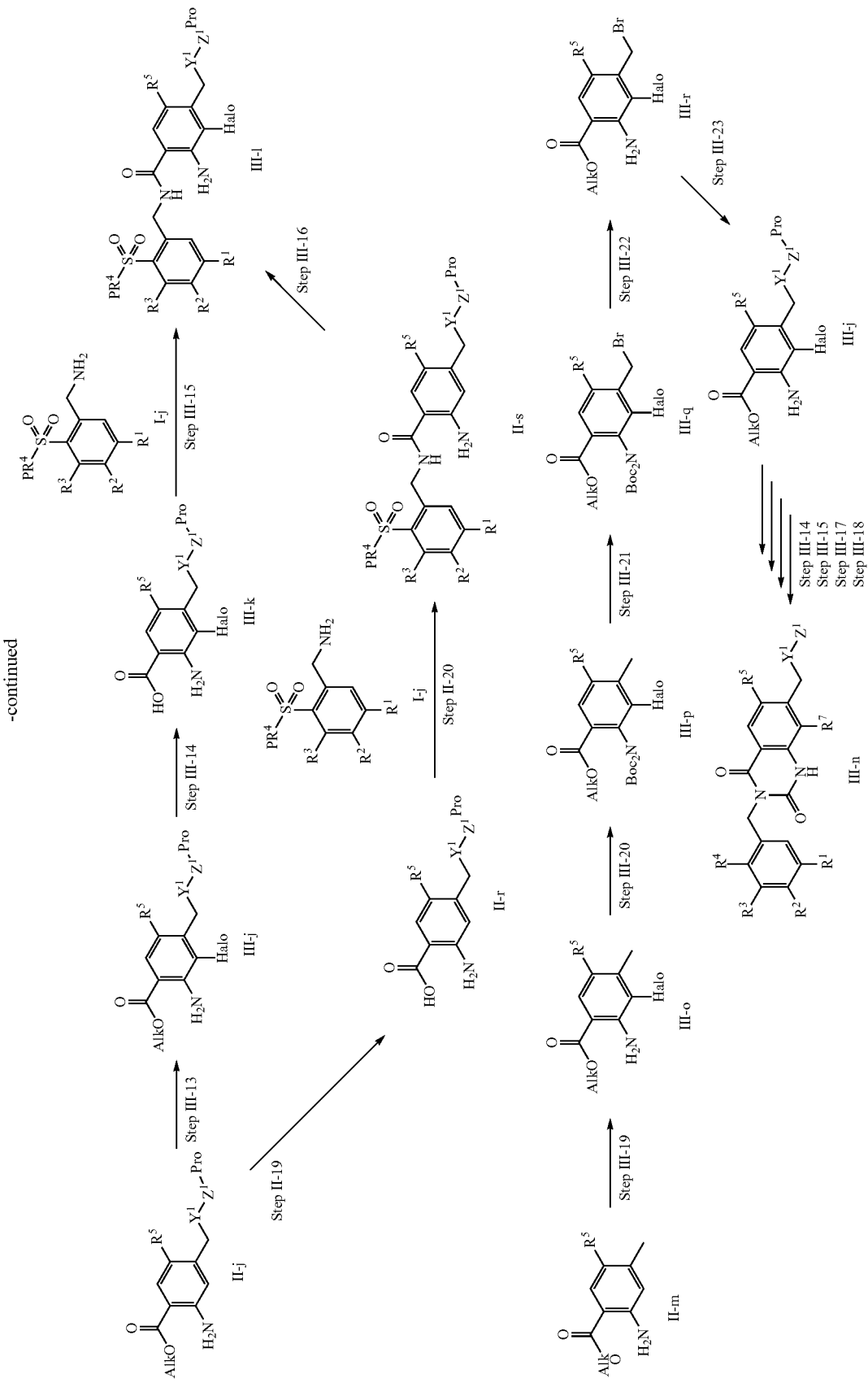

Step III-1

The step is halogenation of a benzaldehyde derivative II-h. This step can be performed by reacting the benzaldehyde derivative II-h with a halogenating agent under heating. An acid or a catalytic amount of a radical initiator can be added when the reaction proceeds slowly. Examples of the halogenating agent include N-halosuccinimides, sulfuryl halides, and chlorine, bromine, and iodine under acidic conditions or in the presence of reduced iron powder. N-Halosuccinimides such as NBS and NCS are preferred. Examples of the solvent include aprotic polar solvents, halomethane solvents, ether solvents, alcohols, and water. DMF is preferred.

Step III-2

The step is saponification (hydrolysis) of a benzoate derivative III-a. This step can be performed by reacting the benzoate derivative III-a with an inorganic base. The conditions to be selected in this step such as the reaction reagent and solvent are the same as those in Step II-19.

Step III-3

The step is condensation (amidation) of a benzoic acid derivative III-b. This step can be performed by reacting the benzoic acid derivative III-b with a corresponding benzylamine derivative I-j in the presence of a condensing agent and a base. A condensing additive may be added as necessary. The conditions to be selected in this step such as the reaction reagent and solvent are the same as those in Step I-16.

Step III-4

This step is cyclization of a 2-aminobenzamide derivative III-c (to a quinazolinedione). This step can be performed by reacting the 2-aminobenzamide derivative III-c with a carbonylating agent in the presence of a base. The conditions to be selected in this step such as the reaction reagent and solvent are the same as those in Step I-17.

Step III-5

The step is introduction of a protecting group into the benzaldehyde derivative III-a by converting the aldehyde group into a 1,3-dioxolanyl group. This step can be performed by reacting the benzaldehyde derivative III-a with ethylene glycol by heating under acidic conditions. The step can be performed using, for example, the method of J. Am. Chem. Soc., 76, 1728 (1954). Examples of the acid include p-toluenesulfonic acid hydrate, pyridinium p-toluenesulfonate, hydrochloric acid, boron trifluoride-dimethyl ether complex, aluminum chloride, trimethylsilyl chloride, and trimethylsilyl trifluoromethanesulfonate. It is preferably p-toluenesulfonic acid hydrate. Examples of the solvent include aromatic solvents, alcohols, and halomethane solvents. Toluene is preferred. The heating condition is preferably under reflux while removing water from the system using a Dean-Stark apparatus.

Step III-6

The step is saponification (hydrolysis) of a benzoate derivative III-e. This step can be performed by reacting the benzoate derivative III-e with an inorganic base. The conditions to be selected in this step such as the reaction reagent and solvent are the same as those in Step II-19.

Step III-7

The step is condensation (amidation) of a benzoic acid derivative III-f. This step can be performed by reacting the benzoic acid derivative III-f with a corresponding benzylamine derivative I-j in the presence of a condensing agent and a base. A condensing additive may be added as necessary. The conditions to be selected in this step such as the reaction reagent and solvent are the same as those in Step I-16.

Step III-8

This step is cyclization of a 2-aminobenzamide derivative III-g (to a quinazolinedione). This step can be performed by reacting the 2-aminobenzamide derivative III-g with a carbonylating agent in the presence of a base. The conditions to be selected in this step such as the reaction reagent and solvent are the same as those in Step I-17.

Step III-9

The step is deprotection of the aldehyde protecting group of a sulfonylquinazolinedione derivative III-h. This step can be performed by reacting the sulfonylquinazolinedione derivative III-h with an acid in an aqueous solvent. Examples of the acid include p-toluenesulfonic acid hydrate, pyridinium p-toluenesulfonate, sulfuric acid, hydrochloric acid, acetic acid, and trimethylsilyl iodide. Concentrated sulfuric acid is preferred. Examples of the aqueous solvent include mixed solvents of water-soluble solvents such as acetone, THF, and N-methylpyrolidone and water. An aqueous N-methylpyrolidone solution is preferred.

Step III-10

This step is production of a C—N bond from a quinazolinedione aldehyde derivative III-d by reductive amination. This step can be performed by reacting the quinazolinedione aldehyde derivative III-d with a primary or secondary amine which corresponds to Y1-Z1-Pro in the presence of a reducing agent. The conditions to be selected in this step such as the reaction reagent and solvent are the same as those in Step II-8.

Step III-11

The step is conversion of the quinazolinedione aldehyde derivative III-d to a quinazolinedione derivative III-i in two steps. This step can be performed by carrying out hydroxylation of the quinazolinedione aldehyde derivative III-d by reaction with a reducing agent, isolation and purification, and subsequent introduction of a leaving group. Examples of the reducing agent in the hydroxylation include metal reducing agents such as lithium aluminum hydride, diisobutylaluminum hydride, Selectride, Super-Hydride, and sodium borohydride; and boron reducing agents such as borane-THF complex and borane-dimethyl sulfide complex. Sodium borohydride is preferred. Examples of the solvent include ether solvents, halomethane solvents, and alcohols. THF is preferred. Examples of the leaving group in the introduction of a leaving group include sulfonates by sulfonating reagents. Specific examples include methanesulfonates, p-toluenesulfonates, and triflate groups. Preferred examples include methanesulfonates that can be provided by reaction with methanesulfonyl chloride in the presence of tertiary amines such as triethylamine. Examples of the solvent include halomethane solvents, ether solvents, and aprotic polar solvents. Dichloromethane is preferred.

Step III-12

This step is production of a C—N bond from a quinazolinedione derivative III-i by substitution reaction. This step can be performed by reacting the quinazolinedione derivative III-i with a primary or secondary amine which corresponds to Y1-Z1-Pro. A base is preferably added when the reaction is slow. The conditions to be selected in this step such as the reaction reagent and solvent are the same as those in Step II-16.

Step III-13

The step is halogenation of a benzoate derivative II-j. This step can be performed by reacting the benzoate derivative II-j with a halogenating agent under heating. An acid or a catalytic amount of a radical initiator can be added when the reaction proceeds slowly. The conditions to be selected in this step such as the reaction reagent and solvent are the same as those in Step III-1.

Step III-14

The step is saponification (hydrolysis) of a halobenzoate derivative III-j. This step can be performed by reacting the halobenzoate derivative III-j with an inorganic base. The conditions to be selected in this step such as the reaction reagent and solvent are the same as those in Step II-19.

Step III-15

The step is condensation (amidation) of a halobenzoic acid derivative III-k. This step can be performed by reacting the halobenzoic acid derivative III-k with a corresponding benzylamine derivative I-j in the presence of a condensing agent and a base. A condensing additive may be added as necessary. The conditions to be selected in this step such as the reaction reagent and solvent are the same as those in Step I-16.

Step III-16

The step is halogenation of a 2-aminobenzamide derivative II-s. This step can be performed by reacting the 2-aminobenzamide derivative II-s with a halogenating agent under heating. An acid or a catalytic amount of a radical initiator can be added when the reaction proceeds slowly. The conditions to be selected in this step such as the reaction reagent and solvent are the same as those in Step III-1.

Step III-17

This step is cyclization of a 2-aminobenzamide derivative III-l (to a quinazolinedione). This step can be performed by reacting the 2-aminobenzamide derivative III-l with a carbonylating agent in the presence of a base. The conditions to be selected in this step such as the reaction reagent and solvent are the same as those in Step I-17.

Step III-18

This step is deprotection of the amine protecting group of a protected aminosulfonylquinazolinedione derivative III-m. Here, the protecting group mainly refers to a Boc group. This step can be performed by reacting the protected aminosulfonylquinazolinedione derivative III-m under strongly acidic conditions. The conditions to be selected in this step such as the reaction reagent and solvent are the same as those in Step II-22.

Step III-19

The step is halogenation of a toluene derivative II-m. This step can be performed by reacting the toluene derivative II-m with a halogenating agent under heating. An acid or a catalytic amount of a radical initiator can be added when the reaction proceeds slowly. The conditions to be selected in this step such as the reaction reagent and solvent are the same as those in Step III-1.

Step III-20

The step is protection of the amino group of a halobenzoate derivative III-o with a diBoc group. This step can be performed by reacting the halobenzoate derivative III-o with di-tert-butyl dicarbonate in the presence of a base. The conditions to be selected in this step such as the reaction reagent and solvent are the same as those in Step II-13.

Step III-21

The step is bromination of a halotoluene derivative III-p (Wohl-Ziegler reaction). This step can be performed by reacting the halotoluene derivative III-p with a brominating agent under heating in the presence of a catalytic amount of a radical initiator. The conditions to be selected in this step such as the reaction reagent and solvent are the same as those in Step I-8.

Step III-22

The step is deprotection of the diBoc group of a diBoc amine derivative III-q. This step can be performed by reacting the diBoc amine derivative III-q under strongly acidic conditions. The conditions to be selected in this step such as the reaction reagent and solvent are the same as those in Step II-15.

Step III-23

This step is production of a C—N bond from a benzyl bromide derivative III-r by substitution reaction. This step can be performed by reacting the benzyl bromide derivative III-r with a primary or secondary amine which corresponds to Y1-Z1-Pro. A base is preferably added when the reaction is slow. The conditions to be selected in this step such as the reaction reagent and solvent are the same as those in Step II-16.

Production Method IV

The method is a method for forming a backbone of formula (I), where Q is NH; $A^1$, $A^2$, and $A^3$ are $CR^1$, $CR^2$, and $CR^3$, respectively; and $R^4$ is a sulfonyl group.

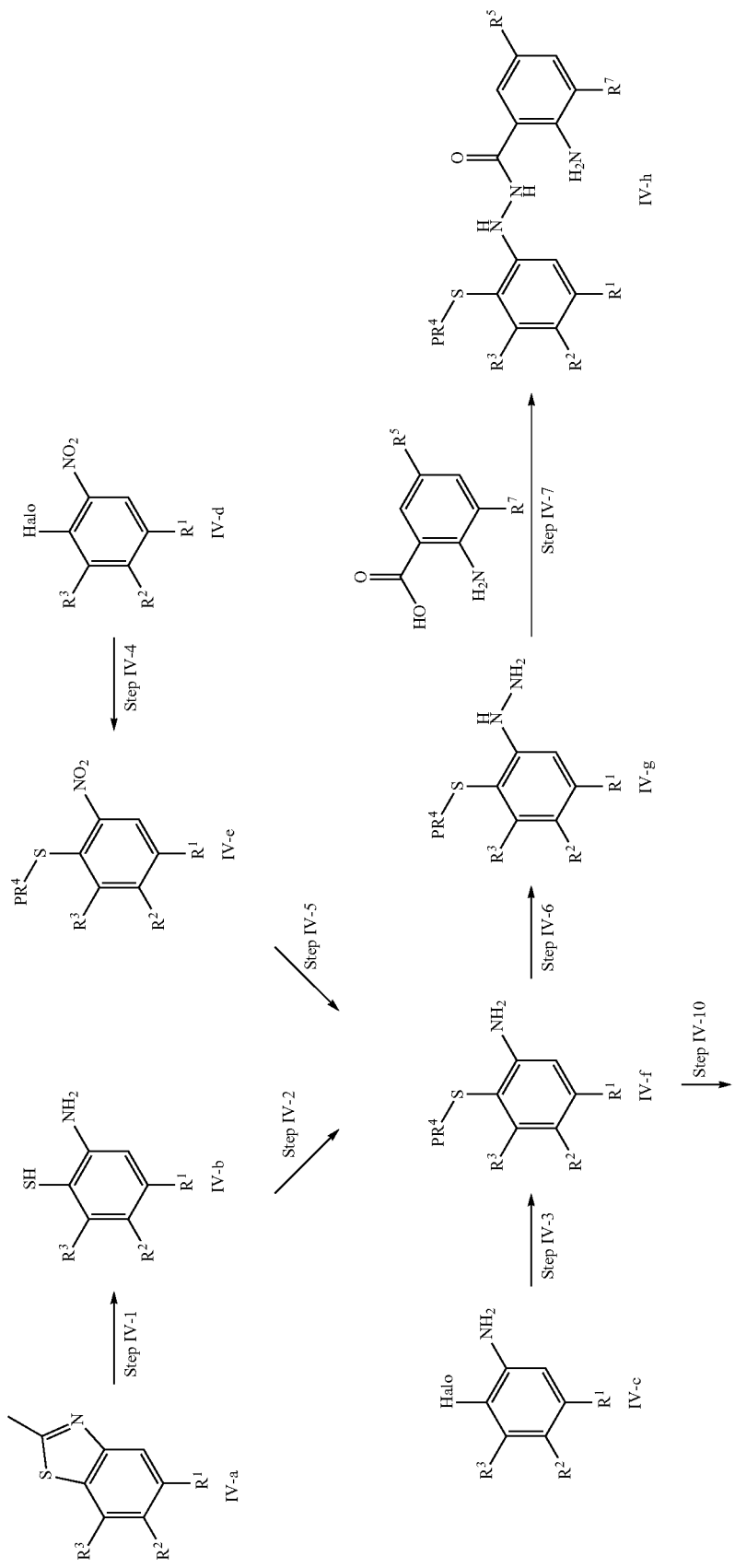

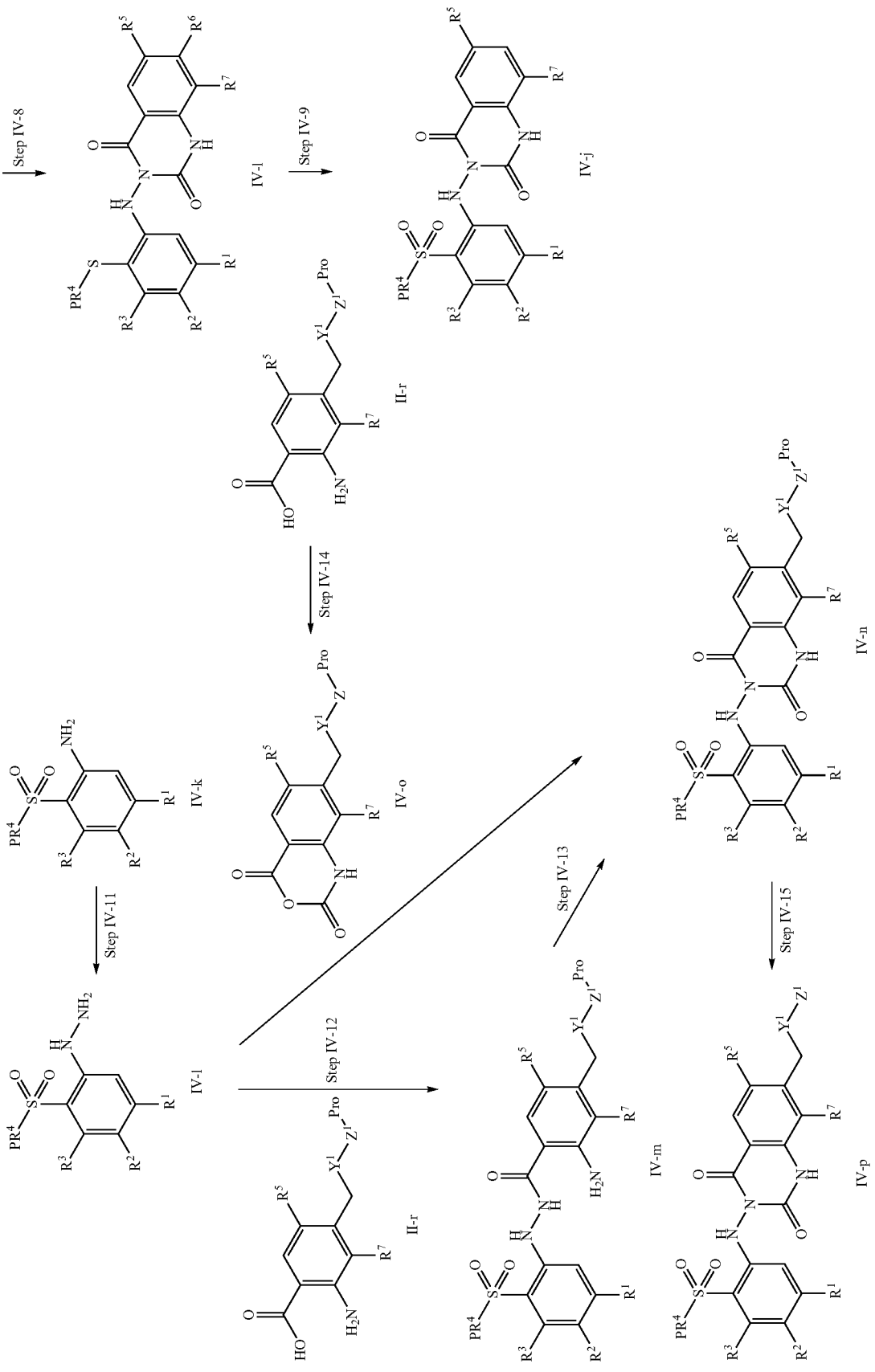

Step IV-1

The step is cleavage of the thiazole ring off a benzothiazole derivative IV-a by hydrolysis. This step can be performed by hydrolyzing the benzothiazole derivative IV-a by reaction with an inorganic base under heating. The step can be performed using, for example, the method of J. Med. Chem. 2002, 45, 2229-2239. Examples of the inorganic base include sodium hydroxide, lithium hydroxide, and potassium hydroxide. Sodium hydroxide is preferred. Examples of the solvent include ethylene glycol, water, dimethoxyethane, and mixed solvents thereof. A mixed solvent of ethylene glycol and water is preferred. The heating is preferably performed at 100° C. or higher.

Step IV-2

The step is alkylation of a thiophenol derivative IV-b. This step can be performed by reacting the thiophenol derivative IV-b with an alkylating agent which corresponds to $PR^4$ in the presence of a base and a phase-transfer catalyst. Examples of the alkylating agent include alkyl iodides, alkyl bromides, alkyl triflates, and alkyl mesylates. Alkyl iodides such as ethyl iodide are preferred. Examples of the base include inorganic bases such as potassium carbonate, sodium carbonate, cesium carbonate, and lithium carbonate; and organic bases such as DBU, t-BuOK, LDA, LiHMDS, and N,N-dimethyl-4-aminopyridine. Cesium carbonate, potassium carbonate, and DBU are preferred. Examples of the phase-transfer catalyst include tetrabutylammonium iodide and tetrabutylammonium bromide. Examples of the solvent include aprotic polar solvents and ether solvents. DMF and THF are preferred.

Step IV-3

The step is sulfanylation of a haloaniline derivative IV-c. This step can be performed by reacting the haloaniline derivative IV-c with a metal alkyl/aryl thiolate which corresponds to $PR^4$ under heating with reference to, for example, the method described in WO 2009/131245. The conditions to be selected in this step such as the reaction reagent and solvent are the same as those in Step I-6.

Step IV-4

The step is sulfanylation of a halonitrobenzene derivative IV-d. This step can be performed by reacting the halonitrobenzene derivative IV-d with an alkylthiol or arylthiol reagent which corresponds to $PR^4$ in the presence of a base. Examples of the thiol reagent include acyclic alkylthiols such as methanethiol, ethanethiol, n-propylthiol, and i-propylthiol; cyclic alkylthiols such as cyclopentylthiol; and arylthiols such as phenylthiol. Examples of the base include inorganic bases such as potassium carbonate, sodium carbonate, cesium carbonate, calcium carbonate, and sodium hydride; and organic bases such as t-BuOK, LDA, LiHMDS, N,N-dimethyl-4-aminopyridine, and DBU. Potassium carbonate and sodium carbonate are preferred. Examples of the solvent include DMF, DMA, DMSO, dichloromethane, THF, acetonitrile, and mixtures thereof. DMF is preferred.

Step IV-5

The step is amination (reduction) of a sulfanylnitrobenzene derivative IV-e. This step can be performed by reacting the sulfanylnitrobenzene derivative IV-e with a metal-reducing agent under acidic conditions. The step can be performed by referring to, for example, the method described in a patent (EP 1065204). Examples of the reducing agent include iron powder, zinc powder, and tin reagents. Iron powder is preferred. Examples of the acid to be added include ammonium chloride, acetic acid, and hydrochloric acid. Ammonium chloride is preferred. Examples of the solvent include protic alcohol solvents, water, and mixed solvents thereof. A mixed solvent of ethanol and water is preferred.

Step IV-6

The step is conversion of a sulfanylaniline derivative IV-f to a hydrazine. This step can be performed by converting the sulfanylaniline derivative IV-f to a diazonium salt using a nitrite under strongly acidic conditions (Griess reaction), and then reacting it with a metal-reducing agent without isolation. The nitrite used for the conversion to a diazonium salt is preferably sodium nitrite. The metal-reducing agent used for the reduction of a diazonium salt to a phenylhydrazine is preferably tin(II) chloride. Examples of the solvent include protic acidic solvents. An aqueous hydrochloric acid solution is preferred.

Step IV-7

The step is amidation of a sulfanylphenylhydrazine derivative IV-g. This step can be performed by reacting the sulfanylphenylhydrazine derivative IV-g with a corresponding carboxylic acid in the presence of a condensing agent. A condensing additive can be added as necessary. Examples of the condensing agent include WSCDI, HBTU, HATU, BOP, DCC, DPPA, and DMT-MM. WSCDI, HBTU, and HATU are preferred. Examples of the condensing additive include HOBT and HOOBT. HOBT is preferred. Examples of the solvent include aprotic solvents. Dichloromethane, THF, DMF, and the like are preferred.

Step IV-8

This step is cyclization of an aminoketohydrazide derivative IV-h (to a quinazolinedione). This step can be performed by reacting the aminoketohydrazide derivative IV-h with a carbonylating agent in the presence of a base. The conditions to be selected in this step such as the reaction reagent and solvent are the same as those in Step I-17.

Step IV-9

The step is oxidation of a sulfanylquinazolinedione derivative IV-i to a sulfoxide. This step can be performed by reacting the sulfanylquinazolinedione derivative IV-i with an oxidizing agent. The conditions to be selected in this step such as the reaction reagent and solvent are the same as those in Step I-13.

Step IV-10

The step is oxidation of the sulfanylaniline derivative IV-f to a sulfoxide. This step can be performed by reacting the sulfanylaniline derivative IV-f with an oxidizing agent. The conditions to be selected in this step such as the reaction reagent and solvent are the same as those in Step I-13.

Step IV-11

The step is conversion of a sulfonylaniline derivative IV-k to a hydrazine. This step can be performed by converting the sulfonylaniline derivative IV-k to a diazonium salt using a nitrite under strongly acidic conditions (Griess reaction), and then reacting it with a metal-reducing agent without isolation. The conditions to be selected in this step such as the reaction reagent and solvent are the same as those in Step IV-6.

Step IV-12

This step is cyclization (carbonylation) of an anthranilic acid derivative II-r. This step can be performed by reacting the anthranilic acid derivative II-r with a carbonylating agent in the presence of a base. The conditions to be selected in this step such as the reaction reagent and solvent are the same as those in Step I-17.

Step IV-13

The step is conversion of a sulfonylhydrazide derivative IV-i to a quinazolinedione. This step can be performed by reacting the sulfonylhydrazide derivative IV-l with a benzoxazinedione derivative IV-m by heating in a sealed tube. Examples of the solvent include ether solvents and aprotic polar solvents. THF is preferred. The heating condition is preferably 100° C.

Step IV-14

This step is deprotection of the amine protecting group of a protected aminosulfonylquinazolinedione derivative IV-n. Here, the protecting group mainly refers to a Boc group. This step can be performed by reacting the protected aminosulfonylquinazolinedione derivative IV-n under strongly acidic conditions. The conditions to be selected in this step such as the reaction reagent and solvent are the same as those in Step II-22.

EXAMPLES

Herein below, the present invention will be more specifically described with reference to the Examples, but it is not to be construed as being limited thereto.

NMR Analysis

NMR analysis was performed using either ARX 300 (300 MHz) manufactured by Bruker Corporation, AVANCEIII600 (600 MHz) manufactured by Bruker Corporation, JNM-GSX 400 (400 MHz) manufactured by JEOL Corporation, JNM-EX 270 (270 MHz) manufactured by JEOL Corporation, ECA-400 (400 MHz) manufactured by JEOL Corporation or 400MR (400 MHz) manufactured by Varian Corporation. NMR data are shown in ppm (parts per million) (δ) and refers to the deuterium lock signal from the sample solvent.

Data from Mass Spectrometry with High Performance Liquid Chromatography (LC-MS)

The data were obtained using a Micromass (SQD) equipped with an Acquity gradient ultra high performance liquid chromatography system (manufactured by Waters Corporation), SQD2 Mass Spectrometer paired with Acquity Gradient Ultra High Performance Liquid Chromatography (manufactured by Waters Corporation), a Micromass (ZQ) equipped with a 2525 gradient high performance liquid chromatography system (manufactured by Waters Corporation), or a Micromass (SQD) equipped with a 2524 gradient high performance liquid chromatography system (manufactured by Waters Corporation).

Any one of the conditions shown in Table 1 below was used for high performance liquid chromatography.

TABLE 1

| Analysis condition | Equipment | Column used | Column temperature | Mobile phase, gradient | Flow rate (mL/min) | Detection wavelength (PDA total) |
|---|---|---|---|---|---|---|
| A | Acquity SQD | Ascentis Express C18 HPLC column, 5 cm × 2.1 mm, 2.7 μm | Room temp. | A) 10 mM AcONH4, B) MeOH, A/B = 95/5 → 0/100 (1 min) → 100 (0.4 min) | 1 | 210-400 nm |
| B | SQD | Sunfire C18 (Waters) 4.5 mm I.D. × 50 mm, 5 um | Room Temp. | A) 0.05% TFA, CH3CN, B) 0.05% TFA, H2O, A/B = 10/90 → 95/5 (3.5 min) → 10/90 (1 min) → 95/5 (0.5 min) | 4 | 210-370 nm |
| C | ZQ | Sunfire C18 (Waters) 4.6 mm I.D. × 50 mm, 5 um | Room Temp. | A) 0.05% TFA, CH3CN, B) 0.05% TFA, H2O, A/B = 10/90 → 95/5 (3.5 min) → 10/90 (1 min) → 95/5 (0.5 min) | 4 | 210-400 nm |
| D | Acquity SQD | Ascentis Express C18 HPLC column, 5 cm × 2.1 mm, 2.7 μm | 35° C. | A) 0.1% FA, CH3CN, B) 0.1% FA, H2O, A/B = 5/95 to 100/0 (1 min) → 100/0 (0.4 min) | 1 | 210-400 nm |
| E | Acquity SQD | Ascentis Express C18 HPLC column, 5 cm × 2.1 mm, 2.7 μm | Room Temp. | A) 0.05% TFA, CH3CN, B) 0.05% TFA, H2O, A/B = 5/95 to 100/0 (1 min) → 100/0 (0.4 min) | 1 | 210-400 nm |
| F | Acquity SQD | Ascentis Express C18 HPLC column, 5 cm × 2.1 mm, 2.7 μm | Room Temp. | A) 0.1% FA, CH3CN, B) 0.1% FA, H2O, A/B = 5/95 → 70/30 (1 min) → 70/30 (0.4 min) | 1 | 210-400 nm |
| G | Acquity SQD | Ascentis Express C18 HPLC column, 5 cm × 2.1 mm, 2.7 μm | Room Temp. | A) 0.05% TFA, CH3CN, B) 0.05% TFA, H2O, A/B = 10/90 → 98/2 (1 min) → 98/2 (0.4 min) | 1 | 210-400 nm |
| H | Acquity SQD | Ascentis Express C18 | Room Temp. | A) 0.1% FA, CH3CN, B) | | |

TABLE 1-continued

| Analysis condition | Equipment | Column used | Column temperature | Mobile phase, gradient | Flow rate (mL/min) | Detection wavelength (PDA total) |
|---|---|---|---|---|---|---|
| | | HPLC column, 5 cm × 2.1 mm, 2.7 μm | | 0.1% FA, H2O, A/B = 10/90→ 98/2 (1 min) → 98/2 (0.4 min) | | |
| I | ZQ | Wakosil-II 3C18 AR, 4.6 mm * 30 mm | Room Temp. | A) 0.05% TFA, CH3CN, B) 0.05% TFA, H2O, A/B = 10/90 → 10/90 (0.2 min) → 95/5 (3.1 min) → 95/5 (1.4 min) | 2 | 210-400 nm |
| J | SQD | ACE 5 C18, 4.5 mm I.D. × 50 mm, 5 um | Room Temp. | A) 0.05% TFA, CH3CN, B) 0.05% TFA, H2O, A/B = 10/90 → 95/5 (3.5 min) → 10/90 (1 min) → 95/5 (0.5 min) | 4 | 210-370 nm |
| K | Acquity I-Class SQD2 | Ascentis Express C18 HPLC column, 5 cm × 2.1 mm, 2.7 μm | 35° C. | A) 0.1% FA, CH3CN, B) 0.1% FA, H2O, A/B = 5/95 to 100/0 (1 min) → 100/0 (0.4 min) | 1 | 210-400 nm |

Commercially available reagents were used without further purification. "Room temperature" refers to a temperature within the range of about 20-25° C. All nonaqueous reactions were performed in anhydrous solvents. Concentration under reduced pressure or solvent evaporation was performed using a rotary evaporator. For the HPLC fractionation, the products of interest were isolated, then neutralized as necessary, and obtained as free forms.

When an undesirable side reaction could occur in the preparation of a compound, a functional group was protected by a protecting group as necessary, and the protecting group was removed after preparing the target molecule. Selection and detachment of the protecting group was performed, for example, by a method described in Greene and Wuts, "Protective Groups in Organic Synthesis" (Fourth edition, John Wiley & Sons 2007).

Example 1

Compound 1

5-Chloro-2-ethylsulfanyl-benzonitrile

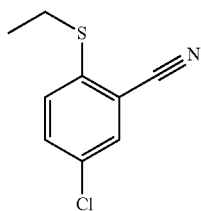

A solution of 5-chloro-2-fluoro-benzonitrile (3.60 g, 23.1 mmol) in DMF (46 ml) was cooled to 0° C. Potassium carbonate (9.60 g, 69.4 mmol) was added thereto under nitrogen atmosphere, and the mixture was stirred at room temperature for five minutes. Ethanethiol (2.05 ml, 27.8 mmol) was added thereto, and the mixture was stirred at room temperature for three hours. Ethyl acetate was added to the reaction mixture. After washing with brine, the organic layer was dried over anhydrous magnesium sulfate. The drying agent was removed by filtration, and the residue obtained after concentration under reduced pressure was purified by silica gel column chromatography (ethyl acetate/hexane) to give the title compound (4.57 g, quant.) as a colorless solid.

HPLC retention time: 2.47 min (analysis condition C)
$^1$H-NMR (400 MHz, DMSO-$d_6$) δ: 8.01 (1H, d, J=2.2 Hz), 7.73 (1H, dd, J=2.2, 8.8 Hz), 7.58 (1H, d, J=8.8 Hz), 3.14 (2H, q, J=7.7 Hz), 1.27 (3H, t, J=7.7 Hz).

Example 2

Compound 2

5-Chloro-2-ethylsulfanyl-benzylamine

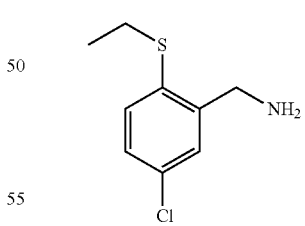

Lithium aluminum hydride (2.63 g, 69.4 mmol) was added to a solution of 5-chloro-2-ethylsulfanyl-benzonitrile (Compound 1, 4.57 g, 23.1 mmol) in THF (40 ml) under cooling at 0° C. The mixture was stirred at 0° C. for 30 minutes and then at room temperature for one hour. Under cooling at 0° C., water was added to the reaction mixture, and this was subjected to filtration through celite. The filtrate was dried over anhydrous magnesium sulfate. The drying agent was removed by filtration, and the residue obtained by concentration under reduced pressure was purified by silica gel column chromatography (ethyl acetate/hexane) to give the title compound (4.00 g, 85%) as a yellow oily substance.

LCMS: m/z 202 [M+H]+

HPLC retention time: 0.97 min (analysis condition C)

Example 3

Compound 3

5-Chloro-2-ethanesulfonyl-benzylamine hydrochloride

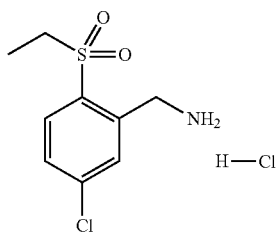

Compound 3 was synthesized from 5-chloro-2-ethylsulfanyl-benzylamine (Compound 2) according to the method described in a patent (WO 2009131245).

LCMS: m/z 234 [M+H]+

HPLC retention time: 0.57 min (analysis condition C)

Example 4

Compound 4

5-Bromo-2-ethylsulfanyl-benzaldehyde

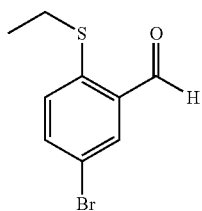

Sodium ethanethiolate (362 mg, 4.3 mmol) was added to a solution of 5-bromo-2-fluorobenzaldehyde (546 mg, 2.7 mmol) in DMF (1.08 ml), and the mixture was stirred at 60° C. After one hour, sodium ethanethiolate (123 mg, 1.5 mmol) was added thereto. After 15 minutes, the reaction solution was returned to room temperature, and a 1 N aqueous hydrochloric acid solution was added thereto, and extraction was performed with ethyl acetate. The organic layer was sequentially washed with a saturated aqueous sodium bicarbonate solution and brine, and dried over anhydrous sodium sulfate. The drying agent was removed by filtration, and the residue obtained by concentration under reduced pressure was purified by silica gel column chromatography (ethyl acetate/hexane) to give the title compound (163 mg, 24%) as a yellow oil.

HPLC retention time: 0.91 min (analysis condition D)

$^1$H-NMR (400 MHz, CDCl$_3$) δ: 10.33 (1H, s), 7.95 (1H, d, J=2.2 Hz), 7.62 (1H, dd, J=2.2, 8.4 Hz), 7.30 (1H, d, J=8.4 Hz), 2.97 (2H, q, J=7.5 Hz), 1.36 (3H, t, J=7.5 Hz).

Example 5

Compound 5

5-Bromo-2-ethylsulfanyl-benzaldehyde O-methyl-oxime

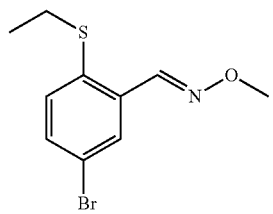

Hydroxylamine methyl ether hydrochloride (61 mg, 0.73 mmol) was added to a solution of 5-bromo-2-ethylsulfanyl-benzaldehyde (Compound 4, 163 mg, 0.66 mmol) in pyridine (0.42 ml), and the mixture was stirred at room temperature for two hours. Water was added to the reaction mixture, and extraction was performed with ethyl acetate. The organic layer was washed with a 1 N aqueous hydrochloric acid solution twice and then with brine, and then dried over anhydrous sodium sulfate. After the drying agent was removed by filtration, concentration was performed under reduced pressure to give a crude product of the title compound.

LCMS: m/z 274 [M+H]+

HPLC retention time: 1.10 min (analysis condition D)

Example 6

Compound 6

5-Bromo-2-ethylsulfanyl-benzylamine

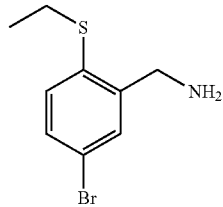

A 1 mol/l solution of borane-THF complex in THF (1.66 ml, 1.7 mmol) was added to a solution of the crude product of 5-bromo-2-ethylsulfanyl-benzaldehyde O-methyl-oxime (Compound 5, 182 mg, 0.66 mmol) in THF, and the mixture was stirred at 80° C. for 2.5 hours. The reaction mixture was cooled to 0° C., and crushed ice and a 1 N aqueous hydrochloric acid solution (3 ml) were added thereto, and this was stirred at 90° C. for one hour. The reaction solution was cooled to room temperature, and separated by adding water and ethyl acetate. The aqueous layer was made basic with a 5 N aqueous sodium hydroxide solution, and extraction was performed with dichloromethane three times. The organic layers were combined and dried over anhydrous sodium sulfate. After the drying agent was removed by filtration, concentration was performed under reduced pressure to give a crude product of the title compound.

HPLC retention time: 0.48 min (analysis condition D)
$^1$H-NMR (400 MHz, CDCl$_3$) δ: 7.48 (1H, d, J=2.2 Hz), 7.33 (1H, dd, J=2.2, 8.4 Hz), 7.17 (1H, d, J=8.4 Hz), 3.89 (2H, s), 2.93 (2H, q, J=7.5 Hz), 1.32 (3H, t, J=7.5 Hz).

Example 7

Compound 7

(5-Bromo-2-ethylsulfanyl-benzyl)-carbamic acid tert-butyl ester

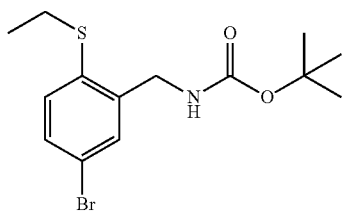 [SMILES: CCSc1ccc(Br)cc1CNC(=O)OC(C)(C)C]

Boc$_2$O (0.148 ml, 0.64 mmol) was added to a solution of the crude product of 5-bromo-2-ethylsulfanyl-benzylamine (Compound 6) in THF (2 ml), and the mixture was stirred at room temperature for one hour. Water was added to the reaction mixture, and extraction was performed with ethyl acetate. The organic layer was washed with brine and then dried over anhydrous sodium sulfate. The drying agent was removed by filtration, and the residue obtained by concentration under reduced pressure was purified by silica gel column chromatography (ethyl acetate/hexane) to give the title compound (168 mg, total yield from Compound 4 in three steps: 73%) as a yellow oily substance.

HPLC retention time: 1.01 min (analysis condition D)
$^1$H-NMR (400 MHz, CDCl$_3$) δ: 7.46 (1H, d, J=2.2 Hz), 7.35 (1H, dd, J=2.2, 8.4 Hz), 7.184 (1H, d, J=8.4 Hz), 4.97 (1H, bs), 4.38 (2H, bd, J=5.7 Hz), 2.91 (2H, q, J=7.5 Hz), 1.46 (9H, s), 1.30 (3H, t, J=7.5 Hz).

Example 8

Compound 8

(5-Bromo-2-ethanesulfonyl-benzyl)-carbamic acid tert-butyl ester

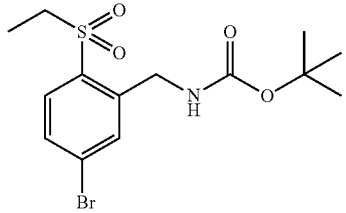 [SMILES: CCS(=O)(=O)c1ccc(Br)cc1CNC(=O)OC(C)(C)C]

mCPBA (234 mg, 1.02 mmol) was added to a solution of (5-bromo-2-ethylsulfanyl-benzyl)-carbamic acid tert-butyl ester (Compound 7, 168 mg, 0.49 mmol) in dichloromethane (2.4 ml) under cooling at 0° C. The mixture was then returned to room temperature and stirred for four hours. A saturated aqueous sodium bicarbonate solution was added to the reaction mixture, and extraction was performed with ethyl acetate. The organic layer was washed with brine and then dried over anhydrous sodium sulfate. The drying agent was removed by filtration, and the residue obtained by concentration under reduced pressure was purified by silica gel column chromatography (ethyl acetate/hexane) to give the title compound (180 mg, yield: 98%) as a yellow oily substance.

LCMS: m/z 322 [M-(2-methylpropene)+H]$^+$
HPLC retention time: 0.84 min (analysis condition D)

Example 9

Compound 9

5-Bromo-2-ethanesulfonyl-benzylamine hydrochloride

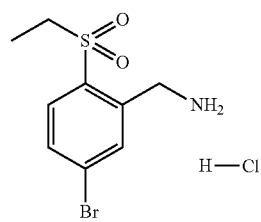

A 4 N solution of hydrochloric acid in ethyl acetate (2.4 ml) was added to (5-bromo-2-ethanesulfonyl-benzyl)-carbamic acid tert-butyl ester (Compound 8, 180 mg, 0.48 mmol), and the mixture was stirred at room temperature for 1.5 hours. The reaction solution was concentrated under reduced pressure to give the title compound (130 mg, yield: 87%) as a colorless solid.

LCMS: m/z 278 [M+H]$^+$
HPLC retention time: 0.38 min (analysis condition D)

Example 10

Compound 10

4-Ethylsulfanyl-3-methyl-benzonitrile

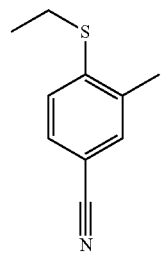

The title compound was synthesized from 4-fluoro-3-methyl-benzonitrile under the same conditions as for Compound 1.

Example 11

Compound 11

4-Ethanesulfonyl-3-methyl-benzonitrile

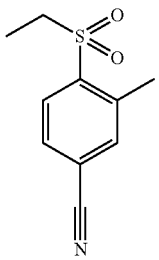

mCPBA (15.0 g, 67.0 mmol) was added to a solution of 4-ethylsulfanyl-3-methyl-benzonitrile (Compound 10, 3.96 g, 22.3 mmol) in DCM (100 ml), and the mixture was stirred at room temperature overnight. The reaction mixture was concentrated under reduced pressure, and the resulting residue was dissolved in ethyl acetate, and this was washed with water. The organic layer was filtered using amino silica gel, and the filtrate was concentrated under reduced pressure. The resulting residue was purified by amino silica gel column chromatography (ethyl acetate/hexane) to give the title compound (4.51 g, yield: 97%).

HPLC retention time: 1.58 min (analysis condition C)
$^1$H-NMR (270 MHz, CDCl$_3$) δ: 8.13 (1H, d, J=8.1 Hz), 7.69 (1H, dt, J=0.8, 8.1 Hz), 7.66 (1H, d, J=0.8 Hz), 3.19 (2H, q, J=7.6 Hz), 2.75 (3H, s), 1.29 (3H, t, J=7.6 Hz).

Example 12

Compound 12

3-Bromomethyl-4-ethanesulfonyl-benzonitrile

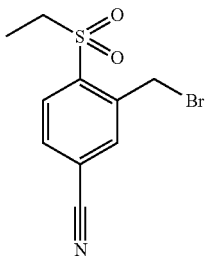

70% benzoyl peroxide (746 mg, 2.2 mmol) was added to a solution of 4-ethanesulfonyl-3-methyl-benzonitrile (Compound 11, 4.51 g, 21.6 mmol) and NBS (4.22 g, 23.7 mmol) in carbon tetrachloride (100 ml), and the mixture was stirred at 80° C. for four hours. The reaction mixture was concentrated under reduced pressure, and the resulting residue was dissolved in DCM. The solution was filtered using silica gel and amino silica gel. The filtrate was concentrated under reduced pressure, and the resulting solid was suspended in and washed with a mixed solvent of diisopropyl ether and DCM to give the title compound (4.14 g, 64%) as a colorless solid.

HPLC retention time: 1.87 min (analysis condition C)
$^1$H-NMR (270 MHz, CDCl$_3$) δ: 8.15 (1H, d, J=8.1 Hz), 7.91 (1H, d, J=1.4 Hz), 7.80 (1H, dd, J=1.4, 8.1 Hz), 5.04 (2H, s), 3.41 (2H, q, J=7.3 Hz), 1.33 (3H, t, J=7.3 Hz).

Example 13

Compound 13

3-Aminomethyl-4-ethanesulfonyl-benzonitrile

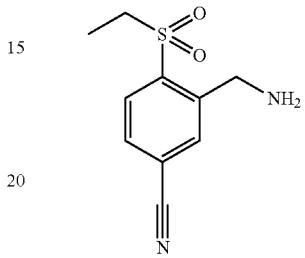

A 25% aqueous ammonia solution (2.5 ml) was added to a solution of 3-bromomethyl-4-ethanesulfonyl-benzonitrile (Compound 12, 250 mg, 0.87 mmol) in EtOH (12.5 ml), and the mixture was stirred at room temperature for 2.5 hours. The reaction mixture was concentrated under reduced pressure, and the resulting residue was purified by silica gel column chromatography (MeOH/DCM) to give the title compound (102 mg, 46%) as a colorless solid.

LCMS: m/z 225 [M+H]$^+$
HPLC retention time: 0.25 min (analysis condition D)

Example 14

Compound 14

5-Chloro-2-ethylsulfanyl-phenylamine

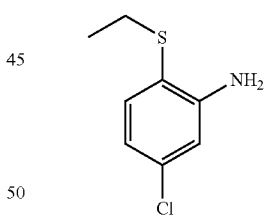

Ethyl iodide (0.66 ml, 8.3 mmol) was added to a suspension of 2-amino-4-chloro-benzenethiol (1.13 g, 7.9 mmol), cesium carbonate (3.09 g, 9.5 mmol), and tetra-n-butylammonium iodide (3.21 g, 8.7 mmol) in DMF (10 ml) under nitrogen atmosphere, and this was stirred for 2.5 hours. Ethyl acetate was added to the reaction mixture. After washing with a saturated aqueous sodium chloride solution, the organic layer was dried over anhydrous sodium sulfate. The drying agent was removed by filtration, and the residue obtained by concentration under reduced pressure was purified by silica gel column chromatography (ethyl acetate/hexane) to give the title compound (1.19 g, 88%) as a colorless oily substance.

LCMS: m/z 188 [M+H]$^+$
HPLC retention time: 0.87 min (analysis condition K)

Example 15

Compound 15

5-Chloro-2-ethanesulfonyl-phenylamine

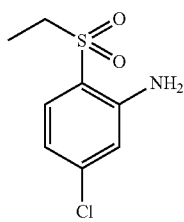

The title compound was synthesized from 5-chloro-2-ethylsulfanyl-phenylamine (Compound 14) under the same conditions as for Compound 11.

Example 16

Compound 16

(5-Chloro-2-ethanesulfonyl-phenyl)-hydrazine

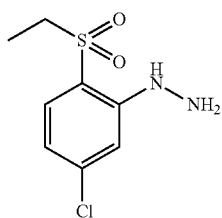

A solution of 5-chloro-2-ethanesulfonyl-phenylamine (Compound 15, 5.33 g, 24.3 mmol) in concentrated hydrochloric acid (26.6 ml) was added to an aqueous solution (13.3 ml) of sodium nitrite (2.5 g, 36.4 mmol) under cooling at 0° C., and the mixture was stirred at 0° C. for one hour. A solution of stannous chloride (11.5 g, 60.7 mmol) in concentrated hydrochloric acid (26.6 ml) was added thereto under cooling at 0° C., and this was stirred for further one hour. The reaction mixture was adjusted to pH 8 to 8.5 by adding a 5 N aqueous sodium hydroxide solution, and extraction was performed with ethyl acetate. The organic layer was dried over anhydrous magnesium sulfate. The drying agent was removed by filtration, and the residue obtained by concentration under reduced pressure was purified by silica gel column chromatography (ethyl acetate/hexane) to give the title compound (4.80 g, 84%).

LCMS: m/z 235 [M+H]$^+$

HPLC retention time: 0.57 min (analysis condition K)

Example 17

Compound 17

4-(Bis(tert-butoxycarbonyl)amino)-5-bromo-2-chloro-1-trifluoromethylbenzene

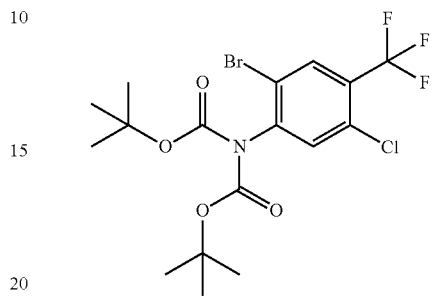

Boc$_2$O (53.3 ml, 240 mmol) was added to a suspension of 2-bromo-5-chloro-4-trifluoromethyl-phenylamine (26.8 g, 98 mmol) and DMAP (2.39 g, 20 mmol) in THF (500 ml), and the mixture was stirred at room temperature for 2.5 hours. The reaction solution was concentrated under reduced pressure, and the resulting residue was purified by silica gel column chromatography (ethyl acetate/hexane) to give the title compound (45.9 g, 99%) as a colorless solid.

HPLC retention time: 1.12 min (analysis condition D)

$^1$H-NMR (400 MHz, CDCl$_3$) δ: 7.92 (1H, s), 7.40 (1H, s), 1.43 (18H, s).

Example 18

Compound 18

2-tert-Butoxycarbonylamino-4-chloro-5-trifluoromethyl-benzoic acid tert-butyl ester

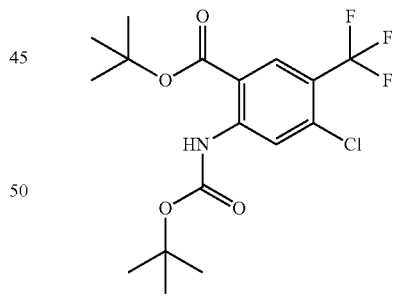

A 1.57 M solution of n-BuLi in hexane (33 ml, 52 mmol) was added to a solution of 4-(bis(tert-butoxycarbonyl)amino)-5-bromo-2-chloro-1-trifluoromethylbenzene (Compound 17, 20.5 g, 43 mmol) in THF (430 ml) at −78° C. over 10 minutes, and this was stirred for one hour. A saturated aqueous ammonium chloride solution (200 ml) was added thereto, and the mixture was then warmed to room temperature. Ethyl acetate (400 ml) was added thereto, and this was washed with a saturated aqueous sodium chloride solution. The organic layer was dried over anhydrous sodium sulfate. The drying agent was removed by filtration, and the residue obtained by concentration under reduced pressure was purified by silica gel column chromatography (ethyl acetate/hexane) to give the title compound (13.9 g, 82%) as a colorless solid.

HPLC retention time: 1.29 min (analysis condition D)

$^1$H-NMR (400 MHz, CDCl$_3$) δ: 10.55 (1H, s), 8.72 (1H, s), 8.22 (1H, s), 1.62 (9H, s), 1.55 (9H, s).

Example 19

Compound 19

2-Amino-4-chloro-5-trifluoromethyl-benzoic acid

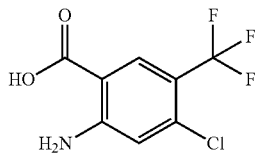

Trifluoroacetic acid (88 ml) was added to a solution of 2-tert-butoxycarbonylamino-4-chloro-5-trifluoromethyl-benzoic acid tert-butyl ester (Compound 18, 13.9 g, 35 mmol) in DCM (350 ml), and the mixture was stirred at room temperature for 15 hours. The reaction solution was concentrated under reduced pressure to give the title compound as a crude product.

LCMS: m/z 240 [M+H]$^+$

HPLC retention time: 0.71 min (analysis condition D)

Example 20

Compound 20

2-Amino-4-chloro-5-trifluoromethyl-benzoic acid ethyl ester

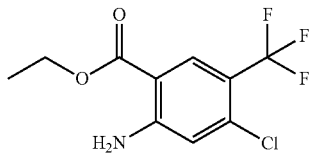 [SMILES: CCOC(=O)c1cc(C(F)(F)F)c(Cl)cc1N]

Potassium carbonate (19.4 g, 141 mmol) and ethyl iodide (4.22 ml, 53 mmol) were added to a solution of the crude product of 2-amino-4-chloro-5-trifluoromethyl-benzoic acid (Compound 19), which was obtained as mentioned above, in DMF (176 ml), and the mixture was stirred at room temperature for two hours. Water (170 ml) was added to the reaction solution, and extraction was performed with ethyl acetate. The extract was washed with a saturated aqueous sodium chloride solution and dried over anhydrous sodium sulfate. The drying agent was removed by filtration, and the residue obtained by concentration under reduced pressure was purified by silica gel column chromatography (ethyl acetate/hexane) to give the title compound (5.89 g, yield from Compound 18 in two steps: 63%) as a yellow solid.

LCMS: m/z 268 [M+H]$^+$

HPLC retention time: 0.93 min (analysis condition D)

Example 21

Compound 21

2-Amino-5-trifluoromethyl-4-vinyl-benzoic acid ethyl ester

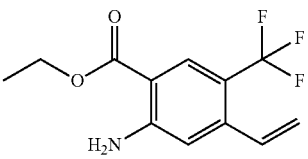 [SMILES: C=Cc1cc(N)c(C(=O)OCC)cc1C(F)(F)F]

Distilled water (112 ml) was added to a suspension of 2-amino-4-chloro-5-trifluoromethyl-benzoic acid ethyl ester (Compound 20, 9.00 g, 34 mmol), potassium vinyltrifluoroborate (6.31 g, 47 mmol), BuPAd$_2$ (1.21 g, 3.4 mmol), palladium acetate (378 mg, 1.7 mmol), and potassium carbonate (13.9 g, 100 mmol) in toluene (336 ml), and the mixture was stirred at 90° C. under argon atmosphere for 18 hours. The reaction solution was cooled to room temperature, and ethyl acetate was then added thereto, and this was washed with water. The organic layer was dried over anhydrous sodium sulfate. The drying agent was removed by filtration, and the residue obtained by concentration under reduced pressure was purified by silica gel column chromatography (ethyl acetate/hexane) to give the title compound (7.93 g, 91%) as a yellow solid.

LCMS: m/z 260 [M+H]$^+$

HPLC retention time: 0.94 min (analysis condition D)

Example 22

Compound 22

2-Amino-4-(1,2-dihydroxy-ethyl)-5-trifluoromethyl-benzoic acid ethyl ester

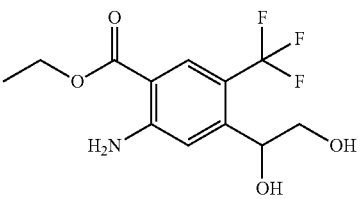 [SMILES: CCOC(=O)c1cc(C(F)(F)F)c(C(O)CO)cc1N]

Water (140 ml) was added to a solution of AD-mixα (manufactured by Aldrich) (61.3 g) in t-butyl alcohol (140 ml), and the mixture was stirred at room temperature for five minutes. A solution of 2-amino-5-trifluoromethyl-4-vinyl-benzoic acid ethyl ester (Compound 21, 14.4 g, 56 mmol) in TBME (140 ml) and water (140 ml) were added to this reaction solution, and the mixture was stirred at room temperature for 0.5 hour. Sodium nitrite (35.1 g, 509 mmol) was added to the reaction mixture, and the mixture was stirred at room temperature for one hour. Ethyl acetate was added to the reaction mixture. After washing with a saturated aqueous sodium chloride solution, the organic layer was dried over anhydrous sodium sulfate. After the drying agent was removed by filtration, concentration was performed under reduced pressure. The resulting solid was washed with DCM to give the title compound (12.9 g, 79%) as a colorless solid.

LCMS: m/z 294 [M+H]$^+$
HPLC retention time: 0.63 min (analysis condition D)

Example 23

Compound 23

2-Amino-4-formyl-5-trifluoromethyl-benzoic acid ethyl ester

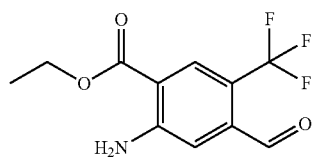

Water (273 ml) and sodium periodate (16.4 g, 76 mmol) were added to a solution of 2-amino-4-(1,2-dihydroxy-ethyl)-5-trifluoromethyl-benzoic acid ethyl ester (Compound 22, 16.0 g, 54 mmol) in TBME (546 ml), and the mixture was stirred at room temperature for seven hours. TBME was added to the reaction mixture. After washing with a saturated aqueous sodium chloride solution, the organic layer was dried over anhydrous sodium sulfate. After the drying agent was removed by filtration, concentration was performed under reduced pressure to give the title compound (14.1 g, 99%) as a yellow solid.

LCMS: m/z 262 [M+H]$^+$
HPLC retention time: 0.87 min (analysis condition D)

Example 24

Compound 24

2-Amino-3-chloro-4-formyl-5-trifluoromethyl-benzoic acid ethyl ester

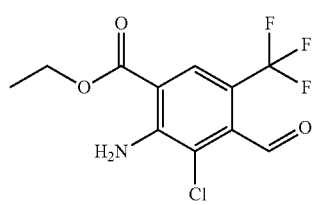 [SMILES: CCOC(=O)c1cc(C(F)(F)F)c(C=O)c(Cl)c1N]

NCS (3.71 g, 14 mmol) was added to a solution of 2-amino-4-formyl-5-trifluoromethyl-benzoic acid ethyl ester (Compound 23, 3.63 g, 14 mmol) in DMF (42 mL), and the mixture was stirred at 70° C. for 0.5 hour. Water (40 mL) was added thereto, and extraction was performed with TBME. The extract was dried over anhydrous sodium sulfate. The drying agent was removed by filtration, and the residue obtained by concentration under reduced pressure was purified by silica gel column chromatography (ethyl acetate/hexane) to give the title compound (3.47 g, 85%) as a yellow solid.

LCMS: m/z 296 [M+H]$^+$
HPLC retention time: 0.89 min (analysis condition D)

Example 25

Compound 25

2-Amino-3-chloro-4-formyl-5-trifluoromethyl-benzoic acid

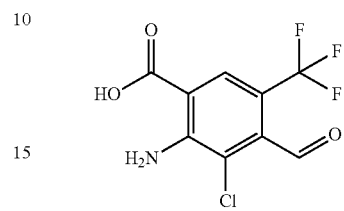

A 1 N aqueous sodium hydroxide solution (23 ml) was added to a solution of 2-amino-3-chloro-4-formyl-5-trifluoromethyl-benzoic acid ethyl ester (Compound 24, 3.47 g, 12 mmol) in ethanol (117 ml), and the mixture was stirred at 60° C. for one hour. After cooling to room temperature, a 1 N aqueous hydrochloric acid solution (23 ml) was added, and the reaction solution was concentrated under reduced pressure to give a crude product of the title compound.

LCMS: m/z 266 [M−H]$^-$
HPLC retention time: 0.67 min (analysis condition D)

Example 26

Compound 26

2-Amino-3-chloro-N-(5-chloro-2-ethanesulfonyl-benzyl)-4-formyl-5-trifluoromethyl-benzamide

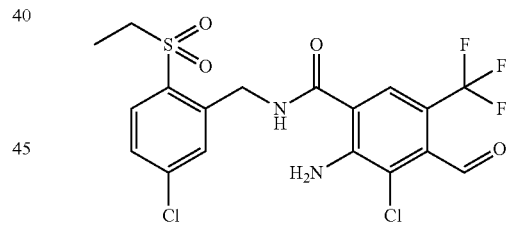

WSCDI (2.48 g, 12.9 mmol) was added to a suspension of the crude product of 2-amino-3-chloro-4-formyl-5-trifluoromethyl-benzoic acid (Compound 25, 11.7 mmol) and HOBT (1.98 g, 12.9 mmol) in DCM (58.7 ml), and the mixture was stirred at room temperature for 0.5 hour. 5-Chloro-2-ethanesulfonyl-benzylamine hydrochloride (Compound 3, 3.17 g, 11.7 mmol) and DIPEA (2.25 ml, 12.9 mmol) were added to this reaction solution, and the mixture was stirred at room temperature for 11 hours. A 1 N aqueous hydrochloric acid solution (5.9 ml) was added to the reaction solution, and the mixture was stirred for 20 minutes at room temperature. Then, a 1 N aqueous sodium hydroxide solution (5.4 ml) was added thereto. The reaction solution was extracted with DCM, and the extract was washed with a saturated aqueous sodium chloride solution and then dried over anhydrous sodium sulfate. The drying agent was removed by filtration, and the residue obtained by concentration under reduced pressure was purified by silica gel column chromatography (ethyl acetate/hexane) to give the title compound (4.84 g, 85%) as a pale yellow foamy substance.

LCMS: m/z 483 [M+H]+

HPLC retention time: 0.87 min (analysis condition D)

Example 27

Compound 27

4-Bromo-2-nitro-5-trifluoromethoxy-benzoic acid

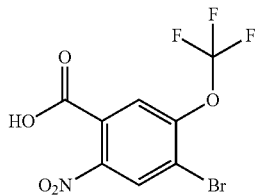

A solution of 2-nitro-5-trifluoromethoxy-benzoic acid (25.3 g, 0.10 mol) in concentrated sulfuric acid (75 ml) was warmed to 80° C., and NBS (18 g, 0.10 mol) was added thereto in three portions at 15 min intervals. After stirring at 80° C. for two hours, NBS (9.0 g, 0.050 mol) and concentrated sulfuric acid (25 ml) were added thereto, and the mixture was stirred at 80° C. for further three hours. The reaction mixture was cooled to room temperature and then added to ice water, and the solid was collected by filtration. This was washed with $H_2O$ and methanol, and a $H_2O$/methanol=5/1 solution (120 ml) was then added thereto, and this was stirred at 0° C. for 30 minutes. The solid was collected by filtration, and washed with a $H_2O$/methanol=5/1 solution, and dried to give the title compound as a crude product.

Example 28

Compound 28

4-Bromo-2-nitro-5-trifluoromethoxy-benzoic acid ethyl ester

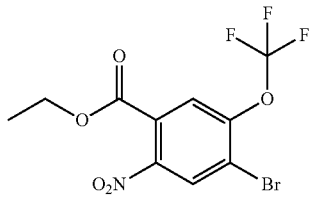

The title compound was synthesized from 4-bromo-2-nitro-5-trifluoromethoxy-benzoic acid (Compound 27) under the same conditions as for Compound 20.

Example 29

Compound 29

2-Nitro-5-trifluoromethoxy-4-vinyl-benzoic acid ethyl ester

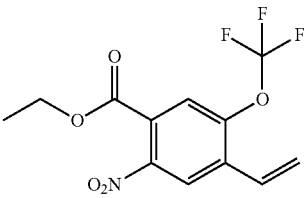

The title compound was synthesized from 4-bromo-2-nitro-5-trifluoromethoxy-benzoic acid ethyl ester (Compound 28) under the same conditions as for Compound 21.

Example 30

Compound 30

2-Amino-5-trifluoromethoxy-4-vinyl-benzoic acid ethyl ester

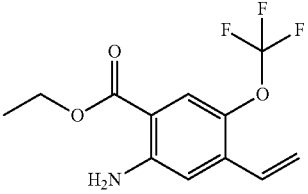 [SMILES: C=Cc1cc([N+](=O)[O-])c(C(=O)OCC)cc1OC(F)(F)F]

Zinc powder (904 mg, 13.8 mmol) was added to 2-nitro-5-trifluoromethoxy-4-vinyl-benzoic acid ethyl ester (Compound 29, 841 mg, 2.8 mmol) in 2-PrOH (4.2 ml) and a saturated aqueous ammonium chloride solution (4.2 ml), and the mixture was stirred at 60° C. for 2.5 hours. The reaction mixture was filtered through celite, and this was washed with MeOH. The filtrate was concentrated under reduced pressure, and water was added to the resulting residue, and extraction was performed with ethyl acetate. The organic layer was then washed with brine and dried over anhydrous sodium sulfate. The drying agent was removed by filtration, and the residue obtained by concentration under reduced pressure was purified by silica gel column chromatography (ethyl acetate/hexane) to give the title compound (683 mg, 89%) as a yellow solid.

LCMS: m/z 276 [M+H]+

HPLC retention time: 0.95 min (analysis condition D)

Example 31

Compound 31

2-Amino-4-(1,2-dihydroxy-ethyl)-5-trifluoromethoxy-benzoic acid ethyl ester

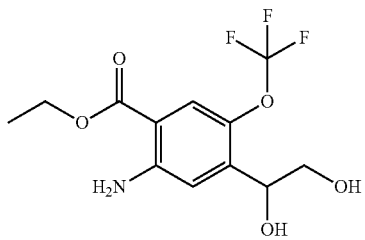 [SMILES: CCOC(=O)c1cc(OC(F)(F)F)c(C(O)CO)cc1N]

The title compound was synthesized from 2-amino-5-trifluoromethoxy-4-vinyl-benzoic acid ethyl ester (Compound 30) under the same conditions as for Compound 22.

Example 32

Compound 32

2-Amino-4-formyl-5-trifluoromethoxy-benzoic acid ethyl ester

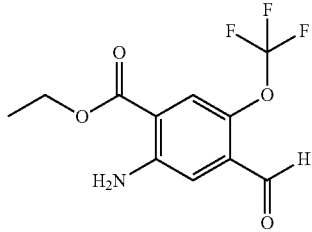 [SMILES: CCOC(=O)c1cc(OC(F)(F)F)c(C=O)cc1N]

The title compound was synthesized from 2-amino-4-(1,2-dihydroxy-ethyl)-5-trifluoromethoxy-benzoic acid ethyl ester (Compound 31) under the same conditions as for Compound 23.

Example 33

Compound 33

2-Amino-3-chloro-4-formyl-5-trifluoromethoxy-benzoic acid ethyl ester

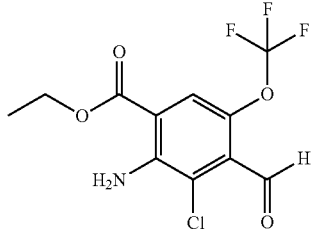 [SMILES: CCOC(=O)c1cc(OC(F)(F)F)c(C=O)c(Cl)c1N]

The title compound was synthesized from 2-amino-4-formyl-5-trifluoromethoxy-benzoic acid ethyl ester (Compound 32) under the same conditions as for Compound 24.

Example 34

Compound 34

2-Amino-3-chloro-4-[1,3]dioxolan-2-yl-5-trifluoromethoxy-benzoic acid ethyl ester

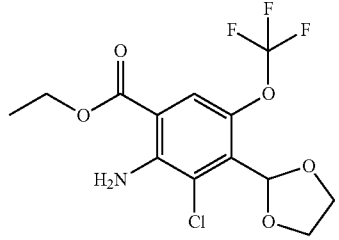 [SMILES: CCOC(=O)c1cc(OC(F)(F)F)c(C2OCCO2)c(Cl)c1N]

Ethylene glycol (387 ul, 6.9 mmol) and PTSA/H$_2$O (132 mg, 0.69 mmol) were added to a solution of 2-amino-3-chloro-4-formyl-5-trifluoromethoxy-benzoic acid ethyl ester (Compound 33, 1.08 g, 3.5 mmol) in toluene (20 ml), and the mixture was stirred at 90° C. for one hour. A saturated aqueous sodium bicarbonate solution was added to the reaction mixture, and extraction was performed with ethyl acetate. The organic layer was then washed with brine and dried over anhydrous sodium sulfate. The drying agent was removed by filtration, and the residue obtained by concentration under reduced pressure was purified by silica gel column chromatography (ethyl acetate/hexane) to give the title compound (1.13 g, 92%) as an orange solid.

LCMS: m/z 356 [M+H]$^+$

HPLC retention time: 0.92 min (analysis condition D)

Example 35

Compound 35

2-Amino-3-chloro-4-[1,3]dioxolan-2-yl-5-trifluoromethoxy-benzoic acid

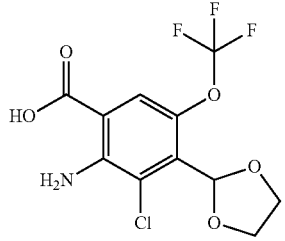 [SMILES: Nc1c(C(=O)O)cc(OC(F)(F)F)c(C2OCCO2)c1Cl]

The title compound was synthesized from 2-amino-3-chloro-4-[1,3]dioxolan-2-yl-5-trifluoromethoxy-benzoic acid ethyl ester (Compound 34) under the same conditions as for Compound 25.

Example 36

Compound 36

2-Amino-3-chloro-N-(5-chloro-2-ethanesulfonyl-benzyl)-4-[1,3]dioxolan-2-yl-5-trifluoromethoxy-benzamide

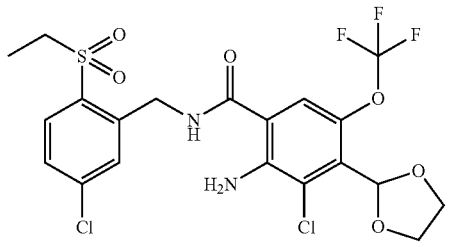 [SMILES: CCS(=O)(=O)c1ccc(Cl)cc1CNC(=O)c1cc(OC(F)(F)F)c(C2OCCO2)c(Cl)c1N]

The title compound was synthesized from 2-amino-3-chloro-4-[1,3]dioxolan-2-yl-5-trifluoromethoxy-benzoic acid (Compound 35) under the same conditions as for Compound 26.

Example 37

Compound 37

8-Chloro-3-(5-chloro-2-ethanesulfonyl-benzyl)-7-[1,3]dioxolan-2-yl-6-trifluoromethoxy-1H-quinazoline-2,4-dione

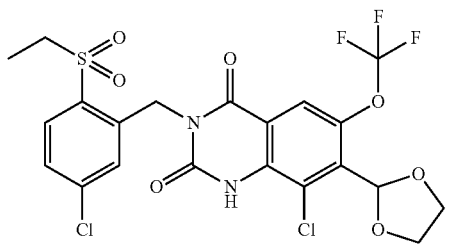 [SMILES: CCS(=O)(=O)c1ccc(Cl)cc1Cn1c(=O)[nH]c2c(Cl)c(C3OCCO3)c(OC(F)(F)F)cc2c1=O]

A solution of triphosgene (4.4 mg, 0.015 mmol) in DCM (0.5 ml) was slowly added to a solution of 2-amino-3-chloro-N-(5-chloro-2-ethanesulfonyl-benzyl)-4-[1,3]dioxolan-2-yl-5-trifluoromethoxy-benzamide (Compound 36, 8.1 mg, 0.015 mmol) and pyridine (8.4 ul, 0.10 mmol) in DCM (0.5 ml) under cooling in an ice water bath, and the mixture was stirred at 0° C. for one hour. A solution of triphosgene (1.1 mg, 0.037 mmol) in DCM (0.5 ml) was slowly added thereto, and the mixture was stirred at 0° C. for one hour. A saturated aqueous sodium bicarbonate solution was added to the reaction mixture, and extraction was performed with ethyl acetate. The organic layer was then washed with brine and dried over anhydrous sodium sulfate. The drying agent was removed by filtration, and the residue obtained by concentration under reduced pressure was purified by silica gel column chromatography (ethyl acetate/hexane) to give the title compound (6.7 mg, 79%) as a white solid.

LCMS: m/z 569 [M+H]$^+$

HPLC retention time: 0.87 min (analysis condition D)

Example 38

Compound 38

8-Chloro-3-(5-chloro-2-ethanesulfonyl-benzyl)-2,4-dioxo-6-trifluoromethoxy-1,2,3,4-tetrahydro-quinazoline-7-carbaldehyde

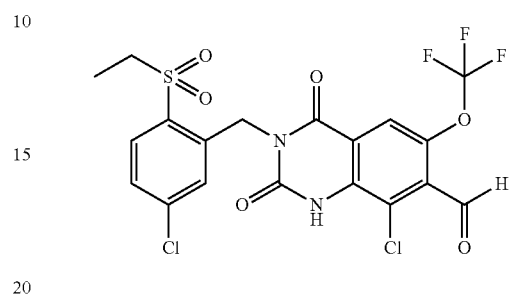

Concentrated sulfuric acid (2 ml) was added to a mixed solution of 8-chloro-3-(5-chloro-2-ethanesulfonyl-benzyl)-7-[1,3]dioxolan-2-yl-6-trifluoromethoxy-1H-quinazoline-2,4-dione (Compound 37, 986 mg, 1.73 mmol) in NMP (20 ml) and H$_2$O (2 ml), and the mixture was stirred at 75° C. for one hour. NMP (20 ml) was added thereto, and the mixture was stirred at 75° C. for two hours. H$_2$O (2 ml) and concentrated sulfuric acid (2 ml) were further added thereto, and the mixture was stirred at 90° C. for 14 hours. H$_2$O was added to the reaction mixture, and the resulting solid was washed with H$_2$O and dried to give the title compound as a crude product.

Example 39

Compound 39

4-Methyl-2-nitro-benzoic acid ethyl ester

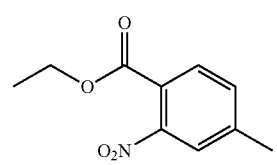

The title compound was synthesized from 4-methyl-2-nitro-benzoic acid under the same conditions as for Compound 20.

Example 40

Compound 40

2-Amino-4-methyl-benzoic acid ethyl ester

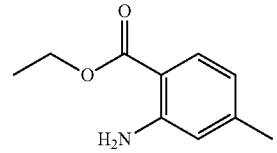

10% palladium carbon (638 mg) was added to a solution of 4-methyl-2-nitro-benzoic acid ethyl ester (Compound 39, 6.38 g, 30.5 mmol) in MeOH (64 ml), and the mixture was stirred at room temperature under hydrogen atmosphere for 17 hours. DCM was added to the reaction mixture, and this was filtrated through celite. The filtrate was concentrated under reduced pressure to give the title compound as a crude product.

Example 41

Compound 41

2-Amino-5-bromo-4-methyl-benzoic acid ethyl ester

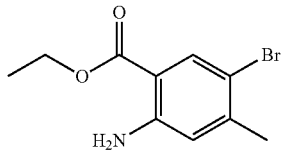

The title compound was synthesized from 2-amino-4-methyl-benzoic acid ethyl ester (Compound 40) under the same conditions as for Compound 24. However, NBS was used in place of NCS.

Example 42

Compound 42

2-(Bis(tert-butoxycarbonyl)amino)-5-bromo-4-methyl-benzoic acid ethyl ester

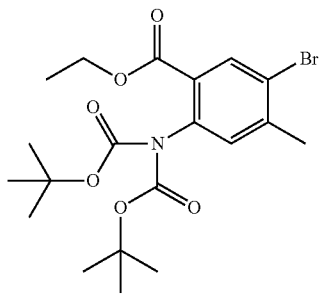 [SMILES: CCOC(=O)c1cc(Br)c(C)cc1N(C(=O)OC(C)(C)C)C(=O)OC(C)(C)C]

The title compound was synthesized from 2-amino-5-bromo-4-methyl-benzoic acid ethyl ester (Compound 41) under the same conditions as for Compound 17. However, acetonitrile was used as a solvent.

Example 43

Compound 43

2-(Bis(tert-butoxycarbonyl)amino)-5-bromo-4-bromomethyl-benzoic acid ethyl ester

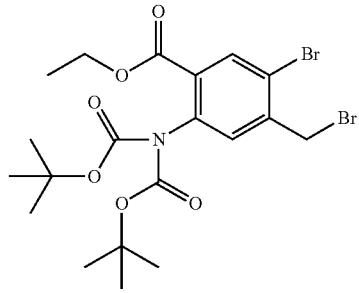 [SMILES: CCOC(=O)c1cc(Br)c(CBr)cc1N(C(=O)OC(C)(C)C)C(=O)OC(C)(C)C]

The title compound was synthesized from 2-(bis(tert-butoxycarbonyl)amino)-5-bromo-4-methyl-benzoic acid ethyl ester (Compound 42) under the same conditions as for Compound 12.

Example 44

Compound 44

2-Amino-5-chloro-4-methyl-benzoic acid ethyl ester

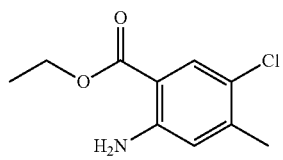

The title compound was synthesized from 2-amino-4-methyl-benzoic acid ethyl ester (Compound 40) under the same conditions as for Compound 24.

Example 45

Compound 45

2-(Bis(tert-butoxycarbonyl)amino)-5-chloro-4-methyl-benzoic acid ethyl ester

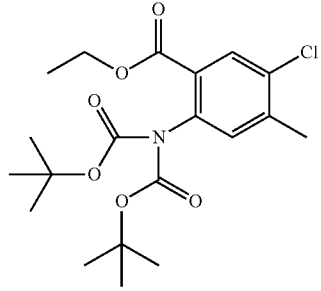 [SMILES: CCOC(=O)c1cc(Cl)c(C)cc1N(C(=O)OC(C)(C)C)C(=O)OC(C)(C)C]

The title compound was synthesized from 2-amino-5-chloro-4-methyl-benzoic acid ethyl ester (Compound 44) under the same conditions as for Compound 17. However, acetonitrile was used as a solvent.

Example 46

Compound 46

2-(Bis(tert-butoxycarbonyl)amino)-4-bromomethyl-5-chloro-benzoic acid ethyl ester

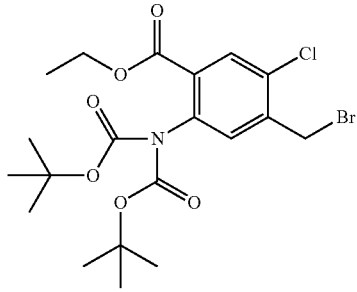 [SMILES: CCOC(=O)c1cc(Cl)c(CBr)cc1N(C(=O)OC(C)(C)C)C(=O)OC(C)(C)C]

The title compound was synthesized from 2-(bis(tert-butoxycarbonyl)amino)-5-chloro-4-methyl-benzoic acid ethyl ester (Compound 45) under the same conditions as for Compound 12.

Example 47

Compound a1

(5-Chloro-2-ethylsulfanyl-phenyl)-hydrazine

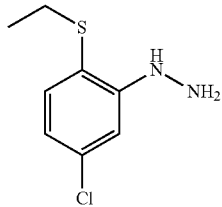

The title compound was synthesized from 5-chloro-2-ethylsulfanyl-phenylamine (Compound 14) under the same conditions as for Compound 16.

Example 48

Compound a2

2-Amino-3-bromo-5-methyl-benzoic acid N'-(5-chloro-2-ethylsulfanyl-phenyl)-hydrazide

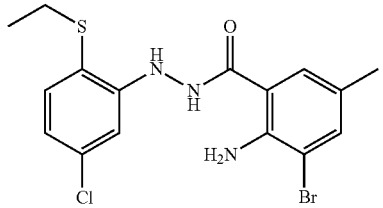 [SMILES: CCSc1ccc(Cl)cc1NNC(=O)c1cc(C)cc(Br)c1N]

The title compound was synthesized from 2-amino-3-bromo-5-methyl-benzoic acid using (5-chloro-2-ethylsulfanyl-phenyl)-hydrazine (Compound a1) in place of 5-chloro-2-ethanesulfonyl-benzylamine hydrochloride (Compound 3) under the same conditions as for Compound 26. However, the reaction was performed without adding HOBT and DIPEA.

Example 49

Compound a3

8-Bromo-3-(5-chloro-2-ethylsulfanyl-phenylamino)-6-methyl-3H-quinazolin-4-one

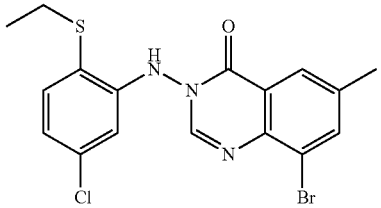 [SMILES: CCSc1ccc(Cl)cc1Nn1cnc2c(Br)cc(C)cc2c1=O]

A solution of 2-amino-3-bromo-5-methyl-benzoic acid N'-(5-chloro-2-ethylsulfanyl-phenyl)-hydrazide (Compound a2, 2.44 g, 5.9 mmol) in formic acid (10 mL) was heated at 100-110° C. Water (10 mL) was added to the reaction mixture, and the mixture was then neutralized to pH 7-8 by adding a 6 N aqueous sodium hydroxide solution. The reaction solution was extracted with DCM, and the extract was washed with brine and then dried over anhydrous magnesium sulfate. The drying agent was removed by filtration, and the residue obtained by concentration under reduced pressure was purified by silica gel column chromatography (ethyl acetate/hexane) to give the title compound (1.28 g, 51%) as a solid.
LCMS: m/z 424 [M+H]$^+$
HPLC retention time: 3.95 min (analysis condition B)

Example 50

Compound a4

(8-Bromo-6-methyl-4-oxo-4H-quinazolin-3-yl)-(5-chloro-2-ethylsulfanyl-phenyl)-carbamic acid tert-butyl ester

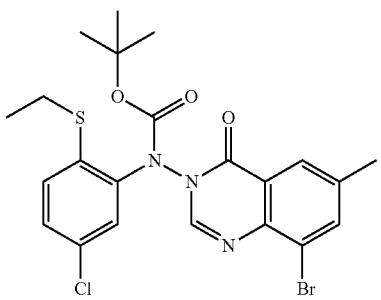 [SMILES: CCSc1ccc(Cl)cc1N(C(=O)OC(C)(C)C)n1cnc2c(Br)cc(C)cc2c1=O]

A 60% dispersion of sodium hydride in mineral oil (100 mg, 2.5 mmol) was added to a solution of 8-bromo-3-(5-chloro-2-ethylsulfanyl-phenylamino)-6-methyl-3H-quinazolin-4-one (Compound a3, 530 mg, 1.3 mmol) in DMF (25 mL). Subsequently, Boc$_2$O (409 mg, 1.9 mmol) and DMAP (76 mg, 0.63 mmol) were added thereto, and the mixture was stirred at room temperature for four hours. The reaction mixture was cooled to 0° C., and water was added thereto, and extraction was performed with ethyl acetate. The organic layer was then washed with brine and dried over anhydrous magnesium sulfate. The drying agent was removed by filtration, and the residue obtained by concentration under reduced pressure was purified by silica gel column chromatography (ethyl acetate/hexane) to give the title compound as a pale yellow solid. $^1$H-NMR (300 MHz, CDCl$_3$) δ: 8.73 (1H, d, J=17.7 Hz), 8.13 (1H, s), 7.89 (2H, s), 7.26-7.29 (2H, m), 2.99 (2H, q, J=7.2 Hz), 2.49 (3H, s), 1.44-1.46 (9H, m), 1.37 (3H, t, J=7.2 Hz).

Example 51

Compound a5

(8-Bromo-6-methyl-4-oxo-4H-quinazolin-3-yl)-(5-chloro-2-ethanesulfonyl-phenyl)-carbamic acid tert-butyl ester

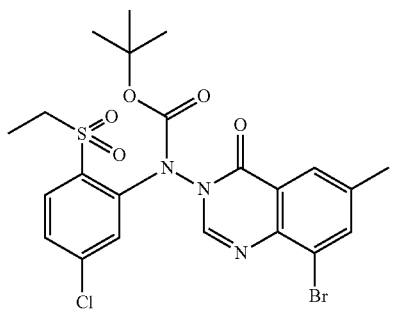 [SMILES: CCS(=O)(=O)c1ccc(Cl)cc1N(C(=O)OC(C)(C)C)n1cnc2c(Br)cc(C)cc2c1=O]

The title compound was synthesized from (8-bromo-6-methyl-4-oxo-4H-quinazolin-3-yl)-(5-chloro-2-ethylsulfanyl-phenyl)-carbamic acid tert-butyl ester (Compound a4) under the same conditions as for Compound 11.

Example 52

Compound A-1

8-Bromo-3-(5-chloro-2-ethylsulfonyl-phenyl amino)-6-methyl-1H-quinazoline-2,4-dione

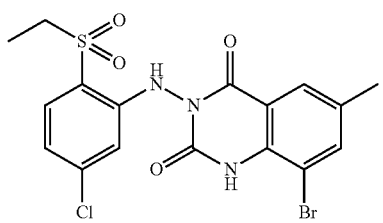 [SMILES: CCS(=O)(=O)c1ccc(Cl)cc1Nn1c(=O)[nH]c2c(Br)cc(C)cc2c1=O]

Sodium hydroxide (240 mg, 6.0 mmol) was added to a mixed solution of (8-bromo-6-methyl-4-oxo-4H-quinazolin-3-yl)-(5-chloro-2-ethanesulfonyl-phenyl)-carbamic acid tert-butyl ester (Compound a5, 120 mg, 0.22 mmol) in THF (10 mL) and water (2 ml), and the mixture was stirred at 100° C. for 18 hours. The reaction mixture was neutralized to pH 6 by adding a 1 N aqueous hydrochloric acid solution. The reaction solution was extracted with DCM, and the extract was washed with brine and then dried over anhydrous magnesium sulfate. The drying agent was removed by filtration, and the residue obtained by concentration under reduced pressure was purified by silica gel column chromatography (ethyl acetate/hexane) to give the title compound (69 mg, 68%) as a solid.

LCMS: m/z 472 [M+H]$^+$

HPLC retention time: 3.47 min (analysis condition B)

Example 53

Compound a6

3-Amino-4-ethylsulfanyl-benzonitrile

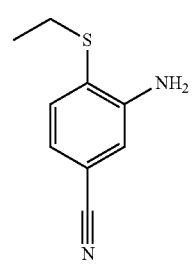

The title compound was synthesized from 3-amino-4-chloro-benzonitrile under the same conditions as for Compound 4. However, the reaction was performed by heating at 80° C. with microwave irradiation.

Example 54

Compound a7

4-Ethylsulfanyl-3-hydrazino-benzonitrile

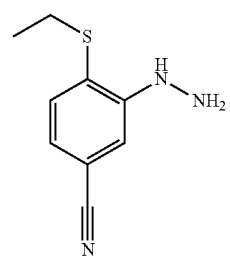

The title compound was synthesized from 3-amino-4-ethylsulfanyl-benzonitrile (Compound a6) under the same conditions as for Compound 16.

Example 55

Compound a8

2-Amino-3-bromo-5-trifluoromethyl-benzoic acid N'-(5-cyano-2-ethylsulfanyl-phenyl)-hydrazide

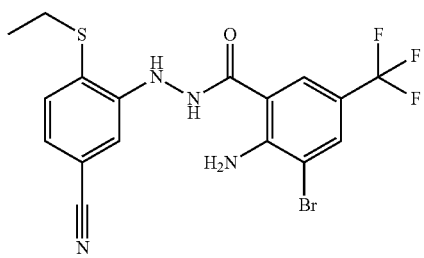 [SMILES: CCSc1ccc(C#N)cc1NNC(=O)c1cc(C(F)(F)F)cc(Br)c1N]

The title compound was synthesized from 2-amino-3-bromo-5-trifluoromethyl-benzoic acid (Compound a10) using 4-ethylsulfanyl-3-hydrazino-benzonitrile (Compound a7) in place of 5-chloro-2-ethanesulfonyl-benzylamine hydrochloride (Compound 3) under the same conditions as for Compound 26. However, the reaction was performed without adding HOBT and DIPEA.

Example 56

Compound a9

2-Amino-3-bromo-5-trifluoromethyl-benzoic acid ethyl ester

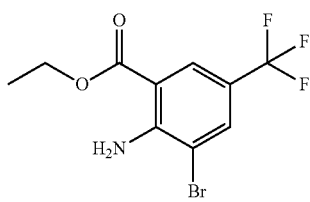 [SMILES: CCOC(=O)c1cc(C(F)(F)F)cc(Br)c1N]

Bromine (3.43 mL, 130 mmol) was added to a solution of 2-amino-5-trifluoromethyl-benzoic acid ethyl ester (5.34 g, 23 mmol) in DCM (26.5 mL) at room temperature. A saturated aqueous sodium thiosulfate solution (30 mL) was added thereto under ice-cooling, and extraction was performed with ethyl acetate. The extract was washed with brine and then dried over anhydrous sodium sulfate. The drying agent was removed by filtration, and the residue obtained by concentration under reduced pressure was purified by silica gel column chromatography (ethyl acetate/hexane) to give the title compound (6.97 g, 97%) as a pale yellow oily substance.

LCMS: m/z 312 [M+H]$^+$

HPLC retention time: 1.02 min (analysis condition D)

Example 57

Compound a10

2-Amino-3-bromo-5-trifluoromethyl-benzoic acid

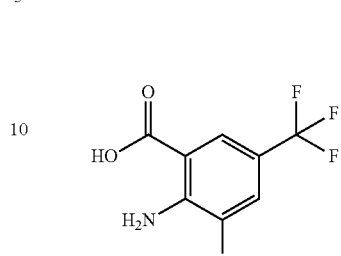

The title compound was synthesized from 2-amino-3-bromo-5-trifluoromethyl-benzoic acid ethyl ester (Compound a9) under the same conditions as for Compound 25.

Example 58

Compound A-2

3-(8-Bromo-2,4-dioxo-6-trifluoromethyl-1,4-dihydro-2H-quinazolin-3-ylamino)-4-ethylsulfanyl-benzonitrile

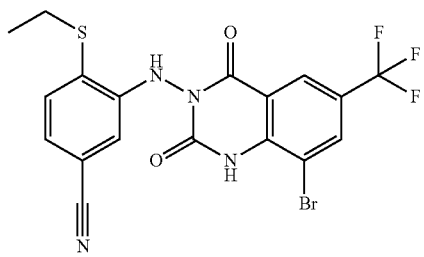 [SMILES: CCSc1ccc(C#N)cc1Nn1c(=O)[nH]c2c(Br)cc(C(F)(F)F)cc2c1=O]

The title compound was synthesized from 2-amino-3-bromo-5-trifluoromethyl-benzoic acid N'-(5-cyano-2-ethylsulfanyl-phenyl)-hydrazide (Compound a8) under the same conditions as for Compound 37.

LCMS: m/z 485 [M+H]$^+$

HPLC retention time: 0.85 min (analysis condition D)

Example 59

Compound A-3

3-(8-Bromo-2,4-dioxo-6-trifluoromethyl-1,4-dihydro-2H-quinazolin-3-ylamino)-4-ethanesulfonyl-benzonitrile

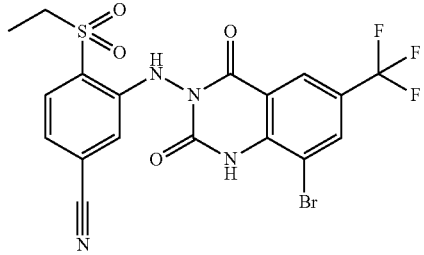 [SMILES: CCS(=O)(=O)c1ccc(C#N)cc1Nn1c(=O)[nH]c2c(Br)cc(C(F)(F)F)cc2c1=O]

The title compound was synthesized from 3-(8-bromo-2,4-dioxo-6-trifluoromethyl-1,4-dihydro-2H-quinazolin-3-ylamino)-4-ethylsulfanyl-benzonitrile (Compound A-2) under the same conditions as for Compound 11.

LCMS: m/z 517 [M+H]$^+$
HPLC retention time: 0.78 min (analysis condition D)

Example 60

Compound a11

2-Amino-N-(5-chloro-2-ethanesulfonyl-benzyl)-5-trifluoromethyl-benzamide

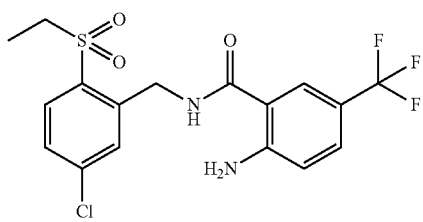 [SMILES: CCS(=O)(=O)c1ccc(Cl)cc1CNC(=O)c1cc(C(F)(F)F)ccc1N]

The title compound was synthesized from 2-amino-5-trifluoromethyl-benzoic acid under the same conditions as for Compound 26.

Example 61

Compound A-4

3-(5-Chloro-2-ethanesulfonyl-benzyl)-6-trifluoromethyl-1H-quinazoline-2,4-dione

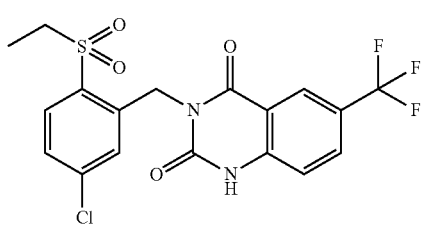 [SMILES: CCS(=O)(=O)c1ccc(Cl)cc1Cn1c(=O)[nH]c2ccc(C(F)(F)F)cc2c1=O]

CDI (58.3 mg, 0.36 mmol) and DBU (21.7 μL, 0.14 mmol) were added to a solution of 2-amino-N-(5-chloro-2-ethanesulfonyl-benzyl)-5-trifluoromethyl-benzamide (Compound a11, 50.4 mg, 0.12 mmol) in DMF (0.6 mL) at room temperature, and the mixture was stirred at room temperature for 18 hours. A 1 N aqueous hydrochloric acid solution was added thereto, and the resulting solid was collected by filtration, and then washed with water and dried under reduced pressure to give the title compound (50.0 mg, 93%) as a colorless solid.

LCMS: m/z 447 [M+H]$^+$
HPLC retention time: 0.86 min (analysis condition D)

Example 62

Compound a12

2-Amino-N-(5-chloro-2-ethanesulfonyl-benzyl)-5-trifluoromethoxy-benzamide

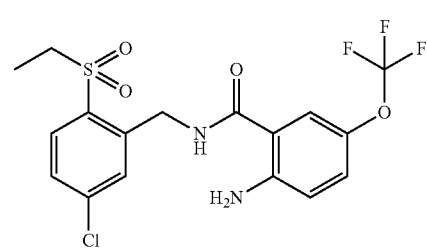 [SMILES: CCS(=O)(=O)c1ccc(Cl)cc1CNC(=O)c1cc(OC(F)(F)F)ccc1N]

The title compound was synthesized from 2-amino-5-trifluoromethoxy-benzoic acid under the same conditions as for Compound 26.

Example 63

Compound A-5

3-(5-Chloro-2-ethanesulfonyl-benzyl)-6-trifluoromethoxy-1H-quinazoline-2,4-dione

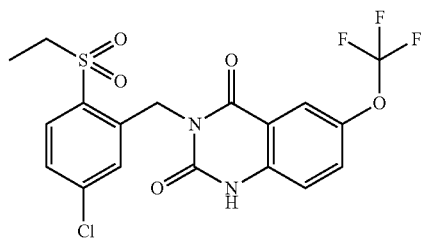 [SMILES: CCS(=O)(=O)c1ccc(Cl)cc1Cn1c(=O)[nH]c2ccc(OC(F)(F)F)cc2c1=O]

The title compound was synthesized from 2-amino-N-(5-chloro-2-ethanesulfonyl-benzyl)-5-trifluoromethoxy-benzamide (Compound a12) under the same conditions as for Compound A-4.

LCMS: m/z 463 [M+H]$^+$
HPLC retention time: 0.87 min (analysis condition D)

Example 64

Compound a13

2-Amino-4-bromo-5-trifluoromethoxy-benzoic acid

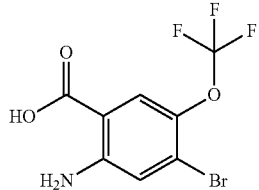 [SMILES: Nc1cc(Br)c(OC(F)(F)F)cc1C(=O)O]

The title compound was synthesized from 4-bromo-2-nitro-5-trifluoromethoxy-benzoic acid (Compound 27) under the same conditions as for Compound 30. However, the reaction was performed at 100° C. using iron in place of zinc.

Example 65

Compound a14

2-Amino-4-bromo-N-(5-chloro-2-ethanesulfonyl-benzyl)-5-trifluoromethoxy-benzamide

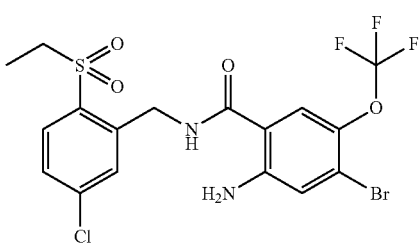 [SMILES: CCS(=O)(=O)c1ccc(Cl)cc1CNC(=O)c1cc(OC(F)(F)F)c(Br)cc1N]

The title compound was synthesized from 2-amino-4-bromo-5-trifluoromethoxy-benzoic acid (Compound a13) under the same conditions as for Compound 26.

Example 66

Compound A-6

7-Bromo-3-(5-chloro-2-ethanesulfonyl-benzyl)-6-trifluoromethoxy-1H-quinazoline-2,4-dione

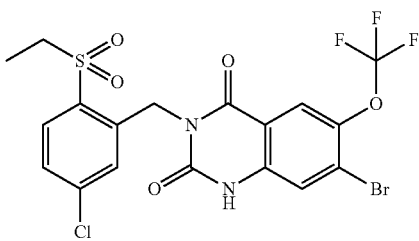 [SMILES: CCS(=O)(=O)c1ccc(Cl)cc1Cn1c(=O)[nH]c2cc(Br)c(OC(F)(F)F)cc2c1=O]

TEA (1.07 ml, 7.6 mmol) was added to a solution of 2-amino-4-bromo-N-(5-chloro-2-ethanesulfonyl-benzyl)-5-trifluoromethoxy-benzamide (Compound a14, 657 mg, 1.3 mmol) in THF (33 ml), and the mixture was cooled to 0° C. A solution of triphosgene (755 mg, 2.5 mmol) in THF (6.6 ml) was added dropwise to this reaction mixture over 10 minutes, and the mixture was stirred at 0° C. for two hours. A saturated aqueous sodium bicarbonate solution (3.3 ml) was added to the reaction mixture at 0° C., and THF was concentrated under reduced pressure. The resulting residue was extracted with ethyl acetate, and the organic layer was then washed with water and brine, and dried over anhydrous sodium sulfate. The drying agent was removed by filtration, and the residue obtained by concentration under reduced pressure was purified by silica gel column chromatography (ethyl acetate/hexane) to give the title compound (473 mg, 69%) as an orange solid.
LCMS: m/z 541 [M+H]$^+$
HPLC retention time: 0.90 min (analysis condition D)

Example 67

Compound a15

2-Amino-5-bromo-4-methyl-benzoic acid

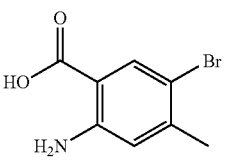

The title compound was synthesized from 2-amino-5-bromo-4-methyl-benzoic acid ethyl ester (Compound 41) under the same conditions as for Compound 25.

Example 68

Compound a16

2-Amino-5-bromo-N-(5-chloro-2-ethanesulfonyl-benzyl)-4-methyl-benzamide

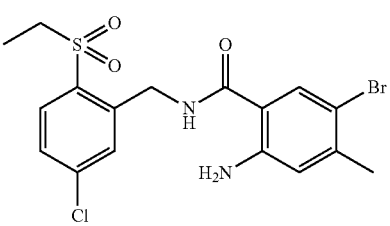 [SMILES: CCS(=O)(=O)c1ccc(Cl)cc1CNC(=O)c1cc(Br)c(C)cc1N]

The title compound was synthesized from 2-amino-5-bromo-4-methyl-benzoic acid (Compound a15) under the same conditions as for Compound 26.

Example 69

Compound A-7

6-Bromo-3-(5-chloro-2-ethanesulfonyl-benzyl)-7-methyl-1H-quinazoline-2,4-dione

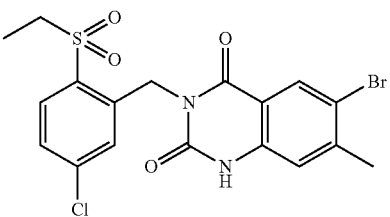 [SMILES: CCS(=O)(=O)c1ccc(Cl)cc1Cn1c(=O)[nH]c2cc(C)c(Br)cc2c1=O]

The title compound was synthesized from 2-amino-5-bromo-N-(5-chloro-2-ethanesulfonyl-benzyl)-4-methyl-benzamide (Compound a16) under the same conditions as for Compound A-6.
LCMS: m/z 471 [M+H]$^+$
HPLC retention time: 0.87 min (analysis condition H)

Example 70

Compound a17

2-Amino-3-bromo-N-(5-chloro-2-ethylsulfanyl-benzyl)-5-methyl-benzamide

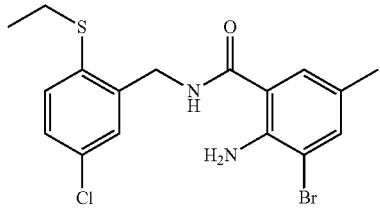 [SMILES: CCSc1ccc(Cl)cc1CNC(=O)c1cc(C)cc(Br)c1N]

The title compound was synthesized from 2-amino-3-bromo-5-methyl-benzoic acid under the same conditions as for Compound 26. However, the reaction was performed using 5-chloro-2-ethylsulfanyl-benzylamine (Compound 2) and TEA in place of 5-chloro-2-ethanesulfonyl-benzylamine hydrochloride (Compound 3) and DIPEA and without adding HOBT.

Example 71

Compound A-8

8-Bromo-3-(5-chloro-2-ethylsulfanyl-benzyl)-6-methyl-1H-quinazoline-2,4-dione

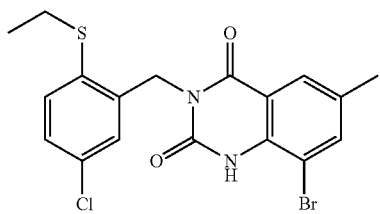 [SMILES: CCSc1ccc(Cl)cc1Cn1c(=O)[nH]c2c(Br)cc(C)cc2c1=O]

The title compound was synthesized from 2-amino-3-bromo-N-(5-chloro-2-ethylsulfanyl-benzyl)-5-methyl-benzamide (Compound a17) under the same conditions as for Compound 37. However, the reaction was performed using ethyl chloroformate in place of triphosgene.

LCMS: m/z 439 [M+H]$^+$
HPLC retention time: 1.03 min (analysis condition A)

Example 72

Compound A-9

8-Bromo-3-(5-chloro-2-ethanesulfonyl-benzyl)-6-methyl-1H-quinazoline-2,4-dione

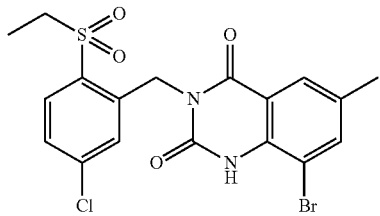 [SMILES: CCS(=O)(=O)c1ccc(Cl)cc1Cn1c(=O)[nH]c2c(Br)cc(C)cc2c1=O]

The title compound was synthesized from 8-bromo-3-(5-chloro-2-ethylsulfanyl-benzyl)-6-methyl-1H-quinazoline-2,4-dione (Compound A-8) under the same conditions as for Compound 11.

LCMS: m/z 471 [M+H]$^+$
HPLC retention time: 3.62 min (analysis condition B)

Example 73

Compound a18

2-Amino-3-chloro-5-trifluoromethyl-benzoic acid ethyl ester

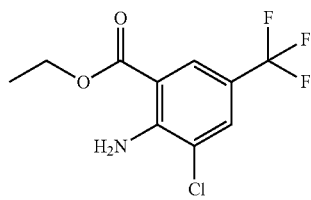 [SMILES: CCOC(=O)c1cc(C(F)(F)F)cc(Cl)c1N]

The title compound was synthesized from 2-amino-5-trifluoromethyl-benzoic acid ethyl ester under the same conditions as for Compound 24.

Example 74

Compound a19

2-Amino-3-chloro-5-trifluoromethyl-benzoic acid

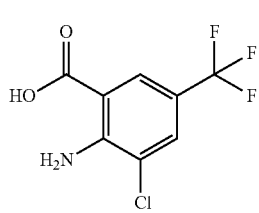 [SMILES: Nc1c(Cl)cc(C(F)(F)F)cc1C(=O)O]

The title compound was synthesized from 2-amino-3-chloro-5-trifluoromethyl-benzoic acid ethyl ester (Compound a18) under the same conditions as for Compound 25. However, the reaction was performed using a 2 N aqueous sodium hydroxide solution in place of a 1 N aqueous sodium hydroxide solution.

Example 75

Compound a20

2-Amino-3-chloro-N-(5-chloro-2-ethylsulfanyl-benzyl)-5-trifluoromethyl-benzamide

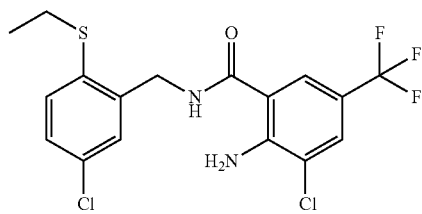 [SMILES: CCSc1ccc(Cl)cc1CNC(=O)c1cc(C(F)(F)F)cc(Cl)c1N]

The title compound was synthesized from 2-amino-3-chloro-5-trifluoromethyl-benzoic acid (Compound a19) under the same conditions as for Compound 26. However, the reaction was performed using 5-chloro-2-ethylsulfanyl-benzylamine (Compound 2) in place of 5-chloro-2-ethane-sulfonyl-benzylamine hydrochloride (Compound 3) and without adding HOBT.

Example 76

Compound A-10

8-Chloro-3-(5-chloro-2-ethylsulfanyl-benzyl)-6-trifluoromethyl-1H-quinazoline-2,4-dione

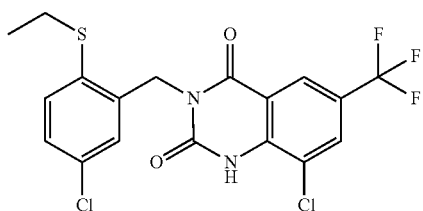 [SMILES: CCSc1ccc(Cl)cc1Cn1c(=O)[nH]c2c(Cl)cc(C(F)(F)F)cc2c1=O]

The title compound was synthesized from 2-amino-3-chloro-N-(5-chloro-2-ethylsulfanyl-benzyl)-5-trifluoromethyl-benzamide (Compound a20) under the same conditions as for Compound 37.

LCMS: m/z 449 [M+H]$^+$

HPLC retention time: 1.02 min (analysis condition D)

Example 77

Compound A-11

8-Chloro-3-(5-chloro-2-ethanesulfonyl-benzyl)-6-trifluoromethyl-1H-quinazoline-2,4-dione

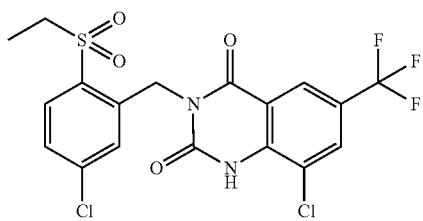 [SMILES: CCS(=O)(=O)c1ccc(Cl)cc1Cn1c(=O)[nH]c2c(Cl)cc(C(F)(F)F)cc2c1=O]

The title compound was synthesized from 8-chloro-3-(5-chloro-2-ethylsulfanyl-benzyl)-6-trifluoromethyl-1H-quinazoline-2,4-dione (Compound A-10) under the same conditions as for Compound 11.

LCMS: m/z 481 [M+H]$^+$

HPLC retention time: 0.88 min (analysis condition D)

Example 78

Compound a21

2-Amino-3-bromo-N-(5-chloro-2-ethylsulfanyl-benzyl)-5-trifluoromethyl-benzamide

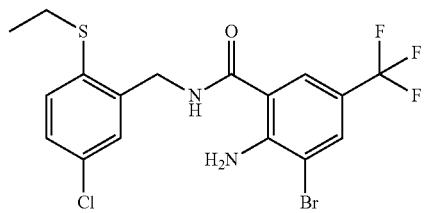 [SMILES: CCSc1ccc(Cl)cc1CNC(=O)c1cc(C(F)(F)F)cc(Br)c1N]

The title compound was synthesized from 2-amino-3-bromo-5-trifluoromethyl-benzoic acid (Compound a10) under the same conditions as for Compound 26. However, the reaction was performed using 5-chloro-2-ethylsulfanyl-benzylamine (Compound 2) in place of 5-chloro-2-ethane-sulfonyl-benzylamine hydrochloride (Compound 3) and using DMF in place of DCM as a solvent.

Example 79

Compound A-12

8-Bromo-3-(5-chloro-2-ethylsulfanyl-benzyl-6-trifluoromethyl-1H-quinazoline-2,4-dione

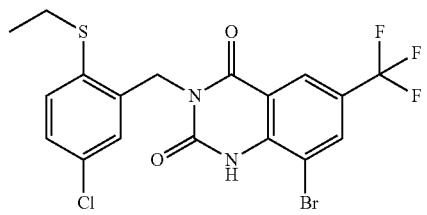 [SMILES: CCSc1ccc(Cl)cc1Cn1c(=O)[nH]c2c(Br)cc(C(F)(F)F)cc2c1=O]

The title compound was synthesized from 2-amino-3-bromo-N-(5-chloro-2-ethylsulfanyl-benzyl)-5-trifluoromethyl-benzamide (Compound a21) under the same conditions as for Compound 37.

LCMS: m/z 493 [M+H]$^+$

HPLC retention time: 1.04 min (analysis condition D)

Example 80

Compound A-13

8-Bromo-3-(5-chloro-2-ethanesulfonyl-benzyl)-6-trifluoromethyl-1H-quinazoline-2,4-dione

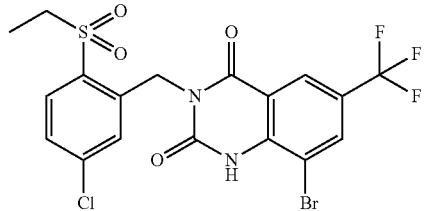 [SMILES: CCS(=O)(=O)c1ccc(Cl)cc1Cn1c(=O)[nH]c2c(Br)cc(C(F)(F)F)cc2c1=O]

The title compound was synthesized from 8-bromo-3-(5-chloro-2-ethylsulfanyl-benzyl)-6-trifluoromethyl-1H-quinazoline-2,4-dione (Compound A-12) under the same conditions as for Compound 11.

LCMS: m/z 525 [M+H]⁺
HPLC retention time: 0.90 min (analysis condition D)

Example 81

Compound a22

2-Amino-3-chloro-5-trifluoromethoxy-benzoic acid

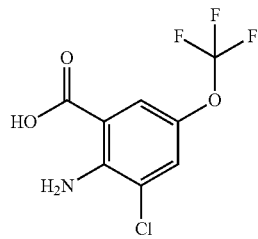 [SMILES: Nc1c(Cl)cc(OC(F)(F)F)cc1C(=O)O]

The title compound was synthesized from 2-amino-3-chloro-5-trifluoromethoxy-benzoic acid methyl ester under the same conditions as for Compound 25. However, the reaction was performed using a 2 N aqueous sodium hydroxide solution in place of a 1 N aqueous sodium hydroxide solution.

Example 82

Compound a23

2-Amino-3-chloro-N-(5-chloro-2-ethylsulfanyl-benzyl)-5-trifluoromethoxy-benzamide

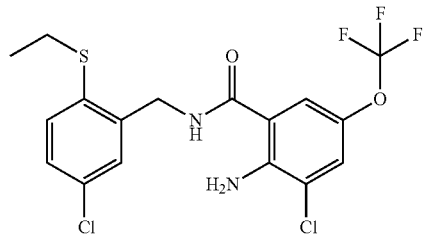 [SMILES: CCSc1ccc(Cl)cc1CNC(=O)c1cc(OC(F)(F)F)cc(Cl)c1N]

The title compound was synthesized from 2-amino-3-chloro-5-trifluoromethoxy-benzoic acid (Compound a22) under the same conditions as for Compound 26. However, the reaction was performed using 5-chloro-2-ethylsulfanyl-benzylamine (Compound 2) in place of 5-chloro-2-ethanesulfonyl-benzylamine hydrochloride (Compound 3) and using DMF in place of DCM as a solvent.

Example 83

Compound A-14

8-Chloro-3-(5-chloro-2-ethylsulfanyl-benzyl)-6-trifluoromethoxy-1H-quinazoline-2,4-dione

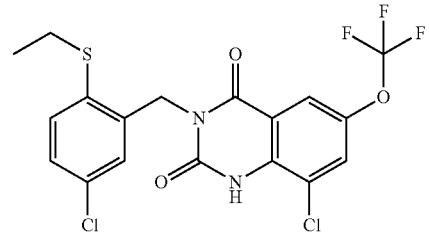

The title compound was synthesized from 2-amino-3-chloro-N-(5-chloro-2-ethylsulfanyl-benzyl)-5-trifluoromethoxy-benzamide (Compound a23) under the same conditions as for Compound 37.
LCMS: m/z 465 [M+H]⁺
HPLC retention time: 1.04 min (analysis condition D)

Example 84

Compound A-15

8-Chloro-3-(5-chloro-2-ethanesulfonyl-benzyl)-6-trifluoromethoxy-1H-quinazoline-2,4-dione

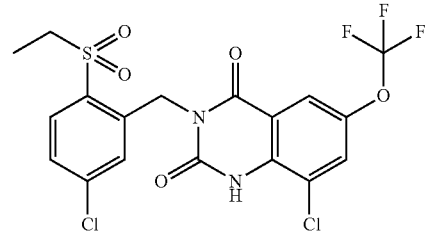

The title compound was synthesized from 8-chloro-3-(5-chloro-2-ethylsulfanyl-benzyl)-6-trifluoromethoxy-1H-quinazoline-2,4-dione (Compound A-14) under the same conditions as for Compound 11.
LCMS: m/z 497 [M+H]⁺
HPLC retention time: 0.90 min (analysis condition D)

Example 85

Compound a24

2-Amino-3-bromo-N-(5-chloro-2-ethylsulfanyl-benzyl)-5-trifluoromethoxy-benzamide

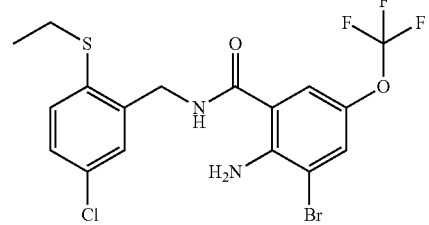

The title compound was synthesized from 2-amino-3-bromo-5-trifluoromethoxy-benzoic acid under the same conditions as for Compound 26. However, the reaction was performed using 5-chloro-2-ethylsulfanyl-benzylamine (Compound 2) in place of 5-chloro-2-ethanesulfonyl-benzylamine hydrochloride (Compound 3) and using DMF in place of DCM as a solvent.

Example 86

Compound A-16

8-Bromo-3-(5-chloro-2-ethylsulfanyl-benzyl)-6-trifluoromethoxy-1H-quinazoline-2,4-dione

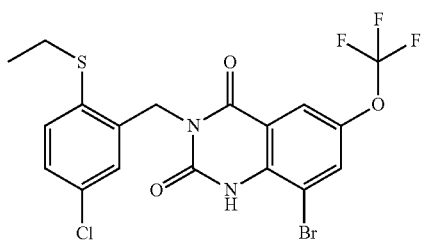 [SMILES: CCSc1ccc(Cl)cc1Cn1c(=O)[nH]c2c(Br)cc(OC(F)(F)F)cc2c1=O]

The title compound was synthesized from 2-amino-3-bromo-N-(5-chloro-2-ethylsulfanyl-benzyl)-5-trifluoromethoxy-benzamide (Compound a24) under the same conditions as for Compound 37.

LCMS: m/z 509 [M+H]$^+$

HPLC retention time: 1.05 min (analysis condition D)

Example 87

Compound A-17

8-Bromo-3-(5-chloro-2-ethanesulfonyl-benzyl)-6-trifluoromethoxy-1H-quinazoline-2,4-dione

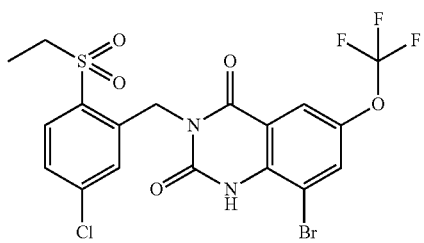 [SMILES: CCS(=O)(=O)c1ccc(Cl)cc1Cn1c(=O)[nH]c2c(Br)cc(OC(F)(F)F)cc2c1=O]

The title compound was synthesized from 8-bromo-3-(5-chloro-2-ethylsulfanyl-benzyl)-6-trifluoromethoxy-1H-quinazoline-2,4-dione (Compound A-16) under the same conditions as for Compound 11.

LCMS: m/z 541 [M+H]$^+$

HPLC retention time: 0.91 min (analysis condition D)

Example 88

Compound a25

2-Ethylsulfanyl-benzonitrile

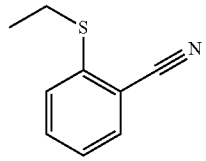

The title compound was synthesized from 2-fluoro-benzonitrile under the same conditions as for Compound 4.

Example 89

Compound a26

2-Ethylsulfanyl-benzylamine

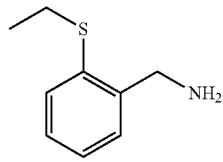

The title compound was synthesized from 2-ethylsulfanyl-benzonitrile (Compound a25) under the same conditions as for Compound 2.

Example 90

Compound a27

2-Amino-N-(2-ethylsulfanyl-benzyl)-5-trifluoromethyl-benzamide

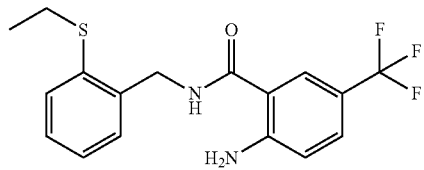 [SMILES: CCSc1ccccc1CNC(=O)c1cc(C(F)(F)F)ccc1N]

The title compound was synthesized from 2-amino-5-trifluoromethyl-benzoic acid under the same conditions as for Compound 26. However, the reaction was performed using 2-ethylsulfanyl-benzylamine (Compound a26) in place of 5-chloro-2-ethanesulfonyl-benzylamine hydrochloride (Compound 3) and without adding DIPEA.

Example 91

Compound A-18

3-(2-Ethylsulfanyl-benzyl)-6-trifluoromethyl-1H-quinazoline-2,4-dione

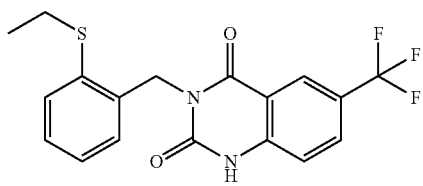 [SMILES: CCSc1ccccc1Cn1c(=O)[nH]c2ccc(C(F)(F)F)cc2c1=O]

The title compound was synthesized from 2-amino-N-(2-ethylsulfanyl-benzyl)-5-trifluoromethyl-benzamide (Compound a27) under the same conditions as for Compound A-4.
LCMS: m/z 381 [M+H]$^+$
HPLC retention time: 0.93 min (analysis condition D)

Example 92

Compound a28

2-Ethanesulfonyl-benzylamine hydrochloride

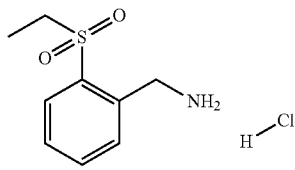

10% Pd/C (10 mg) was added to a solution of 5-chloro-2-ethanesulfonyl-benzylamine hydrochloride (Compound 3, 100 mg, 0.37 mmol) in methanol (1.8 ml), and the mixture was stirred under hydrogen atmosphere for three hours. Pd/C was removed by filtration, and the filtrate was then concentrated under reduced pressure to give the title compound (87 mg, quant.) as a yellow solid.
LCMS: m/z 200 [M+H]$^+$
HPLC retention time: 0.25 min (analysis condition D)

Example 93

Compound a29

2-Amino-N-(2-ethanesulfonyl-benzyl)-5-trifluoromethyl-benzamide

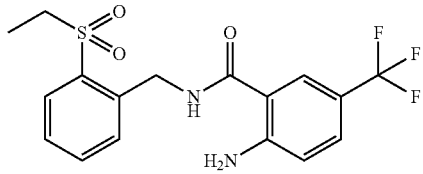 [SMILES: CCS(=O)(=O)c1ccccc1CNC(=O)c1cc(C(F)(F)F)ccc1N]

The title compound was synthesized from 2-amino-5-trifluoromethyl-benzoic acid using 2-ethanesulfonyl-benzylamine hydrochloride (Compound a28) in place of 5-chloro-2-ethanesulfonyl-benzylamine hydrochloride (Compound 3) under the same conditions as for Compound 26.

Example 94

Compound A-19

3-(2-Ethanesulfonyl-benzyl)-6-trifluoromethyl-1H-quinazoline-2,4-dione

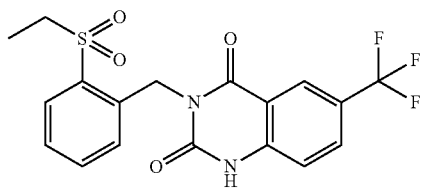 [SMILES: CCS(=O)(=O)c1ccccc1Cn1c(=O)[nH]c2ccc(C(F)(F)F)cc2c1=O]

The title compound was synthesized from 2-amino-N-(2-ethanesulfonyl-benzyl)-5-trifluoromethyl-benzamide (Compound a29) under the same conditions as for Compound A-4.
LCMS: m/z 413 [M+H]$^+$
HPLC retention time: 0.77 min (analysis condition D)

Example 95

Compound a30

2-Propylsulfanyl-benzonitrile

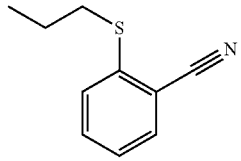

The title compound was synthesized from 2-fluoro-benzonitrile under the same conditions as for Compound 4. However, the reaction was performed using sodium propanethiolate in place of sodium ethanethiolate.

Example 96

Compound A-20

3-(2-Propylsulfanyl-benzyl)-6-trifluoromethyl-1H-quinazoline-2,4-dione

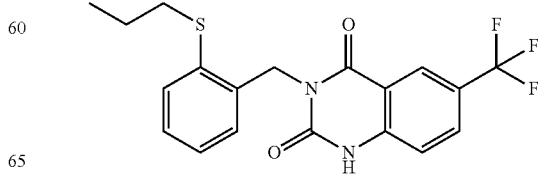

The title compound was synthesized from 2-propylsulfanyl-benzonitrile (Compound a30) under the same conditions as for Compounds a26, a27, and A-18.

LCMS: m/z 395 [M+H]$^+$

HPLC retention time: 0.98 min (analysis condition D)

Example 97

Compound a31

5-Fluoro-2-methylsulfanyl-benzonitrile

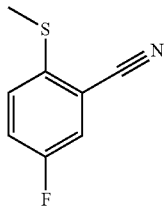

The title compound was synthesized from 2,5-difluorobenzonitrile under the same conditions as for Compound 4. However, the reaction was performed using sodium methanethiolate in place of sodium ethanethiolate.

Example 98

Compound a32

3-(5-Fluoro-2-methylsulfanyl-benzyl)-6-trifluoromethyl-1H-quinazoline-2,4-dione

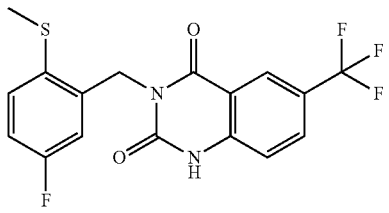 [SMILES: CSc1ccc(F)cc1Cn1c(=O)[nH]c2ccc(C(F)(F)F)cc2c1=O]

The title compound was synthesized from 5-fluoro-2-methylsulfanyl-benzonitrile (Compound a31) under the same conditions as for Compounds a26, a27, and A-18.

Example 99

Compound A-21

3-(5-Fluoro-2-methanesulfonyl-benzyl)-6-trifluoromethyl-1H-quinazoline-2,4-dione

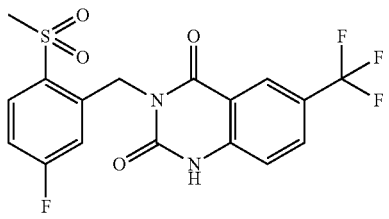 [SMILES: CS(=O)(=O)c1ccc(F)cc1Cn1c(=O)[nH]c2ccc(C(F)(F)F)cc2c1=O]

The title compound was synthesized from 3-(5-fluoro-2-methylsulfanyl-benzyl)-6-trifluoromethyl-1H-quinazoline-2,4-dione (Compound a32) under the same conditions as for Compound 11.

LCMS: m/z 417 [M+H]$^+$

HPLC retention time: 0.82 min (analysis condition D)

Example 100

Compound a33

2-Ethylsulfanyl-5-fluoro-benzonitrile

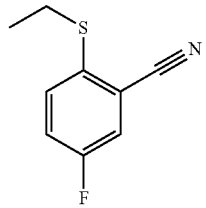

The title compound was synthesized from 2,5-difluorobenzonitrile under the same conditions as for Compound 1. However, the reaction was performed at 90° C. instead of room temperature.

Example 101

Compound A-22

3-(2-Ethylsulfanyl-5-fluoro-benzyl)-6-trifluoromethyl-1H-quinazoline-2,4-dione

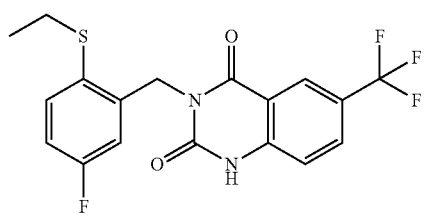 [SMILES: CCSc1ccc(F)cc1Cn1c(=O)[nH]c2ccc(C(F)(F)F)cc2c1=O]

The title compound was synthesized from 2-ethylsulfanyl-5-fluoro-benzonitrile (Compound a33) under the same conditions as for Compounds a26, a27, and A-18.

LCMS: m/z 399 [M+H]$^+$

HPLC retention time: 0.94 min (analysis condition D)

Example 102

Compound A-23

3-(2-Ethanesulfonyl-5-fluoro-benzyl)-6-trifluoromethyl-1H-quinazoline-2,4-dione

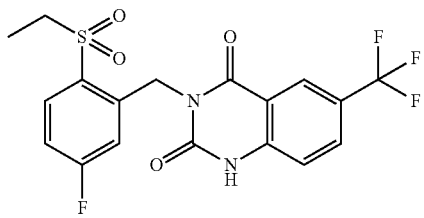

The title compound was synthesized from 3-(2-ethylsulfanyl-5-fluoro-benzyl)-6-trifluoromethyl-1H-quinazoline-2,4-dione (Compound A-22) under the same conditions as for Compound 11.
LCMS: m/z 431 [M+H]$^+$
HPLC retention time: 0.80 min (analysis condition D)

Example 103

Compound a34

2-Amino-N-(5-bromo-2-ethanesulfonyl-benzyl)-5-trifluoromethyl-benzamide

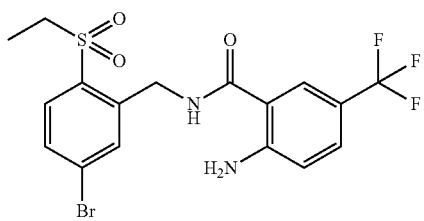

The title compound was synthesized from 2-amino-5-trifluoromethyl-benzoic acid under the same conditions as for Compound 26. However, the reaction was performed using 5-bromo-2-ethanesulfonyl-benzylamine hydrochloride (Compound 9) and HBTU in place of 5-chloro-2-ethanesulfonyl-benzylamine hydrochloride (Compound 3), WSCDI and HOBT.

Example 104

Compound A-24

3-(5-Bromo-2-ethanesulfonyl-benzyl)-6-trifluoromethyl-1H-quinazoline-2,4-dione

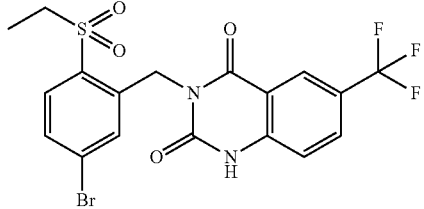 [SMILES: CCS(=O)(=O)c1ccc(Br)cc1Cn1c(=O)[nH]c2ccc(C(F)(F)F)cc2c1=O]

The title compound was synthesized from 2-amino-N-(5-bromo-2-ethanesulfonyl-benzyl)-5-trifluoromethyl-benzamide (Compound a34) under the same conditions as for Compound A-4.
LCMS: m/z 491 [M+H]$^+$
HPLC retention time: 0.85 min (analysis condition D)

Example 105

Compound A-25

3-(5-Bromo-2-ethanesulfonyl-benzyl)-8-chloro-6-trifluoromethyl-1H-quinazoline-2,4-dione

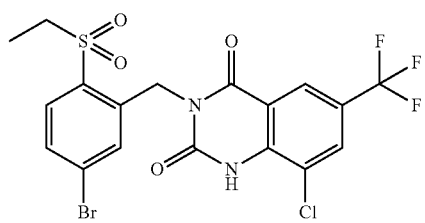 [SMILES: CCS(=O)(=O)c1ccc(Br)cc1Cn1c(=O)[nH]c2c(Cl)cc(C(F)(F)F)cc2c1=O]

The title compound was synthesized from 2-amino-3-chloro-5-trifluoromethyl-benzoic acid (Compound a19) under the same conditions as for Compounds a34 and A-24.
LCMS: m/z 525 [M+H]$^+$
HPLC retention time: 0.91 min (analysis condition D)

Example 106

Compound A-26

3-(5-Bromo-2-ethanesulfonyl-benzyl)-6-trifluoromethoxy-1H-quinazoline-2,4-dione

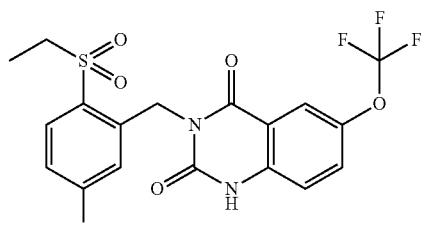

The title compound was synthesized from 2-amino-5-trifluoromethoxy-benzoic acid under the same conditions as for Compounds a34 and A-24.
LCMS: m/z 507 [M+H]$^+$
HPLC retention time: 0.86 min (analysis condition D)

Example 107

Compound A-27

3-(5-Bromo-2-ethanesulfonyl-benzyl)-8-chloro-6-trifluoromethoxy-1H-quinazoline-2,4-dione

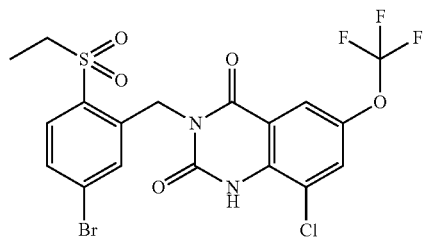

The title compound was synthesized from 2-amino-3-chloro-5-trifluoromethoxy-benzoic acid (Compound a22) under the same conditions as for Compounds a34 and A-24.

LCMS: m/z 541 [M+H]$^+$

HPLC retention time: 0.92 min (analysis condition D)

Example 108

Compound a35

2-Ethylsulfanyl-4-methyl-benzonitrile

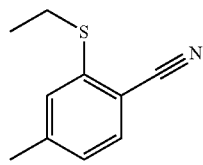

The title compound was synthesized from 2-bromo-4-methyl-benzonitrile under the same conditions as for Compound 1. However, the reaction was performed at 90° C. instead of room temperature.

Example 109

Compound a36

2-Ethylsulfanyl-4-methyl-benzylamine

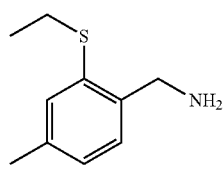

The title compound was synthesized from 2-ethylsulfanyl-4-methyl-benzonitrile (Compound a35) under the same conditions as for Compound 2.

Example 110

Compound a37

2-Amino-N-(2-ethylsulfanyl-4-methyl-benzyl)-5-trifluoromethyl-benzamide

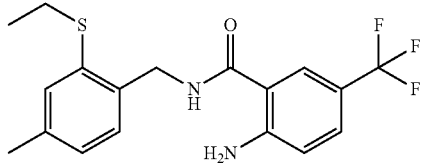 [SMILES: CCSc1cc(C)ccc1CNC(=O)c1cc(C(F)(F)F)ccc1N]

The title compound was synthesized from 2-amino-5-trifluoromethyl-benzoic acid using 2-ethylsulfanyl-4-methyl-benzylamine (Compound a36) in place of 5-chloro-2-ethanesulfonyl-benzylamine hydrochloride (Compound 3) under the same conditions as for Compound 26. However, the reaction was performed without adding DIPEA.

Example 111

Compound a38

3-(2-Ethylsulfanyl-4-methyl-benzyl)-6-trifluoromethyl-1H-quinazoline-2,4-dione

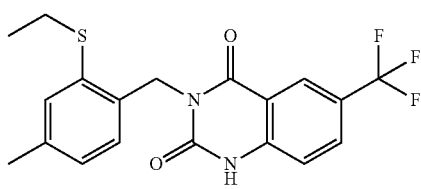 [SMILES: CCSc1cc(C)ccc1Cn1c(=O)[nH]c2ccc(C(F)(F)F)cc2c1=O]

The title compound was synthesized from 2-amino-N-(2-ethylsulfanyl-4-methyl-benzyl)-5-trifluoromethyl-benzamide (Compound a37) under the same conditions as for Compound A-4.

Example 112

Compound A-28

3-(2-Ethanesulfonyl-4-methyl-benzyl)-6-trifluoromethyl-1H-quinazoline-2,4-dione

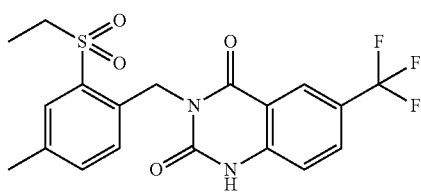 [SMILES: CCS(=O)(=O)c1cc(C)ccc1Cn1c(=O)[nH]c2ccc(C(F)(F)F)cc2c1=O]

The title compound was synthesized from 3-(2-ethylsulfanyl-4-methyl-benzyl)-6-trifluoromethyl-1H-quinazoline-2,4-dione (Compound a38) under the same conditions as for Compound 11.

LCMS: m/z 427 [M+H]+
HPLC retention time: 0.85 min (analysis condition D)

Example 113

Compound a39

1-(Methanesulfonyl)-1H-pyrrole-2-carbonitrile

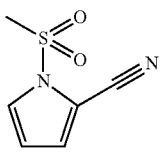

Methanesulfonyl chloride (0.68 ml, 8.70 mmol) was added to a mixed solution of 1H-pyrrole-2-carbonitrile (157 mg, 1.71 mmol) and TEA (2.14 ml, 15.4 mmol) in THF (2 ml) and DCM (2 ml), and this was stirred for three hours. A saturated aqueous sodium chloride solution was added to the reaction mixture, and extraction was performed with DCM. The organic layer was then dried over anhydrous sodium sulfate. The drying agent was removed by filtration, and the residue obtained by concentration under reduced pressure was purified by silica gel column chromatography (ethyl acetate/hexane) to give the title compound (245 mg, 84%) as a colorless oily substance.

LCMS: m/z 171 [M+H]+
HPLC retention time: 0.54 min (analysis condition D)

Example 114

Compound a40

((1-(Methanesulfonyl)-1H-pyrrol-2-yl)methyl)carbamic acid tert-butyl ester

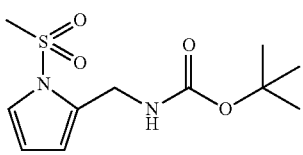 [SMILES: CC(C)(C)OC(=O)NCc1cccn1S(C)(=O)=O]

Sodium borohydride (308 mg, 8.1 mmol) was added in five portions at five-minute intervals to a solution of 1-(methylsulfonyl)-1H-pyrrole-2-carbonitrile (Compound a39, 173 mg, 1.02 mmol), Boc₂O (0.467 ml, 2.03 mmol) and nickel(II) chloride hexahydrate (60.4 mg, 0.25 mmol) in MeOH under cooling at 0° C., and the mixture was stirred at 0° C. for one hour. A saturated aqueous sodium bicarbonate solution was added to the reaction mixture, and extraction was performed with ethyl acetate. The organic layer was washed with brine and then dried over anhydrous sodium sulfate. The drying agent was removed by filtration, and the residue obtained by concentration under reduced pressure was purified by silica gel column chromatography (ethyl acetate/hexane) to give the title compound (168 mg, 60%) as a colorless solid.

LCMS: m/z 219 [M-(2-methylpropene)+H]+
HPLC retention time: 0.72 min (analysis condition D)

Example 115

Compound a41

C-(1-Methanesulfonyl-1H-pyrrol-2-yl)-methylamine hydrochloride

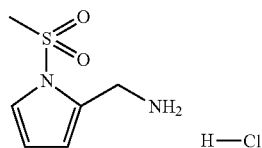

A 4 N solution of hydrochloric acid in ethyl acetate (3 ml) was added to (1-methanesulfonyl-1H-pyrrol-2-ylmethyl)-carbamic acid tert-butyl ester (Compound a40, 168 mg, 0.61 mmol), and the mixture was stirred at room temperature for 30 minutes. The reaction mixture was concentrated under reduced pressure to give a crude product of the title compound as a brown solid.

Example 116

Compound a42

2-Amino-N-(1-methanesulfonyl-1H-pyrrol-2-ylmethyl)-5-trifluoromethyl-benzamide

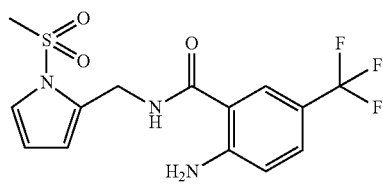 [SMILES: CS(=O)(=O)n1cccc1CNC(=O)c1cc(C(F)(F)F)ccc1N]

The title compound was synthesized from 2-amino-5-trifluoromethyl-benzoic acid using C-(1-methanesulfonyl-1H-pyrrol-2-yl)-methylamine hydrochloride (Compound a41) in place of 5-chloro-2-ethanesulfonyl-benzylamine hydrochloride (Compound 3) under the same conditions as for Compound 26.

Example 117

Compound A-29

3-(1-Methanesulfonyl-1H-pyrrol-2-ylmethyl)-6-trifluoromethyl-1H-quinazoline-2,4-dione

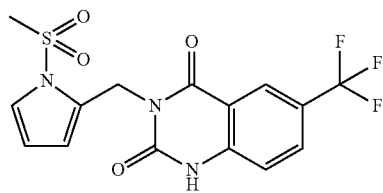 [SMILES: CS(=O)(=O)n1cccc1Cn1c(=O)[nH]c2ccc(C(F)(F)F)cc2c1=O]

The title compound was synthesized from 2-amino-N-(1-methanesulfonyl-1H-pyrrol-2-ylmethyl)-5-trifluoromethyl-benzamide (Compound a42) under the same conditions as for Compound A-4.

LCMS: m/z 388 [M+H]$^+$

HPLC retention time: 0.77 min (analysis condition D)

Example 118

Compound a43

1-Ethanesulfonyl-1H-pyrrole-2-carbonitrile

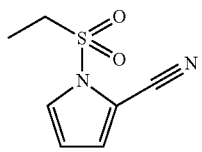

The title compound was synthesized from 1H-pyrrole-2-carbonitrile under the same conditions as for Compound a39. However, the reaction was performed using ethanesulfonyl chloride in place of methanesulfonyl chloride and using only THF as a solvent.

Example 119

Compound a44

(1-Ethanesulfonyl-1H-pyrrol-2-ylmethyl)-carbamic acid tert-butyl ester

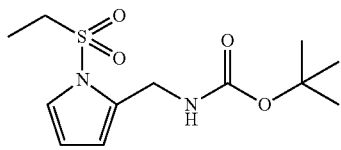 [SMILES: CCS(=O)(=O)n1cccc1CNC(=O)OC(C)(C)C]

The title compound was synthesized from 1-ethanesulfonyl-1H-pyrrole-2-carbonitrile (Compound 43) under the same conditions as for Compound a40.

Example 120

Compound a45

C-(1-Ethanesulfonyl-1H-pyrrol-2-yl)-methylamine hydrochloride

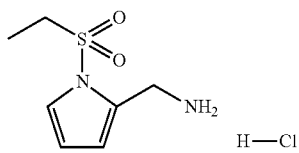

The title compound was synthesized from (1-ethanesulfonyl-1H-pyrrol-2-ylmethyl)-carbamic acid tert-butyl ester (Compound a44) under the same conditions as for Compound a41.

Example 121

Compound a46

2-Amino-N-(1-ethanesulfonyl-1H-pyrrol-2-ylmethyl)-5-trifluoromethyl-benzamide

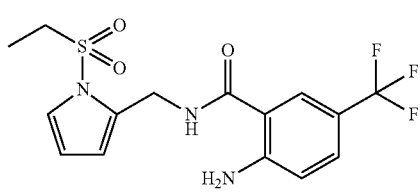 [SMILES: CCS(=O)(=O)n1cccc1CNC(=O)c1cc(C(F)(F)F)ccc1N]

The title compound was synthesized from 2-amino-5-trifluoromethyl-benzoic acid using C-(1-ethanesulfonyl-1H-pyrrol-2-yl)-methylamine hydrochloride (a45) in place of 5-chloro-2-ethanesulfonyl-benzylamine hydrochloride (Compound 3) under the same conditions as for Compound 26.

Example 122

Compound A-30

3-(1-Ethanesulfonyl-1H-pyrrol-2-ylmethyl)-6-trifluoromethyl-1H-quinazoline-2,4-dione

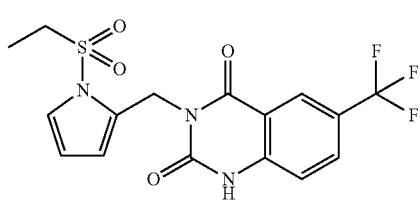 [SMILES: CCS(=O)(=O)n1cccc1Cn1c(=O)[nH]c2ccc(C(F)(F)F)cc2c1=O]

The title compound was synthesized from 2-amino-N-(1-ethanesulfonyl-1H-pyrrol-2-ylmethyl)-5-trifluoromethyl-benzamide (Compound a46) under the same conditions as for Compound A-4.

LCMS: m/z 402 [M+H]$^+$

HPLC retention time: 0.80 min (analysis condition D)

Example 123

Compound b1

4-(5-Amino-4-ethoxycarbonyl-2-trifluoromethyl-benzyl)-piperazine-1-carboxylic acid tert-butyl ester

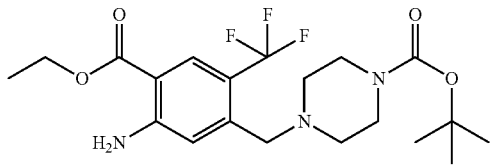 [SMILES: CCOC(=O)c1cc(C(F)(F)F)c(CN2CCN(C(=O)OC(C)(C)C)CC2)cc1N]

A mixture of 2-amino-4-chloro-5-trifluoromethyl-benzoic acid ethyl ester (Compound 20, 1.07 g, 4.0 mmol), potassium (4-tert-butoxycarbonylpiperazin-1-yl)methyltrifluoroborate (1.71 g, 5.6 mmol), palladium acetate (44.9 mg, 0.2 mmol), X-Phos (191 mg, 0.4 mmol), and cesium carbonate (3.91 g, 12 mmol) in THF (40 mL) and water (20 mL) was stirred at 90° C. for three hours. The reaction solution was extracted with ethyl acetate, and the extract was dried over anhydrous sodium sulfate. The drying agent was removed by filtration, and the residue obtained by concentration under reduced pressure was purified by silica gel column chromatography (ethyl acetate/hexane) to give the title compound (1.49 g, 86%) as a pale yellow solid.

LCMS: m/z 432 [M+H]$^+$

HPLC retention time: 0.75 min (analysis condition D)

Example 124

Compound b2

4-(5-Amino-4-carboxy-2-trifluoromethyl-benzyl)-piperazine-1-carboxylic acid tert-butyl ester

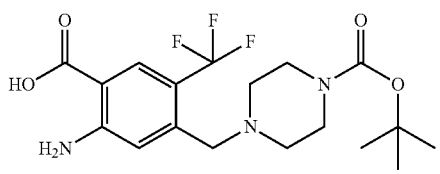 [SMILES: CC(C)(C)OC(=O)N1CCN(Cc2cc(N)c(C(=O)O)cc2C(F)(F)F)CC1]

The title compound was synthesized from 4-(5-amino-4-ethoxycarbonyl-2-trifluoromethyl-benzyl)-piperazine-1-carboxylic acid tert-butyl ester (Compound b1) under the same conditions as for Compound 25.

Example 125

Compound b3

4-[5-Amino-4-(5-chloro-2-ethanesulfonyl-benzylcarbamoyl)-2-trifluoromethyl-benzyl]-piperazine-1-carboxylic acid tert-butyl ester

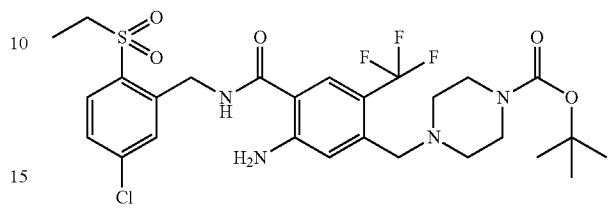

The title compound was synthesized from 4-(5-amino-4-carboxy-2-trifluoromethyl-benzyl)-piperazine-1-carboxylic acid tert-butyl ester (Compound b2) under the same conditions as for Compound 26. However, the reaction was performed without using HOBT and DIPEA.

Example 126

Compound b4

4-[3-(5-Chloro-2-ethanesulfonyl-benzyl)-2,4-dioxo-6-trifluoromethyl-1,2,3,4-tetrahydro-quinazolin-7-ylmethyl]-piperazine-1-carboxylic acid tert-butyl ester

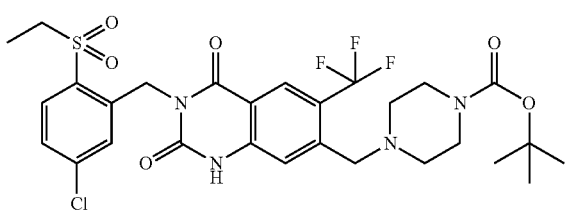 [SMILES: CCS(=O)(=O)c1ccc(Cl)cc1Cn1c(=O)[nH]c2cc(CN3CCN(C(=O)OC(C)(C)C)CC3)c(C(F)(F)F)cc2c1=O]

The title compound was synthesized from 4-[5-amino-4-(5-chloro-2-ethanesulfonyl-benzylcarbamoyl)-2-trifluoromethyl-benzyl]-piperazine-1-carboxylic acid tert-butyl ester (Compound b3) under the same conditions as for Compound 37.

Example 127

Compound B-1

3-(5-Chloro-2-ethanesulfonyl-benzyl)-7-piperazin-1-ylmethyl-6-trifluoromethyl-1H-quinazoline-2,4-dione

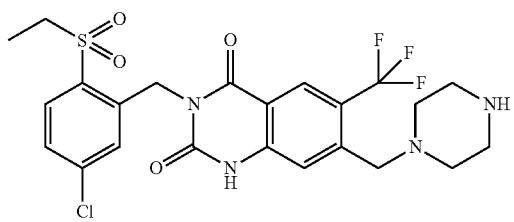 [SMILES: CCS(=O)(=O)c1ccc(Cl)cc1Cn1c(=O)[nH]c2cc(CN3CCNCC3)c(C(F)(F)F)cc2c1=O]

TFA (0.5 ml) was added to 4-[3-(5-chloro-2-ethanesulfonyl-benzyl)-2,4-dioxo-6-trifluoromethyl-1,2,3,4-tetrahydroquinazolin-7-ylmethyl]-piperazine-1-carboxylic acid tert-butyl ester (Compound b4, 41.0 mg, 0.064 mmol) in dichloromethane (1 ml) in an ice bath, and the mixture was warmed to room temperature and then stirred for one hour. This was concentrated under reduced pressure and then dissolved in dichloromethane. This was washed with a saturated aqueous sodium bicarbonate solution and brine, and dried over anhydrous sodium sulfate. The drying agent was removed by filtration, and the residue obtained by concentration under reduced pressure was purified by amino silica gel column chromatography (methanol/dichloromethane) to give the title compound (32.0 mg, 92%) as a colorless amorphous.

LCMS: m/z 545 [M+H]$^+$

HPLC retention time: 0.56 min (analysis condition D)

Example 128

Compound B-2

3-(5-Chloro-2-ethanesulfonyl-benzyl)-7-(4-methyl-piperazin-1-ylmethyl)-6-trifluoromethyl-1H-quinazoline-2,4-dione

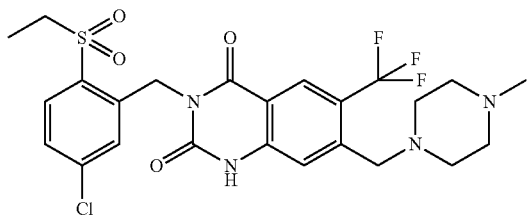 [SMILES: CCS(=O)(=O)c1ccc(Cl)cc1Cn1c(=O)[nH]c2cc(CN3CCN(C)CC3)c(C(F)(F)F)cc2c1=O]

Paraformaldehyde (10.1 mg, 0.32 mmol) and sodium triacetoxyborohydride (51.8 mg, 0.24 mmol) were added to a solution of 3-(5-chloro-2-ethanesulfonyl-benzyl)-7-piperazin-1-ylmethyl-6-trifluoromethyl-1H-quinazoline-2,4-dione (Compound B-1, 43.1 mg, 0.079 mmol) in THF (3 ml), and the mixture was stirred at 50° C. for 3.5 hours. Paraformaldehyde (5.05 mg, 0.16 mmol) and sodium triacetoxyborohydride (25.9 mg, 0.12 mmol) were added thereto, and the mixture was stirred at 50° C. for further one hour. A saturated aqueous sodium bicarbonate solution was added to the reaction mixture, and extraction was performed with ethyl acetate. The organic layer was then washed with brine and dried over anhydrous sodium sulfate. The drying agent was removed by filtration, and the residue obtained by concentration under reduced pressure was purified by amino silica gel column chromatography (methanol/dichloromethane) to give the title compound (26.6 mg, 60%) as a white amorphous.

LCMS: m/z 559 [M+H]$^+$

HPLC retention time: 0.57 min (analysis condition D)

Example 129

Compound B-3

3-(5-Chloro-2-ethanesulfonyl-benzyl)-7-(4-ethyl-piperazin-1-ylmethyl)-6-trifluoromethyl-1H-quinazoline-2,4-dione

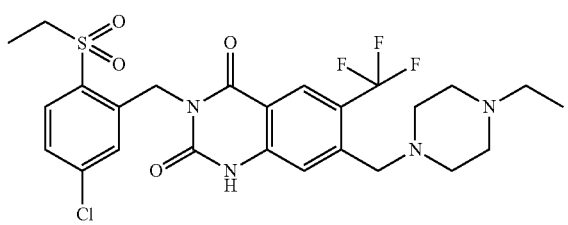 [SMILES: CCN1CCN(Cc2cc3[nH]c(=O)n(Cc4cc(Cl)ccc4S(=O)(=O)CC)c(=O)c3cc2C(F)(F)F)CC1]

Ethyl iodide (10.6 μl, 0.13 mmol) was added to a solution of 3-(5-chloro-2-ethanesulfonyl-benzyl)-7-piperazin-1-ylmethyl-6-trifluoromethyl-1H-quinazoline-2,4-dione (Compound B-1, 60.3 mg, 0.11 mmol) and potassium carbonate (45.9 mg, 0.33 mmol) in DMF (0.603 ml), and the mixture was stirred at room temperature for one hour. Ethyl acetate was added to the reaction mixture, and the organic layer was then washed with water and brine, respectively, and dried over anhydrous sodium sulfate. The drying agent was removed by filtration, and the residue obtained by concentration under reduced pressure was purified by silica gel column chromatography (methanol/dichloromethane) to give the title compound (37.4 mg, 59%) as a colorless solid.

LCMS: m/z 573 [M+H]$^+$

HPLC retention time: 0.57 min (analysis condition D)

Example 130

Compound B-4

3-(5-Chloro-2-ethanesulfonyl-benzyl)-7-(4-isopropyl-piperazin-1-ylmethyl)-6-trifluoromethyl-1H-quinazoline-2,4-dione

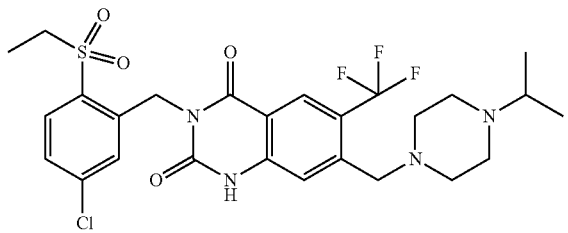 [SMILES: CCS(=O)(=O)c1ccc(Cl)cc1Cn1c(=O)[nH]c2cc(CN3CCN(C(C)C)CC3)c(C(F)(F)F)cc2c1=O]

Sodium triacetoxyborohydride (60.1 mg, 0.28 mmol) was added to a solution of 3-(5-chloro-2-ethanesulfonyl-benzyl)-7-piperazin-1-ylmethyl-6-trifluoromethyl-1H-quinazoline-2,4-dione (Compound B-1, 50.0 mg, 0.092 mmol) and acetone (0.250 ml, 3.4 mmol) in THF (2.5 ml), and the mixture was stirred at 50° C. for one hour. A saturated aqueous sodium bicarbonate solution was added to the reaction mixture, and extraction was performed with ethyl acetate. The organic layer was washed with brine and then dried over anhydrous sodium sulfate. The drying agent was removed by filtration, and the residue obtained by concen-

Example 131

Compound B-5

3-(5-Chloro-2-ethanesulfonyl-benzyl)-7-[4-(tetrahydro-pyran-4-yl)-piperazin-1-ylmethyl]-6-trifluoromethyl-1H-quinazoline-2,4-dione

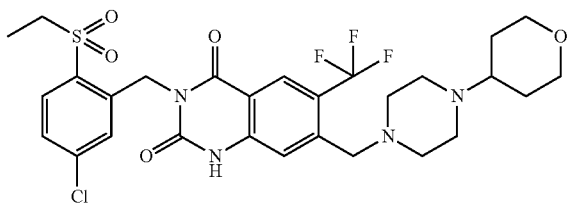 [SMILES: CCS(=O)(=O)c1ccc(Cl)cc1Cn1c(=O)[nH]c2cc(CN3CCN(C4CCOCC4)CC3)c(C(F)(F)F)cc2c1=O]

Sodium triacetoxyborohydride (45.7 mg, 0.22 mmol) was added to a solution of 3-(5-chloro-2-ethanesulfonyl-benzyl)-7-piperazin-1-ylmethyl-6-trifluoromethyl-1H-quinazoline-2,4-dione (Compound B-1, 38.0 mg, 0.072 mmol) and tetrahydro-4H-pyran-4-one (0.0260 ml, 0.28 mmol) in THF (1.0 ml), and the mixture was stirred at 50° C. for 1.5 hours. A saturated aqueous sodium bicarbonate solution was added to the reaction mixture, and extraction was performed with ethyl acetate. The organic layer was washed with brine and then dried over anhydrous sodium sulfate. The drying agent was removed by filtration, and the residue obtained by concentration under reduced pressure was purified by preparative HPLC (water/acetonitrile, 0.05% TFA) to give the title compound (6.0 mg, yield: 13%) as a colorless solid.

LCMS: m/z 629 [M+H]$^+$
HPLC retention time: 2.08 min (analysis condition I)

Example 132

Compound B-6

7-(4-Acetyl-piperazin-1-ylmethyl)-3-(5-chloro-2-ethanesulfonyl-benzyl)-6-trifluoromethyl-1H-quinazoline-2,4-dione

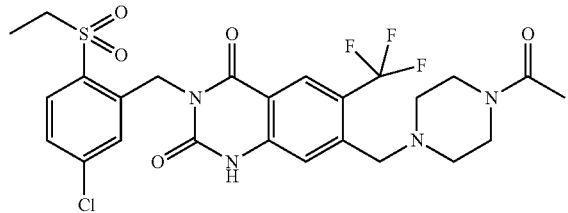 [SMILES: CCS(=O)(=O)c1ccc(Cl)cc1Cn1c(=O)[nH]c2cc(CN3CCN(C(C)=O)CC3)c(C(F)(F)F)cc2c1=O]

7.1 μl of acetyl chloride (0.10 mmol) was added to a mixed solution of 3-(5-chloro-2-ethanesulfonyl-benzyl)-7-piperazin-1-ylmethyl-6-trifluoromethyl-1H-quinazoline-2,4-dione (Compound B-1, 27.3 mg, 0.050 mmol) in DCM (1.5 ml) and pyridine (1.5 ml), and this was stirred for three hours. The reaction mixture was concentrated under reduced pressure, and the resulting residue was purified by silica gel column chromatography (methanol/ethyl acetate) to give the title compound (23.4 mg, 80%) as a colorless solid.

LCMS: m/z 587 [M+H]$^+$
HPLC retention time: 0.69 min (analysis condition D)

Example 133

Compound B-7

3-(5-Chloro-2-ethanesulfonyl-benzyl)-7-(4-methanesulfonyl-piperazin-1-ylmethyl)-6-trifluoromethyl-1H-quinazoline-2,4-dione

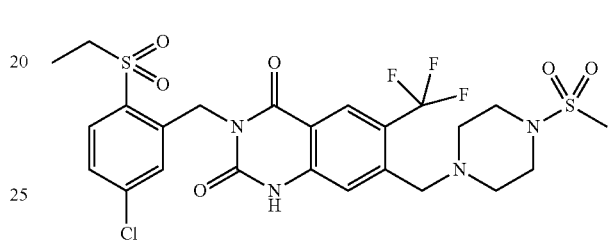

3.1 μl of methanesulfonyl chloride (0.039 mmol) was added to a mixed solution of 3-(5-chloro-2-ethanesulfonyl-benzyl)-7-piperazin-1-ylmethyl-6-trifluoromethyl-1H-quinazoline-2,4-dione (Compound B-1, 21.4 mg, 0.039 mmol) in DCM (2 ml) and pyridine (2 ml), and this was stirred for three hours. The reaction mixture was concentrated under reduced pressure, and the resulting residue was purified by preparative amino silica gel TLC (methanol/ethyl acetate) to give the title compound (15.7 mg, 64%) as a colorless solid.

LCMS: m/z 623 [M+H]$^+$
HPLC retention time: 0.82 min (analysis condition D)

Example 134

Compound b5

1,5-Dichloro-2-ethanesulfonyl-3-methylbenzene

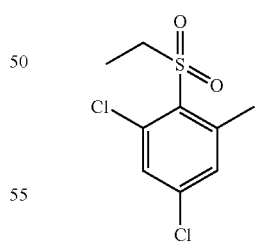

2,4-Dichloro-6-methyl-benzenesulfonyl chloride (1.00 g, 3.9 mmol) was added to a solution of sodium sulfite (534 mg, 4.24 mmol) and sodium bicarbonate (712 mg, 8.48 mmol) in water (5 ml), and the mixture was stirred at 75° C. for one hour. Iodoethane (1.98 ml, 19 mmol) was added thereto, and the mixture was stirred at 100° C. for 11 hours. Iodoethane (0.988 ml, 9.6 mmol) was added thereto, and the mixture was stirred at 100° C. for further three hours. The reaction mixture was extracted with DCM, and the organic layer was washed with a saturated aqueous sodium thiosulfate solution and dried over anhydrous sodium sulfate. The drying agent was removed by filtration, and the residue obtained by concentration under reduced pressure was purified by silica gel column chromatography (ethyl acetate/hexane) to give the title compound (664 mg, 68%) as a colorless oily substance.

LCMS: m/z 253 [M+H]$^+$

HPLC retention time: 0.79 min (analysis condition D)

Example 135

Compound b6

1-Bromomethyl-3,5-dichloro-2-ethanesulfonyl-benzene

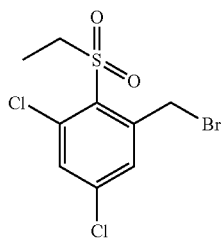

The title compound was synthesized from 1,5-dichloro-2-ethanesulfonyl-3-methylbenzene (Compound b5) under the same conditions as for Compound 12. However, the reaction was performed using acetonitrile in place of methane tetrachloride as a solvent.

Example 136

Compound b7

3,5-Dichloro-2-ethanesulfonyl-benzylamine

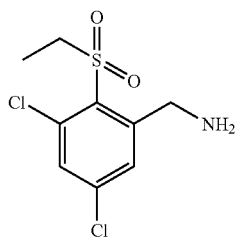

The title compound was synthesized from 1-bromomethyl-3,5-dichloro-2-ethanesulfonyl-benzene (Compound b6) under the same conditions as for Compound 13.

Example 137

Compound b8

4-[5-Amino-4-(3, 5-dichloro-2-ethanesulfonyl-benzylcarbamoyl)-2-trifluoromethyl-benzyl]-piperazine-1-carboxylic acid tert-butyl ester

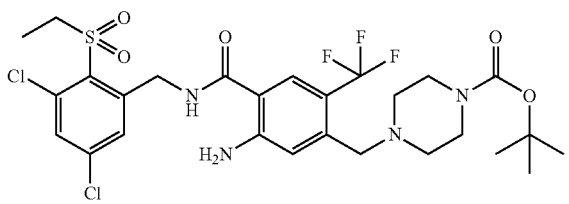 [SMILES: CCS(=O)(=O)c1c(Cl)cc(Cl)cc1CNC(=O)c1cc(C(F)(F)F)c(CN2CCN(C(=O)OC(C)(C)C)CC2)cc1N]

The title compound was synthesized from 4-(5-amino-4-carboxy-2-trifluoromethyl-benzyl)-piperazine-1-carboxylic acid tert-butyl ester (Compound b2) using 3,5-dichloro-2-ethanesulfonyl-benzylamine (Compound b7) in place of 5-chloro-2-ethanesulfonyl-benzylamine hydrochloride (Compound 3) under the same conditions as for Compound 26. However, the reaction was performed without using HOBT.

Example 138

Compound b9

4-[3-(3,5-Dichloro-2-ethanesulfonyl-benzyl)-2,4-dioxo-6-trifluoromethyl-1,2,3,4-tetrahydro-quinazolin-7-ylmethyl]-piperazine-1-carboxylic acid tert-butyl ester

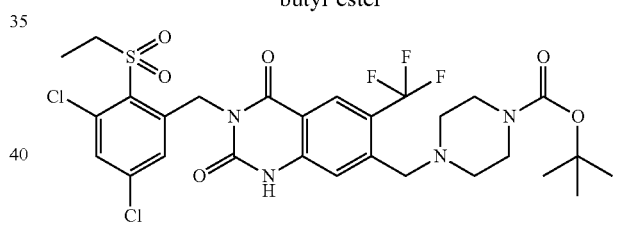

The title compound was synthesized from 4-[5-amino-4-(3,5-dichloro-2-ethanesulfonyl-benzylcarbamoyl)-2-trifluoromethyl-benzyl]-piperazine-1-carboxylic acid tert-butyl ester (Compound b8) under the same conditions as for Compound A-6.

Example 139

Compound B-8

3-(3,5-Dichloro-2-ethanesulfonyl-benzyl)-7-piperazin-1-ylmethyl-6-trifluoromethyl-1H-quinazoline-2,4-dione

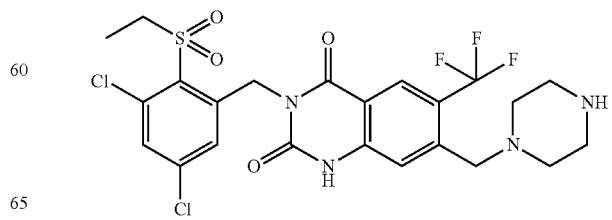

The title compound was synthesized from 4-[3-(3,5-dichloro-2-ethanesulfonyl-benzyl)-2,4-dioxo-6-trifluoromethyl-1,2,3,4-tetrahydro-quinazolin-7-ylmethyl]-piperazine-1-carboxylic acid tert-butyl ester (Compound b9) under the same conditions as for Compound a41.
LCMS: m/z 579 [M+H]$^+$
HPLC retention time: 0.57 min (analysis condition D)

Example 140

Compound B-9

3-(3,5-Dichloro-2-ethanesulfonyl-benzyl)-7-(4-methyl-piperazin-1-ylmethyl)-6-trifluoromethyl-1H-quinazoline-2,4-dione

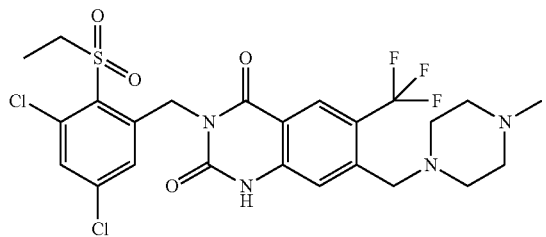 [SMILES: CCS(=O)(=O)c1c(Cl)cc(Cl)cc1Cn1c(=O)[nH]c2cc(CN3CCN(C)CC3)c(C(F)(F)F)cc2c1=O]

A solution of 3-(3,5-dichloro-2-ethanesulfonyl-benzyl)-7-piperazin-1-ylmethyl-6-trifluoromethyl-1H-quinazoline-2,4-dione (Compound B-8, 43.5 mg, 0.075 mmol) and paraformaldehyde (7.2 mg, 0.22 mmol) in formic acid (1.0 ml) was stirred at 60° C. for two hours. Paraformaldehyde (2.4 mg, 0.075 mmol) was added thereto, and the mixture was stirred at 60° C. for further one hour. A saturated aqueous sodium bicarbonate solution was added to the reaction mixture, and extraction was performed with dichloromethane. The organic layer was then washed with brine and dried over anhydrous sodium sulfate. The drying agent was removed by filtration, and the residue obtained by concentration under reduced pressure was purified by amino silica gel column chromatography (methanol/dichloromethane) to give the title compound (28.9 mg, 65%) as a colorless amorphous.
LCMS: m/z 593 [M+H]$^+$
HPLC retention time: 0.58 min (analysis condition D)

Example 141

Compound b10

4-[5-Amino-4-(5-cyano-2-ethanesulfonyl-benzylcarbamoyl)-2-trifluoromethyl-benzyl]-piperazine-1-carboxylic acid tert-butyl ester

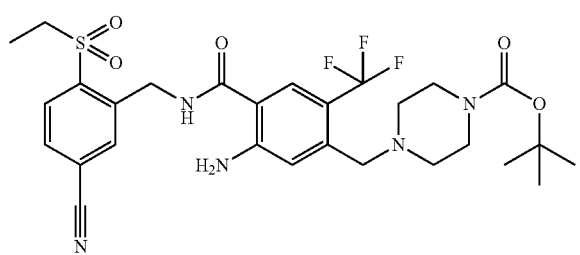 [SMILES: CCS(=O)(=O)c1ccc(C#N)cc1CNC(=O)c1cc(C(F)(F)F)c(CN2CCN(C(=O)OC(C)(C)C)CC2)cc1N]

The title compound was synthesized from 4-(5-amino-4-carboxy-2-trifluoromethyl-benzyl)-piperazine-1-carboxylic acid tert-butyl ester (Compound b2) using 3-aminomethyl-4-ethanesulfonyl-benzonitrile (Compound 13) in place of 5-chloro-2-ethanesulfonyl-benzylamine hydrochloride (Compound 3) under the same conditions as for Compound 26. However, the reaction was performed without using HOBT.

Example 142

Compound b11

4-[3-(5-Cyano-2-ethanesulfonyl-benzyl)-2,4-dioxo-6-trifluoromethyl-1,2,3,4-tetrahydro-quinazolin-7-ylmethyl]-piperazine-1-carboxylic acid tert-butyl ester

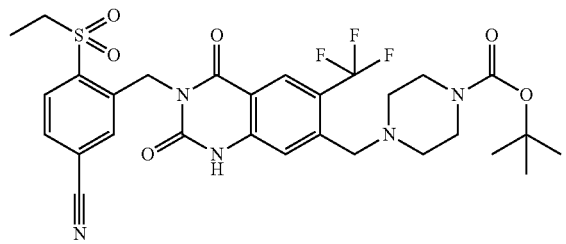 [SMILES: CCS(=O)(=O)c1ccc(C#N)cc1Cn1c(=O)[nH]c2cc(CN3CCN(C(=O)OC(C)(C)C)CC3)c(C(F)(F)F)cc2c1=O]

The title compound was synthesized from 4-[5-amino-4-(5-cyano-2-ethanesulfonyl-benzylcarbamoyl)-2-trifluoromethyl-benzyl]-piperazine-1-carboxylic acid tert-butyl ester (Compound b10) under the same conditions as for Compound A-6.

Example 143

Compound B-10

3-(2,4-Dioxo-7-piperazin-1-ylmethyl-6-trifluoromethyl-1,4-dihydro-2H-quinazolin-3-ylmethyl)-4-ethanesulfonyl-benzonitrile

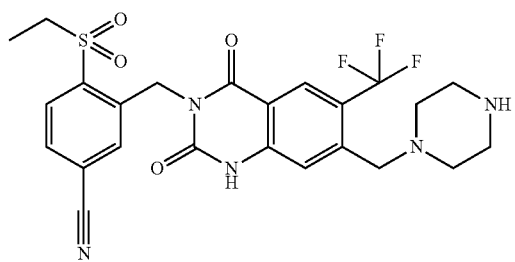 [SMILES: CCS(=O)(=O)c1ccc(C#N)cc1Cn1c(=O)[nH]c2cc(CN3CCNCC3)c(C(F)(F)F)cc2c1=O]

The title compound was synthesized from 4-[3-(5-cyano-2-ethanesulfonyl-benzyl)-2,4-dioxo-6-trifluoromethyl-1,2,3,4-tetrahydro-quinazolin-7-ylmethyl]-piperazine-1-carboxylic acid tert-butyl ester (Compound b11) under the same conditions as for Compound B-1.
LCMS: m/z 536 [M+H]$^+$
HPLC retention time: 0.53 min (analysis condition D)

Example 144

Compound b12

2-Amino-4-((S)-3-tert-butoxycarbonylamino-pyrrolidin-1-ylmethyl)-5-trifluoromethyl-benzoic acid ethyl ester

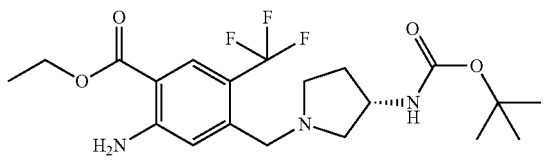 [SMILES: CCOC(=O)c1cc(C(F)(F)F)c(CN2CC[C@H](NC(=O)OC(C)(C)C)C2)cc1N]

Sodium triacetoxyborohydride (487 mg, 2.3 mmol) was added to a solution of 2-amino-4-formyl-5-trifluoromethyl-benzoic acid ethyl ester (Compound 23, 200 mg, 0.77 mmol) and (S)-pyrrolidin-3-yl-carbamic acid tert-butyl ester (428 mg, 2.3 mmol) in THF (3.6 ml), and the mixture was stirred at room temperature for 0.5 hour. A saturated aqueous sodium bicarbonate solution was added to the reaction solution, and extraction was performed with ethyl acetate. The extract was then dried over anhydrous sodium sulfate. The drying agent was removed by filtration, and the residue obtained by concentration under reduced pressure was purified by silica gel column chromatography (ethyl acetate/hexane) to give the title compound (328 mg, 99%) as a colorless foamy substance.

LCMS: m/z 432 [M+H]$^+$

HPLC retention time: 0.59 min (analysis condition D)

Example 145

Compound b13

2-Amino-4-((S)-3-tert-butoxycarbonylamino-pyrrolidin-1-ylmethyl)-5-trifluoromethyl-benzoic acid

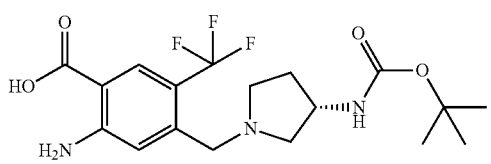 [SMILES: CC(C)(C)OC(=O)N[C@H]1CCN(Cc2cc(N)c(C(=O)O)cc2C(F)(F)F)C1]

The title compound was synthesized from 2-amino-4-((S)-3-tert-butoxycarbonylamino-pyrrolidin-1-ylmethyl)-5-trifluoromethyl-benzoic acid ethyl ester (Compound b12) under the same conditions as for Compound 25.

Example 146

Compound b14

{(S)-1-[5-Amino-4-(5-chloro-2-ethanesulfonyl-benzylcarbamoyl)-2-trifluoromethyl-benzyl]-pyrrolidin-3-yl}-carbamic acid tert-butyl ester

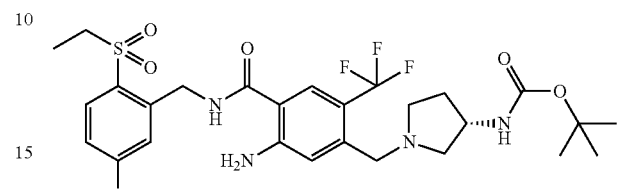

The title compound was synthesized from 2-amino-4-((S)-3-tert-butoxycarbonylamino-pyrrolidin-1-ylmethyl)-5-trifluoromethyl-benzoic acid (Compound b13) under the same conditions as for Compound 26. However, the reaction was performed without using HOBT.

Example 147

Compound b15

{(S)-1-[3-(5-Chloro-2-ethanesulfonyl-benzyl)-2,4-dioxo-6-trifluoromethyl-1,2,3,4-tetrahydro-quinazolin-7-ylmethyl]-pyrrolidin-3-yl}-carbamic acid tert-butyl ester

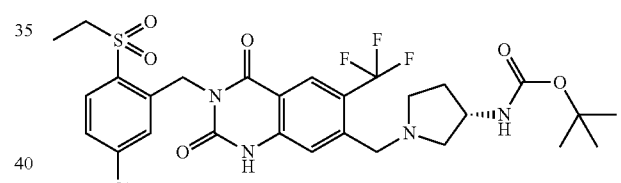

The title compound was synthesized from {(S)-1-[5-amino-4-(5-chloro-2-ethanesulfonyl-benzylcarbamoyl)-2-trifluoromethyl-benzyl]-pyrrolidin-3-yl}-carbamic acid tert-butyl ester (Compound b14) under the same conditions as for Compound A-6.

Example 148

Compound B-11

7-((S)-3-Amino-pyrrolidin-1-ylmethyl)-3-(5-chloro-2-ethanesulfonyl-benzyl)-6-trifluoromethyl-1H-quinazoline-2,4-dione

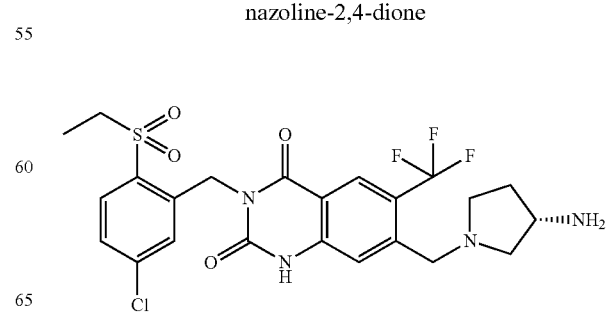

The title compound was synthesized from {(S)-1-[3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-carbamic acid tert-butyl ester (Compound b15) under the same conditions as for Compound a41.

LCMS: m/z 545 [M+H]$^+$

HPLC retention time: 0.53 min (analysis condition D)

Example 149

Compound B-12

3-(5-Chloro-2-ethanesulfonyl-benzyl)-7-((S)-3-dimethylamino-pyrrolidin-1-ylmethyl)-6-trifluoromethyl-1H-quinazoline-2,4-dione

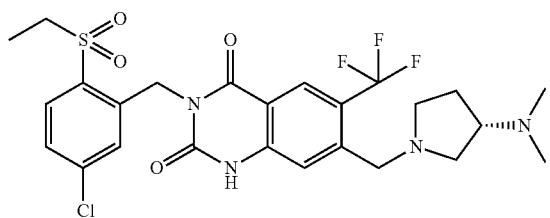 [SMILES: CCS(=O)(=O)c1ccc(Cl)cc1Cn1c(=O)[nH]c2cc(CN3CC[C@H](N(C)C)C3)c(C(F)(F)F)cc2c1=O]

The title compound was synthesized from 7-((S)-3-amino-pyrrolidin-1-ylmethyl)-3-(5-chloro-2-ethanesulfonyl-benzyl)-6-trifluoromethyl-1H-quinazoline-2,4-dione (Compound B-11) under the same conditions as for Compound B-9.

LCMS: m/z 573 [M+H]$^+$

HPLC retention time: 0.57 min (analysis condition D)

Example 150

Compound b16

4-((S)-3-Acetylamino-pyrrolidin-1-ylmethyl)-2-amino-N-(5-chloro-2-ethanesulfonyl-benzyl)-5-trifluoromethyl-benzamide

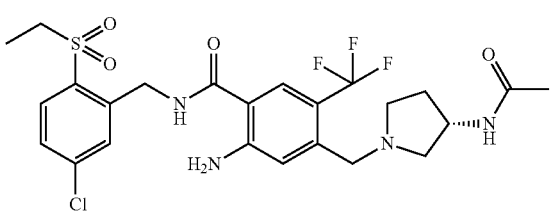 [SMILES: CCS(=O)(=O)c1ccc(Cl)cc1CNC(=O)c1cc(C(F)(F)F)c(CN2CC[C@H](NC(C)=O)C2)cc1N]

The title compound was synthesized from 2-amino-4-formyl-5-trifluoromethyl-benzoic acid ethyl ester (Compound 23) under the same conditions as for Compounds b12, b13, and b14. However, the reaction was performed using (S)-N-pyrrolidin-3-yl-acetamide in place of (S)-pyrrolidin-3-yl-carbamic acid tert-butyl ester under the conditions for Compound b12.

Example 151

Compound B-13

N-{(S)-1-[3-(5-Chloro-2-ethanesulfonyl-benzyl)-2,4-dioxo-6-trifluoromethyl-1,2,34-tetrahydro-quinazolin-7-ylmethyl]-pyrrolidin-3-yl}-acetamide

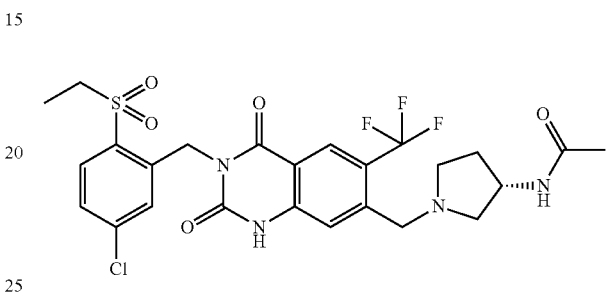

The title compound was synthesized from 4-((S)-3-acetylamino-pyrrolidin-1-ylmethyl)-2-amino-N-(5-chloro-2-ethanesulfonyl-benzyl)-5-trifluoromethyl-benzamide (Compound b16) under the same conditions as for Compound A-4.

LCMS: m/z 587 [M+H]$^+$

HPLC retention time: 0.52 min (analysis condition D)

Example 152

Compound B-14

7-((R)-3-Amino-pyrrolidin-1-ylmethyl)-3-(5-chloro-2-ethanesulfonyl-benzyl)-6-trifluoromethyl-1 H-quinazoline-2,4-dione

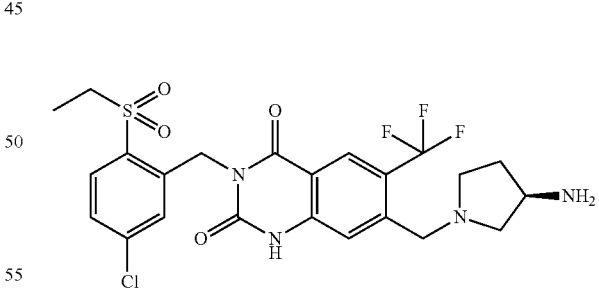

The title compound was synthesized from 2-amino-4-formyl-5-trifluoromethyl-benzoic acid ethyl ester (Compound 23) under the same conditions as for Compounds b12, b13, b14, b15, and B-11. However, the reaction was performed using (R)-pyrrolidin-3-yl-carbamic acid tert-butyl ester in place of (S)-pyrrolidin-3-yl-carbamic acid tert-butyl ester under the conditions for Compound b12.

LCMS: m/z 545 [M+H]$^+$

HPLC retention time: 0.53 min (analysis condition D)

Example 153

Compound B-15

3-(5-Chloro-2-ethanesulfonyl-benzyl)-7-((R)-3-dimethylamino-pyrrolidin-1-ylmethyl)-6-trifluoromethyl-1H-quinazoline-2,4-dione

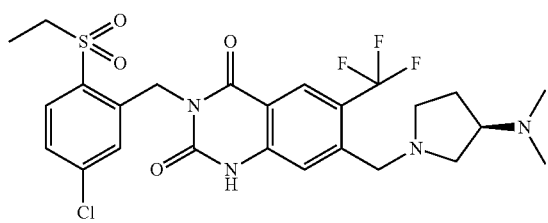 [SMILES: CCS(=O)(=O)c1ccc(Cl)cc1Cn1c(=O)[nH]c2cc(CN3CC[C@@H](N(C)C)C3)c(C(F)(F)F)cc2c1=O]

The title compound was synthesized from 7-((R)-3-amino-pyrrolidin-1-ylmethyl)-3-(5-chloro-2-ethanesulfonyl-benzyl)-6-trifluoromethyl-1H-quinazoline-2,4-dione (Compound B-14) under the same conditions as for Compound B-9.

LCMS: m/z 573 [M+H]$^+$

HPLC retention time: 0.57 min (analysis condition D)

Example 154

Compound B-16

N-{(R)-1-[3-(5-Chloro-2-ethanesulfonyl-benzyl)-2,4-dioxo-6-trifluoromethyl-1,2,3,4-tetrahydro-quinazolin-7-ylmethyl]-pyrrolidin-3-yl}-acetamide

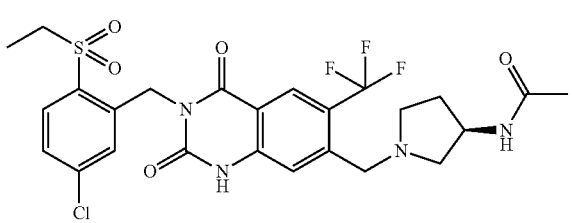 [SMILES: CCS(=O)(=O)c1ccc(Cl)cc1Cn1c(=O)[nH]c2cc(CN3CC[C@@H](NC(C)=O)C3)c(C(F)(F)F)cc2c1=O]

The title compound was synthesized from 2-amino-4-formyl-5-trifluoromethyl-benzoic acid ethyl ester (Compound 23) under the same conditions as for Compounds b12, b13, b14, and b15. However, the reaction was performed using (R)—N-pyrrolidin-3-yl-acetamide in place of (S)-pyrrolidin-3-yl-carbamic acid tert-butyl ester under the conditions for Compound b12.

LCMS: m/z 587 [M+H]$^+$

HPLC retention time: 0.52 min (analysis condition D)

Example 155

Compound b17

2-Amino-4-[(R)-3-(tert-butoxycarbonyl-methyl-amino)-pyrrolidin-1-ylmethyl]-5-trifluoromethyl-benzoic acid ethyl ester

The title compound was synthesized from 2-amino-4-formyl-5-trifluoromethyl-benzoic acid ethyl ester (Compound 23) under the same conditions as for Compound b12. However, the reaction was performed using methyl-(R)-pyrrolidin-3-yl-carbamic acid tert-butyl ester in place of (S)-pyrrolidin-3-yl-carbamic acid tert-butyl ester.

Example 156

Compound b18

2-Amino-4-[(R)-3-(tert-butoxycarbonyl-methyl-amino)-pyrrolidin-1-ylmethyl]-5-trifluoromethyl-benzoic acid

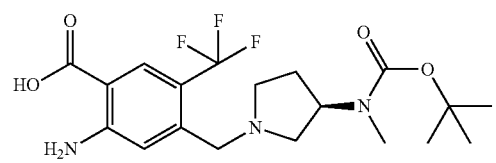 [SMILES: CN(C(=O)OC(C)(C)C)[C@@H]1CCN(Cc2cc(N)c(C(=O)O)cc2C(F)(F)F)C1]

The title compound was synthesized from 2-amino-4-[(R)-3-(tert-butoxycarbonyl-methyl-amino)-pyrrolidin-1-ylmethyl]-5-trifluoromethyl-benzoic acid ethyl ester (Compound b17) under the same conditions as for Compound 25.

Example 157

Compound b19

{(R)-1-[5-Amino-4-(5-chloro-2-ethanesulfonyl-benzylcarbamyl)-2-trifluoromethyl-benzyl]-pyrrolidin-3-yl}-methyl-carbamic acid tert-butyl ester

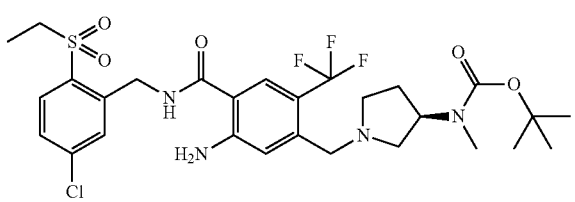 [SMILES: CCS(=O)(=O)c1ccc(Cl)cc1CNC(=O)c1cc(C(F)(F)F)c(CN2CC[C@@H](N(C)C(=O)OC(C)(C)C)C2)cc1N]

The title compound was synthesized from 2-amino-4-[(R)-3-(tert-butoxycarbonyl-methyl-amino)-pyrrolidin-1-ylmethyl]-5-trifluoromethyl-benzoic acid (Compound b18) under the same conditions as for Compound 26.

Example 158

Compound b20

{(R)-1-[3-(5-Chloro-2-ethanesulfonyl-benzyl)-2,4-dioxo-6-trifluoromethyl-1,2,3,4-tetrahydro-quinazolin-7-ylmethyl]-pyrrolidin-3-yl}-methyl-carbamic acid tert-butyl ester

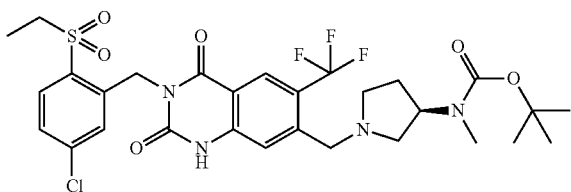 [SMILES: CCS(=O)(=O)c1ccc(Cl)cc1Cn1c(=O)[nH]c2cc(CN3CC[C@@H](N(C)C(=O)OC(C)(C)C)C3)c(C(F)(F)F)cc2c1=O]

The title compound was synthesized from {(R)-1-[5-amino-4-(5-chloro-2-ethanesulfonyl-benzylcarbamoyl)-2-trifluoromethyl-benzyl]-pyrrolidin-3-yl}-methyl-carbamic acid tert-butyl ester (Compound b19) under the same conditions as for Compound A-6.

Example 159

Compound B-17

3-(5-Chloro-2-ethanesulfonyl-benzyl)-7-((R)-3-methylamino-pyrrolidin-1-ylmethyl)-6-trifluoromethyl-1H-quinazoline-2,4-dione

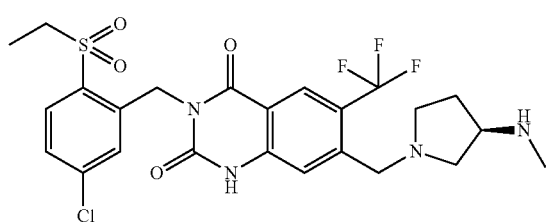 [SMILES: CCS(=O)(=O)c1ccc(Cl)cc1Cn1c(=O)[nH]c2cc(CN3CC[C@@H](NC)C3)c(C(F)(F)F)cc2c1=O]

The title compound was synthesized from {(R)-1-[3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-methyl-carbamic acid tert-butyl ester (Compound b20) under the same conditions as for Compound B-1.

LCMS: m/z 559 [M+H]$^+$

HPLC retention time: 0.55 min (analysis condition H)

Example 160

Compound B-18

N-{(R)-1-[3-(5-Chloro-2-ethanesulfonyl-benzyl)-2,4-dioxo-6-trifluoromethyl-1,2,3,4-tetrahydro-quinazolin-7-ylmethyl]-pyrrolidin-3-yl}-N-methyl-acetamide

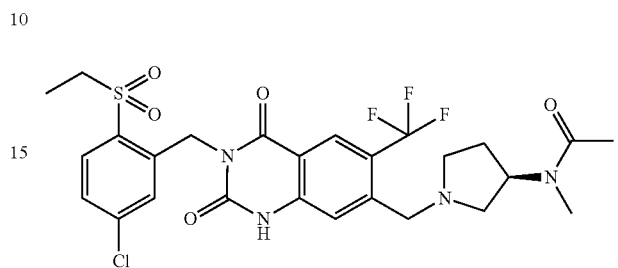

Acetic anhydride (9.89 μL, 0.11 mmol) was added to a solution of 3-(5-chloro-2-ethanesulfonyl-benzyl)-7-((R)-3-methylamino-pyrrolidin-1-ylmethyl)-6-trifluoromethyl-1H-quinazoline-2,4-dione (Compound B-17, 39.0 mg, 0.070 mmol) and triethylamine (0.0292 ml, 0.21 mmol) in DMF (1 ml), and the mixture was stirred at room temperature for six hours. Water was added to the reaction mixture, followed by extraction with ethyl acetate. The organic layer was washed with brine and then dried over anhydrous sodium sulfate. The drying agent was removed by filtration, and the residue obtained after concentration under reduced pressure was purified by preparative HPLC (water/acetonitrile, 0.05% TFA) to give the title compound (37.8 mg, yield: 90%) as a colorless solid.

LCMS: m/z 601 [M+H]$^+$

HPLC retention time: 0.54 min (analysis condition H)

Example 161

Compound b21

{(S)-1-[3-(5-Chloro-2-ethanesulfonyl-benzyl)-2,4-dioxo-6-trifluoromethyl-1,2,3,4-tetrahydro-quinazolin-7-ylmethyl]-pyrrolidin-3-ylmethyl}-carbamic acid tert-butyl ester

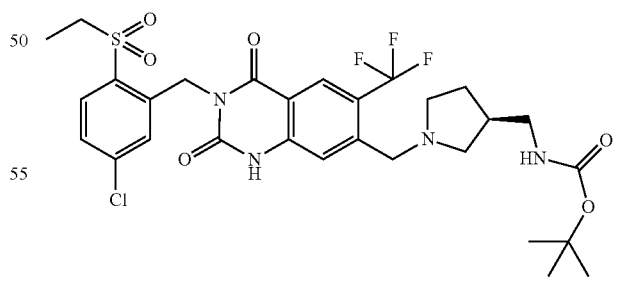

The title compound was synthesized from 2-amino-4-formyl-5-trifluoromethyl-benzoic acid ethyl ester (Compound 23) under the same conditions as for Compounds b12, b13, b14, and b15. However, the reaction was performed using (R)-1-pyrrolidin-3-ylmethyl-carbamic acid tert-butyl ester in place of (S)-1-pyrrolidin-3-yl-carbamic acid tert-butyl ester under the conditions for Compound b12.

Example 162

Compound B-19

7-((S)-3-Aminomethyl-pyrrolidin-1-ylmethyl)-3-(5-chloro-2-ethanesulfonyl-benzyl)-6-trifluoromethyl-1H-quinazoline-2,4-dione

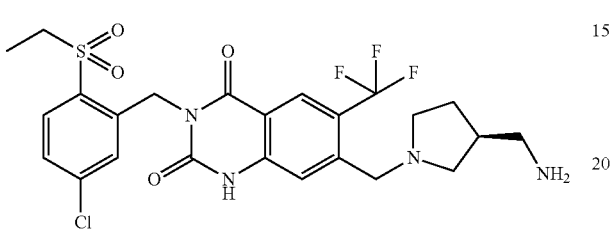

The title compound was synthesized from {(S)-1-[3-(5-chloro-2-ethanesulfonyl-benzyl)-2,4-dioxo-6-trifluoromethyl-1,2,3,4-tetrahydro-quinazolin-7-ylmethyl]-pyrrolidin-3-ylmethyl}-carbamic acid tert-butyl ester (Compound b21) under the same conditions as for Compound B-1.

LCMS: m/z 559 [M+H]$^+$

HPLC retention time: 0.43 min (analysis condition D)

Example 163

Compound B-20

3-(5-Chloro-2-ethanesulfonyl-benzyl)-7-((S)-3-dimethylaminomethyl-pyrrolidin-1-ylmethyl)-6-trifluoromethyl-1H-quinazoline-2,4-dione

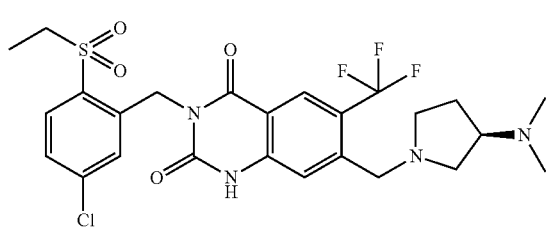 [SMILES: CCS(=O)(=O)c1ccc(Cl)cc1Cn1c(=O)[nH]c2cc(CN3CC[C@@H](N(C)C)C3)c(C(F)(F)F)cc2c1=O]

The title compound was synthesized from 7-((S)-3-aminomethyl-pyrrolidin-1-ylmethyl)-3-(5-chloro-2-ethanesulfonyl-benzyl)-6-trifluoromethyl-1H-quinazoline-2,4-dione (Compound B-19) under the same conditions as for Compound B-9.

LCMS: m/z 587 [M+H]$^+$

HPLC retention time: 0.45 min (analysis condition D)

Example 164

Compound b22

2-Amino-3-bromo-5-trifluoromethyl-benzoic acid ethyl ester

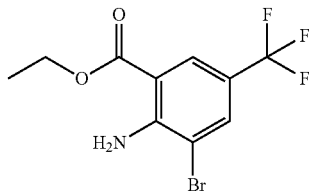

The title compound was synthesized from 2-amino-5-trifluoromethyl-benzoic acid ethyl ester under the same conditions as for Compound a9.

Example 165

Compound B-21

4-[3-(5-Chloro-2-ethanesulfonyl-benzyl)-2,4-dioxo-6-trifluoromethyl-1,2,3,4-tetrahydro-quinazolin-8-ylmethyl]-piperazine-1-carboxylic acid tert-butyl ester

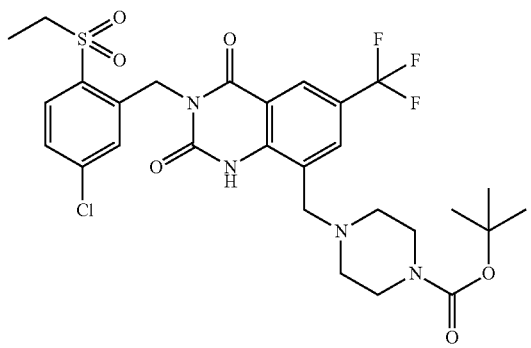 [SMILES: CCS(=O)(=O)c1ccc(Cl)cc1Cn1c(=O)[nH]c2c(CN3CCN(C(=O)OC(C)(C)C)CC3)cc(C(F)(F)F)cc2c1=O]

The title compound was synthesized from 2-amino-3-bromo-5-trifluoromethyl-benzoic acid ethyl ester (Compound b22) under the same conditions as for Compounds b1, b2, b3, and b4. However, the reaction was performed by adding HOBT and using DMF in place of DCM as a solvent under the conditions for Compound b3.

LCMS: m/z 645 [M+H]$^+$

HPLC retention time: 1.01 min (analysis condition D)

Example 166

Compound B-22

3-(5-Chloro-2-ethanesulfonyl-benzyl)-8-piperazin-1-ylmethyl-6-trifluoromethyl-1H-quinazoline-2,4-dione

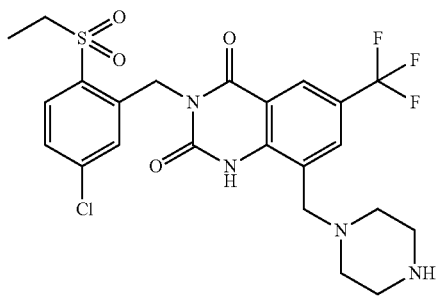 [SMILES: CCS(=O)(=O)c1ccc(Cl)cc1Cn1c(=O)[nH]c2c(CN3CCNCC3)cc(C(F)(F)F)cc2c1=O]

The title compound was synthesized from 4-[3-(5-chloro-2-ethanesulfonyl-benzyl)-2,4-dioxo-6-trifluoromethyl-1,2,3,4-tetrahydro-quinazolin-8-ylmethyl]-piperazine-1-carboxylic acid tert-butyl ester (Compound B-21) under the same conditions as for Compound B-1.

LCMS: m/z 545 [M+H]$^+$

HPLC retention time: 0.58 min (analysis condition D)

Example 167

Compound b23

2-tert-Butoxycarbonyl amino-5-trifluoromethyl-4-vinyl-benzoic acid tert-butyl ester

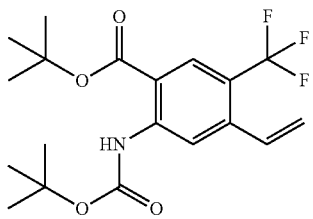 [SMILES: C=Cc1cc(NC(=O)OC(C)(C)C)c(C(=O)OC(C)(C)C)cc1C(F)(F)F]

The title compound was synthesized from 2-tert-butoxycarbonylamino-4-chloro-5-trifluoromethyl-benzoic acid tert-butyl ester (Compound 18) under the same conditions as for Compound 21.

Example 168

Compound b24

2-Amino-5-trifluoromethyl-4-vinyl-benzoic acid

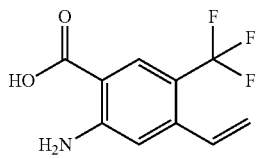

p-Toluenesulfonic acid monohydrate (167 mg, 0.88 mmol) was added to a solution of 2-tert-butoxycarbonylamino-5-trifluoromethyl-4-vinyl-benzoic acid tert-butyl ester (Compound b23, 0.88 mmol) in toluene (4.4 mL), and the mixture was stirred at 70° C. for four hours and then cooled to room temperature. The resulting solid was collected by filtration, and then washed with toluene and dried under reduced pressure to give the title compound as a crude product.

Example 169

Compound b25

2-Amino-N-(5-chloro-2-ethanesulfonyl-benzyl)-5-trifluoromethyl-4-vinyl-benzamide

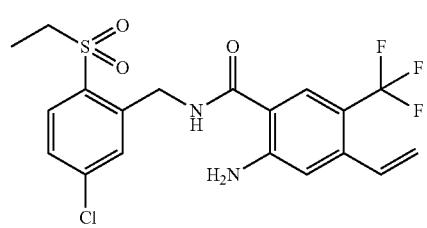 [SMILES: C=Cc1cc(N)c(C(=O)NCc2cc(Cl)ccc2S(=O)(=O)CC)cc1C(F)(F)F]

The title compound was synthesized from the crude product of 2-amino-5-trifluoromethyl-4-vinyl-benzoic acid (Compound b24) under the same conditions as for Compound 26. However, the reaction was performed without using HOBT.

Example 170

Compound b26

3-(5-Chloro-2-ethanesulfonyl-benzyl)-6-trifluoromethyl-7-vinyl-1H-quinazoline-2,4-dione

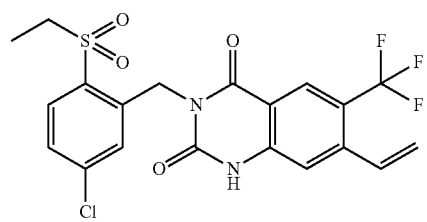 [SMILES: C=Cc1cc2[nH]c(=O)n(Cc3cc(Cl)ccc3S(=O)(=O)CC)c(=O)c2cc1C(F)(F)F]

The title compound was synthesized from 2-amino-N-(5-chloro-2-ethanesulfonyl-benzyl)-5-trifluoromethyl-4-vinyl-benzamide (Compound b25) under the same conditions as for Compound A-6.

Example 171

Compound B-23

3-(5-Chloro-2-ethanesulfonyl-benzyl)-7-(1,2-dihydroxy-ethyl)-6-trifluoromethyl-1H-quinazoline-2,4-dione

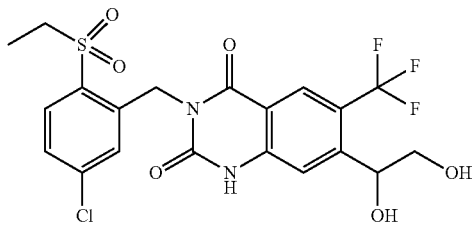 [SMILES: CCS(=O)(=O)c1ccc(Cl)cc1Cn1c(=O)[nH]c2cc(C(O)CO)c(C(F)(F)F)cc2c1=O]

The title compound was synthesized as an enantiomeric mixture from 3-(5-chloro-2-ethanesulfonyl-benzyl)-6-trifluoromethyl-7-vinyl-1H-quinazoline-2,4-dione (Compound b26) under the same conditions as for Compound 22. However, the reaction was performed by adding methanesulfonamide.
LCMS: m/z 507 [M+H]$^+$
HPLC retention time: 0.66 min (analysis condition D)

Example 172

Compound c1

4-(4-Ethoxycarbonyl-5-nitro-2-trifluoromethoxy-benzyl)-piperazine-1-carboxylic acid tert-butyl ester

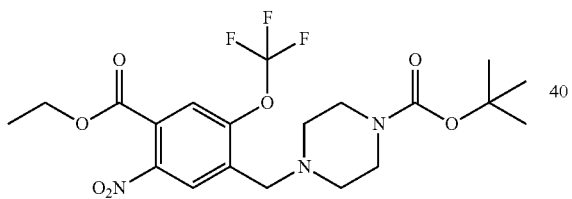

The title compound was synthesized from 4-bromo-2-nitro-5-trifluoromethoxy-benzoic acid ethyl ester (Compound 28) under the same conditions as for Compound b1.

Example 173

Compound c2

4-(5-Amino-4-ethoxycarbonyl-2-trifluoromethoxy-benzyl)-piperazine-1-carboxylic acid tert-butyl ester

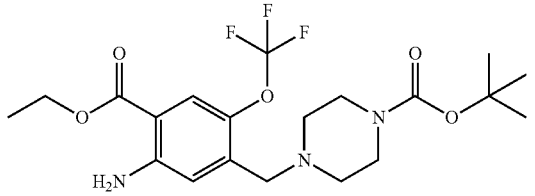 [SMILES: CCOC(=O)c1cc(OC(F)(F)F)c(CN2CCN(C(=O)OC(C)(C)C)CC2)cc1[N+](=O)[O-]]

The title compound was synthesized from 4-(4-ethoxycarbonyl-5-nitro-2-trifluoromethoxy-benzyl)-piperazine-1-carboxylic acid tert-butyl ester (Compound c1) under the same conditions as for Compound 30.

Example 174

Compound c3

4-(5-Amino-4-carboxy-2-trifluoromethoxy-benzyl)-piperazine-1-carboxylic acid tert-butyl ester

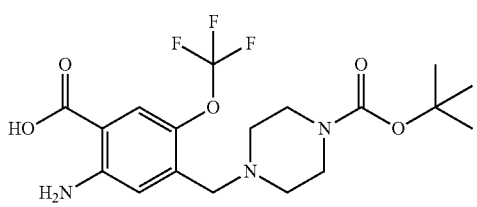 [SMILES: CC(C)(C)OC(=O)N1CCN(Cc2cc(N)c(C(=O)O)cc2OC(F)(F)F)CC1]

The title compound was synthesized from 4-(5-amino-4-ethoxycarbonyl-2-trifluoromethoxy-benzyl)-piperazine-1-carboxylic acid tert-butyl ester (Compound c2) under the same conditions as for Compound 25.

Example 175

Compound c4

4-[5-Amino-4-(5-chloro-2-ethanesulfonyl-benzylcarbamoyl)-2-trifluoromethoxy-benzyl]-piperazine-1-carboxylic acid tert-butyl ester

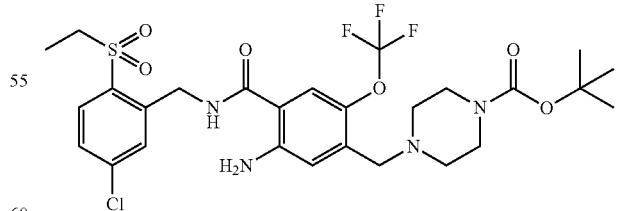

The title compound was synthesized from 4-(5-amino-4-carboxy-2-trifluoromethoxy-benzyl)-piperazine-1-carboxylic acid tert-butyl ester (Compound c3) under the same conditions as for Compound 26. However, the reaction was performed without adding HOBT.

Example 176

Compound c5

4-[3-(5-Chloro-2-ethanesulfonyl-benzyl)-2,4-dioxo-6-trifluoromethoxy-1,2,3,4-tetrahydro-quinazolin-7-ylmethyl]-piperazine-1-carboxylic acid tert-butyl ester

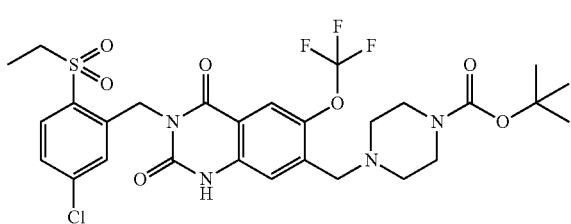 [SMILES: CCS(=O)(=O)c1ccc(Cl)cc1Cn1c(=O)[nH]c2cc(CN3CCN(C(=O)OC(C)(C)C)CC3)c(OC(F)(F)F)cc2c1=O]

The title compound was synthesized from 4-[5-amino-4-(5-chloro-2-ethanesulfonyl-benzylcarbamoyl)-2-trifluoromethoxy-benzyl]-piperazine-1-carboxylic acid tert-butyl ester (Compound c4) under the same conditions as for Compound 37.

Example 177

Compound C-1

3-(5-Chloro-2-ethanesulfonyl-benzyl)-7-piperazin-1-ylmethyl-6-trifluoromethoxy-1H-quinazoline-2,4-dione

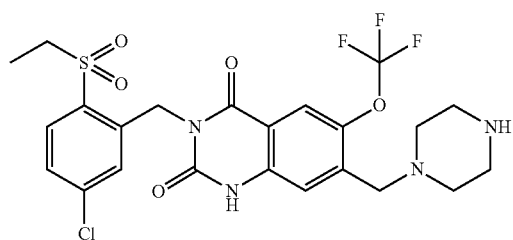 [SMILES: CCS(=O)(=O)c1ccc(Cl)cc1Cn1c(=O)[nH]c2cc(CN3CCNCC3)c(OC(F)(F)F)cc2c1=O]

The title compound was synthesized from 4-[3-(5-chloro-2-ethanesulfonyl-benzyl)-2,4-dioxo-6-trifluoromethoxy-1,2,3,4-tetrahydro-quinazolin-7-ylmethyl]-piperazine-1-carboxylic acid tert-butyl ester (Compound c5) under the same conditions as for Compound B-1.

LCMS: m/z 561 [M+H]$^+$

HPLC retention time: 0.54 min (analysis condition D)

Example 178

Compound C-2

3-(5-Chloro-2-ethanesulfonyl-benzyl)-7-(4-methyl-piperazin-1-ylmethyl)-6-trifluoromethoxy-1H-quinazoline-2,4-dione

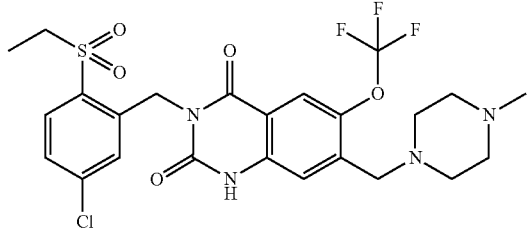 [SMILES: CCS(=O)(=O)c1ccc(Cl)cc1Cn1c(=O)[nH]c2cc(CN3CCN(C)CC3)c(OC(F)(F)F)cc2c1=O]

The title compound was synthesized from 3-(5-chloro-2-ethanesulfonyl-benzyl)-7-piperazin-1-ylmethyl-6-trifluoromethoxy-1H-quinazoline-2,4-dione (Compound C-1) under the same conditions as for Compound B-2.

LCMS: m/z 575 [M+H]$^+$

HPLC retention time: 0.56 min (analysis condition D)

Example 179

Compound C-3

3-(5-Chloro-2-ethanesulfonyl-benzyl)-7-(4-ethyl-piperazin-1-ylmethyl)-6-trifluoromethoxy-1H-quinazoline-2,4-dione

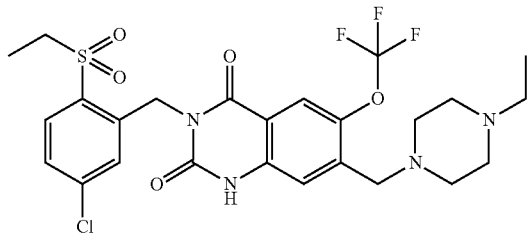 [SMILES: CCN1CCN(Cc2cc3[nH]c(=O)n(Cc4cc(Cl)ccc4S(=O)(=O)CC)c(=O)c3cc2OC(F)(F)F)CC1]

The title compound was synthesized from 3-(5-chloro-2-ethanesulfonyl-benzyl)-7-piperazin-1-ylmethyl-6-trifluoromethoxy-1H-quinazoline-2,4-dione (Compound C-1) under the same conditions as for Compound B-3.

LCMS: m/z 589 [M+H]$^+$

HPLC retention time: 0.50 min (analysis condition H)

Example 180

Compound C-4

3-(5-Chloro-2-ethanesulfonyl-benzyl)-7-(4-isopropyl-piperazin-1-ylmethyl)-6-trifluoromethoxy-1H-quinazoline-2,4-dione

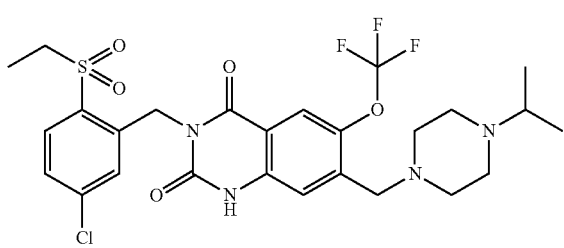 [SMILES: CCS(=O)(=O)c1ccc(Cl)cc1Cn1c(=O)[nH]c2cc(CN3CCN(C(C)C)CC3)c(OC(F)(F)F)cc2c1=O]

The title compound was synthesized from 3-(5-chloro-2-ethanesulfonyl-benzyl)-7-piperazin-1-ylmethyl-6-trifluoromethoxy-1H-quinazoline-2,4-dione (Compound C-1) under the same conditions as for Compound B-4.

LCMS: m/z 603 [M+H]$^+$

HPLC retention time: 0.58 min (analysis condition D)

Example 181

Compound C-5

3-(5-Chloro-2-ethanesulfonyl-benzyl)-7-[4-(tetrahydro-pyran-4-yl)-piperazin-1-ylmethyl]-6-trifluoromethoxy-1H-quinazoline-2,4-dione

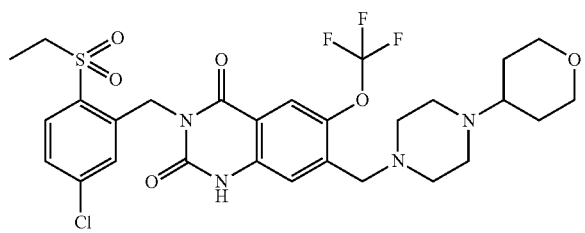 [SMILES: CCS(=O)(=O)c1ccc(Cl)cc1Cn1c(=O)[nH]c2cc(CN3CCN(C4CCOCC4)CC3)c(OC(F)(F)F)cc2c1=O]

The title compound was synthesized from 3-(5-chloro-2-ethanesulfonyl-benzyl)-7-piperazin-1-ylmethyl-6-trifluoromethoxy-1H-quinazoline-2,4-dione (Compound C-1) under the same conditions as for Compound B-5.

LCMS: m/z 645 [M+H]$^+$

HPLC retention time: 0.57 min (analysis condition D)

Example 182

Compound C-6

3-(5-Chloro-2-ethanesulfonyl-benzyl)-7-(4-methanesulfonyl-piperazin-1-ylmethyl)-6-trifluoromethoxy-1H-quinazoline-2,4-dione

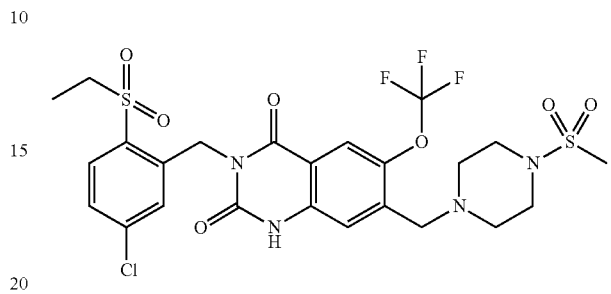

Methanesulfonyl chloride (0.14 ul, mmol) was added to a solution of 3-(5-chloro-2-ethanesulfonyl-benzyl)-7-piperazin-1-ylmethyl-6-trifluoromethoxy-1H-quinazoline-2,4-dione (Compound C-1, 20.0 mg, 0.036 mmol) and DIPEA (18.3 ul, 0.11 mmol) in DMF (1 ml), and the mixture was stirred at room temperature for 3.5 hours. Water was added to the reaction mixture, followed by extraction with hexane/ethyl acetate. The organic layer was then washed with water and brine, and dried over anhydrous sodium sulfate. This was concentrated under reduced pressure, and the resulting residue was purified by amino silica gel column chromatography (methanol/dichloromethane) to give the title compound (18.7 mg, 82%) as a colorless powder.

LCMS: m/z 639 [M+H]$^+$

HPLC retention time: 0.76 min (analysis condition D)

Example 183

Compound C-7

3-(5-Chloro-2-ethanesulfonyl-benzyl)-7-(4-cyclobutyl-piperazin-1-ylmethyl)-6-trifluoromethoxy-1H-quinazoline-2,4-dione

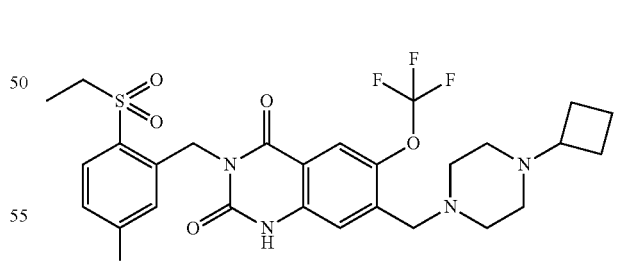

The title compound was synthesized from 3-(5-chloro-2-ethanesulfonyl-benzyl)-7-piperazin-1-ylmethyl-6-trifluoromethoxy-1H-quinazoline-2,4-dione (Compound C-1) under the same conditions as for Compound B-5. However, the reaction was performed using cyclobutanone in place of tetrahydro-4H-pyran-4-one.

LCMS: m/z 615 [M+H]$^+$

HPLC retention time: 0.59 min (analysis condition D)

Example 184

Compound C-8

3-(5-Chloro-2-ethanesulfonyl-benzyl)-7-(4-cyclohexyl-piperazin-1-ylmethyl)-6-trifluoromethoxy-1H-quinazoline-2,4-dione

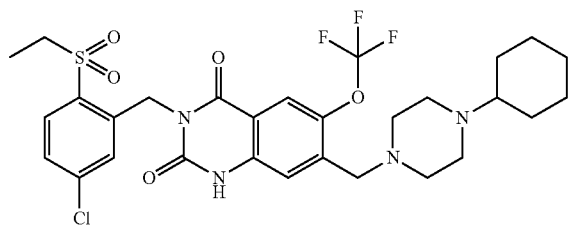 [SMILES: CCS(=O)(=O)c1ccc(Cl)cc1Cn1c(=O)[nH]c2cc(CN3CCN(C4CCCCC4)CC3)c(OC(F)(F)F)cc2c1=O]

The title compound was synthesized from 3-(5-chloro-2-ethanesulfonyl-benzyl)-7-piperazin-1-ylmethyl-6-trifluoromethoxy-1H-quinazoline-2,4-dione (Compound C-1) under the same conditions as for Compound B-5. However, the reaction was performed using cyclohexanone in place of tetrahydro-4H-pyran-4-one.

LCMS: m/z 643 [M+H]$^+$

HPLC retention time: 0.62 min (analysis condition D)

Example 185

Compound c6

4-((R)-3-tert-Butoxycarbonylamino-pyrrolidin-1-ylmethyl)-2-nitro-5-trifluoromethoxy-benzoic acid ethyl ester

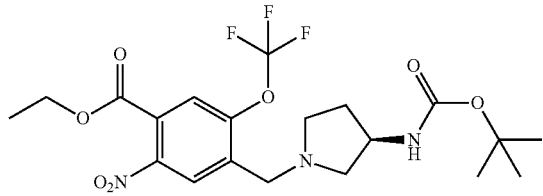

A mixture of 4-bromo-2-nitro-5-trifluoromethoxy-benzoic acid ethyl ester (Compound 28, 750 mg, 2.1 mmol), potassium (R)-({3-[(tert-butoxycarbonyl)amino]pyrrolidin-1-yl}methyl)trifluoroborate (898 mg, 2.9 mmol), palladium acetate (23.5 mg, 0.10 mmol), Ru-Phos (97.7 mg, 0.21 mmol), and potassium carbonate (869 mg, 6.3 mmol) in toluene (7.0 mL) and water (3.5 mL) was refluxed for five hours. Water was added to the reaction solution, followed by extraction with ethyl acetate. The extract was dried over anhydrous sodium sulfate. The drying agent was removed by filtration, and the residue obtained after concentration under reduced pressure was purified by silica gel column chromatography (ethyl acetate/hexane) to give the title compound (847 mg, 85%) as a pale yellow solid.

LCMS: m/z 478 [M+H]$^+$

HPLC retention time: 0.60 min (analysis condition D)

Example 186

Compound c7

{(R)-1-[3-(5-Chloro-2-ethanesulfonyl-benzyl)-2,4-dioxo-6-trifluoromethoxy-1,2,3,4-tetrahydro-quinazolin-7-ylmethyl]-pyrrolidin-3-yl}-carbamic acid tert-butyl ester

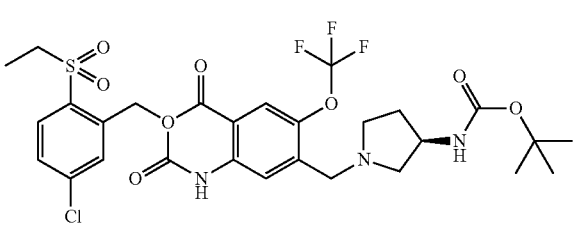

The title compound was synthesized from 4-((R)-3-tert-butoxycarbonylamino-pyrrolidin-1-ylmethyl)-2-nitro-5-trifluoromethoxy-benzoic acid ethyl ester (Compound c6) under the same conditions as for Compounds c2, c3, c4, and c5. However, with regard to the conditions for Compound c5, TEA was used in place of pyridine, and as solvent, THF was used in place of DCM.

Example 187

Compound C-9

7-((R)-3-Amino-pyrrolidin-1-ylmethyl)-3-(5-chloro-2-ethanesulfonyl-benzyl)-6-trifluoromethoxy-1H-quinazoline-2,4-dione

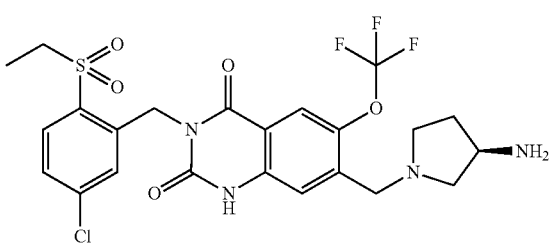 [SMILES: CCS(=O)(=O)c1ccc(Cl)cc1Cn1c(=O)[nH]c2cc(CN3CC[C@@H](N)C3)c(OC(F)(F)F)cc2c1=O]

The title compound was synthesized from {(R)-1-[3-(5-chloro-2-ethanesulfonyl-benzyl)-2,4-dioxo-6-trifluoromethoxy-1,2,3,4-tetrahydro-quinazolin-7-ylmethyl]-pyrrolidin-3-yl}-carbamic acid tert-butyl ester (Compound c7) under the same conditions as for Compound a41.

LCMS: m/z 561 [M+H]$^+$

HPLC retention time: 0.50 min (analysis condition D)

Example 188

Compound C-10

3-(5-Chloro-2-ethanesulfonyl-benzyl)-7-((R)-3-dimethylamino-pyrrolidin-1-ylmethyl)-6-trifluoromethoxy-1H-quinazoline-2,4-dione

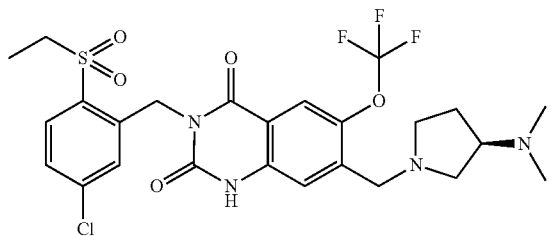 [SMILES: CCS(=O)(=O)c1ccc(Cl)cc1Cn1c(=O)[nH]c2cc(CN3CC[C@@H](N(C)C)C3)c(OC(F)(F)F)cc2c1=O]

The title compound was synthesized from 7-((R)-3-amino-pyrrolidin-1-ylmethyl)-3-(5-chloro-2-ethanesulfonyl-benzyl)-6-trifluoromethoxy-1H-quinazoline-2,4-dione (Compound C-9) under the same conditions as for Compound B-9.

LCMS: m/z 589 [M+H]$^+$

HPLC retention time: 0.55 min (analysis condition D)

Example 189

Compound C-11

N-{(R)-1-[3-(5-Chloro-2-ethanesulfonyl-benzyl)-2,4-dioxo-6-trifluoromethoxy-1,2,3,4-tetrahydro-quinazolin-7-ylmethyl]-pyrrolidin-3-yl}-acetamide

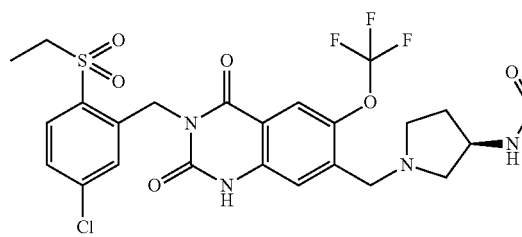

The title compound was synthesized from 7-((R)-3-amino-pyrrolidin-1-ylmethyl)-3-(5-chloro-2-ethanesulfonyl-benzyl)-6-trifluoromethoxy-1H-quinazoline-2,4-dione (Compound C-9) under the same conditions as for Compound B-6.

LCMS: m/z 603 [M+H]$^+$

HPLC retention time: 0.52 min (analysis condition D)

Example 190

Compound c8

4-[(R)-3-(tert-Butoxycarbonyl-methyl-amino)-pyrrolidin-1-ylmethyl]-2-nitro-5-trifluoromethoxy-benzoic acid ethyl ester

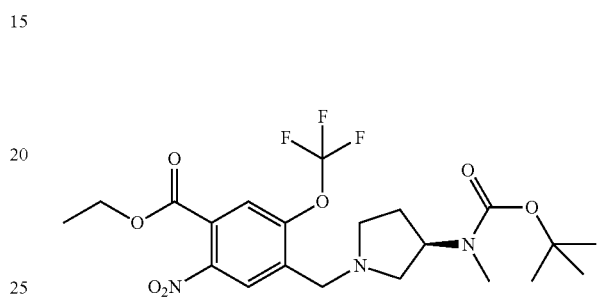

The title compound was synthesized from 4-bromo-2-nitro-5-trifluoromethoxy-benzoic acid ethyl ester (Compound 28) under the same conditions as for Compound c6. However, the reaction was performed using potassium (R)-({3-[(tert-butoxycarbonyl)-methyl-amino]pyrrolidin-1-yl}methyl)trifluoroborate in place of potassium (R)-({(3-[(tert-butoxycarbonyl)amino]pyrrolidin-1-yl}methyl) trifluoroborate and using BuPAd2 in place of Ru-Phos.

Example 191

Compound c9

{(R)-1-[5-Amino-4-(5-chloro-2-ethanesulfonyl-benzylcarbamoyl)-2-trifluoromethoxy-benzyl]-pyrrolidin-3-yl}-methyl-carbamic acid tert-butyl ester

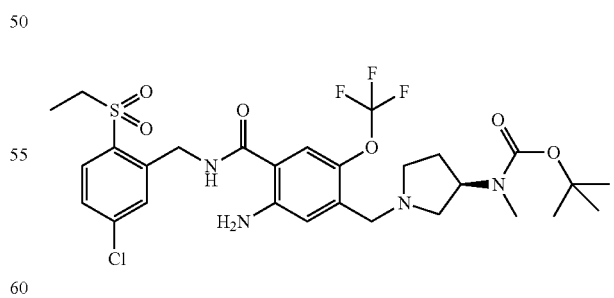

The title compound was synthesized from 4-[(R)-3-(tert-butoxycarbonyl-methyl-amino)-pyrrolidin-1-ylmethyl]-2-nitro-5-trifluoromethoxy-benzoic acid ethyl ester (Compound c8) under the same conditions as for Compounds c2, c3, and c4. However, the reaction was performed by adding HOBT under the conditions for c4.

Example 192

Compound c10

{(R)-1-[3-(5-Chloro-2-ethanesulfonyl-benzyl)-2,4-dioxo-6-trifluoromethoxy-1,2,3,4-tetrahydro-quinazolin-7-ylmethyl]-pyrrolidin-3-yl}-methyl-carbamic acid tert-butyl ester

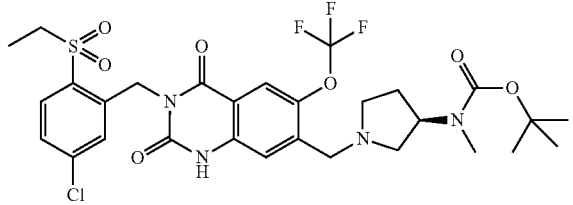 [SMILES: CCS(=O)(=O)c1ccc(Cl)cc1Cn1c(=O)[nH]c2cc(CN3CC[C@@H](N(C)C(=O)OC(C)(C)C)C3)c(OC(F)(F)F)cc2c1=O]

The title compound was synthesized from {(R)-1-[5-amino-4-(5-chloro-2-ethanesulfonyl-benzylcarbamoyl)-2-trifluoromethoxy-benzyl]-pyrrolidin-3-yl}-methyl-carbamic acid tert-butyl ester (Compound c9) under the same conditions as for Compound A-6.

Example 193

Compound C-12

3-(5-Chloro-2-ethanesulfonyl-benzyl)-7-((R)-3-methylamino-pyrrolidin-1-ylmethyl)-6-trifluoromethoxy-1H-quinazoline-2,4-dione

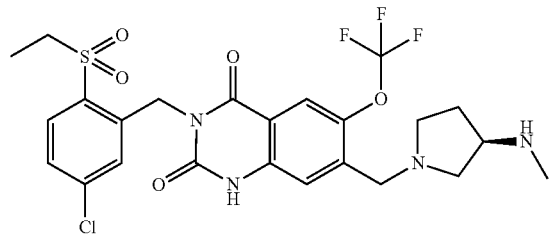 [SMILES: CCS(=O)(=O)c1ccc(Cl)cc1Cn1c(=O)[nH]c2cc(CN3CC[C@@H](NC)C3)c(OC(F)(F)F)cc2c1=O]

The title compound was synthesized from {(R)-1-[3-(5-chloro-2-ethanesulfonyl-benzyl)-2,4-dioxo-6-trifluoromethoxy-1,2,3,4-tetrahydro-quinazolin-7-ylmethyl]-pyrrolidin-3-yl}-methyl-carbamic acid tert-butyl ester (Compound c10) under the same conditions as for Compound B-1.

LCMS: m/z 575 [M+H]$^+$

HPLC retention time: 0.53 min (analysis condition D)

Example 194

Compound c11

2-Amino-3-bromo-5-trifluoromethoxy-benzoic acid ethyl ester

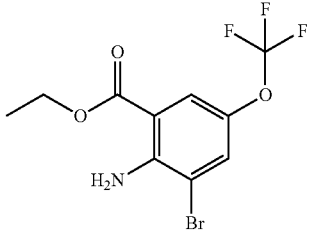 [SMILES: CCOC(=O)c1cc(OC(F)(F)F)cc(Br)c1N]

Sulfuric acid (0.6 mL) was added to a solution of 2-amino-3-bromo-5-trifluoromethoxy-benzoic acid (900 mg, 3.0 mmol) in EtOH (2.7 mL), and the mixture was stirred under reflux for 11 hours. EtOH (2.7 mL) and sulfuric acid (0.6 mL) were added, and the mixture was stirred under reflux for further eight hours. The reaction solution was ice-cooled, and a 5 N aqueous sodium hydroxide solution (9 mL) was added, followed by extraction with ethyl acetate. The extract was washed with brine and dried over anhydrous sodium sulfate. The drying agent was removed by filtration, and the residue obtained after concentration under reduced pressure was purified by silica gel column chromatography (ethyl acetate/hexane) to give the title compound (753 mg, 77%) as a pale brown oily substance.

LCMS: m/z 328 [M+H]$^+$

HPLC retention time: 1.05 min (analysis condition D)

Example 195

Compound c12

4-(2-Amino-3-ethoxycarbonyl-5-trifluoromethoxy-benzyl)-piperazine-1-carboxylic acid tert-butyl ester

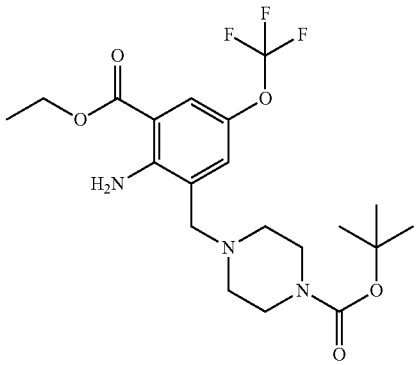 [SMILES: CCOC(=O)c1cc(OC(F)(F)F)cc(CN2CCN(C(=O)OC(C)(C)C)CC2)c1N]

The title compound was synthesized from 2-amino-3-bromo-5-trifluoromethoxy-benzoic acid ethyl ester (Compound c11) under the same conditions as for Compound b1.

Example 196

Compound C-13

4-[3-(5-Chloro-2-ethanesulfonyl-benzyl)-2, 4-dioxo-6-trifluoromethoxy-1,2,3,4-tetrahydro-quinazolin-8-ylmethyl]-piperazine-1-carboxylic acid tert-butyl ester

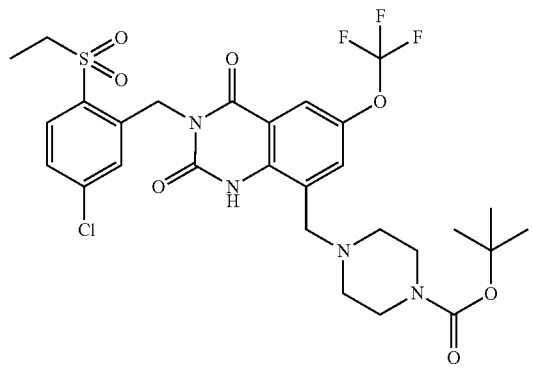 [SMILES: CCS(=O)(=O)c1ccc(Cl)cc1Cn1c(=O)[nH]c2c(CN3CCN(C(=O)OC(C)(C)C)CC3)cc(OC(F)(F)F)cc2c1=O]

The title compound was synthesized from 4-(2-amino-3-ethoxycarbonyl-5-trifluoromethoxy-benzyl)-piperazine-1-carboxylic acid tert-butyl ester (Compound c12) under the same conditions as for Compounds c3, c4, and c5. However, the reaction was performed without adding DIPEA.

LCMS: m/z 661 [M+H]$^+$

HPLC retention time: 1.02 min (analysis condition D)

Example 197

Compound C-14

3-(5-Chloro-2-ethanesulfonyl-benzyl)-8-piperazin-1-ylmethyl-6-trifluoromethoxy-1H-quinazoline-2,4-dione

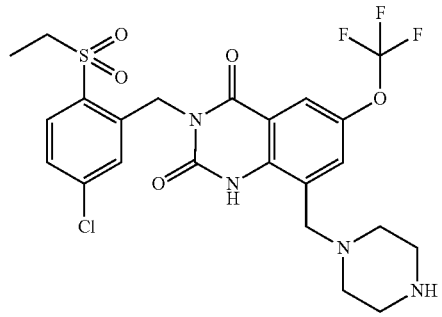 [SMILES: CCS(=O)(=O)c1ccc(Cl)cc1Cn1c(=O)[nH]c2c(CN3CCNCC3)cc(OC(F)(F)F)cc2c1=O]

The title compound was synthesized from 4-[3-(5-chloro-2-ethanesulfonyl-benzyl)-2,4-dioxo-6-trifluoromethoxy-1,2,3,4-tetrahydro-quinazolin-8-ylmethyl]-piperazine-1-carboxylic acid tert-butyl ester (Compound C-13) under the same conditions as for Compound B-1.

LCMS: m/z 561 [M+H]$^+$

HPLC retention time: 0.58 min (analysis condition D)

Example 198

Compound d1

4-(5-(Bis(tert-butoxycarbonyl)amino)-2-chloro-4-(ethoxycarbonyl)benzyl)piperazine-1-carboxylic acid tert-butyl ester

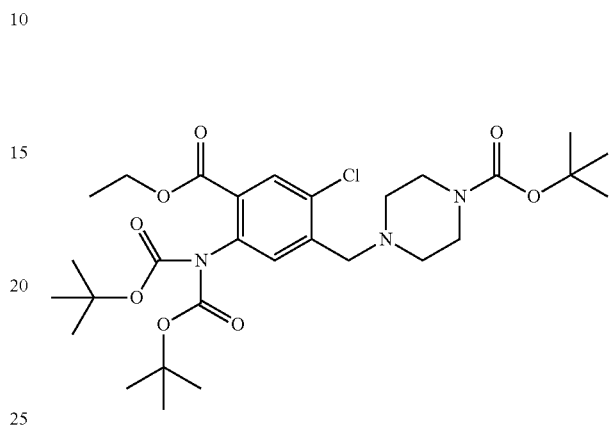

1-(tert-Butoxycarbonyl)piperazine (493 mg, 2.7 mmol) was added to a solution of 2-(bis(tert-butoxycarbonyl)amino)-4-(bromomethyl)-5-chlorobenzoic acid ethyl ester (Compound 46, 604 mg, 0.88 mol) in THF (6.1 ml), and the mixture was stirred at 50-75° C. for 6.5 hours. Water was added to the reaction mixture, followed by extraction with ethyl acetate. The organic layer was washed with brine and then dried over anhydrous sodium sulfate. The drying agent was removed by filtration, and the residue obtained after concentration under reduced pressure was purified by silica gel column chromatography (ethyl acetate/hexane) to give the title compound (498 mg, yield: 94%) as a colorless amorphous.

LCMS: m/z 598 [M+H]$^+$

HPLC retention time: 0.97 min (analysis condition H)

Example 199

Compound d2

2-Amino-5-chloro-4-piperazin-1-ylmethyl-benzoic acid ethyl ester

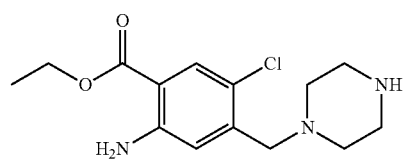 [SMILES: CCOC(=O)c1cc(Cl)c(CN2CCNCC2)cc1N]

The title compound was synthesized from 4-(5-(bis(tert-butoxycarbonyl)amino)-2-chloro-4-(ethoxycarbonyl)benzyl)piperazine-1-carboxylic acid tert-butyl ester (Compound d1) under the same conditions as for Compound a41.

Example 200

Compound d3

4-(5-Amino-2-chloro-4-ethoxycarbonyl-benzyl)-piperazine-1-carboxylic acid tert-butyl ester

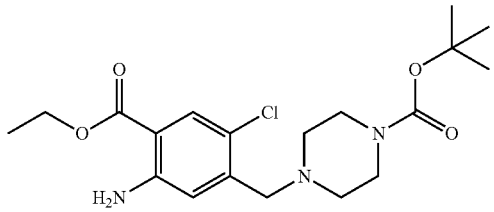 [SMILES: CCOC(=O)c1cc(Cl)c(CN2CCN(C(=O)OC(C)(C)C)CC2)cc1N]

A solution of 2-amino-5-chloro-4-piperazin-1-ylmethyl-benzoic acid ethyl ester (Compound d2, 241 mg, 0.83 mmol) and triethylamine (0.350 ml, 2.5 mmol) in DCM (8 ml) was cooled to 0° C., and Boc$_2$O (0.230 ml, 1.0 mmol) was added, and then stirred at 0° C. for 30 minutes. Water was added to the reaction mixture, followed by extraction with ethyl acetate. The organic layer was washed with brine and then dried over anhydrous sodium sulfate. The drying agent was removed by filtration, and the residue obtained after concentration under reduced pressure was purified by silica gel column chromatography (ethyl acetate/hexane) to give the title compound (287 mg, yield: 86%) as a yellow solid.

LCMS: m/z 398 [M+H]$^+$

HPLC retention time: 0.57 min (analysis condition H)

Example 201

Compound d4

4-(5-Amino-4-carboxy-2-chloro-benzyl)-piperazine-1-carboxylic acid tert-butyl ester

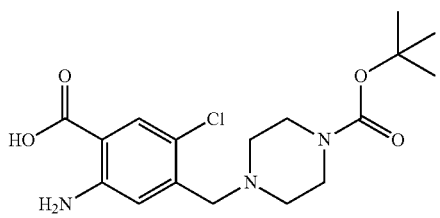

The title compound was synthesized from 4-(5-amino-2-chloro-4-ethoxycarbonyl-benzyl)-piperazine-1-carboxylic acid tert-butyl ester (Compound d3) under the same conditions as for Compound 25.

Example 202

Compound d5

4-[5-Amino-2-chloro-4-(5-chloro-2-ethanesulfonyl-benzylcarbamoyl)-benzyl]-piperazine-1-carboxylic acid tert-butyl ester

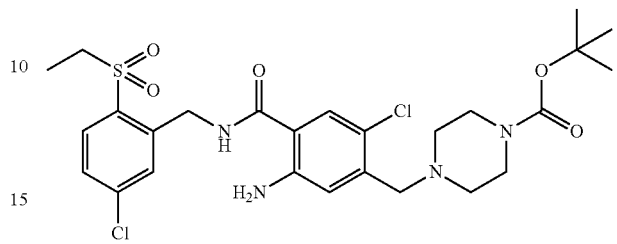

The title compound was synthesized from 4-(5-amino-4-carboxy-2-chloro-benzyl)-piperazine-1-carboxylic acid tert-butyl ester (Compound d4) under the same conditions as for Compound 26. However, the reaction was performed without using HOBT.

Example 203

Compound d6

4-[6-Chloro-3-(5-chloro-2-ethanesulfonyl-benzyl)-2,4-dioxo-1,2,3,4-tetrahydro-quinazolin-7-ylmethyl]-piperazine-1-carboxylic acid tert-butyl ester

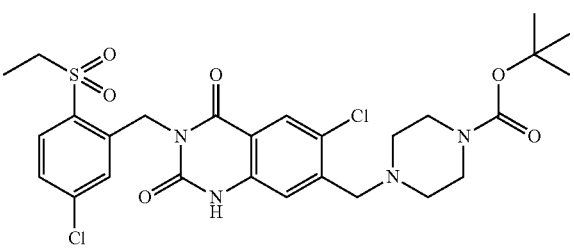 [SMILES: CCS(=O)(=O)c1ccc(Cl)cc1Cn1c(=O)[nH]c2cc(CN3CCN(C(=O)OC(C)(C)C)CC3)c(Cl)cc2c1=O]

The title compound was synthesized from 4-[5-amino-2-chloro-4-(5-chloro-2-ethanesulfonyl-benzylcarbamoyl)-benzyl]-piperazine-1-carboxylic acid tert-butyl ester (Compound d5) under the same conditions as for Compound A-6.

Example 204

Compound D-1

6-Chloro-3-(5-chloro-2-ethanesulfonyl-benzyl)-7-piperazin-1-ylmethyl-1H-quinazoline-2,4-dione

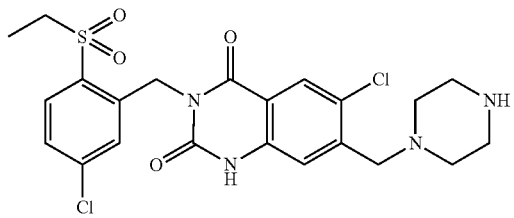 [SMILES: CCS(=O)(=O)c1ccc(Cl)cc1Cn1c(=O)[nH]c2cc(CN3CCNCC3)c(Cl)cc2c1=O]

The title compound was synthesized from 4-[6-chloro-3-(5-chloro-2-ethanesulfonyl-benzyl)-2,4-dioxo-1,2,3,4-tetrahydro-quinazolin-7-ylmethyl]-piperazine-1-carboxylic acid tert-butyl ester (Compound d6) under the same conditions as for Compound B-1.

LCMS: m/z 511 [M+H]$^+$

HPLC retention time: 0.54 min (analysis condition G)

Example 205

Compound D-2

6-Chloro-3-(5-chloro-2-ethanesulfonyl-benzyl)-7-(4-methyl-piperazin-1-ylmethyl)-1H-quinazoline-2,4-dione

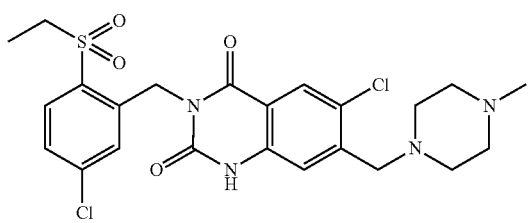 [SMILES: CCS(=O)(=O)c1ccc(Cl)cc1Cn1c(=O)[nH]c2cc(CN3CCN(C)CC3)c(Cl)cc2c1=O]

The title compound was synthesized from 6-chloro-3-(5-chloro-2-ethanesulfonyl-benzyl)-7-piperazin-1-ylmethyl-1H-quinazoline-2,4-dione (Compound D-1) under the same conditions as for Compound B-9.

LCMS: m/z 525 [M+H]$^+$

HPLC retention time: 0.56 min (analysis condition G)

Example 206

Compound d7

2-Bis(tert-butoxycarbonyl)amino-4-((R)-3-tert-butoxycarbonylamino-pyrrolidin-1-ylmethyl)-5-chloro-benzoic acid ethyl ester

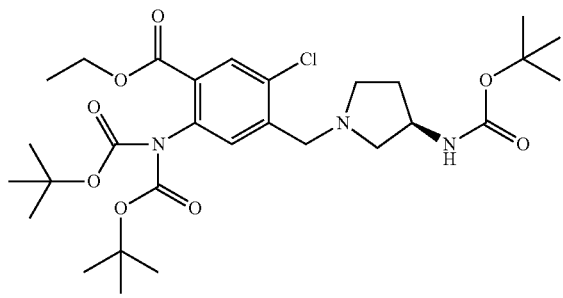 [SMILES: CCOC(=O)c1cc(Cl)c(CN2CC[C@@H](NC(=O)OC(C)(C)C)C2)cc1N(C(=O)OC(C)(C)C)C(=O)OC(C)(C)C]

The title compound was synthesized from 2-(bis(tert-butoxycarbonyl)amino)-4-(bromomethyl)-5-chlorobenzoic acid ethyl ester (Compound 46) under the same conditions as for Compound d1. However, the reaction was performed by adding potassium carbonate and using (R)-pyrrolidin-3-yl-carbamic acid tert-butyl ester in place of 1-(tert-butoxycarbonyl)piperazine.

Example 207

Compound d8

2-Amino-4-((R)-3-amino-pyrrolidin-1-ylmethyl)-5-chloro-benzoic acid ethyl ester

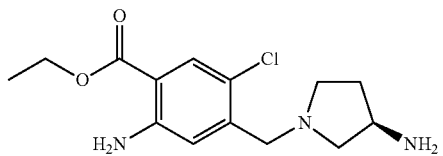 [SMILES: CCOC(=O)c1cc(Cl)c(CN2CC[C@@H](N)C2)cc1N]

The title compound was synthesized from 2-bis(tert-butoxycarbonyl)amino-4-((R)-3-tert-butoxycarbonylamino-pyrrolidin-1-ylmethyl)-5-chloro-benzoic acid ethyl ester (Compound d7) under the same conditions as for Compound B-1.

Example 208

Compound d9

2-Amino-4-((R)-3-tert-butoxycarbonylamino-pyrrolidin-1-ylmethyl)-5-chloro-benzoic acid ethyl ester

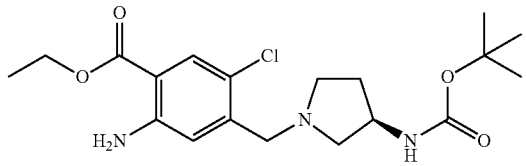 [SMILES: CCOC(=O)c1cc(Cl)c(CN2CC[C@@H](NC(=O)OC(C)(C)C)C2)cc1N]

The title compound was synthesized from 2-amino-4-((R)-3-amino-pyrrolidin-1-ylmethyl)-5-chloro-benzoic acid ethyl ester (Compound d8) under the same conditions as for Compound d3.

Example 209

Compound d10

2-Amino-4-((R)-3-tert-butoxycarbonylamino-pyrrolidin-1-ylmethyl)-5-chloro-benzoic acid

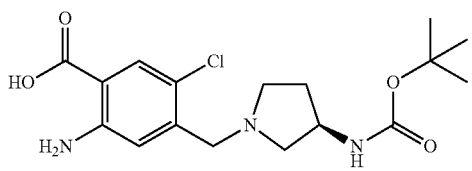 [SMILES: CC(C)(C)OC(=O)N[C@@H]1CCN(Cc2cc(N)c(C(=O)O)cc2Cl)C1]

The title compound was synthesized from 2-amino-4-((R)-3-tert-butoxycarbonylamino-pyrrolidin-1-ylmethyl)-5- chloro-benzoic acid ethyl ester (Compound d9) under the same conditions as for Compound 25.

Example 210

Compound d11

{(R)-1-[5-Amino-2-chloro-4-(5-chloro-2-ethanesulfonyl-benzylcarbamoyl)-benzyl]-pyrrolidin-3-yl}-carbamic acid tert-butyl ester

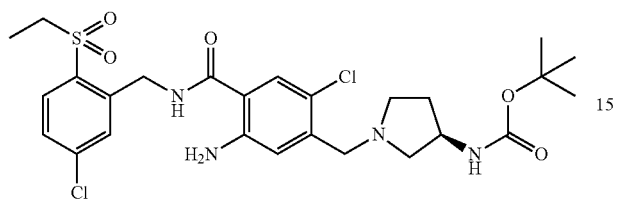

The title compound was synthesized from 2-amino-4-((R)-3-tert-butoxycarbonylamino-pyrrolidin-1-ylmethyl)-5-chloro-benzoic acid (Compound d10) under the same conditions as for Compound 26.

Example 211

Compound d12

{(R)-1-[6-Chloro-3-(5-chloro-2-ethanesulfonyl-benzyl)-2,4-dioxo-1,2,3,4-tetrahydro-quinazolin-7-ylmethyl]-pyrrolidin-3-yl}-carbamic acid tert-butyl ester

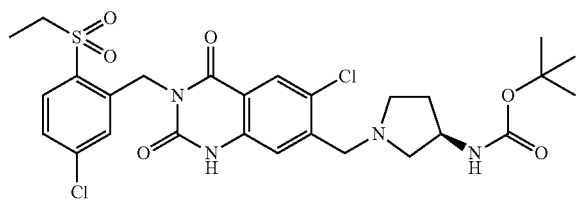 [SMILES: CCS(=O)(=O)c1ccc(Cl)cc1Cn1c(=O)[nH]c2cc(CN3CC[C@@H](NC(=O)OC(C)(C)C)C3)c(Cl)cc2c1=O]

The title compound was synthesized from {(R)-1-[5-amino-2-chloro-4-(5-chloro-2-ethanesulfonyl-benzylcarbamoyl)-benzyl]-pyrrolidin-3-yl}-carbamic acid tert-butyl ester (Compound d11) under the same conditions as for Compound A-6.

Example 212

Compound D-3

7-((R)-3-Amino-pyrrolidin-1-ylmethyl)-6-chloro-3-(5-chloro-2-ethanesulfonyl-benzyl)-1H-quinazoline-2,4-dione

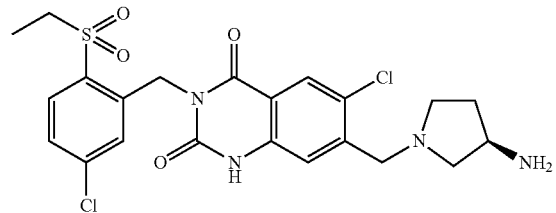 [SMILES: CCS(=O)(=O)c1ccc(Cl)cc1Cn1c(=O)[nH]c2cc(CN3CC[C@@H](N)C3)c(Cl)cc2c1=O]

The title compound was synthesized from {(R)-1-[6-chloro-3-(5-chloro-2-ethanesulfonyl-benzyl)-2,4-dioxo-1,2,3,4-tetrahydro-quinazolin-7-ylmethyl]-pyrrolidin-3-yl}-carbamic acid tert-butyl ester (Compound d12) under the same conditions as for Compound a41.

LCMS: m/z 511 [M+H]$^+$

HPLC retention time: 0.45 min (analysis condition D)

Example 213

Compound D-4

7-((S)-3-Amino-pyrrolidin-1-ylmethyl)-6-chloro-3-(5-chloro-2-ethanesulfonyl-benzyl)-1H-quinazoline-2,4-dione

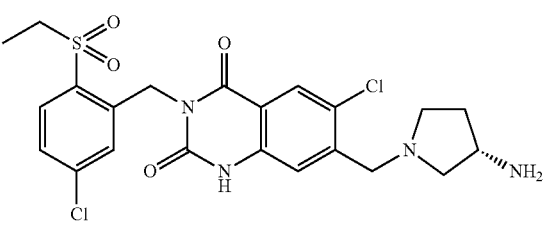 [SMILES: CCS(=O)(=O)c1ccc(Cl)cc1Cn1c(=O)[nH]c2cc(CN3CC[C@H](N)C3)c(Cl)cc2c1=O]

The title compound was synthesized from 2-(bis(tert-butoxycarbonyl)amino)-4-(bromomethyl)-5-chlorobenzoic acid ethyl ester (Compound 46) under the same conditions as for Compounds d7, d8, d9, d10, d11, d12, and D-3. However, the reaction was performed using (S)-pyrrolidin-3-yl-carbamic acid tert-butyl ester in place of (R)-pyrrolidin-3-yl-carbamic acid tert-butyl ester under the conditions for Compound d7.

LCMS: m/z 511 [M+H]$^+$

HPLC retention time: 0.45 min (analysis condition D)

Example 214

Compound d13

2-Amino-5-chloro-3-methyl-benzoic acid ethyl ester

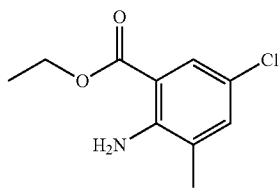

The title compound was synthesized from 2-amino-5-chloro-3-methyl-benzoic acid under the same conditions as for Compound c11.

Example 215

Compound d14

2-Bis(tert-butoxycarbonyl)amino-5-chloro-3-methyl-benzoic acid ethyl ester

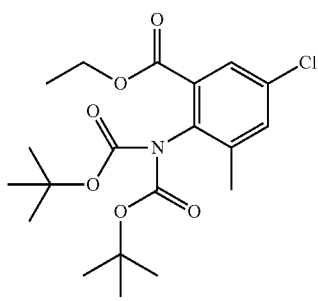 [SMILES: CCOC(=O)c1cc(Cl)cc(C)c1N(C(=O)OC(C)(C)C)C(=O)OC(C)(C)C]

The title compound was synthesized from 2-amino-5-chloro-3-methyl-benzoic acid ethyl ester (Compound d13) under the same conditions as for Compound 17. However, the reaction was performed using acetonitrile in place of THF as a solvent.

Example 216

Compound d15

2-Bis(tert-butoxycarbonyl)amino-3-bromomethyl-5-chloro-benzoic acid ethyl ester

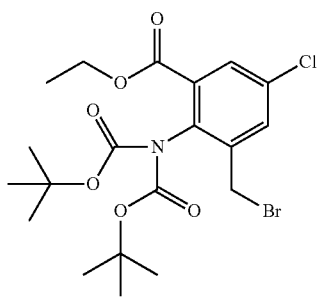 [SMILES: CCOC(=O)c1cc(Cl)cc(CBr)c1N(C(=O)OC(C)(C)C)C(=O)OC(C)(C)C]

The title compound was synthesized from 2-bis(tert-butoxycarbonyl)amino-5-chloro-3-methyl-benzoic acid ethyl ester (Compound d14) under the same conditions as for Compound 12.

Example 217

Compound d16

4-(2-Bis(tert-butoxycarbonyl)amino-5-chloro-3-ethoxycarbonyl-benzyl)-piperazine-1-carboxylic acid tert-butyl ester

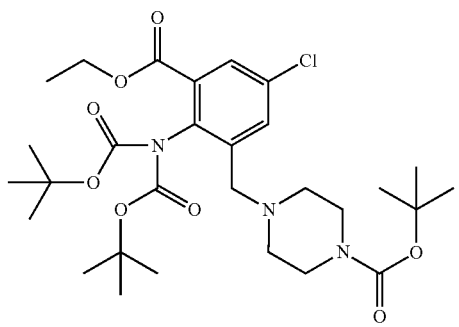 [SMILES: CCOC(=O)c1cc(Cl)cc(CN2CCN(C(=O)OC(C)(C)C)CC2)c1N(C(=O)OC(C)(C)C)C(=O)OC(C)(C)C]

The title compound was synthesized from 2-bis(tert-butoxycarbonyl)amino-3-bromomethyl-5-chloro-benzoic acid ethyl ester (Compound d15) under the same conditions as for Compound d1.

Example 218

Compound d17

2-Amino-5-chloro-3-piperazin-1-ylmethyl-benzoic acid ethyl ester

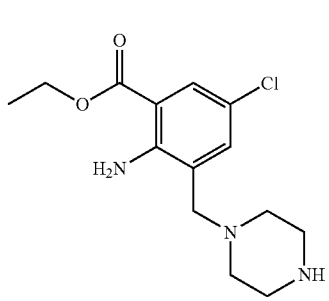 [SMILES: CCOC(=O)c1cc(Cl)cc(CN2CCNCC2)c1N]

The title compound was synthesized from 4-(2-bis(tert-butoxycarbonyl)amino-5-chloro-3-ethoxycarbonyl-benzyl)-piperazine-1-carboxylic acid tert-butyl ester (Compound d16) under the same conditions as for Compound a41.

Example 219

Compound D-5

6-Chloro-3-(5-chloro-2-ethanesulfonyl-benzyl)-8-piperazin-1-ylmethyl-1H-quinazoline-2,4-dione

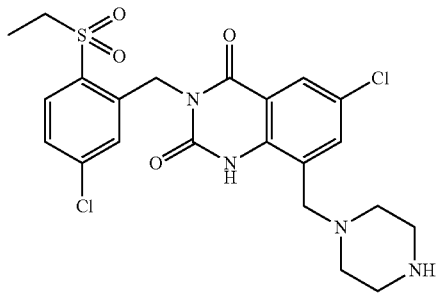

The title compound was synthesized from 2-amino-5-chloro-3-piperazin-1-ylmethyl-benzoic acid ethyl ester (Compound d17) under the same conditions as for Compounds d9, d10, d11, d12, and D-3. However, the reaction was performed without using HOBT under the conditions for Compound d11.

LCMS: m/z 511 [M+H]$^+$

HPLC retention time: 0.52 min (analysis condition H)

Example 220

Compound d18

2-Bis(tert-butoxycarbonyl)amino-5-chloro-3-(4-methyl-piperazin-1-ylmethyl)-benzoic acid ethyl ester

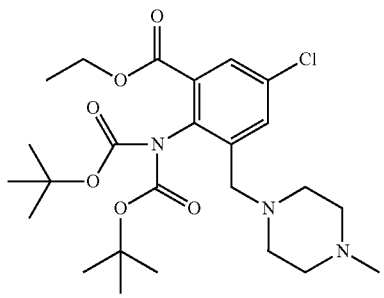 [SMILES: CCOC(=O)c1cc(Cl)cc(CN2CCN(C)CC2)c1N(C(=O)OC(C)(C)C)C(=O)OC(C)(C)C]

The title compound was synthesized from 2-bis(tert-butoxycarbonyl)amino-3-bromomethyl-5-chloro-benzoic acid ethyl ester (Compound d15) under the same conditions as for Compound d1. However, the reaction was performed using 1-methyl-piperazine in place of 1-(tert-butoxycarbonyl)piperazine.

Example 221

Compound d19

2-Amino-5-chloro-3-(4-methyl-piperazin-1-ylmethyl)-benzoic acid ethyl ester

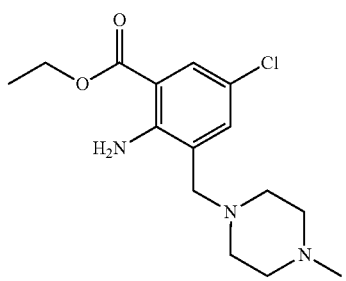 [SMILES: CCOC(=O)c1cc(Cl)cc(CN2CCN(C)CC2)c1N]

The title compound was synthesized from 2-bis(tert-butoxycarbonyl)amino-5-chloro-3-(4-methyl-piperazin-1-ylmethyl)-benzoic acid ethyl ester (Compound d18) under the same conditions as for Compound a41.

Example 222

Compound D-6

6-Chloro-3-(5-chloro-2-ethanesulfonyl-benzyl)-8-(4-methyl-piperazin-1-ylmethyl)-1H-quinazoline-2,4-dione

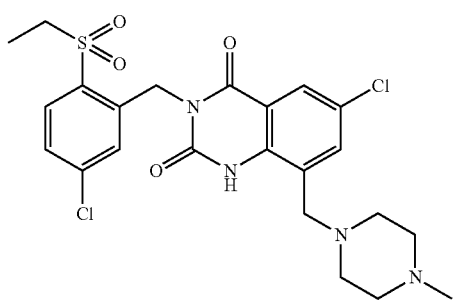 [SMILES: CCS(=O)(=O)c1ccc(Cl)cc1Cn1c(=O)[nH]c2c(CN3CCN(C)CC3)cc(Cl)cc2c1=O]

The title compound was synthesized from 2-amino-5-chloro-3-(4-methyl-piperazin-1-ylmethyl)-benzoic acid ethyl ester (Compound d19) under the same conditions as for Compounds d4, d5, and d6.

LCMS: m/z 525 [M+H]$^+$

HPLC retention time: 2.02 min (analysis condition I)

Example 223

Compound e1

2-Amino-5-bromo-4-bromomethyl-benzoic acid ethyl ester

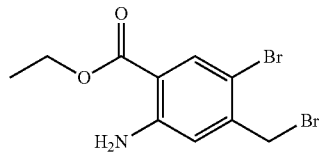

The title compound was synthesized from 2-(bis(tert-butoxycarbonyl)amino)-5-bromo-4-bromomethyl-benzoic acid ethyl ester (Compound 43) under the same conditions as for Compound B-1.

Example 224

Compound e2

4-(5-Amino-2-bromo-4-ethoxycarbonyl-benzyl)-piperazine-1-carboxylic acid tert-butyl ester

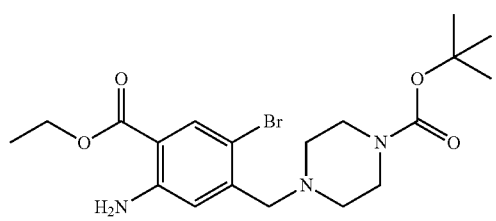

The title compound was synthesized from 2-amino-5-bromo-4-bromomethyl-benzoic acid ethyl ester (Compound e1) under the same conditions as for Compound d1. However, DCM was used as a solvent, and triethylamine was added.

Example 225

Compound e3

4-(5-Amino-2-bromo-4-carboxy-benzyl)-piperazine-1-carboxylic acid tert-butyl ester

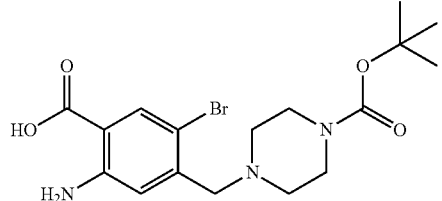

The title compound was synthesized from 4-(5-amino-2-bromo-4-ethoxycarbonyl-benzyl)-piperazine-1-carboxylic acid tert-butyl ester (Compound e2) under the same conditions as for Compound 25.

Example 226

Compound e4

4-[5-Amino-2-bromo-4-(5-chloro-2-ethanesulfonyl-benzylcarbamoyl-benzyl]-piperazine-1-carboxylic acid tert-butyl ester

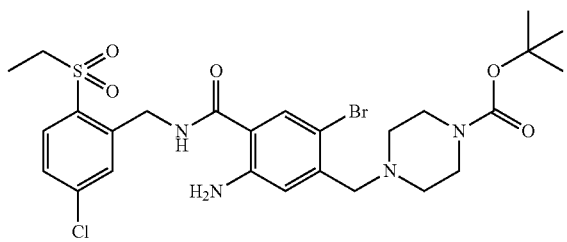 [SMILES: CCS(=O)(=O)c1ccc(Cl)cc1CNC(=O)c1cc(Br)c(CN2CCN(C(=O)OC(C)(C)C)CC2)cc1N]

The title compound was synthesized from 4-(5-amino-2-bromo-4-carboxy-benzyl)-piperazine-1-carboxylic acid tert-butyl ester (Compound e3) under the same conditions as for Compound 26. However, DMF was used as a solvent.

Example 227

Compound e5

4-[6-Bromo-3-(5-chloro-2-ethanesulfonyl-benzyl)-2,4-dioxo-1,2,3,4-tetrahydro-quinazolin-7-ylmethyl]-piperazine-1-carboxylic acid tert-butyl ester The title compound was synthesized from 4-[5-amino-2-bromo-4-(5-chloro-2-ethanesulfonyl-benzylcarbamoyl)-benzyl]-piperazine-1-carboxylic acid tert-butyl ester (Compound e4) under the same conditions as for Compound 37.

Example 228

Compound E-1

6-Bromo-3-(5-chloro-2-ethanesulfonyl-benzyl)-7-piperazin-1-ylmethyl-1H-quinazoline-2,4-dione

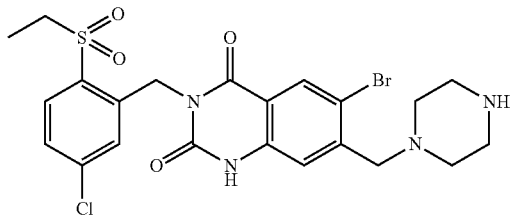 [SMILES: CCS(=O)(=O)c1ccc(Cl)cc1Cn1c(=O)[nH]c2cc(CN3CCNCC3)c(Br)cc2c1=O]

The title compound was synthesized from 4-[6-bromo-3-(5-chloro-2-ethanesulfonyl-benzyl)-2,4-dioxo-1,2,3,4-tetrahydro-quinazolin-7-ylmethyl]-piperazine-1-carboxylic acid tert-butyl ester (Compound e5) under the same conditions as for Compound B-1.

LCMS: m/z 555 [M+H]$^+$

HPLC retention time: 0.52 min (analysis condition D)

Example 229

Compound E-2

6-Bromo-3-(5-chloro-2-ethanesulfonyl-benzyl)-7-(4-methyl-piperazin-1-ylmethyl)-1H-quinazoline-2,4-dione

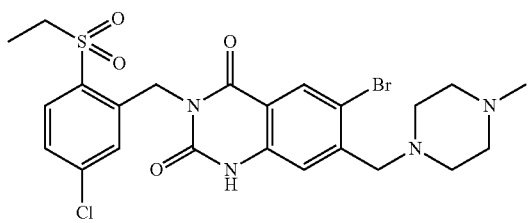 [SMILES: CCS(=O)(=O)c1ccc(Cl)cc1Cn1c(=O)[nH]c2cc(CN3CCN(C)CC3)c(Br)cc2c1=O]

The title compound was synthesized from 6-bromo-3-(5-chloro-2-ethanesulfonyl-benzyl)-7-piperazin-1-ylmethyl-1H-quinazoline-2,4-dione (Compound E-1) under the same conditions as for Compound B-9.

LCMS: m/z 569 [M+H]$^+$

HPLC retention time: 0.54 min (analysis condition D)

Example 230

Compound E-3

6-Bromo-3-(5-chloro-2-ethanesulfonyl-benzyl)-7-(4-isopropyl-piperazin-1-ylmethyl)-1H-quinazoline-2,4-dione

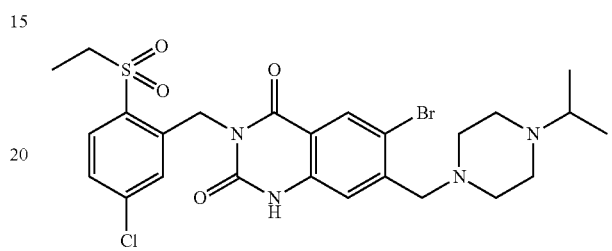

The title compound was synthesized from 6-bromo-3-(5-chloro-2-ethanesulfonyl-benzyl)-7-piperazin-1-ylmethyl-1H-quinazoline-2,4-dione (Compound E-1) under the same conditions as for Compound B-4.

LCMS: m/z 597 [M+H]$^+$

HPLC retention time: 0.55 min (analysis condition D)

Example 231

Compound E-4

6-Bromo-3 (5-chloro-2-ethanesulfonyl-benzyl)-7-[4-(tetrahydro-pyran-4-yl)-piperazin-1-ylmethyl]-1H-quinazoline-2,4-dione

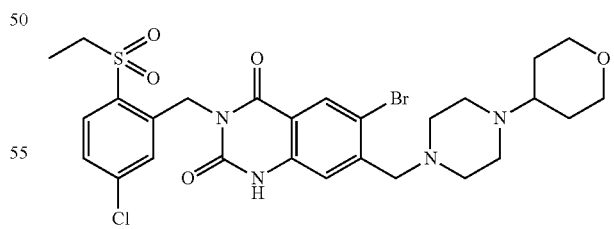

The title compound was synthesized from 6-bromo-3-(5-chloro-2-ethanesulfonyl-benzyl)-7-piperazin-1-ylmethyl-1H-quinazoline-2,4-dione (Compound E-1) under the same conditions as for Compound B-5.

LCMS: m/z 639 [M+H]$^+$

HPLC retention time: 0.54 min (analysis condition D)

Example 232

Compound e6

2-(Bis(tert-butoxycarbonyl)amino)-5-bromo-4-((R)-3-tert-butoxycarbonylamino-pyrrolidin-1-ylmethyl)-benzoic acid ethyl ester

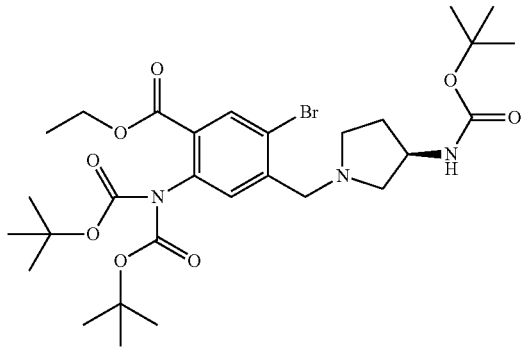 [SMILES: CCOC(=O)c1cc(Br)c(CN2CC[C@@H](NC(=O)OC(C)(C)C)C2)cc1N(C(=O)OC(C)(C)C)C(=O)OC(C)(C)C]

The title compound was synthesized from 2-(bis(tert-butoxycarbonyl)amino)-5-bromo-4-bromomethyl-benzoic acid ethyl ester (Compound 43) and (R)-pyrrolidin-3-yl-carbamic acid tert-butyl ester under the same conditions as for Compound d1. However, DMF was used as a solvent, and potassium carbonate was added.

Example 233

Compound e7

2-Amino-4-((R)-3-amino-pyrrolidin-1-ylmethyl)-5-bromo-benzoic acid ethyl ester

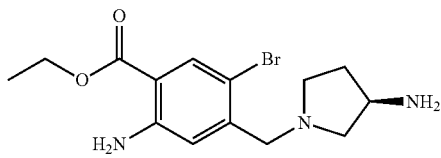 [SMILES: CCOC(=O)c1cc(Br)c(CN2CC[C@@H](N)C2)cc1N]

The title compound was synthesized from 2-(bis(tert-butoxycarbonyl)amino)-5-bromo-4-((R)-3-tert-butoxycarbonylamino-pyrrolidin-1-ylmethyl)-benzoic acid ethyl ester (Compound e6) under the same conditions as for Compound B-1.

Example 234

Compound e8

2-Amino-5-bromo-4-((R)-3-tert-butoxycarbonylamino-pyrrolidin-1-ylmethyl)-benzoic acid ethyl ester

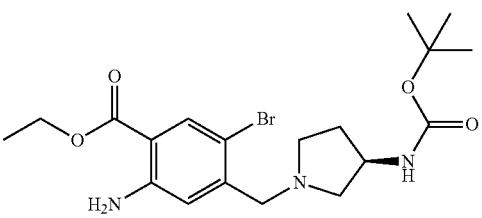 [SMILES: CCOC(=O)c1cc(Br)c(CN2CC[C@@H](NC(=O)OC(C)(C)C)C2)cc1N]

The title compound was synthesized from 2-amino-4-((R)-3-amino-pyrrolidin-1-ylmethyl)-5-bromo-benzoic acid ethyl ester (Compound e7) under the same conditions as for Compound d3.

Example 235

Compound e9

2-Amino-5-bromo-4-((R)-3-tert-butoxycarbonyl amino-pyrrolidin-1-ylmethyl)-benzoic acid

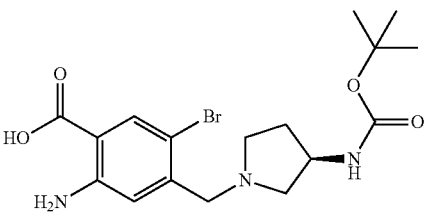 [SMILES: CC(C)(C)OC(=O)N[C@@H]1CCN(Cc2cc(N)c(C(=O)O)cc2Br)C1]

The title compound was synthesized from 2-amino-5-bromo-4-((R)-3-tert-butoxycarbonylamino-pyrrolidin-1-ylmethyl)-benzoic acid ethyl ester (Compound e8) under the same conditions as for Compound 25.

Example 236

Compound e10

{(R)-1-[5-Amino-2-bromo-4-(5-chloro-2-ethanesulfonyl-benzylcarbamoyl)-benzyl]-pyrrolidin-3-yl}-carbamic acid tert-butyl ester

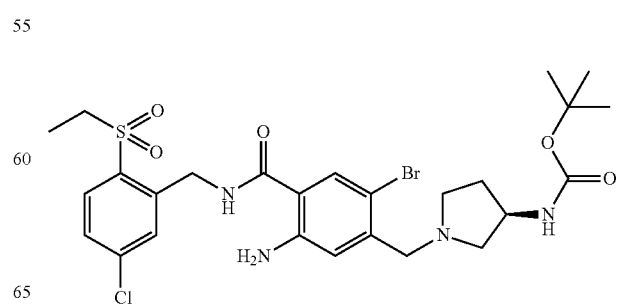

The title compound was synthesized from 2-amino-5-bromo-4-((R)-3-tert-butoxycarbonylamino-pyrrolidin-1-ylmethyl)-benzoic acid (Compound e9) under the same conditions as for Compound 26.

Example 237

Compound E-5

{(R)-1-[6-Bromo-3-(5-chloro-2-ethanesulfonyl-benzyl)-2,4-dioxo-1,2,3,4-tetrahydro-quinazolin-7-ylmethyl]-pyrrolidin-3-yl}-carbamic acid tert-butyl ester

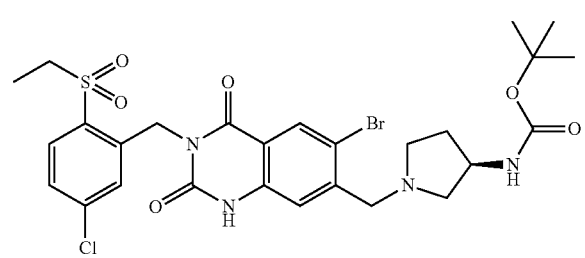 [SMILES: CCS(=O)(=O)c1ccc(Cl)cc1Cn1c(=O)[nH]c2cc(CN3CC[C@@H](NC(=O)OC(C)(C)C)C3)c(Br)cc2c1=O]

The title compound was synthesized from {(R)-1-[5-amino-2-bromo-4-(5-chloro-2-ethanesulfonyl-benzyl carbamoyl)-benzyl]-pyrrolidin-3-yl}-carbamic acid tert-butyl ester (Compound e10) under the same conditions as for Compound A-6.

LCMS: m/z 655 [M+H]$^+$

HPLC retention time: 0.59 min (analysis condition H)

Example 238

Compound E-6

7-((R)-3-Amino-pyrrolidin-1-ylmethyl)-6-bromo-3-(5-chloro-2-ethanesulfonyl-benzyl)-1H-quinazoline-2,4-dione

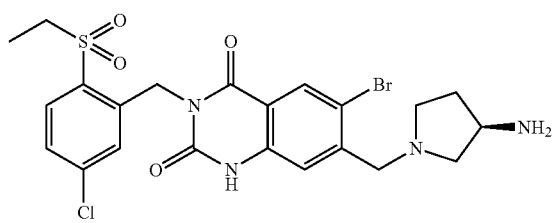 [SMILES: CCS(=O)(=O)c1ccc(Cl)cc1Cn1c(=O)[nH]c2cc(CN3CC[C@@H](N)C3)c(Br)cc2c1=O]

The title compound was synthesized from {(R)-1-[6-bromo-3-(5-chloro-2-ethanesulfonyl-benzyl)-2,4-di oxo-1,2,3,4-tetrahydro-quinazolin-7-ylmethyl]-pyrrolidin-3-yl}-carbamic acid tert-butyl ester (Compound E-5) under the same conditions as for Compound B-1.

LCMS: m/z 555 [M+H]$^+$

HPLC retention time: 0.47 min (analysis condition G)

Example 239

Compound E-7

6-Bromo-3-(5-chloro-2-ethanesulfonyl-benzyl)-7-((R)-3-dimethylamino-pyrrolidin-1-ylmethyl)-1H-quinazoline-2,4-dione

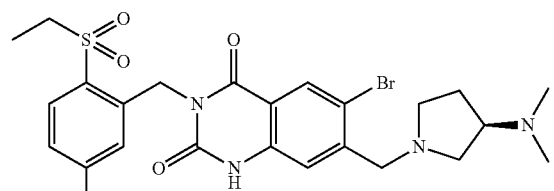

The title compound was synthesized from 7-((R)-3-amino-pyrrolidin-1-ylmethyl)-6-bromo-3-(5-chloro-2-ethanesulfonyl-benzyl)-1H-quinazoline-2,4-dione (Compound E-6) under the same conditions as for Compound B-9.

LCMS: m/z 583 [M+H]$^+$

HPLC retention time: 0.51 min (analysis condition H)

Example 240

Compound E-8

N-{(R)-1-[6-Bromo-3-(5-chloro-2-ethanesulfonyl-benzyl)-2,4-dioxo-1,2,3,4-tetrahydro-quinazolin-7-ylmethyl]-pyrrolidin-3-yl}-acetamide The title compound was synthesized from 7-((R)-3-amino-pyrrolidin-1-ylmethyl)-6-bromo-3-(5-chloro-2-ethanesulfonyl-benzyl)-1H-quinazoline-2,4-dione (Compound E-6) under the same conditions as for Compound B-18.

LCMS: m/z 597 [M+H]$^+$

HPLC retention time: 0.47 min (analysis condition H)

Example 241

Compound E-9

N-{(R)-1-[6-Bromo-3-(5-chloro-2-ethanesulfonyl-benzyl)-2,4-dioxo-1,2,3,4-tetrahydro-quinazolin-7-ylmethyl]-pyrrolidin-3-yl}-methanesulfonamide

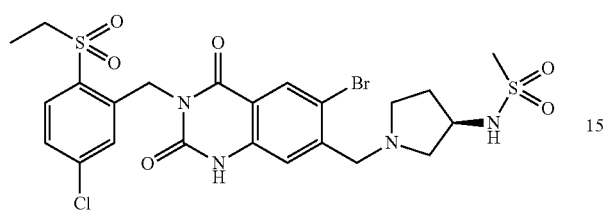

The title compound was synthesized from 7-((R)-3-amino-pyrrolidin-1-ylmethyl)-6-bromo-3-(5-chloro-2-ethanesulfonyl-benzyl)-1H-quinazoline-2,4-dione (Compound E-6) under the same conditions as for Compound C-6.

LCMS: m/z 633 [M+H]$^+$
HPLC retention time: 0.50 min (analysis condition H)

Example 242

Compound E-10

N-{(R)-1-[6-Bromo-3-(5-chloro-2-ethanesulfonyl-benzyl)-2,4-dioxo-1,2,3,4-tetrahydro-quinazolin-7-ylmethyl]-pyrrolidin-3-yl}-dimethylaminosulfonamide

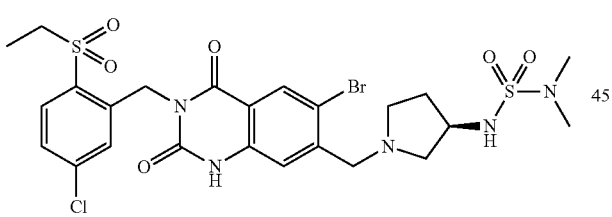

Dimethylsulfamoyl chloride (7.18 μl, 0.067 mmol) was added to a solution of 7-((R)-3-amino-pyrrolidin-1-ylmethyl)-6-bromo-3-(5-chloro-2-ethanesulfonyl-benzyl)-1H-quinazoline-2,4-dione (Compound E-6, 25.0 mg, 0.045 mmol) and triethylamine (18.8 μl, 0.14 mmol) in DMA (1.0 ml), and the mixture was stirred at room temperature for three hours. A saturated aqueous sodium bicarbonate solution was added to the reaction mixture, followed by extraction with ethyl acetate. The organic layer was washed with brine and then dried over anhydrous sodium sulfate. The drying agent was removed by filtration, and the residue obtained after concentration under reduced pressure was purified by preparative HPLC (water/acetonitrile, 0.05% TFA) to give the title compound (15.7 mg, yield: 52%) as a colorless solid.

LCMS: m/z 662 [M+H]$^+$
HPLC retention time: 0.54 min (analysis condition H)

Example 243

Compound e1

2-(Bis(tert-butoxycarbonyl)amino)-5-bromo-4-((R)-3-tert-butoxycarbonyl-methyl-amino-pyrrolidin-1-ylmethyl)-benzoic acid ethyl ester

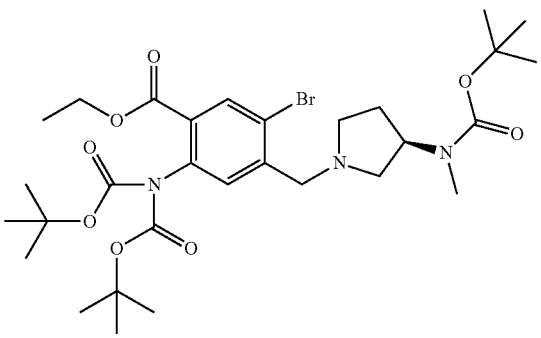 [SMILES: CCOC(=O)c1cc(Br)c(CN2CC[C@@H](N(C)C(=O)OC(C)(C)C)C2)cc1N(C(=O)OC(C)(C)C)C(=O)OC(C)(C)C]

The title compound was synthesized from 2-(bis(tert-butoxycarbonyl)amino)-5-bromo-4-bromomethyl-benzoic acid ethyl ester (Compound 43) using methyl-(R)-pyrrolidin-3-yl-carbamic acid tert-butyl ester in place of 1-(tert-butoxycarbonyl)piperazine under the same conditions as for Compound d1. However, the reaction was performed at room temperature.

Example 244

Compound e12

2-Amino-5-bromo-4-((R)-3-methylamino-pyrrolidin-1-ylmethyl)-benzoic acid ethyl ester

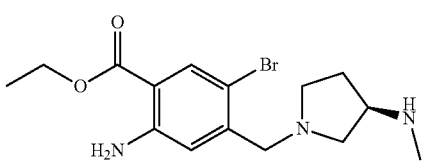 [SMILES: CCOC(=O)c1cc(Br)c(CN2CC[C@@H](NC)C2)cc1N]

The title compound was synthesized from 2-(bis(tert-butoxycarbonyl)amino)-5-bromo-4-((R)-3-tert-butoxycarbonyl-methyl-amino-pyrrolidin-1-ylmethyl)-benzoic acid ethyl ester (Compound e11) under the same conditions as for Compound B-1.

Example 245

Compound e13

2-Amino-5-bromo-4-[(R)-3-(tert-butoxycarbonyl-methyl-amino)-pyrrolidin-1-ylmethyl]-benzoic acid ethyl ester

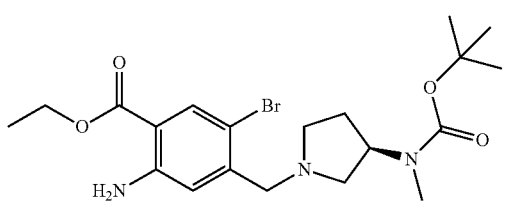 [SMILES: CCOC(=O)c1cc(Br)c(CN2CC[C@@H](N(C)C(=O)OC(C)(C)C)C2)cc1N]

The title compound was synthesized from 2-amino-5-bromo-4-((R)-3-methylamino-pyrrolidin-1-ylmethyl)-benzoic acid ethyl ester (Compound e12) under the same conditions as for Compound d3.

Example 246

Compound e14

2-Amino-5-bromo-4-[(R)-3-(tert-butoxycarbonyl-methyl-amino)-pyrrolidin-1-ylmethyl]-benzoic acid

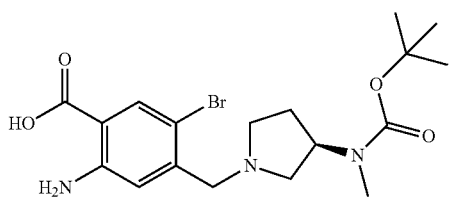 [SMILES: CN(C(=O)OC(C)(C)C)[C@@H]1CCN(Cc2cc(N)c(C(=O)O)cc2Br)C1]

The title compound was synthesized from 2-amino-5-bromo-4-[(R)-3-(tert-butoxycarbonyl-methyl-amino)-pyrrolidin-1-ylmethyl]-benzoic acid ethyl ester (Compound e13) under the same conditions as for Compound 25.

Example 247

Compound e15

{(R)-1-[5-Amino-2-bromo-4-(5-chloro-2-ethanesulfonyl-benzylcarbamyl)-benzyl]-pyrrolidin-3-yl}-methyl-carbamic acid tert-butyl ester

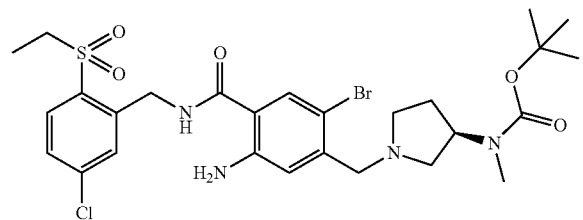 [SMILES: CCS(=O)(=O)c1ccc(Cl)cc1CNC(=O)c1cc(Br)c(CN2CC[C@@H](N(C)C(=O)OC(C)(C)C)C2)cc1N]

The title compound was synthesized from 2-amino-5-bromo-4-[(R)-3-(tert-butoxycarbonyl-methyl-amino)-pyrrolidin-1-ylmethyl]-benzoic acid (Compound e14) under the same conditions as for Compound 26.

Example 248

Compound e16

{(R)-1-[6-Bromo-3-(5-chloro-2-ethanesulfonyl-benzyl)-2,4-dioxo-1,2,3,4-tetrahydro-quinazolin-7-ylmethyl]-pyrrolidin-3-yl}-methyl-carbamic acid tert-butyl ester

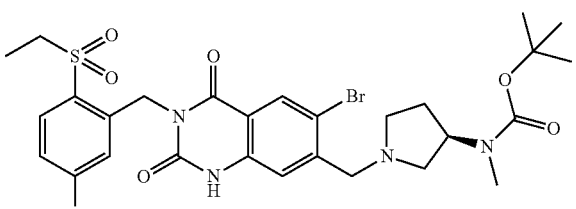

The title compound was synthesized from {(R)-1-[5-amino-2-bromo-4-(5-chloro-2-ethanesulfonyl-benzylcarbamoyl)-benzyl]-pyrrolidin-3-yl}-methyl-carbamic acid tert-butyl ester (Compound e15) under the same conditions as for Compound A-6.

Example 249

Compound E-11

6-Bromo-3-(5-chloro-2-ethanesulfonyl-benzyl)-7-((R)-3-methylamino-pyrrolidin-1-ylmethyl)-1H-quinazoline-2,4-dione

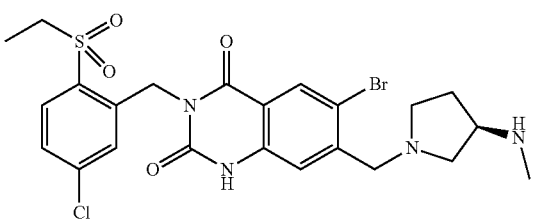 [SMILES: CCS(=O)(=O)c1ccc(Cl)cc1Cn1c(=O)[nH]c2cc(CN3CC[C@@H](NC)C3)c(Br)cc2c1=O]

The title compound was synthesized from {(R)-1-[6-bromo-3-(5-chloro-2-ethanesulfonyl-benzyl)-2,4-dioxo-1,2,3,4-tetrahydro-quinazolin-7-ylmethyl]-pyrrolidin-3-yl}-methyl-carbamic acid tert-butyl ester (Compound e16) under the same conditions as for Compound B-1.
LCMS: m/z 569 [M+H]$^+$
HPLC retention time: 0.48 min (analysis condition H)

Examples 250 to 253

The following compounds of Table 2 were synthesized from 2-(bis(tert-butoxycarbonyl)amino)-5-bromo-4-bromomethyl-benzoic acid ethyl ester (Compound 43) and corresponding amines under the same conditions as for Compounds e11, e12, e13, e14, e15, e16, and E-11.

TABLE 2

| Example | Compound number | Structure | Compound name | HPLC condition | Retention time (min) | m/z [M + H]+ |
|---|---|---|---|---|---|---|
| 250 | E-12 | 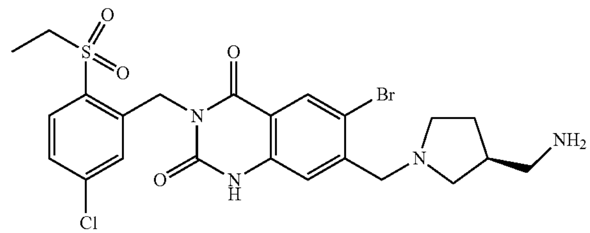 [SMILES: CCS(=O)(=O)c1ccc(Cl)cc1Cn1c(=O)[nH]c2cc(CN3CC[C@@H](CN)C3)c(Br)cc2c1=O] | 7-((S)-3-Aminomethyl-pyrrolidin-1-ylmethyl)-6-bromo-3-(5-chloro-2-ethanesulfonyl-benzyl)-1H-quinazoline-2,4-dione | H | 0.39 | 569 |
| 251 | E-14 | 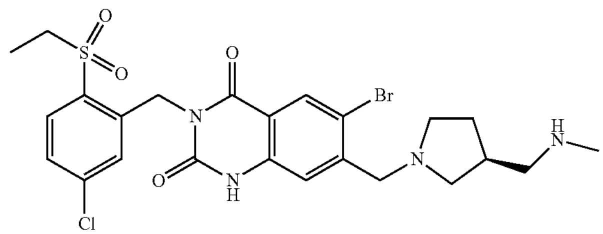 [SMILES: CCS(=O)(=O)c1ccc(Cl)cc1Cn1c(=O)[nH]c2cc(CN3CC[C@@H](CNC)C3)c(Br)cc2c1=O] | 6-Bromo-3-(5-chloro-2-ethanesulfonyl-benzyl)-7-((S)-3-methylaminomethyl-pyrrolidin-1-ylmethyl)-1H-quinazoline-2,4-dione | H | 0.39 | 583 |
| 252 | E-15 | 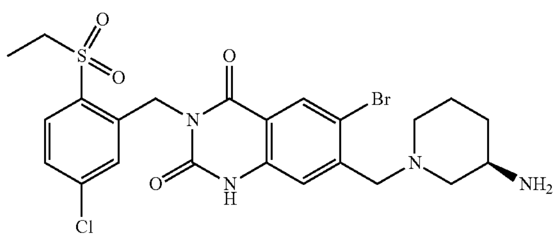 [SMILES: CCS(=O)(=O)c1ccc(Cl)cc1Cn1c(=O)[nH]c2cc(CN3CCC[C@@H](N)C3)c(Br)cc2c1=O] | 7-((R)-3-Amino-piperidin-1-ylmethyl)-6-bromo-3-(5-chloro-2-ethanesulfonyl-benzyl)-1H-quinazoline-2,4-dione | H | 0.49 | 569 |
| 253 | E-17 | 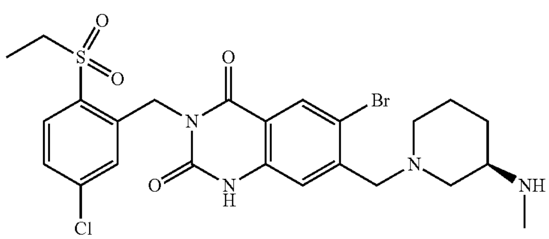 [SMILES: CCS(=O)(=O)c1ccc(Cl)cc1Cn1c(=O)[nH]c2cc(CN3CCC[C@@H](NC)C3)c(Br)cc2c1=O] | 6-Bromo-3-(5-chloro-2-ethanesulfonyl-benzyl)-7-((R)-3-methylamino-piperidin-1-ylmethyl)-1H-quinazoline-2,4-dione | H | 0.52 | 583 |

Example 254

Compound E-13

6-Bromo-3-(5-chloro-2-ethanesulfonyl-benzyl)-7-((S)-3-dimethylaminomethyl-pyrrolidin-1-ylmethyl)-1H-quinazoline-2,4-dione

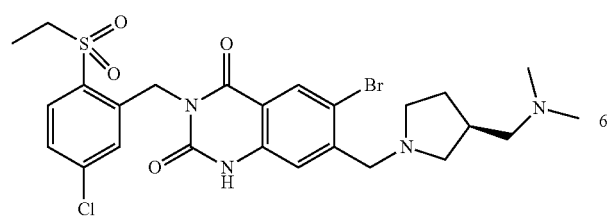

The title compound was synthesized from 7-((S)-3-aminomethyl-pyrrolidin-1-ylmethyl)-6-bromo-3-(5-chloro-2-ethanesulfonyl-benzyl)-1H-quinazoline-2,4-dione (Compound E-12) under the same conditions as for Compound B-9.

LCMS: m/z 597 [M+H]+

HPLC retention time: 0.52 min (analysis condition F)

Example 255

Compound E-16

6-Bromo-3-(5-chloro-2-ethanesulfonyl-benzyl)-7-((R)-3-dimethylamino-piperidin-1-ylmethyl)-1H-quinazoline-2,4-dione

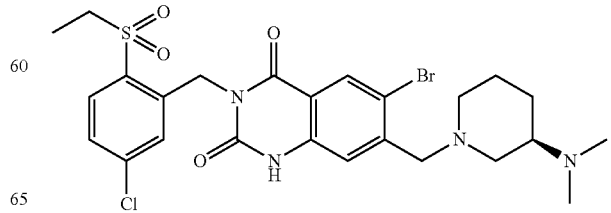

The title compound was synthesized from 7-((R)-3-amino-piperidin-1-ylmethyl)-6-bromo-3-(5-chloro-2-ethanesulfonyl-benzyl)-1H-quinazoline-2,4-dione (Compound E-15) under the same conditions as for Compound B-9.

LCMS: m/z 597 [M+H]+

HPLC retention time: 0.69 min (analysis condition F)

Example 256

Compound e17

2-(Bis(tert-butoxycarbonyl)amino)-5-bromo-4-(3-piperidin-1-yl-pyrrolidin-1-ylmethyl)-benzoic acid ethyl ester

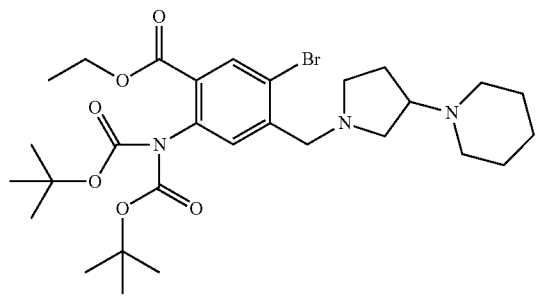 [SMILES: CCOC(=O)c1cc(Br)c(CN2CCC(N3CCCCC3)C2)cc1N(C(=O)OC(C)(C)C)C(=O)OC(C)(C)C]

The title compound was synthesized from 2-(bis(tert-butoxycarbonyl)amino)-5-bromo-4-bromomethyl-benzoic acid ethyl ester (Compound 43) using 1-pyrrolidin-3-yl-piperidine in place of 1-(tert-butoxycarbonyl)piperazine under the same conditions as for Compound d1. However, DMF was used as a solvent, and potassium carbonate was added.

Example 257

Compound e18

2-Amino-5-bromo-4-(3-piperidin-1-yl-pyrrolidin-1-ylmethyl)-benzoic acid ethyl ester

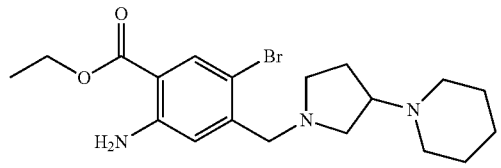 [SMILES: CCOC(=O)c1cc(Br)c(CN2CCC(N3CCCCC3)C2)cc1N]

The title compound was synthesized from 2-(bis(tert-butoxycarbonyl)amino)-5-bromo-4-(3-piperidin-1-yl-pyrrolidin-1-ylmethyl)-benzoic acid ethyl ester (Compound e17) under the same conditions as for Compound B-1.

Example 258

Compound e19

2-Amino-5-bromo-4-(3-piperidin-1-yl-pyrrolidin-1-ylmethyl)-benzoic acid

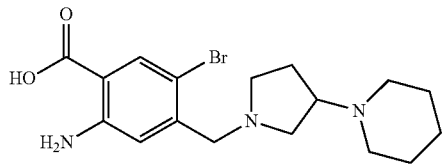 [SMILES: Nc1cc(CN2CCC(N3CCCCC3)C2)c(Br)cc1C(=O)O]

The title compound was synthesized from 2-amino-5-bromo-4-(3-piperidin-1-yl-pyrrolidin-1-ylmethyl)-benzoic acid ethyl ester (Compound e18) under the same conditions as for Compound 25.

Example 259

Compound e20

2-Amino-5-bromo-N-(5-chloro-2-ethanesulfonyl-benzyl)-4-(3-piperidin-1-yl-pyrrolidin-1-ylmethyl)-benzamide

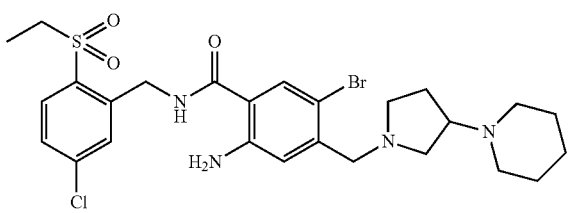 [SMILES: CCS(=O)(=O)c1ccc(Cl)cc1CNC(=O)c1cc(Br)c(CN2CCC(N3CCCCC3)C2)cc1N]

The title compound was synthesized from 2-amino-5-bromo-4-(3-piperidin-1-yl-pyrrolidin-1-ylmethyl)-benzoic acid (Compound e19) under the same conditions as for Compound 26.

Example 260

Compound E-18

6-Bromo-3-(5-chloro-2-ethanesulfonyl-benzyl)-7-(3-piperidin-1-yl-pyrrolidin-1-ylmethyl)-1H-quinazoline-2,4-dione

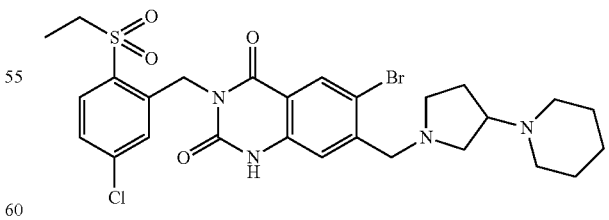

The title compound was synthesized from 2-amino-5-bromo-N-(5-chloro-2-ethanesulfonyl-benzyl)-4-(3-piperidin-1-yl-pyrrolidin-1-ylmethyl)-benzamide (Compound e20) under the same conditions as for Compound A-6.

LCMS: m/z 623 [M+H]+

HPLC retention time: 0.53 min (analysis condition G)

Examples 261 to 268

The following compounds of Table 3 were synthesized from 2-(bis(tert-butoxycarbonyl)amino)-5-bromo-4-bromomethyl-benzoic acid ethyl ester (Compound 43) and corresponding amines under the same conditions as for Compounds e17, e18, e19, e20, and E-18.

TABLE 3

| Example | Compound number | Structure | Compound name | HPLC condition | Retention time (min) | m/z [M + H]+ |
|---|---|---|---|---|---|---|
| 261 | E-19 | 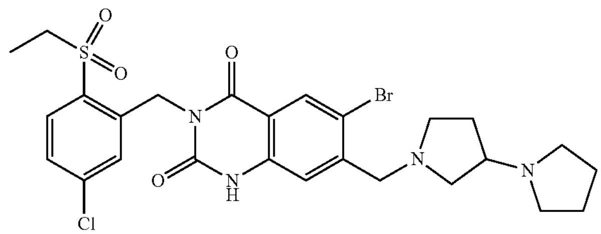 [SMILES: CCS(=O)(=O)c1ccc(Cl)cc1Cn1c(=O)[nH]c2cc(CN3CCC(N4CCCC4)C3)c(Br)cc2c1=O] | 7-[1,3']Bipyrrolidinyl-1'-ylmethyl-6-bromo-3-(5-chloro-2-ethanesulfonyl-benzyl)-1H-quinazoline-2,4-dione | H | 0.52 | 609 |
| 262 | E-20 | 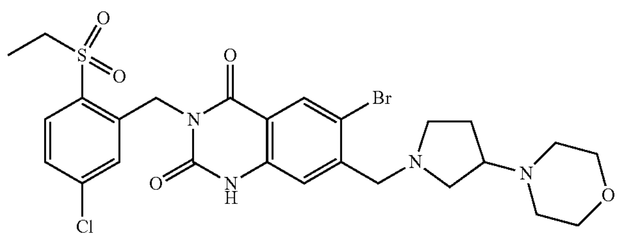 [SMILES: CCS(=O)(=O)c1ccc(Cl)cc1Cn1c(=O)[nH]c2cc(CN3CCC(N4CCOCC4)C3)c(Br)cc2c1=O] | 6-Bromo-3-(5-chloro-2-ethanesulfonyl-benzyl)-7-(3-morpholin-4-yl-pyrrolidin-1-ylmethyl)-1H-quinazoline-2,4-dione | H | 0.52 | 625 |
| 263 | E-21 | 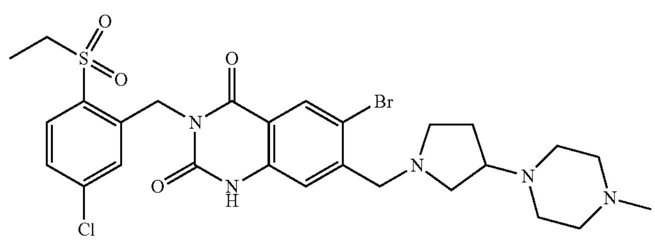 [SMILES: CCS(=O)(=O)c1ccc(Cl)cc1Cn1c(=O)[nH]c2cc(CN3CCC(N4CCN(C)CC4)C3)c(Br)cc2c1=O] | 6-Bromo-3-(5-chloro-2-ethanesulfonyl-benzyl-7-[3-(4-methyl-piperazin-1-yl)-pyrrolidin-1-ylmethyl]-1H-quinazoline-2,4-dione | H | 0.53 | 638 |
| 264 | E-22 | 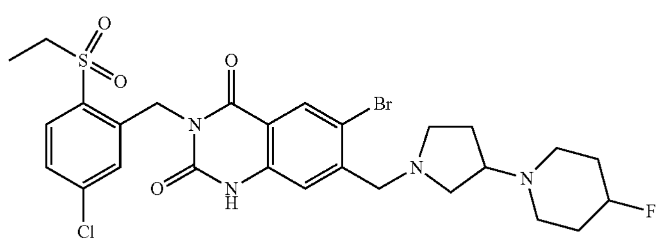 [SMILES: CCS(=O)(=O)c1ccc(Cl)cc1Cn1c(=O)[nH]c2cc(CN3CCC(N4CCC(F)CC4)C3)c(Br)cc2c1=O] | 6-Bromo-3-(5-chloro-2-ethanesulfonyl-benzyl-7-[3-(4-fluoro-piperidin-1-yl)-pyrrolidin-1-ylmethyl]-1H-quinazoline-2,4-dione | H | 0.55 | 641 |
| 265 | E-23 | 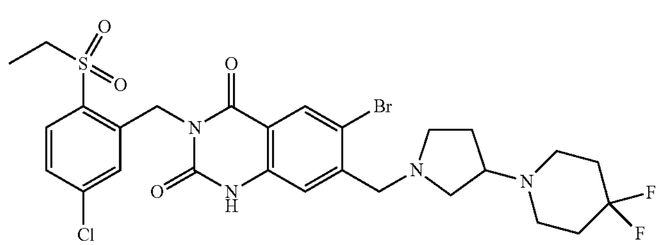 [SMILES: CCS(=O)(=O)c1ccc(Cl)cc1Cn1c(=O)[nH]c2cc(CN3CCC(N4CCC(F)(F)CC4)C3)c(Br)cc2c1=O] | 6-Bromo-3-(5-chloro-2-ethanesulfonyl-benzyl)-7-[3-(4,4-difluoro-piperidin-1-yl)-pyrrolidin-1-ylmethyl]-1H-quinazoline-2,4-dione | H | 0.57 | 659 |

TABLE 3-continued

| Example | Compound number | Structure | Compound name | HPLC condition | Retention time (min) | m/z [M + H]+ |
|---|---|---|---|---|---|---|
| 266 | E-24 | 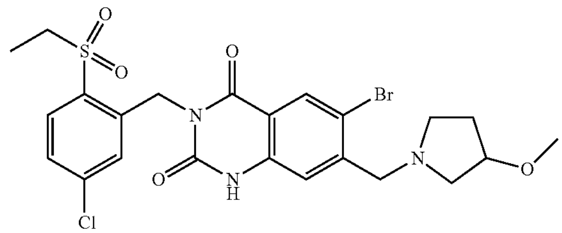 [SMILES: CCS(=O)(=O)c1ccc(Cl)cc1Cn1c(=O)[nH]c2cc(CN3CCC(OC)C3)c(Br)cc2c1=O] | 6-Bromo-3-(5-chloro-2-ethanesulfonyl-benzyl)-7-((R)-3-methoxy-pyrrolidin-1-ylmethyl)-1H-quinazoline-2,4-dione | H | 0.66 | 570 |
| 267 | E-25 | 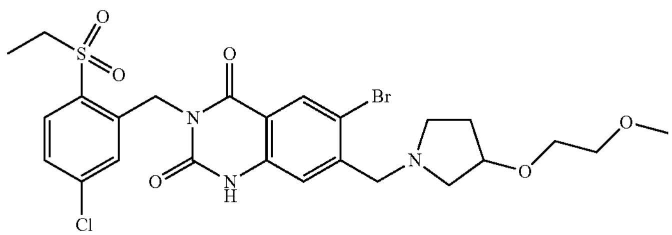 [SMILES: CCS(=O)(=O)c1ccc(Cl)cc1Cn1c(=O)[nH]c2cc(CN3CCC(OCCOC)C3)c(Br)cc2c1=O] | 6-Bromo-3-(5-chloro-2-ethanesulfonyl-benzyl)-7-[(R)-3-(2-methoxy-ethoxy)-pyrrolidin-1-ylmethyl]-1H-quinazoline-2,4-dione | H | 0.67 | 614 |
| 268 | E-26 | 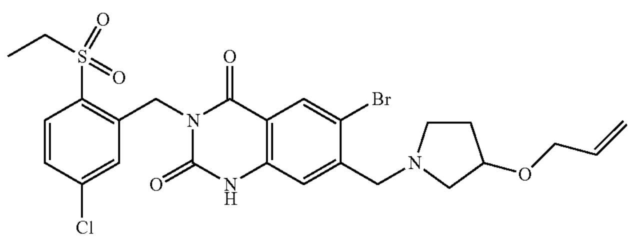 [SMILES: C=CCOC1CCN(Cc2cc3[nH]c(=O)n(Cc4cc(Cl)ccc4S(=O)(=O)CC)c(=O)c3cc2Br)C1] | 7-((R)-3-Allyloxy-pyrrolidin-1-ylmethyl)-6-bromo-3-(5-chloro-2-ethanesulfonyl-benzyl)-1H-quinazoline-2,4-dione | G | 0.62 | 596 |

Example 269

Compound e21

2-(Bis(tert-butoxycarbonyl)amino)-5-bromo-4-((R)-3-hydroxy-pyrrolidin-1-ylmethyl)-benzoic acid ethyl ester

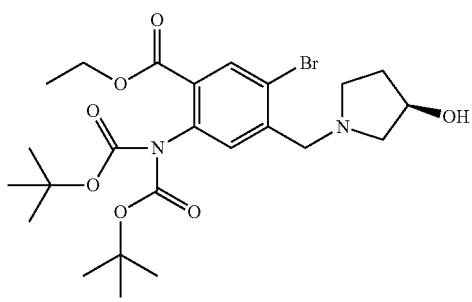 [SMILES: CCOC(=O)c1cc(Br)c(CN2CC[C@@H](O)C2)cc1N(C(=O)OC(C)(C)C)C(=O)OC(C)(C)C]

The title compound was synthesized from 2-(bis(tert-butoxycarbonyl)amino)-5-bromo-4-bromomethyl-benzoic acid ethyl ester (Compound 43) using (R)-pyrrolidin-3-ol in place of 1-(tert-butoxycarbonyl)piperazine under the same conditions as for Compound d1. However, the reaction was performed at room temperature.

Example 270

Compound e22

2-Amino-5-bromo-4-((R)-3-hydroxy-pyrrolidin-1-ylmethyl)-benzoic acid ethyl ester

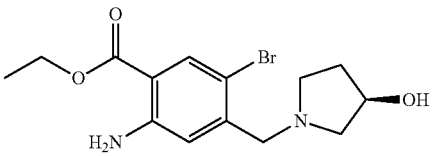 [SMILES: CCOC(=O)c1cc(Br)c(CN2CC[C@@H](O)C2)cc1N]

The title compound was synthesized from 2-(bis(tert-butoxycarbonyl)amino)-5-bromo-4-((R)-3-hydroxy-pyrrolidin-1-ylmethyl)-benzoic acid ethyl ester (Compound e21) under the same conditions as for Compound B-1.

Example 271

Compound e23

2-Amino-5-bromo-4-((R)-3-hydroxy-pyrrolidin-1-ylmethyl)-benzoic acid

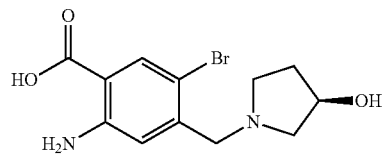 [SMILES: Nc1cc(CN2CC[C@@H](O)C2)c(Br)cc1C(=O)O]

The title compound was synthesized from 2-amino-5-bromo-4-((R)-3-hydroxy-pyrrolidin-1-ylmethyl)-benzoic acid ethyl ester (Compound e22) under the same conditions as for Compound 25.

Example 272

Compound e24

2-Amino-5-bromo-N-(5-chloro-2-ethanesulfonyl-benzyl)-4-((R)-3-hydroxy-pyrrolidin-1-ylmethyl)-benzamide

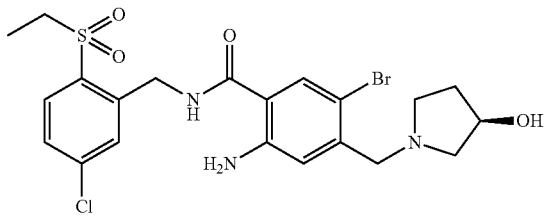 [SMILES: CCS(=O)(=O)c1ccc(Cl)cc1CNC(=O)c1cc(Br)c(CN2CC[C@@H](O)C2)cc1N]

The title compound was synthesized from 2-amino-5-bromo-4-((R)-3-hydroxy-pyrrolidin-1-ylmethyl)-benzoic acid (Compound e23) under the same conditions as for Compound 26.

Example 273

Compound e25

2-Amino-5-bromo-4-[(R)-3-(tert-butyl-dimethyl-silanyloxy)-pyrrolidin-1-ylmethyl]-N-(5-chloro-2-ethanesulfonyl-benzyl)-benzamide

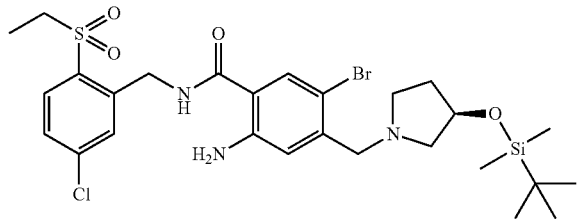 [SMILES: CCS(=O)(=O)c1ccc(Cl)cc1CNC(=O)c1cc(Br)c(CN2CC[C@@H](O[Si](C)(C)C(C)(C)C)C2)cc1N]

tert-Butyldimethylchlorosilane (23.8 mg, 0.16 mmol) was added to a solution of 2-amino-5-bromo-N-(5-chloro-2-ethanesulfonyl-benzyl)-4-((R)-3-hydroxy-pyrrolidin-1-ylmethyl)-benzamide (Compound e24, 55.9 mg, 0.11 mmol) and imidazole (21.5 mg, 0.32 mmol) in dichloromethane (0.50 ml), and then stirred at room temperature. After three hours, imidazole (21.0 mg, 0.31 mmol) and tert-butyldimethylchlorosilane (23.0 mg, 0.15 mmol) were further added, and the mixture was further stirred at room temperature for 1.5 hours. Water was added to the reaction mixture, followed by extraction with ethyl acetate. The organic layer was washed with brine and then dried over anhydrous sodium sulfate. The drying agent was removed by filtration, and the residue obtained after concentration under reduced pressure was purified by silica gel column chromatography (ethyl acetate/hexane) to give the title compound (63.9 mg, yield: 94%) as a colorless solid.
LCMS: m/z 644 [M+H]$^+$
HPLC retention time: 0.70 min (analysis condition H)

Example 274

Compound e26

6-Bromo-7-[(R)-3-(tert-butyl-dimethyl-silanyloxy)-pyrrolidin-1-ylmethyl]-3-(5-chloro-2-ethanesulfonyl-benzyl)-1H-quinazoline-2,4-dione

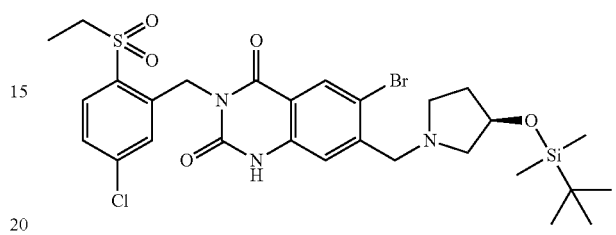

The title compound was synthesized from 2-amino-5-bromo-4-[(R)-3-(tert-butyl-dimethyl-silanyloxy)-pyrrolidin-1-ylmethyl]-N-(5-chloro-2-ethanesulfonyl-benzyl)-benzamide (Compound e25) under the same conditions as for Compound A-6.

Example 275

Compound E-27

6-Bromo-3-(5-chloro-2-ethanesulfonyl-benzyl)-7-((R)-3-hydroxy-pyrrolidin-1-ylmethyl)-1H-quinazoline-2,4-dione

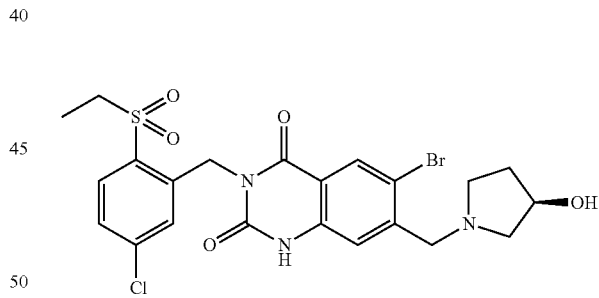

A 1N solution of tetrabutylammonium fluoride in THF (0.101 ml, 0.10 mmol) was added to a solution of 6-bromo-7-[(R)-3-(tert-butyl-dimethyl-silanyloxy)-pyrrolidin-1-ylmethyl]-3-(5-chloro-2-ethanesulfonyl-benzyl)-1H-quinazoline-2,4-dione (Compound e26, 45.1 mg, 0.067 mmol) in THF (0.60 ml) at 0° C., and the mixture was stirred at room temperature for 54.5 hours. The reaction mixture was concentrated under reduced pressure, and the resulting residue was purified by preparative HPLC (water/acetonitrile, 0.05% TFA) to give the title compound (29.1 mg, yield: 77%) as a colorless solid.
LCMS: m/z 556 [M+H]$^+$
HPLC retention time: 0.47 min (analysis condition H)

Example 276

Compound e27

2-Amino-5-bromo-3-methyl-benzoic acid

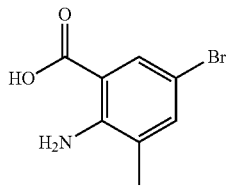

The title compound was synthesized from 2-amino-3-methyl-benzoic acid under the same conditions as for Compound a9. However, acetic acid was used in place of DCM as a solvent.

Example 277

Compound e28

2-Amino-5-bromo-3-methyl-benzoic acid ethyl ester

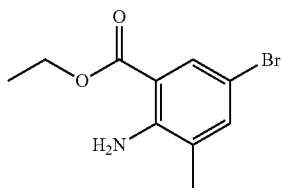

The title compound was synthesized from 2-amino-5-bromo-3-methyl-benzoic acid (Compound e27) under the conditions for Compound 20.

Example 278

Compound e29

2-(Bis(tert-butoxycarbonyl)amino)-5-bromo-3-methyl-benzoic acid ethyl ester

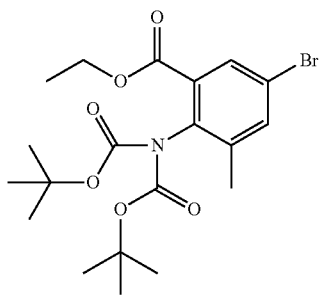 [SMILES: CCOC(=O)c1cc(Br)cc(C)c1N(C(=O)OC(C)(C)C)C(=O)OC(C)(C)C]

The title compound was synthesized from 2-amino-5-bromo-3-methyl-benzoic acid ethyl ester (Compound e28) under the same conditions as for Compound 17. However, acetonitrile was used in place of THF as a solvent.

Example 279

Compound e30

2-(Bis(tert-butoxycarbonyl)amino)-5-bromo-3-bromomethyl-benzoic acid ethyl ester

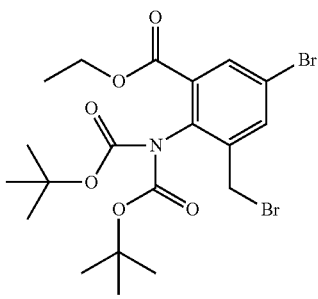 [SMILES: CCOC(=O)c1cc(Br)cc(CBr)c1N(C(=O)OC(C)(C)C)C(=O)OC(C)(C)C]

The title compound was synthesized from 2-(bis(tert-butoxycarbonyl)amino)-5-bromo-3-methyl-benzoic acid ethyl ester (Compound e29) under the same conditions as for Compound 12.

Example 280

Compound e31

4-(5-Bromo-2-(bis(tert-butoxycarbonyl)amino)-3-ethoxycarbonyl-benzyl)-piperazine-1-carboxylic acid tert-butyl ester

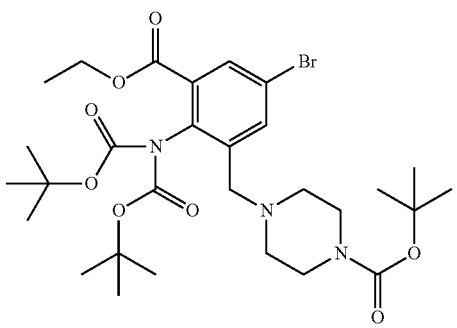 [SMILES: CCOC(=O)c1cc(Br)cc(CN2CCN(C(=O)OC(C)(C)C)CC2)c1N(C(=O)OC(C)(C)C)C(=O)OC(C)(C)C]

The title compound was synthesized from 2-(bis(tert-butoxycarbonyl)amino)-5-bromo-3-bromomethyl-benzoic acid ethyl ester (Compound e30) under the same conditions as for Compound d1. However, DCM was used in place of THF as a solvent, and triethylamine was added.

Example 281

Compound e32

4-(5-Bromo-2-(bis(tert-butoxycarbonyl)amino)-3-carboxy-benzyl)-piperazine-1-carboxylic acid tert-butyl ester

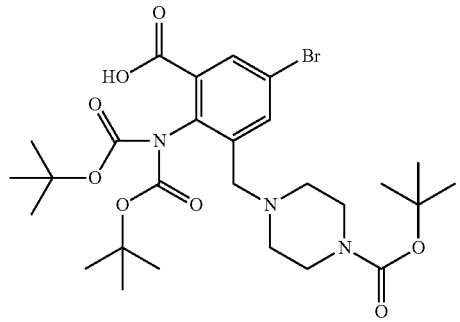 [SMILES: CC(C)(C)OC(=O)N1CCN(Cc2cc(Br)cc(C(=O)O)c2N(C(=O)OC(C)(C)C)C(=O)OC(C)(C)C)CC1]

The title compound was synthesized from 4-(5-bromo-2-(bis(tert-butoxycarbonyl)amino)-3-ethoxycarbonyl-benzyl)-piperazine-1-carboxylic acid tert-butyl ester (Compound e31) under the same conditions as for Compound 25. However, a 6N aqueous sodium hydroxide solution was used in place of a 1N aqueous sodium hydroxide solution.

Example 282

Compound e33

4-[5-Bromo-2-(bis(tert-butoxycarbonyl)amino)-3-(5-chloro-2-ethanesulfonyl-benzylcarbamoyl)-benzyl]-piperazine-1-carboxylic acid tert-butyl ester

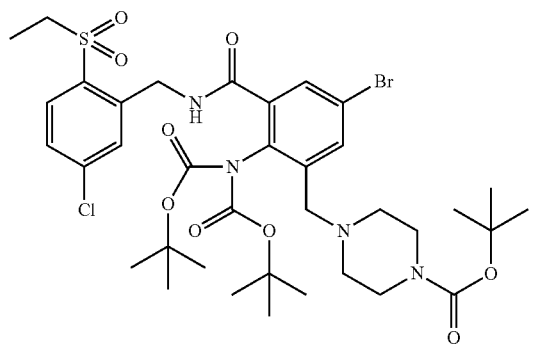 [SMILES: CCS(=O)(=O)c1ccc(Cl)cc1CNC(=O)c1cc(Br)cc(CN2CCN(C(=O)OC(C)(C)C)CC2)c1N(C(=O)OC(C)(C)C)C(=O)OC(C)(C)C]

The title compound was synthesized from 4-(5-bromo-2-(bis(tert-butoxycarbonyl)amino)-3-carboxy-benzyl)-piperazine-1-carboxylic acid tert-butyl ester (Compound e32) under the same conditions as for Compound 26. However, DMF was used in place of DCM as a solvent.

Example 283

Compound e34

2-Amino-5-bromo-N-(5-chloro-2-ethanesulfonyl-benzyl)-3-piperazin-1-ylmethyl-benzamide

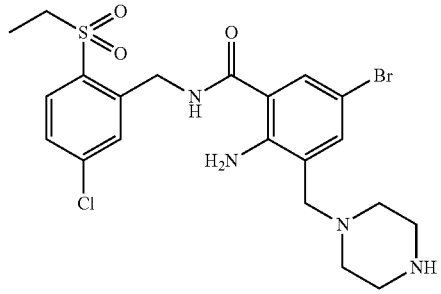 [SMILES: CCS(=O)(=O)c1ccc(Cl)cc1CNC(=O)c1cc(Br)cc(CN2CCNCC2)c1N]

The title compound was synthesized from 4-[5-bromo-2-(bis(tert-butoxycarbonyl)amino)-3-(5-chloro-2-ethanesulfonyl-benzylcarbamoyl)-benzyl]-piperazine-1-carboxylic acid tert-butyl ester (Compound e33) under the same conditions as for Compound B-1.

Example 284

Compound e35

4-[2-Amino-5-bromo-3-(5-chloro-2-ethanesulfonyl-benzylcarbamoyl)-benzyl]-piperazine-1-carboxylic acid tert-butyl ester

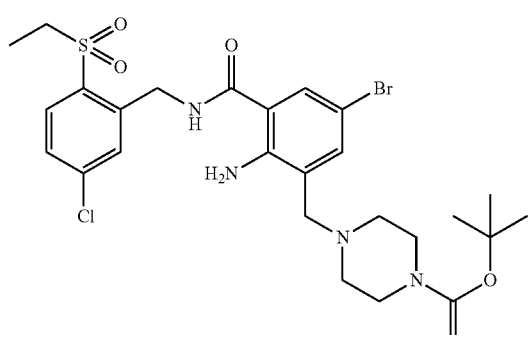

The title compound was synthesized from 2-amino-5-bromo-N-(5-chloro-2-ethanesulfonyl-benzyl)-3-piperazin-1-ylmethyl-benzamide (Compound e34) under the same conditions as for Compound d3. However, THF was used in place of DCM as a solvent.

Example 285

Compound e36

4-[6-Bromo-3-(5-chloro-2-ethanesulfonyl-benzyl)-2,4-dioxo-1,2,3,4-tetrahydro-quinazolin-8-ylmethyl]-piperazine-1-carboxylic acid tert-butyl ester

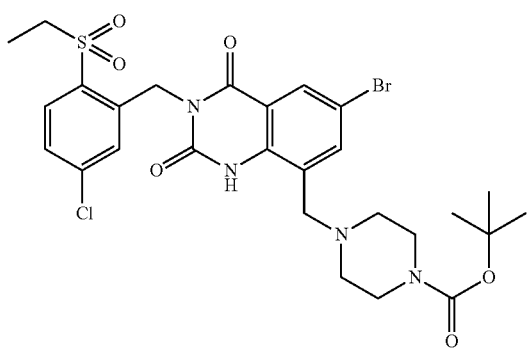 [SMILES: CCS(=O)(=O)c1ccc(Cl)cc1Cn1c(=O)[nH]c2c(CN3CCN(C(=O)OC(C)(C)C)CC3)cc(Br)cc2c1=O]

The title compound was synthesized from 4-[2-amino-5-bromo-3-(5-chloro-2-ethanesulfonyl-benzylcarbamoyl)-benzyl]-piperazine-1-carboxylic acid tert-butyl ester (Compound e35) under the same conditions as for Compound 37.

Example 286

Compound E-28

6-Bromo-3-(5-chloro-2-ethanesulfonyl-benzyl)-8-piperazin-1-ylmethyl-1H-quinazoline-2,4-dione

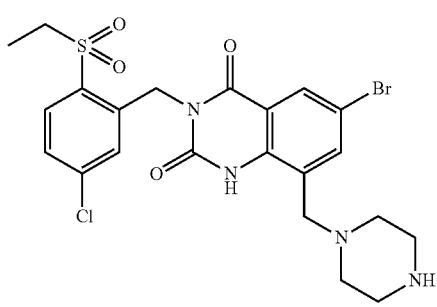 [SMILES: CCS(=O)(=O)c1ccc(Cl)cc1Cn1c(=O)[nH]c2c(CN3CCNCC3)cc(Br)cc2c1=O]

The title compound was synthesized from 4-[6-bromo-3-(5-chloro-2-ethanesulfonyl-benzyl)-2,4-dioxo-1,2,3,4-tetrahydro-quinazolin-8-ylmethyl]-piperazine-1-carboxylic acid tert-butyl ester (Compound e36) under the same conditions as for Compound B-1.
LCMS: m/z 555 [M+H]$^+$
HPLC retention time: 0.56 min (analysis condition D)

Example 287

Compound E-29

6-Bromo-3-(5-chloro-2-ethanesulfonyl-benzyl)-8-(4-methyl-piperazin 1-ylmethyl)-1H-quinazoline-2,4-dione

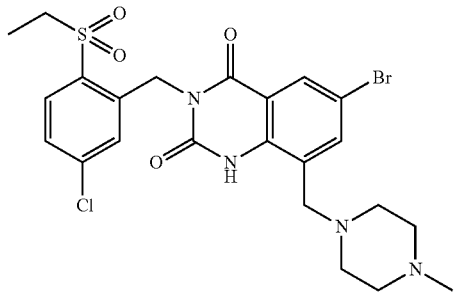

The title compound was synthesized from 6-bromo-3-(5-chloro-2-ethanesulfonyl-benzyl)-8-piperazin-1-ylmethyl-1H-quinazoline-2,4-dione (Compound E-28) under the same conditions as for Compound B-9.
LCMS: m/z 569 [M+H]$^+$
HPLC retention time: 0.55 min (analysis condition D)

Example 288

Compound f1

4-(3-Amino-2-chloro-4-ethoxycarbonyl-6-trifluoromethyl-benzyl)-piperazine-1-carboxylic acid tert-butyl ester

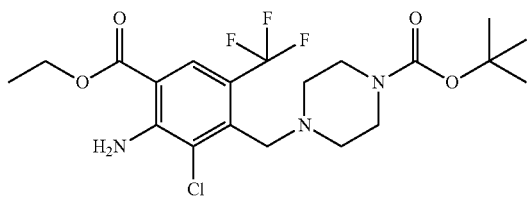 [SMILES: CCOC(=O)c1cc(C(F)(F)F)c(CN2CCN(C(=O)OC(C)(C)C)CC2)c(Cl)c1N]

The title compound was synthesized from 4-(5-amino-4-ethoxycarbonyl-2-trifluoromethyl-benzyl)-piperazine-1-carboxylic acid tert-butyl ester (Compound b1) under the same conditions as for Compound 24.

Example 289

Compound f2

4-(3-Amino-4-carboxy-2-chloro-6-trifluoromethyl-benzyl)-piperazine-1-carboxylic acid tert-butyl ester

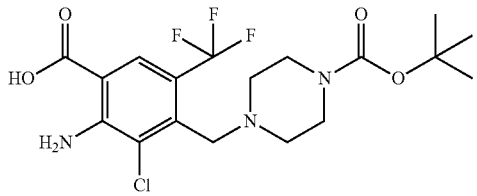

The title compound was synthesized from 4-(3-amino-2-chloro-4-ethoxycarbonyl-6-trifluoromethyl-benzyl)-piperazine-1-carboxylic acid tert-butyl ester (Compound f1) under the same conditions as for Compound 25.

Example 290

Compound f3

4-[3-Amino-2-chloro-4-(5-chloro-2-ethanesulfonyl-benzylcarbamyl)-6-trifluoromethyl-benzyl]-piperazine-1-carboxylic acid tert-butyl ester

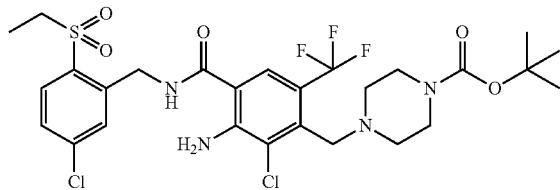 [SMILES: CCS(=O)(=O)c1ccc(Cl)cc1CNC(=O)c1cc(C(F)(F)F)c(CN2CCN(C(=O)OC(C)(C)C)CC2)c(Cl)c1N]

The title compound was synthesized from 4-(3-amino-4-carboxy-2-chloro-6-trifluoromethyl-benzyl)-piperazine-1-carboxylic acid tert-butyl ester (Compound f2) under the same conditions as for Compound 26.

Example 291

Compound f4

4-[8-Chloro-3-(5-chloro-2-ethanesulfonyl-benzyl)-2,4-dioxo-6-trifluoromethyl-1,2,3,4-tetrahydro-quinazolin-7-ylmethyl]-piperazine-1-carboxylic acid tert-butyl ester

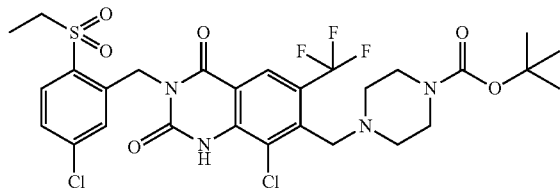 [SMILES: CCS(=O)(=O)c1ccc(Cl)cc1Cn1c(=O)[nH]c2c(Cl)c(CN3CCN(C(=O)OC(C)(C)C)CC3)c(C(F)(F)F)cc2c1=O]

The title compound was synthesized from 4-[3-amino-2-chloro-4-(5-chloro-2-ethanesulfonyl-benzylcarbamoyl)-6-trifluoromethyl-benzyl]-piperazine-1-carboxylic acid tert-butyl ester (Compound f3) under the same conditions as for Compound 37.

Example 292

Compound F-1

8-Chloro-3-(5-chloro-2-ethanesulfonyl-benzyl)-7-piperazin-1-ylmethyl-6-trifluoromethyl-1H-quinazoline-2,4-dione

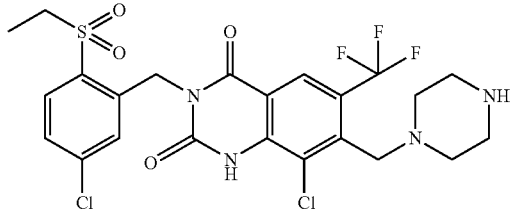

The title compound was synthesized from 4-[8-chloro-3-(5-chloro-2-ethanesulfonyl-benzyl)-2,4-dioxo-6-trifluoromethyl-1,2,3,4-tetrahydro-quinazolin-7-ylmethyl]-piperazine-1-carboxylic acid tert-butyl ester (Compound f4) under the same conditions as for Compound B-1.

LCMS: m/z 579 [M+H]$^+$
HPLC retention time: 0.57 min (analysis condition D)

Example 293

Compound F-2

8-Chloro-3-(5-chloro-2-ethanesulfonyl-benzyl)-7-(4-methyl-piperazin-1-ylmethyl)-6-trifluoromethyl-1H-quinazoline-2,4-dione

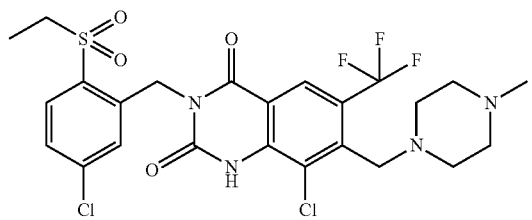

The title compound was synthesized from 8-chloro-3-(5-chloro-2-ethanesulfonyl-benzyl)-7-piperazin-1-ylmethyl-6-trifluoromethyl-1H-quinazoline-2,4-dione (Compound F-1) under the same conditions as for Compound B-9.

LCMS: m/z 593 [M+H]$^+$
HPLC retention time: 0.57 min (analysis condition D)

Example 294

Compound F-3

4-[8-Chloro-3-(5-chloro-2-ethanesulfonyl-benzyl)-2,4-dioxo-6-trifluoromethyl-1,2,3,4-tetrahydro-quinazolin-7-ylmethyl]-piperazine-1-carboxylic acid amide

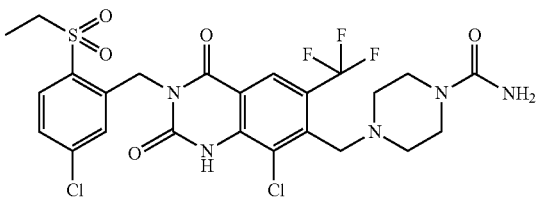 [SMILES: CCS(=O)(=O)c1ccc(Cl)cc1Cn1c(=O)[nH]c2c(Cl)c(CN3CCN(C(N)=O)CC3)c(C(F)(F)F)cc2c1=O]

Trimethylsilyl isocyanate (12.0 µl, 0.10 mmol) was added to a solution of 8-chloro-3-(5-chloro-2-ethanesulfonyl-benzyl)-7-piperazin-1-ylmethyl-6-trifluoromethyl-1H-quinazoline-2,4-dione (Compound F-1, 20.0 mg, 0.035 mmol) in acetonitrile (1.0 ml), and then stirred at room temperature. After six hours, trimethylsilyl isocyanate (12.0 µl, 0.10 mmol) was further added, and the mixture was further stirred at room temperature for 15 hours. The same experimental procedure was performed using DMF as a solvent. These reaction mixtures were combined and diluted with DMSO, followed by purification by preparative HPLC (water/acetonitrile, 0.05% TFA) to give the title compound (17.2 mg, yield: 39%) as a colorless solid.

LCMS: m/z 622 [M+H]$^+$
HPLC retention time: 0.66 min (analysis condition D)

Example 295

Compound F-4

4-[8-Chloro-3-(5-chloro-2-ethanesulfonyl-benzyl)-2,4-dioxo-6-trifluoromethyl-1,2,3,4-tetrahydro-quinazolin-7-ylmethyl]-piperazine-1-sulfonic acid methylamide

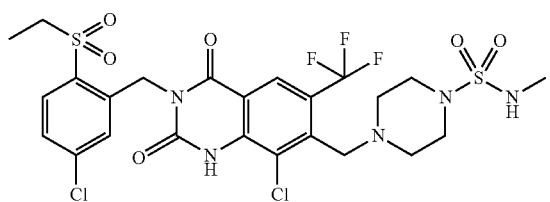 [SMILES: CCS(=O)(=O)c1ccc(Cl)cc1Cn1c(=O)[nH]c2c(Cl)c(CN3CCN(S(=O)(=O)NC)CC3)c(C(F)(F)F)cc2c1=O]

2-Oxo-oxazoline-3-sulfonic acid methylamine (8.09 mg, 0.045 mmol) was added to a solution of 8-chloro-3-(5-chloro-2-ethanesulfonyl-benzyl)-7-piperazin-1-ylmethyl-6-trifluoromethyl-1H-quinazoline-2,4-dione (Compound F-1, 20.0 mg, 0.035 mmol) and triethylamine (0.0105 ml, 0.10 mmol) in DMF (1.0 ml), and then stirred at 90° C. After two hours, triethylamine (0.020 ml, 0.14 mmol) and 2-oxo-oxazoline-3-sulfonic acid methylamine (10.0 mg, 0.056 mmol) were further added, and then stirred at 90° C. After three hours, triethylamine (0.020 ml, 0.14 mmol) and 2-oxo-oxazoline-3-sulfonic acid methylamine (18.0 mg, 0.100 mmol) were further added, and the mixture was stirred at 90° C. for further 1.5 hours. The reaction mixture was cooled to room temperature and diluted with DMSO, followed by purification by preparative HPLC (water/acetonitrile, 0.05% TFA) to give the title compound (5.8 mg, yield: 24%) as a brown solid. However, 2-oxo-oxazoline-3-sulfonic acid methylamine was synthesized following the method described in a patent (WO 2009080638).

LCMS: m/z 672 [M+H]$^+$

HPLC retention time: 0.85 min (analysis condition D)

Example 296

Compound F-5

7-[4-(2-Amino-acetyl)-piperazin-1-ylmethyl]-8-chloro-3-(5-chloro-2-ethanesulfonyl-benzyl)-6-trifluoromethyl-1H-quinazoline-2,4-dione

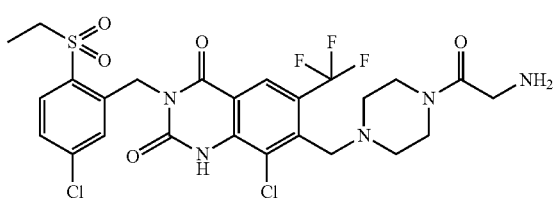 [SMILES: CCS(=O)(=O)c1ccc(Cl)cc1Cn1c(=O)[nH]c2c(Cl)c(CN3CCN(C(=O)CN)CC3)c(C(F)(F)F)cc2c1=O]

HBTU (25.5 mg, 0.067 mmol) was added to a solution of 8-chloro-3-(5-chloro-2-ethanesulfonyl-benzyl)-7-piperazin-1-ylmethyl-6-trifluoromethyl-1H-quinazoline-2,4-dione (Compound F-1, 30.0 mg, 0.052 mmol), N-(tert-butoxycarbonyl)glycine (9.98 mg, 0.057 mmol), and DIPEA (8.80 μl, 0.052 mmol) in DMF (0.5 ml), and then stirred at room temperature. After two hours, N-(tert-butoxycarbonyl)glycine (5.00 mg, 0.029 mmol) and HBTU (12.0 mg, 0.032 mmol) were further added, and the mixture was further stirred at room temperature for two hours. Water was added to the reaction mixture, followed by extraction with ethyl acetate. The organic layer was washed with brine and then dried over anhydrous sodium sulfate. The drying agent was removed by filtration, and the residue obtained after concentration under reduced pressure was purified by silica gel column chromatography (ethyl acetate/hexane) to give an N-Boc protected product of the title compound (30.3 mg, yield: 79%) as a colorless solid.

TFA (0.4 ml) was added to a solution of the resulting N-Boc protected product in dichloromethane (0.6 ml), and the mixture was stirred at room temperature for one hour. The reaction mixture was concentrated under reduced pressure, and the resulting residue was dissolved in ethyl acetate and water, followed by washing with a saturated aqueous sodium bicarbonate solution. The organic layer was washed with brine and then dried over anhydrous sodium sulfate. The drying agent was removed by filtration, and the title compound (17.4 mg, quant.) was obtained as a colorless solid by concentration under reduced pressure.

LCMS: m/z 636 [M+H]$^+$

HPLC retention time: 0.57 min (analysis condition E)

Example 297

Compound F-6

7-[4-(3-Amino-propionyl)-piperazin-1-ylmethyl]-8-chloro-3-(5-chloro-2-ethanesulfonyl-benzyl)-6-trifluoromethyl-1H-quinazoline-2,4-dione

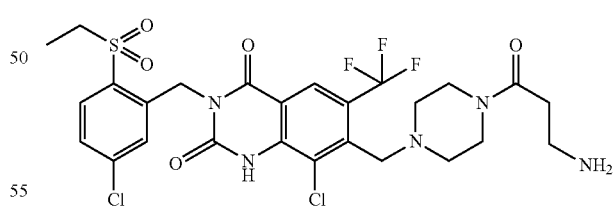

The title compound was synthesized from 8-chloro-3-(5-chloro-2-ethanesulfonyl-benzyl)-7-piperazin-1-ylmethyl-6-trifluoromethyl-1H-quinazoline-2,4-dione (Compound F-1) under the same conditions as for Compound F-5. However, 3-tert-butoxycarbonylamino-propionic acid was used in place of N-(tert-butoxycarbonyl)glycine.

LCMS: m/z 650 [M+H]$^+$

HPLC retention time: 0.56 min (analysis condition E)

Example 298

Compound F-7

8-Chloro-3-(5-chloro-2-ethanesulfonyl-benzyl)-7-(4-prop-2-ynyl-piperazin-1-ylmethyl)-6-trifluoromethyl-1H-quinazoline-2,4-dione

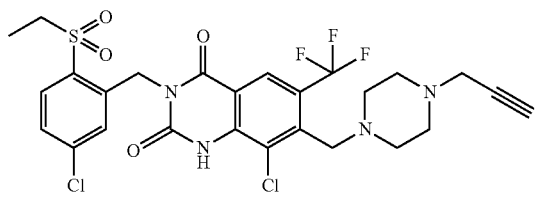 [SMILES: C#CCN1CCN(Cc2c(C(F)(F)F)cc3c(=O)n(Cc4cc(Cl)ccc4S(=O)(=O)CC)c(=O)[nH]c3c2Cl)CC1]

Propargyl bromide (5.40 µl, 0.061 mmol) was added to a solution of 8-chloro-3-(5-chloro-2-ethanesulfonyl-benzyl)-7-piperazin-1-ylmethyl-6-trifluoromethyl-1H-quinazoline-2,4-dione (Compound F-1, 31.8 mg, 0.055 mmol) and DIPEA (12.4 µl, 0.071 mmol) in chloroform (0.275 ml), and the mixture was stirred at room temperature for two hours. Ethyl acetate (15 ml) and THF (5 ml) were added to the reaction mixture, and the organic layer was washed with a saturated aqueous ammonium chloride solution and brine, and dried over anhydrous sodium sulfate. The drying agent was removed by filtration, the residue obtained by concentration under reduced pressure was purified by amino silica gel column chromatography (MeOH/DCM) to give the title compound (13.9 mg, 41%) as a yellow solid.

LCMS: m/z 617 [M+H]$^+$

HPLC retention time: 0.59 min (analysis condition D)

Example 299

Compound F-8

{4-[8-Chloro-3-(5-chloro-2-ethanesulfonyl-benzyl)-2,4-dioxo-6-trifluoromethyl-1,2,3,4-tetrahydro-quinazolin-7-ylmethyl]-piperazin-1-yl}-acetonitrile

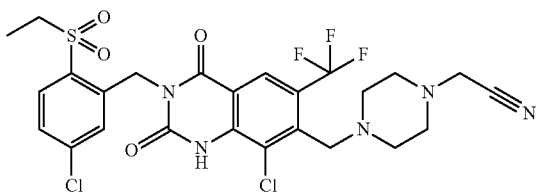 [SMILES: CCS(=O)(=O)c1ccc(Cl)cc1Cn1c(=O)[nH]c2c(Cl)c(CN3CCN(CC#N)CC3)c(C(F)(F)F)cc2c1=O]

Iodoacetonitrile (4.30 µl, 0.059 mmol) was added to a solution of 8-chloro-3-(5-chloro-2-ethanesulfonyl-benzyl)-7-piperazin-1-ylmethyl-6-trifluoromethyl-1H-quinazoline-2,4-dione (Compound F-1, 30.8 mg, 0.053 mmol) and DIPEA (10.2 µl, 0.059 mmol) in chloroform (0.265 ml), and the mixture was stirred at room temperature for 8.5 hours. DIPEA (8.33 µl, 0.048 mmol), iodoacetonitrile (3.46 µl, 0.048 mmol), and chloroform (0.265 ml) were further added to this reaction solution, and the mixture was stirred at room temperature for 14.5 hours. Ethyl acetate (15 ml) and THF (15 ml) were added to the reaction mixture, and the organic layer was washed with a saturated aqueous ammonium chloride solution and brine, and dried over anhydrous sodium sulfate. The drying agent was removed by filtration, and the residue obtained by concentration under reduced pressure was purified by amino silica gel column chromatography (MeOH/DCM) to give the title compound (29.3 mg, 89%) as a colorless amorphous.

LCMS: m/z 618 [M+H]$^+$

HPLC retention time: 1.77 min (analysis condition C)

Example 300

Compound F-9

8-Chloro-3-(5-chloro-2-ethanesulfonyl-benzyl)-7-(4-oxetan-3-yl-piperazin-1-ylmethyl)-6-trifluoromethyl-1H-quinazoline-2,4-dione

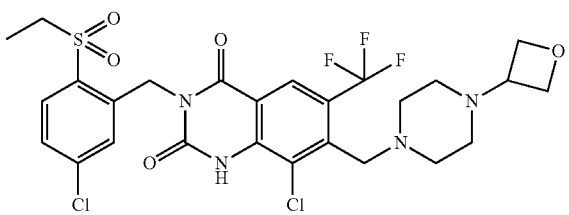 [SMILES: CCS(=O)(=O)c1ccc(Cl)cc1Cn1c(=O)[nH]c2c(Cl)c(CN3CCN(C4COC4)CC3)c(C(F)(F)F)cc2c1=O]

The title compound was synthesized from 8-chloro-3-(5-chloro-2-ethanesulfonyl-benzyl)-7-piperazin-1-ylmethyl-6-trifluoromethyl-1H-quinazoline-2,4-dione (Compound F-1) under the same conditions as for Compound B-5. However, the reaction was performed using DCM in place of THF as a solvent and using oxetan-3-one in place of tetrahydro-4H-pyran-4-one.

LCMS: m/z 635 [M+H]$^+$

HPLC retention time: 0.56 min (analysis condition D)

Example 301

Compound F-10

2-{4-[8-Chloro-3-(5-chloro-2-ethanesulfonyl-benzyl)-2,4-dioxo-6-trifluoromethyl-1,2,3,4-tetrahydro-quinazolin-7-ylmethyl]-piperazin-1-yl}-acetamide

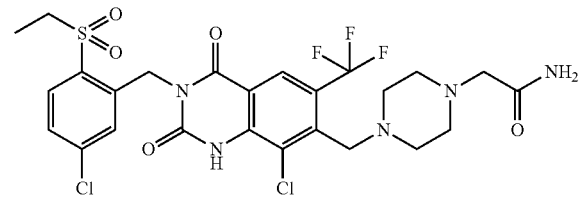 [SMILES: CCS(=O)(=O)c1ccc(Cl)cc1Cn1c(=O)[nH]c2c(Cl)c(CN3CCN(CC(N)=O)CC3)c(C(F)(F)F)cc2c1=O]

2-Bromoacetamide (11.8 mg, 0.085 mmol) was added to a solution of 8-chloro-3-(5-chloro-2-ethanesulfonyl-benzyl)-7-piperazin-1-ylmethyl-6-trifluoromethyl-1H-quinazoline-2,4-dione (Compound F-1, 32.8 mg, 0.057 mmol) and DIPEA (14.8 µl, 0.085 mmol) in chloroform (0.566 ml), and the mixture was stirred at room temperature for 4.5 hours. A saturated aqueous ammonium chloride solution was added to the reaction mixture, followed by extraction with DCM. The organic layer was then dried over anhydrous sodium sulfate. The drying agent was removed by filtration, and the residue obtained by concentration under reduced pressure was purified by silica gel column chromatography (MeOH/DCM) to give the title compound (27.7 mg, 77%) as a colorless solid.

LCMS: m/z 636 [M+H]$^+$

HPLC retention time: 0.56 min (analysis condition D)

Example 302

Compound F-11

8-Chloro-3-(5-chloro-2-ethanesulfonyl-benzyl)-7-[4-(2,2,2-trifluoro-ethyl)-piperazin-1-ylmethyl]-6-trifluoromethyl-1H-quinazoline-2,4-dione

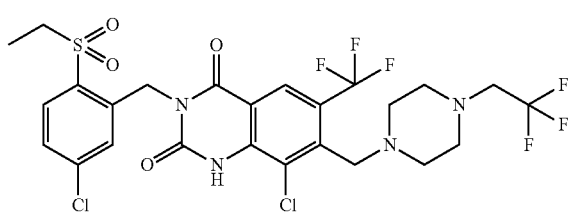 [SMILES: CCS(=O)(=O)c1ccc(Cl)cc1Cn1c(=O)[nH]c2c(Cl)c(CN3CCN(CC(F)(F)F)CC3)c(C(F)(F)F)cc2c1=O]

2,2,2-Trifluoroethyl p-toluenesulfonate (9.60 µl, 0.067 mmol) was added to a solution of 8-chloro-3-(5-chloro-2-ethanesulfonyl-benzyl)-7-piperazin-1-ylmethyl-6-trifluoromethyl-1H-quinazoline-2,4-dione (Compound F-1, 32.1 mg, 0.055 mmol) and DIPEA (11.6 µl, 0.067 mmol) in DMF (0.642 ml), and the mixture was stirred at 70° C. for 20 minutes. The reaction mixture was purified by preparative HPLC (water/acetonitrile, 0.05% TFA) to give the title compound (21.1 mg, 58%) as a colorless solid.

LCMS: m/z 661 [M+H]$^+$

HPLC retention time: 0.92 min (analysis condition D)

Example 303

Compound f5

4-[3-Amino-2-chloro-4-(5-cyano-2-ethanesulfonyl-benzylcarbamoyl)-6-trifluoromethyl-benzyl]-piperazine-1-carboxylic acid tert-butyl ester

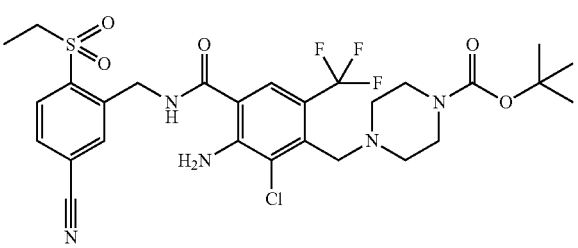 [SMILES: CCS(=O)(=O)c1ccc(C#N)cc1CNC(=O)c1cc(C(F)(F)F)c(CN2CCN(C(=O)OC(C)(C)C)CC2)c(Cl)c1N]

The title compound was synthesized from 4-[5-amino-4-(5-cyano-2-ethanesulfonyl-benzylcarbamoyl)-2-trifluoromethyl-benzyl]-piperazine-1-carboxylic acid tert-butyl ester (Compound b10) under the same conditions as for Compound 24.

Example 304

Compound f6

4-[8-Chloro-3-(5-cyano-2-ethanesulfonyl-benzyl)-2,4-dioxo-6-trifluoromethyl-1,2,3,4-tetrahydro-quinazolin-7-ylmethyl]-piperazine-1-carboxylic acid tert-butyl ester

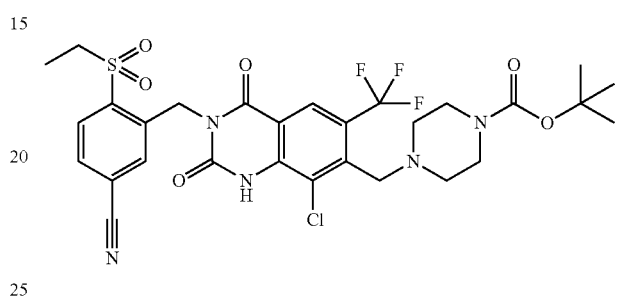

The title compound was synthesized from 4-[3-amino-2-chloro-4-(5-cyano-2-ethanesulfonyl-benzylcarbamoyl)-6-trifluoromethyl-benzyl]-piperazine-1-carboxylic acid tert-butyl ester (Compound f5) under the same conditions as for Compound A-6.

Example 305

Compound F-12

3-(8-Chloro-2,4-dioxo-7-piperazin-1-ylmethyl-6-trifluoromethyl-, 4-dihydro-2H-quinazolin-3-ylmethyl)-4-ethanesulfonyl-benzonitrile

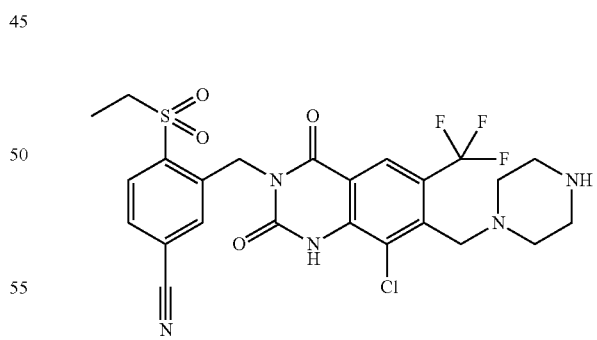

The title compound was synthesized from 4-[8-chloro-3-(5-cyano-2-ethanesulfonyl-benzyl)-2,4-dioxo-6-trifluoromethyl-1,2,3,4-tetrahydro-quinazolin-7-ylmethyl]-piperazine-1-carboxylic acid tert-butyl ester (Compound f6) under the same conditions as for Compound B-1.

LCMS: m/z 570 [M+H]$^+$

HPLC retention time: 0.52 min (analysis condition D)

Example 306

Compound f7

4-(8-Chloro-2,4-dioxo-6-trifluoromethyl-1,4-dihydro-2H-benzo[d][1,3]oxazin-7-ylmethyl)-piperazine-1-carboxylic acid tert-butyl ester

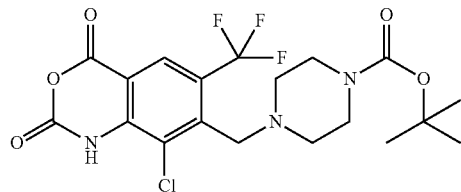 [SMILES: CC(C)(C)OC(=O)N1CCN(Cc2c(C(F)(F)F)cc3c(=O)oc(=O)[nH]c3c2Cl)CC1]

DBU (171 μl, 1.1 mmol) was added to a solution of 4-(3-amino-4-carboxy-2-chloro-6-trifluoromethyl-benzyl)-piperazine-1-carboxylic acid tert-butyl ester (Compound f2, 127 mg, 0.23 mmol) in THF (4 ml), and a solution of triphosgene (102 mg, 0.34 mmol) in THF (0.5 ml) was slowly added while cooling in an ice water bath. After stirring at 0° C. for 1.5 hours, a saturated aqueous sodium bicarbonate solution was added to the reaction mixture, followed by extraction with ethyl acetate. The organic layer was then washed with brine and dried over anhydrous sodium sulfate. The drying agent was removed by filtration, followed by concentration under reduced pressure to give the title compound as a crude product.

Example 307

Compound f8

4-[8-Chloro-3-(5-chloro-2-ethanesulfonyl-phenylamino)-2,4-dioxo-6-trifluoromethyl-1,2,3,4-tetrahydro-quinazolin-7-ylmethyl]-piperazine-1-carboxylic acid tert-butyl ester

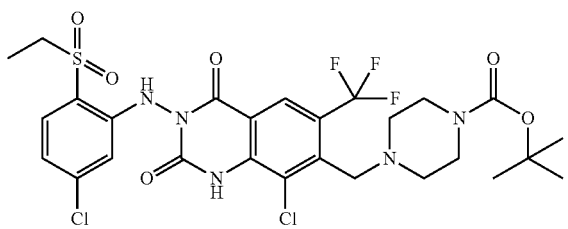 [SMILES: CCS(=O)(=O)c1ccc(Cl)cc1Nn1c(=O)[nH]c2c(Cl)c(CN3CCN(C(=O)OC(C)(C)C)CC3)c(C(F)(F)F)cc2c1=O]

A solution of 4-(8-chloro-2,4-dioxo-6-trifluoromethyl-1,4-dihydro-2H-benzo[d][1,3]oxazin-7-ylmethyl)-piperazine-1-carboxylic acid tert-butyl ester (Compound f7, 197.7 mg, 0.43 mmol) and (5-chloro-2-ethanesulfonyl-phenyl)-hydrazine (Compound 16, 120 mg, 0.51 mmol) in THF (4 ml) was stirred in a sealed tube at 100° C. for 3.5 hours. This was concentrated under reduced pressure, and the resulting residue was purified by silica gel column chromatography (ethyl acetate/hexane) to give the title compound (68.7 mg, 24%).

LCMS: m/z 680 [M+H]$^+$

HPLC retention time: 1.00 min (analysis condition D)

Example 308

Compound F-13

8-Chloro-3-(5-chloro-2-ethanesulfonyl-phenylamino)-7-piperazin-1-ylmethyl-6-trifluoromethyl-1H-quinazoline-2,4-dione

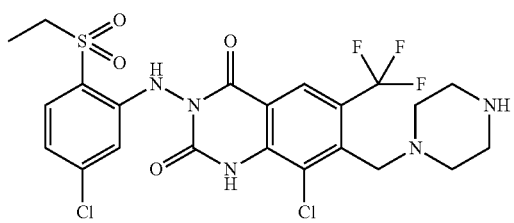 [SMILES: CCS(=O)(=O)c1ccc(Cl)cc1Nn1c(=O)[nH]c2c(Cl)c(CN3CCNCC3)c(C(F)(F)F)cc2c1=O]

The title compound was synthesized from 4-[8-chloro-3-(5-chloro-2-ethanesulfonyl-phenylamino)-2,4-dioxo-6-trifluoromethyl-1,2,3,4-tetrahydro-quinazolin-7-ylmethyl]-piperazine-1-carboxylic acid tert-butyl ester (Compound f8) under the same conditions as for Compound a41.

LCMS: m/z 580 [M+H]$^+$

HPLC retention time: 0.54 min (analysis condition D)

Example 309

Compound F-14

8-Chloro-3-(5-chloro-2-ethanesulfonyl-phenylamino)-7-(4-methyl-piperazin-1-ylmethyl)-6-trifluoromethyl-1H-quinazoline-2,4-dione

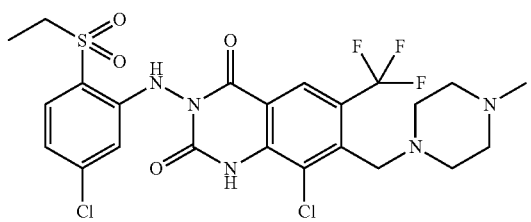 [SMILES: CCS(=O)(=O)c1ccc(Cl)cc1Nn1c(=O)[nH]c2c(Cl)c(CN3CCN(C)CC3)c(C(F)(F)F)cc2c1=O]

The title compound was synthesized from 8-chloro-3-(5-chloro-2-ethanesulfonyl-phenylamino)-7-piperazin-1-ylmethyl-6-trifluoromethyl-1H-quinazoline-2,4-dione (Compound F-13) under the same conditions as for Compound B-9. However, (R)-pyrrolidin-3-yl-carbamic acid tert-butyl ester was used in place of (S)-pyrrolidin-3-yl-carbamic acid tert-butyl ester.

LCMS: m/z 594 [M+H]$^+$

HPLC retention time: 0.55 min (analysis condition D)

Example 310

Compound f9

2-Amino-4-((R)-3-tert-butoxycarbonylamino-pyrrolidin-1-ylmethyl)-5-trifluoromethyl-benzoic acid ethyl ester

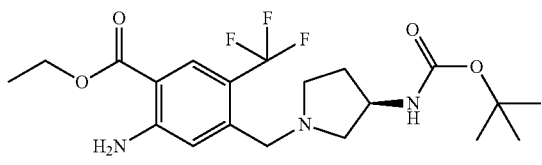 [SMILES: CCOC(=O)c1cc(C(F)(F)F)c(CN2CC[C@@H](NC(=O)OC(C)(C)C)C2)cc1N]

The title compound was synthesized from 2-amino-4-formyl-5-trifluoromethyl-benzoic acid ethyl ester (Compound 23) under the same conditions as for Compound b12. However, (R)-pyrrolidin-3-yl-carbamic acid tert-butyl ester was used in place of (S)-pyrrolidin-3-yl-carbamic acid tert-butyl ester.

Example 311

Compound f10

2-Amino-4-((R)-3-tert-butoxycarbonylamino-pyrrolidin-1-ylmethyl)-5-trifluoromethyl-benzoic acid

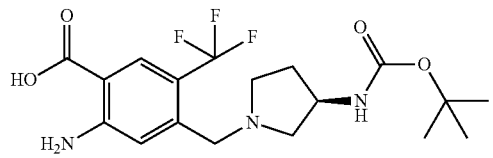 [SMILES: CC(C)(C)OC(=O)N[C@@H]1CCN(Cc2cc(N)c(C(=O)O)cc2C(F)(F)F)C1]

The title compound was synthesized from 2-amino-4-((R)-3-tert-butoxycarbonylamino-pyrrolidin-1-ylmethyl)-5-trifluoromethyl-benzoic acid ethyl ester (Compound f9) under the same conditions as for Compound 25.

Example 312

Compound f11

{(R)-1-[5-Amino-4-(5-chloro-2-ethanesulfonyl-benzylcarbamoyl)-2-trifluoromethyl-benzyl]-pyrrolidin-3-yl}-carbamic acid tert-butyl ester

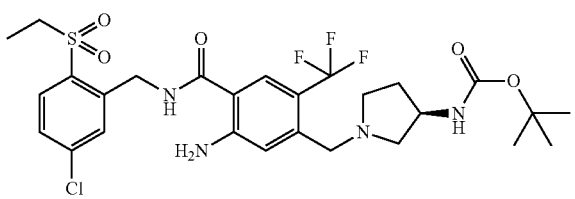 [SMILES: CCS(=O)(=O)c1ccc(Cl)cc1CNC(=O)c1cc(C(F)(F)F)c(CN2CC[C@@H](NC(=O)OC(C)(C)C)C2)cc1N]

The title compound was synthesized from 2-amino-4-((R)-3-tert-butoxycarbonylamino-pyrrolidin-1-ylmethyl)-5-trifluoromethyl-benzoic acid (Compound f10) under the same conditions as for Compound 26. However, the reaction was performed without adding HOBT.

Example 313

Compound f12

{(R)-1-[3-Amino-2-chloro-4-(5-chloro-2-ethanesulfonyl-benzylcarbamoyl)-6-trifluoromethyl-benzyl]-pyrrolidin-3-yl}-carbamic acid tert-butyl ester

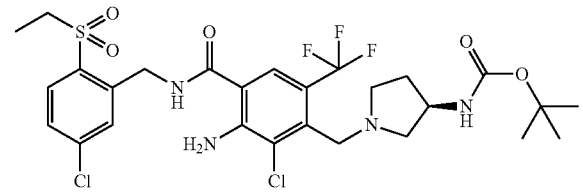 [SMILES: CCS(=O)(=O)c1ccc(Cl)cc1CNC(=O)c1cc(C(F)(F)F)c(CN2CC[C@@H](NC(=O)OC(C)(C)C)C2)c(Cl)c1N]

The title compound was synthesized from {(R)-1-[5-amino-4-(5-chloro-2-ethanesulfonyl-benzylcarbamoyl)-2-trifluoromethyl-benzyl]-pyrrolidin-3-yl}-carbamic acid tert-butyl ester (Compound f11) under the same conditions as for Compound 24.

Example 314

Compound f13

{(R)-1-[8-Chloro-3-(5-chloro-2-ethanesulfonyl-benzyl)-2,4-dioxo-6-trifluoromethyl-1,2,3,4-tetrahydroquinazolin-7-ylmethyl]-pyrrolidin-3-yl}-carbamic acid tert-butyl ester

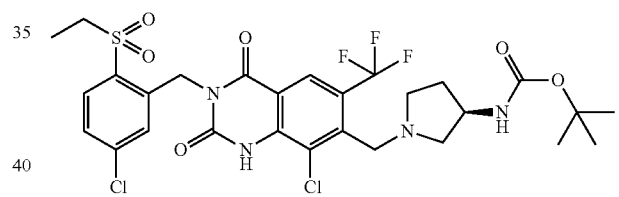

The title compound was synthesized from {(R)-1-[3-amino-2-chloro-4-(5-chloro-2-ethanesulfonyl-benzylcarbamoyl)-6-trifluoromethyl-benzyl]-pyrrolidin-3-yl}-carbamic acid tert-butyl ester (Compound f12) under the same conditions as for Compound 37.

Example 315

Compound F-15

7-((R)-3-Amino-pyrrolidin-1-ylmethyl)-8-chloro-3-(5-chloro-2-ethanesulfonyl-benzyl)-6-trifluoromethyl-1H-quinazoline-2,4-dione

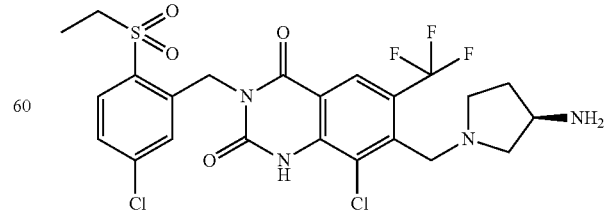

The title compound was synthesized from {(R)-1-[8-chloro-3-(5-chloro-2-ethanesulfonyl-benzyl)-2,4-dioxo-6- trifluoromethyl-1,2,3,4-tetrahydro-quinazolin-7-ylmethyl]-pyrrolidin-3-yl}-carbamic acid tert-butyl ester (Compound f13) under the same conditions as for Compound a41.

LCMS: m/z 579 [M+H]+

HPLC retention time: 0.54 min (analysis condition D)

Example 316

Compound F-16

8-Chloro-3-(5-chloro-2-ethanesulfonyl-benzyl)-7-((R)-3-dimethylamino-pyrrolidin-1-ylmethyl)-6-trifluoromethyl-1H-quinazoline-2,4-dione

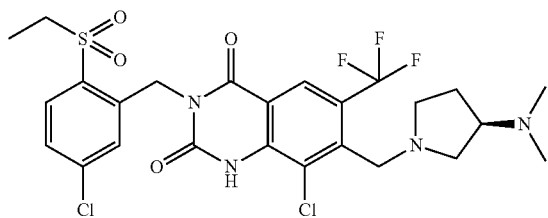

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound B-9.

LCMS: m/z 607 [M+H]+

HPLC retention time: 0.57 min (analysis condition D)

Example 317

Compound F-17

N-{(R)-1-[8-Chloro-3-(5-chloro-2-ethanesulfonyl-benzyl-2,4-dioxo-6-trifluoromethyl-1,2,3,4-tetrahydro-quinazolin-7-ylmethyl]-pyrrolidin-3-yl}-methanesulfonamide

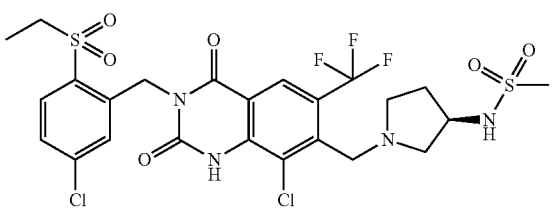 [SMILES: CCS(=O)(=O)c1ccc(Cl)cc1Cn1c(=O)[nH]c2c(Cl)c(CN3CC[C@@H](NS(C)(=O)=O)C3)c(C(F)(F)F)cc2c1=O]

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound B-7. However, the reaction was performed using TEA in place of pyridine.

LCMS: m/z 657 [M+H]+

HPLC retention time: 0.58 min (analysis condition D)

Example 318

Compound F-18

N-{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-dimethylaminesulfonamide

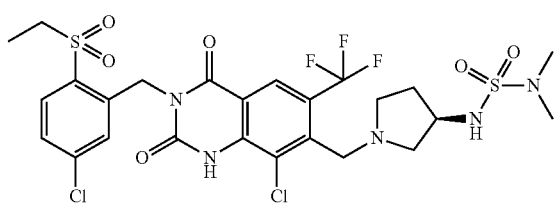 [SMILES: CCS(=O)(=O)c1ccc(Cl)cc1Cn1c(=O)[nH]c2c(Cl)c(CN3CC[C@@H](NS(=O)(=O)N(C)C)C3)c(C(F)(F)F)cc2c1=O]

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound E-10. However, the reaction was performed using DMF in place of DMA.

LCMS: m/z 686 [M+H]+

HPLC retention time: 0.64 min (analysis condition D)

Example 319

Compound F-19

N-{(R)-1-[8-Chloro-3-(5-chloro-2-ethanesulfonyl-benzyl)-2, 4-dioxo-6-trifluoromethyl-1,2,3,4-tetrahydro-quinazolin-7-ylmethyl]-pyrrolidin-3-yl}-2-dimethylamino-acetamide

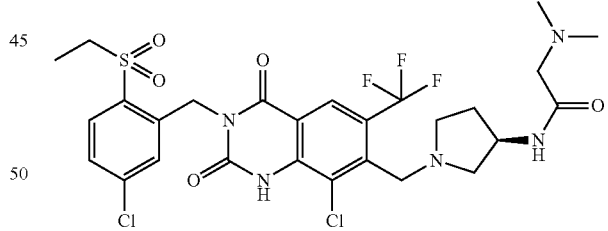

A solution of 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15, 20.0 mg, 0.035 mmol), N,N-dimethylglycine (3.92 mg, 0.038 mmol), HOBT (5.90 mg, 0.038 mmol), and DIPEA (0.0119 ml, 0.069 mmol) in DCM (1 ml) was cooled to 0° C. WSCDI (7.28 mg, 0.038 mmol) was added, and the mixture was stirred at room temperature for 63 hours. The reaction mixture was diluted with DMSO, then purified by preparative HPLC (water/acetonitrile, 0.05% TFA) to give the title compound (14.1 mg, yield: 61%) as a colorless solid.

LCMS: m/z 664 [M+H]+

HPLC retention time: 0.51 min (analysis condition E)

Example 320

Compound F-20

N-{(R)-1-[8-Chloro-3-(5-chloro-2-ethanesulfonyl-benzyl)-2,4-dioxo-6-trifluoromethyl-1,2,3,4-tetra-hydro-quinazolin-7-ylmethyl]-pyrrolidin-3-yl}-isobutylamide

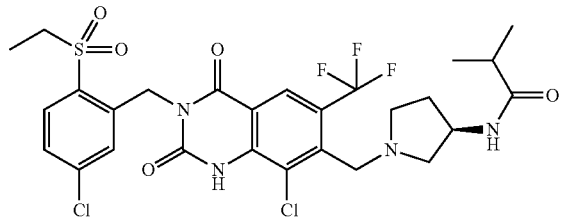 [SMILES: CCS(=O)(=O)c1ccc(Cl)cc1Cn1c(=O)[nH]c2c(Cl)c(CN3CC[C@@H](NC(=O)C(C)C)C3)c(C(F)(F)F)cc2c1=O]

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound B-6. However, the reaction was performed using isobutyryl chloride, DIPEA, and DMF in place of acetyl chloride, pyridine, and DCM.

LCMS: m/z 649 [M+H]$^+$

HPLC retention time: 0.62 min (analysis condition E)

Example 321

Compound F-21

Cyclopentanecarboxylic acid {(R)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-amide

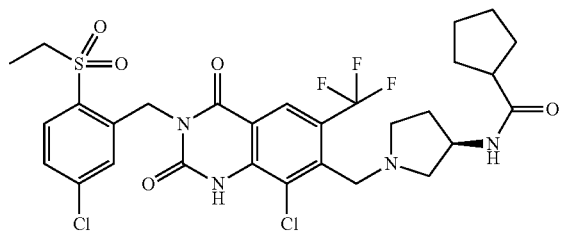 [SMILES: CCS(=O)(=O)c1ccc(Cl)cc1Cn1c(=O)[nH]c2c(Cl)c(CN3CC[C@@H](NC(=O)C4CCCC4)C3)c(C(F)(F)F)cc2c1=O]

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound F-19. However, the reaction was performed using cyclopentanecarboxylic acid, HATU, and DMF in place of N,N-dimethylglycine, WSCDI, HOBT, and DCM.

LCMS: m/z 675 [M+H]$^+$

HPLC retention time: 0.66 min (analysis condition E)

Example 322

Compound F-22

N-{(R)-1-[8-Chloro-3-(5-chloro-2-ethanesulfonyl-benzyl)-2,4-dioxo-6-trifluoromethyl-1,2,3,4-tetra-hydro-quinazolin-7-ylmethyl]-pyrrolidin-3-yl}-2-cyclohexyl-acetamide

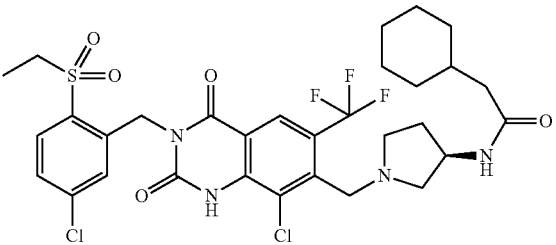 [SMILES: CCS(=O)(=O)c1ccc(Cl)cc1Cn1c(=O)[nH]c2c(Cl)c(CN3CC[C@@H](NC(=O)CC4CCCCC4)C3)c(C(F)(F)F)cc2c1=O]

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound F-19. However, the reaction was performed using cyclohexylacetic acid, HATU, and DMF in place of N,N-dimethylglycine, WSCDI, HOBT, and DCM.

LCMS: m/z 703 [M+H]$^+$

HPLC retention time: 0.71 min (analysis condition E)

Example 323

Compound F-23

(S)-2-Amino-N-{(R)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-propionamide

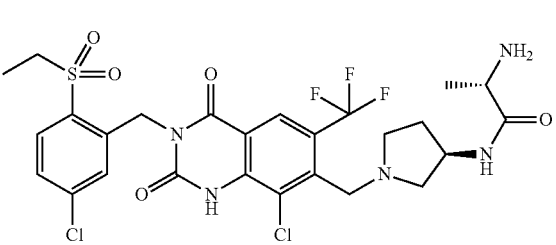 [SMILES: CCS(=O)(=O)c1ccc(Cl)cc1Cn1c(=O)[nH]c2c(Cl)c(CN3CC[C@@H](NC(=O)[C@H](C)N)C3)c(C(F)(F)F)cc2c1=O]

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound F-5. However, the reaction was performed using (S)-2-(tert-butoxycarbonylamino)propanoic acid and HATU in place of N-(tert-butoxycarbonyl)glycine and HBTU.

LCMS: m/z 650 [M+H]$^+$

HPLC retention time: 0.50 min (analysis condition E)

Example 324

Compound F-24

(R)-2-Amino-N-{(R)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-propionamide

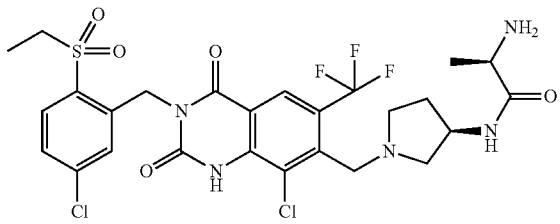 [SMILES: CCS(=O)(=O)c1ccc(Cl)cc1Cn1c(=O)[nH]c2c(Cl)c(CN3CC[C@@H](NC(=O)[C@@H](C)N)C3)c(C(F)(F)F)cc2c1=O]

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound F-5. However, the reaction was performed using (R)-2-(tert-butoxycarbonylamino)propanoic acid and HATU in place of N-(tert-butoxycarbonyl)glycine and HBTU.

LCMS: m/z 650 [M+H]$^+$

HPLC retention time: 0.50 min (analysis condition E)

Example 325

Compound F-25

2-Amino-N-{(R)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-2-methyl-propionamide

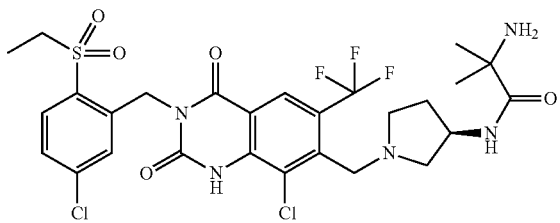 [SMILES: CCS(=O)(=O)c1ccc(Cl)cc1Cn1c(=O)[nH]c2c(Cl)c(CN3CC[C@@H](NC(=O)C(C)(C)N)C3)c(C(F)(F)F)cc2c1=O]

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound F-5. However, the reaction was performed using 2-tert-butoxycarbonylamino-2-methyl-propionic acid and HATU in place of N-(tert-butoxycarbonyl)glycine and HBTU.

LCMS: m/z 664 [M+H]$^+$

HPLC retention time: 0.51 min (analysis condition E)

Example 326

Compound F-26

3-Amino-N-{(R)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-propionamide

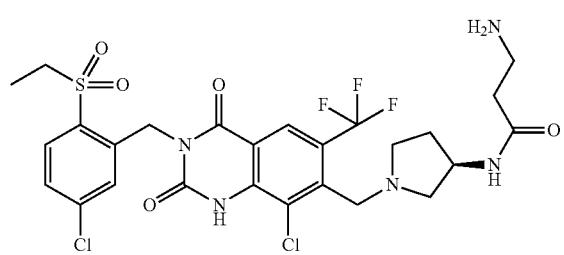 [SMILES: CCS(=O)(=O)c1ccc(Cl)cc1Cn1c(=O)[nH]c2c(Cl)c(CN3CC[C@@H](NC(=O)CCN)C3)c(C(F)(F)F)cc2c1=O]

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound F-5. However, the reaction was performed using 3-tert-butoxycarbonylamino-propionic acid in place of N-(tert-butoxycarbonyl)glycine.

LCMS: m/z 650 [M+H]$^+$

HPLC retention time: 0.50 min (analysis condition E)

Example 327

Compound F-27

2-Amino-N-{(R)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-acetamide

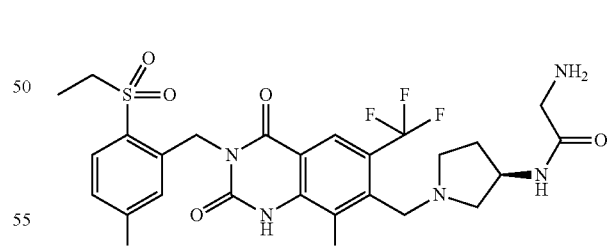

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound F-5. However, the reaction was performed using HATU in place of HBTU.

LCMS: m/z 636 [M+H]$^+$

HPLC retention time: 0.50 min (analysis condition E)

Example 328

Compound F-28

N-{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-2-methylamino-acetamide

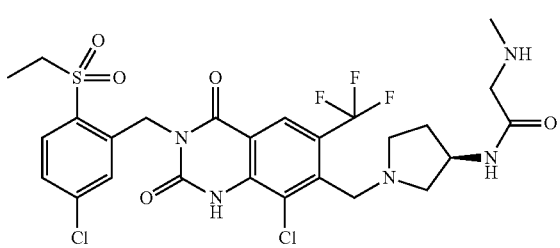 [SMILES: CCS(=O)(=O)c1ccc(Cl)cc1Cn1c(=O)[nH]c2c(Cl)c(CN3CC[C@@H](NC(=O)CNC)C3)c(C(F)(F)F)cc2c1=O]

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound F-5. However, the reaction was performed using (tert-butoxycarbonyl-methyl-amino)-acetic acid and HATU in place of N-(tert-butoxycarbonyl)glycine and HBTU.

LCMS: m/z 650 [M+H]$^+$

HPLC retention time: 0.48 min (analysis condition E)

Example 329

Compound F-29

{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-urea

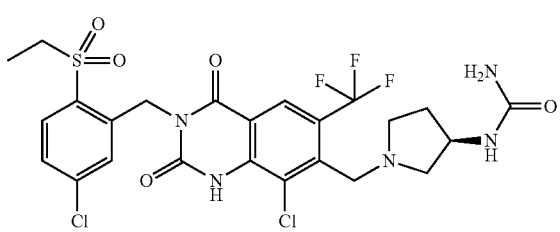 [SMILES: CCS(=O)(=O)c1ccc(Cl)cc1Cn1c(=O)[nH]c2c(Cl)c(CN3CC[C@@H](NC(N)=O)C3)c(C(F)(F)F)cc2c1=O]

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound F-3. However, the reaction was performed using DMF in place of acetonitrile.

LCMS: m/z 622 [M+H]$^+$

HPLC retention time: 0.52 min (analysis condition D)

Example 330

Compound F-30

8-Chloro-3-(5-chloro-2-ethanesulfonyl-benzyl)-7-[(R)-3-(2,2,2-trifluoro-ethylamino)-pyrrolidin-1-ylmethyl]-6-trifluoromethyl-1H-quinazoline-2,4-dione

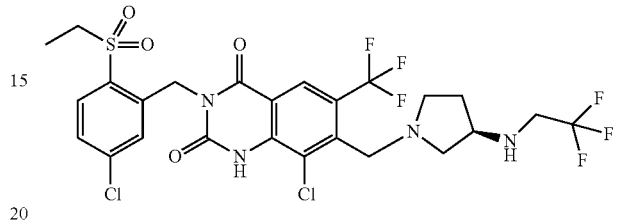

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound F-11. However, the reaction was performed using THF in place of DMF.

LCMS: m/z 661 [M+H]$^+$

HPLC retention time: 0.61 min (analysis condition D)

Example 331

Compound F-31

8-Chloro-3-(5-chloro-2-ethanesulfonyl-benzyl)-7-[(R)-3-(2,2-difluoro-ethylamino)-pyrrolidin-1-ylmethyl]-6-trifluoromethyl-1H-quinazoline-2,4-dione

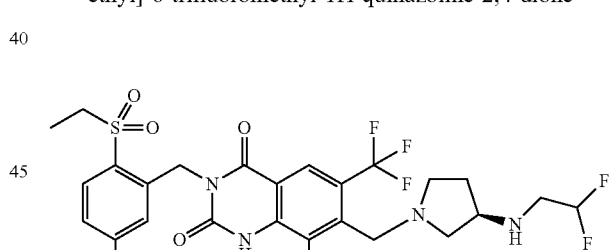

2,2-Difluoroethyl p-toluenesulfonate (15.6 mg, 0.073 mmol) was added to a solution of 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15, 30.3 mg, 0.052 mmol) and DIPEA (10.9 μl, 0.063 mmol) in THF (0.6 ml), and the mixture was stirred at 70° C. for one hour. Ethyl acetate was added to the reaction mixture, and the organic layer was then washed with a saturated aqueous ammonium chloride solution and brine, and dried over anhydrous sodium sulfate. The drying agent was removed by filtration, and the residue obtained by concentration under reduced pressure was purified by amino silica gel column chromatography (MeOH/DCM) to give the title compound (29.8 mg, 89%) as a colorless amorphous.

LCMS: m/z 643 [M+H]$^+$

HPLC retention time: 1.57 min (analysis condition C)

Example 332

Compound F-32

{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-ylamino}-acetonitrile

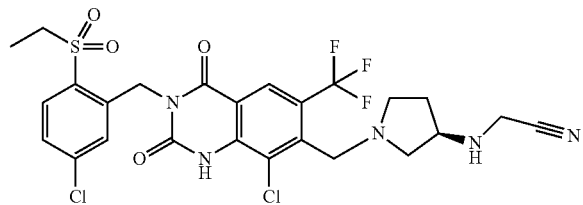 [SMILES: CCS(=O)(=O)c1ccc(Cl)cc1Cn1c(=O)[nH]c2c(Cl)c(CN3CC[C@@H](NCC#N)C3)c(C(F)(F)F)cc2c1=O]

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound F-8.

LCMS: m/z 618 [M+H]$^+$

HPLC retention time: 1.48 min (analysis condition C)

Example 333

Compound F-33

8-Chloro-3-(5-chloro-2-ethanesulfonyl-benzyl)-7-[(R)-3-(oxetan-3-ylamino)-pyrrolidin-1-ylmethyl]-6-trifluoromethyl-1H-quinazoline-2,4-dione

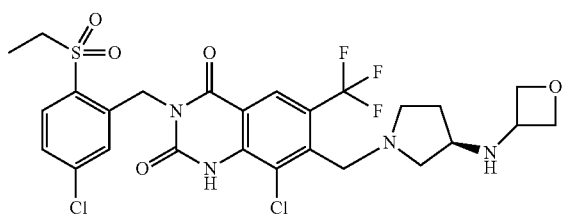 [SMILES: CCS(=O)(=O)c1ccc(Cl)cc1Cn1c(=O)[nH]c2c(Cl)c(CN3CC[C@@H](NC4COC4)C3)c(C(F)(F)F)cc2c1=O]

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound B-5. However, the reaction was performed using oxetan-3-one and DCM in place of tetrahydro-4H-pyran-4-one and THF.

LCMS: m/z 635 [M+H]$^+$

HPLC retention time: 0.57 min (analysis condition D)

Example 334

Compound F-34

2-{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-ylamino}-acetamide

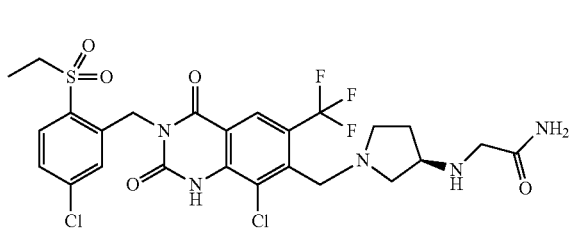 [SMILES: CCS(=O)(=O)c1ccc(Cl)cc1Cn1c(=O)[nH]c2c(Cl)c(CN3CC[C@@H](NCC(N)=O)C3)c(C(F)(F)F)cc2c1=O]

The title compound was synthesized from 7-((R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound F-10.

LCMS: m/z 636 [M+H]$^+$

HPLC retention time: 0.56 min (analysis condition D)

Example 335

Compound F-35

8-Chloro-3-(5-chloro-2-ethanesulfonyl-benzyl)-7-((R)-3-prop-2-ynylamino-pyrrolidin-1-ylmethyl)-6-trifluoromethyl-1H-quinazoline-2,4-dione

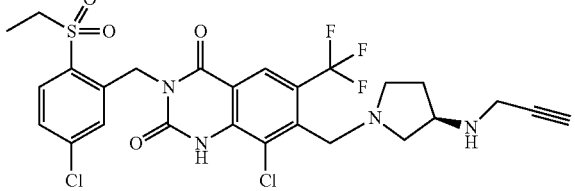

The title compound was synthesized from 7-(R)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-15) under the same conditions as for Compound F-7.

LCMS: m/z 617 [M+H]$^+$

HPLC retention time: 1.53 min (analysis condition C)

Example 336

Compound f14

4-((R)-3-Acetylamino-pyrrolidin-1-ylmethyl)-2-amino-5-trifluoromethyl-benzoic acid ethyl ester

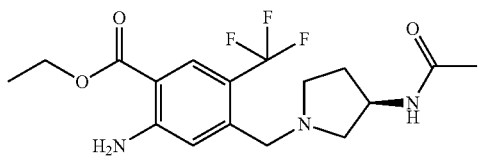 [SMILES: CCOC(=O)c1cc(C(F)(F)F)c(CN2CC[C@@H](NC(C)=O)C2)cc1N]

The title compound was synthesized from 2-amino-4-formyl-5-trifluoromethyl-benzoic acid ethyl ester (Compound 23) under the same conditions as for Compound b12. However, the reaction was carried out by using N-[(3R)-pyrrolidin-3-yl]acetamide in place of (S)-pyrrolidin-3-yl-carbamic acid tert-butyl ester.

Example 337

Compound f15

4-((R)-3-Acetylamino-pyrrolidin-1-ylmethyl)-2-amino-5-trifluoromethyl-benzoic acid

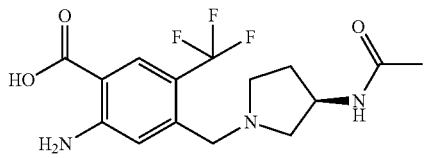 [SMILES: CC(=O)N[C@@H]1CCN(Cc2cc(N)c(C(=O)O)cc2C(F)(F)F)C1]

The title compound was synthesized from 4-((R)-3-acetylamino-pyrrolidin-1-ylmethyl)-2-amino-5-trifluoromethyl-benzoic acid ethyl ester (Compound f14) under the same conditions as for Compound 25.

Example 338

Compound f16

4-((R)-3-Acetylamino-pyrrolidin-1-ylmethyl)-2-amino-N-(5-chloro-2-ethanesulfonyl-benzyl)-5-trifluoromethyl-benzamide

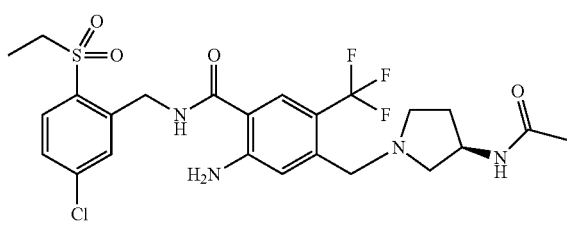 [SMILES: CCS(=O)(=O)c1ccc(Cl)cc1CNC(=O)c1cc(C(F)(F)F)c(CN2CC[C@@H](NC(C)=O)C2)cc1N]

The title compound was synthesized from 4-((R)-3-acetylamino-pyrrolidin-1-ylmethyl)-2-amino-5-trifluoromethyl-benzoic acid (Compound f15) under the same conditions as for Compound 26. However, the reaction was performed without adding HOBT.

Example 339

Compound f17

4-((R)-3-Acetylamino-pyrrolidin-1-ylmethyl)-2-amino-3-chloro-N-(5-chloro-2-ethanesulfonyl-benzyl)-5-trifluoromethyl-benzamide

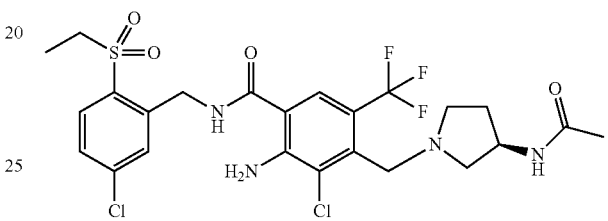

The title compound was synthesized from 4-((R)-3-acetylamino-pyrrolidin-1-ylmethyl)-2-amino-N-(5-chloro-2-ethanesulfonyl-benzyl)-5-trifluoromethyl-benzamide (Compound f16) under the same conditions as for Compound 24.

Example 340

Compound F-36

N-{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-acetamide

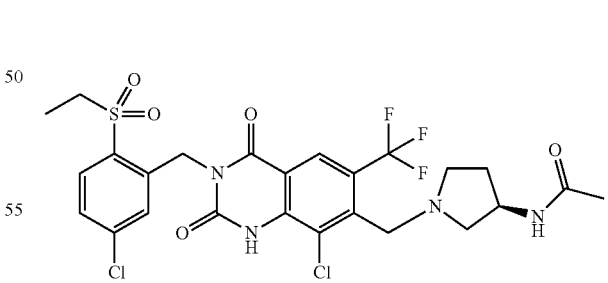

The title compound was synthesized from 4-((R)-3-acetylamino-pyrrolidin-1-ylmethyl)-2-amino-3-chloro-N-(5-chloro-2-ethanesulfonyl-benzyl)-5-trifluoromethyl-benzamide (Compound f17) under the same conditions as for Compound 37.

LCMS: m/z 621 [M+H]$^+$

HPLC retention time: 0.52 min (analysis condition D)

Example 341

Compound f18

{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-methyl-carbamic acid tert-butyl ester

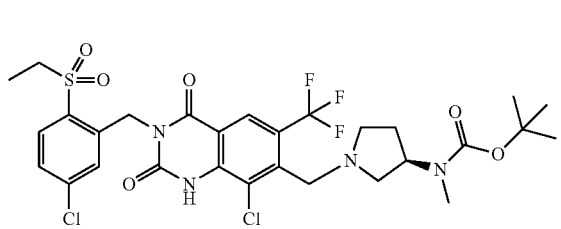 [SMILES: CCS(=O)(=O)c1ccc(Cl)cc1Cn1c(=O)[nH]c2c(Cl)c(CN3CC[C@@H](N(C)C(=O)OC(C)(C)C)C3)c(C(F)(F)F)cc2c1=O]

The title compound was synthesized from {(R)-1-[5-amino-4-(5-chloro-2-ethanesulfonyl-benzylcarbamoyl)-2-trifluoromethyl-benzyl]-pyrrolidin-3-yl}-methyl-carbamic acid tert-butyl ester (Compound b19) under the same conditions as for Compounds f17 and F-36.

Example 342

Compound F-37

8-Chloro-3-(5-chloro-2-ethanesulfonyl-benzyl)-7-((R)-3-methylamino-pyrrolidin-1-ylmethyl)-6-trifluoromethyl-1H-quinazoline-2,4-dione

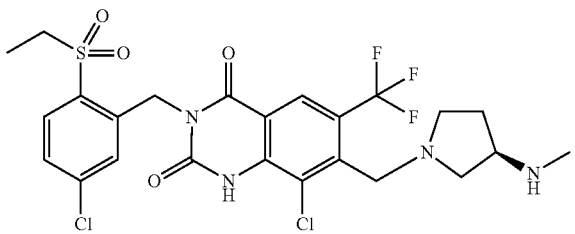 [SMILES: CCS(=O)(=O)c1ccc(Cl)cc1Cn1c(=O)[nH]c2c(Cl)c(CN3CC[C@@H](NC)C3)c(C(F)(F)F)cc2c1=O]

The title compound was synthesized from {(R)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-methyl-carbamic acid tert-butyl ester (Compound f18) under the same conditions as for Compound a41.

LCMS: m/z 593 [M+H]$^+$

HPLC retention time: 0.56 min (analysis condition D)

Example 343

Compound F-38

N-{(R)-1-[8-Chloro-3-(5-chloro-2-ethanesulfonyl-benzyl)-2,4-dioxo-6-trifluoromethyl-1,2,34-tetrahydro-quinazolin-7-ylmethyl]-pyrrolidin-3-yl}-N-methyl-acetamide

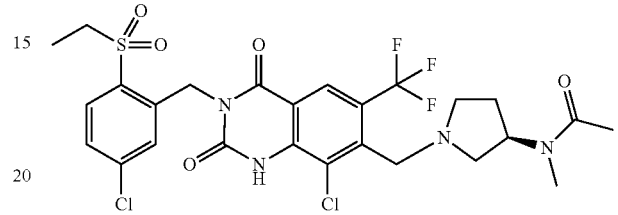

The title compound was synthesized from 8-chloro-3-(5-chloro-2-ethanesulfonyl-benzyl)-7-((R)-3-methylamino-pyrrolidin-1-ylmethyl)-6-trifluoromethyl-1H-quinazoline-2,4-dione (Compound F-37) under the same conditions as for Compound B-18.

LCMS: m/z 635 [M+H]$^+$

HPLC retention time: 0.56 min (analysis condition D)

Example 344

Compound F-39

N-{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-N-methyl-methanesulfonamide

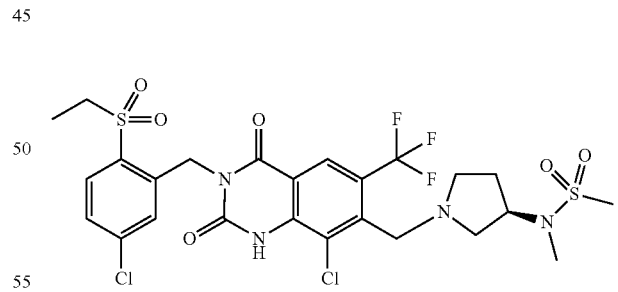

The title compound was synthesized from 8-chloro-3-(5-chloro-2-ethanesulfonyl-benzyl)-7-((R)-3-methylamino-pyrrolidin-1-ylmethyl)-6-trifluoromethyl-1H-quinazoline-2,4-dione (Compound F-37) under the same conditions as for Compound C-6. However, the reaction was performed using TEA in place of DIPEA.

LCMS: m/z 671 [M+H]$^+$

HPLC retention time: 0.74 min (analysis condition D)

Example 345

Compound f19

2-Amino-3-chloro-4-[(S)-1-(hexahydro-pyrrolo[1,2-a]pyrazin-2-yl)methyl]-5-trifluoromethyl-benzoic acid ethyl ester

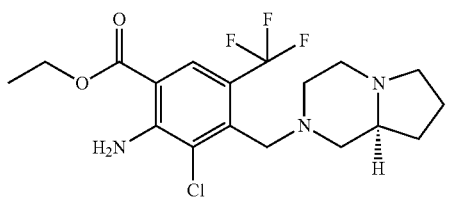 [SMILES: CCOC(=O)c1cc(C(F)(F)F)c(CN2CCN3CCC[C@H]3C2)c(Cl)c1N]

The title compound was synthesized from 2-amino-3-chloro-4-formyl-5-trifluoromethyl-benzoic acid ethyl ester (Compound 24) and (S)-octahydro-pyrrolo[1,2-a]pyrazine under the same conditions as for Compound b12.

Example 346

Compound f20

2-Amino-3-chloro-4-[(S)-1-(hexahydro-pyrrolo[1,2-a]pyrazin-2-yl)methyl]-5-trifluoromethyl-benzoic acid

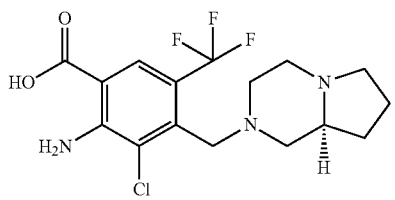 [SMILES: Nc1c(C(=O)O)cc(C(F)(F)F)c(CN2CCN3CCC[C@H]3C2)c1Cl]

The title compound was synthesized from 2-amino-3-chloro-4-[(S)-1-(hexahydro-pyrrolo[1,2-a]pyrazin-2-yl)methyl]-5-trifluoromethyl-benzoic acid ethyl ester (Compound f19) under the same conditions as for Compound 25.

Example 347

Compound f21

2-Amino-3-chloro-N-(5-chloro-2-ethanesulfonyl-benzyl)-4-[(S)-1-(hexahydro-pyrrolo[1,2-a]pyrazin-2-yl)methyl]-5-trifluoromethyl-benzamide

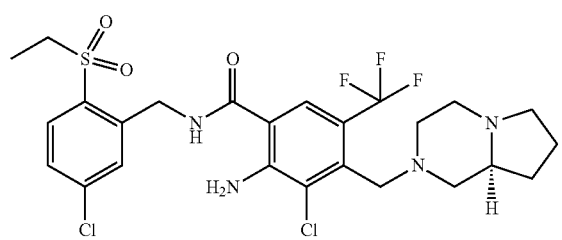 [SMILES: CCS(=O)(=O)c1ccc(Cl)cc1CNC(=O)c1cc(C(F)(F)F)c(CN2CCN3CCC[C@H]3C2)c(Cl)c1N]

The title compound was synthesized from 2-amino-3-chloro-4-[(S)-1-(hexahydro-pyrrolo[1,2-a]pyrazin-2-yl)methyl]-5-trifluoromethyl-benzoic acid (Compound f20) under the same conditions as for Compound 26. However, the reaction was performed without adding HOBT.

Example 348

Compound F-41

8-Chloro-3-(5-chloro-2-ethanesulfonyl-benzyl)-7-[(S)-1-(hexahydro-pyrrolo[1,2-a]pyrazin-2-yl)methyl]-6-trifluoromethyl-1H-quinazoline-2,4-dione

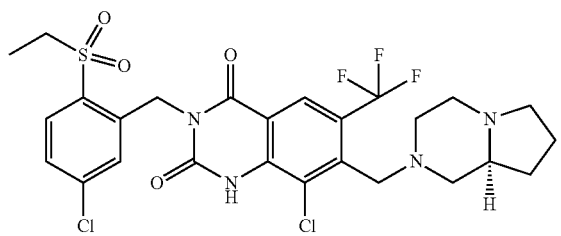 [SMILES: CCS(=O)(=O)c1ccc(Cl)cc1Cn1c(=O)[nH]c2c(Cl)c(CN3CCN4CCC[C@H]4C3)c(C(F)(F)F)cc2c1=O]

The title compound was synthesized from 2-amino-3-chloro-N-(5-chloro-2-ethanesulfonyl-benzyl)-4-[(S)-1-(hexahydro-pyrrolo[1,2-a]pyrazin-2-yl)methyl]-5-trifluoromethyl-benzamide (Compound f21) under the same conditions as for Compound 37.

LCMS: m/z 619 [M+H]$^+$

HPLC retention time: 0.58 min (analysis condition D)

Example 349

Compound F-42

8-Chloro-3-(5-chloro-2-ethanesulfonyl-benzyl)-7-[(R)-1-(hexahydro-pyrrolo[1,2-a]pyrazin-2-yl)methyl]-6-trifluoromethyl-1H-quinazoline-2,4-dione

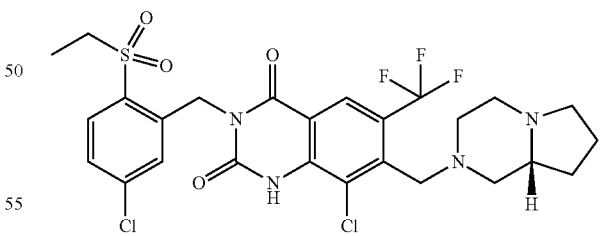

The title compound was synthesized from 2-amino-3-chloro-4-formyl-5-trifluoromethyl-benzoic acid ethyl ester (Compound 24) under the same conditions as for Compounds f19, f20, f21, and F-41. However, the reaction was performed using (R)-octahydro-pyrrolo[1,2-a]pyrazine in place of (S)-octahydro-pyrrolo[1,2-a]pyrazine under the conditions for Compound f19.

LCMS: m/z 619 [M+H]$^+$

HPLC retention time: 0.59 min (analysis condition D)

Example 350

Compound f22

{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-ylmethyl}-methyl-carbamic acid tert-butyl ester

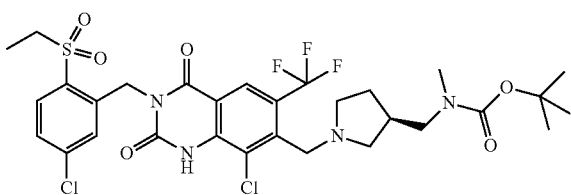 [SMILES: CCS(=O)(=O)c1ccc(Cl)cc1Cn1c(=O)[nH]c2c(Cl)c(CN3CC[C@@H](CN(C)C(=O)OC(C)(C)C)C3)c(C(F)(F)F)cc2c1=O]

The title compound was synthesized from 2-amino-3-chloro-4-formyl-5-trifluoromethyl-benzoic acid ethyl ester (Compound 24) under the same conditions as for Compounds f19, f20, f21, and F-41. However, the reaction was performed using methyl-(R)-1-pyrrolidin-3-ylmethyl-carbamic acid tert-butyl ester in place of (S)-octahydro-pyrrolo[1,2-a]pyrazine under the conditions for Compound f19.

Example 351

Compound F-43

8-Chloro-3-(5-chloro-2-ethanesulfonyl-benzyl)-7-((S)-3-methylaminomethyl-pyrrolidin-1-ylmethyl)-6-trifluoromethyl-1H-quinazoline-2,4-dione

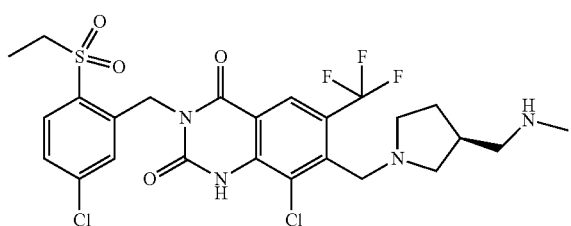 [SMILES: CCS(=O)(=O)c1ccc(Cl)cc1Cn1c(=O)[nH]c2c(Cl)c(CN3CC[C@@H](CNC)C3)c(C(F)(F)F)cc2c1=O]

The title compound was synthesized from {(R)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-ylmethyl}-methyl-carbamic acid tert-butyl ester (Compound f22) under the same conditions as for Compound a41.

LCMS: m/z 607 [M+H]$^+$

HPLC retention time: 0.43 min (analysis condition D)

Example 352

Compound f23

{(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-ylmethyl}-methyl-carbamic acid tert-butyl ester

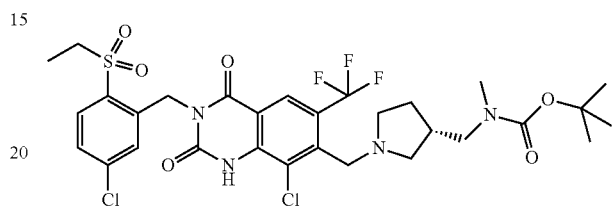

The title compound was synthesized from 2-amino-3-chloro-4-formyl-5-trifluoromethyl-benzoic acid ethyl ester (Compound 24) under the same conditions as for Compounds f19, f20, f21, and F-41. However, the reaction was performed using methyl-(S)-1-pyrrolidin-3-ylmethyl-carbamic acid tert-butyl ester in place of (S)-octahydro-pyrrolo[1,2-a]pyrazine under the conditions for Compound f19.

Example 353

Compound F-44

8-Chloro-3-(5-chloro-2-ethanesulfonyl-benzyl)-7-((R)-3-methylaminomethyl-pyrrolidin-1-ylmethyl)-6-trifluoromethyl-1H-quinazoline-2,4-dione

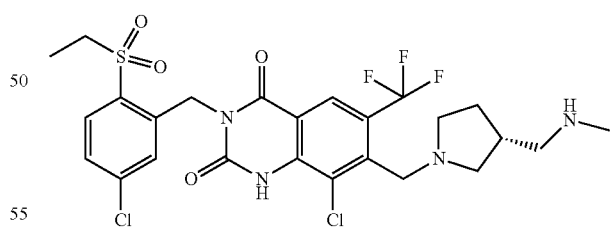

The title compound was synthesized from {(S)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-ylmethyl}-methyl-carbamic acid tert-butyl ester (Compound f23) under the same conditions as for Compound a41.

LCMS: m/z 607 [M+H]$^+$

HPLC retention time: 0.45 min (analysis condition D)

Example 354

Compound F-45

8-Chloro-3-(5-chloro-2-ethanesulfonyl-benzyl)-2,4-dioxo-6-trifluoromethyl-1,2,3,4-tetrahydro-quinazoline-7-carbaldehyde

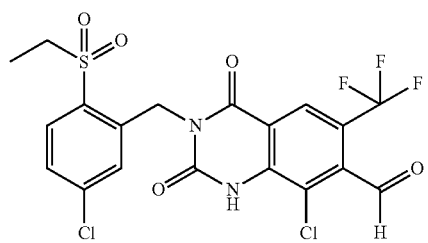 [SMILES: CCS(=O)(=O)c1ccc(Cl)cc1Cn1c(=O)[nH]c2c(Cl)c(C=O)c(C(F)(F)F)cc2c1=O]

The title compound was synthesized from 2-amino-3-chloro-N-(5-chloro-2-ethanesulfonyl-benzyl)-4-formyl-5-trifluoromethyl-benzamide (Compound 26) under the same conditions as for Compound A-4.

LCMS: m/z 509 [M+H]$^+$

HPLC retention time: 0.85 min (analysis condition D)

Example 355

Compound F-46

{(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-carbamic acid tert-butyl ester

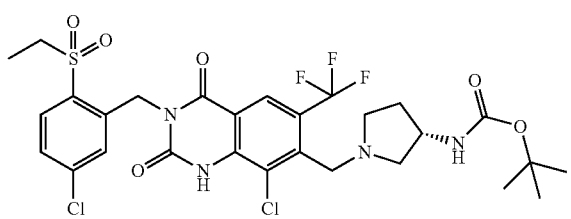 [SMILES: CCS(=O)(=O)c1ccc(Cl)cc1Cn1c(=O)[nH]c2c(Cl)c(CN3CC[C@H](NC(=O)OC(C)(C)C)C3)c(C(F)(F)F)cc2c1=O]

The title compound was synthesized from 8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and (S)-pyrrolidin-3-yl-carbamic acid tert-butyl ester under the same conditions as for Compound b12.

LCMS: m/z 679 [M+H]$^+$

HPLC retention time: 0.68 min (analysis condition D)

Example 356

Compound F-47

7-((S)-3-Amino-pyrrolidin-1-ylmethyl)-8-chloro-3-(5-chloro-2-ethanesulfonyl-benzyl)-6-trifluoromethyl-1H-quinazoline-2,4-dione

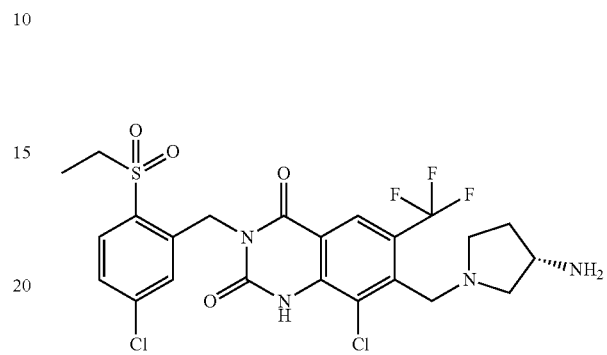

The title compound was synthesized from {(S)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-carbamic acid tert-butyl ester (Compound F-46) under the same conditions as for Compound a41.

LCMS: m/z 579 [M+H]$^+$

HPLC retention time: 0.56 min (analysis condition D)

Example 357

Compound F-48

8-Chloro-3-(5-chloro-2-ethanesulfonyl-benzyl)-7-((S)-3-dimethylamino-pyrrolidin-1-ylmethyl)-6-trifluoromethyl-1H-quinazoline-2,4-dione

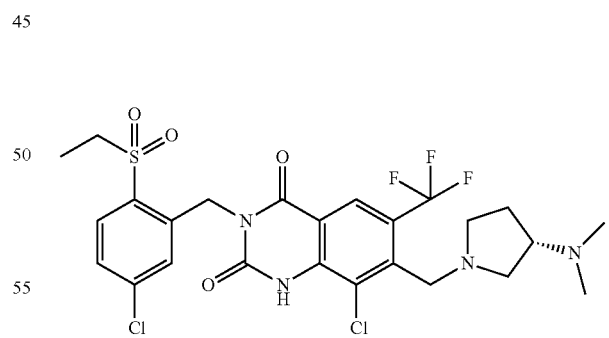

The title compound was synthesized from 7-((S)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-47) under the same conditions as for Compound B-9.

LCMS: m/z 607 [M+H]$^+$

HPLC retention time: 0.61 min (analysis condition D)

Example 358

Compound F-49

N-{(S)-1-[8-Chloro-3-(5-chloro-2-ethanesulfonyl-benzyl)-2,4-dioxo-6-trifluoromethyl-1,2,3,4-tetra-hydro-quinazolin-7-ylmethyl]-pyrrolidin-3-yl}-acet-amide

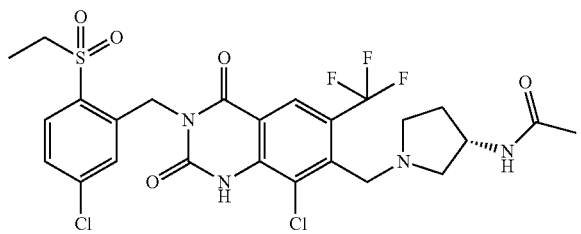 [SMILES: CCS(=O)(=O)c1ccc(Cl)cc1Cn1c(=O)[nH]c2c(Cl)c(CN3CC[C@H](NC(C)=O)C3)c(C(F)(F)F)cc2c1=O]

The title compound was synthesized from 7-((S)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-47) under the same conditions as for Compound B-18.

LCMS: m/z 621 [M+H]$^+$

HPLC retention time: 0.53 min (analysis condition D)

Example 359

Compound F-50

N-{(S)-1-[8-Chloro-3-(5-chloro-2-ethanesulfonyl-benzyl)-2,4-dioxo-6-trifluoromethyl-1,2,3,4-tetra-hydro-quinazolin-7-ylmethyl]-pyrrolidin-3-yl}-methanesulfonamide

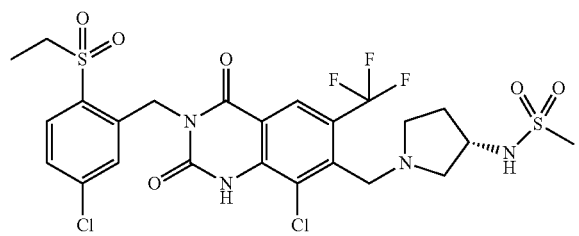 [SMILES: CCS(=O)(=O)c1ccc(Cl)cc1Cn1c(=O)[nH]c2c(Cl)c(CN3CC[C@H](NS(C)(=O)=O)C3)c(C(F)(F)F)cc2c1=O]

The title compound was synthesized from 7-((S)-3-amino-pyrrolidin-1-ylmethyl)-8-chloro-3-(5-chloro-2-ethanesulfonyl-benzyl)-6-trifluoromethyl-1H-quinazoline-2,4-dione (Compound F-47) under the same conditions as for Compound C-6. However, the reaction was performed using TEA in place of DIPEA.

LCMS: m/z 657 [M+H]$^+$

HPLC retention time: 0.56 min (analysis condition D)

Example 360

Compound F-51

{(S)-1-[8-Chloro-3-(5-chloro-2-ethanesulfonyl-ben-zyl)-2,4-dioxo-6-trifluoromethyl-1,2, 3,4-tetrahydro-quinazolin-7-ylmethyl]-pyrrolidin-3-yl}-methyl-carbamic acid tert-butyl ester

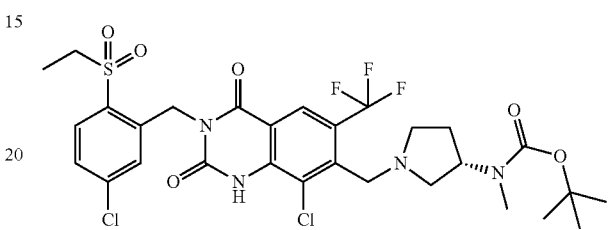

The title compound was synthesized from 8-chloro-3-(5-chloro-2-ethanesulfonyl-benzyl)-2,4-dioxo-6-trifluorom-ethyl-1,2,3,4-tetrahydro-quinazoline-7-carbaldehyde (Compound F-45) and methyl-(S)-pyrrolidin-3-yl-carbamic acid tert-butyl ester under the same conditions as for Compound b12.

LCMS: m/z 693 [M+H]$^+$

HPLC retention time: 0.76 min (analysis condition D)

Example 361

Compound F-52

8-Chloro-3-(5-chloro-2-ethanesulfonyl-benzyl)-7-((S)-3-methylamino-pyrrolidin-1-ylmethyl)-6-trif-luoromethyl-1H-quinazoline-2,4-dione

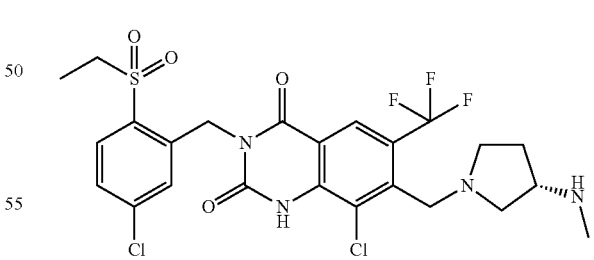

The title compound was synthesized from {(S)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-methyl-carbamic acid tert-butyl ester (Compound F-51) under the same conditions as for Compound a41.

LCMS: m/z 593 [M+H]$^+$

HPLC retention time: 0.60 min (analysis condition D)

Example 362

Compound F-53

{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-3-yl}-carbamic acid tert-butyl ester

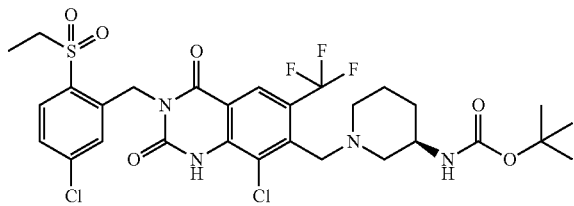 [SMILES: CCS(=O)(=O)c1ccc(Cl)cc1Cn1c(=O)[nH]c2c(Cl)c(CN3CCC[C@@H](NC(=O)OC(C)(C)C)C3)c(C(F)(F)F)cc2c1=O]

The title compound was synthesized from 8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and (R)-piperidin-3-yl-carbamic acid tert-butyl ester under the same conditions as for Compound b12.

LCMS: m/z 693 [M+H]$^+$

HPLC retention time: 0.87 min (analysis condition D)

Example 363

Compound F-54

7-((R)-3-Amino-piperidin-1-ylmethyl)-8-chloro-3-(5-chloro-2-ethanesulfonyl-benzyl)-6-trifluoromethyl-1H-quinazoline-2,4-dione

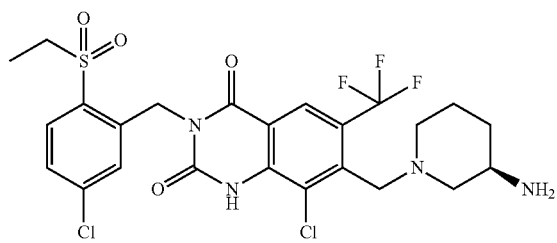 [SMILES: CCS(=O)(=O)c1ccc(Cl)cc1Cn1c(=O)[nH]c2c(Cl)c(CN3CCC[C@@H](N)C3)c(C(F)(F)F)cc2c1=O]

The title compound was synthesized from {(R)-1-[8-chloro-3-(5-chloro-2-ethanesulfonyl-benzyl)-2,4-di oxo-6-trifluoromethyl-1,2,3,4-tetrahydro-quinazolin-7-ylmethyl]-piperidin-3-yl}-carbamic acid tert-butyl ester (Compound F-53) under the same conditions as for Compound a41.

LCMS: m/z 593 [M+H]$^+$

HPLC retention time: 0.54 min (analysis condition H)

Example 364

Compound F-55

8-Chloro-3-(5-chloro-2-ethanesulfonyl-benzyl)-7-((R)-3-dimethylamino-piperidin-1-ylmethyl)-6-trifluoromethyl-1H-quinazoline-2,4-dione

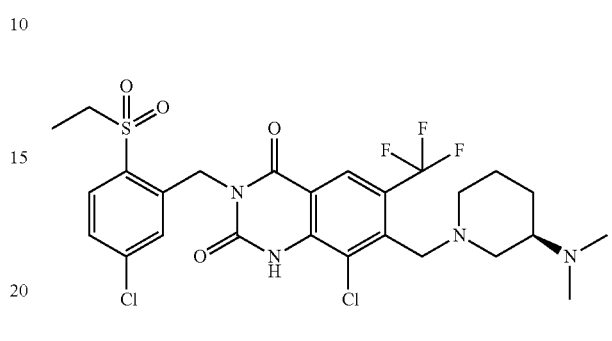

The title compound was synthesized from 7-((R)-3-amino-piperidin-1-ylmethyl)-8-chloro-3-(5-chloro-2-ethanesulfonyl-benzyl)-6-trifluoromethyl-1H-quinazoline-2,4-dione (Compound F-54) under the same conditions as for Compound B-9.

LCMS: m/z 621 [M+H]$^+$

HPLC retention time: 0.60 min (analysis condition D)

Example 365

Compound F-56

N-{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-3-yl}-acetamide

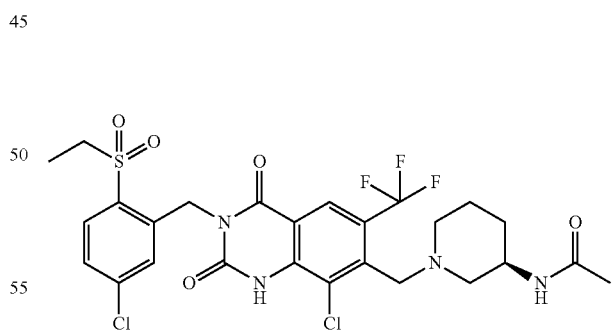

The title compound was synthesized from 7-((R)-3-amino-piperidin-1-ylmethyl)-8-chloro-3-(5-chloro-2-ethanesulfonyl-benzyl)-6-trifluoromethyl-1H-quinazoline-2,4-dione (Compound F-54) under the same conditions as for Compound B-18.

LCMS: m/z 635 [M+H]$^+$

HPLC retention time: 0.61 min (analysis condition D)

Example 366

Compound F-57

N-{(R)-1-[8-Chloro-3-(5-chloro-2-ethanesulfonyl-benzyl)-2,4-dioxo-6-trifluoromethyl-1,2,3,4-tetra-hydro-quinazolin-7-ylmethyl]-piperidin-3-yl}-methanesulfonamide

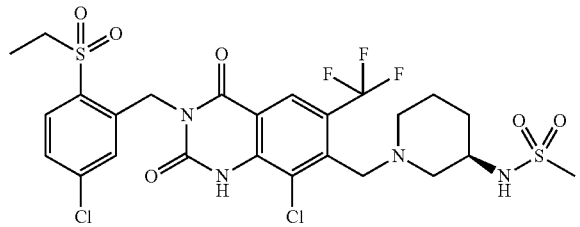 [SMILES: CCS(=O)(=O)c1ccc(Cl)cc1Cn1c(=O)[nH]c2c(Cl)c(CN3CCC[C@@H](NS(C)(=O)=O)C3)c(C(F)(F)F)cc2c1=O]

The title compound was synthesized from 7-((R)-3-amino-piperidin-1-ylmethyl)-8-chloro-3-(5-chloro-2-ethanesulfonyl-benzyl)-6-trifluoromethyl-1H-quinazoline-2,4-dione (Compound F-54) under the same conditions as for Compound C-6. However, the reaction was performed using TEA in place of DIPEA.

LCMS: m/z 671 [M+H]$^+$

HPLC retention time: 0.72 min (analysis condition D)

Example 367

Compound F-58

{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-3-yl}-methyl-carbamic acid tert-butyl ester

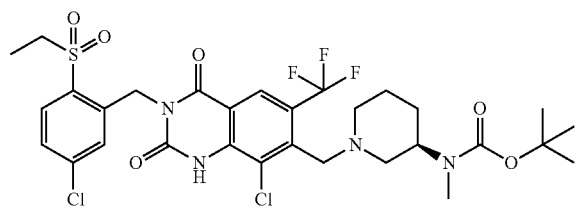 [SMILES: CCS(=O)(=O)c1ccc(Cl)cc1Cn1c(=O)[nH]c2c(Cl)c(CN3CCC[C@@H](N(C)C(=O)OC(C)(C)C)C3)c(C(F)(F)F)cc2c1=O]

The title compound was synthesized from (8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and methyl-(R)-piperidin-3-yl-carbamic acid tert-butyl ester under the same conditions as for Compound b12. However, the reaction was performed using DCM in place of THF.

LCMS: m/z 707 [M+H]$^+$

HPLC retention time: 0.91 min (analysis condition D)

Example 368

Compound F-59

8-Chloro-3-(5-chloro-2-ethanesulfonyl-benzyl)-7-((R)-3-methylamino-piperidin-1-ylmethyl)-6-trifluoromethyl-1H-quinazoline-2,4-dione

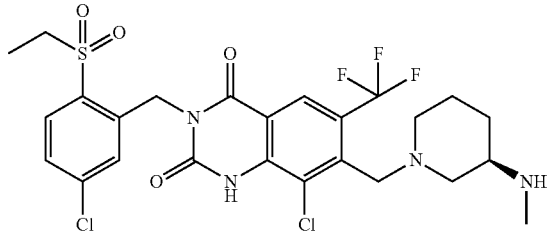 [SMILES: CCS(=O)(=O)c1ccc(Cl)cc1Cn1c(=O)[nH]c2c(Cl)c(CN3CCC[C@@H](NC)C3)c(C(F)(F)F)cc2c1=O]

The title compound was synthesized from {(R)-1-[8-chloro-3-(5-chloro-2-ethanesulfonyl-benzyl)-2,4-dioxo-6-trifluoromethyl-1,2,3,4-tetrahydro-quinazolin-7-ylmethyl]-piperidin-3-yl}-methyl-carbamic acid tert-butyl ester (F-58) under the same conditions as for Compound a41.

LCMS: m/z 607 [M+H]$^+$

HPLC retention time: 0.59 min (analysis condition D)

Example 369

Compound F-60

{(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-3-yl}-carbamic acid tert-butyl ester

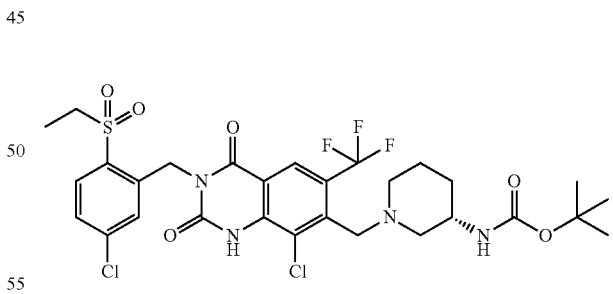

The title compound was synthesized from 8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and (S)-piperidin-3-yl-carbamic acid tert-butyl ester under the same conditions as for Compound b12. However, the reaction was performed using chloroform in place of THF.

LCMS: m/z 693 [M+H]$^+$

HPLC retention time: 0.86 min (analysis condition D)

Example 370

Compound F-61

7-((S)-3-Amino-piperidin-1-ylmethyl)-8-chloro-3-(5-chloro-2-ethanesulfonyl-benzyl)-6-trifluoromethyl-1H-quinazoline-2,4-dione

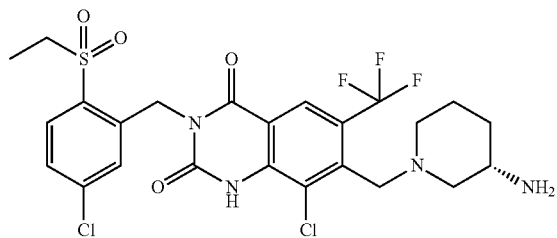 [SMILES: CCS(=O)(=O)c1ccc(Cl)cc1Cn1c(=O)[nH]c2c(Cl)c(CN3CCC[C@H](N)C3)c(C(F)(F)F)cc2c1=O]

The title compound was synthesized from {(S)-1-[8-chloro-3-(5-chloro-2-ethanesulfonyl-benzyl)-2,4-dioxo-6-trifluoromethyl-1,2,3,4-tetrahydro-quinazolin-7-ylmethyl]-piperidin-3-yl}-carbamic acid tert-butyl ester (Compound F-60) under the same conditions as for Compound a41.

LCMS: m/z 593 [M+H]$^+$

HPLC retention time: 0.59 min (analysis condition D)

Example 371

Compound F-62

8-Chloro-3-(5-chloro-2-ethanesulfonyl-benzyl)-7-((S)-3-dimethylamino-piperidin-1-ylmethyl)-6-trifluoromethyl-1H-quinazoline-2,4-dione

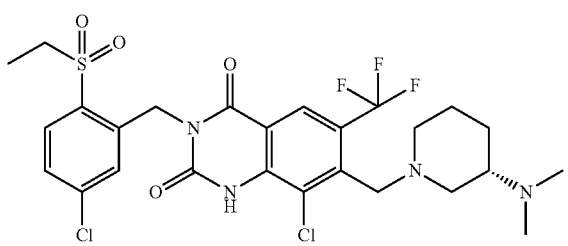 [SMILES: CCS(=O)(=O)c1ccc(Cl)cc1Cn1c(=O)[nH]c2c(Cl)c(CN3CCC[C@H](N(C)C)C3)c(C(F)(F)F)cc2c1=O]

The title compound was synthesized from 7-((S)-3-amino-piperidin-1-ylmethyl)-8-chloro-3-(5-chloro-2-ethanesulfonyl-benzyl)-6-trifluoromethyl-1H-quinazoline-2,4-dione (Compound F-61) under the same conditions as for Compound B-9.

LCMS: m/z 621 [M+H]$^+$

HPLC retention time: 0.61 min (analysis condition D)

Example 372

Compound F-63

N-{(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-3-yl}-acetamide

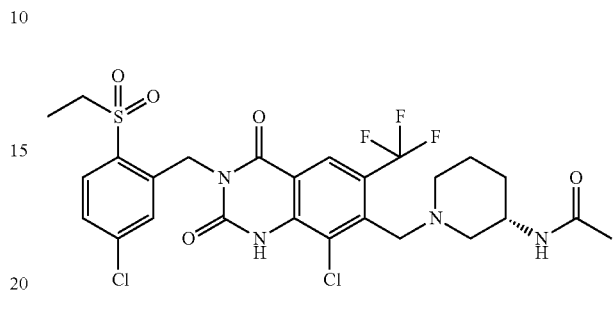

The title compound was synthesized from 7-((S)-3-amino-piperidin-1-ylmethyl)-8-chloro-3-(5-chloro-2-ethanesulfonyl-benzyl)-6-trifluoromethyl-1H-quinazoline-2,4-dione (Compound F-61) under the same conditions as for Compound B-18.

LCMS: m/z 635 [M+H]$^+$

HPLC retention time: 0.61 min (analysis condition D)

Example 373

Compound F-64

N-{(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-3-yl}-methanesulfonamide

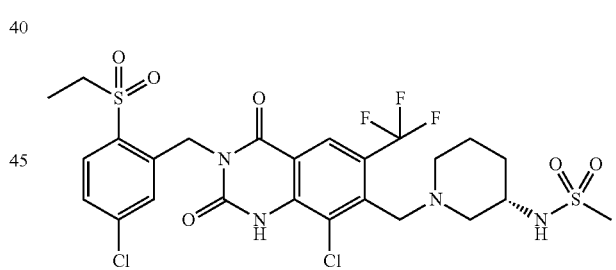

The title compound was synthesized from 7-((S)-3-amino-piperidin-1-ylmethyl)-8-chloro-3-(5-chloro-2-ethanesulfonyl-benzyl)-6-trifluoromethyl-1H-quinazoline-2,4-dione (Compound F-61) under the same conditions as for Compound C-6. However, the reaction was performed using TEA in place of DIPEA.

LCMS: m/z 671 [M+H]$^+$

HPLC retention time: 0.72 min (analysis condition D)

Examples 374 to 377

The following compounds of Table 4 were synthesized using 7-((S)-3-amino-piperidin-1-ylmethyl)-8-chloro-3-(5-chloro-2-ethanesulfonyl-benzyl)-6-trifluoromethyl-1H-quinazoline-2,4-dione (Compound F-61) and corresponding amino acids under the same conditions as for Compound F-5.

TABLE 4

| Example | Compound No. | Structure | Compound name | HPLC cond. | Retention time (min) | m/z [M + H]+ |
|---|---|---|---|---|---|---|
| 374 | F-65 | 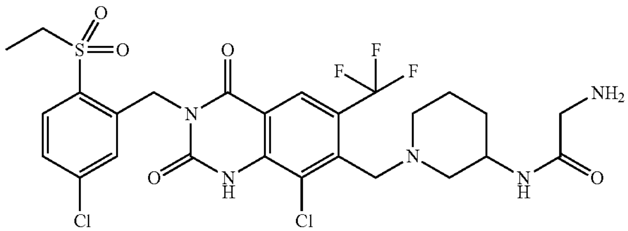 [SMILES: CCS(=O)(=O)c1ccc(Cl)cc1Cn1c(=O)[nH]c2c(Cl)c(CN3CCCC(NC(=O)CN)C3)c(C(F)(F)F)cc2c1=O] | 2-Amino-N-{(S)-1-[8-chloro-3-(5-chloro-2-ethanesulfonyl-benzyl)-2,4-dioxo-6-trifluoromethyl-1,2,3,4-tetrahydro-quinazolin-7-ylmethyl]-piperidin-3-yl}-acetamide | E | 0.50 | 650 |
| 375 | F-66 | 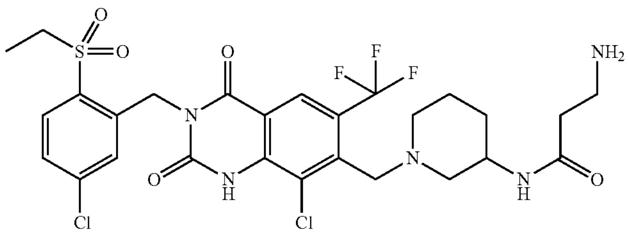 [SMILES: CCS(=O)(=O)c1ccc(Cl)cc1Cn1c(=O)[nH]c2c(Cl)c(CN3CCCC(NC(=O)CCN)C3)c(C(F)(F)F)cc2c1=O] | 3-Amino-N-{(S)-1-[8-chloro-3-(5-chloro-2-ethanesulfonyl-benzyl)-2,4-dioxo-6-trifluoromethyl-1,2,3,4-tetrahydro-quinazolin-7-ylmethyl]-piperidin-3-yl}-propionamide | E | 0.51 | 664 |
| 376 | F-67 | 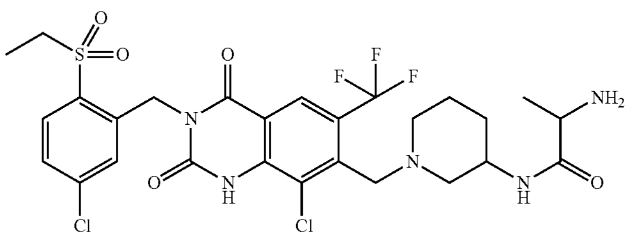 [SMILES: CCS(=O)(=O)c1ccc(Cl)cc1Cn1c(=O)[nH]c2c(Cl)c(CN3CCCC(NC(=O)C(C)N)C3)c(C(F)(F)F)cc2c1=O] | (R)-2-Amino-N-{(S)-1-[8-chloro-3-(5-chloro-2-ethanesulfonyl-benzyl)-2,4-dioxo-6-trifluoromethyl-1,2,3,4-tetrahydro-quinazolin-7-ylmethyl]-piperidin-3-yl}-propionamide | E | 0.52 | 664 |
| 377 | F-68 | 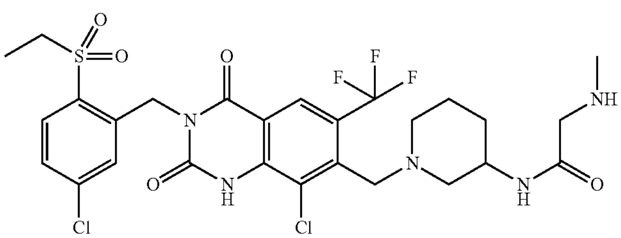 [SMILES: CCS(=O)(=O)c1ccc(Cl)cc1Cn1c(=O)[nH]c2c(Cl)c(CN3CCCC(NC(=O)CNC)C3)c(C(F)(F)F)cc2c1=O] | N-{(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-3-yl}-2-methylamino-acetamide | D | 0.51 | 664 |

Example 378

Compound F-69

{(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-3-yl}1-methyl-carbamic acid tert-butyl ester

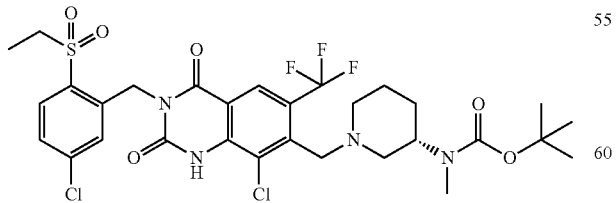

The title compound was synthesized from (8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and methyl-(S)-piperidin-3-yl-carbamic acid tert-butyl ester under the same conditions as for Compound b12. However, the reaction was performed using chloroform in place of THF.
LCMS: m/z 707 [M+H]+
HPLC retention time: 0.90 min (analysis condition D)

Example 379

Compound F-70

8-Chloro-3-(5-chloro-2-ethanesulfonyl-benzyl)-7-((S)-3-methylamino-piperidin-1-ylmethyl)-6-trifluoromethyl-1H-quinazoline-2,4-dione

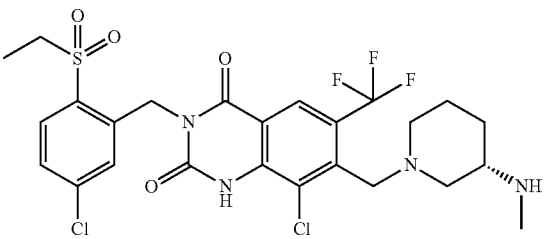 [SMILES: CCS(=O)(=O)c1ccc(Cl)cc1Cn1c(=O)[nH]c2c(Cl)c(CN3CCC[C@H](NC)C3)c(C(F)(F)F)cc2c1=O]

The title compound was synthesized from {(S)-1-[8-chloro-3-(5-chloro-2-ethanesulfonyl-benzyl)-2,4-dioxo-6-trifluoromethyl-1,2,3,4-tetrahydro-quinazolin-7-ylmethyl]-piperidin-3-yl}-methyl-carbamic acid tert-butyl ester (F-69) under the same conditions as for Compound a41.
LCMS: m/z 607 [M+H]⁺
HPLC retention time: 0.60 min (analysis condition D)

Example 380

Compound F-71

{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-2-ylmethyl}-carbamic acid tert-butyl ester

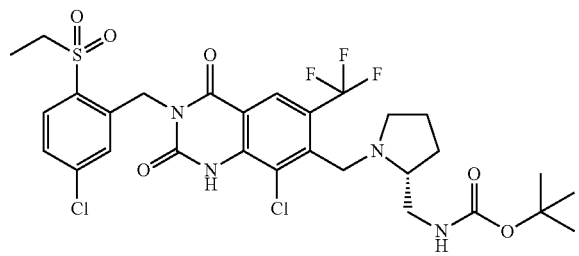 [SMILES: CCS(=O)(=O)c1ccc(Cl)cc1Cn1c(=O)[nH]c2c(Cl)c(CN3CCC[C@@H]3CNC(=O)OC(C)(C)C)c(C(F)(F)F)cc2c1=O]

The title compound was synthesized from (8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and (R)-1-pyrrolidin-2-ylmethyl-carbamic acid tert-butyl ester under the same conditions as for Compound b12. However, the reaction was performed using chloroform in place of THF.
LCMS: m/z 693 [M+H]⁺
HPLC retention time: 0.70 min (analysis condition D)

Example 381

Compound F-72

7-((R)-2-Aminomethyl-pyrrolidin-1-ylmethyl)-8-chloro-3-(5-chloro-2-ethanesulfonyl-benzyl)-6-trifluoromethyl-1H-quinazoline-2,4-dione

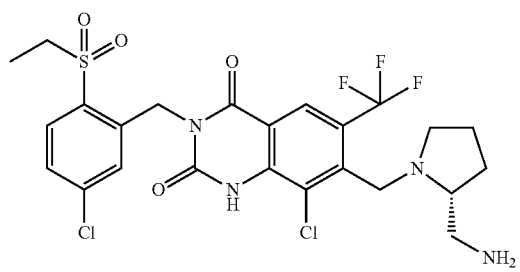 [SMILES: CCS(=O)(=O)c1ccc(Cl)cc1Cn1c(=O)[nH]c2c(Cl)c(CN3CCC[C@@H]3CN)c(C(F)(F)F)cc2c1=O]

The title compound was synthesized from {(R)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-2-ylmethyl}-carbamic acid tert-butyl ester (Compound F-71) under the same conditions as for Compound a41.
LCMS: m/z 593 [M+H]⁺
HPLC retention time: 0.59 min (analysis condition D)

Example 382

Compound F-73

8-Chloro-3-(5-chloro-2-ethanesulfonyl-benzyl)-7-((R)-2-dimethylaminomethyl-pyrrolidin-1-ylmethyl)-6-trifluoromethyl-1H-quinazoline-2,4-dione

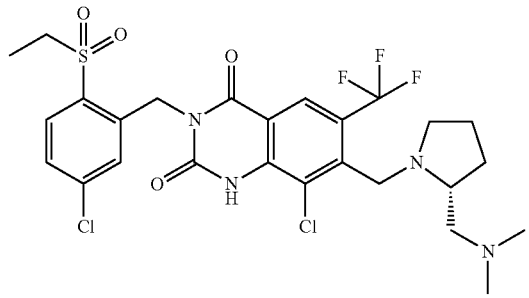 [SMILES: CCS(=O)(=O)c1ccc(Cl)cc1Cn1c(=O)[nH]c2c(Cl)c(CN3CCC[C@@H]3CN(C)C)c(C(F)(F)F)cc2c1=O]

The title compound was synthesized from 7-((R)-2-aminomethyl-pyrrolidin-1-ylmethyl)-8-chloro-3-(5-chloro-2-ethanesulfonyl-benzyl)-6-trifluoromethyl-1H-quinazoline-2,4-dione (Compound F-72) under the same conditions as for Compound B-9.
LCMS: m/z 621 [M+H]⁺
HPLC retention time: 0.63 min (analysis condition D)

Example 383

Compound F-74

N-{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-2-ylmethyl}-acetamide

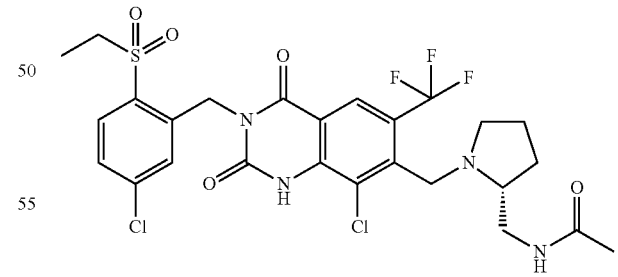

The title compound was synthesized from 7-((R)-2-aminomethyl-pyrrolidin-1-ylmethyl)-8-chloro-3-(5-chloro-2-ethanesulfonyl-benzyl)-6-trifluoromethyl-1H-quinazoline-2,4-dione (Compound F-72) under the same conditions as for Compound B-18.
LCMS: m/z 635 [M+H]⁺
HPLC retention time: 0.56 min (analysis condition D)

Example 384

Compound F-75

N-{(R)-1-[8-Chloro-3-(5-chloro-2-ethanesulfonyl-benzyl)-2,4-dioxo-6-trifluoromethyl-1,2,3,4-tetra-hydro-quinazolin-7-ylmethyl]-pyrrolidin-2-ylmethyl}-methanesulfonamide

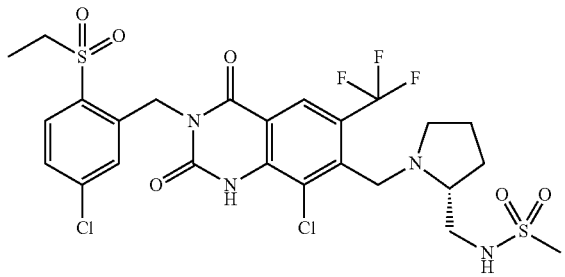 [SMILES: CCS(=O)(=O)c1ccc(Cl)cc1Cn1c(=O)[nH]c2c(Cl)c(CN3CCC[C@@H]3CNS(C)(=O)=O)c(C(F)(F)F)cc2c1=O]

The title compound was synthesized from 7-((R)-2-aminomethyl-pyrrolidin-1-ylmethyl)-8-chloro-3-(5-chloro-2-ethanesulfonyl-benzyl)-6-trifluoromethyl-1H-quinazoline-2,4-dione (Compound F-72) under the same conditions as for Compound C-6. However, the reaction was performed using TEA in place of DIPEA.

LCMS: m/z 671 [M+H]$^+$

HPLC retention time: 0.59 min (analysis condition D)

Example 385

Compound F-76

{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-2-ylmethyl}-methyl-carbamic acid tert-butyl ester

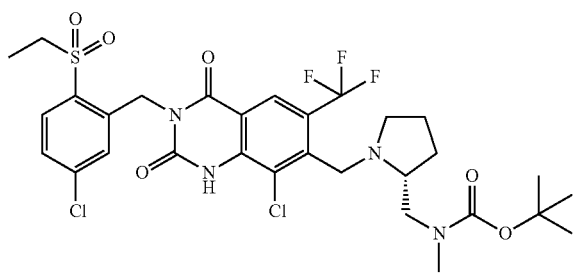 [SMILES: CCS(=O)(=O)c1ccc(Cl)cc1Cn1c(=O)[nH]c2c(Cl)c(CN3CCC[C@@H]3CN(C)C(=O)OC(C)(C)C)c(C(F)(F)F)cc2c1=O]

The title compound was synthesized from (8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and methyl-(R)-1-pyrrolidin-2-ylmethyl-carbamic acid tert-butyl ester under the same conditions as for Compound b12. However, the reaction was performed using chloroform in place of THF.

LCMS: m/z 707 [M+H]$^+$

HPLC retention time: 0.75 min (analysis condition D)

Example 386

Compound F-77

8-Chloro-3-(5-chloro-2-ethanesulfonyl-benzyl)-7-((R)-2-methylaminomethyl-pyrrolidin-1-ylmethyl)-6-trifluoromethyl-1H-quinazoline-2,4-dione

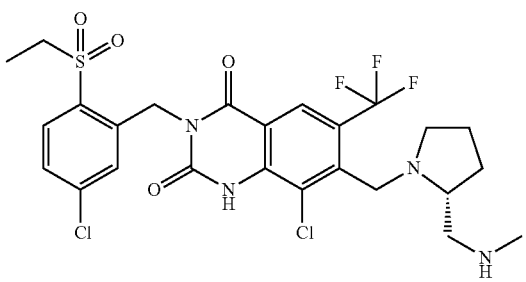 [SMILES: CCS(=O)(=O)c1ccc(Cl)cc1Cn1c(=O)[nH]c2c(Cl)c(CN3CCC[C@@H]3CNC)c(C(F)(F)F)cc2c1=O]

The title compound was synthesized from {(R)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-2-ylmethyl}-methyl-carbamic acid tert-butyl ester (Compound F-76) under the same conditions as for Compound a41.

LCMS: m/z 607 [M+H]$^+$

HPLC retention time: 0.60 min (analysis condition D)

Example 387

Compound F-78

{(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-2-ylmethyl}-carbamic acid tert-butyl ester

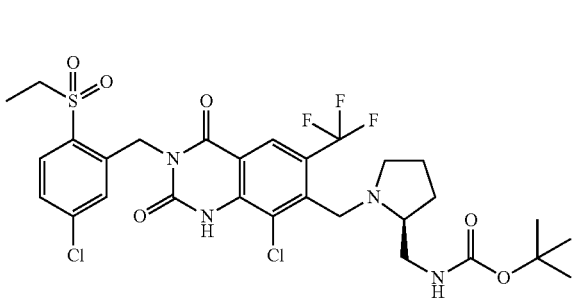 [SMILES: CCS(=O)(=O)c1ccc(Cl)cc1Cn1c(=O)[nH]c2c(Cl)c(CN3CCC[C@H]3CNC(=O)OC(C)(C)C)c(C(F)(F)F)cc2c1=O]

The title compound was synthesized from (8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and (S)-1-pyrrolidin-2-ylmethyl-carbamic acid tert-butyl ester under the same conditions as for Compound b12. However, the reaction was performed using chloroform in place of THF.

LCMS: m/z 693 [M+H]$^+$

HPLC retention time: 0.70 min (analysis condition D)

Example 388

Compound F-79

7-((S)-2-Aminomethyl-pyrrolidin-1-ylmethyl)-8-chloro-3-(5-chloro-2-ethanesulfonyl-benzyl)-6-trifluoromethyl-1H-quinazoline-2,4-dione

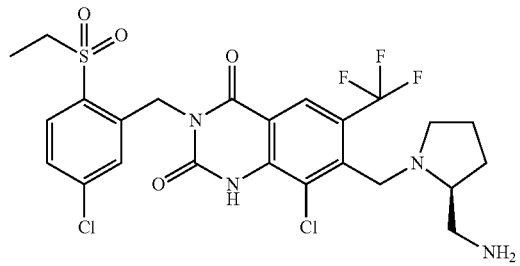 [SMILES: CCS(=O)(=O)c1ccc(Cl)cc1Cn1c(=O)[nH]c2c(Cl)c(CN3CCC[C@H]3CN)c(C(F)(F)F)cc2c1=O]

The title compound was synthesized from {(S)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-2-ylmethyl}-carbamic acid tert-butyl ester (Compound F-78) under the same conditions as for Compound a41.

LCMS: m/z 593 [M+H]+

HPLC retention time: 0.59 min (analysis condition D)

Example 389

Compound F-80

8-Chloro-3-(5-chloro-2-ethanesulfonyl-benzyl)-7-((S)-2-dimethylaminomethyl-pyrrolidin-1-ylmethyl)-6-trifluoromethyl-1H-quinazoline-2,4-dione

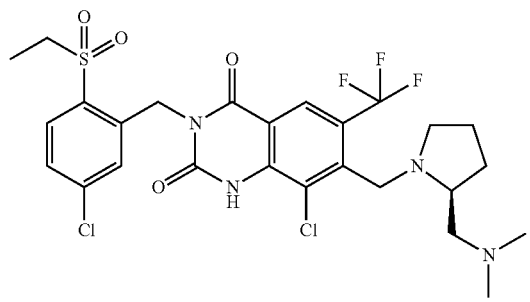 [SMILES: CCS(=O)(=O)c1ccc(Cl)cc1Cn1c(=O)[nH]c2c(Cl)c(CN3CCC[C@H]3CN(C)C)c(C(F)(F)F)cc2c1=O]

The title compound was synthesized from 7-((S)-2-aminomethyl-pyrrolidin-1-ylmethyl)-8-chloro-3-(5-chloro-2-ethanesulfonyl-benzyl)-6-trifluoromethyl-1H-quinazoline-2,4-dione (Compound F-79) under the same conditions as for Compound B-9.

LCMS: m/z 621 [M+H]+

HPLC retention time: 0.61 min (analysis condition D)

Example 390

Compound F-81

N-{(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-2-ylmethyl}-acetamide

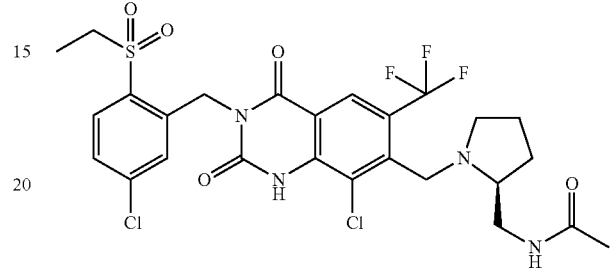

The title compound was synthesized from 7-((S)-2-aminomethyl-pyrrolidin-1-ylmethyl)-8-chloro-3-(5-chloro-2-ethanesulfonyl-benzyl)-6-trifluoromethyl-1H-quinazoline-2,4-dione (Compound F-79) under the same conditions as for Compound B-18.

LCMS: m/z 635 [M+H]+

HPLC retention time: 0.54 min (analysis condition D)

Example 391

Compound F-82

N-{(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-2-ylmethyl}-methanesulfonamide

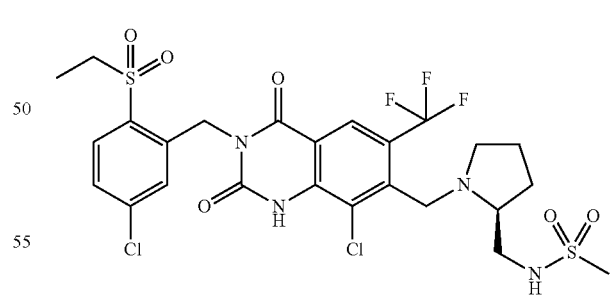

The title compound was synthesized from 7-((S)-2-aminomethyl-pyrrolidin-1-ylmethyl)-8-chloro-3-(5-chloro-2-ethanesulfonyl-benzyl)-6-trifluoromethyl-1H-quinazoline-2,4-dione (Compound F-79) under the same conditions as for Compound C-6. However, the reaction was performed using TEA in place of DIPEA.

LCMS: m/z 671 [M+H]+

HPLC retention time: 0.58 min (analysis condition D)

Example 392

Compound F-83

{(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-2-ylmethyl}-methyl-carbamic acid tert-butyl ester

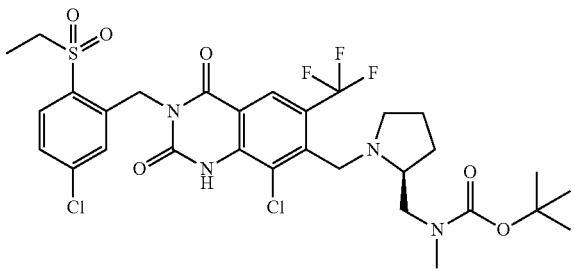

The title compound was synthesized from (8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and methyl-(S)-1-pyrrolidin-2-ylmethyl-carbamic acid tert-butyl ester under the same conditions as for Compound b12. However, the reaction was performed using chloroform in place of THF.

LCMS: m/z 707 [M+H]$^+$

HPLC retention time: 0.76 min (analysis condition D)

Example 393

Compound F-84

8-Chloro-3-(5-chloro-2-ethanesulfonyl-benzyl)-7-((S)-2-methylaminomethyl-pyrrolidin-1-ylmethyl)-6-trifluoromethyl-1H-quinazoline-2,4-dione

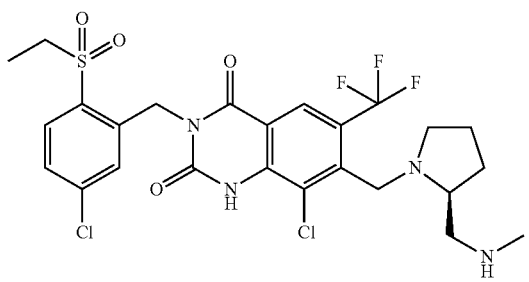 [SMILES: CCS(=O)(=O)c1ccc(Cl)cc1Cn1c(=O)[nH]c2c(Cl)c(CN3CCC[C@H]3CNC)c(C(F)(F)F)cc2c1=O]

The title compound was synthesized from {(S)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-2-ylmethyl}-methyl-carbamic acid tert-butyl ester (Compound F-83) under the same conditions as for Compound a41.

LCMS: m/z 607 [M+H]$^+$

HPLC retention time: 0.61 min (analysis condition D)

Example 394

Compound F-85

{(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-ylmethyl}-carbamic acid tert-butyl ester

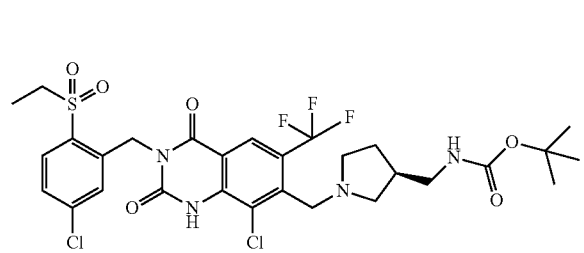 [SMILES: CCS(=O)(=O)c1ccc(Cl)cc1Cn1c(=O)[nH]c2c(Cl)c(CN3CC[C@@H](CNC(=O)OC(C)(C)C)C3)c(C(F)(F)F)cc2c1=O]

The title compound was synthesized from (8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and (R)-1-pyrrolidin-3-ylmethyl-carbamic acid tert-butyl ester under the same conditions as for Compound b12. However, the reaction was performed using chloroform in place of THF.

LCMS: m/z 693 [M+H]$^+$

HPLC retention time: 0.61 min (analysis condition D)

Example 395

Compound F-86

7-((S)-3-Aminomethyl-pyrrolidin-1-ylmethyl)-8-chloro-3-(5-chloro-2-ethanesulfonyl-benzyl)-6-trifluoromethyl-1H-quinazoline-2,4-dione

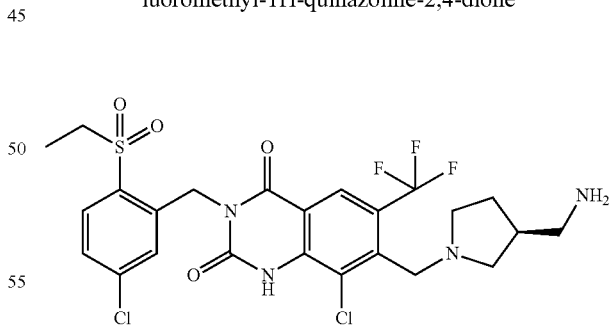

The title compound was synthesized from {(S)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-ylmethyl}-carbamic acid tert-butyl ester (Compound F-85) under the same conditions as for Compound a41.

LCMS: m/z 593 [M+H]$^+$

HPLC retention time: 0.44 min (analysis condition D)

Example 396

Compound F-87

8-Chloro-3-(5-chloro-2-ethanesulfonyl-benzyl)-7-((S)-3-dimethylaminoethyl-pyrrolidin-1-ylmethyl)-6-trifluoromethyl-1H-quinazoline-2,4-dione

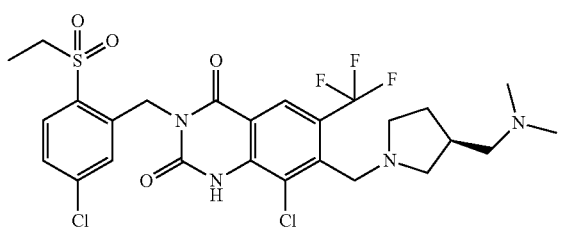 [SMILES: CCS(=O)(=O)c1ccc(Cl)cc1Cn1c(=O)[nH]c2c(Cl)c(CN3CC[C@@H](CN(C)C)C3)c(C(F)(F)F)cc2c1=O]

The title compound was synthesized from 7-((S)-3-aminomethyl-pyrrolidin-1-ylmethyl)-8-chloro-3-(5-chloro-2-ethanesulfonyl-benzyl)-6-trifluoromethyl-1H-quinazoline-2,4-dione (Compound F-86) under the same conditions as for Compound B-9.

LCMS: m/z 621 [M+H]$^+$

HPLC retention time: 0.44 min (analysis condition D)

Example 397

Compound F-88

N-{(S)-1-[8-Chloro-3-(5-chloro-2-ethanesulfonyl-benz)-2,4-dioxo-6-trifluoromethyl-1,2,3,4-tetrahydro-quinazolin-7-ylmethyl]-pyrrolidin-3-ylmethyl}-acetamide

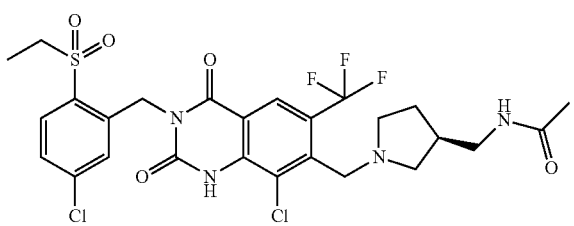 [SMILES: CCS(=O)(=O)c1ccc(Cl)cc1Cn1c(=O)[nH]c2c(Cl)c(CN3CC[C@@H](CNC(C)=O)C3)c(C(F)(F)F)cc2c1=O]

The title compound was synthesized from 7-((S)-3-aminomethyl-pyrrolidin-1-ylmethyl)-8-chloro-3-(5-chloro-2-ethanesulfonyl-benzyl)-6-trifluoromethyl-1H-quinazoline-2,4-dione (Compound F-86) under the same conditions as for Compound B-18.

LCMS: m/z 635 [M+H]$^+$

HPLC retention time: 0.51 min (analysis condition D)

Example 398

Compound F-89

N-{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-ylmethyl}-methanesulfonamide

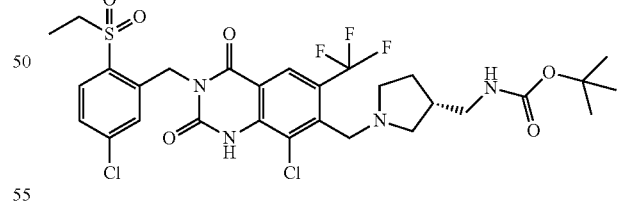

The title compound was synthesized from 7-((S)-3-aminomethyl-pyrrolidin-1-ylmethyl)-8-chloro-3-(5-chloro-2-ethanesulfonyl-benzyl)-6-trifluoromethyl-1H-quinazoline-2,4-dione (Compound F-86) under the same conditions as for Compound C-6. However, the reaction was performed using TEA in place of DIPEA.

LCMS: m/z 671 [M+H]$^+$

HPLC retention time: 0.53 min (analysis condition D)

Example 399

Compound F-90

{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-ylmethyl}-carbamic acid tert-butyl ester The title compound was synthesized from (8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and (S)-1-pyrrolidin-3-ylmethyl-carbamic acid tert-butyl ester under the same conditions as for Compound b12. However, the reaction was performed using chloroform in place of THF.

LCMS: m/z 693 [M+H]$^+$

HPLC retention time: 0.63 min (analysis condition D)

Example 400

Compound F-91

7-((R)-3-Aminomethyl-pyrrolidin-1-ylmethyl)-8-chloro-3-(5-chloro-2-ethanesulfonyl-benzyl)-6-trifluoromethyl-1H-quinazoline-2,4-dione

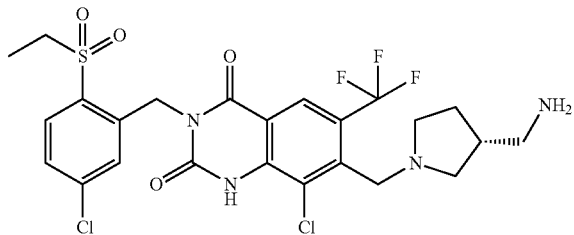 [SMILES: CCS(=O)(=O)c1ccc(Cl)cc1Cn1c(=O)[nH]c2c(Cl)c(CN3CC[C@H](CN)C3)c(C(F)(F)F)cc2c1=O]

The title compound was synthesized from {(R)-1-[8-chloro-3-(5-chloro-2-ethanesulfonyl-benzyl)-2,4-di oxo-6-trifluoromethyl-1,2,3,4-tetrahydro-quinazolin-7-ylmethyl]-pyrrolidin-3-ylmethyl}-carbamic acid tert-butyl ester (Compound F-90) under the same conditions as for Compound a41.

LCMS: m/z 593 [M+H]$^+$

HPLC retention time: 0.46 min (analysis condition D)

Example 401

Compound F-92

8-Chloro-3-(5-chloro-2-ethanesulfonyl-benzyl)-7-((R)-3-dimethylaminomethyl-pyrrolidin-1-ylmethyl)-6-trifluoromethyl-1H-quinazoline-2,4-dione

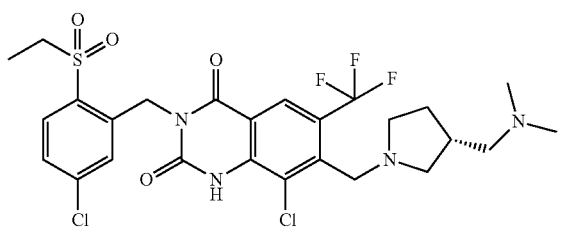 [SMILES: CCS(=O)(=O)c1ccc(Cl)cc1Cn1c(=O)[nH]c2c(Cl)c(CN3CC[C@H](CN(C)C)C3)c(C(F)(F)F)cc2c1=O]

The title compound was synthesized from 7-((R)-3-aminomethyl-pyrrolidin-1-ylmethyl)-8-chloro-3-(5-chloro-2-ethanesulfonyl-benzyl)-6-trifluoromethyl-1H-quinazoline-2,4-dione (Compound F-91) under the same conditions as for Compound B-9.

LCMS: m/z 621 [M+H]$^+$

HPLC retention time: 0.48 min (analysis condition D)

Example 402

Compound F-93

N-{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-ylmethyl-acetamide

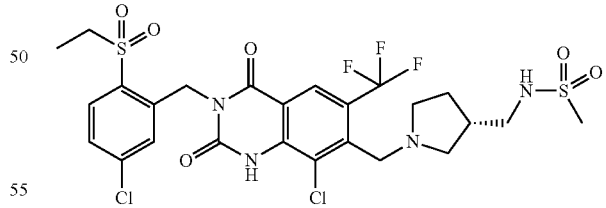

The title compound was synthesized from 7-((R)-3-aminomethyl-pyrrolidin-1-ylmethyl)-8-chloro-3-(5-chloro-2-ethanesulfonyl-benzyl)-6-trifluoromethyl-1H-quinazoline-2,4-dione (Compound F-91) under the same conditions as for Compound B-18.

LCMS: m/z 635 [M+H]$^+$

HPLC retention time: 0.51 min (analysis condition D)

Example 403

Compound F-94

N—(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-ylmethyl}-methanesulfonamide The title compound was synthesized from 7-((R)-3-aminomethyl-pyrrolidin-1-ylmethyl)-8-chloro-3-(5-chloro-2-ethanesulfonyl-benzyl)-6-trifluoromethyl-1H-quinazoline-2,4-dione (Compound F-91) under the same conditions as for Compound C-6. However, the reaction was performed using TEA in place of DIPEA.

LCMS: m/z 671 [M+H]$^+$

HPLC retention time: 0.53 min (analysis condition D)

Example 404

Compound F-95

{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-3-ylmethyl}-carbamic acid tert-butyl ester

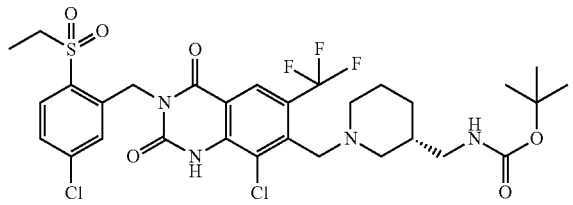 [SMILES: CCS(=O)(=O)c1ccc(Cl)cc1Cn1c(=O)[nH]c2c(Cl)c(CN3CCC[C@H](CNC(=O)OC(C)(C)C)C3)c(C(F)(F)F)cc2c1=O]

The title compound was synthesized from (8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and (S)-1-piperidin-3-ylmethyl-carbamic acid tert-butyl ester under the same conditions as for Compound b12. However, the reaction was performed using chloroform in place of THF.

LCMS: m/z 707 [M+H]$^+$

HPLC retention time: 0.68 min (analysis condition D)

Example 405

Compound F-96

7-((R)-3-Aminomethyl-piperidin-1-ylmethyl)-8-chloro-3-(5-chloro-2-ethanesulfonyl-benzyl)-6-trifluoromethyl-1H-quinazoline-2,4-dione

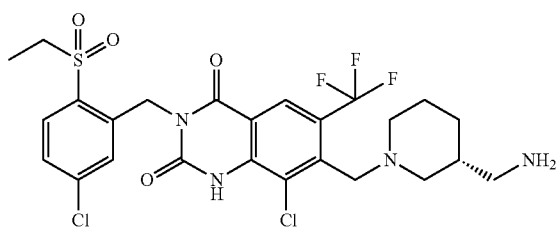 [SMILES: CCS(=O)(=O)c1ccc(Cl)cc1Cn1c(=O)[nH]c2c(Cl)c(CN3CCC[C@H](CN)C3)c(C(F)(F)F)cc2c1=O]

The title compound was synthesized from {(R)-1-[8-chloro-3-(5-chloro-2-ethanesulfonyl-benzyl)-2,4-dioxo-6-trifluoromethyl-1,2,3,4-tetrahydro-quinazolin-7-ylmethyl]-piperidin-3-ylmethyl}-carbamic acid tert-butyl ester (Compound F-95) under the same conditions as for Compound a41.

LCMS: m/z 607 [M+H]$^+$

HPLC retention time: 0.47 min (analysis condition D)

Example 406

Compound F-97

8-Chloro-3-(5-chloro-2-ethanesulfonyl-benzyl)-7-((R)-3-dimethylaminomethyl-piperidin-1-ylmethyl)-6-trifluoromethyl-1H-quinazoline-2,4-dione

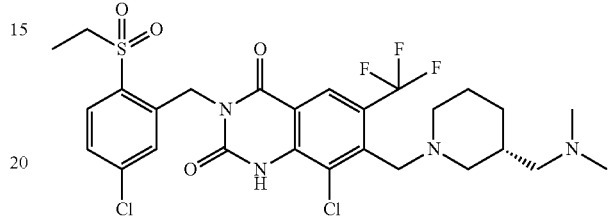

The title compound was synthesized from 7-((R)-3-aminomethyl-piperidin-1-ylmethyl)-8-chloro-3-(5-chloro-2-ethanesulfonyl-benzyl)-6-trifluoromethyl-1H-quinazoline-2,4-dione (Compound F-96) under the same conditions as for Compound B-9.

LCMS: m/z 635 [M+H]$^+$

HPLC retention time: 0.52 min (analysis condition E)

Example 407

Compound F-98

N-{(R) 1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-3-ylmethyl}-acetamide

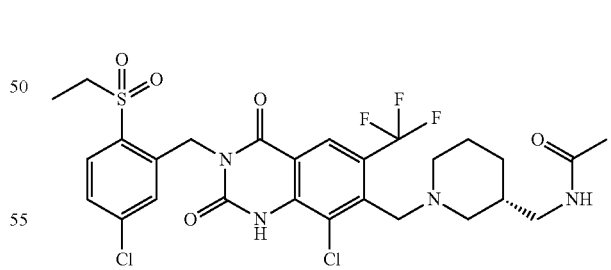

The title compound was synthesized from 7-((R)-3-aminomethyl-piperidin-1-ylmethyl)-8-chloro-3-(5-chloro-2-ethanesulfonyl-benzyl)-6-trifluoromethyl-1H-quinazoline-2,4-dione (Compound F-96) under the same conditions as for Compound B-18.

LCMS: m/z 649 [M+H];

HPLC retention time: 0.53 min (analysis condition D)

Example 408

Compound F-99

N-{(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-3-ylmethyl}-methanesulfonamide

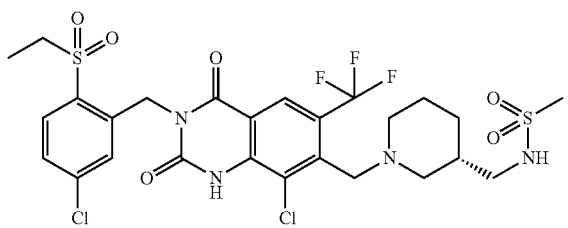 [SMILES: CCS(=O)(=O)c1ccc(Cl)cc1Cn1c(=O)[nH]c2c(Cl)c(CN3CCC[C@H](CNS(C)(=O)=O)C3)c(C(F)(F)F)cc2c1=O]

The title compound was synthesized from 7-((R)-3-aminomethyl-piperidin-1-ylmethyl)-8-chloro-3-(5-chloro-2-ethanesulfonyl-benzyl)-6-trifluoromethyl-1H-quinazoline-2,4-dione (Compound F-96) under the same conditions as for Compound C-6. However, the reaction was performed using TEA in place of DIPEA.

LCMS: m/z 685 [M+H]$^+$

HPLC retention time: 0.57 min (analysis condition D)

Example 409

Compound F-100

{(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-3-ylmethyl}-methyl-carbamic acid tert-butyl ester

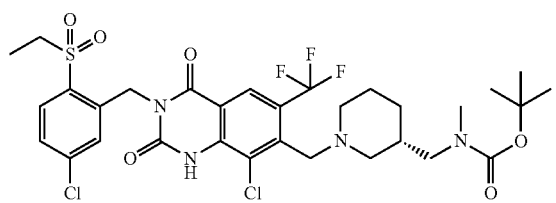 [SMILES: CCS(=O)(=O)c1ccc(Cl)cc1Cn1c(=O)[nH]c2c(Cl)c(CN3CCC[C@H](CN(C)C(=O)OC(C)(C)C)C3)c(C(F)(F)F)cc2c1=O]

The title compound was synthesized from (8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and methyl-(S)-1-piperidin-3-ylmethyl-carbamic acid tert-butyl ester under the same conditions as for Compound b12. However, the reaction was performed using chloroform in place of THF.

LCMS: m/z 721 [M+H]$^+$

HPLC retention time: 0.76 min (analysis condition D)

Example 410

Compound F-101

8-Chloro-3-(5-chloro-2-ethanesulfonyl-benzyl)-7-((R)-3-methylaminomethyl-piperidin-1-ylmethyl)-6-trifluoromethyl-1H-quinazoline-2,4-dione

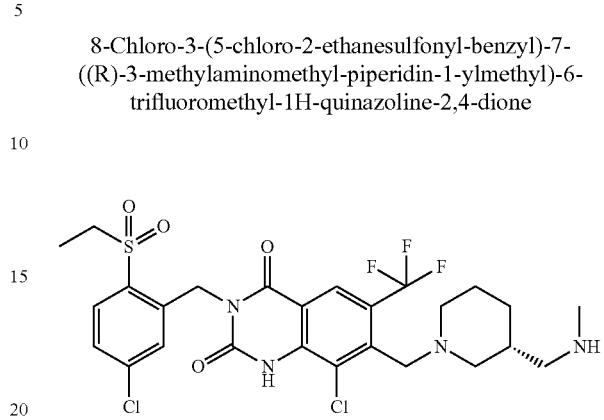

The title compound was synthesized from {(S)-1-[8-chloro-3-(5-chloro-2-ethanesulfonyl-benzyl)-2,4-dioxo-6-trifluoromethyl-1,2,3,4-tetrahydro-quinazolin-7-ylmethyl]-piperidin-3-ylmethyl}-methyl-carbamic acid tert-butyl ester (Compound F-100) under the same conditions as for Compound a41.

LCMS: m/z 621 [M+H]$^1$

HPLC retention time: 0.51 min (analysis condition D)

Example 411

Compound F-102

{(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-3-ylmethyl}-carbamic acid tert-butyl ester

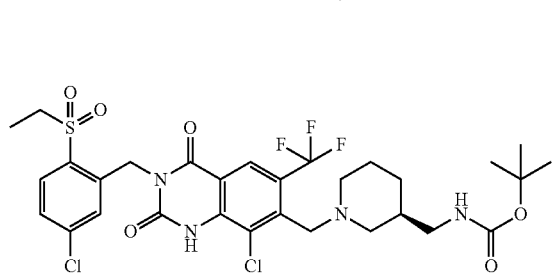 [SMILES: CCS(=O)(=O)c1ccc(Cl)cc1Cn1c(=O)[nH]c2c(Cl)c(CN3CCC[C@@H](CNC(=O)OC(C)(C)C)C3)c(C(F)(F)F)cc2c1=O]

The title compound was synthesized from (8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and (R)-1-piperidin-3-ylmethyl-carbamic acid tert-butyl ester under the same conditions as for Compound b12. However, the reaction was performed using chloroform in place of THF.

LCMS: m/z 707 [M+H]$^+$

HPLC retention time: 0.68 min (analysis condition D)

Example 412

Compound F-103

7-((S)-3-Aminomethyl-piperidin-1-ylmethyl)-8-chloro-3-(5-chloro-2-ethanesulfonyl-benzyl)-6-trifluoromethyl-1H-quinazoline-2,4-dione

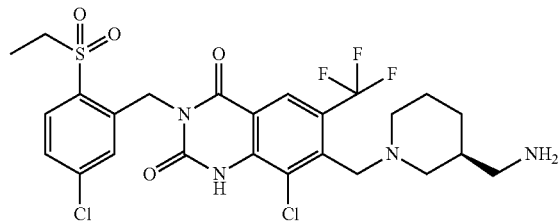 [SMILES: CCS(=O)(=O)c1ccc(Cl)cc1Cn1c(=O)[nH]c2c(Cl)c(CN3CCC[C@@H](CN)C3)c(C(F)(F)F)cc2c1=O]

The title compound was synthesized from {(S)-1-[8-chloro-3-(5-chloro-2-ethanesulfonyl-benzyl)-2,4-dioxo-6-trifluoromethyl-1,2,3,4-tetrahydro-quinazolin-7-ylmethyl]-piperidin-3-ylmethyl}-carbamic acid tert-butyl ester (Compound F-102) under the same conditions as for Compound a41.

LCMS: m/z 607 [M+H]+

HPLC retention time: 0.47 min (analysis condition D)

Example 413

Compound F-104

8-Chloro-3-(5-chloro-2-ethanesulfonyl-benzyl)-7-((S)-3-dimethylaminomethyl-piperidin-1-ylmethyl)-6-trifluoromethyl-1H-quinazoline-2,4-dione

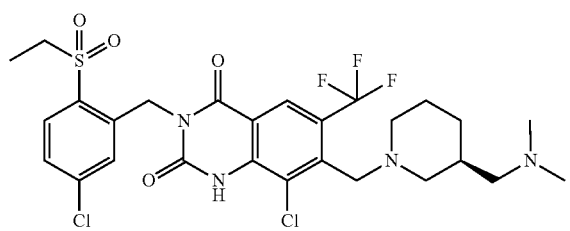 [SMILES: CCS(=O)(=O)c1ccc(Cl)cc1Cn1c(=O)[nH]c2c(Cl)c(CN3CCC[C@@H](CN(C)C)C3)c(C(F)(F)F)cc2c1=O]

The title compound was synthesized from 7-((S)-3-aminomethyl-piperidin-1-ylmethyl)-8-chloro-3-(5-chloro-2-ethanesulfonyl-benzyl)-6-trifluoromethyl-1H-quinazoline-2,4-dione (Compound F-103) under the same conditions as for Compound B-9.

LCMS: m/z 635 [M+H]+

HPLC retention time: 1.11 min (analysis condition A)

Example 414

Compound F-105

N-{(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-3-ylmethyl}-acetamide

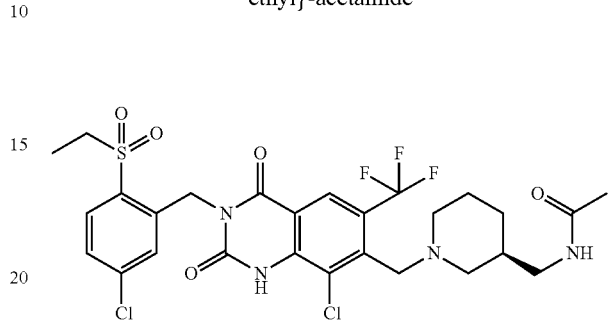

The title compound was synthesized from 7-((S)-3-aminomethyl-piperidin-1-ylmethyl)-8-chloro-3-(5-chloro-2-ethanesulfonyl-benzyl)-6-trifluoromethyl-1H-quinazoline-2,4-dione (Compound F-103) under the same conditions as for Compound B-18.

LCMS: m/z 649 [M+H]+

HPLC retention time: 0.54 min (analysis condition D)

Example 415

Compound F-106

N-{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-3-ylmethyl}-methanesulfonamide

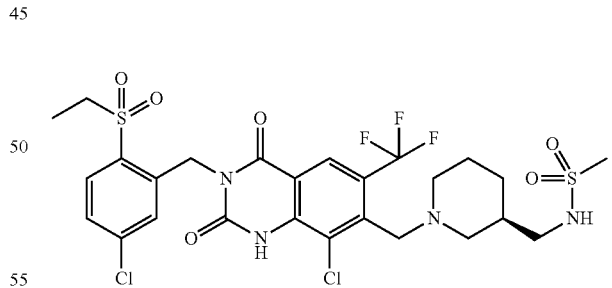

The title compound was synthesized from 7-((S)-3-aminomethyl-piperidin-1-ylmethyl)-8-chloro-3-(5-chloro-2-ethanesulfonyl-benzyl)-6-trifluoromethyl-1H-quinazoline-2,4-dione (Compound F-103) under the same conditions as for Compound C-6. However, the reaction was performed using TEA in place of DIPEA.

LCMS: m/z 685 [M+H]+

HPLC retention time: 0.58 min (analysis condition D)

Example 416

Compound F-107

{(R)-1-[8-Chloro-3-(5-chloro-2-ethanesulfonyl-benzyl)-2,4-dioxo-6-trifluoromethyl-1,2,3,4-tetrahydroquinazolin-7-ylmethyl]-piperidin-3-ylmethyl}-methyl-carbamic acid tert-butyl ester

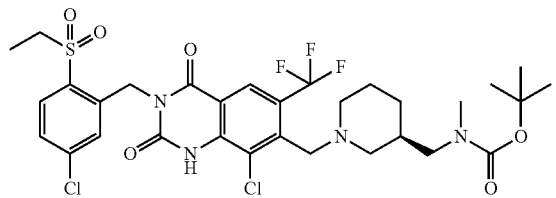 [SMILES: CCS(=O)(=O)c1ccc(Cl)cc1Cn1c(=O)[nH]c2c(Cl)c(CN3CCC[C@@H](CN(C)C(=O)OC(C)(C)C)C3)c(C(F)(F)F)cc2c1=O]

The title compound was synthesized from (8-chloro-3-(5-chloro-2-ethanesulfonyl-benzyl)-2,4-di oxo-6-trifluoromethyl-1,2,3,4-tetrahydro-quinazoline-7-carbaldehyde (Compound F-45) and methyl-(R)-1-piperidin-3-ylmethyl-carbamic acid tert-butyl ester under the same conditions as for Compound b12. However, the reaction was performed using chloroform in place of THF.

LCMS: m/z 721 [M+H]$^+$

HPLC retention time: 0.75 min (analysis condition D)

Example 417

Compound F-108

8-Chloro-3-(5-chloro-2-ethanesulfonyl-benzyl)-7-((S)-3-methylaminomethyl-piperidin-1-ylmethyl)-6-trifluoromethyl-1H-quinazoline-2,4-dione

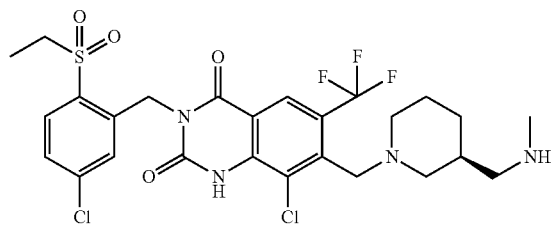 [SMILES: CCS(=O)(=O)c1ccc(Cl)cc1Cn1c(=O)[nH]c2c(Cl)c(CN3CCC[C@@H](CNC)C3)c(C(F)(F)F)cc2c1=O]

The title compound was synthesized from {(R)-1-[8-chloro-3-(5-chloro-2-ethanesulfonyl-benzyl)-2,4-dioxo-6-trifluoromethyl-1,2,3,4-tetrahydro-quinazolin-7-ylmethyl]-piperidin-3-ylmethyl}-methyl-carbamic acid tert-butyl ester (Compound F-107) under the same conditions as for Compound a41.

LCMS: m/z 621 [M+H]$^+$

HPLC retention time: 0.51 min (analysis condition D)

Example 418

Compound F-109

{1-[8-Chloro-3-(5-chloro-2-ethanesulfonyl-benzyl)-2,4-dioxo-6-trifluoromethyl-1,2,3,4-tetrahydro-quinazolin-7-ylmethyl]-azetidin-3-yl}-carbamic acid tert-butyl ester

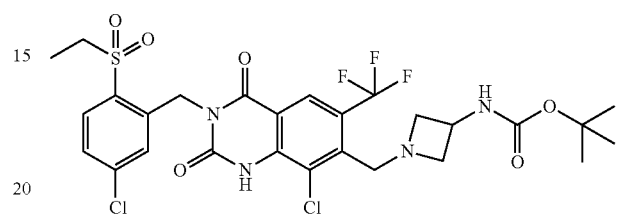

The title compound was synthesized from (8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and azetidin-3-yl-carbamic acid tert-butyl ester under the same conditions as for Compound b12. However, the reaction was performed using chloroform in place of THF.

LCMS: m/z 665 [M+H]$^+$

HPLC retention time: 0.62 min (analysis condition D)

Example 419

Compound F-110

7-(3-Amino-azetidin-1-ylmethyl)-8-chloro-3-(5-chloro-2-ethanesulfonyl-benzyl)-6-trifluoromethyl-1H-quinazoline-2,4-dione

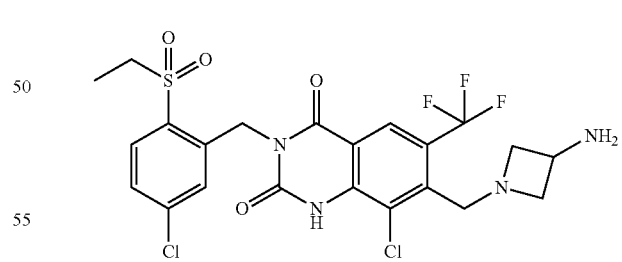

The title compound was synthesized from {1-[8-chloro-3-(5-chloro-2-ethanesulfonyl-benzyl)-2,4-dioxo-6-trifluoromethyl-1,2,3,4-tetrahydro-quinazolin-7-ylmethyl]-azetidin-3-yl}-carbamic acid tert-butyl ester (Compound F-109) under the same conditions as for Compound a41.

LCMS: m/z 565 [M+H]$^+$

HPLC retention time: 0.50 min (analysis condition D)

Example 420

Compound F-111

N-{1-[8-Chloro-3-(5-chloro-2-ethanesulfonyl-benzyl)-2,4-dioxo-6-trifluoromethyl-1,2,3,4-tetrahydroquinazolin-7-ylmethyl]-azetidin-3-yl}-acetamide

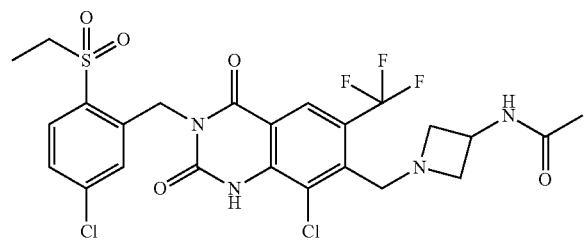 [SMILES: CCS(=O)(=O)c1ccc(Cl)cc1Cn1c(=O)[nH]c2c(Cl)c(CN3CC(NC(C)=O)C3)c(C(F)(F)F)cc2c1=O]

The title compound was synthesized from 7-(3-aminoazetidin-1-ylmethyl)-8-chloro-3-(5-chloro-2-ethanesulfonyl-benzyl)-6-trifluoromethyl-1H-quinazoline-2,4-dione (Compound F-110) under the same conditions as for Compound B-18.

LCMS: m/z 607 [M+H]$^+$

HPLC retention time: 0.53 min (analysis condition D)

Example 421

Compound F-112

N-{1-[8-Chloro-3-(5-chloro-2-ethanesulfonyl-benzyl)-2,4-dioxo-6-trifluoromethyl-1,2,3,4-tetrahydroquinazolin-7-ylmethyl]-azetidin-3-yl}-methanesulfonamide

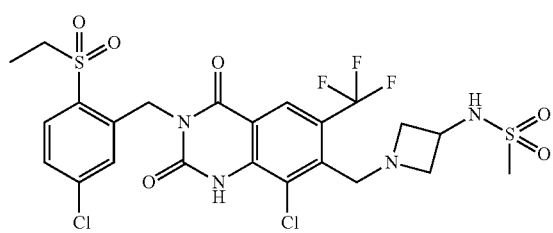 [SMILES: CCS(=O)(=O)c1ccc(Cl)cc1Cn1c(=O)[nH]c2c(Cl)c(CN3CC(NS(C)(=O)=O)C3)c(C(F)(F)F)cc2c1=O]

The title compound was synthesized from 7-(3-aminoazetidin-1-ylmethyl)-8-chloro-3-(5-chloro-2-ethanesulfonyl-benzyl)-6-trifluoromethyl-1H-quinazoline-2,4-dione (Compound F-110) under the same conditions as for Compound C-6. However, the reaction was performed using TEA in place of DIPEA.

LCMS: m/z 643 [M+H]$^+$

HPLC retention time: 0.57 min (analysis condition D)

Example 422

Compound F-113

8-Chloro-3-(5-chloro-2-ethanesulfonyl-benzyl)-7-[4-(2,2-difluoro-ethyl)-piperazin-1-ylmethyl]-6-trifluoromethyl-1H-quinazoline-2,4-dione

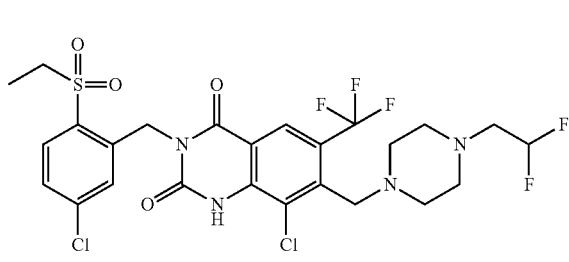 [SMILES: CCS(=O)(=O)c1ccc(Cl)cc1Cn1c(=O)[nH]c2c(Cl)c(CN3CCN(CC(F)F)CC3)c(C(F)(F)F)cc2c1=O]

The title compound was synthesized from 8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and 1-(2,2-difluoro-ethyl)-piperazine under the same conditions as for Compound b12. However, DCM was used in place of THF as a solvent.

LCMS: m/z 643 [M+H]$^+$

HPLC retention time: 0.68 min (analysis condition D)

Example 423

Compound F-114

8-Chloro-3-(5-chloro-2-ethanesulfonyl-benzyl)-7-((R)-3-hydroxy-pyrrolidin-1-ylmethyl)-6-trifluoromethyl-1H-quinazoline-2,4-dione

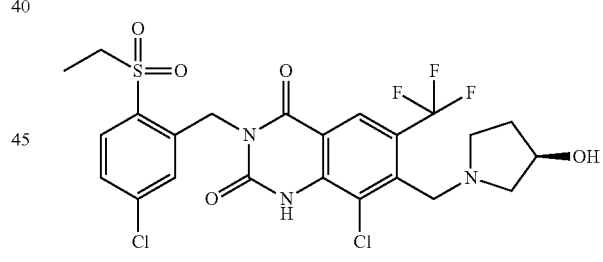

The title compound was synthesized from 8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and (R)-pyrrolidin-3-ol under the same conditions as for Compound b12. However, chloroform was used in place of THF as a solvent.

LCMS: m/z 580 [M+H]$^+$

HPLC retention time: 0.51 min (analysis condition D)

Examples 424 to 425

The following compounds of Table 5 were synthesized from 8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and corresponding amines under the same conditions as for Compound F-114.

TABLE 5

| Example | Compound No. | Structure | Compound name | HPLC cond. | Retention time (min) | m/z [M + H]+ |
|---------|--------------|-----------|---------------|------------|----------------------|--------------|
| 424 | F-115 | 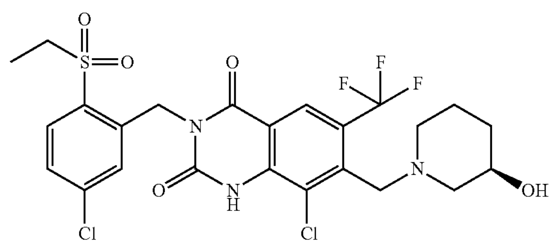 [SMILES: CCS(=O)(=O)c1ccc(Cl)cc1Cn1c(=O)[nH]c2c(Cl)c(CN3CCC[C@@H](O)C3)c(C(F)(F)F)cc2c1=O] | 8-Chloro-3-(5-chloro-2-ethanesulfonyl-benzyl)-7-((R)-3-hydroxy-piperidin-1-ylmethyl)-6-trifluoromethyl-1H-quinazoline-2,4-dione | D | 0.54 | 594 |
| 425 | F-116 | 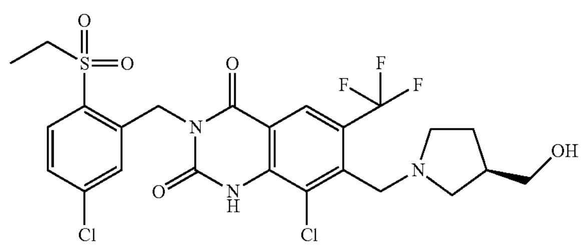 [SMILES: CCS(=O)(=O)c1ccc(Cl)cc1Cn1c(=O)[nH]c2c(Cl)c(CN3CC[C@@H](CO)C3)c(C(F)(F)F)cc2c1=O] | 8-Chloro-3-(5-chloro-2-ethanesulfonyl-benzyl)-7-((R)-3-hydroxymethyl-pyrrolidin-1-ylmethyl)-6-trifluoromethyl-1H-quinazoline-2,4-dione | A | 1.07 | 594 |

Example 426

Compound F-117

8-Chloro-3-(5-chloro-2-ethanesulfonyl-benzyl)-7-((R)-2-oxo-[1,3']bipyrrolidinyl-1'-ylmethyl)-6-trifluoromethyl-1H-quinazoline-2,4-dione The title compound was synthesized from 8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and (R)-[1,3']bipyrrolidinyl-2-one under the same conditions as for Compound b12. However, the reaction was performed at a reaction temperature of 50° C.

LCMS: m/z 647 [M+H]+

HPLC retention time: 0.54 min (analysis condition H)

Example 427

Compound F-118

8-Chloro-3-(5-chloro-2-ethanesulfonyl-benzyl-7-(3-oxo-piperazin-1-ylmethyl)-6-trifluoromethyl-1H-quinazoline-2,4-dione The title compound was synthesized from 8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and piperazin-2-one under the same conditions as for Compound b12.

LCMS: m/z 593 [M+H]+

HPLC retention time: 0.71 min (analysis condition H)

Examples 428 to 433

The following compounds of Table 6 were synthesized from 8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and corresponding amines under the same conditions as for Compound F-118.

TABLE 6

| Example | Compound No. | Structure | Compound name | HPLC cond. | Retention time (min) | m/z [M + H]+ |
|---|---|---|---|---|---|---|
| 428 | F-119 | 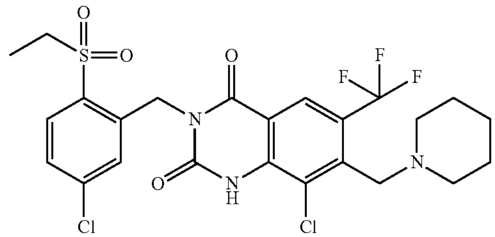 [SMILES: CCS(=O)(=O)c1ccc(Cl)cc1Cn1c(=O)[nH]c2c(Cl)c(CN3CCCCC3)c(C(F)(F)F)cc2c1=O] | 8-Chloro-3-(5-chloro-2-ethanesulfonyl-benzyl)-7-piperidin-1-ylmethyl-6-trifluoromethyl-1H-quinazoline-2,4-dione | H | 0.53 | 578 |
| 429 | F-120 | 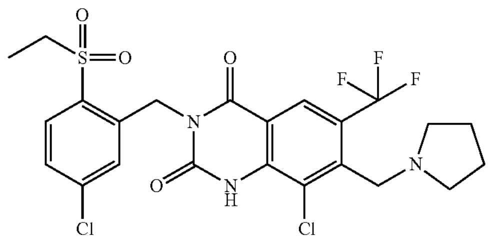 [SMILES: CCS(=O)(=O)c1ccc(Cl)cc1Cn1c(=O)[nH]c2c(Cl)c(CN3CCCC3)c(C(F)(F)F)cc2c1=O] | 8-Chloro-3-(5-chloro-2-ethanesulfonyl-benzyl)-7-pyrrolidin-1-ylmethyl-6-trifluoromethyl-1H-quinazoline-2,4-dione | H | 0.48 | 564 |
| 430 | F-121 | 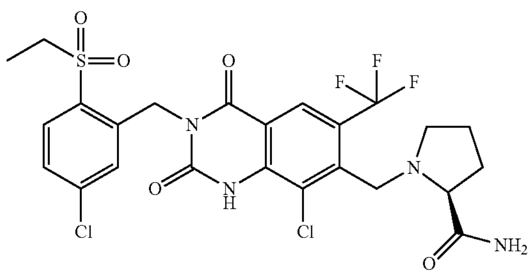 [SMILES: CCS(=O)(=O)c1ccc(Cl)cc1Cn1c(=O)[nH]c2c(Cl)c(CN3CCC[C@H]3C(N)=O)c(C(F)(F)F)cc2c1=O] | (S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidine-2-carboxylic acid amide | H | 0.61 | 607 |
| 431 | F-122 | 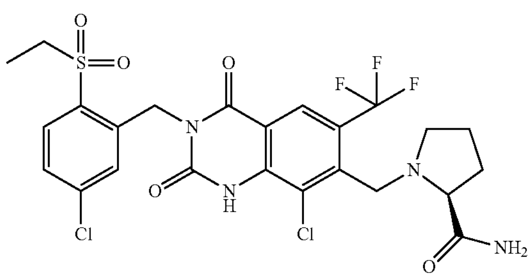 [SMILES: CCS(=O)(=O)c1ccc(Cl)cc1Cn1c(=O)[nH]c2c(Cl)c(CN3CCC[C@H]3C(N)=O)c(C(F)(F)F)cc2c1=O] | (R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidine-2-carboxylic acid amide | H | 0.61 | 607 |
| 432 | F-123 | 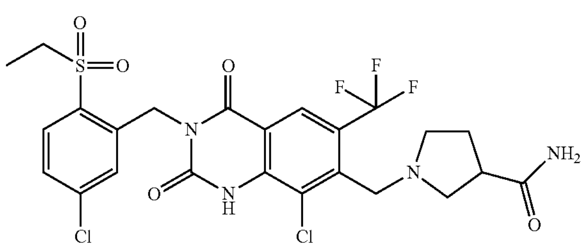 [SMILES: CCS(=O)(=O)c1ccc(Cl)cc1Cn1c(=O)[nH]c2c(Cl)c(CN3CCC(C(N)=O)C3)c(C(F)(F)F)cc2c1=O] | 1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidine-3-carboxylic acid amide | H | 0.49 | 607 |
| 433 | F-124 | 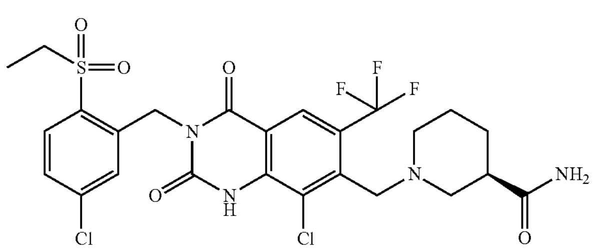 [SMILES: CCS(=O)(=O)c1ccc(Cl)cc1Cn1c(=O)[nH]c2c(Cl)c(CN3CCC[C@@H](C(N)=O)C3)c(C(F)(F)F)cc2c1=O] | (R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidine-3-carboxylic acid amide | H | 0.51 | 621 |

Example 434

Compound f24

{1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-4-ylmethyl}-carbamic acid tert-butyl ester

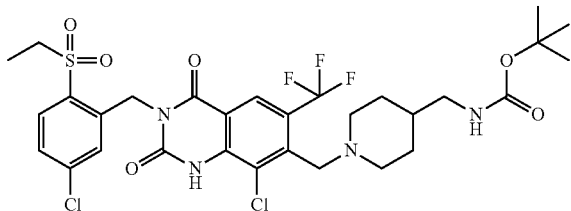 [SMILES: CCS(=O)(=O)c1ccc(Cl)cc1Cn1c(=O)[nH]c2c(Cl)c(CN3CCC(CNC(=O)OC(C)(C)C)CC3)c(C(F)(F)F)cc2c1=O]

The title compound was synthesized from 8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45) and piperidin-4-ylmethyl-carbamic acid tert-butyl ester under the same conditions as for Compound b12. However, the reaction was performed using chloroform in place of THF as a solvent and at a reaction temperature of 0° C.

Example 435

Compound F-125

7-(4-Aminomethyl-piperidin-1-ylmethyl)-8-chloro-3-(5-chloro-2-ethanesulfonyl-benzyl)-6-trifluoromethyl-1H-quinazoline-2,4-dione

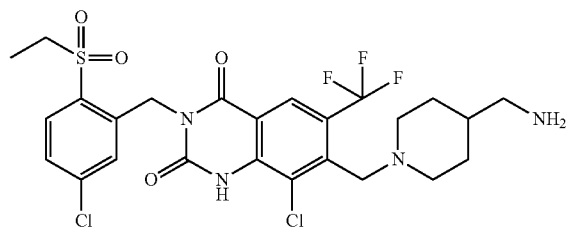 [SMILES: CCS(=O)(=O)c1ccc(Cl)cc1Cn1c(=O)[nH]c2c(Cl)c(CN3CCC(CN)CC3)c(C(F)(F)F)cc2c1=O]

The title compound was synthesized from {1-[8 chloro-3-(5-chloro-2-ethanesulfonyl-benzyl)-2,4-dioxo-6-trifluoromethyl-1,2,3,4-tetrahydro-quinazolin-7-ylmethyl]-piperidin-4-ylmethyl}-carbamic acid tert-butyl ester (Compound f24) under the same conditions as for Compound B-1.

LCMS: m/z 607 [M+H]$^+$

HPLC retention time: 0.50 min (analysis condition E)

Example 436

Compound F-126

8-Chloro-3-(5-chloro-2-ethanesulfonyl-benzyl)-7-hydroxymethyl-6-trifluoromethyl-1H-quinazoline-2,4-dione

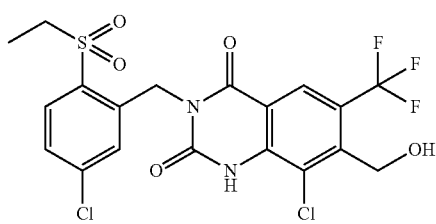 [SMILES: CCS(=O)(=O)c1ccc(Cl)cc1Cn1c(=O)[nH]c2c(Cl)c(CO)c(C(F)(F)F)cc2c1=O]

Sodium borohydride (53.0 mg, 1.3 mmol) was added to a solution of 8-chloro-3-(5-chloro-2-ethanesulfonyl-benzyl)-2,4-dioxo-6-trifluoromethyl-1,2,3,4-tetrahydro-quinazoline-7-carbaldehyde (Compound F-45, 243 mg, 0.48 mmol) in THF (2.9 ml), and the mixture was stirred at room temperature for one hour. Water was added to the reaction mixture, followed by extraction with ethyl acetate. The organic layer was washed with brine and then dried over anhydrous sodium sulfate. The drying agent was removed by filtration, and the residue obtained by concentration under reduced pressure was purified by silica gel column chromatography (ethyl acetate/hexane) to give the title compound (221 mg, yield: 90%) as a colorless solid.

LCMS: m/z 511 [M+H]$^+$

HPLC retention time: 0.75 min (analysis condition D)

Example 437

Compound F-127

Methanesulfonic acid 8-chloro-3-(5-chloro-2-ethanesulfonyl-benzyl)-2,4-dioxo-6-trifluoromethyl-1,2,3,4-tetrahydro-quinazolin-7-ylmethyl ester

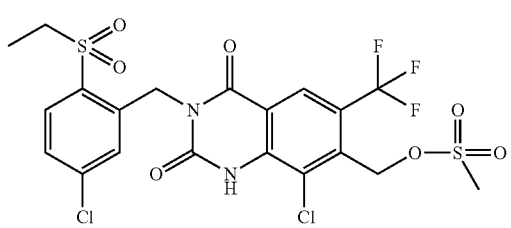 [SMILES: CCS(=O)(=O)c1ccc(Cl)cc1Cn1c(=O)[nH]c2c(Cl)c(COS(C)(=O)=O)c(C(F)(F)F)cc2c1=O]

Methanesulfonyl chloride (0.042 ml, 0.54 mmol) was added to a solution of 8-chloro-3-(5-chloro-2-ethanesulfonyl-benzyl)-7-hydroxymethyl-6-trifluoromethyl-1H-quinazoline-2,4-dione (Compound F-126, 214 mg, 0.42 mmol) and triethylamine (0.127 ml, 1.3 mmol) in DCM (4.2 ml) under cooling at 0° C., and the mixture was stirred at 0° C. for one hour. Water was added to the reaction mixture, followed by extraction with ethyl acetate. The organic layer was washed with brine and then dried over anhydrous sodium sulfate. The drying agent was removed by filtration, and the residue obtained by concentration under reduced pressure was purified by silica gel column chromatography (ethyl acetate/hexane) to give the title compound (230 mg, yield: 93%) as a colorless solid.
LCMS: m/z 589 [M+H]$^+$
HPLC retention time: 0.81 min (analysis condition H)

Example 438

Compound f25

{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-2-ylmethyl}-carbamic acid tert-butyl ester

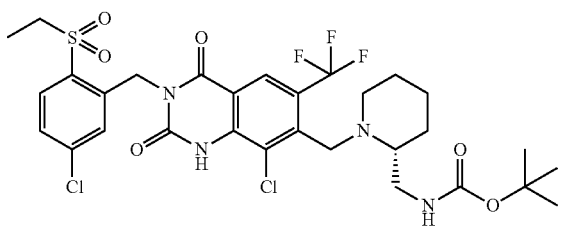 [SMILES: CCS(=O)(=O)c1ccc(Cl)cc1Cn1c(=O)[nH]c2c(Cl)c(CN3CCCC[C@@H]3CNC(=O)OC(C)(C)C)c(C(F)(F)F)cc2c1=O]

Methanesulfonic acid 8-chloro-3-(5-chloro-2-ethanesulfonyl-benzyl)-2,4-dioxo-6-trifluoromethyl-1,2,3,4-tetrahydro-quinazolin-7-ylmethyl ester (Compound F-127, 33.0 mg, 0.056 mmol) was added to a solution of (R)-1-piperidin-2-ylmethyl-carbamic acid tert-butyl ester (36.0 mg, 0.17 mmol) in DMF (0.5 ml), and the mixture was stirred at 50° C. for three hours. The reaction solution was cooled to room temperature and then purified by preparative HPLC (water/acetonitrile, 0.05% TFA) to give the title compound (15.5 mg, 39%) as a colorless amorphous.
LCMS: m/z 707 [M+H]$^+$
HPLC retention time: 0.78 min (analysis condition D)

Example 439

Compound F-128

7-((R)-2-Aminomethyl-piperidin-1-ylmethyl)-8-chloro-3-(5-chloro-2-ethanesulfonyl-benzyl)-6-trifluoromethyl-1H-quinazoline-2,4-dione

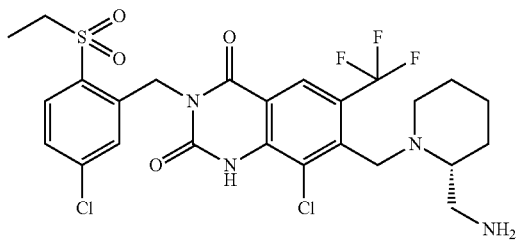 [SMILES: CCS(=O)(=O)c1ccc(Cl)cc1Cn1c(=O)[nH]c2c(Cl)c(CN3CCCC[C@@H]3CN)c(C(F)(F)F)cc2c1=O]

The title compound was synthesized from {(R)-1-[8-chloro-3-(5-chloro-2-ethanesulfonyl-benzyl)-2,4-dioxo-6-trifluoromethyl-1,2,3,4-tetrahydro-quinazolin-7-ylmethyl]-piperidin-2-ylmethyl}-carbamic acid tert-butyl ester (Compound f25) under the same conditions as for Compound a41.
LCMS: m/z 607 [M+H]$^+$
HPLC retention time: 0.60 min (analysis condition D)

Example 440

Compound F-129

7-((S)-2-Aminomethyl-piperidin-1-ylmethyl)-8-chloro-3-(5-chloro-2-ethanesulfonyl-benzyl)-6-trifluoromethyl-1H-quinazoline-2,4-dione

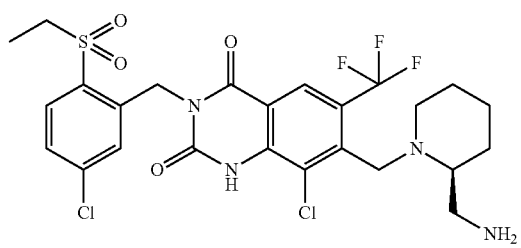 [SMILES: CCS(=O)(=O)c1ccc(Cl)cc1Cn1c(=O)[nH]c2c(Cl)c(CN3CCCC[C@H]3CN)c(C(F)(F)F)cc2c1=O]

The title compound was synthesized from methanesulfonic acid 8-chloro-3-(5-chloro-2-ethanesulfonyl-benzyl)-2,4-dioxo-6-trifluoromethyl-1,2,3,4-tetrahydro-quinazolin-7-ylmethyl ester (Compound F-127) and (S)-1-piperidin-2-ylmethyl-carbamic acid tert-butyl ester under the same conditions as for Compounds f25 and F-128.
LCMS: m/z 607 [M+H]$^+$
HPLC retention time: 0.62 min (analysis condition D)

Example 441

Compound F-130

8-Chloro-3-(5-chloro-2-ethanesulfonyl-benzyl)-7-((S)-2-hydroxymethyl-pyrrolidin-1-ylmethyl)-6-trifluoromethyl-1H-quinazoline-2,4-dione

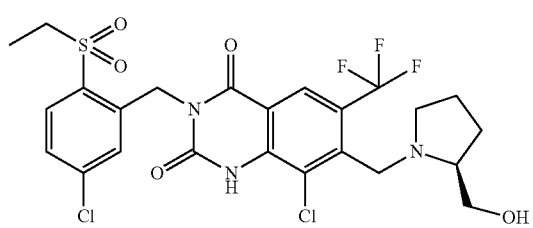 [SMILES: CCS(=O)(=O)c1ccc(Cl)cc1Cn1c(=O)[nH]c2c(Cl)c(CN3CCC[C@H]3CO)c(C(F)(F)F)cc2c1=O]

The title compound was synthesized from methanesulfonic acid 8-chloro-3-(5-chloro-2-ethanesulfonyl-benzyl)-2,4-dioxo-6-trifluoromethyl-1,2,3,4-tetrahydro-quinazolin-7-ylmethyl ester (Compound F-127) and (S)-1-pyrrolidin-2-yl-methanol under the same conditions as for Compound f25.
LCMS: m/z 594 [M+H]$^+$
HPLC retention time: 0.54 min (analysis condition D)

Examples 442 to 455

The following compounds in Table 7 were synthesized from methanesulfonic acid 8-chloro-3-(5-chloro-2-ethanesulfonyl-benzyl)-2,4-dioxo-6-trifluoromethyl-1,2,3,4-tetrahydro-quinazolin-7-ylmethyl ester (Compound F-127) and corresponding amines under the same conditions as for Compound F-130.

TABLE 7

| Example | Compound No. | Structure | Compound name | HPLC cond. | Retention time (min) | m/z [M + H]+ |
|---|---|---|---|---|---|---|
| 442 | F-131 | 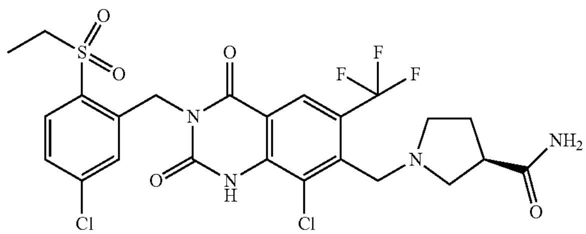 [SMILES: CCS(=O)(=O)c1ccc(Cl)cc1Cn1c(=O)[nH]c2c(Cl)c(CN3CC[C@@H](C(N)=O)C3)c(C(F)(F)F)cc2c1=O] | (R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidine-3-carboxylic acid amide | D | 0.52 | 607 |
| 443 | F-132 | 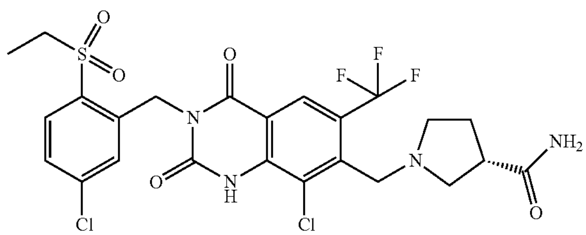 [SMILES: CCS(=O)(=O)c1ccc(Cl)cc1Cn1c(=O)[nH]c2c(Cl)c(CN3CC[C@H](C(N)=O)C3)c(C(F)(F)F)cc2c1=O] | (S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidine-3-carboxylic acid amide | D | 0.52 | 607 |
| 444 | F-133 | 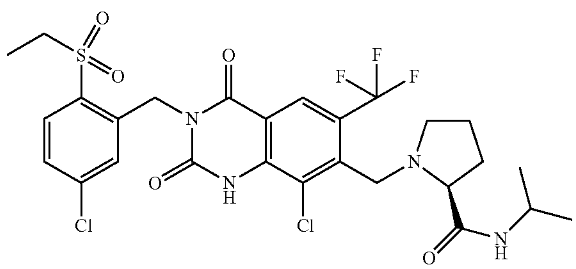 [SMILES: CCS(=O)(=O)c1ccc(Cl)cc1Cn1c(=O)[nH]c2c(Cl)c(CN3CCC[C@H]3C(=O)NC(C)C)c(C(F)(F)F)cc2c1=O] | (S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidine-2-carboxylic acid isopropylamide | D | 0.78 | 649 |
| 445 | F-135 | 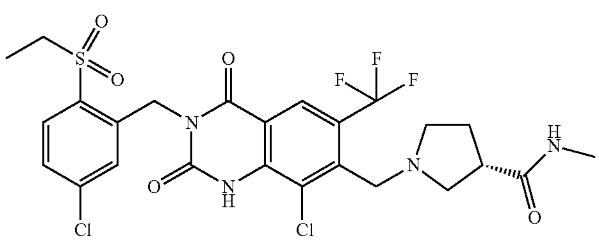 [SMILES: CCS(=O)(=O)c1ccc(Cl)cc1Cn1c(=O)[nH]c2c(Cl)c(CN3CC[C@H](C(=O)NC)C3)c(C(F)(F)F)cc2c1=O] | (S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidine-3-carboxylic acid methylamide | E | 0.57 | 621 |
| 446 | F-136 | 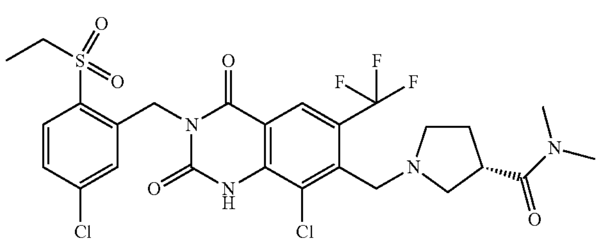 [SMILES: CCS(=O)(=O)c1ccc(Cl)cc1Cn1c(=O)[nH]c2c(Cl)c(CN3CC[C@H](C(=O)N(C)C)C3)c(C(F)(F)F)cc2c1=O] | (S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidine-3-carboxylic acid dimethylamide | E | 0.59 | 635 |
| 447 | F-137 | 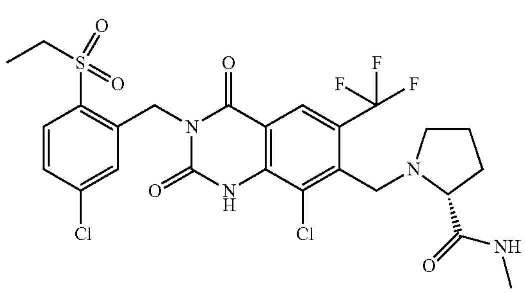 [SMILES: CCS(=O)(=O)c1ccc(Cl)cc1Cn1c(=O)[nH]c2c(Cl)c(CN3CCC[C@@H]3C(=O)NC)c(C(F)(F)F)cc2c1=O] | (R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidine-2-carboxylic acid methylamide | D | 0.70 | 621 |

TABLE 7-continued

| Example | Compound No. | Structure | Compound name | HPLC cond. | Retention time (min) | m/z [M + H]+ |
|---|---|---|---|---|---|---|
| 448 | F-138 | 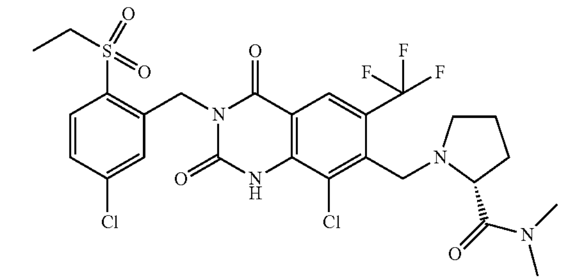 [SMILES: CCS(=O)(=O)c1ccc(Cl)cc1Cn1c(=O)[nH]c2c(Cl)c(CN3CCC[C@@H]3C(=O)N(C)C)c(C(F)(F)F)cc2c1=O] | (R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidine-2-carboxylic acid dimethylamide | D | 0.55 | 635 |
| 449 | F-139 | 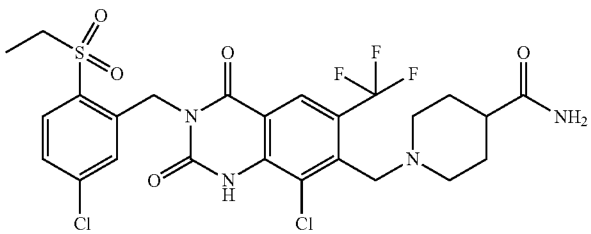 [SMILES: CCS(=O)(=O)c1ccc(Cl)cc1Cn1c(=O)[nH]c2c(Cl)c(CN3CCC(C(N)=O)CC3)c(C(F)(F)F)cc2c1=O] | 1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidine-4-carboxylic acid amide | E | 0.55 | 621 |
| 450 | F-141 | 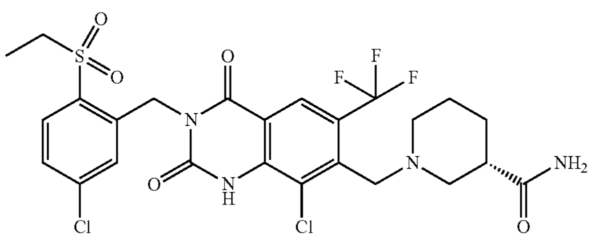 [SMILES: CCS(=O)(=O)c1ccc(Cl)cc1Cn1c(=O)[nH]c2c(Cl)c(CN3CCC[C@H](C(N)=O)C3)c(C(F)(F)F)cc2c1=O] | (S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidine-3-carboxylic acid amide | H | 0.51 | 621 |
| 451 | F-144 | 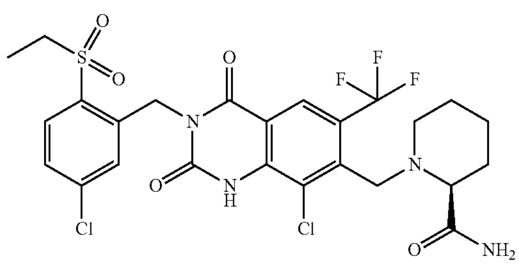 [SMILES: CCS(=O)(=O)c1ccc(Cl)cc1Cn1c(=O)[nH]c2c(Cl)c(CN3CCCC[C@H]3C(N)=O)c(C(F)(F)F)cc2c1=O] | (S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidine-2-carboxylic acid amide | H | 0.70 | 621 |
| 452 | F-145 | 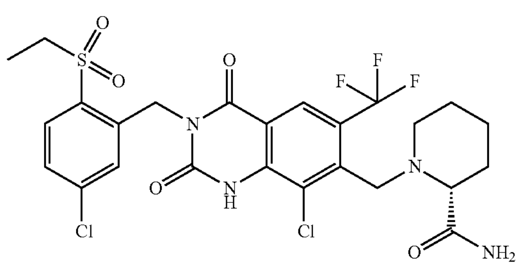 [SMILES: CCS(=O)(=O)c1ccc(Cl)cc1Cn1c(=O)[nH]c2c(Cl)c(CN3CCCC[C@@H]3C(N)=O)c(C(F)(F)F)cc2c1=O] | (R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidine-2-carboxylic acid amide | D | 0.73 | 621 |
| 453 | F-146 | 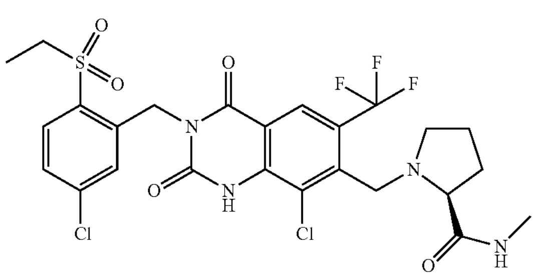 [SMILES: CCS(=O)(=O)c1ccc(Cl)cc1Cn1c(=O)[nH]c2c(Cl)c(CN3CCC[C@H]3C(=O)NC)c(C(F)(F)F)cc2c1=O] | (S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidine-2-carboxylic acid methylamide | D | 0.70 | 621 |

TABLE 7-continued

| Example | Compound No. | Structure | Compound name | HPLC cond. | Retention time (min) | m/z [M + H]+ |
|---|---|---|---|---|---|---|
| 454 | F-147 | 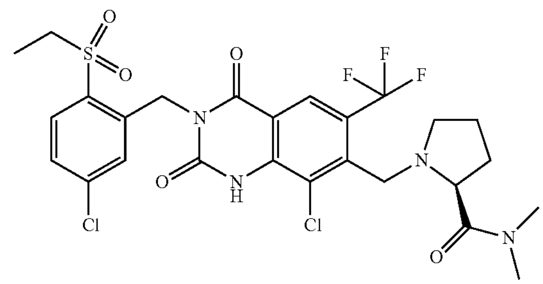 [SMILES: CCS(=O)(=O)c1ccc(Cl)cc1Cn1c(=O)[nH]c2c(Cl)c(CN3CCC[C@H]3C(=O)N(C)C)c(C(F)(F)F)cc2c1=O] | (S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidine-2-carboxylic acid dimethylamide | D | 0.56 | 635 |
| 455 | F-148 | 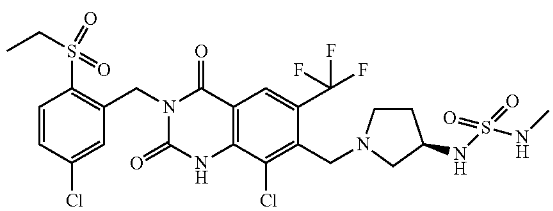 [SMILES: CCS(=O)(=O)c1ccc(Cl)cc1Cn1c(=O)[nH]c2c(Cl)c(CN3CC[C@@H](NS(=O)(=O)NC)C3)c(C(F)(F)F)cc2c1=O] | N-{(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-methylaminesulfonamide | D | 0.58 | 672 |

Example 456

Compound F-134

(S)-1-[8-Chloro-3-(5-chloro-2-ethanesulfonyl-benzyl)-2, 4-dioxo-6-trifluoromethyl-1,2,3,4-tetrahydro-quinazolin-7-ylmethyl]-2-methyl-pyrrolidine-2-carboxylic acid amide

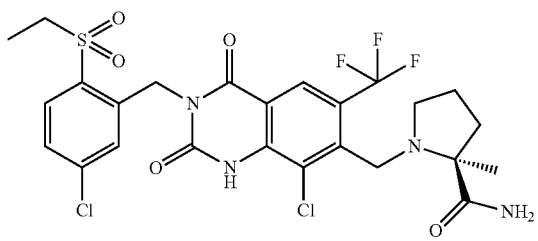 [SMILES: CCS(=O)(=O)c1ccc(Cl)cc1Cn1c(=O)[nH]c2c(Cl)c(CN3CCC[C@@]3(C)C(N)=O)c(C(F)(F)F)cc2c1=O]

The title compound was synthesized from methanesulfonic acid 8-chloro-3-(5-chloro-2-ethanesulfonyl-benzyl)-2,4-dioxo-6-trifluoromethyl-1,2,3,4-tetrahydro-quinazolin-7-ylmethyl ester (Compound F-127) and (S)-2-methyl-pyrrolidine-2-carboxylic acid amide under the same conditions as for Compound f25. However, the reaction was performed at 50° C. to 90° C.

LCMS: m/z 621 [M+H]+

HPLC retention time: 0.72 min (analysis condition D)

Example 457

Compound f26

{1-[8-Chloro-3-(5-chloro-2-ethanesulfonyl-benzyl)-2,4-dioxo-6-trifluoromethyl-1,2,3,4-tetrahydro-quinazolin-7-ylmethyl]-piperidin-4-yl}-carbamic acid tert-butyl ester

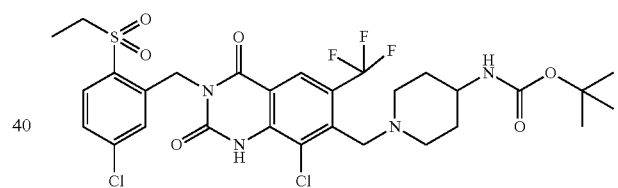

The title compound was synthesized from methanesulfonic acid 8-chloro-3-(5-chloro-2-ethanesulfonyl-benzyl)-2,4-dioxo-6-trifluoromethyl-1,2,3,4-tetrahydro-quinazolin-7-ylmethyl ester (Compound F-127) and piperidin-4-yl-carbamic acid tert-butyl ester under the same conditions as for Compound f25.

Example 458

Compound F-140

7-(4-Amino-piperidin-1-ylmethyl)-8-chloro-3-(5-chloro-2-ethanesulfonyl-benzyl)-6-trifluoromethyl-1H-quinazoline-2,4-dione

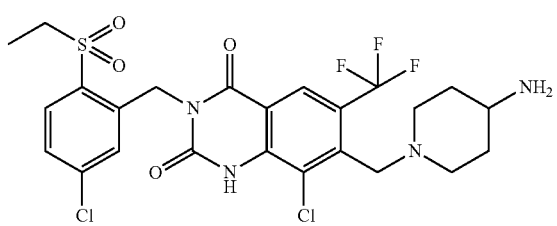 [SMILES: CCS(=O)(=O)c1ccc(Cl)cc1Cn1c(=O)[nH]c2c(Cl)c(CN3CCC(N)CC3)c(C(F)(F)F)cc2c1=O]

The title compound was synthesized from {1-[8-chloro-3-(5-chloro-2-ethanesulfonyl-benzyl)-2,4-dioxo-6-trifluoromethyl-1,2,3,4-tetrahydro-quinazolin-7-ylmethyl]-piperidin-4-yl}-carbamic acid tert-butyl ester (Compound f26) under the same conditions as for Compound B-1.
LCMS: m/z 593 [M+H]+
HPLC retention time: 0.51 min (analysis condition E)

Example 459

Compound F-142

(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidine-2-carboxylic acid tert-butyl ester

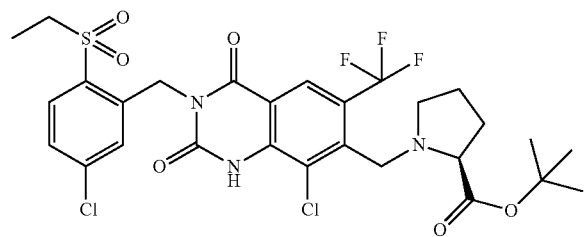 [SMILES: CCS(=O)(=O)c1ccc(Cl)cc1Cn1c(=O)[nH]c2c(Cl)c(CN3CCC[C@H]3C(=O)OC(C)(C)C)c(C(F)(F)F)cc2c1=O]

The title compound was synthesized from methanesulfonic acid 8-chloro-3-(5-chloro-2-ethanesulfonyl-benzyl)-2,4-dioxo-6-trifluoromethyl-1,2,3,4-tetrahydro-quinazolin-7-ylmethyl ester (Compound F-127) and (S)-pyrrolidin-2-carboxylic acid tert-butyl ester under the same conditions as for Compound f25.
LCMS: m/z 664 [M+H]+
HPLC retention time: 1.06 min (analysis condition H)

Example 460

Compound F-143

(S)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidine-2-carboxylic acid

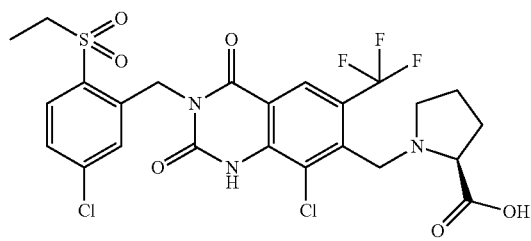 [SMILES: CCS(=O)(=O)c1ccc(Cl)cc1Cn1c(=O)[nH]c2c(Cl)c(CN3CCC[C@H]3C(=O)O)c(C(F)(F)F)cc2c1=O]

TFA (0.4 ml) was added to a solution of (S)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidine-2-carboxylic acid tert-butyl ester (Compound F-142, 30.0 mg, 0.045 mmol) in DCM (0.6 ml), and the mixture was stirred at room temperature for six hours. The reaction mixture was concentrated under reduced pressure, and the resulting residue was purified by preparative HPLC (water/ acetonitrile, 0.05% TFA) to give the title compound (18.8 mg, yield: 67%) as a colorless solid.
LCMS: m/z 608 [M+H]+
HPLC retention time: 0.57 min (analysis condition D)

Example 461

Compound f27

[({(R)-1-[8-Chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-methyl-carbamoyl)-methyl]-carbamic acid tert-butyl ester

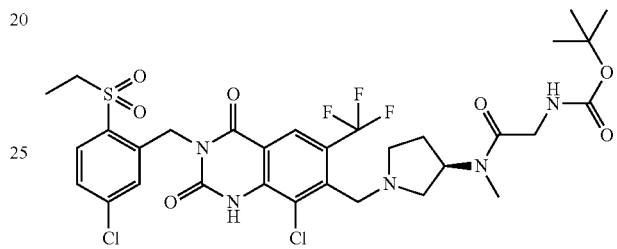

The title compound was synthesized from methanesulfonic acid 8-chloro-3-(5-chloro-2-ethanesulfonyl-benzyl)-2,4-dioxo-6-trifluoromethyl-1,2,3,4-tetrahydro-quinazolin-7-ylmethyl ester (Compound F-127) and [((R)-methyl-pyrrolidin-3-yl-carbamoyl)-methyl]-carbamic acid tert-butyl ester under the same conditions as for Compound f25.

Example 462

Compound F-40

2-Amino-N-{(R)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-N-methyl-acetamide

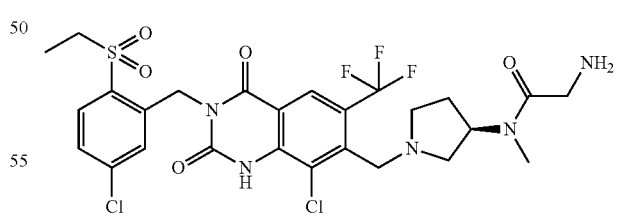

The title compound was synthesized from [({(R)-1-[8-chloro-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-methyl-carbamoyl)-methyl]-carbamic acid tert-butyl ester (Compound f27) under the same conditions as for Compound B-1.
LCMS: m/z 650 [M+H]+
HPLC retention time: 0.50 min (analysis condition E)

Example 463

Compound f28

2-Amino-3-chloro-5-trifluoromethyl-4-vinyl-benzoic acid

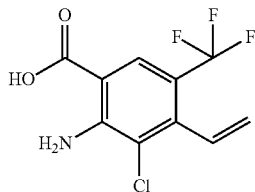

The title compound was synthesized from 2-amino-5-trifluoromethyl-4-vinyl-benzoic acid (Compound b24) under the same conditions as for Compound 24.

Example 464

Compound f29

2-Amino-3-chloro-N-(5-chloro-2-ethanesulfonyl-benzyl)-5-trifluoromethyl-4-vinyl-benzamide

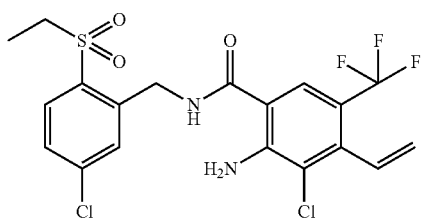 [SMILES: C=Cc1c(C(F)(F)F)cc(C(=O)NCc2cc(Cl)ccc2S(=O)(=O)CC)c(N)c1Cl]

The title compound was synthesized from 2-amino-3-chloro-5-trifluoromethyl-4-vinyl-benzoic acid (Compound f28) under the same conditions as for Compound 26. However, the reaction was performed using DMF in place of DCM.

Example 465

Compound F-149

8-Chloro-3-(5-chloro-2-ethanesulfonyl-benzyl)-6-trifluoromethyl-7-vinyl-1H-quinazoline-2,4-dione

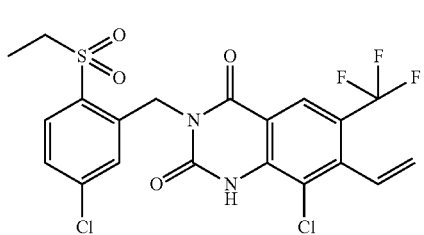 [SMILES: C=Cc1c(C(F)(F)F)cc2c(=O)n(Cc3cc(Cl)ccc3S(=O)(=O)CC)c(=O)[nH]c2c1Cl]

The title compound was synthesized from 2-amino-3-chloro-N-(5-chloro-2-ethanesulfonyl-benzyl)-5-trifluoromethyl-4-vinyl-benzamide (Compound f29) under the same conditions as for Compound 37.

LCMS: m/z 507 [M+H]$^+$
HPLC retention time: 0.96 min (analysis condition H)

Example 466

Compound f30

2-Amino-3-chloro-4-[1,3]dioxolan-2-yl-5-trifluoromethyl-benzoic acid ethyl ester

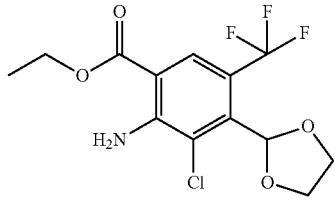 [SMILES: CCOC(=O)c1cc(C(F)(F)F)c(C2OCCO2)c(Cl)c1N]

The title compound was synthesized from 2-amino-3-chloro-4-formyl-5-trifluoromethyl-benzoic acid ethyl ester (Compound 24) under the same conditions as for Compound 34.

Example 467

Compound f31

2-Amino-3-chloro-4-[1,3]dioxolan-2-yl-5-trifluoromethyl-benzoic acid

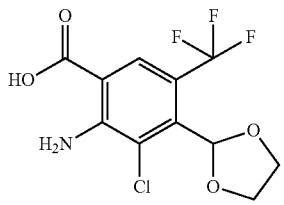 [SMILES: Nc1c(C(=O)O)cc(C(F)(F)F)c(C2OCCO2)c1Cl]

The title compound was synthesized from 2-amino-3-chloro-4-[1,3]dioxolan-2-yl-5-trifluoromethyl-benzoic acid ethyl ester (Compound f30) under the same conditions as for Compound 25.

Example 468

Compound f32

2-Amino-3-chloro-N-(5-chloro-2-ethanesulfonyl-benzyl)-4-[1.3]dioxolan-2-yl-5-trifluoromethyl-benzamide

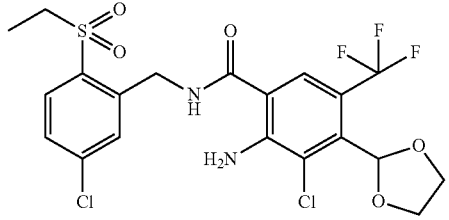 [SMILES: CCS(=O)(=O)c1ccc(Cl)cc1CNC(=O)c1cc(C(F)(F)F)c(C2OCCO2)c(Cl)c1N]

The title compound was synthesized from 2-amino-3-chloro-4-[1,3]dioxolan-2-yl-5-trifluoromethyl-benzoic acid (Compound f31) under the same conditions as for Compound 26.

Example 469

Compound F-150

8-Chloro-3-(5-chloro-2-ethanesulfonyl-benzyl)-7-[1,3]dioxolan-2-yl-6-trifluoromethyl-1H-quinazoline-2,4-dione

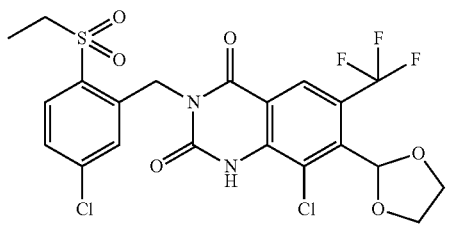 [SMILES: CCS(=O)(=O)c1ccc(Cl)cc1Cn1c(=O)[nH]c2c(Cl)c(C3OCCO3)c(C(F)(F)F)cc2c1=O]

The title compound was synthesized from 2-amino-3-chloro-N-(5-chloro-2-ethanesulfonyl-benzyl)-4-[1,3]dioxolan-2-yl-5-trifluoromethyl-benzamide (Compound f32) under the same conditions as for Compound 37.

LCMS: m/z 553 [M+H]$^+$
HPLC retention time: 0.87 min (analysis condition H)

Example 470

Compound g1

4-(3-Amino-2-chloro-4-ethoxycarbonyl-6-trifluoromethoxy-benzyl)-piperazine-1-carboxylic acid tert-butyl ester

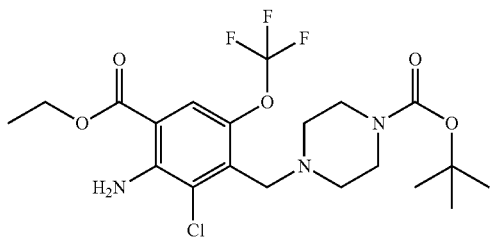 [SMILES: CCOC(=O)c1cc(OC(F)(F)F)c(CN2CCN(C(=O)OC(C)(C)C)CC2)c(Cl)c1N]

The title compound was synthesized from 4-(5-amino-4-ethoxycarbonyl-2-trifluoromethoxy-benzyl)-piperazine-1-carboxylic acid tert-butyl ester (Compound c2) under the same conditions as for Compound 24.

Example 471

Compound g2

4-(3-Amino-4-carboxy-2-chloro-6-trifluoromethoxy-benzyl)-piperazine-1-carboxylic acid tert-butyl ester

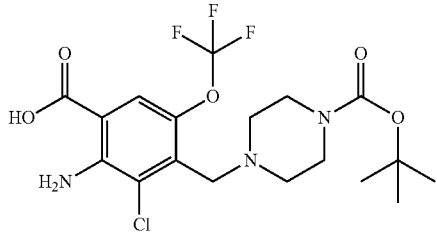 [SMILES: CC(C)(C)OC(=O)N1CCN(Cc2c(OC(F)(F)F)cc(C(=O)O)c(N)c2Cl)CC1]

The title compound was synthesized from 4-(3-amino-2-chloro-4-ethoxycarbonyl-6-trifluoromethoxy-benzyl)-piperazine-1-carboxylic acid tert-butyl ester (Compound g1) under the same conditions as for Compound 25.

Example 472

Compound g3

4-[3-Amino-2-chloro-4-(5-chloro-2-ethanesulfonyl-benzylcarbamoyl)-6-trifluoromethoxy-benzyl]-piperazine-1-carboxylic acid tert-butyl ester

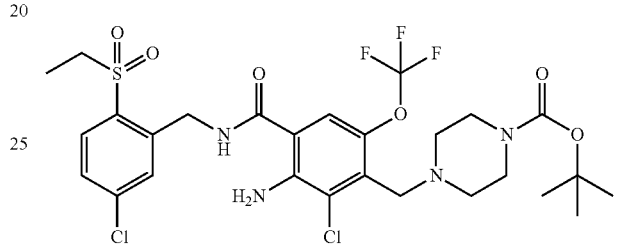

The title compound was synthesized from 4-(3-amino-4-carboxy-2-chloro-6-trifluoromethoxy-benzyl)-piperazine-1-carboxylic acid tert-butyl ester (Compound g2) without using HOBt under the same conditions as for Compound 26.

Example 473

Compound g4

4-[8-Chloro-3-(5-chloro-2-ethanesulfonyl-benzyl)-2,4-dioxo-6-trifluoromethoxy-1,2,3,4-tetrahydro-quinazolin-7-ylmethyl]-piperazine-1-carboxylic acid tert-butyl ester

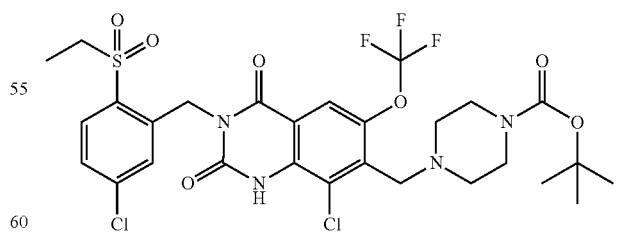

The title compound was synthesized from 4-[3-amino-2-chloro-4-(5-chloro-2-ethanesulfonyl-benzylcarbamoyl)-6-trifluoromethoxy-benzyl]-piperazine-1-carboxylic acid tert-butyl ester (Compound g3) under the same conditions as for Compound 37.

Example 474

Compound G-1

8-Chloro-3-(5-chloro-2-ethanesulfonyl-benzyl)-7-piperazin-1-ylmethyl-6-trifluoromethoxy-1H-quinazoline-2,4-dione

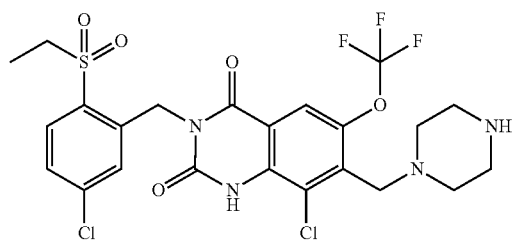 [SMILES: CCS(=O)(=O)c1ccc(Cl)cc1Cn1c(=O)[nH]c2c(Cl)c(CN3CCNCC3)c(OC(F)(F)F)cc2c1=O]

The title compound was synthesized from 4-[8-chloro-3-(5-chloro-2-ethanesulfonyl-benzyl)-2,4-dioxo-6-trifluoromethoxy-1,2,3,4-tetrahydro-quinazolin-7-ylmethyl]-piperazine-1-carboxylic acid tert-butyl ester (Compound g4) under the same conditions as for Compound B-1.

LCMS: m/z 595 [M+H]$^+$

HPLC retention time: 1.62 min (analysis condition C)

Example 475

Compound G-2

8-Chloro-3-(5-chloro-2-ethanesulfonyl-benzyl)-7-(4-methyl-piperazin-1-ylmethyl)-6-trifluoromethoxy-1H-quinazoline-2,4-dione

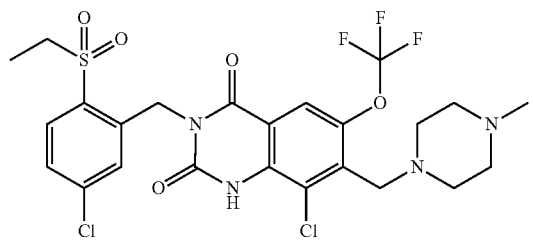 [SMILES: CCS(=O)(=O)c1ccc(Cl)cc1Cn1c(=O)[nH]c2c(Cl)c(CN3CCN(C)CC3)c(OC(F)(F)F)cc2c1=O]

The title compound was synthesized from 8-chloro-3-(5-chloro-2-ethanesulfonyl-benzyl)-7-piperazin-1-ylmethyl-6-trifluoromethoxy-1H-quinazoline-2,4-dione (Compound G-1) under the same conditions as for Compound B-2.

LCMS: m/z 609 [M+H]$^+$

HPLC retention time: 0.56 min (analysis condition D)

Example 476

Compound G-3

8-Chloro-3-(5-chloro-2-ethanesulfonyl-benzyl)-7-(4-isopropyl-piperazin-1-ylmethyl)-6-trifluoromethoxy-1H-quinazoline-2,4-dione

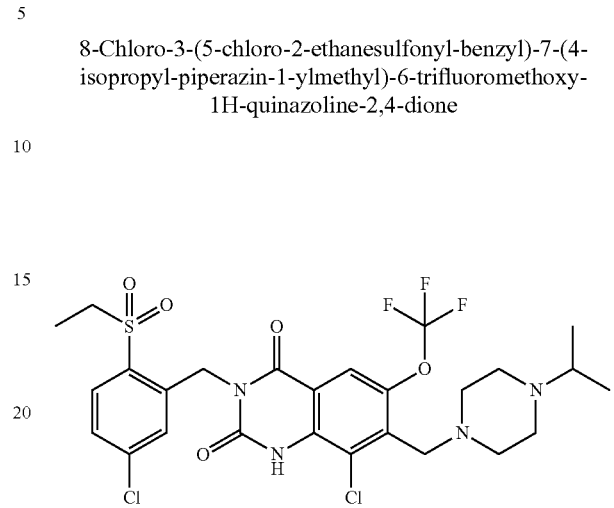

The title compound was synthesized from 8-chloro-3-(5-chloro-2-ethanesulfonyl-benzyl)-7-piperazin-1-ylmethyl-6-trifluoromethoxy-1H-quinazoline-2,4-dione (Compound G-1) under the same conditions as for Compound B-4.

LCMS: m/z 637 [M+H]$^+$

HPLC retention time: 0.59 min (analysis condition D)

Example 477

Compound G-4

8-Chloro-3-(5-chloro-2-ethanesulfonyl-benzyl)-7-[4-(tetrahydro-pyran-4-yl)-piperazin-1-ylmethyl]-6-trifluoromethoxy-1H-quinazoline-2,4-dione

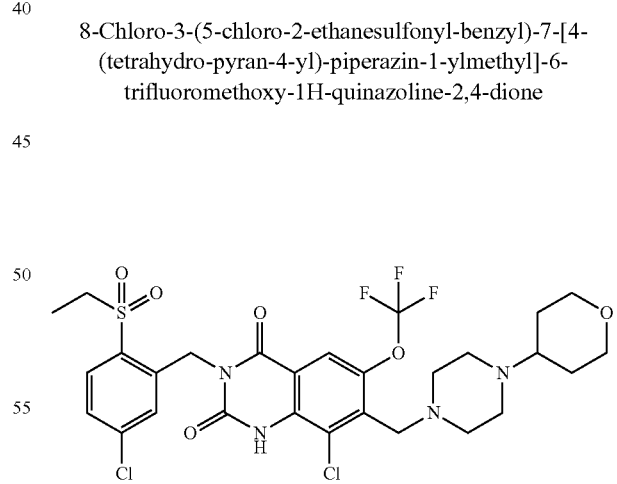

The title compound was synthesized from 8-chloro-3-(5-chloro-2-ethanesulfonyl-benzyl)-7-piperazin-1-ylmethyl-6-trifluoromethoxy-1H-quinazoline-2,4-dione (Compound G-1) under the same conditions as for Compound B-5.

LCMS: m/z 679 [M+H]$^+$

HPLC retention time: 0.57 min (analysis condition D)

Example 478

Compound g5

2-Amino-4-((R)-3-tert-butoxycarbonylamino-pyrrolidin-1-ylmethyl)-5-trifluoromethoxy-benzoic acid ethyl ester

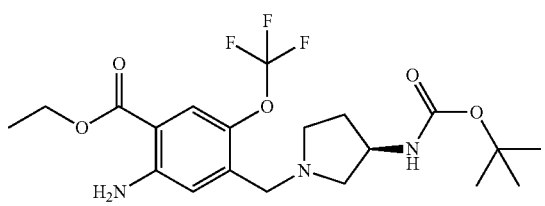 [SMILES: CCOC(=O)c1cc(OC(F)(F)F)c(CN2CC[C@@H](NC(=O)OC(C)(C)C)C2)cc1N]

The title compound was synthesized from 4-((R)-3-tert-butoxycarbonylamino-pyrrolidin-1-ylmethyl)-2-nitro-5-trifluoromethoxy-benzoic acid ethyl ester (Compound c6) under the same conditions as for Compound 30.

Example 479

Compound g6

2-Amino-4-((R)-3-tert-butoxycarbonylamino-pyrrolidin-1-ylmethyl)-5-trifluoromethoxy-benzoic acid

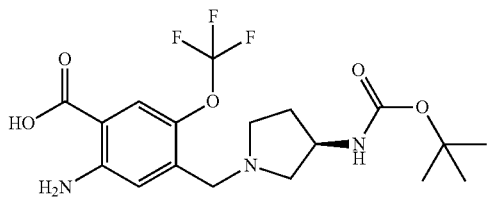 [SMILES: CC(C)(C)OC(=O)N[C@@H]1CCN(Cc2cc(N)c(C(=O)O)cc2OC(F)(F)F)C1]

The title compound was synthesized from 2-amino-4-((R)-3-tert-butoxycarbonylamino-pyrrolidin-1-ylmethyl)-5-trifluoromethoxy-benzoic acid ethyl ester (Compound g5) under the same conditions as for Compound 25.

Example 480

Compound g7

{(R)-1-[5-Amino-4-(5-chloro-2-ethanesulfonyl-benzylcarbamoyl)-2-trifluoromethoxy-benzyl]-pyrrolidin-3-yl}-carbamic acid tert-butyl ester

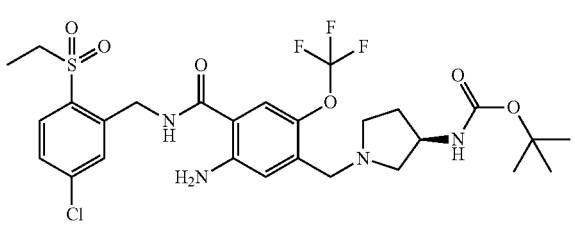 [SMILES: CCS(=O)(=O)c1ccc(Cl)cc1CNC(=O)c1cc(OC(F)(F)F)c(CN2CC[C@@H](NC(=O)OC(C)(C)C)C2)cc1N]

The title compound was synthesized from 2-amino-4-((R)-3-tert-butoxycarbonylamino-pyrrolidin-1-ylmethyl)-5-trifluoromethoxy-benzoic acid (Compound g6) under the same conditions as for Compound 26. However, the reaction was performed without using HOBt.

Example 481

Compound g8

{(R)-1-[3-Amino-2-chloro-4-(5-chloro-2-ethanesulfonyl-benzylcarbamoyl)-6-trifluoromethoxy-benzyl]-pyrrolidin-3-yl}-carbamic acid tert-butyl ester

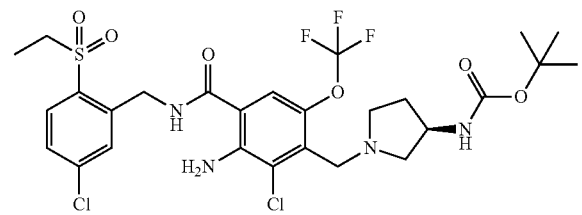 [SMILES: CCS(=O)(=O)c1ccc(Cl)cc1CNC(=O)c1cc(OC(F)(F)F)c(CN2CC[C@@H](NC(=O)OC(C)(C)C)C2)c(Cl)c1N]

The title compound was synthesized from {(R)-1-[5-amino-4-(5-chloro-2-ethanesulfonyl-benzylcarbamoyl)-2-trifluoromethoxy-benzyl]-pyrrolidin-3-yl}-carbamic acid tert-butyl ester (Compound g7) under the same conditions as for Compound 24.

Example 482

Compound G-5

7-((R)-3-Amino-pyrrolidin-1-ylmethyl)-8-chloro-3-(5-chloro-2-ethanesulfonyl-benzyl)-6-trifluoromethoxy-1H-quinazoline-2,4-dione

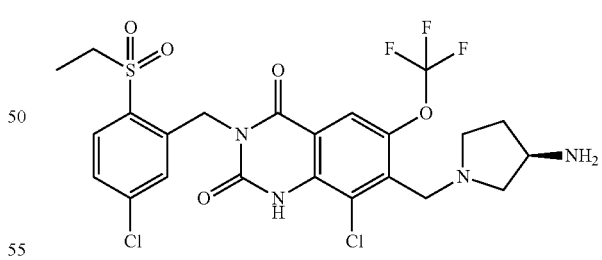

The title compound was synthesized from {(R)-1-[3-amino-2-chloro-4-(5-chloro-2-ethanesulfonyl-benzylcarbamoyl)-6-trifluoromethoxy-benzyl]-pyrrolidin-3-yl}-carbamic acid tert-butyl ester (Compound g8) under the same conditions as for Compounds g4 and G-1. However, the reaction was performed using a 4N hydrochloric acid/ethyl acetate solution in place of TFA/DCM under the conditions for Compound G-1.

LCMS: m/z 595 [M+H]$^+$

HPLC retention time: 0.52 min (analysis condition D)

Example 483

Compound G-6

8-Chloro-3-(5-chloro-2-ethanesulfonyl-benzyl)-7-((R)-3-dimethylamino-pyrrolidin-1-ylmethyl)-6-trifluoromethoxy-1H-quinazoline-2,4-di one

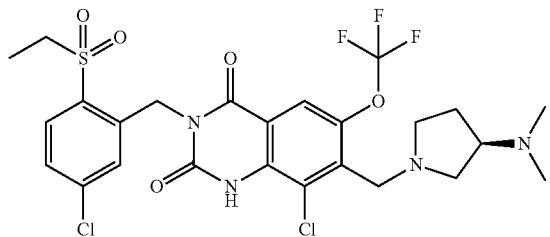 [SMILES: CCS(=O)(=O)c1ccc(Cl)cc1Cn1c(=O)[nH]c2c(Cl)c(CN3CC[C@@H](N(C)C)C3)c(OC(F)(F)F)cc2c1=O]

The title compound was synthesized from 8-chloro-3-(5-chloro-2-ethanesulfonyl-benzyl)-2,4-dioxo-6-trifluoromethoxy-1,2,3,4-tetrahydro-quinazoline-7-carbaldehyde (Compound 38) and dimethyl-(R)-pyrrolidin-3-yl-amine under the same conditions as for Compound b12.

LCMS: m/z 623 [M+H]$^+$

HPLC retention time: 0.57 min (analysis condition D)

Example 484

Compound G-7

{(R)-1-[8-Chloro-3-(5-chloro-2-ethanesulfonyl-benzyl)-2,4-dioxo-6-trifluoromethoxy-1,2,3,4-tetrahydro-quinazolin-7-ylmethyl]-pyrrolidin-3-yl}-methyl-carbamic acid tert-butyl ester

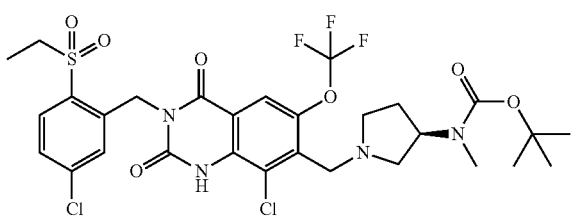 [SMILES: CCS(=O)(=O)c1ccc(Cl)cc1Cn1c(=O)[nH]c2c(Cl)c(CN3CC[C@@H](N(C)C(=O)OC(C)(C)C)C3)c(OC(F)(F)F)cc2c1=O]

The title compound was synthesized from 8-chloro-3-(5-chloro-2-ethanesulfonyl-benzyl)-2,4-dioxo-6-trifluoromethoxy-1,2,3,4-tetrahydro-quinazoline-7-carbaldehyde (Compound 38) and methyl-(R)-pyrrolidin-3-yl-carbamic acid tert-butyl ester under the same conditions as for Compound b12.

LCMS: m/z 709 [M+H]$^+$

HPLC retention time: 0.70 min (analysis condition D)

Example 485

Compound G-8

8-Chloro-3-(5-chloro-2-ethanesulfonyl-benzyl)-7-((R)-3-methylamino-pyrrolidin-1-ylmethyl)-6-trifluoromethoxy-1H-quinazoline-2,4-dione

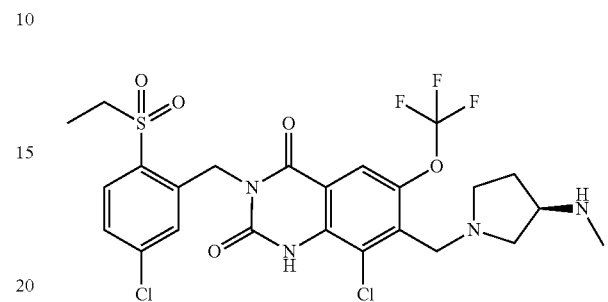

The title compound was synthesized from {(R)-1-[8-chloro-3-(5-chloro-2-ethanesulfonyl-benzyl)-2,4-dioxo-6-trifluoromethoxy-1,2,3,4-tetrahydro-quinazolin-7-ylmethyl]-pyrrolidin-3-yl}-methyl-carbamic acid tert-butyl ester (Compound G-7) under the same conditions as for Compound a41.

LCMS: m/z 609 [M+H]$^+$

HPLC retention time: 0.55 min (analysis condition D)

Example 486

Compound G-9

((R)-1-[8-Chloro-3-(5-chloro-2-ethanesulfonyl-benzyl)-2,4-dioxo-6-trifluoromethoxy-1,2,3,4-tetrahydro-quinazolin-7-ylmethyl]-piperidin-3-yl-carbamic acid tert-butyl ester

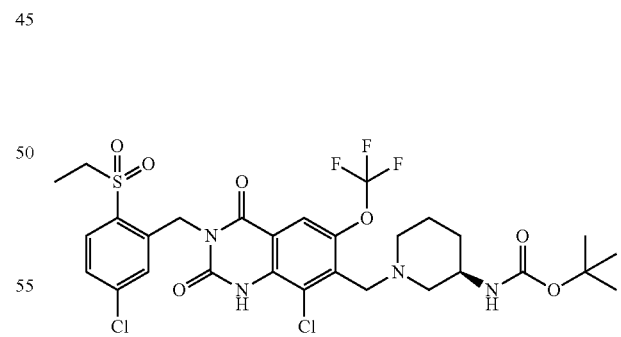

The title compound was synthesized from 8-chloro-3-(5-chloro-2-ethanesulfonyl-benzyl)-2,4-dioxo-6-trifluoromethoxy-1,2,3,4-tetrahydro-quinazoline-7-carbaldehyde (Compound 38) and (R)-piperidin-3-yl-carbamic acid tert-butyl ester under the same conditions as for Compound b12.

LCMS: m/z 709 [M+H]$^+$

HPLC retention time: 0.75 min (analysis condition D)

Example 487

Compound G-10

7-((R)-3-Amino-piperidin-1-ylmethyl)-8-chloro-3-(5-chloro-2-ethanesulfonyl-benzyl)-6-trifluoromethoxy-1H-quinazoline-2,4-dione

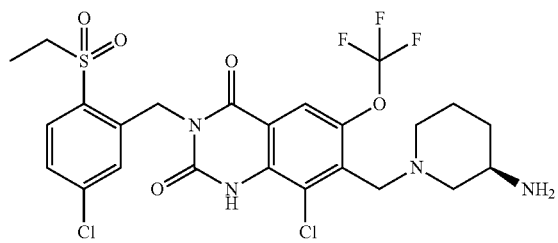 [SMILES: CCS(=O)(=O)c1ccc(Cl)cc1Cn1c(=O)[nH]c2c(Cl)c(CN3CCC[C@@H](N)C3)c(OC(F)(F)F)cc2c1=O]

The title compound was synthesized from {(R)-1-[8-chloro-3-(5-chloro-2-ethanesulfonyl-benzyl)-2,4-dioxo-6-trifluoromethoxy-1,2,3,4-tetrahydro-quinazolin-7-ylmethyl]-piperidin-3-yl}-carbamic acid tert-butyl ester (Compound G-9) under the same conditions as for Compound a41.

LCMS: m/z 609 [M+H]$^+$

HPLC retention time: 0.58 min (analysis condition D)

Example 488

Compound G-11

8-Chloro-3-(5-chloro-2-ethanesulfonyl-benzyl)-7-((R)-3-dimethylamino-piperidin-1-ylmethyl)-6-trifluoromethoxy-1H-quinazoline-2,4-dione

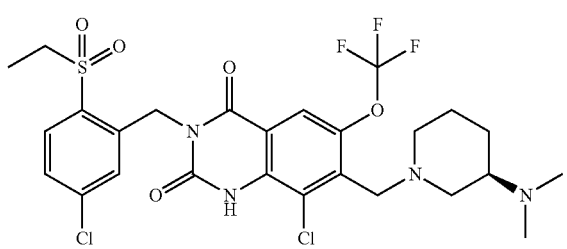 [SMILES: CCS(=O)(=O)c1ccc(Cl)cc1Cn1c(=O)[nH]c2c(Cl)c(CN3CCC[C@@H](N(C)C)C3)c(OC(F)(F)F)cc2c1=O]

The title compound was synthesized from 7-((R)-3-amino-piperidin-1-ylmethyl)-8-chloro-3-(5-chloro-2-ethanesulfonyl-benzyl)-6-trifluoromethoxy-1H-quinazoline-2,4-dione (Compound G-10) under the same conditions as for Compound B-9.

LCMS: m/z 637 [M+H]$^+$

HPLC retention time: 0.59 min (analysis condition D)

Example 489

Compound G-12

N-{(R)-1-[8-Chloro-3-(5-chloro-2-ethanesulfonyl-benzyl)-2,4-dioxo-6-trifluoromethoxy-1,2,3,4-tetrahydro-quinazolin-7-ylmethyl]-piperidin-3-yl}-acetamide

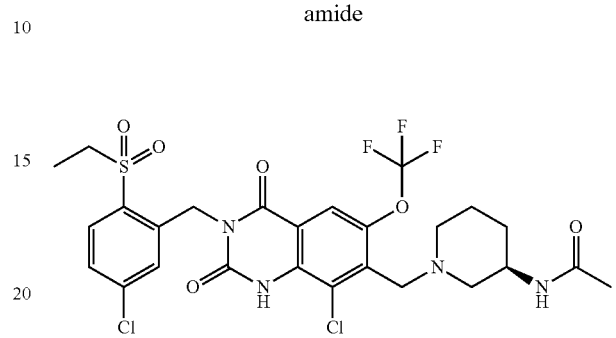

The title compound was synthesized from 7-((R)-3-amino-piperidin-1-ylmethyl)-8-chloro-3-(5-chloro-2-ethanesulfonyl-benzyl)-6-trifluoromethoxy-1H-quinazoline-2,4-dione (Compound G-10) under the same conditions as for Compound B-18.

LCMS: m/z 651 [M+H]$^+$

HPLC retention time: 0.56 min (analysis condition D)

Example 490

Compound G-13

N-{(R)-1-[8-Chloro-3-(5-chloro-2-ethanesulfonyl-benzyl)-2,4-dioxo-6-trifluoromethoxy-1,2,3,4-tetrahydro-quinazolin-7-ylmethyl]-piperidin-3-yl}-methanesulfonamide

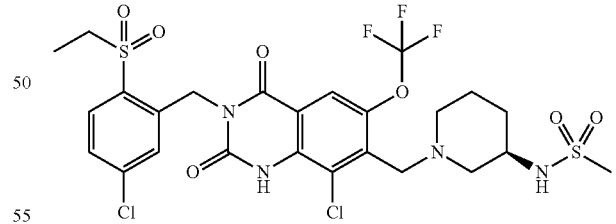

The title compound was synthesized from 7-((R)-3-amino-piperidin-1-ylmethyl)-8-chloro-3-(5-chloro-2-ethanesulfonyl-benzyl)-6-trifluoromethoxy-1H-quinazoline-2,4-dione (Compound G-10) under the same conditions as for Compound C-6. However, the reaction was performed using TEA in place of DIPEA.

LCMS: m/z 687 [M+H]$^+$

HPLC retention time: 0.64 min (analysis condition D)

Example 491

Compound g9

{(R)-1-[8-Chloro-3-(5-chloro-2-ethanesulfonyl-benzyl)-2,4-dioxo-6-trifluoromethoxy-1,2,3,4-tetrahydro-quinazolin-7-ylmethyl]-piperidin-3-yl}-methyl-carbamic acid tert-butyl ester

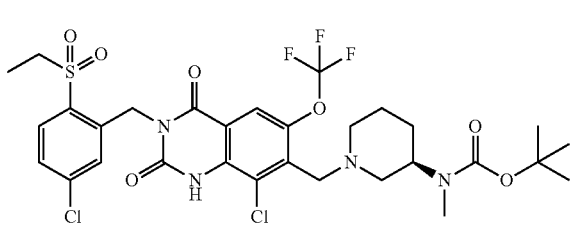 [SMILES: CCS(=O)(=O)c1ccc(Cl)cc1Cn1c(=O)[nH]c2c(Cl)c(CN3CCC[C@@H](N(C)C(=O)OC(C)(C)C)C3)c(OC(F)(F)F)cc2c1=O]

The title compound was synthesized from 8-chloro-3-(5-chloro-2-ethanesulfonyl-benzyl)-2,4-dioxo-6-trifluoromethoxy-1,2,3,4-tetrahydro-quinazoline-7-carbaldehyde (Compound 38) and methyl-(R)-piperidin-3-yl-carbamic acid tert-butyl ester under the same conditions as for Compound b12. However, the reaction was performed by using DCM in place of THF and adding molecular sieves 3A.

Example 492

Compound G-14

8-Chloro-3-(5-chloro-2-ethanesulfonyl-benzyl)-7-((R)-3-methylamino-piperidin-1-ylmethyl)-6-trifluoromethoxy-1H-quinazoline-2,4-dione

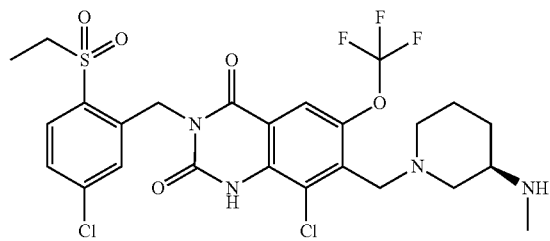 [SMILES: CCS(=O)(=O)c1ccc(Cl)cc1Cn1c(=O)[nH]c2c(Cl)c(CN3CCC[C@@H](NC)C3)c(OC(F)(F)F)cc2c1=O]

The title compound was synthesized from {(R)-1-[8-chloro-3-(5-chloro-2-ethanesulfonyl-benzyl)-2,4-dioxo-6-trifluoromethoxy-1,2,3,4-tetrahydro-quinazolin-7-ylmethyl]-piperidin-3-yl}-methyl-carbamic acid tert-butyl ester (Compound g9) under the same conditions as for Compound a41.

LCMS: m/z 623 [M+H]$^+$

HPLC retention time: 0.57 min (analysis condition D)

Example 493

Compound G-15

{(S)-1-[8-Chloro-3-(5-chloro-2-ethanesulfonyl-benzyl)-2,4-dioxo-6-trifluoromethoxy-1,2,3,4-tetrahydro-quinazolin-7-ylmethyl]-piperidin-3-yl}-carbamic acid tert-butyl ester

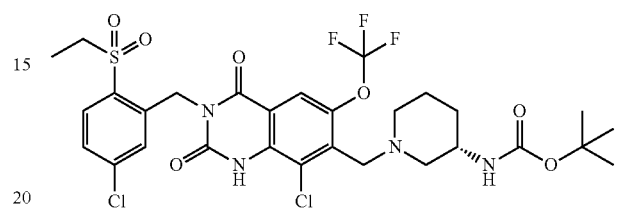

The title compound was synthesized from 8-chloro-3-(5-chloro-2-ethanesulfonyl-benzyl)-2,4-dioxo-6-trifluoromethoxy-1,2,3,4-tetrahydro-quinazoline-7-carbaldehyde (Compound 38) and (S)-piperidin-3-yl-carbamic acid tert-butyl ester under the same conditions as for Compound b12. However, the reaction was performed using chloroform in place of THF.

LCMS: m/z 709 [M+H]$^+$

HPLC retention time: 0.74 min (analysis condition D)

Example 494

Compound G-16

7-((S)-3-Amino-piperidin-1-ylmethyl)-8-chloro-3-(5-chloro-2-ethanesulfonyl-benzyl)-6-trifluoromethoxy-1H-quinazoline-2,4-dione

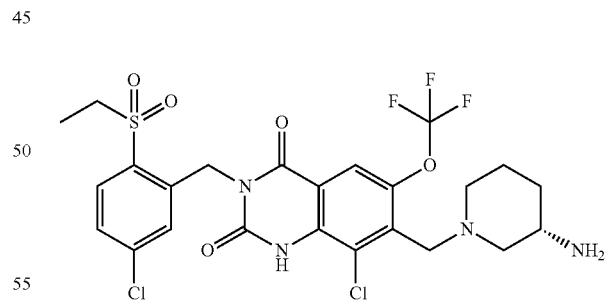

The title compound was synthesized from {(S)-1-[8-chloro-3-(5-chloro-2-ethanesulfonyl-benzyl)-2,4-dioxo-6-trifluoromethoxy-1,2,3,4-tetrahydro-quinazolin-7-ylmethyl]-piperidin-3-yl}-carbamic acid tert-butyl ester (Compound G-15) under the same conditions as for Compound a41.

LCMS: m/z 609 [M+H]$^+$

HPLC retention time: 0.58 min (analysis condition D)

Example 495

Compound G-17

8-Chloro-3-(5-chloro-2-ethanesulfonyl-benzyl)-7-
((S)-3-dimethylamino-piperidin-1-ylmethyl)-6-trif-
luoromethoxy-1H-quinazoline-2,4-dione

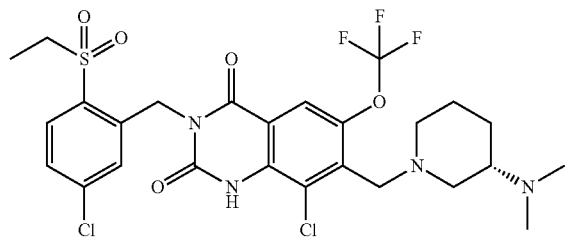 [SMILES: CCS(=O)(=O)c1ccc(Cl)cc1Cn1c(=O)[nH]c2c(Cl)c(CN3CCC[C@H](N(C)C)C3)c(OC(F)(F)F)cc2c1=O]

The title compound was synthesized from 7-((S)-3-amino-piperidin-1-ylmethyl)-8-chloro-3-(5-chloro-2-ethanesulfonyl-benzyl)-6-trifluoromethoxy-1H-quinazoline-2,4-dione (Compound G-16) under the same conditions as for Compound B-9.

LCMS: m/z 637 [M+H]+

HPLC retention time: 0.60 min (analysis condition D)

Example 496

Compound G-18

N-{(S)-1-[8-Chloro-3-(5-chloro-2-ethanesulfonyl-
benzyl)-2,4-dioxo-6-trifluoromethoxy-1,2,3,4-tetra-
hydro-quinazolin-7-ylmethyl]-piperidin-3-yl}-acet-
amide

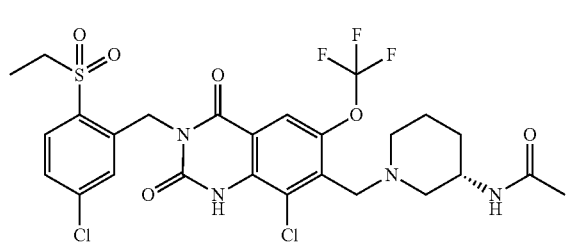 [SMILES: CCS(=O)(=O)c1ccc(Cl)cc1Cn1c(=O)[nH]c2c(Cl)c(CN3CCC[C@H](NC(C)=O)C3)c(OC(F)(F)F)cc2c1=O]

The title compound was synthesized from 7-((S)-3-amino-piperidin-1-ylmethyl)-8-chloro-3-(5-chloro-2-ethanesulfonyl-benzyl)-6-trifluoromethoxy-1H-quinazoline-2,4-dione (Compound G-16) under the same conditions as for Compound B-18.

LCMS: m/z 651 [M+H]+

HPLC retention time: 0.56 min (analysis condition D)

Example 497

Compound G-19

N-{(S)-1-[8-Chloro-3-(5-chloro-2-ethanesulfonyl-
benzyl)-2,4-dioxo-6-trifluoromethoxy-1,2,3,4-tetra-
hydro-quinazolin-7-ylmethyl]-piperidin-3-yl}-meth-
anesulfonamide

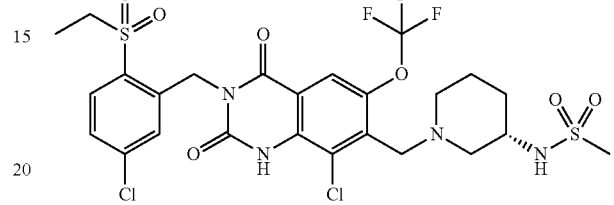

The title compound was synthesized from 7-((S)-3-amino-piperidin-1-ylmethyl)-8-chloro-3-(5-chloro-2-ethanesulfonyl-benzyl)-6-trifluoromethoxy-1H-quinazoline-2,4-dione (Compound G-16) under the same conditions as for Compound C-6. However, the reaction was performed using TEA in place of DIPEA.

LCMS: m/z 687 [M+H]+

HPLC retention time: 0.62 min (analysis condition D)

Example 498

Compound G-20

8-Chloro-3-(5-chloro-2-ethanesulfonyl-benzyl)-7-
((S)-3-methylamino-piperidin-1-ylmethyl)-6-trifluo-
romethoxy-1H-quinazoline-2,4-dione

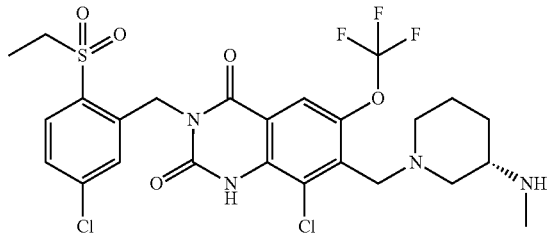 [SMILES: CCS(=O)(=O)c1ccc(Cl)cc1Cn1c(=O)[nH]c2c(Cl)c(CN3CCC[C@H](NC)C3)c(OC(F)(F)F)cc2c1=O]

The title compound was synthesized from 8-chloro-3-(5-chloro-2-ethanesulfonyl-benzyl)-2,4-dioxo-6-trifluoromethoxy-1,2,3,4-tetrahydro-quinazoline-7-carbaldehyde (Compound 38) and methyl-(S)-piperidin-3-yl-carbamic acid tert-butyl ester under the same conditions as for Compounds G-15 and G-16.

LCMS: m/z 623 [M+H]+

HPLC retention time: 0.59 min (analysis condition D)

Example 499

Compound G-21

{(S)-1-[8-Chloro-3-(5-chloro-2-ethanesulfonyl-benzyl)-2,4-dioxo-6-trifluoromethoxy-1,2,3,4-tetrahydro-quinazolin-7-ylmethyl]-pyrrolidin-2-ylmethyl}-carbamic acid tert-butyl ester

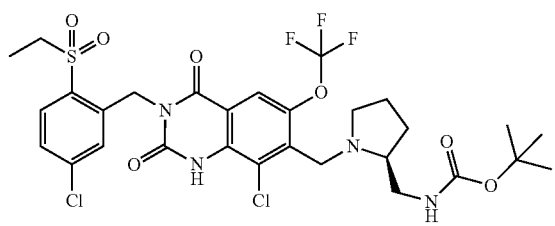 [SMILES: CCS(=O)(=O)c1ccc(Cl)cc1Cn1c(=O)[nH]c2c(Cl)c(CN3CCC[C@H]3CNC(=O)OC(C)(C)C)c(OC(F)(F)F)cc2c1=O]

The title compound was synthesized from 8-chloro-3-(5-chloro-2-ethanesulfonyl-benzyl)-2,4-dioxo-6-trifluoromethoxy-1,2,3,4-tetrahydro-quinazoline-7-carbaldehyde (Compound 38) and (S)-1-pyrrolidin-2-ylmethyl-carbamic acid tert-butyl ester under the same conditions as for Compound b12.

LCMS: m/z 709 [M+H]$^+$

HPLC retention time: 0.68 min (analysis condition D)

Example 500

Compound G-22

7-((S)-2-Aminomethyl-pyrrolidin-1-ylmethyl)-8-chloro-3-(5-chloro-2-ethanesulfonyl-benzyl)-6-trifluoromethoxy-1H-quinazoline-2,4-dione

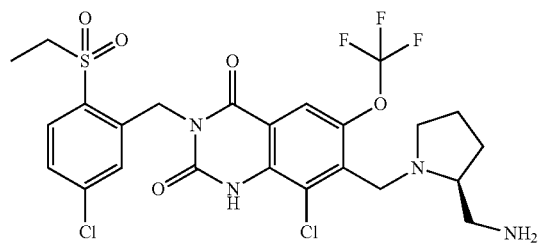 [SMILES: CCS(=O)(=O)c1ccc(Cl)cc1Cn1c(=O)[nH]c2c(Cl)c(CN3CCC[C@H]3CN)c(OC(F)(F)F)cc2c1=O]

The title compound was synthesized from {(S)-1-[8-chloro-3-(5-chloro-2-ethanesulfonyl-benzyl)-2,4-dioxo-6-trifluoromethoxy-1,2,3,4-tetrahydro-quinazolin-7-ylmethyl]-pyrrolidin-2-ylmethyl}-carbamic acid tert-butyl ester (Compound G-21) under the same conditions as for Compound a41.

LCMS: m/z 609 [M+H]$^+$

HPLC retention time: 0.58 min (analysis condition D)

Example 501

Compound G-23

8-Chloro-3-(5-chloro-2-ethanesulfonyl-benzyl)-7-((S)-2-dimethylaminomethyl-pyrrolidin-1-ylmethyl)-6-trifluoromethoxy-1H-quinazoline-2,4-dione

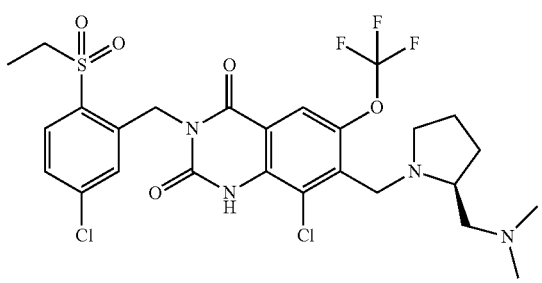 [SMILES: CCS(=O)(=O)c1ccc(Cl)cc1Cn1c(=O)[nH]c2c(Cl)c(CN3CCC[C@H]3CN(C)C)c(OC(F)(F)F)cc2c1=O]

The title compound was synthesized from 7-((S)-2-aminomethyl-pyrrolidin-1-ylmethyl)-8-chloro-3-(5-chloro-2-ethanesulfonyl-benzyl)-6-trifluoromethoxy-1H-quinazoline-2,4-dione (Compound G-22) under the same conditions as for Compound B-9.

LCMS: m/z 637 [M+H]$^+$

HPLC retention time: 0.59 min (analysis condition D)

Example 502

Compound G-24

N-{(S)-1-[8-Chloro-3-(5-chloro-2-ethanesulfonyl-benzyl)-2,4-dioxo-6-trifluoromethoxy-1,2,3,4-tetrahydro-quinazolin-7-ylmethyl]-pyrrolidin-2-ylmethyl}-acetamide

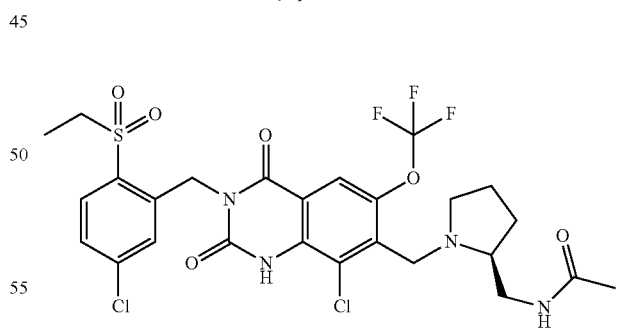

The title compound was synthesized from 7-((S)-2-aminomethyl-pyrrolidin-1-ylmethyl)-8-chloro-3-(5-chloro-2-ethanesulfonyl-benzyl)-6-trifluoromethoxy-1H-quinazoline-2,4-dione (Compound G-22) under the same conditions as for Compound B-18.

LCMS: m/z 651 [M+H]$^+$

HPLC retention time: 0.53 min (analysis condition D)

Example 503

Compound G-25

N-{(S)-1-[8-Chloro-3-(5-chloro-2-ethanesulfonyl-benzyl)-2,4-dioxo-6-trifluoromethoxy-1,2,3,4-tetra-hydro-quinazolin-7-ylmethyl]-pyrrolidin-2-ylmethyl}-methanesulfonamide

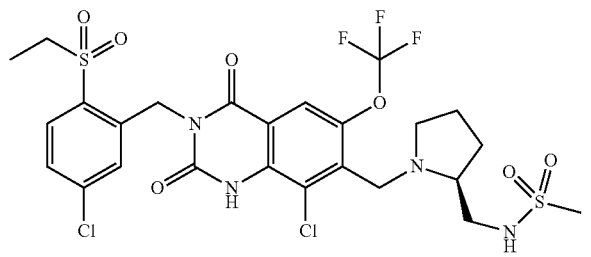 [SMILES: CCS(=O)(=O)c1ccc(Cl)cc1Cn1c(=O)[nH]c2c(Cl)c(CN3CCC[C@H]3CNS(C)(=O)=O)c(OC(F)(F)F)cc2c1=O]

The title compound was synthesized from 7-((S)-2-aminomethyl-pyrrolidin-1-ylmethyl)-8-chloro-3-(5-chloro-2-ethanesulfonyl-benzyl)-6-trifluoromethoxy-1H-quinazoline-2,4-dione (Compound G-22) under the same conditions as for Compound C-6. However, the reaction was performed using TEA in place of DIPEA.

LCMS: m/z 687 [M+H]$^+$

HPLC retention time: 0.57 min (analysis condition D)

Example 504

Compound G-26

{(S)-1-[8-Chloro-3-(5-chloro-2-ethanesulfonyl-benzyl)-2,4-dioxo-6-trifluoromethoxy-1,2,3,4-tetra-hydro-quinazolin-7-ylmethyl]-pyrrolidin-2-ylmethyl}-methyl-carbamic acid tert-butyl ester

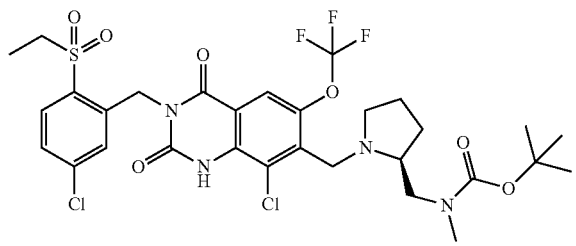 [SMILES: CCS(=O)(=O)c1ccc(Cl)cc1Cn1c(=O)[nH]c2c(Cl)c(CN3CCC[C@H]3CN(C)C(=O)OC(C)(C)C)c(OC(F)(F)F)cc2c1=O]

The title compound was synthesized from 8-chloro-3-(5-chloro-2-ethanesulfonyl-benzyl)-2,4-dioxo-6-trifluoromethoxy-1,2,3,4-tetrahydro-quinazoline-7-carbaldehyde (Compound 38) and methyl-(S)-1-pyrrolidin-2-ylmethyl-carbamic acid tert-butyl ester under the same conditions as for Compound b12. However, the reaction was performed using DCM in place of THF.

LCMS: m/z 723 [M+H]$^+$

HPLC retention time: 0.71 min (analysis condition D)

Example 505

Compound G-27

8-Chloro-3-(5-chloro-2-ethanesulfonyl-benzyl)-7-((S)-2-methylaminomethyl-pyrrolidin-1-ylmethyl)-6-trifluoromethoxy-1H-quinazoline-2,4-dione

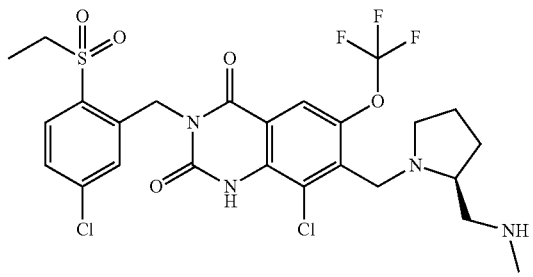 [SMILES: CCS(=O)(=O)c1ccc(Cl)cc1Cn1c(=O)[nH]c2c(Cl)c(CN3CCC[C@H]3CNC)c(OC(F)(F)F)cc2c1=O]

The title compound was synthesized from {(S)-1-[8-chloro-3-(5-chloro-2-ethanesulfonyl-benzyl)-2,4-dioxo-6-trifluoromethoxy-1,2,3,4-tetrahydro-quinazolin-7-ylmethyl]-pyrrolidin-2-ylmethyl}-methyl-carbamic acid tert-butyl ester (Compound G-26) under the same conditions as for Compound a41.

LCMS: m/z 623 [M+H]$^+$

HPLC retention time: 0.58 min (analysis condition D)

Example 506

Compound G-28

7-((R)-2-Aminomethyl-pyrrolidin-1-ylmethyl)-8-chloro-3-(5-chloro-2-ethanesulfonyl-benzyl)-6-trifluoromethoxy-1H-quinazoline-2,4-dione

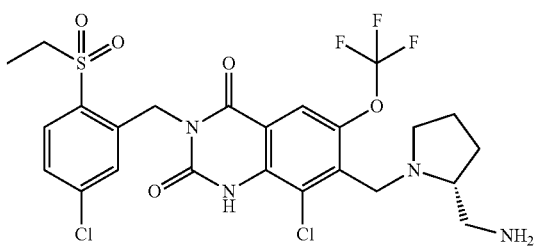 [SMILES: CCS(=O)(=O)c1ccc(Cl)cc1Cn1c(=O)[nH]c2c(Cl)c(CN3CCC[C@@H]3CN)c(OC(F)(F)F)cc2c1=O]

The title compound was synthesized from 8-chloro-3-(5-chloro-2-ethanesulfonyl-benzyl)-2,4-dioxo-6-trifluoromethoxy-1,2,3,4-tetrahydro-quinazoline-7-carbaldehyde (Compound 38) and (R)-1-pyrrolidin-2-ylmethyl-carbamic acid tert-butyl ester under the same conditions as for Compounds G-26 and G-27.

LCMS: m/z 609 [M+H]$^+$

HPLC retention time: 0.58 min (analysis condition D)

Example 507

Compound G-29

8-Chloro-3-(5-chloro-2-ethanesulfonyl-benzyl)-7-((R)-2-dimethylaminomethyl-pyrrolidin-1-ylmethyl)-6-trifluoromethoxy-1H-quinazoline-2,4-dione

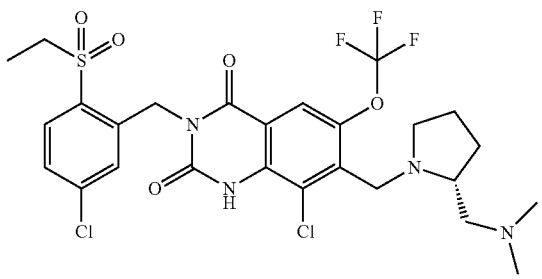 [SMILES: CCS(=O)(=O)c1ccc(Cl)cc1Cn1c(=O)[nH]c2c(Cl)c(CN3CCC[C@@H]3CN(C)C)c(OC(F)(F)F)cc2c1=O]

The title compound was synthesized from 7-((R)-2-aminomethyl-pyrrolidin-1-ylmethyl)-8-chloro-3-(5-chloro-2-ethanesulfonyl-benzyl)-6-trifluoromethoxy-1H-quinazoline-2,4-dione (Compound G-28) under the same conditions as for Compound B-9.

LCMS: m/z 637 [M+H]$^+$

HPLC retention time: 0.59 min (analysis condition D)

Example 508

Compound G-30

N-{(R)-1-[8-Chloro-3-(5-chloro-2-ethanesulfonyl-benzyl)-2,4-dioxo-6-trifluoromethoxy-1,2,3,4-tetrahydro-quinazolin-7-ylmethyl]-pyrrolidin-2-ylmethyl}-acetamide

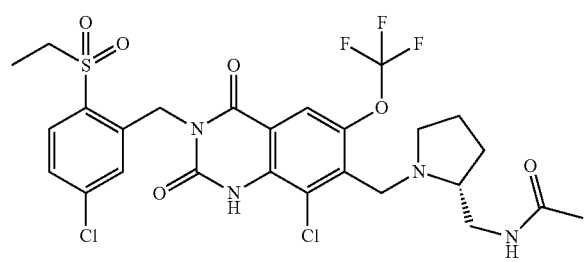 [SMILES: CCS(=O)(=O)c1ccc(Cl)cc1Cn1c(=O)[nH]c2c(Cl)c(CN3CCC[C@@H]3CNC(C)=O)c(OC(F)(F)F)cc2c1=O]

The title compound was synthesized from 7-((R)-2-aminomethyl-pyrrolidin-1-ylmethyl)-8-chloro-3-(5-chloro-2-ethanesulfonyl-benzyl)-6-trifluoromethoxy-1H-quinazoline-2,4-dione (Compound G-28) under the same conditions as for Compound B-18.

LCMS: m/z 651 [M+H]$^+$

HPLC retention time: 0.54 min (analysis condition D)

Example 509

Compound G-31

N-{(R)-1-[8-Chloro-3-(5-chloro-2-ethanesulfonyl-benzyl)-2,4-dioxo-6-trifluoromethoxy-1,2,3,4-tetrahydro-quinazolin-7-ylmethyl]-pyrrolidin-2-ylmethyl}-methanesulfonamide

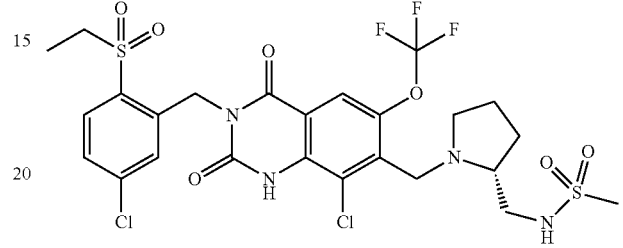

The title compound was synthesized from 7-((R)-2-aminomethyl-pyrrolidin-1-ylmethyl)-8-chloro-3-(5-chloro-2-ethanesulfonyl-benzyl)-6-trifluoromethoxy-1H-quinazoline-2,4-dione (Compound G-28) under the same conditions as for Compound C-6. However, the reaction was performed using TEA in place of DIPEA.

LCMS: m/z 687 [M+H]$^+$

HPLC retention time: 0.56 min (analysis condition D)

Example 510

Compound G-32

8-Chloro-3-(5-chloro-2-ethanesulfonyl-benzyl)-7-((R)-2-methylaminomethyl-pyrrolidin-1-ylmethyl)-6-trifluoromethoxy-1H-quinazoline-2,4-dione

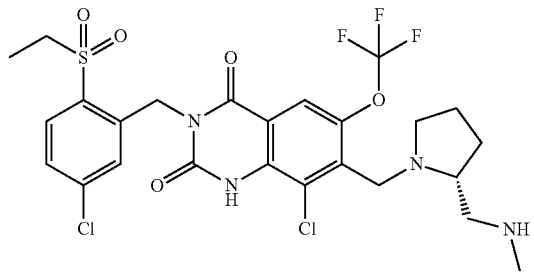 [SMILES: CCS(=O)(=O)c1ccc(Cl)cc1Cn1c(=O)[nH]c2c(Cl)c(CN3CCC[C@@H]3CNC)c(OC(F)(F)F)cc2c1=O]

The title compound was synthesized from 8-chloro-3-(5-chloro-2-ethanesulfonyl-benzyl)-2,4-dioxo-6-trifluoromethoxy-1,2,3,4-tetrahydro-quinazoline-7-carbaldehyde (Compound 38) and methyl-(R)-1-pyrrolidin-2-ylmethyl-carbamic acid tert-butyl ester under the same conditions as for Compounds G-26 and G-27.

LCMS: m/z 623 [M+H]$^+$

HPLC retention time: 0.59 min (analysis condition D)

Example 511

Compound G-33

7-((S)-3-Aminomethyl-pyrrolidin-1-ylmethyl)-8-chloro-3-(5-chloro-2-ethanesulfonyl-benzyl)-6-trifluoromethoxy-1H-quinazoline-2,4-dione

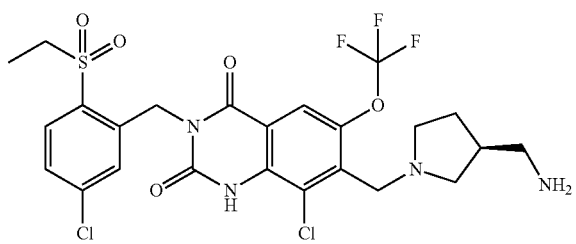 [SMILES: CCS(=O)(=O)c1ccc(Cl)cc1Cn1c(=O)[nH]c2c(Cl)c(CN3CC[C@@H](CN)C3)c(OC(F)(F)F)cc2c1=O]

The title compound was synthesized from 8-chloro-3-(5-chloro-2-ethanesulfonyl-benzyl)-2,4-dioxo-6-trifluoromethoxy-1,2,3,4-tetrahydro-quinazoline-7-carbaldehyde (Compound 38) and (R)-1-pyrrolidin-3-ylmethyl-carbamic acid tert-butyl ester under the same conditions as for Compounds G-15 and G-16.

LCMS: m/z 609 [M+H]$^+$

HPLC retention time: 0.44 min (analysis condition D)

Example 512

Compound G-34

8-Chloro-3-(5-chloro-2-ethanesulfonyl-benzyl)-7-((S)-3-methylaminomethyl-pyrrolidin-1-ylmethyl)-6-trifluoromethoxy-1H-quinazoline-2,4-di one

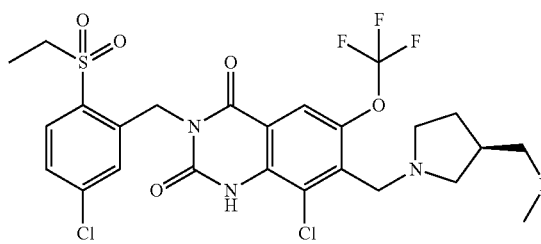

The title compound was synthesized from 8-chloro-3-(5-chloro-2-ethanesulfonyl-benzyl)-2,4-dioxo-6-trifluoromethoxy-1,2,3,4-tetrahydro-quinazoline-7-carbaldehyde (Compound 38) and methyl-(R)-1-pyrrolidin-3-ylmethyl-carbamic acid tert-butyl ester under the same conditions as for Compounds G-15 and G-16.

LCMS: m/z 623 [M+H]$^+$

HPLC retention time: 0.47 min (analysis condition D)

Example 513

Compound g10

(R)-3-[8-Chloro-3-(5-chloro-2-ethanesulfonyl-benzyl)-2,4-dioxo-6-trifluoromethoxy-1,2,3,4-tetrahydro-quinazolin-7-ylmethyl]-5-(2-chloro-ethyl)-2-oxo-imidazolidine-1-carboxylic acid tert-butyl ester

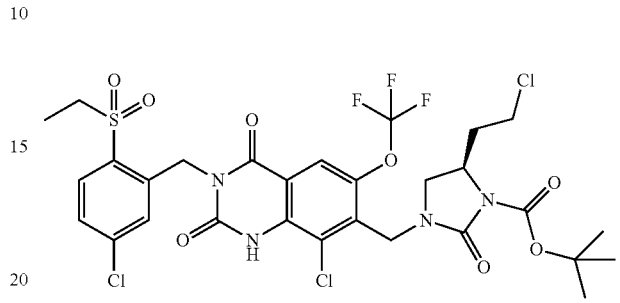

The title compound was obtained as an overreaction product from {(R)-1-[3-amino-2-chloro-4-(5-chloro-2-ethanesulfonyl-benzylcarbamoyl)-6-trifluoromethoxy-benzyl]-pyrrolidin-3-yl}-carbamic acid tert-butyl ester (Compound g8) under the same conditions as for Compound 37.

LCMS: m/z 755 [M−H]$^−$

HPLC retention time: 0.94 min (analysis condition D)

Example 514

Compound g11

(R)-3-[8-Chloro-3-(5-chloro-2-ethanesulfonyl-benzyl)-2,4-dioxo-6-trifluoromethoxy-1,2,3,4-tetrahydro-quinazolin-7-ylmethyl]-5-[2-(2, 4-dimethoxybenzylamino)-ethyl]-2-oxo-imidazolidine-1-carboxylic acid tert-butyl ester

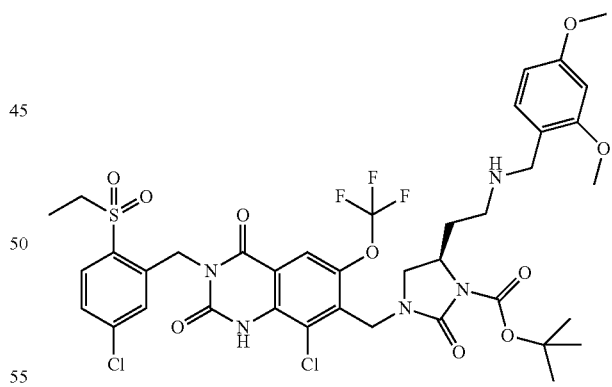

DIPEA (33.9 μl, 0.20 mmol) and 2,4-dimethoxy-benzylamine (29.7 μl, 0.20 mmol) were added to a solution of (R)-3-[8-chloro-3-(5-chloro-2-ethanesulfonyl-benzyl)-2,4-dioxo-6-trifluoromethoxy-1,2,3,4-tetrahydro-quinazolin-7-ylmethyl]-5-(2-chloro-ethyl)-2-oxo-imidazolidine-1-carboxylic acid tert-butyl ester (Compound g10, 50 mg, 0.066 mmol) in acetonitrile (2 ml), and the mixture was stirred under microwave irradiation at 120-130° C. for 5.5 hours. A saturated aqueous ammonium chloride solution was added to the reaction mixture, followed by extraction with ethyl acetate. The organic layer was then washed with brine and dried over anhydrous sodium sulfate. This was concentrated under reduced pressure, and the resulting residue was purified by amino silica gel column chromatography (MeOH/DCM) and further purified by preparative HPLC (water/acetonitrile, 0.05% TFA) to give the title compound (21.8 mg, 37%) as a white powder.

LCMS: m/z 888 [M+H]+

HPLC retention time: 0.68 min (analysis condition D)

Example 515

Compound G-35

7-[(R)-4-(2-Amino-ethyl)-2-oxo-imidazolidin-1-ylmethyl]-8-chloro-3-(5-chloro-2-ethanesulfonyl-benzyl)-6-trifluoromethoxy-1H-quinazoline-2,4-dione

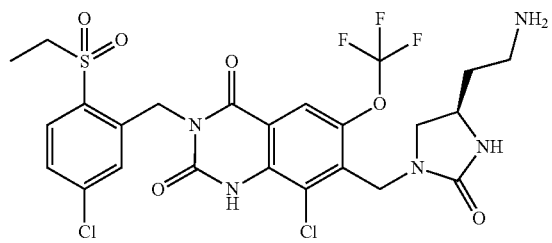 [SMILES: CCS(=O)(=O)c1ccc(Cl)cc1Cn1c(=O)[nH]c2c(Cl)c(CN3C[C@@H](CCN)NC3=O)c(OC(F)(F)F)cc2c1=O]

TFA (1 ml) and N-acetyl-L-cysteine (0.48 mg, 0.0030 mmol) were added to a solution of (R)-3-[8-chloro-3-(5-chloro-2-ethanesulfonyl-benzyl)-2,4-dioxo-6-trifluoromethoxy-1,2,3,4-tetrahydro-quinazolin-7-ylmethyl]-5-[2-(2,4-dimethoxy-benzylamino)-ethyl]-2-oxo-imidazolidine-1-carboxylic acid tert-butyl ester (Compound g11, 10.9 mg, 0.015 mmol) in DCM (1 ml), and the mixture was stirred under microwave irradiation at 100-120° C. for two hours. A saturated aqueous sodium bicarbonate solution was added to the reaction mixture, followed by extraction with ethyl acetate. The organic layer was then washed with brine and dried over anhydrous sodium sulfate. This was purified by preparative HPLC (water/acetonitrile, 0.05% TFA) to give the title compound (2.9 mg, 31%) as a white powder.

LCMS: m/z 638 [M+H]+

HPLC retention time: 0.54 min (analysis condition D)

Example 516

Compound g12

(R)-3-[8-Chloro-3-(5-chloro-2-ethanesulfonyl-benzyl)-2,4-dioxo-6-trifluoromethoxy-1,2,3,4-tetrahydro-quinazolin-7-ylmethyl]-5-{2-[(2,4-dimethoxy-benzyl)-methanesulfonyl-amino]-ethyl}-2-oxo-imidazolidine-1-carboxylic acid tert-butyl ester

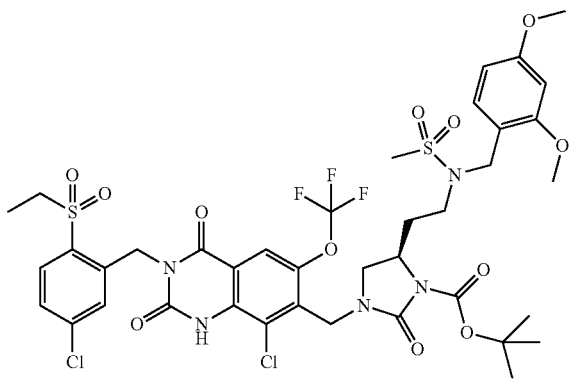 [SMILES: CCS(=O)(=O)c1ccc(Cl)cc1Cn1c(=O)[nH]c2c(Cl)c(CN3C[C@@H](CCN(Cc4ccc(OC)cc4OC)S(C)(=O)=O)N(C(=O)OC(C)(C)C)C3=O)c(OC(F)(F)F)cc2c1=O]

The title compound was synthesized from (R)-3-[8-chloro-3-(5-chloro-2-ethanesulfonyl-benzyl)-2,4-di oxo-6-trifluoromethoxy-1,2,3,4-tetrahydro-quinazolin-7-ylmethyl]-5-[2-(2,4-dimethoxy-benzylamino)-ethyl]-2-oxo-imidazolidine-1-carboxylic acid tert-butyl ester (Compound g11) by adding TEA in place of DIPEA under the same conditions as for Compound C-6. However, the reaction was performed using TEA in place of DIPEA.

Example 517

Compound G-36

N-(2-{(R)-1-[8-Chloro-3-(5-chloro-2-ethanesulfonyl-benzyl)-2,4-dioxo-6-trifluoromethoxy-1,2,3,4-tetrahydro-quinazolin-7-ylmethyl]-2-oxo-imidazolidin-4-yl}-ethyl)-methanesulfonamide

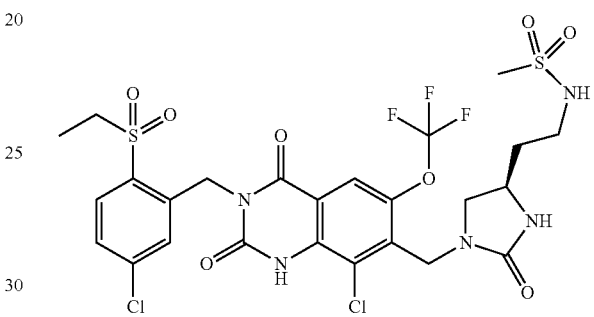

A solution of (R)-3-[8-chloro-3-(5-chloro-2-ethanesulfonyl-benzyl)-2,4-dioxo-6-trifluoromethoxy-1,2,3,4-tetrahydro-quinazolin-7-ylmethyl]-5-{2-[(2,4-dimethoxy-benzyl)-methanesulfonyl-amino]-ethyl}-2-oxo-imidazolidine-1-carboxylic acid tert-butyl ester (Compound g12, 7.9 mg, 0.0085 mmol) in TFA (1.0 ml) was stirred at 60° C. for one hour. This was concentrated under reduced pressure and then dissolved in ethyl acetate. The organic layer was washed with a saturated aqueous sodium bicarbonate solution and brine, and dried over anhydrous sodium sulfate. This was concentrated under reduced pressure, and the resulting residue was purified by amino silica gel column chromatography (dichloromethane/methanol) to give the title compound (5.1 mg, 84%) as a colorless powder.

LCMS: m/z 716 [M+H]+

HPLC retention time: 0.68 min (analysis condition D)

Example 518

Compound h1

2-Amino-4-chloro-3-fluoro-5-trifluoromethyl-benzoic acid ethyl ester

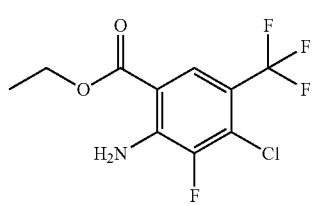 [SMILES: CCOC(=O)c1cc(C(F)(F)F)c(Cl)c(F)c1N]

N-Fluoro-N'-(chloromethyl)triethylenediamine bis(tetrafluoroborate) (1.98 g, 5.3 mmol) was added to a solution of 2-amino-4-chloro-5-trifluoromethyl-benzoic acid ethyl ester (Compound 20, 652 mg, 2.4 mmol) in acetonitrile (13 ml), and the mixture was stirred at room temperature for 43 hours. The reaction mixture was concentrated under reduced pressure, and ethyl acetate was added to the resulting residue. The organic layer was washed with water and brine, and dried over anhydrous sodium sulfate. The drying agent was removed by filtration, and the residue obtained by concentration under reduced pressure was purified by amino silica gel column chromatography (ethyl acetate/hexane) to give the title compound (186 mg, 27%) as a colorless solid.

LCMS: m/z 286 [M+H]$^+$

HPLC retention time: 0.97 min (analysis condition D)

Example 519

Compound h2

4-(3-Amino-4-ethoxycarbonyl-2-fluoro-6-trifluoromethyl-benzyl)-piperazine-1-carboxylic acid tert-butyl ester

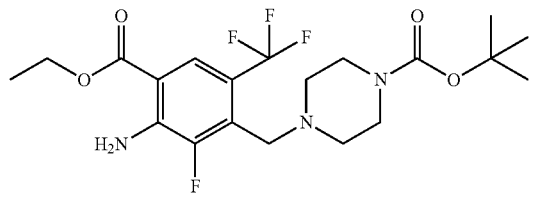

The title compound was synthesized from 2-amino-4-chloro-3-fluoro-5-trifluoromethyl-benzoic acid ethyl ester (Compound h1) under the same conditions as for Compound b1.

Example 520

Compound h3

4-(3-Amino-4-carboxy-2-fluoro-6-trifluoromethyl-benzyl)-piperazine-1-carboxylic acid tert-butyl ester

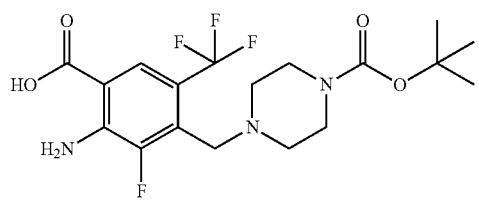 [SMILES: CC(C)(C)OC(=O)N1CCN(Cc2c(C(F)(F)F)cc(C(=O)O)c(N)c2F)CC1]

The title compound was synthesized from 4-(3-amino-4-ethoxycarbonyl-2-fluoro-6-trifluoromethyl-benzyl)-piperazine-1-carboxylic acid tert-butyl ester (Compound h2) under the same conditions as for Compound 25.

Example 521

Compound h4

4-[3-Amino-4-(5-chloro-2-ethanesulfonyl-benzylcarbamoyl)-2-fluoro-6-trifluoromethyl-benzyl]-piperazine-1-carboxylic acid tert-butyl ester

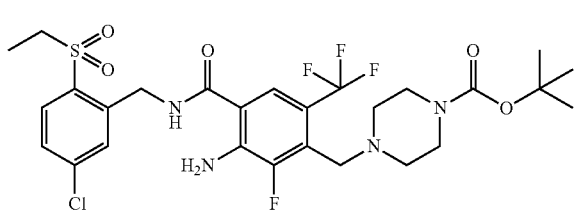 [SMILES: CCS(=O)(=O)c1ccc(Cl)cc1CNC(=O)c1cc(C(F)(F)F)c(CN2CCN(C(=O)OC(C)(C)C)CC2)c(F)c1N]

The title compound was synthesized from 4-(3-amino-4-carboxy-2-fluoro-6-trifluoromethyl-benzyl)-piperazine-1-carboxylic acid tert-butyl ester (Compound h3) under the same conditions as for Compound 26. However, the reaction was performed without using HOBT.

Example 522

Compound h5

4-[3-(5-Chloro-2-ethanesulfonyl-benzyl)-8-fluoro-2,4-dioxo-6-trifluoromethyl-1,2,3,4-tetrahydro-quinazolin-7-ylmethyl]-piperazine-1-carboxylic acid tert-butyl ester

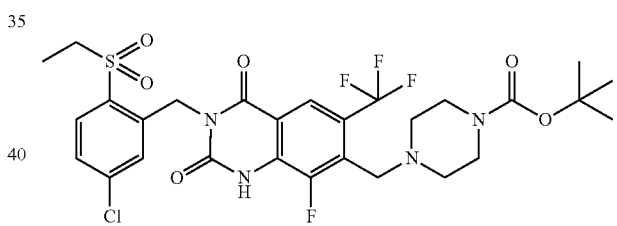

The title compound was synthesized from 4-[3-amino-4-(5-chloro-2-ethanesulfonyl-benzylcarbamoyl)-2-fluoro-6-trifluoromethyl-benzyl]-piperazine-1-carboxylic acid tert-butyl ester (Compound h4) under the same conditions as for Compound 37.

Example 523

Compound H-1

3-(5-Chloro-2-ethanesulfonyl-benzyl)-8-fluoro-7-piperazin-1-ylmethyl-6-trifluoromethyl-1H-quinazoline-2,4-dione

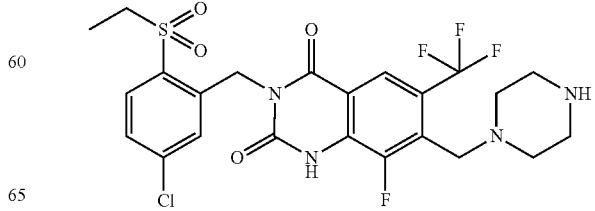

283

The title compound was synthesized from 4-[3-(5-chloro-2-ethanesulfonyl-benzyl)-8-fluoro-2,4-dioxo-6-trifluoromethyl-1,2,3,4-tetrahydro-quinazolin-7-ylmethyl]-piperazine-1-carboxylic acid tert-butyl ester (Compound h5) under the same conditions as for Compound B-1.

LCMS: m/z 563 [M+H]$^+$

HPLC retention time: 1.48 min (analysis condition C)

Example 524

Compound H-2

3-(5-Chloro-2-ethanesulfonyl-benzyl)-8-fluoro-7-(4-methyl-piperazin-1-ylmethyl)-6-trifluoromethyl-1H-quinazoline-2,4-dione

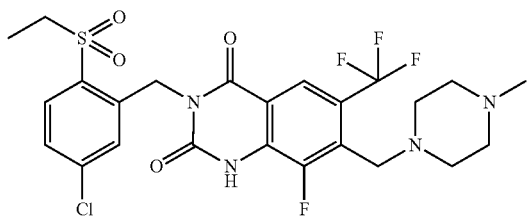 [SMILES: CCS(=O)(=O)c1ccc(Cl)cc1Cn1c(=O)[nH]c2c(F)c(CN3CCN(C)CC3)c(C(F)(F)F)cc2c1=O]

The title compound was synthesized from 3-(5-chloro-2-ethanesulfonyl-benzyl)-8-fluoro-7-piperazin-1-ylmethyl-6-trifluoromethyl-1H-quinazoline-2,4-dione (Compound H-1) under the same conditions as for Compound B-9.

LCMS: m/z 577 [M+H]$^+$

HPLC retention time: 0.52 min (analysis condition D)

Example 525

Compound h6

2-Amino-3-bromo-4-formyl-5-trifluoromethyl-benzoic acid ethyl ester

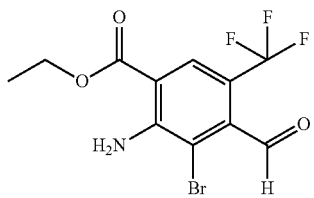 [SMILES: CCOC(=O)c1cc(C(F)(F)F)c(C=O)c(Br)c1N]

The title compound was synthesized from 2-amino-4-formyl-5-trifluoromethyl-benzoic acid ethyl ester (Compound 23) under the same conditions as for Compound 24. However, the reaction was performed using NBS in place of NCS.

284

Example 526

Compound h7

4-(3-Amino-2-bromo-4-ethoxycarbonyl-6-trifluoromethyl-benzyl)-piperazine-1-carboxylic acid tert-butyl ester

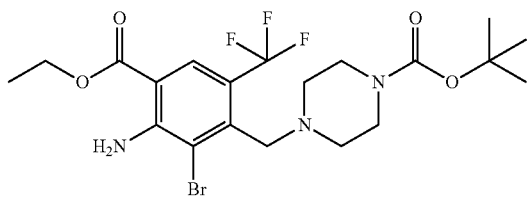

The title compound was synthesized from 2-amino-3-bromo-4-formyl-5-trifluoromethyl-benzoic acid ethyl ester (Compound h6) and piperazine-1-carboxylic acid tert-butyl ester under the same conditions as for Compound b12.

Example 527

Compound h8

4-(3-Amino-2-bromo-4-carboxy-6-trifluoromethyl-benzyl)-piperazine-1-carboxylic acid tert-butyl ester

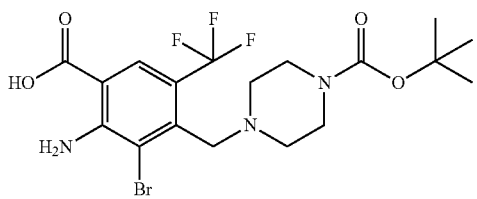 [SMILES: CC(C)(C)OC(=O)N1CCN(Cc2c(C(F)(F)F)cc(C(=O)O)c(N)c2Br)CC1]

The title compound was synthesized from 4-(3-amino-2-bromo-4-ethoxycarbonyl-6-trifluoromethyl-benzyl)-piperazine-1-carboxylic acid tert-butyl ester (Compound h7) under the same conditions as for Compound 25.

Example 528

Compound h9

4-[3-Amino-2-bromo-4-(5-chloro-2-ethanesulfonyl-benzylcarbamoyl)-6-trifluoromethyl-benzyl]-piperazine-1-carboxylic acid tert-butyl ester

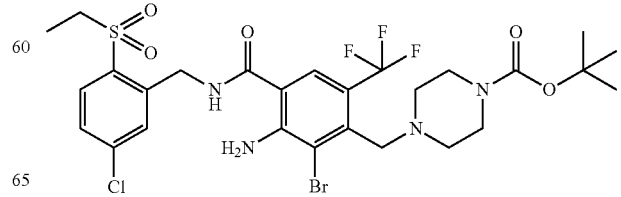

285

The title compound was synthesized from amino-2-bromo-4-carboxy-6-trifluoromethyl-benzyl)-piperazine-1-carboxylic acid tert-butyl ester (Compound h8) under the same conditions as for Compound 26.

Example 529

Compound h10

4-[8-Bromo-3-(5-chloro-2-ethanesulfonyl-benzyl)-2,4-dioxo-6-trifluoromethyl-1,2,34-tetrahydro-quinazolin-7-ylmethyl]-piperazine-1-carboxylic acid tert-butyl ester

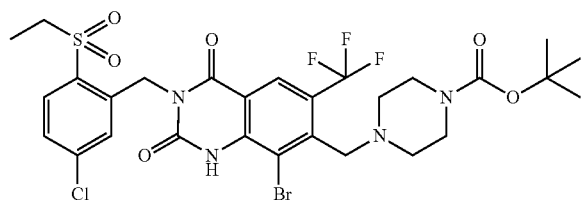 [SMILES: CCS(=O)(=O)c1ccc(Cl)cc1Cn1c(=O)[nH]c2c(Br)c(CN3CCN(C(=O)OC(C)(C)C)CC3)c(C(F)(F)F)cc2c1=O]

The title compound was synthesized from 4-[3-amino-2-bromo-4-(5-chloro-2-ethanesulfonyl-benzylcarbamoyl)-6-trifluoromethyl-benzyl]-piperazine-1-carboxylic acid tert-butyl ester (Compound h9) under the same conditions as for Compound 37.

Example 530

Compound H-3

8-Bromo-3-(5-chloro-2-ethanesulfonyl-benzyl)-7-piperazin-1-ylmethyl-6-trifluoromethyl-1H-quinazoline-2,4-dione

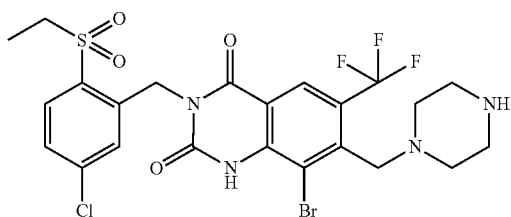

The title compound was synthesized from 4-[8-bromo-3-(5-chloro-2-ethanesulfonyl-benzyl)-2,4-dioxo-6-trifluoromethyl-1,2,3,4-tetrahydro-quinazolin-7-ylmethyl]-piperazine-1-carboxylic acid tert-butyl ester (Compound h10) under the same conditions as for Compound a41.
LCMS: m/z 623 [M+H]$^+$
HPLC retention time: 0.57 min (analysis condition D)

286

Example 531

Compound H-4

8-Bromo-3-(5-chloro-2-ethanesulfonyl-benzyl)-7-(4-methyl-piperazin-1-ylmethyl)-6-trifluoromethyl-1H-quinazoline-2,4-dione

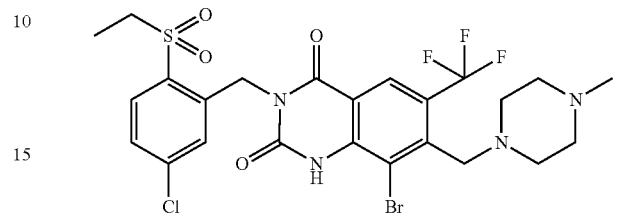

The title compound was synthesized from 8-bromo-3-(5-chloro-2-ethanesulfonyl-benzyl)-7-piperazin-1-ylmethyl-6-trifluoromethyl-1H-quinazoline-2,4-dione (Compound H-3) under the same conditions as for Compound B-9.
LCMS: m/z 637 [M+H]$^+$
HPLC retention time: 0.57 min (analysis condition D)

Example 532

Compound h11

2-Amino-3-bromo-4-[(R)-3-(tert-butoxycarbonyl-methyl-amino)-pyrrolidin-1-ylmethyl]-5-trifluoromethyl-benzoic acid ethyl ester

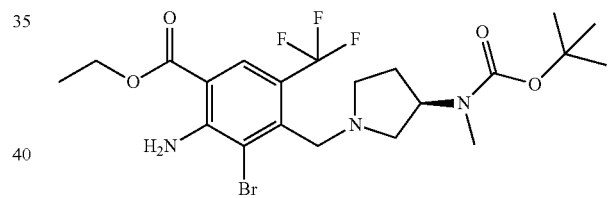

The title compound was synthesized from 2-amino-3-bromo-4-formyl-5-trifluoromethyl-benzoic acid ethyl ester (Compound h6) and methyl-(R)-pyrrolidin-3-yl-carbamic acid tert-butyl ester under the same conditions as for Compound b12. However, the reaction was performed using DCM in place of THF as a solvent.

Example 533

Compound H-5

8-Bromo-3-(5-chloro-2-ethanesulfonyl-benzyl)-7-((R)-3-methylamino-pyrrolidin-1-ylmethyl)-6-trifluoromethyl-1H-quinazoline-2,4-dione

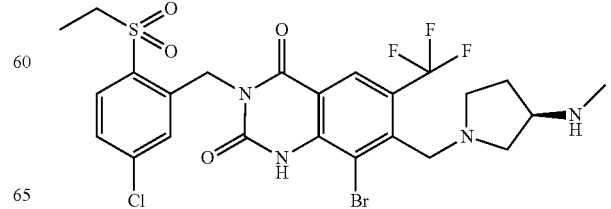

The title compound was synthesized from 2-amino-3-bromo-4-[(R)-3-(tert-butoxycarbonyl-methyl-amino)-pyrrolidin-1-ylmethyl]-5-trifluoromethyl-benzoic acid ethyl ester (Compound h11) under the same conditions as for Compounds h8, h9, h10, and H-3.

LCMS: m/z 637 [M+H]+

HPLC retention time: 0.58 min (analysis condition D)

Example 534

Compound H-6

7-((R)-3-Amino-pyrrolidin-1-ylmethyl)-8-bromo-3-(5-chloro-2-ethanesulfonyl-benzyl)-6-trifluoromethyl-1H-quinazoline-2,4-dione

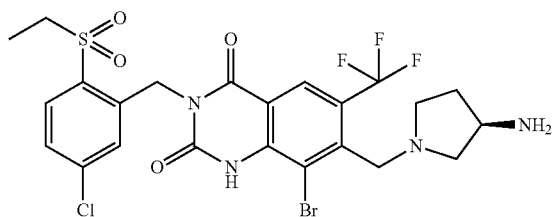 [SMILES: CCS(=O)(=O)c1ccc(Cl)cc1Cn1c(=O)[nH]c2c(Br)c(CN3CC[C@@H](N)C3)c(C(F)(F)F)cc2c1=O]

The title compound was synthesized from 2-amino-3-bromo-4-formyl-5-trifluoromethyl-benzoic acid ethyl ester (Compound h6) under the same conditions as for Compounds h7, h8, h9, h10, and H-3. However, the reaction was performed using (R)-pyrrolidin-3-yl-carbamic acid tert-butyl ester in place of piperazine-1-carboxylic acid tert-butyl ester under the conditions for Compound h7.

LCMS: m/z 623 [M+H]+

HPLC retention time: 0.52 min (analysis condition D)

Example 535

Compound H-7

8-Bromo-3-(5-chloro-2-ethanesulfonyl-benzyl)-7-((R)-3-dimethylamino-pyrrolidin-1-ylmethyl)-6-trifluoromethyl-1H-quinazoline-2,4-dione

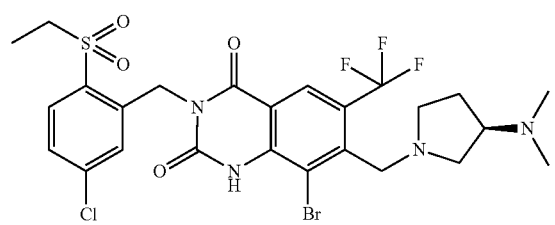 [SMILES: CCS(=O)(=O)c1ccc(Cl)cc1Cn1c(=O)[nH]c2c(Br)c(CN3CC[C@@H](N(C)C)C3)c(C(F)(F)F)cc2c1=O]

The title compound was synthesized from 7-((R)-3-amino-pyrrolidin-1-ylmethyl)-8-bromo-3-(5-chloro-2-ethanesulfonyl-benzyl)-6-trifluoromethyl-1H-quinazoline-2,4-dione (Compound H-6) under the same conditions as for Compound B-9.

LCMS: m/z 651 [M+H]+

HPLC retention time: 0.58 min (analysis condition D)

Example 536

Compound H-8

N-{(R)-1-[8-Bromo-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-methanesulfonamide

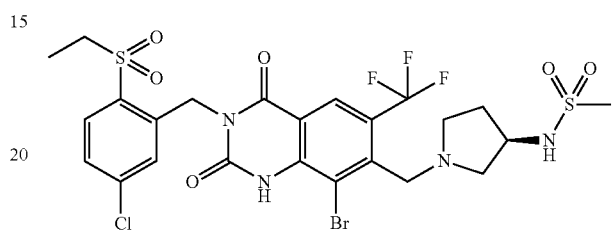

The title compound was synthesized from 7-((R)-3-amino-pyrrolidin-1-ylmethyl)-8-bromo-3-(5-chloro-2-ethanesulfonyl-benzyl)-6-trifluoromethyl-1H-quinazoline-2,4-dione (Compound H-6) under the same conditions as for Compound B-7. However, the reaction was performed using TEA in place of pyridine.

LCMS: m/z 701 [M+H]+

HPLC retention time: 0.61 min (analysis condition D)

Example 537

Compound H-9

N-{(R)-1-[8-Bromo-3-(5-chloro-2-ethanesulfonyl-benzyl)-2,4-dioxo-6-trifluoromethyl-1,2,3,4-tetrahydro-quinazolin-7-ylmethyl]-pyrrolidin-3-yl}-acetamide

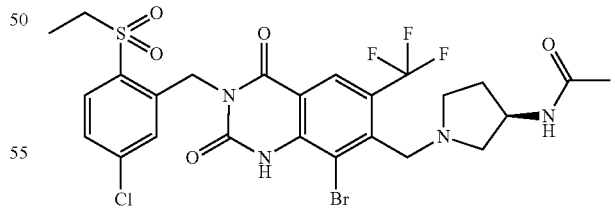

The title compound was synthesized from 7-((R)-3-amino-pyrrolidin-1-ylmethyl)-8-bromo-3-(5-chloro-2-ethanesulfonyl-benzyl)-6-trifluoromethyl-1H-quinazoline-2,4-dione (Compound H-6) under the same conditions as for Compound B-18. However, the reaction was performed using DCM in place of DMF.

LCMS: m/z 665 [M+H]+

HPLC retention time: 0.53 min (analysis condition D)

Example 538

Compound h12

8-Bromo-3-(5-chloro-2-ethanesulfonyl-benzyl)-2,4-dioxo-6-trifluoromethyl-1,2,3,4-tetrahydro-quinazoline-7-carbaldehyde

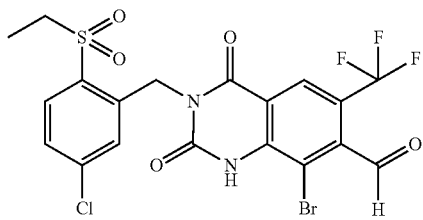 [SMILES: CCS(=O)(=O)c1ccc(Cl)cc1Cn1c(=O)[nH]c2c(Br)c(C=O)c(C(F)(F)F)cc2c1=O]

The title compound was synthesized from 2-amino-3-bromo-4-formyl-5-trifluoromethyl-benzoic acid ethyl ester (Compound h6) under the same conditions as for Compounds h8, h9, and h10.

Example 539

Compound h13

{(S)-1-[8-Bromo-3-(5-chloro-2-ethanesulfonyl-benzyl)-2,4-dioxo-6-trifluoromethyl-1,2,3,4-tetrahydro-quinazolin-7-ylmethyl]-pyrrolidin-3-ylmethyl}-carbamic acid tert-butyl ester

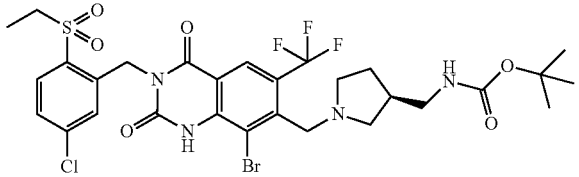 [SMILES: CCS(=O)(=O)c1ccc(Cl)cc1Cn1c(=O)[nH]c2c(Br)c(CN3CC[C@@H](CNC(=O)OC(C)(C)C)C3)c(C(F)(F)F)cc2c1=O]

The title compound was synthesized from 8-bromo-3-(5-chloro-2-ethanesulfonyl-benzyl)-2,4-dioxo-6-trifluoromethyl-1,2,3,4-tetrahydro-quinazoline-7-carbaldehyde (Compound h12) and (R)-1-pyrrolidin-3-ylmethyl-carbamic acid tert-butyl ester under the same conditions as for Compound b12. However, the reaction was performed using DCM in place of THF.

Example 540

Compound H-10

7-((S)-3-Aminomethyl-pyrrolidin-1-ylmethyl)-8-bromo-3-(5-chloro-2-ethanesulfonyl-benzyl)-6-trifluoromethyl-1H-quinazoline-2,4-dione

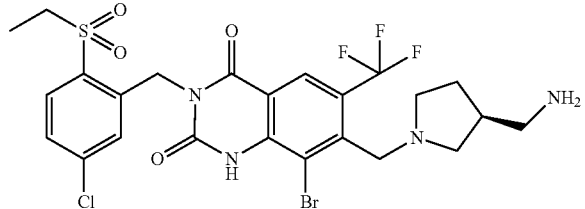 [SMILES: CCS(=O)(=O)c1ccc(Cl)cc1Cn1c(=O)[nH]c2c(Br)c(CN3CC[C@@H](CN)C3)c(C(F)(F)F)cc2c1=O]

The title compound was synthesized from {(S)-1-[8-bromo-3-(5-chloro-2-ethanesulfonyl-benzyl)-2,4-dioxo-6-trifluoromethyl-1,2,3,4-tetrahydro-quinazolin-7-ylmethyl]-pyrrolidin-3-ylmethyl}-carbamic acid tert-butyl ester (Compound h13) under the same conditions as for Compound a41.

LCMS: m/z 637 [M+H]$^+$
HPLC retention time: 0.43 min (analysis condition D)

Example 541

Compound H-11

7-((S)-3-Amino-piperidin-1-ylmethyl)-8-bromo-3-(5-chloro-2-ethanesulfonyl-benzyl)-6-trifluoromethyl-1H-quinazoline-2,4-dione

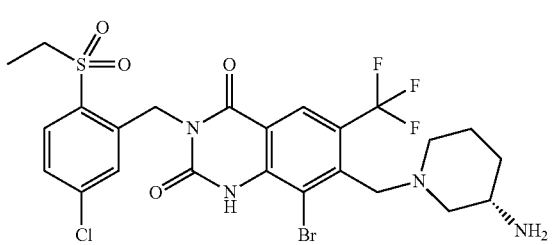 [SMILES: CCS(=O)(=O)c1ccc(Cl)cc1Cn1c(=O)[nH]c2c(Br)c(CN3CCC[C@H](N)C3)c(C(F)(F)F)cc2c1=O]

The title compound was synthesized from 8-bromo-3-(5-chloro-2-ethanesulfonyl-benzyl)-2,4-dioxo-6-trifluoromethyl-1,2,3,4-tetrahydro-quinazoline-7-carbaldehyde (Compound h12) under the same conditions as for Compounds h13 and H-10. However, the reaction was performed using (S)-piperidin-3-yl-carbamic acid tert-butyl ester in place of (R)-1-pyrrolidin-3-ylmethyl-carbamic acid tert-butyl ester under the conditions for Compound h13.

LCMS: m/z 637 [M+H]$^+$
HPLC retention time: 0.59 min (analysis condition D)

Example 542

Compound H-12

8-Bromo-3-(5-chloro-2-ethanesulfonyl-benzyl)-7-((S)-3-methylamino-piperidin-1-ylmethyl)-6-trifluoromethyl-1H-quinazoline-2,4-dione

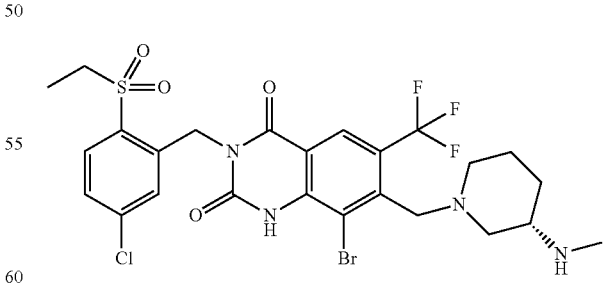

The title compound was synthesized from 8-bromo-3-(5-chloro-2-ethanesulfonyl-benzyl)-2,4-dioxo-6-trifluoromethyl-1,2,3,4-tetrahydro-quinazoline-7-carbaldehyde (Compound h12) under the same conditions as for Compounds h13 and H-10. However, the reaction was performed using methyl-(S)-piperidin-3-yl-carbamic acid tert-butyl ester in place of (R)-1-pyrrolidin-3-ylmethyl-carbamic acid tert-butyl ester under the conditions for Compound h13.
LCMS: m/z 651 [M+H]+
HPLC retention time: 0.61 min (analysis condition D)

Example 543

Compound h14

2-Amino-4-bromo-5-trifluoromethoxy-benzoic acid ethyl ester

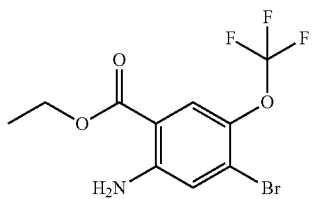

The title compound was synthesized from 4-bromo-2-nitro-5-trifluoromethoxy-benzoic acid ethyl ester (Compound 28) under the same conditions as for Compound 30. However, the reaction was performed at 90° C. using iron in place of zinc.

Example 544

Compound h15

2-Amino-4-bromo-3-fluoro-5-trifluoromethoxy-benzoic acid ethyl ester

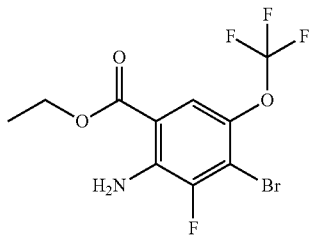 [SMILES: CCOC(=O)c1cc(OC(F)(F)F)c(Br)c(F)c1N]

The title compound was synthesized from 2-amino-4-bromo-5-trifluoromethoxy-benzoic acid ethyl ester (Compound h14) under the same conditions as for Compound h1.

Example 545

Compound h16

4-(3-Amino-4-ethoxycarbonyl-2-fluoro-6-trifluoromethoxy-benzyl)-piperazine-1-carboxylic acid tert-butyl ester

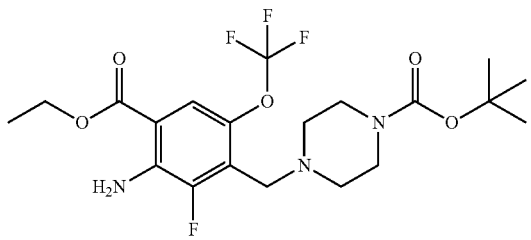 [SMILES: CCOC(=O)c1cc(OC(F)(F)F)c(CN2CCN(C(=O)OC(C)(C)C)CC2)c(F)c1N]

The title compound was synthesized from 2-amino-4-bromo-3-fluoro-5-trifluoromethoxy-benzoic acid ethyl ester (Compound h15) under the same conditions as for Compound b1.

Example 546

Compound h17

4-[3-(5-Chloro-2-ethanesulfonyl-benzyl)-8-fluoro-2,4-dioxo-6-trifluoromethoxy-1,2,3,4-tetrahydro-quinazolin-7-ylmethyl]-piperazine-1-carboxylic acid tert-butyl ester

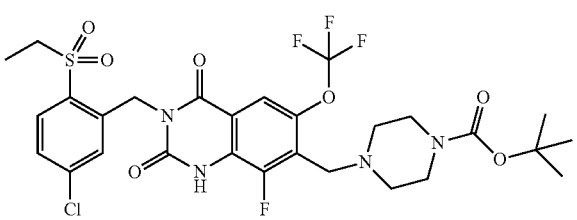 [SMILES: CCS(=O)(=O)c1ccc(Cl)cc1Cn1c(=O)[nH]c2c(F)c(CN3CCN(C(=O)OC(C)(C)C)CC3)c(OC(F)(F)F)cc2c1=O]

The title compound was synthesized from 4-(3-amino-4-ethoxycarbonyl-2-fluoro-6-trifluoromethoxy-benzyl)-piperazine-1-carboxylic acid tert-butyl ester (Compound h16) under the same conditions as for Compounds h8, h9, and h10.

Example 547

Compound H-13

3-(5-Chloro-2-ethanesulfonyl-benzyl)-8-fluoro-7-piperazin-1-ylmethyl-6-trifluoromethoxy-1H-quinazoline-2,4-dione

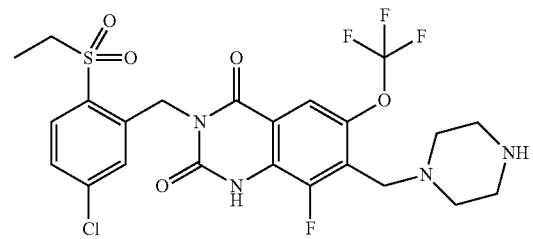 [SMILES: CCS(=O)(=O)c1ccc(Cl)cc1Cn1c(=O)[nH]c2c(F)c(CN3CCNCC3)c(OC(F)(F)F)cc2c1=O]

The title compound was synthesized from 4-[3-(5-chloro-2-ethanesulfonyl-benzyl)-8-fluoro-2,4-dioxo-6-trifluoromethoxy-1,2,3,4-tetrahydro-quinazolin-7-ylmethyl]-piperazine-1-carboxylic acid tert-butyl ester (Compound h17) under the same conditions as for Compound B-1.
LCMS: m/z 579 [M+H]+
HPLC retention time: 0.54 min (analysis condition D)

Example 548

Compound H-14

3-(5-Chloro-2-ethanesulfonyl-benzyl)-8-fluoro-7-(4-methyl-piperazin-1-ylmethyl)-6-trifluoromethoxy-1H-quinazoline-2,4-dione

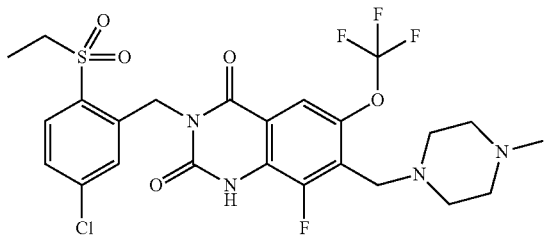 [SMILES: CCS(=O)(=O)c1ccc(Cl)cc1Cn1c(=O)[nH]c2c(F)c(CN3CCN(C)CC3)c(OC(F)(F)F)cc2c1=O]

The title compound was synthesized from 3-(5-chloro-2-ethanesulfonyl-benzyl)-8-fluoro-7-piperazin-1-ylmethyl-6-trifluoromethoxy-1H-quinazoline-2,4-dione (Compound H-13) under the same conditions as for Compound B-9.
LCMS: m/z 593 [M+H]$^+$
HPLC retention time: 0.55 min (analysis condition D)

Example 549

Compound h18

2-Amino-3-bromo-4-formyl-5-trifluoromethoxy-benzoic acid ethyl ester

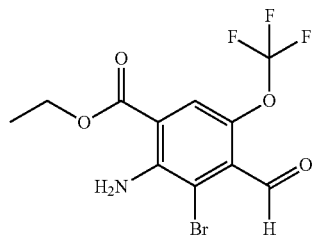 [SMILES: CCOC(=O)c1cc(OC(F)(F)F)c(C=O)c(Br)c1N]

The title compound was synthesized from 2-amino-4-formyl-5-trifluoromethoxy-benzoic acid ethyl ester (Compound 32) under the same conditions as for Compound 24. However, the reaction was performed using NBS in place of NCS.

Example 550

Compound h19

2-Amino-3-bromo-4-[(R)-3-(tert-butoxycarbonyl-methyl-amino)-pyrrolidin-1-ylmethyl]-5-trifluoromethoxy-benzoic acid ethyl ester

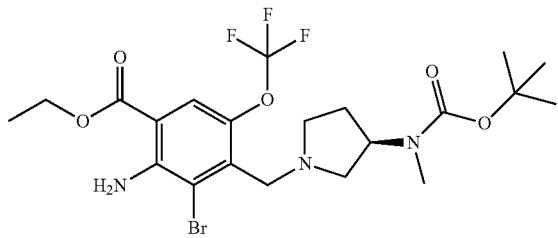 [SMILES: CCOC(=O)c1cc(OC(F)(F)F)c(CN2CC[C@@H](N(C)C(=O)OC(C)(C)C)C2)c(Br)c1N]

The title compound was synthesized from 2-amino-3-bromo-4-formyl-5-trifluoromethoxy-benzoic acid ethyl ester (Compound h18) under the same conditions as for Compound b12. However, the reaction was performed using DCM in place of THF as a solvent and using methyl-(R)-pyrrolidin-3-yl-carbamic acid tert-butyl ester in place of (S)-pyrrolidin-3-yl-carbamic acid tert-butyl ester.

Example 551

Compound H-15

8-Bromo-3-(5-chloro-2-ethanesulfonyl-benzyl)-7-((R)-3-methylamino-pyrrolidin-1-ylmethyl)-6-trifluoromethoxy-1H-quinazoline-2,4-dione

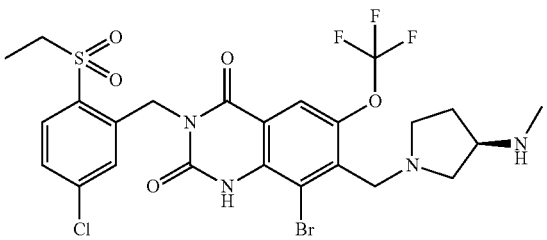 [SMILES: CCS(=O)(=O)c1ccc(Cl)cc1Cn1c(=O)[nH]c2c(Br)c(CN3CC[C@@H](NC)C3)c(OC(F)(F)F)cc2c1=O]

The title compound was synthesized from 2-amino-3-bromo-4-[(R)-3-(tert-butoxycarbonyl-methyl-amino)-pyrrolidin-1-ylmethyl]-5-trifluoromethoxy-benzoic acid ethyl ester (Compound h19) under the same conditions as for Compounds h8, h9, h10, and H-3.
LCMS: m/z 653 [M+H]$^+$
HPLC retention time: 0.55 min (analysis condition D)

Example 552

Compound h20

2-Amino-3-bromo-4-((R)-3-tert-butoxycarbonylamino-pyrrolidin-1-ylmethyl)-5-trifluoromethoxy-benzoic acid ethyl ester

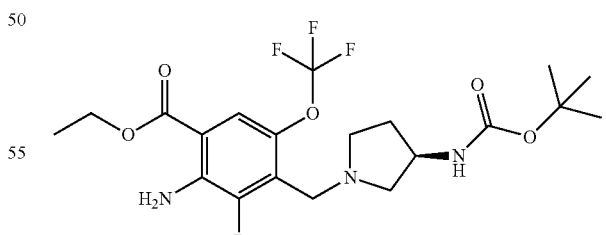

The title compound was synthesized from 2-amino-3-bromo-4-formyl-5-trifluoromethoxy-benzoic acid ethyl ester (Compound h18) under the same conditions as for Compound b12. However, the reaction was performed using DCM in place of THF as a solvent and using (R)-pyrrolidin-3-yl-carbamic acid tert-butyl ester in place of (S)-pyrrolidin-3-yl-carbamic acid tert-butyl ester.

Example 553

Compound H-16

7-((R)-3-Amino-pyrrolidin-1-ylmethyl)-8-bromo-3-(5-chloro-2-ethanesulfonyl-benzyl)-6-trifluoromethoxy-1H-quinazoline-2,4-dione

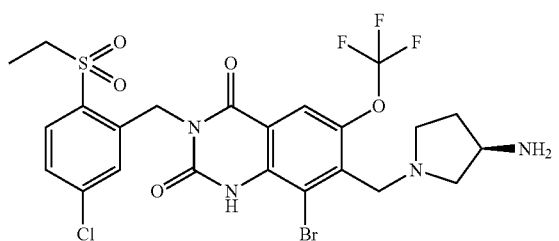 [SMILES: CCS(=O)(=O)c1ccc(Cl)cc1Cn1c(=O)[nH]c2c(Br)c(CN3CC[C@@H](N)C3)c(OC(F)(F)F)cc2c1=O]

The title compound was synthesized from 2-amino-3-bromo-4-((R)-3-tert-butoxycarbonylamino-pyrrolidin-1-ylmethyl)-5-trifluoromethoxy-benzoic acid ethyl ester (Compound h20) under the same conditions as for Compounds h8, h9, h10, and H-3.

LCMS: m/z 639 [M+H]$^+$

HPLC retention time: 0.52 min (analysis condition D)

Example 554

Compound H-17

8-Bromo-3-(5-chloro-2-ethanesulfonyl-benzyl)-7-((R)-3-dimethylamino-pyrrolidin-1-ylmethyl)-6-trifluoromethoxy-1H-quinazoline-2,4-dione

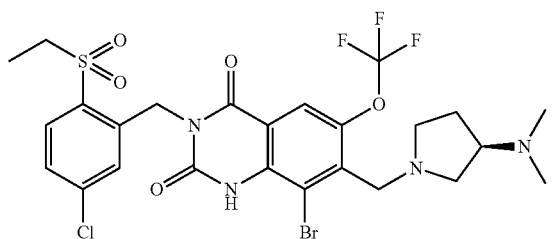 [SMILES: CCS(=O)(=O)c1ccc(Cl)cc1Cn1c(=O)[nH]c2c(Br)c(CN3CC[C@@H](N(C)C)C3)c(OC(F)(F)F)cc2c1=O]

The title compound was synthesized from 7-((R)-3-amino-pyrrolidin-1-ylmethyl)-8-bromo-3-(5-chloro-2-ethanesulfonyl-benzyl)-6-trifluoromethoxy-1H-quinazoline-2,4-dione (Compound H-16) under the same conditions as for Compound B-9.

LCMS: m/z 667 [M+H]$^+$

HPLC retention time: 0.56 min (analysis condition D)

Example 555

Compound H-18

N-{(R)-1-[8-Bromo-3-(5-chloro-2-ethanesulfonyl-benzyl)-2,4-dioxo-6-trifluoromethoxy-1,2,3,4-tetrahydro-quinazolin-7-ylmethyl]-pyrrolidin-3-yl}-acetamide

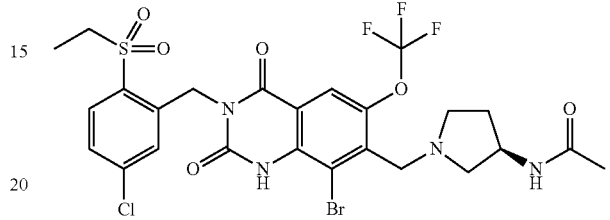

The title compound was synthesized from 7-((R)-3-amino-pyrrolidin-1-ylmethyl)-8-bromo-3-(5-chloro-2-ethanesulfonyl-benzyl)-6-trifluoromethoxy-1H-quinazoline-2,4-dione (Compound H-16) under the same conditions as for Compound B-18. However, the reaction was performed using DCM in place of DMF.

LCMS: m/z 681 [M+H]$^+$

HPLC retention time: 0.53 min (analysis condition D)

Example 556

Compound H-19

N-{(R)-1-[8-Bromo-3-(5-chloro-2-ethanesulfonyl-benzyl)-2,4-dioxo-6-trifluoromethoxy-1,2,3,4-tetrahydro-quinazolin-7-ylmethyl]-pyrrolidin-3-yl}-methanesulfonamide

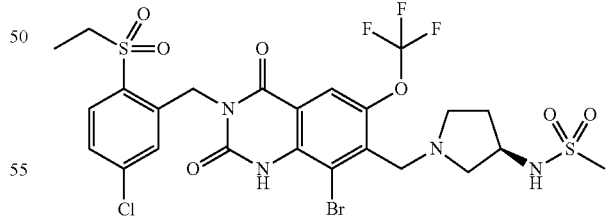

The title compound was synthesized from 7-((R)-3-amino-pyrrolidin-1-ylmethyl)-8-bromo-3-(5-chloro-2-ethanesulfonyl-benzyl)-6-trifluoromethoxy-1H-quinazoline-2,4-dione (Compound H-16) under the same conditions as for Compound B-7. However, the reaction was performed using TEA in place of pyridine.

LCMS: m/z 717 [M+H]$^+$

HPLC retention time: 0.57 min (analysis condition D)

Example 557

Compound i1

2-Amino-3,5-dichloro-4-methyl-benzoic acid ethyl ester

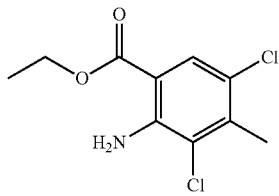

The title compound was synthesized from 2-amino-5-chloro-4-methyl-benzoic acid ethyl ester (Compound 44) under the same conditions as for Compound 24.

Example 558

Compound i2

2-(Bis(tert-butoxycarbonyl)amino)-3,5-dichloro-4-methyl-benzoic acid ethyl ester

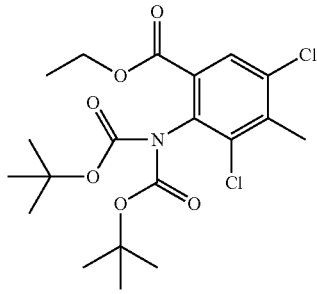 [SMILES: CCOC(=O)c1cc(Cl)c(C)c(Cl)c1N(C(=O)OC(C)(C)C)C(=O)OC(C)(C)C]

The title compound was synthesized from 2-amino-3,5-dichloro-4-methyl-benzoic acid ethyl ester (Compound i1) under the same conditions as for Compound 17. However, the reaction was performed using acetonitrile in place of THF.

Example 559

Compound i3

2-(Bis(tert-butoxycarbonyl)amino)-4-bromomethyl-3,5-dichloro-benzoic acid ethyl ester

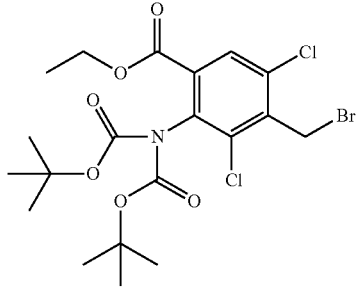 [SMILES: CCOC(=O)c1cc(Cl)c(CBr)c(Cl)c1N(C(=O)OC(C)(C)C)C(=O)OC(C)(C)C]

The title compound was synthesized from 2-(bis(tert-butoxycarbonyl)amino)-3,5-dichloro-4-methyl-benzoic acid ethyl ester (Compound i2) under the same conditions as for Compound 12.

Example 560

Compound i4

4-(3-(Bis(tert-butoxycarbonyl)amino)-2,6-dichloro-4-(ethoxycarbonyl)benzyl)piperazine-1-carboxylic acid tert-butyl ester

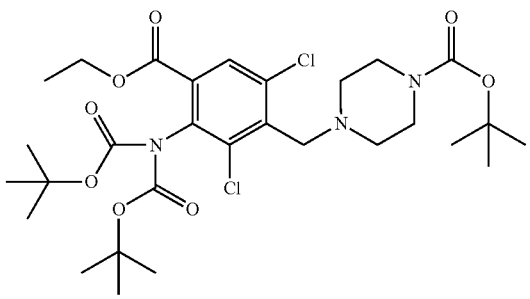 [SMILES: CCOC(=O)c1cc(Cl)c(CN2CCN(C(=O)OC(C)(C)C)CC2)c(Cl)c1N(C(=O)OC(C)(C)C)C(=O)OC(C)(C)C]

The title compound was synthesized from 2-(bis(tert-butoxycarbonyl)amino)-4-bromomethyl-3,5-dichloro-benzoic acid ethyl ester (Compound i3) and piperazine-1-carboxylic acid tert-butyl ester under the same conditions as for Compound d1. However, the reaction was performed by using DCM in place of THF and adding TEA at room temperature.

Example 561

Compound i5

2-Amino-3,5-dichloro-4-piperazin-1-ylmethyl-benzoic acid ethyl ester

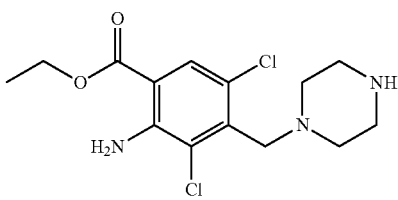 [SMILES: CCOC(=O)c1cc(Cl)c(CN2CCNCC2)c(Cl)c1N]

The title compound was synthesized from 4-(3-(bis(tert-butoxycarbonyl)amino)-2,6-dichloro-4-(ethoxycarbonyl)benzyl)piperazine-1-carboxylic acid tert-butyl ester (Compound i4) under the same conditions as for Compound B-1.

Example 562

Compound i6

4-(3-Amino-2,6-dichloro-4-ethoxycarbonyl-benzyl)-piperazine-1-carboxylic acid tert-butyl ester

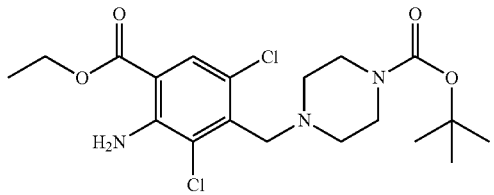 [SMILES: CCOC(=O)c1cc(Cl)c(CN2CCN(C(=O)OC(C)(C)C)CC2)c(Cl)c1N]

The title compound was obtained from 2-amino-3,5-dichloro-4-piperazin-1-ylmethyl-benzoic acid ethyl ester (Compound i5) under the same conditions as for Compound d3.

Example 563

Compound i7

4-(3-Amino-4-carboxy-2, 6-dichloro-benzyl)-piperazine-1-carboxylic acid tert-butyl ester

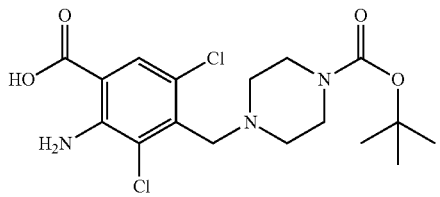

The title compound was obtained from 4-(3-amino-2,6-dichloro-4-ethoxycarbonyl-benzyl)-piperazine-1-carboxylic acid tert-butyl ester (Compound i6) under the same conditions as for Compound 25. However, the reaction was performed using a 6 N aqueous sodium hydroxide solution in place of a 1 N aqueous sodium hydroxide solution.

Example 564

Compound i8

4-[3-Amino-2,6-dichloro-4-(5-chloro-2-ethanesulfonyl-benzylcarbamoyl)-benzyl]-piperazine-1-carboxylic acid tert-butyl ester

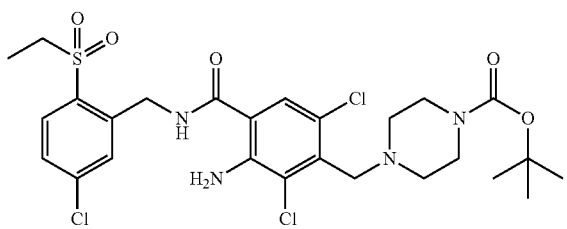 [SMILES: CCS(=O)(=O)c1ccc(Cl)cc1CNC(=O)c1cc(Cl)c(CN2CCN(C(=O)OC(C)(C)C)CC2)c(Cl)c1N]

The title compound was synthesized from 4-(3-amino-4-carboxy-2,6-dichloro-benzyl)-piperazine-1-carboxylic acid tert-butyl ester (Compound i7) under the same conditions as for Compound 26. However, the reaction was performed using DMF in place of DCM.

Example 565

Compound i9

4-[6,8-Dichloro-3-(5-chloro-2-ethanesulfonyl-benzyl)-2,4-dioxo-1,2,3,4-tetrahydro-quinazolin-7-ylmethyl]-piperazine-1-carboxylic acid tert-butyl ester

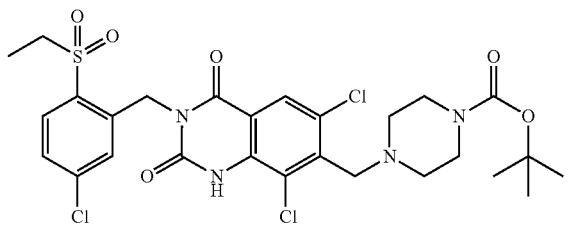 [SMILES: CCS(=O)(=O)c1ccc(Cl)cc1Cn1c(=O)[nH]c2c(Cl)c(CN3CCN(C(=O)OC(C)(C)C)CC3)c(Cl)cc2c1=O]

The title compound was synthesized from 4-[3-amino-2,6-dichloro-4-(5-chloro-2-ethanesulfonyl-benzylcarbamoyl)-benzyl]-piperazine-1-carboxylic acid tert-butyl ester (Compound i8) under the same conditions as for Compound 37.

Example 566

Compound I-1

6,8-Dichloro-3-(5-chloro-2-ethanesulfonyl-benzyl)-7-piperazin-1-ylmethyl-1H-quinazoline-2,4-dione

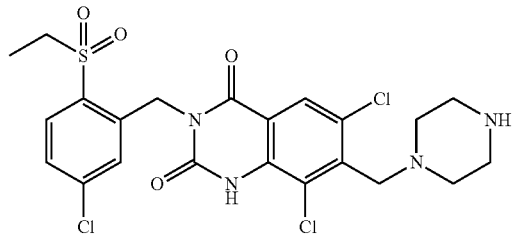

The title compound was synthesized from 4-[6,8-dichloro-3-(5-chloro-2-ethanesulfonyl-benzyl)-2,4-dioxo-1,2,3,4-tetrahydro-quinazolin-7-ylmethyl]-piperazine-1-carboxylic acid tert-butyl ester (Compound i9) under the same conditions as for Compound B-1.

LCMS: m/z 545 [M+H]$^+$

HPLC retention time: 0.52 min (analysis condition D)

Example 567

Compound i10

2-Amino-5-bromo-3-chloro-4-methyl-benzoic acid ethyl ester

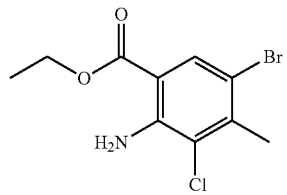

The title compound was synthesized from 2-amino-5-bromo-4-methyl-benzoic acid ethyl ester (Compound 41) under the same conditions as for Compound 24.

Example 568

Compound i11

2-(Bis(tert-butoxycarbonyl)amino)-5-bromo-3-chloro-4-methyl-benzoic acid ethyl ester

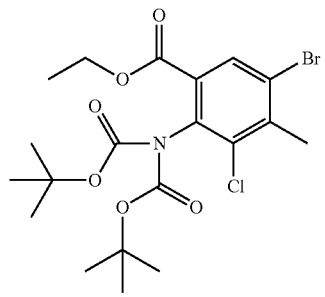 [SMILES: CCOC(=O)c1cc(Br)c(C)c(Cl)c1N(C(=O)OC(C)(C)C)C(=O)OC(C)(C)C]

The title compound was synthesized from 2-amino-5-bromo-3-chloro-4-methyl-benzoic acid ethyl ester (Compound i10) under the same conditions as for Compound 17. However, the reaction was performed using acetonitrile in place of THF.

Example 569

Compound i12

2-(Bis(tert-butoxycarbonyl)amino)-5-bromo-4-bromomethyl-3-chloro-benzoic acid ethyl ester

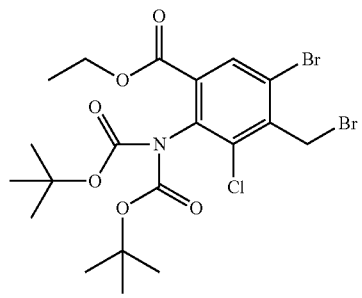 [SMILES: CCOC(=O)c1cc(Br)c(CBr)c(Cl)c1N(C(=O)OC(C)(C)C)C(=O)OC(C)(C)C]

The title compound was obtained from 2-(bis(tert-butoxycarbonyl)amino)-5-bromo-3-chloro-4-methyl-benzoic acid ethyl ester (Compound i11) under the same conditions as for Compound 12.

Example 570

Compound i13

2-Amino-5-bromo-4-bromomethyl-3-chloro-benzoic acid ethyl ester

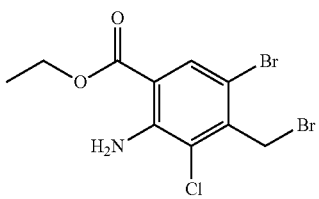 [SMILES: CCOC(=O)c1cc(Br)c(CBr)c(Cl)c1N]

The title compound was synthesized from 2-(bis(tert-butoxycarbonyl)amino)-5-bromo-4-bromomethyl-3-chloro-benzoic acid ethyl ester (Compound i12) under the same conditions as for Compound B-1.

Example 571

Compound i14

4-(3-Amino-6-bromo-2-chloro-4-ethoxycarbonyl-benzyl)-piperazine-1-carboxylic acid tert-butyl ester

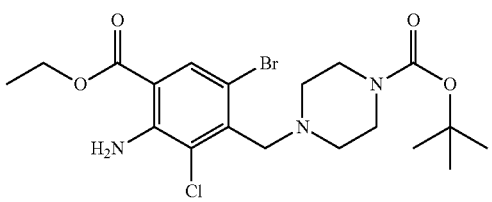 [SMILES: CCOC(=O)c1cc(Br)c(CN2CCN(C(=O)OC(C)(C)C)CC2)c(Cl)c1N]

The title compound was synthesized from 2-amino-5-bromo-4-bromomethyl-3-chloro-benzoic acid ethyl ester (Compound i13) and piperazine-1-carboxylic acid tert-butyl ester under the same conditions as for Compound d1. However, the reaction was performed by using DCM in place of THF and adding TEA at room temperature.

Example 572

Compound i15

4-(3-Amino-6-bromo-4-carboxy-2-chloro-benzyl)-piperazine-1-carboxylic acid tert-butyl ester

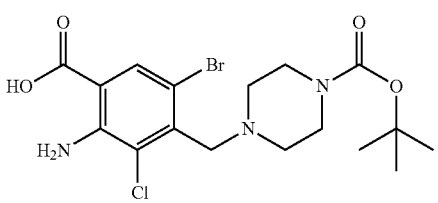

The title compound was obtained from 4-(3-amino-6-bromo-2-chloro-4-ethoxycarbonyl-benzyl)-piperazine-1-carboxylic acid tert-butyl ester (Compound i14) under the same conditions as for Compound 25. However, the reaction was performed using potassium hydroxide in place of a 1 N aqueous sodium hydroxide solution.

Example 573

Compound I-2

6-Bromo-8-chloro-3-(5-chloro-2-ethanesulfonyl-benzyl)-7-piperazin-1-ylmethyl-1H-quinazoline-2,4-dione

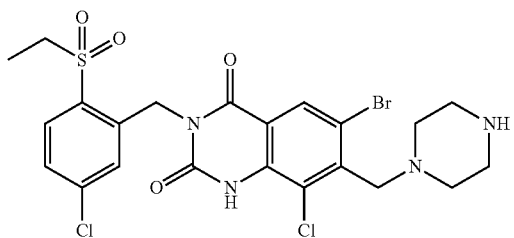

The title compound was synthesized from 4-(3-amino-6-bromo-4-carboxy-2-chloro-benzyl)-piperazine-1-carboxylic acid tert-butyl ester (Compound i15) under the same conditions as for Compounds i8, i9, and I-1.

LCMS: m/z 589 [M+H]+

HPLC retention time: 0.55 min (analysis condition D)

Example 574

Compound I-3

6-Bromo-8-chloro-3-(5-chloro-2-ethanesulfonyl-benzyl)-7-(4-methyl-piperazin-1-ylmethyl)-1H-quinazoline-2,4-dione

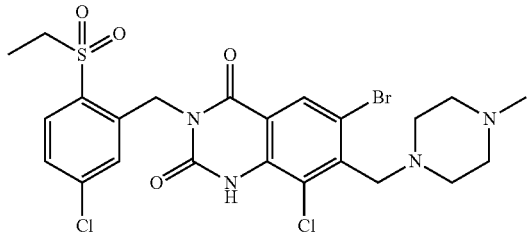 [SMILES: CCS(=O)(=O)c1ccc(Cl)cc1Cn1c(=O)[nH]c2c(Cl)c(CN3CCN(C)CC3)c(Br)cc2c1=O]

The title compound was synthesized from 6-bromo-8-chloro-3-(5-chloro-2-ethanesulfonyl-benzyl)-7-piperazin-1-ylmethyl-1H-quinazoline-2,4-dione (Compound I-2) under the same conditions as for Compound B-2. However, the reaction was performed at 90° C. using 1,4-dioxane in place of THF.

LCMS: m/z 603 [M+H]+

HPLC retention time: 0.54 min (analysis condition D)

Example 575

Compound I-4

6-Bromo-8-chloro-3-(5-chloro-2-ethanesulfonyl-benzyl)-7-(4-isopropyl-piperazin-1-ylmethyl)-1H-quinazoline-2,4-dione

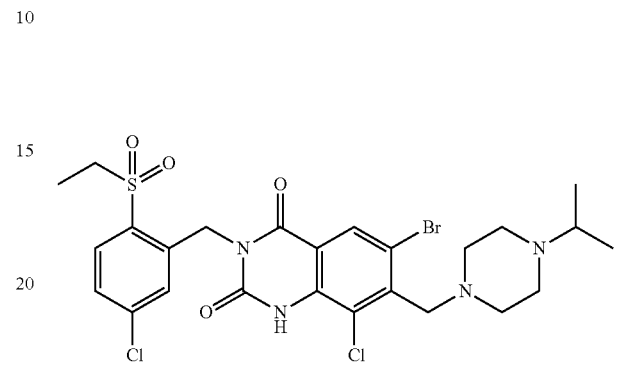

The title compound was synthesized from 6-bromo-8-chloro-3-(5-chloro-2-ethanesulfonyl-benzyl)-7-piperazin-1-ylmethyl-1H-quinazoline-2,4-dione (Compound I-2) under the same conditions as for Compound B-4. However, the reaction was performed at 90° C. using 1,4-dioxane in place of THF.

LCMS: m/z 631 [M+H]+

HPLC retention time: 0.56 min (analysis condition D)

Example 576

Compound I-5

6-Bromo-8-chloro-3-(5-chloro-2-ethanesulfonyl-benzyl)-7-[4-(tetrahydro-pyran-4-yl)-piperazin-1-ylmethyl]-1H-quinazoline-2,4-dione

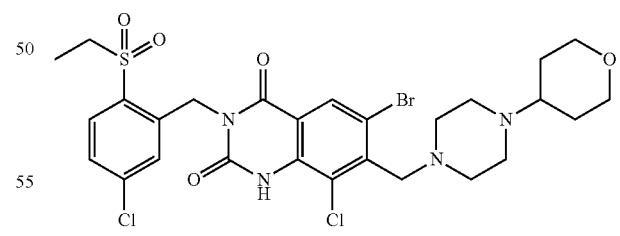

The title compound was synthesized from 6-bromo-8-chloro-3-(5-chloro-2-ethanesulfonyl-benzyl)-7-piperazin-1-ylmethyl-1H-quinazoline-2,4-dione (Compound I-2) by using 1,4-dioxane in place of THF and heating to 90° C. under the same conditions as for Compound B-5.

LCMS: m/z 673 [M+H]+

HPLC retention time: 0.54 min (analysis condition D)

Example 577

Compound i16

2-Amino-3,5-dibromo-4-methyl-benzoic acid ethyl ester

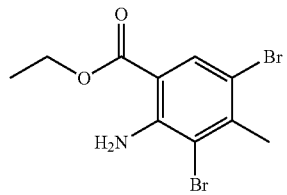

The title compound was synthesized from 2-amino-5-bromo-4-methyl-benzoic acid ethyl ester (Compound 41) under the same conditions as for Compound 12.

Example 578

Compound i17

2-(Bis(tert-butoxycarbonyl)amino)-3, 5-dibromo-4-methyl-benzoic acid ethyl ester

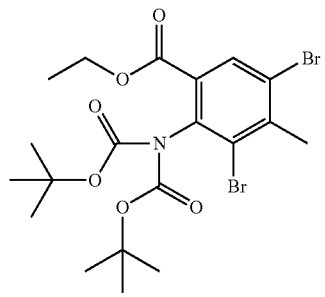 [SMILES: CCOC(=O)c1cc(Br)c(C)c(Br)c1N(C(=O)OC(C)(C)C)C(=O)OC(C)(C)C]

The title compound was synthesized from 2-amino-3,5-dibromo-4-methyl-benzoic acid ethyl ester (Compound i16) under the same conditions as for Compound 17. However, the reaction was performed using acetonitrile in place of THF.

Example 579

Compound i18

2-(Bis(tert-butoxycarbonyl)amino)-3,5-dibromo-4-bromomethyl-benzoic acid ethyl ester

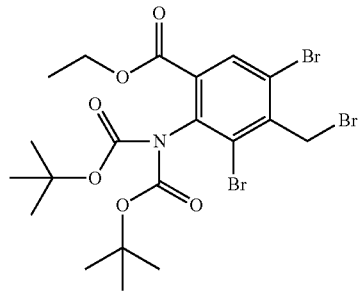 [SMILES: CCOC(=O)c1cc(Br)c(CBr)c(Br)c1N(C(=O)OC(C)(C)C)C(=O)OC(C)(C)C]

The title compound was synthesized from 2-(bis(tert-butoxycarbonyl)amino)-3,5-dibromo-4-methyl-benzoic acid ethyl ester (Compound i17) under the same conditions as for Compound 12.

Example 580

Compound i19

2-Amino-3,5-dibromo-4-bromomethyl-benzoic acid ethyl ester

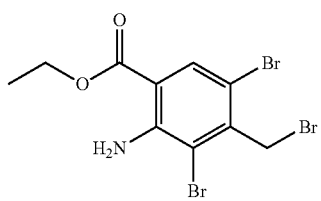 [SMILES: CCOC(=O)c1cc(Br)c(CBr)c(Br)c1N]

The title compound was synthesized from 2-(bis(tert-butoxycarbonyl)amino)-3,5-dibromo-4-bromomethyl-benzoic acid ethyl ester (Compound i18) under the same conditions as for Compound B-1.

Example 581

Compound i20

4-(3-Amino-2,6-dibromo-4-ethoxycarbonyl-benzyl)-piperazine-1-carboxylic acid tert-butyl ester

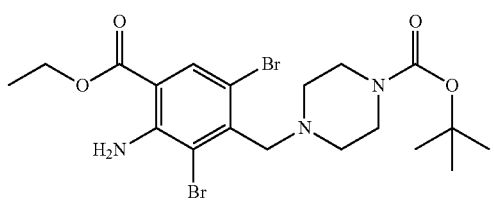 [SMILES: CCOC(=O)c1cc(Br)c(CN2CCN(C(=O)OC(C)(C)C)CC2)c(Br)c1N]

The title compound was synthesized from 2-amino-3,5-dibromo-4-bromomethyl-benzoic acid ethyl ester (Compound i19) and piperazine-1-carboxylic acid tert-butyl ester under the same conditions as for Compound d1. However, the reaction was performed by using DCM in place of THF and adding TEA at room temperature Example 582

Compound i21

4-(3-Amino-2,6-dibromo-4-carboxy-benzyl)-piperazine-1-carboxylic acid tert-butyl ester

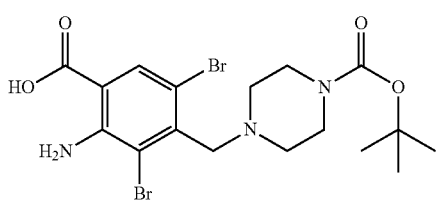 [SMILES: CC(C)(C)OC(=O)N1CCN(Cc2c(Br)cc(C(=O)O)c(N)c2Br)CC1]

The title compound was synthesized from 4-(3-amino-2,6-dibromo-4-ethoxycarbonyl-benzyl)-piperazine-1-carboxylic acid tert-butyl ester (Compound i20) under the same conditions as for Compound 25. However, the reaction was performed using potassium hydroxide in place of a 1 N aqueous sodium hydroxide solution.

Example 583

Compound I-6

6,8-Dibromo-3-(5-chloro-2-ethanesulfonyl-benzyl)-7-piperazin-1-ylmethyl-1H-quinazoline-2,4-dione

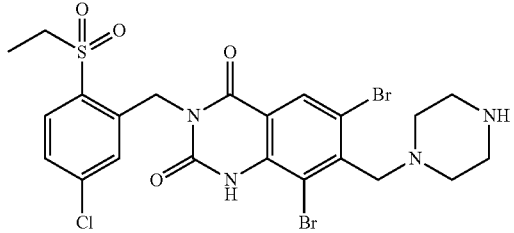 [SMILES: CCS(=O)(=O)c1ccc(Cl)cc1Cn1c(=O)[nH]c2c(Br)c(CN3CCNCC3)c(Br)cc2c1=O]

The title compound was synthesized from 4-(3-amino-2,6-dibromo-4-carboxy-benzyl)-piperazine-1-carboxylic acid tert-butyl ester (Compound i21) under the same conditions as for Compounds i8, i9, and I-1.

LCMS: m/z 633 [M+H]$^+$

HPLC retention time: 0.54 min (analysis condition D)

Example 584

Compound I-7

6,8-Dibromo-3-(5-chloro-2-ethanesulfonyl-benzyl)-7-(4-methyl-piperazin-1-ylmethyl)-1H-quinazoline-2,4-dione

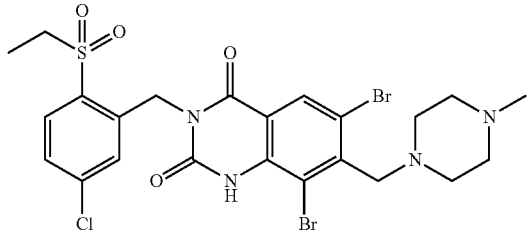 [SMILES: CCS(=O)(=O)c1ccc(Cl)cc1Cn1c(=O)[nH]c2c(Br)c(CN3CCN(C)CC3)c(Br)cc2c1=O]

The title compound was synthesized from 6,8-dibromo-3-(5-chloro-2-ethanesulfonyl-benzyl)-7-piperazin-1-ylmethyl-1H-quinazoline-2,4-dione (Compound I-6) under the same conditions as for Compound B-2.

LCMS: m/z 647 [M+H]$^+$

HPLC retention time: 0.54 min (analysis condition D)

Example 585

Compound I-8

6,8-Dibromo-3-(5-chloro-2-ethanesulfonyl-benzyl)-7-(4-ethyl-piperazin-1-ylmethyl)-1H-quinazoline-2,4-dione

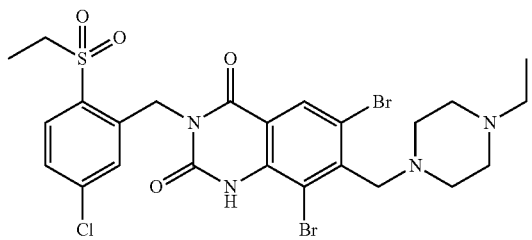 [SMILES: CCN1CCN(Cc2c(Br)cc3c(=O)n(Cc4cc(Cl)ccc4S(=O)(=O)CC)c(=O)[nH]c3c2Br)CC1]

The title compound was synthesized from 6,8-dibromo-3-(5-chloro-2-ethanesulfonyl-benzyl)-7-piperazin-1-ylmethyl-1H-quinazoline-2,4-dione (Compound I-6) under the same conditions as for Compound B-4. However, the reaction was performed using acetaldehyde in place of acetone.

LCMS: m/z 661 [M+H]$^+$

HPLC retention time: 0.55 min (analysis condition D)

Example 586

Compound I-9

6,8-Dibromo-3-(5-chloro-2-ethanesulfonyl-benzyl)-7-(4-isopropyl-piperazin-1-ylmethyl)-1H-quinazoline-2,4-dione

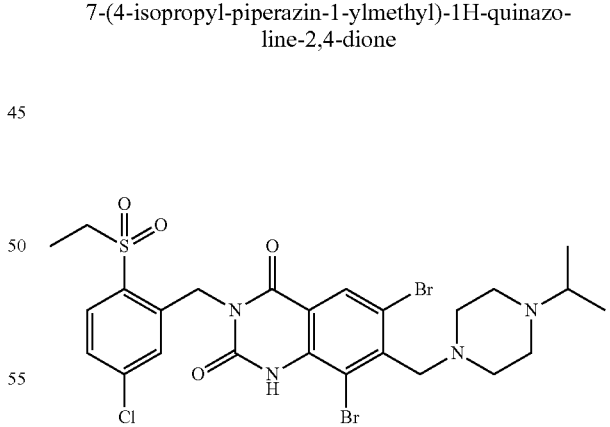

The title compound was synthesized from 6,8-dibromo-3-(5-chloro-2-ethanesulfonyl-benzyl)-7-piperazin-1-ylmethyl-1H-quinazoline-2,4-dione (Compound I-6) under the same conditions as for Compound B-4. However, the reaction was performed using 1,4-dioxane in place of THF.

LCMS: m/z 675 [M+H]$^+$

HPLC retention time: 0.56 min (analysis condition D)

Example 587

Compound I-10

6,8-Dibromo-3-(5-Chloro-2-ethanesulfonyl-benzyl)-7-[4-(tetrahydro-pyran-4-yl)-piperazin-1-ylmethyl]-1H-quinazoline-2,4-dione

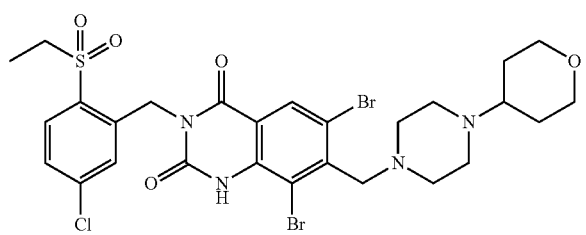

The title compound was synthesized from 6,8-dibromo-3-(5-chloro-2-ethanesulfonyl-benzyl)-7-piperazin-1-ylmethyl-1H-quinazoline-2,4-dione (Compound I-6) under the same conditions as for Compound B-5.
LCMS: m/z 717 [M+H]$^+$
HPLC retention time: 0.55 min (analysis condition D)

Example 588

Compound ff1

Ethyl 2-amino-3-chloro-4-[[(3R)-3-[(2-methylpropan-2-yl)oxycarbonylamino]piperidin-1-yl]methyl]-5-(trifluoromethyl)benzoate

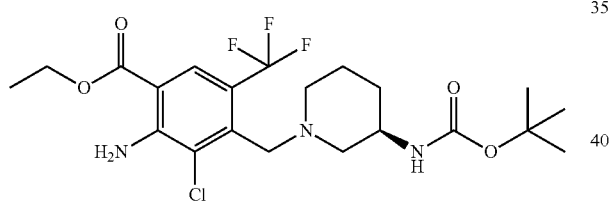

The title compound was synthesized from ethyl 2-amino-3-chloro-4-formyl-5-trifluoromethyl-benzoate (Compound 24) under the same conditions as for Compound b12. However, tert-butyl N-[(3R)-piperidin-3-yl]carbamate was used in place of tert-butyl N-[(3S)-pyrrolidin-3-yl]carbamate, and chloroform was used in place of THF as a solvent.

Example 589

Compound ff2

2-Amino-3-chloro-4-[[(3R)-3-[(2-methylpropan-2-yl)oxycarbonylamino]piperidin-1-yl]methyl]-5-(trifluoromethyl)benzoic acid

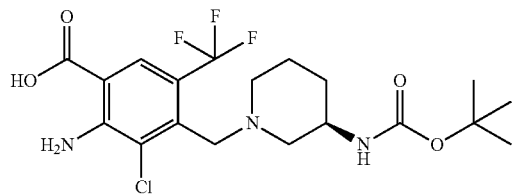 [SMILES: CC(C)(C)OC(=O)N[C@@H]1CCCN(Cc2c(C(F)(F)F)cc(C(=O)O)c(N)c2Cl)C1]

The title compound was synthesized from ethyl 2-amino-3-chloro-4-[[(3R)-3-[(2-methylpropan-2-yl)oxycarbonylamino]piperidin-1-yl]methyl]-5-(trifluoromethyl)benzoate (Compound ff1) under the same conditions as for Compound 25.

Example 590

Compound ff3

5-Chloro-2-propylsulfanylbenzonitrile

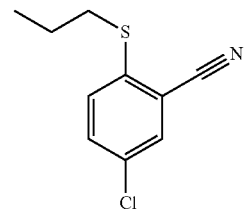

The title compound was synthesized from 5-chloro-2-fluorobenzonitrile under the same conditions as for Compound 1. However, propane-1-thiol was used in place of ethanethiol.

Example 591

Compound ff4

(5-Chloro-2-propylsulfanylphenyl)methanamine

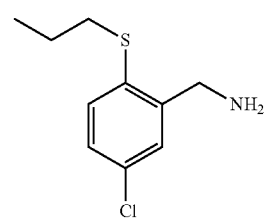

The title compound was synthesized from 5-chloro-2-propylsulfanylbenzonitrile (Compound ff3) under the same conditions as for Compound 2.

Example 592

Compound ff5

(5-Chloro-2-propylsulfonylphenyl)methanamine hydrochloride

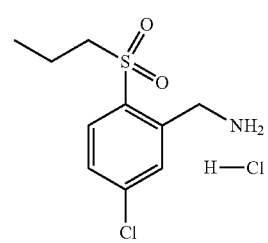

311

The title compound was synthesized from (5-chloro-2-propylsulfanylphenyl)methanamine (Compound ff4) under the same conditions as for Compound 3.

Example 593

Compound ff6 tert-Butyl N-[(3R)-1-[[3-amino-2-chloro-4-[(5-chloro-2-propylsulfonylphenyl)methylcarbamoyl]-6-(trifluoromethyl)phenyl]methyl]piperidin-3-yl]carbamate

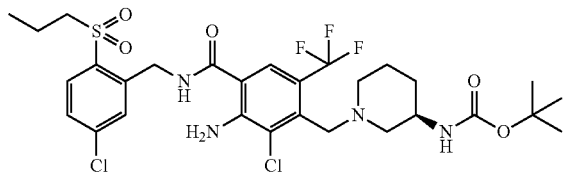 [SMILES: CCCS(=O)(=O)c1ccc(Cl)cc1CNC(=O)c1cc(C(F)(F)F)c(CN2CCC[C@@H](NC(=O)OC(C)(C)C)C2)c(Cl)c1N]

The title compound was synthesized from (5-chloro-2-propylsulfonylphenyl)methanamine hydrochloride (Compound ff5) under the same conditions as for Compound 26. However, 2-amino-3-chloro-4-[[(3R)-3-[(2-methylpropan-2-yl)oxycarbonylamino]piperidin-1-yl]methyl]-5-(trifluoromethyl)benzoic acid (Compound ff2) was used in place of 2-amino-3-chloro-4-formyl-5-trifluoromethyl-benzoic acid (Compound 25).

Example 594

Compound ff7 tert-Butyl N-[(3R)-1-[[8-chloro-3-[(5-chloro-2-propylsulfonylphenyl)methyl]-2,4-dioxo-6-(trifluoromethyl)-1H-quinazolin-7-yl]methyl]piperidin-3-yl]carbamate

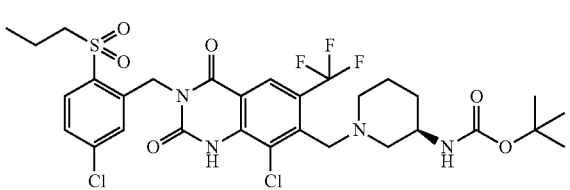 [SMILES: CCCS(=O)(=O)c1ccc(Cl)cc1Cn1c(=O)[nH]c2c(Cl)c(CN3CCC[C@@H](NC(=O)OC(C)(C)C)C3)c(C(F)(F)F)cc2c1=O]

The title compound was synthesized from tert-butyl N-[(3R)-1-[[3-amino-2-chloro-4-[(5-chloro-2-propylsulfonylphenyl)methylcarbamoyl]-6-(trifluoromethyl)phenyl]

312 methyl]piperidin-3-yl]carbamate (Compound ff6) under the same conditions as for Compound 37.

Example 595

Compound FF-1

7-[[(3R)-3-Aminopiperidin-1-yl]methyl]-8-chloro-3-[(5-chloro-2-propylsulfonylphenyl)methyl]-6-(trifluoromethyl)-1H-quinazoline-2,4-dione

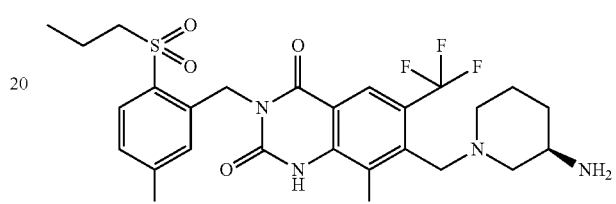

The title compound was synthesized from tert-butyl N-[(3R)-1-[[8-chloro-3-[(5-chloro-2-propylsulfonylphenyl)methyl]-2,4-dioxo-6-(trifluoromethyl)-1H-quinazolin-7-yl]methyl]piperidin-3-yl]carbamate (Compound ff7) under the same conditions as for Compound a41. However, a mixed solvent of 1,4-dioxane/DCM (1:1) was used in place of EtOAc as a solvent.

LCMS: m/z 607 [M+H]+

HPLC retention time: 0.63 min (analysis condition K)

Example 596

Compound ff8

(5-Chloro-2-phenylsulfanylphenyl)methanamine

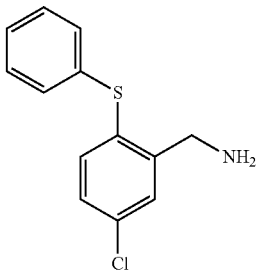 [SMILES: NCc1cc(Cl)ccc1Sc1ccccc1]

The title compound was synthesized from 5-chloro-2-fluorobenzonitrile under the same conditions as for Compounds ff3 and ff4. However, under the ff3 conditions, thiophenol was used in place of propane-1-thiol.

Example 597

Compound ff9

[2-(Benzenesulfonyl)-5-chlorophenyl]methanamine hydrochloride

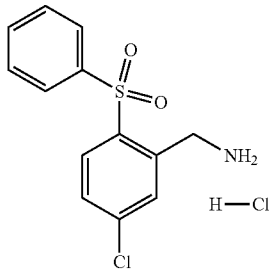

The title compound was synthesized from (5-chloro-2-phenylsulfanylphenyl)methanamine (Compound ff8) under the same conditions as for Compounds 7, 8 and 9. However, under the Compound 7 conditions, the reaction was performed with the addition of TEA.

Example 598

Compound FF-2

7-[[(3R)-3-Aminopiperidin-1-yl]methyl]-3-[[2-(benzenesulfonyl)-5-chlorophenyl]methyl]-8-chloro-6-(trifluoromethyl)-1H-quinazoline-2,4-dione

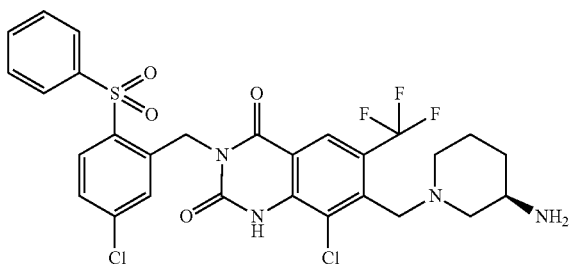 [SMILES: N[C@@H]1CCCN(Cc2c(C(F)(F)F)cc3c(=O)n(Cc4cc(Cl)ccc4S(=O)(=O)c4ccccc4)c(=O)[nH]c3c2Cl)C1]

The title compound was synthesized from [2-(benzenesulfonyl)-5-chlorophenyl]methanamine hydrochloride (Compound ff9) under the same conditions as for Compounds ff6, ff7 and FF-1.
LCMS: m/z 641 [M+H]$^+$
HPLC retention time: 0.64 min (analysis condition K)

Example 599

Compound FF-3

7-[[(3R)-3-Aminopiperidin-1-yl]methyl]-8-chloro-3-[(5-chloro-2-propan-2-ylsulfonylphenyl)methyl]-6-(trifluoromethyl)-1H-quinazoline-2,4-dione

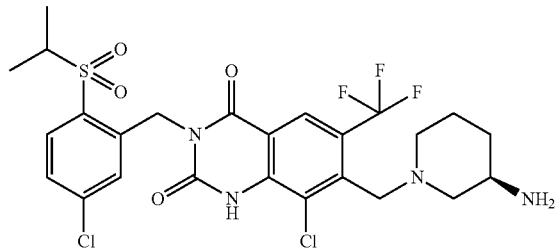 [SMILES: CC(C)S(=O)(=O)c1ccc(Cl)cc1Cn1c(=O)[nH]c2c(Cl)c(CN3CCC[C@@H](N)C3)c(C(F)(F)F)cc2c1=O]

The title compound was synthesized from 5-chloro-2-fluorobenzonitrile under the same conditions as for Compounds ff3, ff4, ff5, ff6, ff7 and FF-1. However, under the Compound ff3 conditions, propane-2-thiol was used in place of propane-1-thiol.
LCMS: m/z 607 [M+H]$^+$
HPLC retention time: 0.60 min (analysis condition K)

Example 600

Compound ff10

(4-Chloro-2-formyl-6-methoxyphenyl) trifluoromethanesulfonate

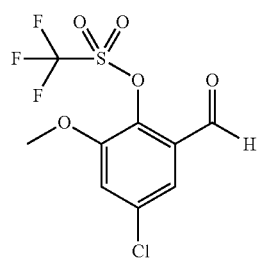 [SMILES: COc1cc(Cl)cc(C=O)c1OS(=O)(=O)C(F)(F)F]

Trifluoromethanesulfonic anhydride (688 mg, 2.44 mmol) was added to a solution of 5-chloro-2-hydroxy-3-methoxybenzaldehyde (403 mg, 2.16 mmol) in pyridine (7 ml), and it was stirred under ice-cooling for 30 minutes under nitrogen atmosphere. Water was added to the reaction mixture, followed by extraction with ethyl acetate. The organic layer was then dried over anhydrous magnesium sulfate. The drying agent was removed by filtration, and the residue obtained by concentration under reduced pressure was purified by silica gel column chromatography (ethyl acetate/n-hexane) to yield the title compound (648 mg, 94%) as a pale yellow oily substance.
LCMS: m/z 319 [M+H]$^+$
HPLC retention time: 0.87 min (analysis condition C)

Example 601

Compound ff11

5-Chloro-2-ethylsulfanyl-3-methoxybenzaldehyde

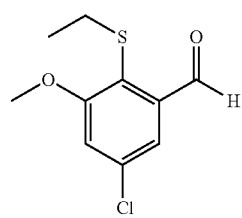

Tris(dibenzylideneacetone)dipalladium(0) (66.8 mg, 0.0729 mmol), (5-diphenylphosphanyl-9, 9-dimethylxanthen-4-yl)-diphenylphosphane (83.9 mg, 0.145 mmol), DIPEA (362 μl, 2.13 mmol) and ethanethiol (210 μl, 2.84 mmol) were added to a solution of (4-chloro-2-formyl-6-methoxyphenyl) trifluoromethanesulfonate (ff10, 319 mg, 0.709 mmol) in 1,4-dioxane (2.5 ml), and it was stirred at 100° C. for 15 minutes. The reaction solution was cooled to room temperature, followed by addition of water and extraction with ethyl acetate. The organic layer was washed with brine and dried over anhydrous magnesium sulfate. The drying agent was removed by filtration, and the residue obtained by concentration under reduced pressure was purified by silica gel column chromatography (ethyl acetate/n-hexane) to yield the title compound (135 mg, 83%) as a yellow oily substance.

LCMS: m/z 231 [M+H]$^+$

HPLC retention time: 2.64 min (analysis condition C)

Example 602

Compound ff12

(5-Chloro-2-ethylsulfanyl-3-methoxyphenyl)methanamine

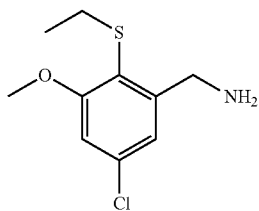

The title compound was synthesized from 5-chloro-2-ethylsulfanyl-3-methoxybenzaldehyde (Compound ff11) under the same conditions as for Compounds 5 and 6.

Example 603

Compound ff13

(5-Chloro-2-ethylsulfonyl-3-methoxyphenyl)methanamine hydrochloride

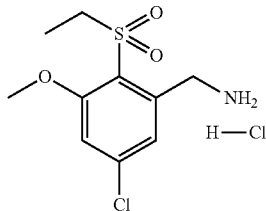

Boc$_2$O (121 mg, 0.553 mmol) was added to a solution of (5-chloro-2-ethylsulfanyl-3-methoxyphenyl)methanamine (Compound ff12, 105 mg, 0.452 mmol) and TEA (94.0 μl, 0.678 mmol) in THF (1.5 ml), and it was stirred at room temperature for 30 minutes under nitrogen atmosphere. A 10% aqueous citric acid solution was added to the reaction mixture, followed by extraction with ethyl acetate. The organic layer was then washed with brine and dried over anhydrous magnesium sulfate. After the drying agent was removed by filtration, a crude product of tert-butyl N-[(5-chloro-2-ethylsulfanyl-3-methoxyphenyl)methyl]carbamate (182 mg) was obtained as a gray solid by concentration under reduced pressure.

LCMS: m/z 332 [M+H]$^+$

HPLC retention time: 0.93 min (analysis condition D)

To a solution of the resultant crude product of tert-butyl N-[(5-chloro-2-ethylsulfanyl-3-methoxyphenyl)methyl]carbamate (148 mg) in EtOAc (1.5 ml), m-CPBA (233 mg, 0.876 mmol) was added under ice-cooling, and it was warmed to room temperature and stirred for 30 minutes under nitrogen atmosphere. A saturated aqueous solution of sodium bicarbonate was added to the reaction mixture, followed by extraction with ethyl acetate. The organic layer was then washed with brine and dried over anhydrous magnesium sulfate. After the drying agent was removed by filtration, a crude product of tert-butyl N-[(5-chloro-2-ethylsulfonyl-3-methoxyphenyl)methyl]carbamate was obtained by concentration under reduced pressure. A 4 N hydrochloric acid/ethyl acetate solution (760 μl, 3.04 mmol) was added to this crude product of tert-butyl N-[(5-chloro-2-ethylsulfonyl-3-methoxyphenyl)methyl]carbamate in MeOH/EtOAc (60 l/750 μl), and it was stirred at 60° C. for three hours. The reaction solution was cooled to room temperature, and the precipitated solid was then washed with ethyl acetate to yield the title compound (99.8 mg, 90%) as a colorless solid.

LCMS: m/z 264 [M+H]$^+$

HPLC retention time: 0.59 min (analysis condition C)

Example 604

Compound ff14 tert-Butyl N-[(3R)-1-[[3-amino-2-chloro-4-[(5-chloro-2-ethylsulfonyl-3-methoxyphenyl)methylcarbamoyl]-6-(trifluoromethyl)phenyl]methyl]piperidin-3-yl]carbamate

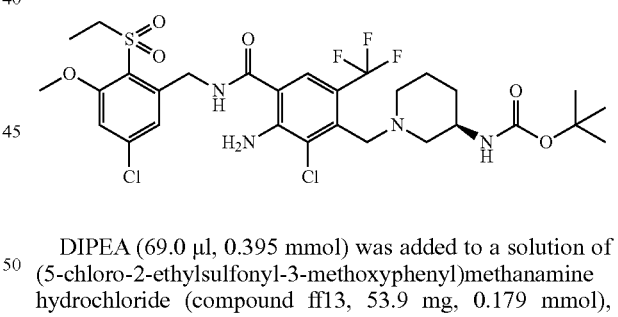

DIPEA (69.0 μl, 0.395 mmol) was added to a solution of (5-chloro-2-ethylsulfonyl-3-methoxyphenyl)methanamine hydrochloride (compound ff13, 53.9 mg, 0.179 mmol), 2-amino-3-chloro-4-[[(3R)-3-[(2-methylpropan-2-yl)oxycarbonylamino]piperidin-1-yl]methyl]-5-(trifluoromethyl)benzoic acid (Compound ff2, 91.4 mg, 0.180 mmol) and HATU (75.8 mg, 0.199 mmol) in DMF (0.7 ml), and it was stirred at room temperature for 30 minutes under nitrogen atmosphere. Water was added to the reaction mixture, followed by extraction with ethyl acetate. The organic layer was then dried over anhydrous sodium sulfate. The drying agent was removed by filtration, followed by concentration under reduced pressure. The resultant residue was purified by silica gel column chromatography (ethyl acetate/n-hexane) to yield the title compound (85.3 mg, 68%) as a colorless oily substance.

LCMS: m/z 697 [M+H]$^+$

HPLC retention time: 1.70 min (analysis condition C)

Example 605

Compound ff15 tert-Butyl N-[(3R)-1-[[8-chloro-3-[(5-chloro-2-eth-ylsulfonyl-3-methoxyphenyl)methyl]-2,4-dioxo-6-(trifluoromethyl)-1H-quinazolin-7-yl]methyl]piperidin-3-yl]carbamate

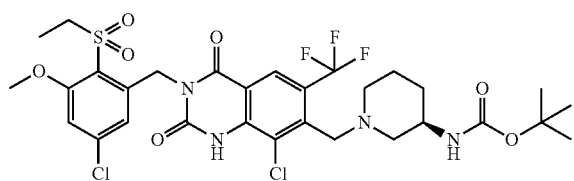 [SMILES: CCS(=O)(=O)c1c(Cn2c(=O)[nH]c3c(Cl)c(CN4CCC[C@@H](NC(=O)OC(C)(C)C)C4)c(C(F)(F)F)cc3c2=O)cc(Cl)cc1OC]

The title compound was synthesized from tert-butyl N-[(3R)-1-[[3-amino-2-chloro-4-[(5-chloro-2-ethylsulfonyl-3-methoxyphenyl)methylcarbamoyl]-6-(trifluoromethyl)phenyl]methyl]piperidin-3-yl]carbamate (Compound ff14) under the same conditions as for Compound A-4.

Example 606

Compound FF-4

7-[[(3R)-3-Aminopiperidin-1-yl]methyl]-8-chloro-3-[(5-chloro-2-ethylsulfonyl-3-methoxyphenyl)methyl]-6-(trifluoromethyl)-1H-quinazoline-2,4-dione

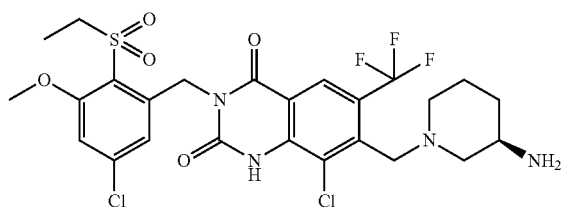 [SMILES: CCS(=O)(=O)c1c(Cn2c(=O)[nH]c3c(Cl)c(CN4CCC[C@@H](N)C4)c(C(F)(F)F)cc3c2=O)cc(Cl)cc1OC]

The title compound was synthesized from tert-butyl N-[(3R)-1-[[8-chloro-3-[(5-chloro-2-ethylsulfonyl-3-methoxyphenyl)methyl]-2,4-dioxo-6-(trifluoromethyl)-1H-quinazolin-7-yl]methyl]piperidin-3-yl]carbamate (Compound ff15) under the same conditions as for Compound a41.

LCMS: m/z 623 [M+H]$^+$

HPLC retention time: 1.48 min (analysis condition C)

Example 607

Compound ff16

2-Iodo-4,5-dimethylaniline

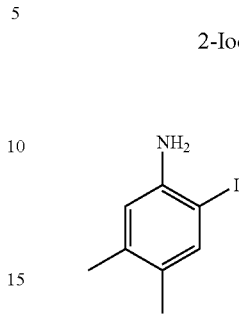

Iodine (2.06 g, 8.11 mmol) was added in 10 parts to a mixed solution of 3,4-dimethylaniline (893 mg, 7.37 mmol) and sodium bicarbonate (683 mg, 8.14 mmol) in MeOH/water (7 ml/7 ml), and it was stirred at room temperature for one hour under nitrogen atmosphere. Followed by addition of water to the reaction mixture and extraction with dichloromethane, the organic layer was then washed with a saturated aqueous solution of sodium thiosulfate and dried over anhydrous magnesium sulfate. The drying agent was removed by filtration, followed by concentration under reduced pressure. The resultant residue was purified by silica gel column chromatography (ethyl acetate/n-hexane) to yield the title compound (1.54 g, 85%) as a brown solid.

LCMS: m/z 248 [M+H]$^+$

HPLC retention time: 1.91 min (analysis condition C)

Example 608

Compound ff17

2-Amino-4,5-dimethylbenzonitrile

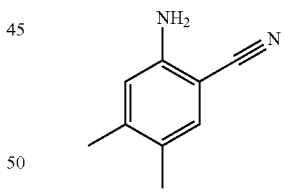

Copper(I) cyanide (1.24 g, 12.4 mmol) was added to a solution of 2-iodo-4,5-dimethylaniline (Compound ff16, 1.53 g, 6.21 mmol) in DMF (20 ml), and it was stirred at 150 to 160° C. for 1.5 hours. After the reaction solution was cooled to room temperature, a 10% aqueous ammonia solution (30 ml) and DCM (30 ml) were added, followed by removal of the insoluble matter through celite, and it was washed with DCM. The organic layer of the filtrate was concentrated under reduced pressure, and the resultant residue was purified by silica gel column chromatography (ethyl acetate/n-hexane) to yield the title compound (796 mg, 88%) as a brown solid.

LCMS: m/z 147 [M+H]$^+$

HPLC retention time: 0.66 min (analysis condition D)

Example 609

Compound ff18

2-Iodo-4,5-dimethylbenzonitrile

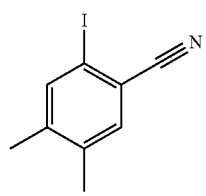

Sodium nitrite (392 mg, 5.68 mmol) dissolved in water (2 ml) was added to a solution of 2-amino-4,5-dimethylbenzonitrile (Compound ff17, 682 mg, 4.67 mmol) in 2,2,2-trifluoroethanol/TFA (27 ml/2.7 ml), and it was stirred at room temperature under nitrogen atmosphere. After 20 minutes, potassium iodide (2.30 g, 13.9 mmol) was added, and it was further stirred for 1.5 hours. Followed by addition of water to the reaction mixture and extraction with ethyl acetate, the organic layer was then washed with a saturated aqueous solution of sodium thiosulfate and dried over anhydrous magnesium sulfate. The drying agent was removed by filtration, followed by concentration under reduced pressure. The resultant residue was purified by silica gel column chromatography (ethyl acetate/n-hexane) to yield the title compound (694 mg, 58%) as a pale yellow solid.

LCMS: m/z 258 [M+H]$^+$

HPLC retention time: 0.85 min (analysis condition D)

Example 610

Compound ff19

2-Ethylsulfanyl-4, 5-dimethylbenzonitrile

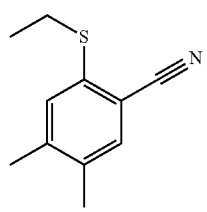

The title compound was synthesized from 2-iodo-4,5-dimethylbenzonitrile (Compound ff18) under the same conditions as for Compound ff11.

Example 611

Compound ff20

(2-Ethylsulfanyl-4,5-dimethylphenyl)methanamine

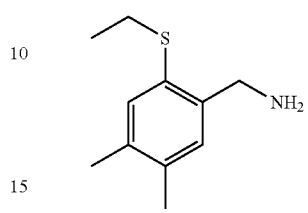

The title compound was synthesized from 2-ethylsulfanyl-4,5-dimethylbenzonitrile (Compound ff19) under the same conditions as for Compound 2.

Example 612

Compound ff21

(2-Ethylsulfonyl-4,5-dimethylphenyl)methanamine hydrochloride

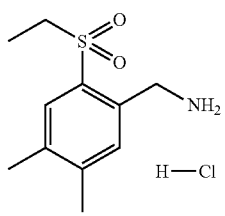

The title compound was synthesized from (2-ethylsulfanyl-4,5-dimethylphenyl)methanamine (Compound ff20) under the same conditions as for Compound ff13.

Example 613

Compound ff22 tert-Butyl N-[(3R)-1-[[3-amino-2-chloro-4-[(2-ethylsulfonyl-4,5-dimethylphenyl)methylcarbamoyl]-6-(trifluoromethyl)phenyl]methyl]piperidin-3-yl]carbamate

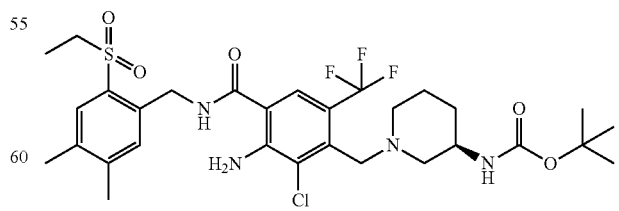

The title compound was synthesized from (2-ethylsulfonyl-4,5-dimethylphenyl)methanamine hydrochloride (Compound ff21) under the same conditions as for Compound ff14.

Example 614

Compound ff23 tert-Butyl N-[(3R)-1-[[8-chloro-3-[(2-ethylsulfonyl-4,5-dimethylphenyl)methyl]-2,4-dioxo-6-(trifluoromethyl)-1H-quinazolin-7-yl]methyl]piperidin-3-yl]carbamate

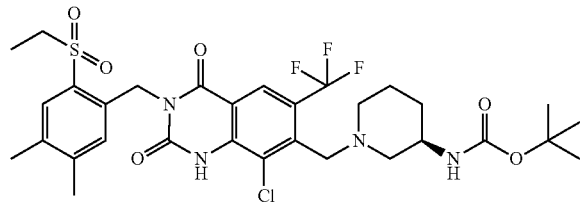 [SMILES: CCS(=O)(=O)c1cc(C)c(C)cc1Cn1c(=O)[nH]c2c(Cl)c(CN3CCC[C@@H](NC(=O)OC(C)(C)C)C3)c(C(F)(F)F)cc2c1=O]

The title compound was synthesized from tert-butyl N-[(3R)-1-[[3-amino-2-chloro-4-[(2-ethylsulfonyl-4, 5-dimethylphenyl)methylcarbamoyl]-6-(trifluoromethyl)phenyl]methyl]piperidin-3-yl]carbamate (Compound ff22) under the same conditions as for Compound A-4.

Example 615

Compound FF-5

7-[[(3R)-3-Aminopiperidin-1-yl]methyl]-8-chloro-3-[(2-ethylsulfonyl-4,5-dimethylphenyl)methyl]-6-(trifluoromethyl)-1H-quinazoline-2,4-dione

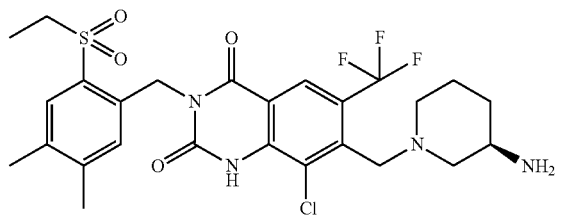 [SMILES: CCS(=O)(=O)c1cc(C)c(C)cc1Cn1c(=O)[nH]c2c(Cl)c(CN3CCC[C@@H](N)C3)c(C(F)(F)F)cc2c1=O]

A 36% aqueous hydrochloric acid solution (0.274 ml, 3.28 mmol) was added to a solution of tert-butyl N-[(3R)-1-[[8-chloro-3-[(2-ethylsulfonyl-4,5-dimethylphenyl)methyl]-2,4-dioxo-6-(trifluoromethyl)-1H-quinazolin-7-yl]methyl]piperidin-3-yl]carbamate (Compound ff23, 37.5 mg, 0.0546 mmol) in THF (1 ml), and it was stirred at room temperature for three hours under nitrogen atmosphere. A saturated aqueous sodium bicarbonate solution was added to the reaction mixture, followed by extraction with ethyl acetate. The organic layer was then washed with brine and dried over anhydrous magnesium sulfate. The drying agent was removed by filtration, followed by concentration under reduced pressure. The resultant residue was purified by amino silica gel column chromatography (methanol/dichloromethane) to yield the title compound (27.1 mg, 84%) as a colorless solid.

LCMS: m/z 587 [M+H]+

HPLC retention time: 1.59 min (analysis condition C)

Example 616

Compound ff24 tert-Butyl N-[(3R)-1-[[8-chloro-3-[(5-chloro-2-ethylsulfonyl-4-methylphenyl)methyl]-2,4-dioxo-6-(trifluoromethyl)-1H-quinazolin-7-yl]methyl]piperidin-3-yl]carbamate

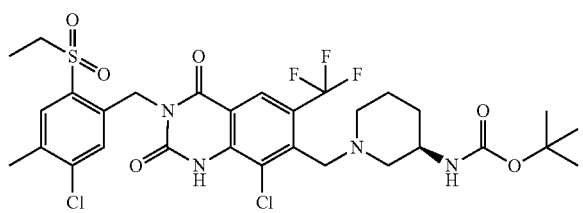 [SMILES: CCS(=O)(=O)c1cc(C)c(Cl)cc1Cn1c(=O)[nH]c2c(Cl)c(CN3CCC[C@@H](NC(=O)OC(C)(C)C)C3)c(C(F)(F)F)cc2c1=O]

The title compound was synthesized from 5-chloro-2-hydroxy-4-methylbenzaldehyde under the same conditions as for Compounds ff10, ff11, ff12, ff13, ff14 and ff15. However, under the Compound ff11 conditions, the reaction was performed at a temperature of 80° C.

Example 617

Compound FF-6

7-[[(3R)-3-Aminopiperidin-1-yl]methyl]-8-chloro-3-[(5-chloro-2-ethylsulfonyl-4-methylphenyl)methyl]-6-(trifluoromethyl)-1H-quinazoline-2,4-dione

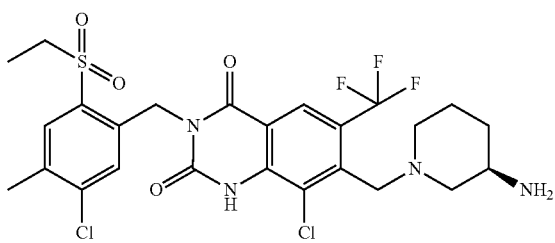 [SMILES: CCS(=O)(=O)c1cc(C)c(Cl)cc1Cn1c(=O)[nH]c2c(Cl)c(CN3CCC[C@@H](N)C3)c(C(F)(F)F)cc2c1=O]

The title compound was synthesized from tert-butyl N-[(3R)-1-[[8-chloro-3-[(5-chloro-2-ethylsulfonyl-4-methylphenyl)methyl]-2,4-dioxo-6-(trifluoromethyl)-1H-quinazolin-7-yl]methyl]piperidin-3-yl]carbamate (Compound ff24) under the same conditions as for Compound FF-5.

LCMS: m/z 607 [M+H]+

HPLC retention time: 1.71 min (analysis condition C)

Example 618

Compound ff25

2-Amino-3-chloro-4-[[3-[(2-methylpropan-2-yl)oxy-carbonylamino]azetidin-1-yl]methyl]-5-(trifluoromethyl)benzoic acid

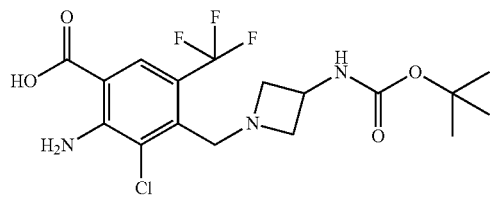 [SMILES: CC(C)(C)OC(=O)NC1CN(Cc2c(C(F)(F)F)cc(C(=O)O)c(N)c2Cl)C1]

The title compound was synthesized from ethyl 2-amino-3-chloro-4-formyl-5-(trifluoromethyl)benzoate (Compound 24) under the same conditions as for Compounds ff1 and ff2. However, under the Compound ff1 conditions, tert-butyl N-(azetidin-3-yl)carbamate was used in place of tert-butyl N-[(3R)-piperidin-3-yl]carbamate, and chloroform was used in place of THF as a solvent.

Example 619

Compound ff26

7-[(3-Aminoazetidin-1-yl)methyl]-8-chloro-3-[(5-chloro-2-ethylsulfonylphenyl)methyl]-6-(trifluoromethyl)-1H-quinazoline-2,4-dione

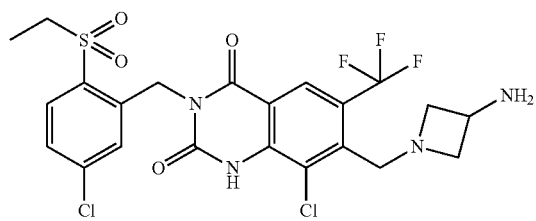 [SMILES: CCS(=O)(=O)c1ccc(Cl)cc1Cn1c(=O)[nH]c2c(Cl)c(CN3CC(N)C3)c(C(F)(F)F)cc2c1=O]

The title compound was synthesized from 5-chloro-2-ethanesulfonyl-benzylamine hydrochloride (Compound 3) under the same conditions as for Compounds ff14, ff15 and FF-4. However, under the Compound ff14 conditions, 2-amino-3-chloro-4-[[3-[(2-methylpropan-2-yl)oxycarbonylamino]azetidin-1-yl]methyl]-5-(trifluoromethyl)benzoic acid (Compound ff25) was used in place of 2-amino-3-chloro-4-[[(3R)-3-[(2-methylpropan-2-yl)oxycarbonylamino]piperidin-1-yl]methyl]-5-(trifluoromethyl)benzoic acid (Compound ff2) as a carboxylic acid.

Example 620

Compound FF-7

8-Chloro-3-[(5-chloro-2-ethylsulfonylphenyl)methyl]-7-[[3-(dimethylsulfamoylamino)azetidin-1-yl]methyl]-2,4-dioxo-6-(trifluoromethyl)-1H-quinazoline

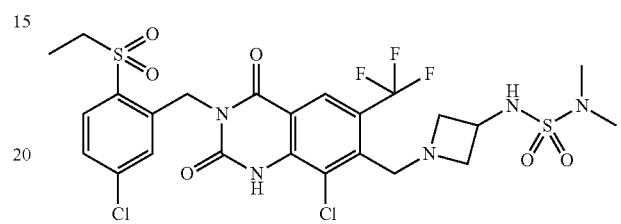

The title compound was synthesized from 7-[(3-aminoazetidin-1-yl)methyl]-8-chloro-3-[(5-chloro-2-ethylsulfonylphenyl)methyl]-6-(trifluoromethyl)-1H-quinazoline-2,4-dione (Compound ff26) under the same conditions as for Compound E-10.

LCMS: m/z 672 [M+H]$^+$

HPLC retention time: 1.64 min (analysis condition C)

Example 621

Compound FF-8

8-Chloro-3-[(5-chloro-2-ethylsulfonylphenyl)methyl]-7-[[3-(methylsulfamoylamino)azetidin-1-yl]methyl]-6-(trifluoromethyl)-1H-quinazoline-2,4-dione

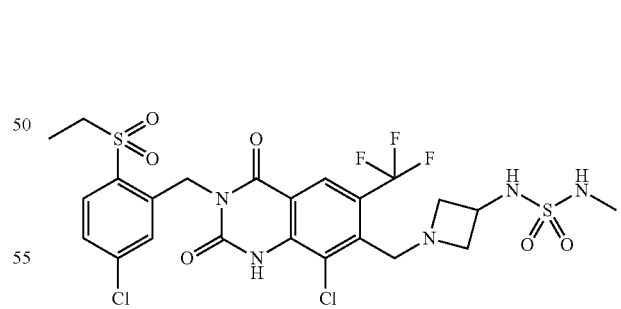

The title compound was synthesized from 7-[(3-aminoazetidin-1-yl)methyl]-8-chloro-3-[(5-chloro-2-ethylsulfonylphenyl)methyl]-6-(trifluoromethyl)-1H-quinazoline-2,4-dione (Compound ff26) under the same conditions as for Compound F-4.

LCMS: m/z 658 [M+H]$^+$

HPLC retention time: 1.55 min (analysis condition C)

Example 622

Compound ff27 tert-Butyl N-[[1-[[8-chloro-3-[(5-chloro-2-ethylsulfonylphenyl)methyl]-2,4-dioxo-6-(trifluoromethyl)-1H-quinazolin-7-yl]methyl]azetidin-3-yl]sulfamoyl]carbamate

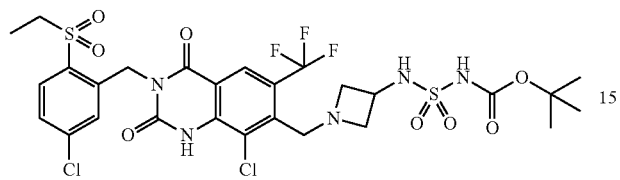

TEA (15.0 µl, 0.104 mmol) was added to a solution of 7-[(3-aminoazetidin-1-yl)methyl]-8-chloro-3-[(5-chloro-2-ethylsulfonylphenyl)methyl]-6-(trifluoromethyl)-1H-quinazoline-2,4-dione (Compound ff26, 29.4 mg, 0.0520 mmol) and (4-dimethylazaniumylidenepyridin-1-yl)sulfonyl-[(2-methylpropan-2-yl)oxycarbonyl]azanide (24.9 mg, 0.0826 mmol) in acetonitrile (1 ml), and it was stirred at 65° C. for two hours. The reaction solution was cooled to room temperature, followed by addition of water and extraction with ethyl acetate. The organic layer was washed with brine and dried over anhydrous magnesium sulfate. The drying agent was removed by filtration, followed by concentration under reduced pressure. The resultant residue was purified by silica gel column chromatography (ethyl acetate/n-hexane) to yield the title compound (18.3 mg, 47%) as a colorless solid. (4-Dimethylazaniumylidenepyridin-1-yl) sulfonyl-[(2-methylpropan-2-yl)oxycarbonyl]azanide was synthesized by following the method described in the literature (Organic Letters, vol. 3, pp. 2241-2243, 2001).

LCMS: m/z 744 [M+H]+

HPLC retention time: 1.70 min (analysis condition C)

Example 623

Compound FF-9

8-Chloro-3-[(5-chloro-2-ethylsulfonylphenyl)methyl]-2,4-dioxo-7-[[3-(sulfamoylamino)azetidin-1-yl]methyl]-6-(trifluoromethyl)-1H-quinazoline

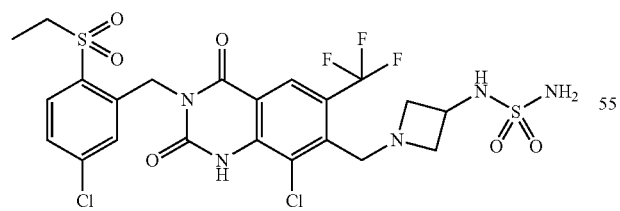

The title compound was synthesized from tert-butyl N-[[1-[[8-chloro-3-[(5-chloro-2-ethylsulfonylphenyl)methyl]-2,4-dioxo-6-(trifluoromethyl)-1H-quinazolin-7-yl]methyl]azetidin-3-yl]sulfamoyl]carbamate (Compound ff27) under the same conditions as for Compound a41.

LCMS: m/z 644 [M+H]+

HPLC retention time: 1.38 min (analysis condition C)

Example 624

Compound j1

Ethyl 2-amino-4-formyl-3-methyl-5-(trifluoromethyl)benzoate

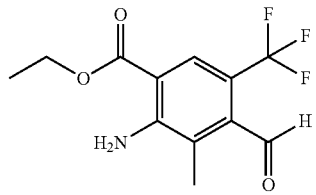 [SMILES: CCOC(=O)c1cc(C(F)(F)F)c(C=O)c(C)c1N]

The title compound was synthesized from ethyl 2-amino-3-bromo-4-formyl-5-(trifluoromethyl)benzoate (Compound h6) under the same conditions as for Compound 21. However, potassium trifluoro(methyl)borate was used in place of potassium vinyltrifluoroborate.

Example 625

Compound j2

Ethyl 2-amino-3-methyl-4-[[(3S)-3-[methyl-[(2-methylpropan-2-yl)oxycarbonyl]amino]piperidin-1-yl]methyl]-5-(trifluoromethyl)benzoate

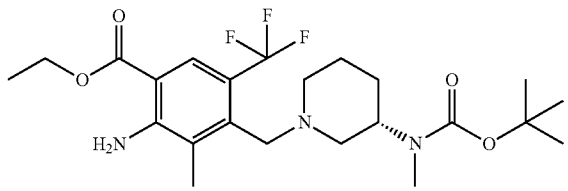 [SMILES: CCOC(=O)c1cc(C(F)(F)F)c(CN2CCC[C@H](N(C)C(=O)OC(C)(C)C)C2)c(C)c1N]

The title compound was synthesized from ethyl 2-amino-4-formyl-3-methyl-5-(trifluoromethyl)benzoate (Compound j1) under the same conditions as for Compound b12. However, tert-butyl N-methyl-N-[(3S)-piperidin-3-yl]carbamate was used in place of tert-butyl (S)-pyrrolidin-3-yl-carbamate. Chloroform was used in place of THF as a solvent.

Example 626

Compound j3

2-Amino-3-methyl-4-[[(3S)-3-[methyl-[(2-methylpropan-2-yl)oxycarbonyl]amino]piperidin-1-yl]methyl]-5-(trifluoromethyl)benzoic acid

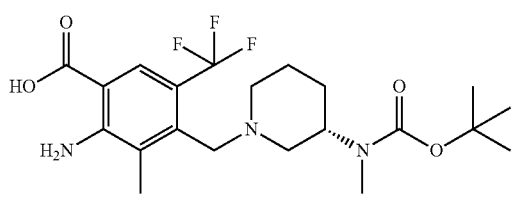 [SMILES: Cc1c(N)c(C(=O)O)cc(C(F)(F)F)c1CN1CCC[C@H](N(C)C(=O)OC(C)(C)C)C1]

The title compound was synthesized from ethyl 2-amino-3-methyl-4-[[(3S)-3-[methyl-[(2-methylpropan-2-yl)oxycarbonyl]amino]piperidin-1-yl]methyl]-5-(trifluoromethyl)benzoate (Compound j2) under the same conditions as for Compound 25.

Example 627

Compound j4 tert-Butyl N-[(3S)-1-[[3-amino-4-[(5-chloro-2-ethylsulfonylphenyl)methylcarbamoyl]-2-methyl-6-(trifluoromethyl)phenyl]methyl]piperidin-3-yl]-N-methylcarbamate

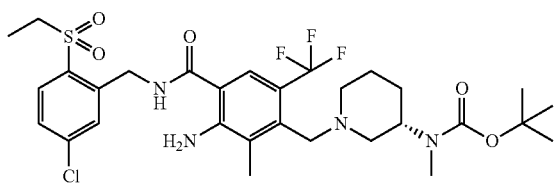 [SMILES: CCS(=O)(=O)c1ccc(Cl)cc1CNC(=O)c1cc(C(F)(F)F)c(CN2CCC[C@H](N(C)C(=O)OC(C)(C)C)C2)c(C)c1N]

The title compound was synthesized from 2-amino-3-methyl-4-[[(3S)-3-[methyl-[(2-methylpropan-2-yl)oxycarbonyl]amino]piperidin-1-yl]methyl]-5-(trifluoromethyl)benzoic acid (Compound j3) under the same conditions as for Compound ff14.

Example 628

Compound j5 tert-Butyl N-[(3S)-1-[[3-[(5-chloro-2-ethylsulfonylphenyl)methyl]-8-methyl-2,4-dioxo-6-(trifluoromethyl)-1H-quinazolin-7-yl]methyl]piperidin-3-yl]-N-methylcarbamate

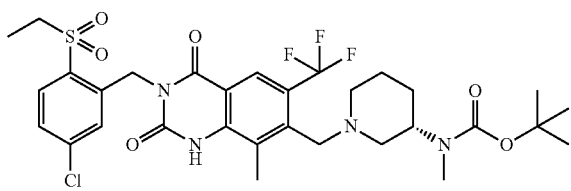 [SMILES: CCS(=O)(=O)c1ccc(Cl)cc1Cn1c(=O)[nH]c2c(C)c(CN3CCC[C@H](N(C)C(=O)OC(C)(C)C)C3)c(C(F)(F)F)cc2c1=O]

The title compound was synthesized from tert-butyl N-[(3S)-1-[[3-amino-4-[(5-chloro-2-ethylsulfonylphenyl)methyl carbamoyl]-2-methyl-6-(trifluoromethyl)phenyl]methyl]piperidin-3-yl]-N-methylcarbamate (Compound j4) under the same conditions as for Compound A-4.

Example 629

Compound J-1

3-[(5-Chloro-2-ethylsulfonylphenyl)methyl]-8-methyl-7-[[(3S)-3-(methylamino)piperidin-1-yl]methyl]-6-(trifluoromethyl)-1H-quinazoline-2,4-dione

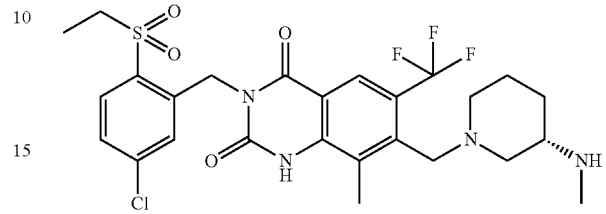

The title compound was synthesized from tert-butyl N-[(3S)-1-[[3-[(5-chloro-2-ethylsulfonylphenyl)methyl]-8-methyl-2,4-dioxo-6-(trifluoromethyl)-1H-quinazolin-7-yl]methyl]piperidin-3-yl]-N-methylcarbamate (Compound j5) under the same conditions as for Compound a41.

LCMS: m/z 587 [M+H]$^+$

HPLC retention time: 0.56 min (analysis condition D)

Example 630

Compound j6

Ethyl 2-amino-3-ethenyl-4-formyl-5-(trifluoromethyl)benzoate

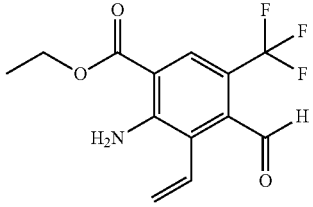 [SMILES: C=Cc1c(N)c(C(=O)OCC)cc(C(F)(F)F)c1C=O]

The title compound was synthesized from ethyl 2-amino-3-bromo-4-formyl-5-(trifluoromethyl)benzoate (Compound h6) under the same conditions as for Compound 21.

Example 631

Compound j7

Ethyl 2-amino-3-ethenyl-4-[[(3S)-3-[methyl-[(2-methylpropan-2-yl)oxycarbonyl]amino]piperidin-1-yl]methyl]-5-(trifluoromethyl)benzoate

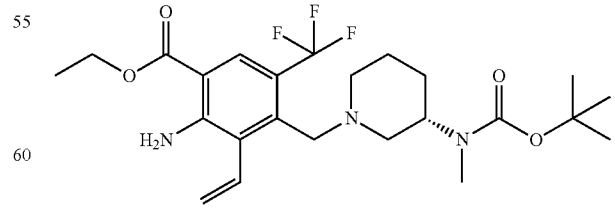

The title compound was synthesized from ethyl 2-amino-3-ethenyl-4-formyl-5-(trifluoromethyl)benzoate (Compound j6) under the same conditions as for Compound b12. However, tert-butyl N-methyl-N-[(3S)-piperidin-3-yl]car-

Example 632

Compound J-2

3-[(5-Chloro-2-ethylsulfonylphenyl)methyl]-8-ethenyl-7-[[(3S)-3-(methylamino)piperidin-1-yl]methyl]-6-(trifluoromethyl)-1H-quinazoline-2,4-dione

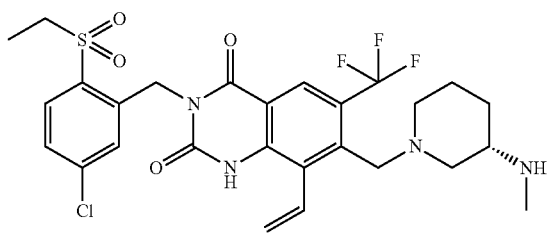 [SMILES: C=Cc1c(CN2CCC[C@H](NC)C2)c(C(F)(F)F)cc2c(=O)n(Cc3cc(Cl)ccc3S(=O)(=O)CC)c(=O)[nH]c12]

The title compound was synthesized from ethyl 2-amino-3-ethenyl-4-[[(3S)-3-[methyl-[(2-methylpropan-2-yl)oxycarbonyl]amino]piperidin-1-yl]methyl]-5-(trifluoromethyl)benzoate (Compound j7) under the same conditions as for Compounds j3, j4, j5 and J-1.

LCMS: m/z 599 [M+H]$^+$

HPLC retention time: 0.57 min (analysis condition D)

Example 633

Compound j8

Ethyl 2-amino-3-ethyl-4-[[(3S)-3-[methyl-[(2-methylpropan-2-yl)oxycarbonyl]amino]piperidin-1-yl]methyl]-5-(trifluoromethyl)benzoate

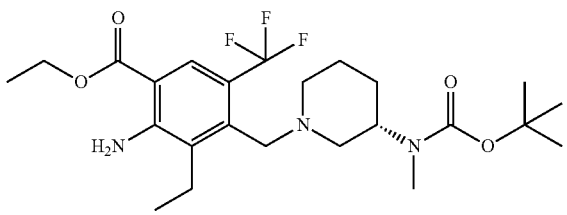 [SMILES: CCOC(=O)c1cc(C(F)(F)F)c(CN2CCC[C@H](N(C)C(=O)OC(C)(C)C)C2)c(CC)c1N]

10% palladium on carbon (6.95 mg) was added to a solution of ethyl 2-amino-3-ethenyl-4-[[(3S)-3-[methyl-[(2-methylpropan-2-yl)oxycarbonyl]amino]piperidin-1-yl]methyl]-5-(trifluoromethyl)benzoate (Compound j7, 72.1 mg, 0.148 mmol) in EtOAc (3.5 ml) at room temperature, and it was stirred at room temperature for 14 hours under hydrogen atmosphere. The palladium was removed by filtration through celite, followed by washing with ethyl acetate. The filtrate and the washings were concentrated under reduced pressure to yield the title compound (69.8 mg, 96%) as a pale yellow oily substance.

LCMS: m/z 488 [M+H]$^+$

HPLC retention time: 0.82 min (analysis condition K)

Example 634

Compound J-3

3-[(5-Chloro-2-ethylsulfonylphenyl)methyl]-8-ethyl-7-[[(3S)-3-(methylamino)piperidin-1-yl]methyl]-6-(trifluoromethyl)-1H-quinazoline-2,4-dione

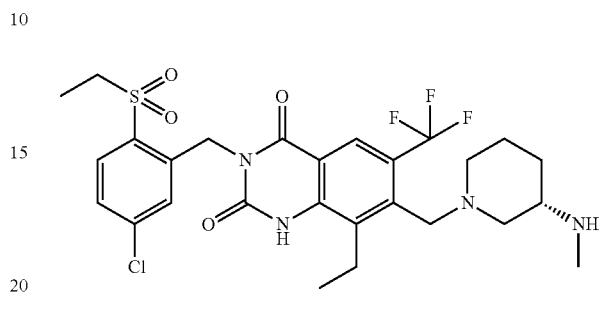

The title compound was synthesized from ethyl 2-amino-3-ethyl-4-[[(3S)-3-[methyl-[(2-methylpropan-2-yl)oxycarbonyl]amino]piperidin-1-yl]methyl]-5-(trifluoromethyl)benzoate (Compound j8) under the same conditions as for Compounds j3, j4, j5 and J-1.

LCMS: m/z 601 [M+H]$^+$

HPLC retention time: 0.58 min (analysis condition D)

Example 635

Sodium methoxide (10.6 mg, 0.196 mmol) was added to a solution of (S)-8-bromo-3-(5-chloro-2-(ethylsulfonyl)benzyl)-7-((3-(methylamino)piperidin-1-yl)methyl)-6-(trifluoromethyl)quinazoline-2,4(1H,3H)-dione (Compound H-12, 42.4 mg, 0.0650 mmol) in MeOH (3.5 ml) at room temperature, and it was stirred at 120° C. under microwave irradiation for 30 minutes. After it was cooled to room temperature, sodium methoxide (21.0 mg, 0.389 mmol) was further added, followed by 30 minutes of stirring at 145° C. under microwave irradiation. After the mixture was cooled to room temperature again, followed by addition of sodium methoxide (21.0 mg, 0.389 mmol), and it was stirred at 170° C. under microwave irradiation for 30 minutes. After the reaction mixture was cooled to room temperature, ethyl acetate was added, and the organic layer was washed with water and brine and then dried over anhydrous sodium sulfate. The drying agent was removed by filtration, followed by concentration under reduced pressure. The resultant residue was purified by preparative HPLC (water/acetonitrile, 0.05% TFA) to yield 3-[(5-chloro-2-ethylsulfonylphenyl)methyl]-8-methoxy-7-[[(3S)-3-(methylamino)piperidin-1-yl]methyl]-6-(trifluoromethyl)-1H-quinazoline-2,4-dione (Compound J-4, 3.8 mg, 10%), 8-bromo-3-[(2-ethylsulfonyl-5-methoxyphenyl)methyl]-7-[[(3S)-3-(methylamino)piperidin-1-yl]methyl]-6-(trifluoromethyl)-1H-quinazoline-2,4-dione (Compound J-5, 19.3 mg, 46%) and 3-[(2-ethylsulfonyl-5-methoxyphenyl)methyl]-8-methoxy-7-[[(3S)-3-(methylamino)piperidin-1-yl]methyl]-6-(trifluoromethyl)-1H-quinazoline-2,4-dione (Compound J-6, 5.1 mg, 13%) as colorless foamy substances.

Compound J-4

3-[(5-Chloro-2-ethylsulfonylphenyl)methyl]-8-methoxy-7-[[(3S)-3-(methylamino)piperidin-1-yl]methyl]-6-(trifluoromethyl)-1H-quinazoline-2,4-dione

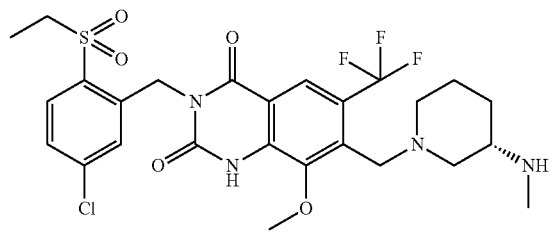 [SMILES: CCS(=O)(=O)c1ccc(Cl)cc1Cn1c(=O)[nH]c2c(OC)c(CN3CCC[C@H](NC)C3)c(C(F)(F)F)cc2c1=O]

LCMS: m/z 603 [M+H]$^+$
HPLC retention time: 0.59 min (analysis condition D)

Compound J-5

8-Bromo-3-[(2-ethylsulfonyl-5-methoxyphenyl)methyl]-7-[[(3S)-3-(methylamino)piperidin-1-yl]methyl]-6-(trifluoromethyl)-1H-quinazoline-2,4-dione

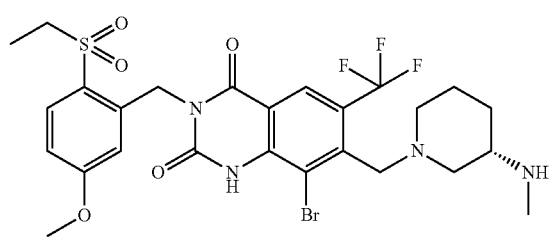 [SMILES: CCS(=O)(=O)c1ccc(OC)cc1Cn1c(=O)[nH]c2c(Br)c(CN3CCC[C@H](NC)C3)c(C(F)(F)F)cc2c1=O]

LCMS: m/z 647 [M+H]$^+$
HPLC retention time: 0.54 min (analysis condition D)

Compound J-6

3-[(2-Ethylsulfonyl-5-methoxyphenyl)methyl]-8-methoxy-7-[[(3S)-3-(methylamino)piperidin-1-yl]methyl]-6-(trifluoromethyl)-1H-quinazoline-2,4-dione

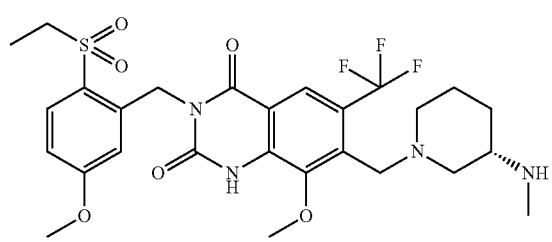 [SMILES: CCS(=O)(=O)c1ccc(OC)cc1Cn1c(=O)[nH]c2c(OC)c(CN3CCC[C@H](NC)C3)c(C(F)(F)F)cc2c1=O]

LCMS: m/z 599 [M+H]$^+$
HPLC retention time: 0.50 min (analysis condition D)

Example 636

Compound J-7

3-[(5-Chloro-2-ethylsulfonylphenyl)methyl]-7-[[(3S)-3-(methylamino)piperidin-1-yl]methyl]-2,4-dioxo-6-(trifluoromethyl)-1H-quinazoline-8-carbonitrile

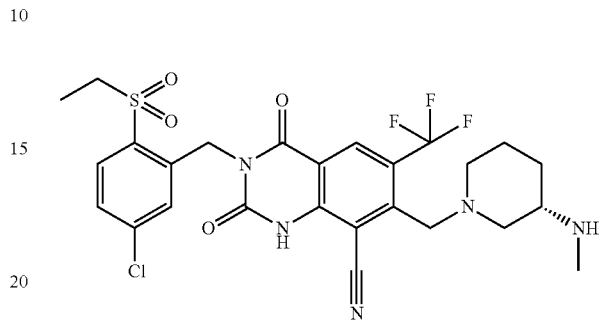

Copper(I) cyanide (12.6 mg, 0.141 mmol) was added to a solution of (S)-8-bromo-3-(5-chloro-2-(ethylsulfonyl)benzyl)-7-((3-(methylamino)piperidin-1-yl)methyl)-6-(trifluoromethyl)quinazoline-2,4(1H,3H)-dione (Compound H-12, 70.8 mg, 0.109 mmol) in DMF (1.5 ml), and it was irradiated with microwaves and stirred at 130 to 150° C. for 20 minutes. After the reaction mixture was cooled to room temperature, it was purified by preparative HPLC (water/acetonitrile, 0.05% TFA) to yield the title compound (25.4 mg, 39%) as a pale yellow foamy substance.

LCMS: m/z 598 [M+H]$^+$
HPLC retention time: 0.57 min (analysis condition K)

Example 637

Compound k1

N-(2-Bromo-5-chloro-4-methylphenyl)acetamide

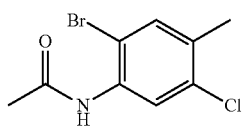

A solution of 3-chloro-4-methylaniline (5.00 g, 35.3 mmol) and pyridine (4.30 ml, 53.0 mmol) in EtOAc (35 ml) was cooled to 0° C., followed by addition of acetic anhydride (5.00 ml, 53.0 mmol), and it was stirred at room temperature for two hours. After addition of ethyl acetate to the reaction mixture and four washes with a 1 N aqueous hydrochloric acid solution, the organic layer was dried over anhydrous magnesium sulfate. The drying agent was removed by filtration, followed by concentration under reduced pressure to yield a crude product of N-(3-chloro-4-methylphenyl)acetamide. The resultant crude product in acetic acid solution (35 ml) was cooled to 0° C., followed by addition of a solution of bromine (3.40 ml, 67.1 mmol) in acetic acid (3.4 ml), and it was stirred at room temperature for 20 hours. Followed by addition of DCM to the reaction mixture, and sequential washing with a saturated aqueous solution of sodium bicarbonate, water and a saturated aqueous sodium thiosulfate solution, the organic layer was dried over anhydrous magnesium sulfate. The drying agent was removed by filtration, followed by concentration under reduced pressure. The resultant solid was recrystallized from a mixed solvent of DCM and n-hexane to yield the title compound (7.90 g, 85%, two steps) as a colorless solid.

1H-NMR (400 MHz, CDCl$_3$) δ: 8.40 (1H, s), 7.49 (1H, brs), 7.39 (1H, s), 2.31 (3H, s), 2.23 (3H, s).

Example 638

Compound k2

2-Acetamido-4-chloro-5-methylbenzoic acid

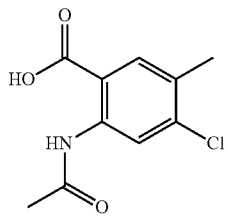

A solution of N-(2-bromo-5-chloro-4-methylphenyl)acetamide (Compound k1, 7.90 g, 30.1 mmol) in THF (150 ml) was cooled to −78° C., followed by addition of a n-butyllithium/n-hexane solution (41.4 ml, 66.2 mmol), and it was stirred for 30 minutes under nitrogen atmosphere. The reaction mixture was bubbled with carbon dioxide gas and then stirred at room temperature for 15 hours. After addition of DCM to the reaction solution which was made acidic by adding a 1 N aqueous hydrochloric acid solution, the organic layer was separated. The organic layer was concentrated under reduced pressure, and the resultant solid was washed with DCM to yield the title compound (2.50 g, 37%) as a pale brown solid.

LCMS: m/z 228 [M+H]$^+$
HPLC retention time: 1.28 min (analysis condition J)

Example 639

Compound k3

2-Amino-4-chloro-5-methylbenzoic acid

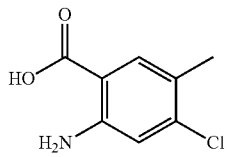

Sodium hydroxide (2.24 g, 56.0 mmol) was added to a solution of 2-acetamido-4-chloro-5-methylbenzoic acid (Compound k2, 2.55 g, 11.2 mmol) in water (12 ml), and it was stirred for 15 hours under reflux. The reaction mixture was cooled to room temperature, and the pH of the solution was then adjusted from 4 to 5 with a 35% aqueous solution of hydrochloric acid. The precipitated solid was collected by filtration and then washed with water to yield the title compound (1.89 g, 91%) as a yellow solid.

1H-NMR (400 MHz, DMSO-d$_6$) δ: 7.63 (1H, s), 6.83 (1H, s), 2.17 (3H, s).

Example 640

Compound k4

Ethyl 2-amino-4-chloro-5-methylbenzoate

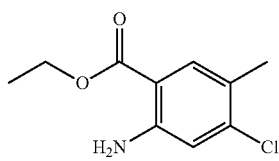

The title compound was synthesized from 2-amino-4-chloro-5-methylbenzoic acid (Compound k3) under the same conditions as for Compound B-3.

Example 641

Compound k5

Ethyl 2-amino-4-formyl-5-methylbenzoate

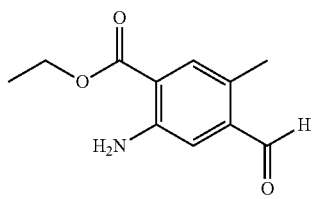

The title compound was synthesized from ethyl 2-amino-4-chloro-5-methylbenzoate (Compound k4) under the same conditions as for Compounds 21, 22, and 23. However, under the Compound 22 conditions, AD-mix-β was used in place of AD-mix-α.

Example 642

Compound k6

Ethyl 2-amino-4-(1,3-dioxolan-2-yl)-5-methylbenzoate

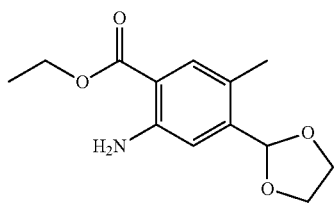 [SMILES: CCOC(=O)c1cc(C)c(C2OCCO2)cc1N]

The title compound was synthesized from ethyl 2-amino-4-formyl-5-methylbenzoate (Compound k5) under the same conditions as for Compound 34. However, the reaction was performed under reflux.

Example 643

Compound k7

Ethyl 2-amino-3-chloro-4-formyl-5-methylbenzoate

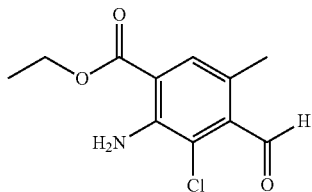 [SMILES: CCOC(=O)c1cc(C)c(C=O)c(Cl)c1N]

The title compound was synthesized from ethyl 2-amino-4-(1,3-dioxolan-2-yl)-5-methylbenzoate (Compound k6) under the same conditions as for Compound 24. However, the reaction was performed at a temperature of 65° C.

Example 644

Compound k8

Ethyl 2-amino-3-chloro-5-methyl-4-[[(3R)-3-[(2-methylpropan-2-yl)oxycarbonylamino]piperidin-1-yl]methyl]benzoate

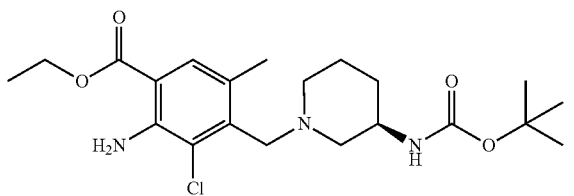 [SMILES: CCOC(=O)c1cc(C)c(CN2CCC[C@@H](NC(=O)OC(C)(C)C)C2)c(Cl)c1N]

The title compound was synthesized from ethyl 2-amino-3-chloro-4-formyl-5-methylbenzoate (Compound k7) under the same conditions as for Compound b12. However, tert-butyl N-[(3R)-piperidin-3-yl]carbamate was used in place of tert-butyl (S)-pyrrolidin-3-yl-carbamate. DCM was used in place of THF as a solvent.

Example 645

Compound k9

2-Amino-3-chloro-5-methyl-4-[[(3R)-3-[(2-methyl-propan-2-yl)oxycarbonylamino]piperidin-1-yl]methyl]benzoic acid

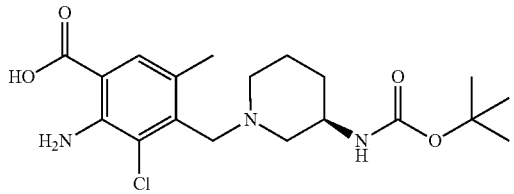 [SMILES: Cc1cc(C(=O)O)c(N)c(Cl)c1CN1CCC[C@@H](NC(=O)OC(C)(C)C)C1]

The title compound was synthesized from ethyl 2-amino-3-chloro-5-methyl-4-[[(3R)-3-[(2-methylpropan-2-yl)oxycarbonylamino]piperidin-1-yl]methyl]benzoate (Compound k8) under the same conditions as for Compound 25.

Example 646

Compound k10 tert-Butyl N-[(3R)-1-[[3-amino-2-chloro-4-[(5-chloro-2-ethylsulfonylphenyl)methylcarbamoyl]-6-methylphenyl]methyl]piperidin-3-yl]carbamate

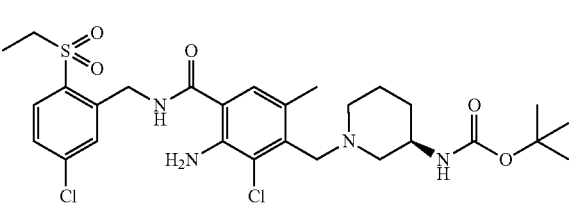 [SMILES: CCS(=O)(=O)c1ccc(Cl)cc1CNC(=O)c1cc(C)c(CN2CCC[C@@H](NC(=O)OC(C)(C)C)C2)c(Cl)c1N]

The title compound was synthesized from 5-chloro-2-ethanesulfonyl-benzylamine hydrochloride (Compound 3) under the same conditions as for Compound 26. However, 2-amino-3-chloro-5-methyl-4-[[(3R)-3-[(2-methylpropan-2-yl)oxycarbonylamino]piperidin-1-yl]methyl]benzoic acid (Compound k9) was used in place of 2-amino-3-chloro-4-formyl-5-trifluoromethyl-benzoic acid (Compound 25), and DMF was used in place of DCM as a solvent.

Example 647

Compound k1 tert-Butyl N-[(3R)-1-[[8-chloro-3-[(5-chloro-2-ethylsulfonylphenyl)methyl]-6-methyl-2,4-dioxo-1H-quinazolin-7-yl]methyl]piperidin-3-yl]carbamate

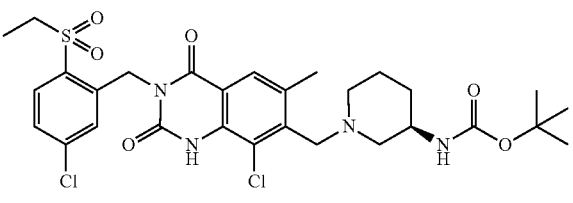 [SMILES: CCS(=O)(=O)c1ccc(Cl)cc1Cn1c(=O)[nH]c2c(Cl)c(CN3CCC[C@@H](NC(=O)OC(C)(C)C)C3)c(C)cc2c1=O]

The title compound was synthesized from tert-butyl N-[(3R)-1-[[3-amino-2-chloro-4-[(5-chloro-2-ethylsulfonylphenyl)methylcarbamoyl]-6-methylphenyl]methyl]piperidin-3-yl]carbamate (Compound k10) under the same conditions as for Compound 37.

Example 648

Compound K-1

7-[[(3R)-3-Aminopiperidin-1-yl]methyl]-8-chloro-3-[(5-chloro-2-ethylsulfonylphenyl)methyl]-6-methyl-1H-quinazoline-2,4-di one

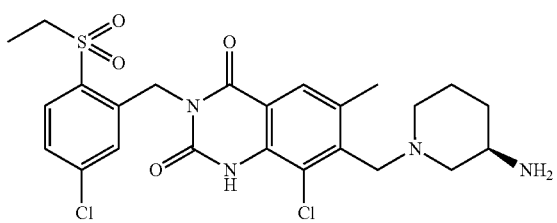 [SMILES: CCS(=O)(=O)c1ccc(Cl)cc1Cn1c(=O)[nH]c2c(Cl)c(CN3CCC[C@@H](N)C3)c(C)cc2c1=O]

The title compound was synthesized from tert-butyl N-[(3R)-1-[[8-chloro-3-[(5-chloro-2-ethylsulfonylphenyl)methyl]-6-methyl-2,4-dioxo-1H-quinazolin-7-yl]methyl]piperidin-3-yl]carbamate (Compound k11) under the same conditions as for Compound a41.

LCMS: m/z 539 [M+H]$^+$

HPLC retention time: 0.49 min (analysis condition K)

Example 649

Compound k12

Ethyl 2-amino-4-methylbenzoate

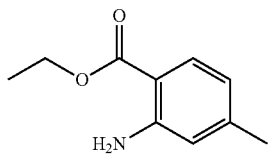

The title compound was synthesized from 2-amino-4-methylbenzoic acid under the same conditions as for Compound B-3.

Example 650

Compound k13

Ethyl 2-amino-5-bromo-4-methylbenzoate

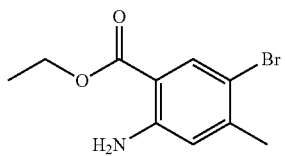

The title compound was synthesized from ethyl 2-amino-4-methylbenzoate (Compound k12) under the same conditions as for Compound 24. However, NBS was used in place of NCS. The reaction was performed at room temperature.

Example 651

Compound k14

Ethyl 2-[bis[(2-methylpropan-2-yl)oxycarbonyl]amino]-5-bromo-4-methylbenzoate

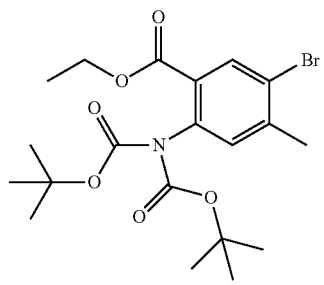 [SMILES: CCOC(=O)c1cc(Br)c(C)cc1N(C(=O)OC(C)(C)C)C(=O)OC(C)(C)C]

The title compound was synthesized from ethyl 2-amino-5-bromo-4-methylbenzoate (Compound k13) under the same conditions as for Compound 17. However, triethylamine was not added.

Example 652

Compound k15

Ethyl 2-[bis[(2-methylpropan-2-yl)oxycarbonyl]amino]-5-bromo-4-(dibromomethyl)benzoate

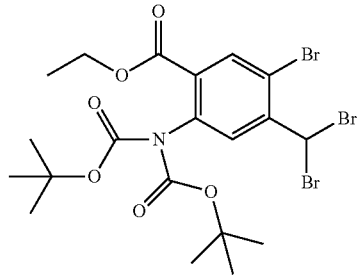 [SMILES: CCOC(=O)c1cc(Br)c(C(Br)Br)cc1N(C(=O)OC(C)(C)C)C(=O)OC(C)(C)C]

The title compound was synthesized from ethyl 2-[bis[(2-methylpropan-2-yl)oxycarbonyl]amino]-5-bromo-4-methylbenzoate (Compound k14) under the same conditions as for Compound 12.

Example 653

Compound k16

Ethyl 2-amino-5-bromo-4-(1,3-dioxolan-2-yl)benzoate

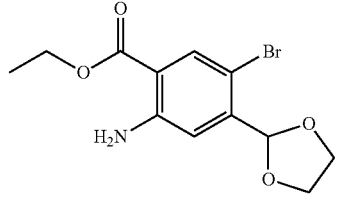 [SMILES: CCOC(=O)c1cc(Br)c(C2OCCO2)cc1N]

Silver(I) nitrate (27.9 g, 164 mmol) was added to a mixed solution of ethyl 2-[bis[(2-methylpropan-2-yl)oxycarbonyl]

amino]-5-bromo-4-(dibromomethyl)benzoate (Compound k15, 20.3 g, 32.9 mmol) in water/acetone (330 ml, 1:2). After one hour of stirring at 65° C., the reaction mixture was extracted with ethyl acetate. The organic layer was sequentially washed with water and brine, and then dried over anhydrous sodium sulfate. The drying agent was removed by filtration, followed by concentration under reduced pressure to yield a mixture of ethyl 2-[bis[(2-methylpropan-2-yl)oxycarbonyl]amino]-5-bromo-4-formylbenzoate and ethyl 2-[(2-methylpropan-2-yl)oxycarbonylamino]-5-bromo-4-formylbenzoate (15.4 g) as a pale yellow solid. Ethylene glycol (0.9 ml, 161 mmol) and p-toluenesulfonic acid (627 mg, 3.29 mmol) were added to a solution of the resultant crude product in toluene (330 ml), followed by stirring under reflux for 15 hours. The reaction mixture was made basic by adding a saturated aqueous solution of sodium bicarbonate, followed by extraction with ethyl acetate. The organic layer was washed with brine, and then dried over anhydrous magnesium sulfate. The drying agent was removed by filtration, followed by concentration under reduced pressure. The resultant residue was purified by silica gel column chromatography (ethyl acetate/n-hexane) to yield the title compound (3.50 g, 34%) as a yellow solid.

1H-NMR (400 MHz, DMSO-$d_6$) δ: 8.03 (1H, s), 6.93 (1H, s), 5.98 (1H, s), 5.78 (2H, brs), 4.33 (2H, q, J=7.1 Hz), 4.05-4.15 (4H, m), 1.39 (3H, t, J=7.1 Hz).

Example 654

Compound k17

Ethyl 2-amino-4-(1,3-dioxolan-2-yl)-5-ethenylbenzoate

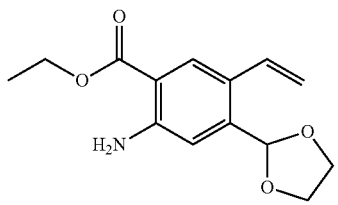 [SMILES: C=Cc1cc(C(=O)OCC)c(N)cc1C1OCCO1]

Tri-n-butyl(ethenyl)tin (1.11 ml, 3.80 mmol) was added to a solution of ethyl 2-amino-5-bromo-4-(1,3-dioxolan-2-yl)benzoate (Compound k16, 1.00 g, 3.16 mmol), tris(dibenzylideneacetone)dipalladium (145 mg, 0.160 mmol) and tris(2-methylphenyl)phosphine (97.0 mg, 0.320 mmol) in acetonitrile (32 ml), and it was stirred at 90° C. for 15 hours. The reaction mixture was cooled to room temperature, and EtOAc was added. After washing with brine, the organic layer was dried over anhydrous magnesium sulfate. The drying agent was removed by filtration, followed by concentration under reduced pressure. The resultant residue was purified by silica gel column chromatography (EtOAc/n-hexane) to yield the title compound (615 mg, 74%) as a yellow solid.

LCMS: m/z 264 [M+H]$^+$

HPLC retention time: 1.59 min (analysis condition J)

Example 655

Compound k18

Ethyl 2-amino-4-(1,3-dioxolan-2-yl)-5-ethylbenzoate

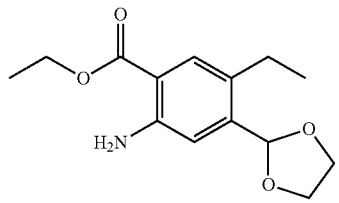 [SMILES: CCOC(=O)c1cc(CC)c(C2OCCO2)cc1N]

The title compound was synthesized from ethyl 2-amino-4-(1,3-dioxolan-2-yl)-5-ethenylbenzoate (Compound k17) under the same conditions as for Compound j8.

Example 656

Compound k19

Ethyl 2-amino-5-ethyl-4-formylbenzoate

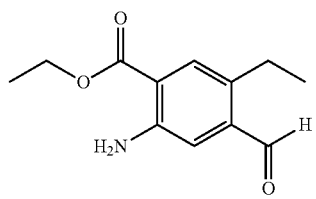 [SMILES: CCOC(=O)c1cc(CC)c(C=O)cc1N]

The title compound was synthesized from ethyl 2-amino-4-(1,3-dioxolan-2-yl)-5-ethylbenzoate (Compound k18) under the same conditions as for Compound 38. However, the reaction was carried out at room temperature.

Example 657

Compound k20 tert-Butyl N-[(3R)-1-[[8-chloro-3-[(5-chloro-2-ethylsulfonylphenyl)methyl]-6-ethyl-2,4-dioxo-1H-quinazolin-7-yl]methyl]piperidin-3-yl]carbamate

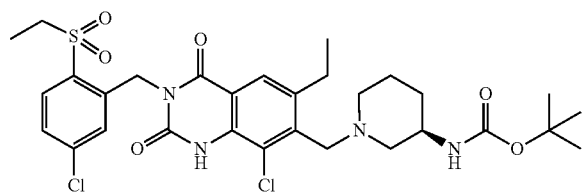 [SMILES: CCc1cc2c(=O)n(Cc3cc(Cl)ccc3S(=O)(=O)CC)c(=O)[nH]c2c(Cl)c1CN1CCC[C@@H](NC(=O)OC(C)(C)C)C1]

The title compound was synthesized from ethyl 2-amino-5-ethyl-4-formylbenzoate (Compound k19) under the same conditions as for Compounds k7, k8, k9, k10 and k11. However, under the Compound k7 conditions, the reaction was performed at room temperature; and under the Compound k8 conditions, chloroform was used in place of DCM as a solvent.

Example 658

Compound K-2

7-[[(3R)-3-Aminopiperidin-1-yl]methyl]-8-chloro-3-[(5-chloro-2-ethylsulfonylphenyl)methyl]-6-ethyl-1H-quinazoline-2,4-dione

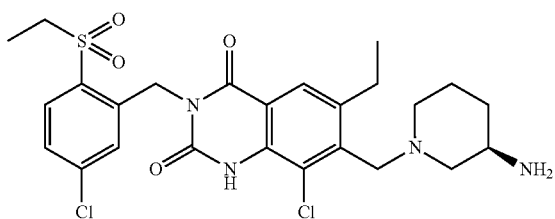 [SMILES: CCc1cc2c(=O)n(Cc3cc(Cl)ccc3S(=O)(=O)CC)c(=O)[nH]c2c(Cl)c1CN1CCC[C@@H](N)C1]

The title compound was synthesized from tert-butyl N-[(3R)-1-[[8-chloro-3-[(5-chloro-2-ethylsulfonylphenyl)methyl]-6-ethyl-2,4-dioxo-1H-quinazolin-7-yl]methyl]piperidin-3-yl]carbamate (Compound k20) under the same conditions as for Compound B-1.
LCMS: m/z 553 [M+H]$^+$
HPLC retention time: 0.52 min (analysis condition K)

Example 659

Compound k21

Ethyl 2-amino-4-formyl-5-bromobenzoate

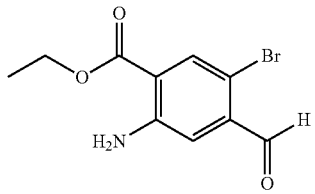

Silver(I) nitrate (9.70 g, 56.8 mmol) was added to a solution of ethyl 2-[bis[(2-methylpropan-2-yl)oxycarbonyl]amino]-5-bromo-4-(dibromomethyl)benzoate (Compound k15, 7.00 g, 11.4 mmol) in a mixture of water/acetone (112 ml, 1:2). After the reaction mixture was stirred at 65° C. for one hour, it was extracted with EtOAc. The organic layer was sequentially washed with water and brine, and then dried over anhydrous sodium sulfate. The drying agent was removed by filtration, followed by concentration under reduced pressure to yield a crude product which is obtained as a mixture of ethyl 2-[bis[(2-methylpropan-2-yl)oxycarbonyl]amino]-5-bromo-4-formylbenzoate and ethyl 2-[(2-methylpropan-2-yl)oxycarbonylamino]-5-bromo-4-formylbenzoate (3.53 g) as a pale brown solid. A 4 N hydrochloric acid/1,4-dioxane solution (9.4 ml) was added to a solution of the obtained crude product in DCM (94 ml), and it was stirred at room temperature for one hour. The reaction mixture was made basic by adding a saturated aqueous solution of sodium bicarbonate, followed by extraction with EtOAc. The organic layer was washed with brine, and then dried over anhydrous magnesium sulfate. The drying agent was removed by filtration, followed by concentration under reduced pressure. The resultant solid was recrystallized from a mixed solvent of DCM and n-hexane to yield the title compound (1.37 g, 51%, two steps) as a yellow solid.
LCMS: m/z 272 [M+H]$^+$
HPLC retention time: 1.79 min (analysis condition J)

Example 660

Compound k22

Ethyl 2-amino-5-bromo-3-chloro-4-formylbenzoate

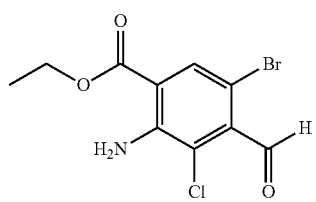 [SMILES: CCOC(=O)c1cc(Br)c(C=O)c(Cl)c1N]

The title compound was synthesized from ethyl 2-amino-4-formyl-5-bromobenzoate (Compound k21) under the same conditions as for Compound 24. However, the reaction was performed at room temperature.

Example 661

Compound k23

Ethyl 2-amino-3-chloro-5-ethenyl-4-formylbenzoate

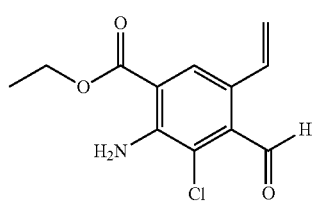 [SMILES: C=Cc1cc(C(=O)OCC)c(N)c(Cl)c1C=O]

The title compound was synthesized from ethyl 2-amino-5-bromo-3-chloro-4-formylbenzoate (Compound k22) under the same conditions as for Compound k17.

Example 662

Compound k24 tert-Butyl N-[(3R)-1-[[8-chloro-3-[(5-chloro-2-ethylsulfonylphenyl)methyl]-6-ethenyl-2,4-dioxo-1H-quinazolin-7-yl]methyl]piperidin-3-yl]carbamate

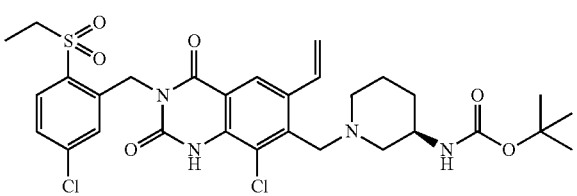 [SMILES: C=Cc1cc2c(=O)n(Cc3cc(Cl)ccc3S(=O)(=O)CC)c(=O)[nH]c2c(Cl)c1CN1CCC[C@@H](NC(=O)OC(C)(C)C)C1]

The title compound was synthesized from ethyl 2-amino-3-chloro-5-ethenyl-4-formylbenzoate (Compound k23) under the same conditions as for Compounds k8, k9, k10 and k11. However, under the Compound k8 conditions, chloroform was used in place of DCM as a solvent.

Example 663

Compound K-3

7-[[(3R)-3-Aminopiperidin-1-yl]methyl]-8-chloro-3-[(5-chloro-2-ethylsulfonylphenyl)methyl]-6-ethenyl-1H-quinazoline-2,4-dione

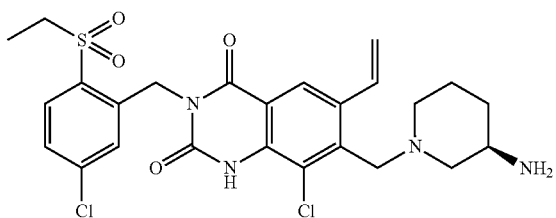 [SMILES: C=Cc1cc2c(=O)n(Cc3cc(Cl)ccc3S(=O)(=O)CC)c(=O)[nH]c2c(Cl)c1CN1CCC[C@@H](N)C1]

The title compound was synthesized from tert-butyl N-[(3R)-1-[[8-chloro-3-[(5-chloro-2-ethylsulfonylphenyl)methyl]-6-ethenyl-2,4-dioxo-1H-quinazolin-7-yl]methyl]piperidin-3-yl]carbamate (Compound k24) under the same conditions as for Compound a41. However, 1,4-dioxane was used in place of ethyl acetate as a solvent.
LCMS: m/z 551 [M+H]$^+$
HPLC retention time: 0.53 min (analysis condition K)

Example 664

Compound 11

4-Chloro-2-iodo-6-methylaniline

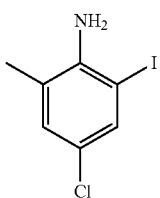

NIS (2.95 g, 13.1 mmol) was added to a solution of 4-chloro-2-methylaniline (1.69 g, 12.0 mmol) in DMF (27 ml), and it was stirred at room temperature for 1.5 hours under nitrogen atmosphere. NIS (738 mg, 3.28 mmol) was added, followed by another 1.5 hours of stirring. Water was added to the reaction mixture, followed by extraction with ethyl acetate. The organic layer was then washed with a saturated aqueous sodium thiosulfate solution, and dried over anhydrous magnesium sulfate. The drying agent was removed by filtration, followed by concentration under reduced pressure. The resultant residue was purified by silica gel column chromatography (ethyl acetate/hexane) to yield the title compound (1.51 g, 47%) as a pale brown solid.
LCMS: m/z 268 [M+H]$^+$
HPLC retention time: 2.68 min (analysis condition C)

Example 665

Compound 12

2-Amino-5-chloro-3-methylbenzonitrile

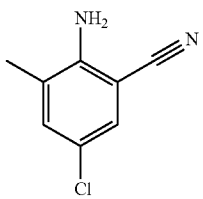

The title compound was synthesized from 4-chloro-2-iodo-6-methylaniline (Compound 11) under the same conditions as for Compound ff17. However, the reaction was performed at a temperature of 150 to 160° C.

Example 666

Compound 13

5-Chloro-2-iodo-3-methylbenzonitrile

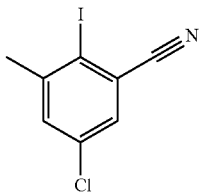

The title compound was synthesized from 2-amino-5-chloro-3-methylbenzonitrile (Compound 12) under the same conditions as for Compound ff18.

Example 667

Compound 14

5-Chloro-2-ethylsulfanyl-3-methylbenzonitrile

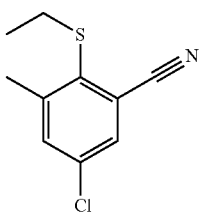

The title compound was synthesized from 5-chloro-2-iodo-3-methylbenzonitrile (Compound 13) under the same conditions as for Compound ff11. However, the reaction was performed at a temperature of 80° C.

Example 668

Compound 15

(5-Chloro-2-ethylsulfanyl-3-methylphenyl)methanamine 2,2,2-trifluoroacetate

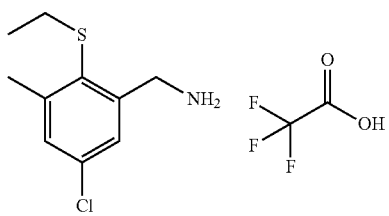

A solution of 5-chloro-2-ethylsulfanyl-3-methylbenzonitrile (Compound 14, 95.4 mg, 0.450 mmol) in THF (2 ml) was added to a solution of lithium aluminum hydride (27.5 mg, 0.579 mmol) in THF (4.5 ml) under ice-cooling, and it was warmed to room temperature and stirred for five hours under nitrogen atmosphere. Lithium aluminum hydride (35.8 mg, 0.754 mmol) was further added under ice-cooling, and the mixture was warmed to room temperature and stirred for 2.5 hours under nitrogen atmosphere. Water (25 μl), a 5 N aqueous sodium hydroxide solution (25 μl), THF (600 μl) and water (60 μl) were added to the reaction suspension under ice-cooling, followed by 30 minutes of stirring and removal of the insoluble matter by filtration through celite, and it was washed with THF. The filtrate was concentrated under reduced pressure, and the resultant residue was purified by preparative HPLC (water/acetonitrile, 0.05% TFA) to yield the title compound (69.3 mg, 47%) as a colorless solid.

LCMS: m/z 216 [M+H]$^+$

HPLC retention time: 0.44 min (analysis condition K)

Example 669

Compound 16

(5-Chloro-2-ethylsulfonyl-3-methylphenyl)methanamine hydrochloride

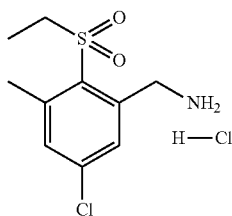

The title compound was synthesized from (5-chloro-2-ethylsulfanyl-3-methylphenyl)methanamine 2,2,2-trifluoroacetate (Compound 15) under the same conditions as for Compound ff13.

Example 670

Compound 17 tert-Butyl N-[(3R)-1-[[3-amino-2-chloro-4-[(5-chloro-2-ethylsulfonyl-3-methylphenyl)methylcarbamoyl]-6-(trifluoromethyl)phenyl]methyl]piperidin-3-yl]carbamate

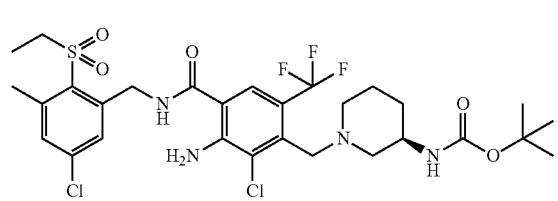 [SMILES: CCS(=O)(=O)c1c(C)cc(Cl)cc1CNC(=O)c1cc(C(F)(F)F)c(CN2CCC[C@@H](NC(=O)OC(C)(C)C)C2)c(Cl)c1N]

The title compound was synthesized from ((5-chloro-2-ethylsulfonyl-3-methylphenyl)methanamine hydrochloride (Compound 16) under the same conditions as for Compound ff14.

Example 671

Compound 18 tert-Butyl N-[(3R)-1-[[8-chloro-3-[(5-chloro-2-ethylsulfonyl-3-methylphenyl)methyl]-2,4-dioxo-6-(trifluoromethyl)-1H-quinazolin-7-yl]methyl]piperidin-3-yl]carbamate

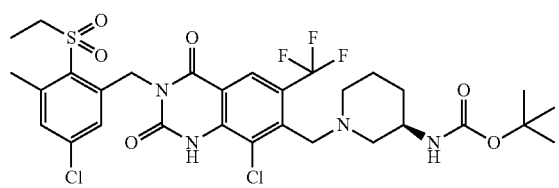 [SMILES: CCS(=O)(=O)c1c(C)cc(Cl)cc1Cn1c(=O)[nH]c2c(Cl)c(CN3CCC[C@@H](NC(=O)OC(C)(C)C)C3)c(C(F)(F)F)cc2c1=O]

The title compound was synthesized from tert-butyl N-[(3R)-1-[[3-amino-2-chloro-4-[(5-chloro-2-ethylsulfonyl-3-methylphenyl)methylcarbamoyl]-6-(trifluoromethyl)phenyl]methyl]piperidin-3-yl]carbamate (Compound 17) under the same conditions as for Compound A-4.

Example 672

Compound L-1

7-[[(3R)-3-Aminopiperidin-1-yl]methyl]-8-chloro-3-[(5-chloro-2-ethylsulfonyl-3-methylphenyl)methyl]-6-(trifluoromethyl)-1H-quinazoline-2,4-dione

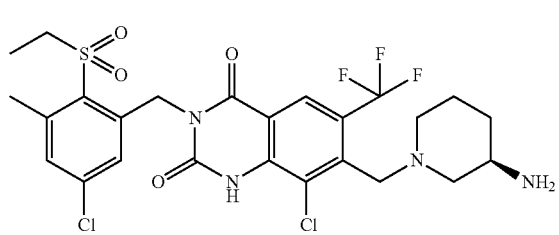 [SMILES: CCS(=O)(=O)c1c(C)cc(Cl)cc1Cn1c(=O)[nH]c2c(Cl)c(CN3CCC[C@@H](N)C3)c(C(F)(F)F)cc2c1=O]

The title compound was synthesized from tert-butyl N-[(3R)-1-[[8-chloro-3-[(5-chloro-2-ethylsulfonyl-3-methylphenyl)methyl]-2,4-dioxo-6-(trifluoromethyl)-1H-quinazolin-7-yl]methyl]piperidin-3-yl]carbamate (Compound 18) under the same conditions as for Compound a41.
LCMS: m/z 607 [M+H]$^+$
HPLC retention time: 0.59 min (analysis condition K)

Example 673

Compound L-2

N-[(3R)-1-[[8-Chloro-3-[(5-chloro-2-ethylsulfonyl-phenyl)methyl]-2,4-dioxo-6-(trifluoromethyl)-1H-quinazolin-7-yl]methyl]piperidin-3-yl]piperidine-4-carboxamide

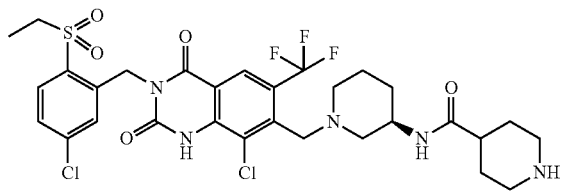 [SMILES: CCS(=O)(=O)c1ccc(Cl)cc1Cn1c(=O)[nH]c2c(Cl)c(CN3CCC[C@@H](NC(=O)C4CCNCC4)C3)c(C(F)(F)F)cc2c1=O]

The title compound was synthesized from 7-[[(3R)-3-aminopiperidin-1-yl]methyl]-8-chloro-3-[(5-chloro-2-ethyl-sulfonylphenyl)methyl]-6-(trifluoromethyl)-1H-quinazoline-2,4-dione (Compound F-54) under the same conditions as for Compound F-5. However, 1-[(2-methylpropan-2-yl)oxycarbonyl]piperidine-4-carboxylic acid was used in place of 2-[(2-methylpropan-2-yl)oxycarbonylamino]acetic acid, and HATU was used in place of HBTU.
LCMS: m/z 704 [M+H]$^+$
HPLC retention time: 0.49 min (analysis condition K)

Example 674

Compound L-3

4-Amino-N-[(3R)-1-[[8-chloro-3-[(5-chloro-2-ethyl-sulfonylphenyl)methyl]-2,4-dioxo-6-(trifluoromethyl)-1H-quinazolin-7-yl]methyl]piperidin-3-yl]butanamide

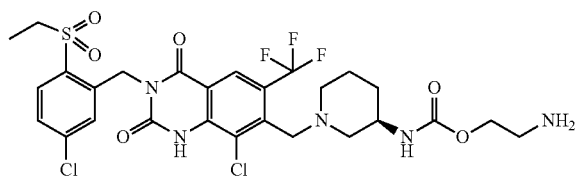 [SMILES: CCS(=O)(=O)c1ccc(Cl)cc1Cn1c(=O)[nH]c2c(Cl)c(CN3CCC[C@@H](NC(=O)OCCN)C3)c(C(F)(F)F)cc2c1=O]

The title compound was synthesized from 7-[[(3R)-3-aminopiperidin-1-yl]methyl]-8-chloro-3-[(5-chloro-2-ethyl-sulfonylphenyl)methyl]-6-(trifluoromethyl)-1H-quinazoline-2,4-dione (Compound F-54) under the same conditions as for Compound L-2. However, 4-[(2-methylpropan-2-yl)oxycarbonylamino]butanoic acid was used in place of 1-[(2-methylpropan-2-yl)oxycarbonyl]piperidine-4-carboxylic acid.
LCMS: m/z 678 [M+H]$^+$
HPLC retention time: 0.48 min (analysis condition K)

Example 675

Compound 19

Ethyl (3R)-1-[[8-chloro-3-[(5-chloro-2-ethylsulfonylphenyl)methyl]-2,4-dioxo-6-(trifluoromethyl)-1H-quinazolin-7-yl]methyl]piperidine-3-carboxylate

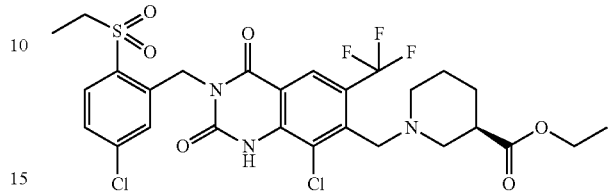

The title compound was synthesized from 8-chloro-3-[(5-chloro-2-ethylsulfonylphenyl)methyl]-2,4-dioxo-6-(trifluoromethyl)-1H-quinazoline-7-carbaldehyde (Compound F-45) under the same conditions as for Compound b12. However, ethyl (3R)-piperidine-3-carboxylate was used in place of tert-butyl N-[(3S)-pyrrolidin-3-yl]carbamate, and chloroform was used in place of THF as a solvent. The reaction was performed at a temperature of 0° C.

Example 676

Compound L-4

(3R)-1-[[8-Chloro-3-[(5-chloro-2-ethylsulfonylphenyl)methyl]-2, 4-dioxo-6-(trifluoromethyl)-1H-quinazolin-7-yl]methyl]piperidine-3-carboxylic acid

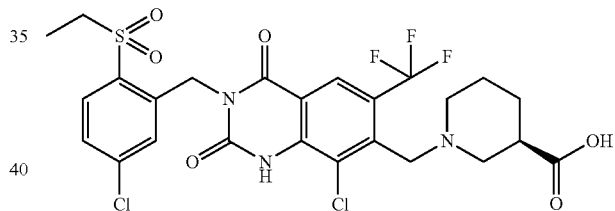

The title compound was synthesized from ethyl (3R)-1-[[8-chloro-3-[(5-chloro-2-ethylsulfonylphenyl)methyl]-2,4-dioxo-6-(trifluoromethyl)-1H-quinazolin-7-yl]methyl]piperidine-3-carboxylate (Compound 19) under the same conditions as for Compound 25.
LCMS: m/z 622 [M+H]$^+$
HPLC retention time: 0.60 min (analysis condition K)

Example 677

Compound L-5

(3R)-1-[[8-Chloro-3-[(5-chloro-2-ethylsulfonylphenyl)methyl]-2,4-dioxo-6-(trifluoromethyl)-1 H-quinazolin-7-yl]methyl]-N-[2-(dimethylamino)ethyl]piperidine-3-carboxamide

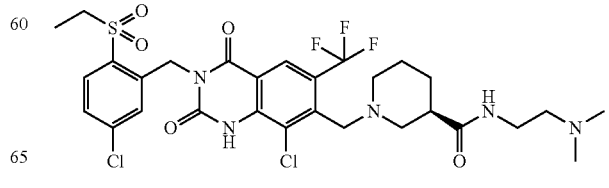

N',N'-Dimethylethane-1,2-diamine (9.3 mg, 0.106 mmol) and DIPEA (46 j L, 0.266 mmol) were added to a solution of (3R)-1-[[8-chloro-3-[(5-chloro-2-ethylsulfonylphenyl)methyl]-2,4-dioxo-6-(trifluoromethyl)-1H-quinazolin-7-yl]methyl]piperidine-3-carboxylic acid (Compound L-4, 55 mg, 0.084 mmol) and HATU (44 mg, 0.116 mmol) in acetonitrile (2 ml), and it was stirred at room temperature for 1.5 hours. Water was added to the reaction mixture, followed by extraction with EtOAc twice. The organic layers were combined, washed with brine, and then dried over anhydrous magnesium sulfate. The drying agent was removed by filtration, followed by concentration under reduced pressure. The resultant residue was purified by amino silica gel column chromatography (MeOH/DCM) to yield the title compound (36 mg, 65%) as a colorless solid.

LCMS: m/z 692 [M+H]⁺

HPLC retention time: 0.45 min (analysis condition K)

Example 678

Compound 110 tert-Butyl N-[2-[[(3R)-1-[[8-chloro-3-[(5-chloro-2-ethylsulfonylphenyl)methyl]-2,4-dioxo-6-(trifluoromethyl)-1H-quinazolin-7-yl]methyl]piperidine-3-carbonyl]amino]ethyl]carbamate

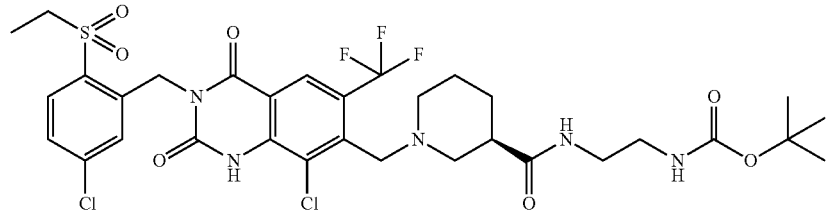 [SMILES: CCS(=O)(=O)c1ccc(Cl)cc1Cn1c(=O)[nH]c2c(Cl)c(CN3CCC[C@@H](C(=O)NCCNC(=O)OC(C)(C)C)C3)c(C(F)(F)F)cc2c1=O]

The title compound was synthesized from (3R)-1-[[8-chloro-3-[(5-chloro-2-ethylsulfonylphenyl)methyl]-2,4-dioxo-6-(trifluoromethyl)-1H-quinazolin-7-yl]methyl]piperidine-3-carboxylic acid (Compound L-4) under the same conditions as for Compound L-5. However, tert-butyl N-(2-aminoethyl)carbamate was used in place of N',N'-dimethylethane-1,2-diamine.

Example 679

Compound L-6

(3R)—N-(2-Aminoethyl)-1-[[8-chloro-3-[(5-chloro-2-ethylsulfonylphenyl)methyl]-2,4-dioxo-6-(trifluoromethyl)-1H-quinazolin-7-yl]methyl]piperidine-3-carboxamide

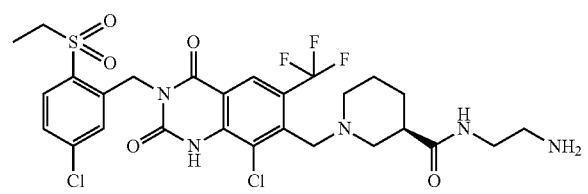 [SMILES: CCS(=O)(=O)c1ccc(Cl)cc1Cn1c(=O)[nH]c2c(Cl)c(CN3CCC[C@@H](C(=O)NCCN)C3)c(C(F)(F)F)cc2c1=O]

The title compound was synthesized from tert-Butyl N-[2-[[(3R)-1-[[8-chloro-3-[(5-chloro-2-ethylsulfonylphenyl)methyl]-2,4-dioxo-6-(trifluoromethyl)-1H-quinazolin-7-yl]methyl]piperidine-3-carbonyl]amino]ethyl]carbamate (Compound 110) under the same conditions as for Compound B-1.

LCMS: m/z 664 [M+H]⁺

HPLC retention time: 0.45 min (analysis condition K)

Example 680

Compound L-7

(3R)-1-[[8-Chloro-3-[(5-chloro-2-ethylsulfonylphenyl)methyl]-2, 4-dioxo-6-(trifluoromethyl)-1H-quinazolin-7-yl]methyl]-N-piperidin-4-ylpiperidine-3-carboxamide

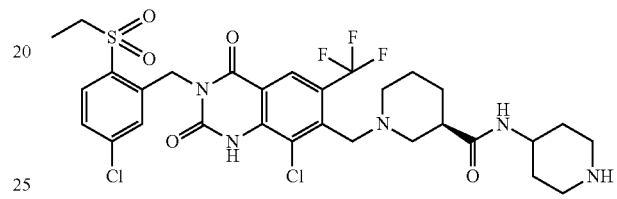

The title compound was synthesized from (3R)-1-[[8-chloro-3-[(5-chloro-2-ethylsulfonylphenyl)methyl]-2,4-dioxo-6-(trifluoromethyl)-1H-quinazolin-7-yl]methyl]piperidine-3-carboxylic acid (Compound L-4) under the same conditions as for Compounds 110 and L-6. However, under the Compound 110 conditions, tert-butyl 4-aminopiperidine-1-carboxylate was used in place of tert-butyl N-(2-aminoethyl)carbamate.

LCMS: m/z 704 [M+H]⁺

HPLC retention time: 0.45 min (analysis condition K)

Example 681

Compound m1 tert-Butyl N-[(5-chloro-2-phenylsulfanylphenyl)methyl]carbamate

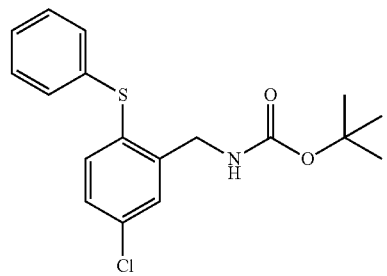 [SMILES: CC(C)(C)OC(=O)NCc1cc(Cl)ccc1Sc1ccccc1]

Boc₂O (454 mg, 2.08 mmol) and TEA (483 μl, 3.48 mmol) were added to a solution of (5-chloro-2-phenylsulfanylphenyl)methanamine (Compound ff8, 435 mg, 1.74 mmol) in THF (17 ml), and it was stirred at room temperature for 30 minutes. The reaction mixture was concentrated under reduced pressure, and the resultant residue was purified by silica gel column chromatography (ethyl acetate/n-hexane) to yield the title compound (510 mg, 84%).

1H-NMR (300 MHz, CDCl₃) δ: 7.17-7.42 (8H, m), 4.91 (1H, brs), 4.39 (2H, d, J=4.5 Hz), 1.44 (9H, s).

Example 682

Compound m2

(5-Chloro-2-phenylsulfanylphenyl)methanamine hydrochloride

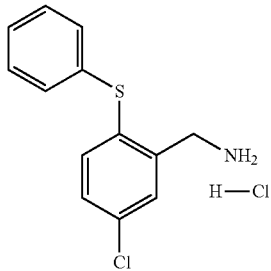

The title compound was synthesized from tert-butyl N-[(5-chloro-2-phenylsulfanylphenyl)methyl]carbamate (Compound m1) under the same conditions as for Compound a41. However, the reaction was performed at a temperature of 40° C.

Example 683

Compound m3

2-Amino-N-[(5-chloro-2-phenylsulfanylphenyl) methyl]-5-(trifluoromethyl)benzamide

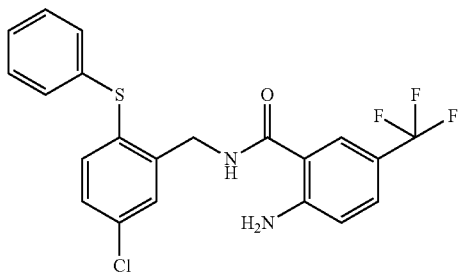 [SMILES: Nc1ccc(C(F)(F)F)cc1C(=O)NCc1cc(Cl)ccc1Sc1ccccc1]

The title compound was synthesized from (5-chloro-2-phenylsulfanylphenyl)methanamine hydrochloride (Compound m2) under the same conditions as for Compound 26. However, 2-amino-5-(trifluoromethyl)benzoic acid was used in place of 2-amino-3-chloro-4-formyl-5-(trifluoromethyl)benzoic acid (Compound 25).

Example 684

Compound M-1

3-[(5-chloro-2-phenylsulfanylphenyl)methyl]-6-(trifluoromethyl)-1H-quinazoline-2,4-dione

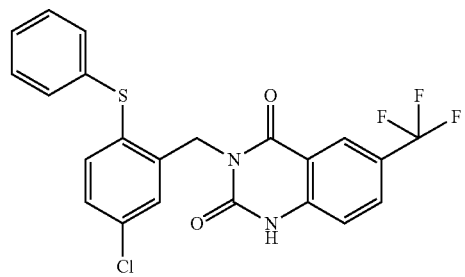 [SMILES: O=c1[nH]c2ccc(C(F)(F)F)cc2c(=O)n1Cc1cc(Cl)ccc1Sc1ccccc1]

The title compound was synthesized from 2-amino-N-[(5-chloro-2-phenylsulfanylphenyl)methyl]-5-(trifluoromethyl) benzamide (Compound m3) under the same conditions as for Compound 37.

LCMS: m/z 463 [M+H]⁺

HPLC retention time: 1.01 min (analysis condition K)

Example 685

Compound M-2

3-[[2-(Benzenesulfinyl)-5-chlorophenyl]methyl]-6-(trifluoromethyl)-1H-quinazoline-2,4-dione

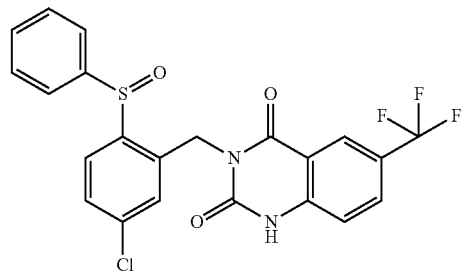 [SMILES: O=c1[nH]c2ccc(C(F)(F)F)cc2c(=O)n1Cc1cc(Cl)ccc1S(=O)c1ccccc1]

m-CPBA (5.8 mg, 0.026 mmol) was added to a solution of 3-[(5-chloro-2-phenylsulfanylphenyl)methyl]-6-(trifluoromethyl)-1H-quinazoline-2,4-dione (Compound M-1, 40 mg, 0.086 mmol) in EtOAc (1.6 ml) under ice-cooling. Two hours later, m-CPBA (5.8 mg, 0.026 mmol) was further added. Two hours later, m-CPBA (6.8 mg, 0.030 mmol) was added once again, and it was stirred under ice-cooling for two hours. The reaction mixture was allowed to pass through an amino silica gel and then concentrated under reduced pressure. The title compound (23.9 mg, 58%) was obtained by purifying the resultant residue by silica gel column chromatography (ethyl acetate/n-hexane).

LCMS: m/z 479 [M+H]⁺

HPLC retention time: 0.83 min (analysis condition K)

Example 686

Compound M-3

3-[(5-chloro-2-ethylsulfinylphenyl)methyl]-6-(trifluoromethyl)-1H-quinazoline-2,4-dione

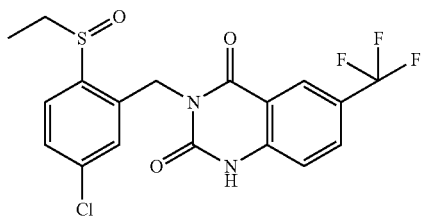 [SMILES: CCS(=O)c1ccc(Cl)cc1Cn1c(=O)[nH]c2ccc(C(F)(F)F)cc2c1=O]

The title compound was synthesized from (5-chloro-2-ethylsulfanylphenyl)methanamine (Compound 2) under the same conditions as for Compounds m1, m2, m3, M-1 and M-2.
LCMS: m/z 431 [M+H]$^+$
HPLC retention time: 0.73 min (analysis condition K)

Example 687

Compound m4

2-Ethylsulfanyl-5-(trifluoromethyl)benzonitrile

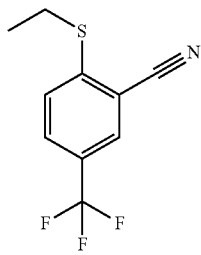

The title compound was synthesized from 2-fluoro-5-(trifluoromethyl)benzonitrile under the same conditions as for Compound 1.

Example 688

Compound m5

[2-Ethylsulfanyl-5-(trifluoromethyl)phenyl]methanamine

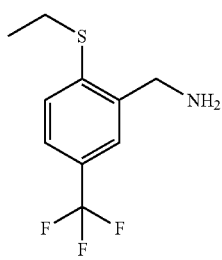

The title compound was synthesized from 2-ethylsulfanyl-5-(trifluoromethyl)benzonitrile (Compound m4) under the same conditions as for Compound 2.

Example 689

Compound m6

[2-Ethylsulfonyl-5-(trifluoromethyl)phenyl]methanamine hydrochloride

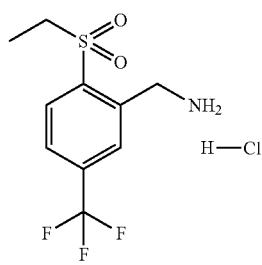

The title compound was synthesized from [2-ethylsulfanyl-5-(trifluoromethyl)phenyl]methanamine (Compound m5) under the same conditions as for Compound ff13.

Example 690

Compound m7

2-Amino-3-chloro-N-[[2-ethylsulfonyl-5-(trifluoromethyl)phenyl]methyl]-5-(trifluoromethyl)benzamide

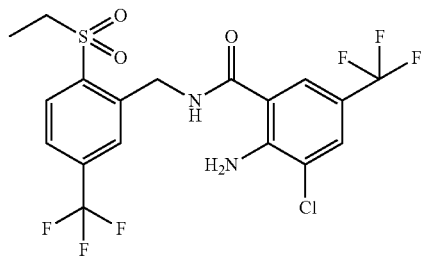 [SMILES: CCS(=O)(=O)c1ccc(C(F)(F)F)cc1CNC(=O)c1cc(C(F)(F)F)cc(Cl)c1N]

The title compound was synthesized from [2-ethylsulfonyl-5-(trifluoromethyl)phenyl]methanamine hydrochloride (Compound m6) under the same conditions as for Compound ff14. However, 2-amino-3-chloro-5-(trifluoromethyl)benzoic acid (Compound a19) was used in place of 2-amino-3-chloro-4-[[(3R)-3-[(2-methylpropan-2-yl)oxycarbonylamino]piperidin-1-yl]methyl]-5-(trifluoromethyl)benzoic acid (Compound ff2).

Example 691

Compound M-4

8-Chloro-3-[[2-ethylsulfonyl-5-(trifluoromethyl)phenyl]methyl]-6-(trifluoromethyl)-1H-quinazoline-2,4-dione

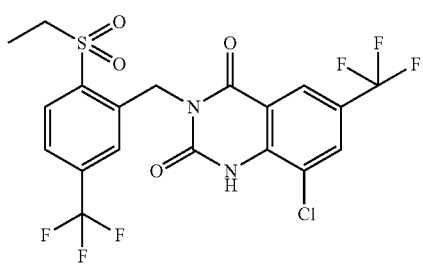 [SMILES: CCS(=O)(=O)c1ccc(C(F)(F)F)cc1Cn1c(=O)[nH]c2c(Cl)cc(C(F)(F)F)cc2c1=O]

The title compound was synthesized from 2-amino-3-chloro-N-[[2-ethylsulfonyl-5-(trifluoromethyl)phenyl]methyl]-5-(trifluoromethyl)benzamide (Compound m7) under the same conditions as for Compound A-4.

LCMS: m/z 515 [M+H]$^+$

HPLC retention time: 0.88 min (analysis condition K)

Example 692

Compound m8

2-Bromo-5-ethoxybenzaldehyde

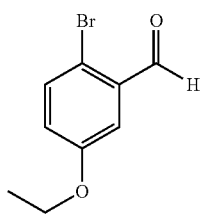

Potassium carbonate (560 mg, 4.05 mmol) and iodoethane (243 μl, 3.03 mmol) were added to a solution of 2-bromo-5-hydroxybenzaldehyde (406 mg, 2.02 mmol) in DMF (1.6 ml), and it was stirred at 50° C. for one hour. Water was added to the reaction mixture, followed by extraction with tert-butyl methyl ether/n-hexane (1:1). The organic layer was washed with a saturated aqueous solution of sodium chloride, and then dried over anhydrous sodium sulfate. The drying agent was removed by filtration, followed by concentration under reduced pressure to yield the title compound as a crude product.

LCMS: m/z 268 [M+H]$^+$

HPLC retention time: 0.93 min (analysis condition K)

Example 693

Compound m9

5-Ethoxy-2-ethylsulfanylbenzaldehyde

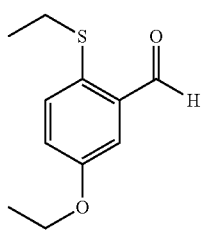

The title compound was synthesized from 2-bromo-5-ethoxybenzaldehyde (Compound m8) under the same conditions as for Compound ff11.

Example 694

Compound m10

(5-Ethoxy-2-ethylsulfanylphenyl)methanamine

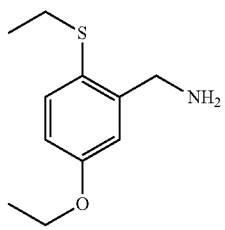

The title compound was synthesized from 5-ethoxy-2-ethylsulfanylbenzaldehyde (Compound m9) under the same conditions as for Compounds 5 and 6.

Example 695

Compound M-5

8-Chloro-3-[(5-ethoxy-2-ethylsulfonylphenyl)methyl]-6-(trifluoromethyl)-1H-quinazoline-2,4-dione

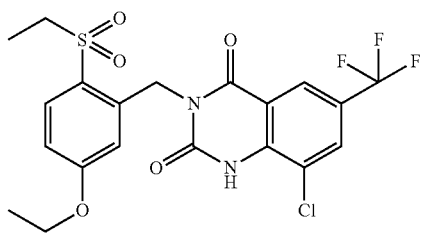 [SMILES: CCOc1ccc(S(=O)(=O)CC)c(Cn2c(=O)[nH]c3c(Cl)cc(C(F)(F)F)cc3c2=O)c1]

The title compound was synthesized from (5-ethoxy-2-ethylsulfanylphenyl)methanamine (Compound m10) under the same conditions as for Compounds m6, m7 and M-4.

LCMS: m/z 491 [M+H]$^+$

HPLC retention time: 0.86 min (analysis condition K)

Example 696

Compound n1

2-Ethylsulfanyl-5-methylbenzonitrile

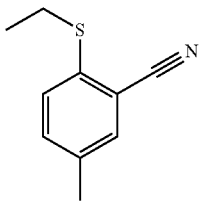

The title compound was synthesized from 2-fluoro-5-methylbenzonitrile under the same conditions as for Compound 1.

Example 697

Compound n2

(2-Ethylsulfanyl-5-methylphenyl)methanamine

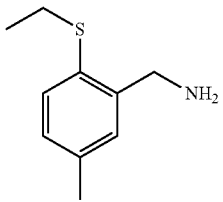

The title compound was synthesized from 2-ethylsulfanyl-5-methylbenzonitrile (Compound n1) under the same conditions as for Compound 2.

Example 698

Compound n3

(2-Ethylsulfonyl-5-methylphenyl)methanamine hydrochloride

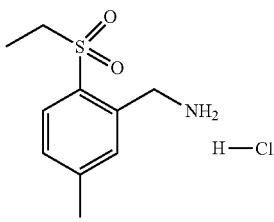

The title compound was synthesized from (2-ethylsulfanyl-5-methylphenyl)methanamine (Compound n2) under the same conditions as for Compound ff13.

Example 699

Compound n4 tert-Butyl N-[(3R)-1-[[3-amino-2-chloro-4-[(2-ethylsulfonyl-5-methylphenyl)methylcarbamoyl]-6-(trifluoromethyl)phenyl]methyl]piperidin-3-yl]carbamate

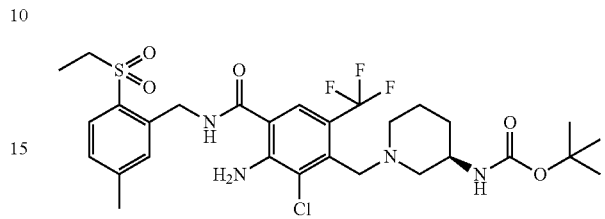

The title compound was synthesized from (2-ethylsulfonyl-5-methylphenyl)methanamine hydrochloride (Compound n3) under the same conditions as for Compound ff14.

Example 700

Compound n5 tert-Butyl N-[(3R)-1-[[8-chloro-3-[(2-ethylsulfonyl-5-methylphenyl)methyl]-2,4-dioxo-6-(trifluoromethyl)-1H-quinazolin-7-yl]methyl]piperidin-3-yl]carbamate

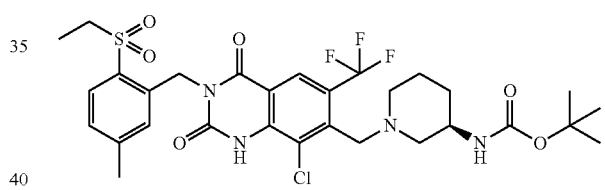

The title compound was synthesized from tert-butyl N-[(3R)-1-[[3-amino-2-chloro-4-[(2-ethylsulfonyl-5-methylphenyl)methylcarbamoyl]-6-(trifluoromethyl)phenyl]methyl]piperidin-3-yl]carbamate (Compound n4) under the same conditions as for Compound A-4.

Example 701

Compound N-1

7-[[(3R)-3-Aminopiperidin-1-yl]methyl]-8-chloro-3-[(2-ethylsulfonyl-5-methylphenyl)methyl]-6-(trifluoromethyl)-1H-quinazoline-2,4-dione

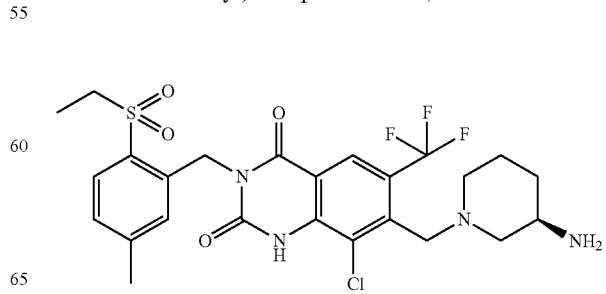

The title compound was synthesized from tert-butyl N-[(3R)-1-[[8-chloro-3-[(2-ethylsulfonyl-5-methylphenyl)methyl]-2,4-dioxo-6-(trifluoromethyl)-1H-quinazolin-7-yl]methyl]piperidin-3-yl]carbamate (Compound n5) under the same conditions as for Compound a41. However, THF was added as a solvent.

LCMS: m/z 573 [M+H]$^+$

HPLC retention time: 0.53 min (analysis condition K)

Example 702

Compound n6

4-Chloropyridine-3-carbonitrile

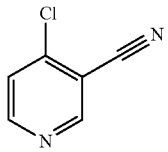

A 48% aqueous tetrafluoroboric acid solution (10 ml) was added to a solution of 4-chloropyridin-3-amine (1.29 g, 10.0 mmol) in ethanol (10 ml) at 0° C. A solution of sodium nitrite (725 mg, 10.5 mmol) in water (10 ml) was added to the resultant mixed solution at the same temperature, and it was stirred at the same temperature for 30 minutes. The precipitate was collected by filtration and washed with ethanol, and the resultant brown solid (1.94 g) was then dissolved in acetonitrile (10 ml). A mixed solution of sodium cyanide (980 mg, 20.0 mmol) and copper(I) cyanide (896 mg, 10.0 mmol) in water (10 ml) and acetonitrile (1 ml) was added to the resultant solution at 0° C., and it was stirred while gradually warming to room temperature for 10 hours. The reaction mixture was cooled to 0° C., after which a saturated aqueous solution of sodium bicarbonate was added, and it was stirred for five minutes. The resultant solution was extracted with ethyl acetate, and the organic layer was then washed with a saturated aqueous solution of sodium chloride and dried over anhydrous magnesium sulfate. The drying agent was removed by filtration, followed by concentration under reduced pressure. The resultant residue was purified by silica gel column chromatography (ethyl acetate/n-hexane) to yield the title compound (605 mg, 44%) as a pale yellow solid.

1H-NMR (300 MHz, CDCl$_3$) δ: 8.87 (1H, s), 8.72 (1H, d, J=3.9 Hz), 7.51 (1H, d, J=3.9 Hz).

Example 703

Compound n7

4-Ethylsulfanyl pyridine-3-carbonitrile

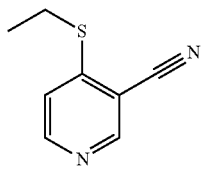

The title compound was synthesized from 4-chloropyridine-3-carbonitrile (Compound n6) under the same conditions as for Compound 1. However, sodium ethanethiolate was used in place of ethanethiol.

Example 704

Compound n8

(4-Ethylsulfanylpyridin-3-yl)methanamine

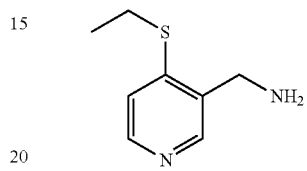

A 2 M solution of ammonia in methanol (6 ml) and a 50% aqueous Raney nickel suspension (6 ml) were added to a solution of 4-ethylsulfanylpyridine-3-carbonitrile (Compound n7, 306 mg, 1.86 mmol) in methanol (20 ml), and the mixture was stirred at 50° C. for 15 hours under hydrogen atmosphere. The reaction mixture was cooled to room temperature, and the insoluble matter was then removed by filtration, followed by washing with methanol. The filtrate and the washings were combined and concentrated under reduced pressure, and ethyl acetate was added to the resulting residue. The resulting solution was washed with brine, and the organic layer was dried over anhydrous magnesium sulfate. The drying agent was removed by filtration, then concentration under reduced pressure was carried out. The resulting residue was purified by silica gel column chromatography (ethyl acetate/n-hexane) to give the title compound (86 mg, 27%).

1H-NMR (300 MHz, CDCl$_3$) δ: 8.38 (1H, s), 8.36 (1H, d, J=3.9 Hz), 7.09 (1H, d, J=3.9 Hz), 3.88 (2H, s), 3.03 (2H, q, J=5.4 Hz), 1.42 (3H, t, J=5.4 Hz).

Example 705

Compound n9

2-Amino-N-[(4-ethylsulfanylpyridin-3-yl)methyl]-5-(trifluoromethyl)benzamide

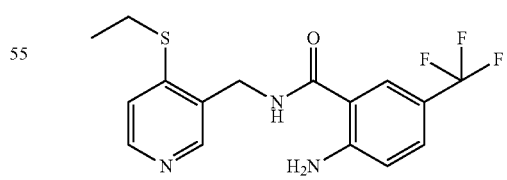

The title compound was synthesized from (4-ethylsulfanylpyridin-3-yl)methanamine (Compound n8) under the same conditions as for Compound 26. However, 2-amino-5-(trifluoromethyl)benzoic acid was used in place of 2-amino-3-chloro-4-formyl-5-(trifluoromethyl)benzoic acid (Compound 25) as a carboxylic acid.

Example 706

Compound n10

3-[(4-Ethylsulfanylpyridin-3-yl)methyl]-6-(trifluoromethyl)-1H-quinazoline-2,4-dione

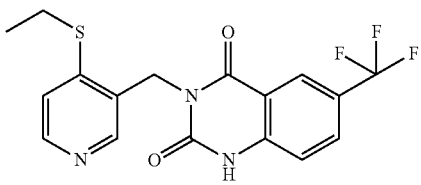 [SMILES: CCSc1ccncc1Cn1c(=O)[nH]c2ccc(C(F)(F)F)cc2c1=O]

The title compound was synthesized from 2-amino-N-[(4-ethylsulfanylpyridin-3-yl)methyl]-5-(trifluoromethyl)benzamide (Compound n9) under the same conditions as for Compound A-4.

Example 707

Compound N-2

3-[(4-Ethylsulfonylpyridin-3-yl)methyl]-6-(trifluoromethyl)-1H-quinazoline-2,4-dione

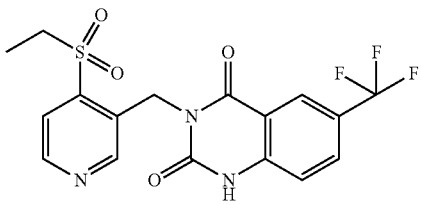 [SMILES: CCS(=O)(=O)c1ccncc1Cn1c(=O)[nH]c2ccc(C(F)(F)F)cc2c1=O]

The title compound was synthesized from 3-[(4-ethylsulfanylpyridin-3-yl)methyl]-6-(trifluoromethyl)-1H-quinazoline-2,4-dione (Compound n10) under the same conditions as for Compound 11. However, the reaction was performed at a temperature of 30° C.
LCMS: m/z 414 [M+H]$^+$
HPLC retention time: 0.67 min (analysis condition K)

Example 708

Compound n11

Methyl 4-fluoro-2-nitrobenzoate

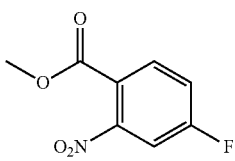

The title compound was synthesized from 4-fluoro-2-nitrobenzoic acid under the same conditions as for Compound c1. However, the reaction was performed using MeOH in place of EtOH as a solvent and at a temperature of 65° C.

Example 709

Compound n12 tert-Butyl 4-(4-methoxycarbonyl-3-nitroanilino)piperidine-1-carboxylate

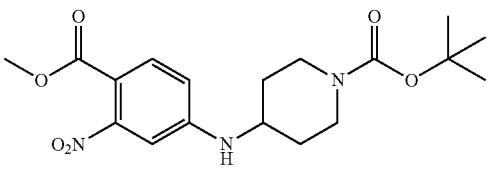 [SMILES: COC(=O)c1ccc(NC2CCN(C(=O)OC(C)(C)C)CC2)cc1[N+](=O)[O-]]

tert-Butyl 4-aminopiperidine-1-carboxylate (104 mg, 0.520 mmol) was added to a solution of methyl 4-fluoro-2-nitrobenzoate (Compound n11, 69.0 mg, 0.346 mmol) and DIPEA (0.181 ml, 1.04 mmol) in DMF (1.7 ml), followed by stirring at room temperature. After 17 hours, the reaction mixture was heated to 70° C. After one hour, tert-butyl 4-aminopiperidine-1-carboxylate (104 mg, 0.520 mmol) and DIPEA (0.181 ml, 1.04 mmol) were added. After further one hour, tert-butyl 4-aminopiperidine-1-carboxylate (104 mg, 0.520 mmol) and DIPEA (0.181 ml, 1.04 mmol) were added. After one hour, the reaction mixture was cooled to room temperature, and water was added, followed by extraction with ethyl acetate. The organic layer was washed with brine and then dried over anhydrous sodium sulfate. The drying agent was removed by filtration, then concentration under reduced pressure was carried out. The resulting residue was purified by silica gel column chromatography (ethyl acetate/n-hexane) to give the title compound (64.0 mg, 49%) as a yellow solid.
LCMS: m/z 324 [M-(2-methylpropene)+H]$^+$
HPLC retention time: 0.86 min (analysis condition K)

Example 710

Compound n13 tert-Butyl 4-[4-methoxycarbonyl-N-[(2-methylpropan-2-yl)oxycarbonyl]-3-nitroanilino]piperidine-1-carboxylate

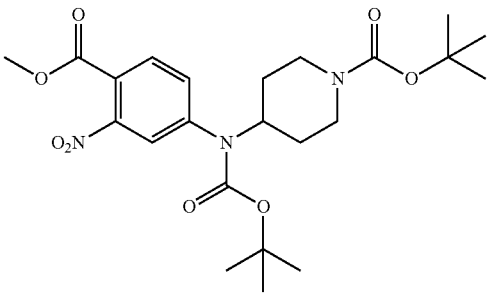 [SMILES: COC(=O)c1ccc(N(C(=O)OC(C)(C)C)C2CCN(C(=O)OC(C)(C)C)CC2)cc1[N+](=O)[O-]]

The title compound was synthesized from tert-butyl 4-(4-methoxycarbonyl-3-nitroanilino)piperidine-1-carboxylate (Compound n12) under the same conditions as for Compound 17. However, the reaction was performed at a temperature of 50° C.

Example 711

Compound n14

2-Amino-4-[(2-methylpropan-2-yl)oxycarbonyl-[1-[(2-methylpropan-2-yl)oxycarbonyl]piperidin-4-yl]amino]benzoic acid

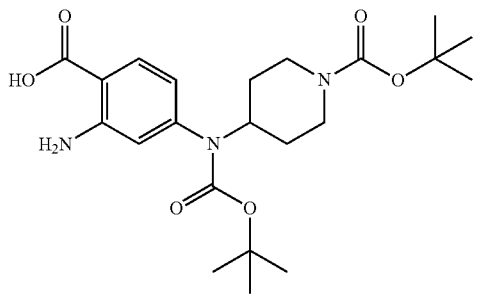 [SMILES: CC(C)(C)OC(=O)N1CCC(N(C(=O)OC(C)(C)C)c2ccc(C(=O)O)c(N)c2)CC1]

The title compound was synthesized from tert-butyl 4-[4-methoxycarbonyl-N-[(2-methylpropan-2-yl)oxycarbonyl]-3-nitroanilino]piperidine-1-carboxylate (Compound n13) under the same conditions as for Compound 30. However, the reaction was performed at a temperature of 80° C.

Example 712

Compound n15

2-Amino-5-bromo-4-[(2-methylpropan-2-yl)oxycarbonyl-[1-[(2-methylpropan-2-yl)oxycarbonyl]piperidin-4-yl]amino]benzoic acid

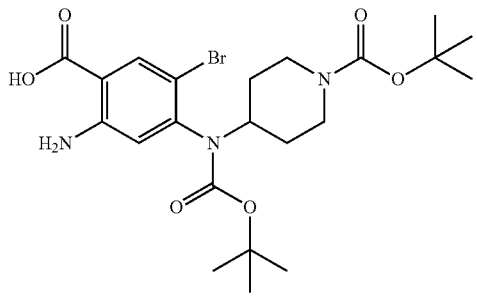 [SMILES: CC(C)(C)OC(=O)N1CCC(N(C(=O)OC(C)(C)C)c2cc(N)c(C(=O)O)cc2Br)CC1]

The title compound was synthesized from 2-amino-4-[(2-methylpropan-2-yl)oxycarbonyl-[1-[(2-methylpropan-2-yl)oxycarbonyl]piperidin-4-yl]amino]benzoic acid (Compound n14) under the same conditions as for Compound 24. However, the reaction was performed using NBS in place of NCS and at room temperature.

Example 713

Compound n16 tert-Butyl 4-[5-amino-2-bromo-4-[(5-chloro-2-ethylsulfonylphenyl)methylcarbamoyl]-N-[(2-methylpropan-2-yl)oxycarbonyl]anilino]piperidine-1-carboxylate

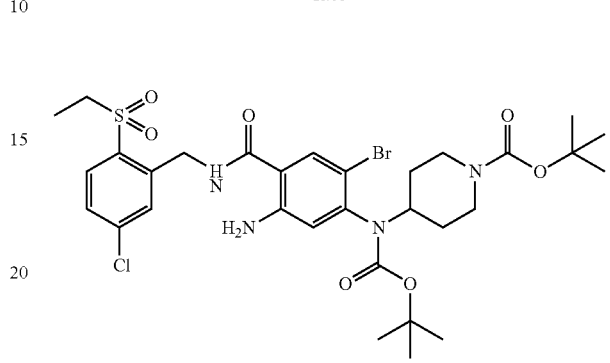

The title compound was synthesized from (5-chloro-2-ethylsulfonylphenyl)methanamine hydrochloride (Compound 3) under the same conditions as for Compound ff14. However, 2-amino-5-bromo-4-[(2-methylpropan-2-yl)oxycarbonyl-[1-[(2-methylpropan-2-yl)oxycarbonyl]piperidin-4-yl]amino]benzoic acid (Compound n15) was used in place of 2-amino-3-chloro-4-[[(3R)-3-[(2-methylpropan-2-yl)oxycarbonylamino]piperidin-1-yl]methyl]-5-(trifluoromethyl)benzoic acid (Compound ff2) as a carboxylic acid, HBTU was used in place of HATU as a condensing agent, and DCM was used in place of DMF as a solvent.

Example 714

Compound n17 tert-Butyl 4-[[6-bromo-3-[(5-chloro-2-ethylsulfonylphenyl)methyl]-2,4-dioxo-1H-quinazolin-7-yl]-[(2-methylpropan-2-yl)oxycarbonyl]amino]piperidine-1-carboxylate

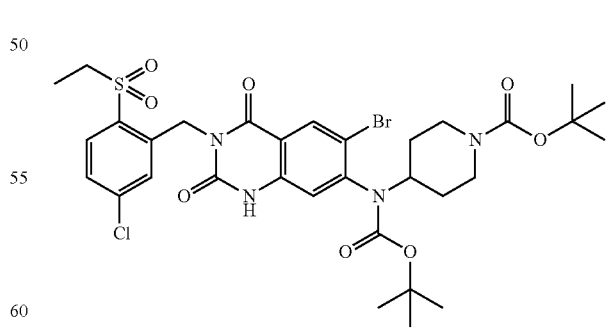

The title compound was synthesized from tert-butyl 4-[5-amino-2-bromo-4-[(5-chloro-2-ethylsulfonylphenyl)methylcarbamoyl]-N-[(2-methylpropan-2-yl)oxycarbonyl]anilino]piperidine-1-carboxylate (Compound n16) by the same method as for Compound A-4.

Example 715

Compound N-3

6-Bromo-3-[(5-chloro-2-ethylsulfonylphenyl)methyl]-7-(piperidin-4-ylamino)-1H-quinazoline-2,4-dione

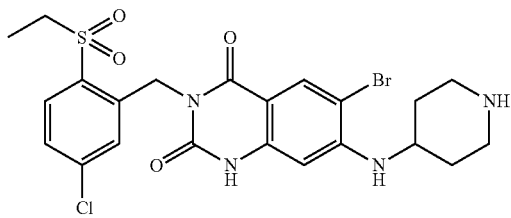 [SMILES: CCS(=O)(=O)c1ccc(Cl)cc1Cn1c(=O)[nH]c2cc(NC3CCNCC3)c(Br)cc2c1=O]

The title compound was synthesized from tert-butyl 4-[[6-bromo-3-[(5-chloro-2-ethylsulfonylphenyl)methyl]-2,4-di-oxo-1H-quinazolin-7-yl]-[(2-methylpropan-2-yl)oxycarbonyl]amino]piperidine-1-carboxylate (Compound n17) under the same conditions as for Compound B-1.

LCMS: m/z 555 [M+H]+

HPLC retention time: 0.50 min (analysis condition K)

Example 716

Compound n18

3-Ethylsulfanylpyridine-4-carbonitrile

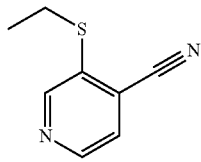

The title compound was synthesized from 3-chloropyridine-4-carbonitrile under the same conditions as for Compound 1. However, sodium ethanethiolate was used in place of ethanethiol.

Example 717

Compound n19

(3-Ethylsulfanylpyridin-4-yl)methanamine

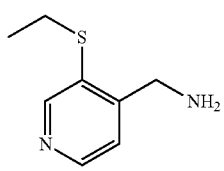

The title compound was synthesized from 3-ethylsulfanylpyridine-4-carbonitrile (Compound n18) under the same conditions as for Compound n8. However, the reaction was performed at room temperature.

Example 718

Compound n20

2-Amino-N-[(3-ethylsulfanylpyridin-4-yl)methyl]-5-(trifluoromethyl)benzamide

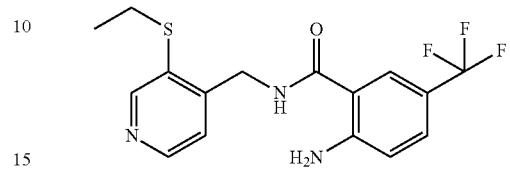

The title compound was synthesized from (3-ethylsulfanylpyridin-4-yl)methanamine (Compound n19) under the same conditions as for Compound 26. However, 2-amino-5-(trifluoromethyl)benzoic acid was used in place of 2-amino-3-chloro-4-formyl-5-(trifluoromethyl)benzoic acid (Compound 25) as a carboxylic acid.

Example 719

Compound n21

3-[(3-Ethylsulfanylpyridin-4-yl)methyl]-6-(trifluoromethyl)-1H-quinazoline-2,4-dione

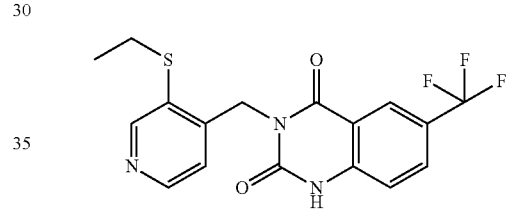

The title compound was synthesized from 2-amino-N-[(3-ethylsulfanylpyridin-4-yl)methyl]-5-(trifluoromethyl)benzamide (Compound n20) under the same conditions as for Compound 37.

Example 720

Compound N-6

3-[(3-Ethylsulfonylpyridin-4-yl)methyl]-6-(trifluoromethyl)-1H-quinazoline-2,4-dione

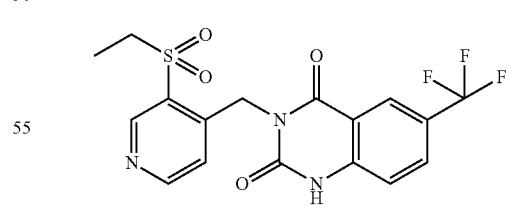

The title compound was synthesized from 3-[(3-ethylsulfanylpyridin-4-yl)methyl]-6-(trifluoromethyl)-1H-quinazoline-2,4-dione (Compound n21) under the same conditions as for Compound 11. However, the reaction was performed using ethyl acetate in place of DCM as a solvent and at a temperature of 0° C.

LCMS: m/z 414 [M+H]+

HPLC retention time: 0.66 min (analysis condition K)

Example 721

Compound n22 tert-Butyl N-[(3S)-1-[[8-chloro-3-[(5-chloro-2-ethyl-sulfonylphenyl)methyl]-2,4-dioxo-6-(trifluoromethyl)-1H-quinazolin-7-yl]methyl]piperidin-3-yl]-N-[2-[methyl-[(2-methylpropan-2-yl)oxycarbonyl]amino]ethyl]carbamate

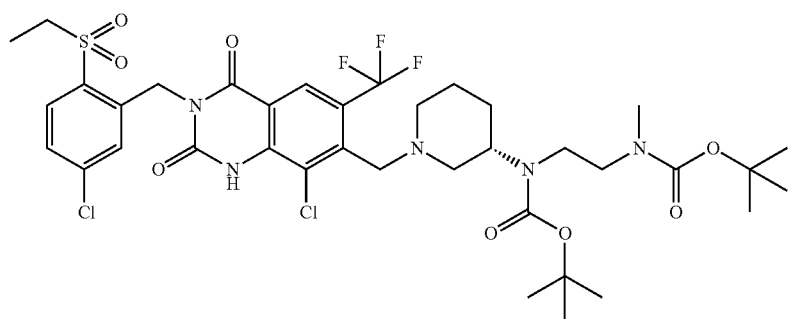 [SMILES: CCS(=O)(=O)c1ccc(Cl)cc1Cn1c(=O)[nH]c2c(Cl)c(CN3CCC[C@H](N(CCN(C)C(=O)OC(C)(C)C)C(=O)OC(C)(C)C)C3)c(C(F)(F)F)cc2c1=O]

The title compound was synthesized from [8-chloro-3-[(5-chloro-2-ethylsulfonylphenyl)methyl]-2,4-dioxo-6-(trifluoromethyl)-1H-quinazolin-7-yl]methyl methanesulfonate (Compound F-127) under the same conditions as for Compound f25. However, tert-butyl N-methyl-N-[2-[(2-methylpropan-2-yl)oxycarbonyl-[(3S)-piperidin-3-yl]amino]ethyl]carbamate was used in place of tert-butyl N-[[(2R)-piperidin-2-yl]methyl]carbamate as an amine, and potassium carbonate was added.

Example 722

Compound N-7

8-Chloro-3-[(5-chloro-2-ethylsulfonylphenyl)methyl]-7-[[(3S)-3-[2-(methylamino)ethylamino]piperidin-1-yl]methyl]-6-(trifluoromethyl)-1H-quinazoline-2,4-dione

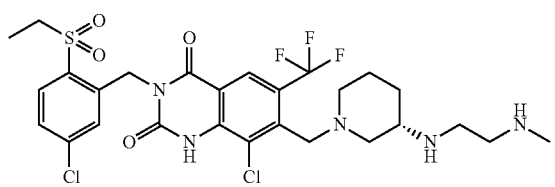 [SMILES: CCS(=O)(=O)c1ccc(Cl)cc1Cn1c(=O)[nH]c2c(Cl)c(CN3CCC[C@H](NCCNC)C3)c(C(F)(F)F)cc2c1=O]

The title compound was synthesized from tert-butyl N-[(3S)-1-[[8-chloro-3-[(5-chloro-2-ethylsulfonylphenyl)methyl]-2,4-dioxo-6-(trifluoromethyl)-1H-quinazolin-7-yl]methyl]piperidin-3-yl]-N-[2-[methyl-[(2-methylpropan-2-yl)oxycarbonyl]amino]ethyl]carbamate (Compound n22) under the same conditions as for Compound B-1.

LCMS: m/z 650 [M+H]$^+$

HPLC retention time: 0.46 min (analysis condition K)

Example 723

Compound n23

Benzyl N-[2-[(3S)-1-[[8-chloro-3-[(5-chloro-2-ethylsulfonylphenyl)methyl]-2,4-dioxo-6-(trifluoromethyl)-1H-quinazolin-7-yl]methyl]piperidin-3-yl]oxyethyl]carbamate

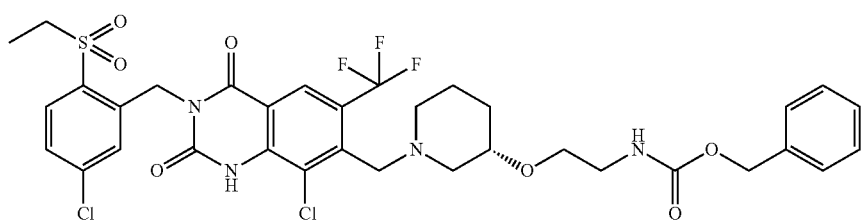 [SMILES: CCS(=O)(=O)c1ccc(Cl)cc1Cn1c(=O)[nH]c2c(Cl)c(CN3CCC[C@H](OCCNC(=O)OCc4ccccc4)C3)c(C(F)(F)F)cc2c1=O]

The title compound was synthesized from [8-chloro-3-[(5-chloro-2-ethylsulfonylphenyl)methyl]-2,4-dioxo-6-(trifluoromethyl)-1H-quinazolin-7-yl]methyl methanesulfonate (Compound F-127) under the same conditions as for Compound f25. However, benzyl N-[2-[(3S)-piperidin-3-yl]oxyethyl]carbamate was used in place of tert-butyl N-[[(2R)-piperidin-2-yl]methyl]carbamate as an amine, and potassium carbonate was added.

Example 724

Compound N-8

7-[[(3S)-3-(2-Aminoethoxy)piperidin-1-yl]methyl]-8-chloro-3-[(5-chloro-2-ethylsulfonylphenyl)methyl]-6-(trifluoromethyl)-1H-quinazoline-2,4-dione

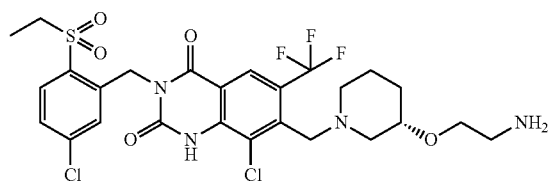 [SMILES: CCS(=O)(=O)c1ccc(Cl)cc1Cn1c(=O)[nH]c2c(Cl)c(CN3CCC[C@H](OCCN)C3)c(C(F)(F)F)cc2c1=O]

A 25% solution of hydrogen bromide in acetic acid (1 ml) was added to benzyl N-[2-[(3S)-1-[[8-chloro-3-[(5-chloro-2-ethylsulfonylphenyl)methyl]-2,4-dioxo-6-(trifluoromethyl)-1H-quinazolin-7-yl]methyl]piperidin-3-yl]oxyethyl]carbamate (Compound n23, 26.0 mg, 0.034 mmol), and the mixture was stirred at room temperature for 1.5 hours. The reaction mixture was diluted with water and DMSO, then purified by preparative HPLC (water/acetonitrile, 0.05% TFA) to give the title compound (13.0 mg, 60%) as a colorless solid.
LCMS: m/z 637 [M+H]$^+$
HPLC retention time: 0.44 min (analysis condition K)

Example 725

Compound N-9

8-Chloro-3-[(5-chloro-2-ethylsulfonylphenyl)methyl]-7-[[(3S)-3-(2-hydroxyethylamino)piperidin-1-yl]methyl]-6-(trifluoromethyl)-1H-quinazoline-2,4-dione

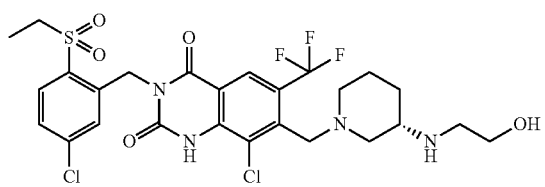 [SMILES: CCS(=O)(=O)c1ccc(Cl)cc1Cn1c(=O)[nH]c2c(Cl)c(CN3CCC[C@H](NCCO)C3)c(C(F)(F)F)cc2c1=O]

The title compound was synthesized from [8-chloro-3-[(5-chloro-2-ethylsulfonylphenyl)methyl]-2,4-dioxo-6-(trifluoromethyl)-1H-quinazolin-7-yl]methyl methanesulfonate (Compound F-127) under the same conditions as for Compounds n22 and N-7. However, tert-butyl N-[2-[tert-butyl(dimethyl)silyl]oxyethyl]-N-[(3S)-piperidin-3-yl]carbamate was used in place of tert-butyl N-methyl-N-[2-[(2-methylpropan-2-yl)oxycarbonyl-[(3S)-piperidin-3-yl]amino]ethyl]carbamate under the conditions for Compound n22.
LCMS: m/z 637 [M+H]$^+$
HPLC retention time: 0.56 min (analysis condition K)

Example 726

Compound n24

Ethyl 2-amino-4-(hydroxymethyl)-5-(trifluoromethyl)benzoate

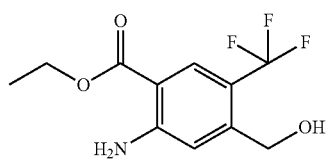

The title compound was synthesized from ethyl 2-amino-4-formyl-5-(trifluoromethyl)benzoate (Compound 23) under the same conditions as for Compound F-126. However, MeOH was used in place of THF as a solvent.

Example 727

Compound n25

2-Amino-4-(hydroxymethyl)-5-(trifluoromethyl)benzoic acid

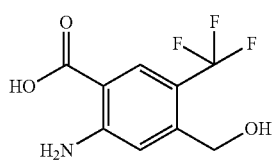

The title compound was synthesized from ethyl 2-amino-4-(hydroxymethyl)-5-(trifluoromethyl)benzoate (Compound n24) under the same conditions as for Compound 25.

Example 728

Compound n26

2-Amino-N-[(5-chloro-2-ethylsulfonylphenyl)methyl]-4-(hydroxymethyl)-5-(trifluoromethyl)benzamide

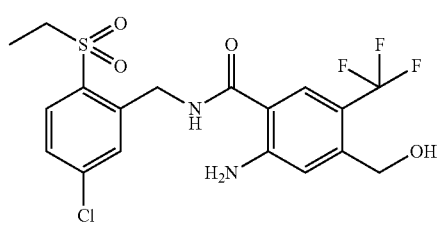 [SMILES: CCS(=O)(=O)c1ccc(Cl)cc1CNC(=O)c1cc(C(F)(F)F)c(CO)cc1N]

The title compound was synthesized from (5-chloro-2-ethylsulfonylphenyl)methanamine hydrochloride (Compound 3) under the same conditions as for Compound ff14. However, 2-amino-4-(hydroxymethyl)-5-(trifluoromethyl) benzoic acid (Compound n25) was used in place of 2-amino-3-chloro-4-[[(3R)-3-[(2-methylpropan-2-yl)oxycarbonylamino]piperidin-1-yl]methyl]-5-(trifluromethyl)benzoic acid (Compound ff2) as a carboxylic acid, HBTU was used in place of HATU as a condensing agent, and DCM was used in place of DMF as a solvent.

Example 729

Compound n27

3-[(5-Chloro-2-ethylsulfonylphenyl)methyl]-7-(hydroxymethyl)-6-(trifluoromethyl)-1H-quinazoline-2,4-dione

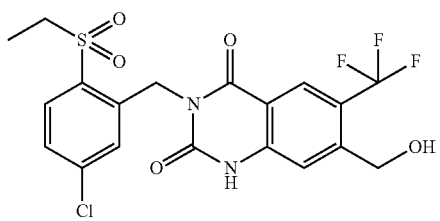 [SMILES: CCS(=O)(=O)c1ccc(Cl)cc1Cn1c(=O)[nH]c2cc(CO)c(C(F)(F)F)cc2c1=O]

DBU (0.080 ml, 0.532 mmol) and CDI (216 mg, 1.33 mmol) were added to a solution of 2-amino-N-[(5-chloro-2-ethylsulfonyl phenyl)methyl]-4-(hydroxymethyl)-5-(trifluoromethyl)benzamide (Compound n26, 100 mg, 0.222 mmol) in DMF (1.7 ml), and the mixture was stirred at room temperature for 16 hours. A 1 N aqueous hydrochloric acid solution was added to the reaction mixture, followed by extraction with a mixed solvent of ethyl acetate and n-hexane. The organic layer was washed with brine and then dried over anhydrous sodium sulfate. The drying agent was removed by filtration, then concentration under reduced pressure was carried out. The resulting residue was dissolved in MeOH (2 ml), a 1 N aqueous sodium hydroxide solution (0.444 ml, 0.444 mmol) was added, and the mixture was stirred at room temperature for 30 minutes. 1 N hydrochloric acid was added to the reaction mixture, then extraction with ethyl acetate was carried out. The organic layer was washed with brine and then dried over anhydrous sodium sulfate. The drying agent was removed by filtration, then concentration under reduced pressure was carried out. The resulting residue was purified by silica gel column chromatography (ethyl acetate/n-hexane) to give the title compound (93.0 mg, 88%) as a colorless solid.

LCMS: m/z 477 [M+H]$^+$

HPLC retention time: 0.73 min (analysis condition K)

Example 730

Compound n28

7-(Bromomethyl)-3-[(5-chloro-2-ethylsulfonylphenyl)methyl]-6-(trifluoromethyl)-1H-quinazoline-2,4-dione

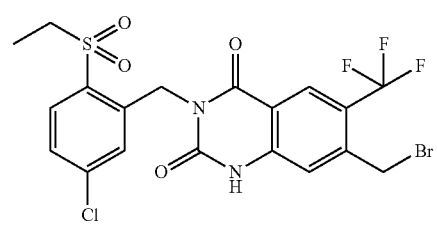 [SMILES: CCS(=O)(=O)c1ccc(Cl)cc1Cn1c(=O)[nH]c2cc(CBr)c(C(F)(F)F)cc2c1=O]

Triphenylphosphine (85.0 mg, 0.324 mmol) was added to a solution of 3-[(5-chloro-2-ethylsulfonylphenyl)methyl]-7-(hydroxymethyl)-6-(trifluoromethyl)-1H-quinazoline-2,4-dione (Compound n27, 103 mg, 0.216 mmol) and carbon tetrabromide (107 mg, 0.324 mmol) in THF (2.1 ml), and the mixture was stirred at room temperature. After three hours, carbon tetrabromide (107 mg, 0.324 mmol) and triphenylphosphine (85.0 mg, 0.324 mmol) were added, and the mixture was stirred for further one hour. The reaction mixture was concentrated under reduced pressure, and the resulting residue was purified by silica gel column chromatography (ethyl acetate/n-hexane) to give the title compound (103 mg, yield: 88%) as a colorless solid.

LCMS: m/z 539 [M+H]$^+$

HPLC retention time: 0.88 min (analysis condition K)

Example 731

Compound N-10

3-[(5-Chloro-2-ethylsulfonylphenyl)methyl]-7-(pyridin-4-ylmethyl)-6-(trifluoromethyl)-1H-quinazoline-2,4-dione

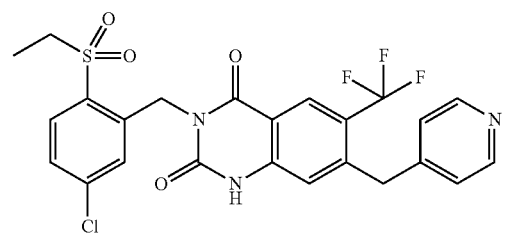 [SMILES: CCS(=O)(=O)c1ccc(Cl)cc1Cn1c(=O)[nH]c2cc(Cc3ccncc3)c(C(F)(F)F)cc2c1=O]

A suspension of 7-(bromomethyl)-3-[(5-chloro-2-ethylsulfonylphenyl)methyl]-6-(trifluoromethyl)-1H-quinazoline-2,4-dione (Compound n28, 50.0 mg, 0.093 mmol), 4-(4,4,5,5-tetramethyl-1,3,2-dioxaborolan-2-yl)pyridine (24.7 mg, 0.120 mmol), potassium carbonate (38.4 mg, 0.278 mmol) and tetrakis(triphenylphosphine)palladium (0) (11.1 mg, 9.64 mol) in a mixed solvent of 1,2-dimethoxyethane/water (2/1) (0.90 mL) was stirred at 70° C. for two hours. Water and ethyl acetate were added to the reaction mixture, and the organic layer was washed with brine and then dried over anhydrous sodium sulfate. The drying agent Example 732

Compound n29

Ethyl 5-bromo-4-methyl-2-[(2-methylpropan-2-yl)oxycarbonylamino]benzoate

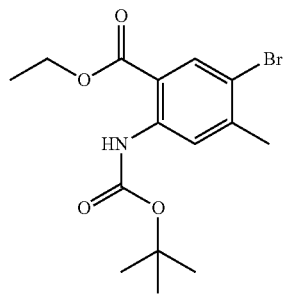 [SMILES: CCOC(=O)c1cc(Br)c(C)cc1NC(=O)OC(C)(C)C]

The title compound was synthesized from ethyl 2-amino-5-bromo-4-methylbenzoate (Compound k13) under the same conditions as for Compound 17.

Example 733

Compound n30

Ethyl 5-bromo-4-(bromomethyl)-2-[(2-methylpropan-2-yl)oxycarbonylamino]benzoate

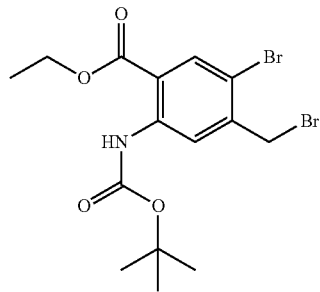 [SMILES: CCOC(=O)c1cc(Br)c(CBr)cc1NC(=O)OC(C)(C)C]

The title compound was synthesized from ethyl 5-bromo-4-methyl-2-[(2-methylpropan-2-yl)oxycarbonylamino]benzoate (Compound n29) under the same conditions as for Compound 12.

Example 734

Compound n31

Ethyl 5-bromo-4-[(4-methylpiperazin-1-yl)methyl]-2-[(2-methylpropan-2-yl)oxycarbonylamino]benzoate

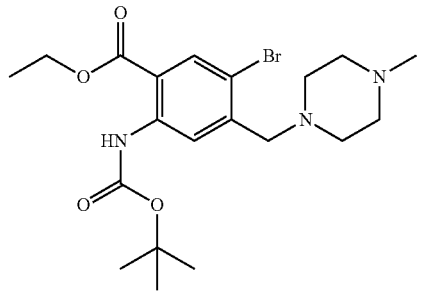 [SMILES: CCOC(=O)c1cc(Br)c(CN2CCN(C)CC2)cc1NC(=O)OC(C)(C)C]

The title compound was synthesized from ethyl 5-bromo-4-(bromomethyl)-2-[(2-methylpropan-2-yl)oxycarbonylamino]benzoate (Compound n30) under the same conditions as for Compound d1. However, 1-methylpiperazine was used in place of tert-butyl piperazine-1-carboxylate as an amine.

Example 735

Compound n32

Ethyl 5-cyano-4-[(4-methylpiperazin-1-yl)methyl]-2-[(2-methylpropan-2-yl)oxycarbonylamino]benzoate

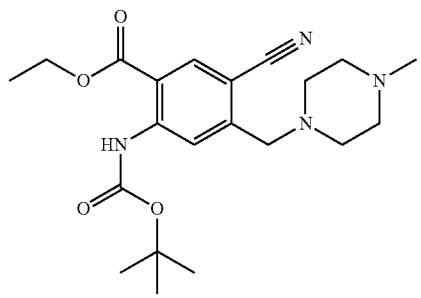 [SMILES: CCOC(=O)c1cc(C#N)c(CN2CCN(C)CC2)cc1NC(=O)OC(C)(C)C]

The title compound was synthesized from ethyl 5-bromo-4-[(4-methylpiperazin-1-yl)methyl]-2-[(2-methylpropan-2-yl)oxycarbonylamino]benzoate (Compound n31) under the same conditions as for Compound J-7. However, the reaction was performed at a temperature of 170° C.

The preceding section (before Example 732):

was removed by filtration, then concentration under reduced pressure was carried out. The resulting residue was purified by preparative HPLC (water/acetonitrile, 0.05% TFA) to give the title compound (7.5 mg, 15%) as a colorless solid.

LCMS: m/z 538 [M+H]$^+$

HPLC retention time: 0.51 min (analysis condition K)

Example 736

Compound n33

Ethyl 2-amino-5-cyano-4-[(4-methylpiperazin-1-yl)methyl]benzoate

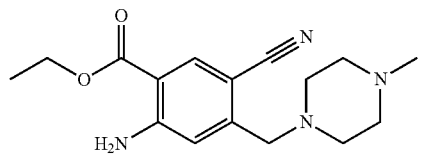 [SMILES: CCOC(=O)c1cc(C#N)c(CN2CCN(C)CC2)cc1N]

The title compound was synthesized from ethyl 5-cyano-4-[(4-methylpiperazin-1-yl)methyl]-2-[(2-methylpropan-2-yl)oxycarbonylamino]benzoate (Compound n32) under the same conditions as for Compound B-1.

Example 737

Compound n34

2-Amino-5-cyano-4-[(4-methylpiperazin-1-yl)methyl]benzoic acid

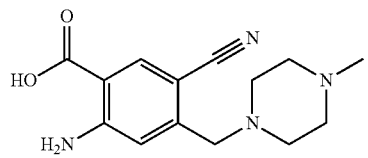

The title compound was synthesized from ethyl 2-amino-5-cyano-4-[(4-methylpiperazin-1-yl)methyl]benzoate (Compound n33) under the same conditions as for Compound 25.

Example 738

Compound n35

2-Amino-N-[(5-chloro-2-ethylsulfonylphenyl)methyl]-5-cyano-4-[(4-methylpiperazin-1-yl)methyl]benzamide

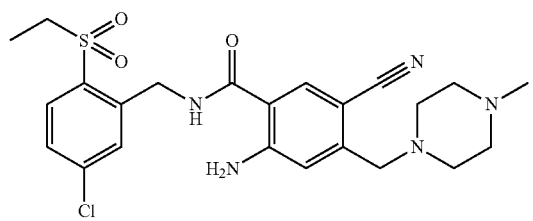 [SMILES: CCS(=O)(=O)c1ccc(Cl)cc1CNC(=O)c1cc(C#N)c(CN2CCN(C)CC2)cc1N]

The title compound was synthesized from (5-chloro-2-ethylsulfonylphenyl)methanamine hydrochloride (Compound 3) under the same conditions as for Compound ff14. However, 2-amino-5-cyano-4-[(4-methylpiperazin-1-yl)methyl]benzoic acid (Compound n34) was used in place of 2-amino-3-chloro-4-[[(3R)-3-[(2-methylpropan-2-yl)oxycarbonylamino]piperidin-1-yl]methyl]-5-(trifluoromethyl)benzoic acid (Compound ff2) as a carboxylic acid.

Example 739

Compound N-11

3-[(5-Chloro-2-ethylsulfonylphenyl)methyl]-7-[(4-methylpiperazin-1-yl)methyl]-2,4-dioxo-1H-quinazoline-6-carbonitrile

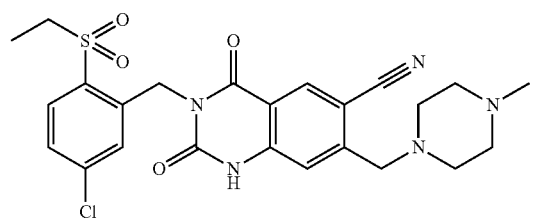 [SMILES: CCS(=O)(=O)c1ccc(Cl)cc1Cn1c(=O)[nH]c2cc(CN3CCN(C)CC3)c(C#N)cc2c1=O]

The title compound was synthesized from 2-amino-N-[(5-chloro-2-ethylsulfonylphenyl)methyl]-5-cyano-4-[(4-methylpiperazin-1-yl)methyl]benzamide (Compound n35) under the same conditions as for Compound A-4.

LCMS: m/z 516 [M+H]$^+$

HPLC retention time: 0.48 min (analysis condition D)

Example 740

Compound N-12

3-[(4-Ethylsulfinylpyridin-3-yl)methyl]-6-(trifluoromethyl)-1H-quinazoline-2,4-dione

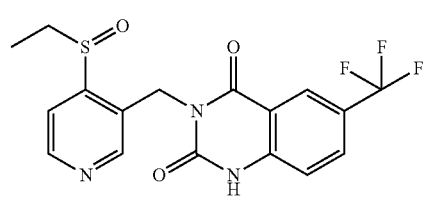 [SMILES: CCS(=O)c1ccncc1Cn1c(=O)[nH]c2ccc(C(F)(F)F)cc2c1=O]

The title compound was synthesized from 3-[(4-ethylsulfanylpyridin-3-yl)methyl]-6-(trifluoromethyl)-1H-quinazoline-2,4-dione (Compound n10) under the same conditions as for Compound M-2. However, the reaction was performed at room temperature.

LCMS: m/z 398 [M+H]$^+$

HPLC retention time: 0.56 min (analysis condition K)

Example 741

Compound N-13

7-[[(3R)-3-Aminopiperidin-1-yl]methyl]-8-chloro-3-[[2-ethylsulfonyl-5-(trifluoromethyl)phenyl]methyl]-6-(trifluoromethyl)-1H-quinazoline-2,4-dione

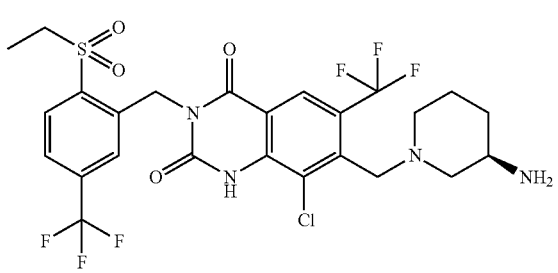 [SMILES: CCS(=O)(=O)c1ccc(C(F)(F)F)cc1Cn1c(=O)[nH]c2c(Cl)c(CN3CCC[C@@H](N)C3)c(C(F)(F)F)cc2c1=O]

The title compound was synthesized from 2-fluoro-5-(trifluoromethyl)benzonitrile under the same conditions as for Compounds n1, n2, n3, n4, n5 and N-1.

LCMS: m/z 627 [M+H]$^+$

HPLC retention time: 0.57 min (analysis condition K)

Example 742

Compound n36

5-Chloro-4-fluoro-2-nitrobenzoic acid

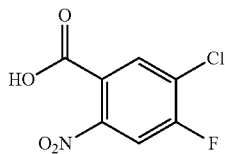

A mixed solution of 3-chloro-4-fluorobenzoic acid (300 mg, 1.72 mmol) in sulfuric acid (1 ml) and DCM (2 ml) was cooled to 0° C., fuming nitric acid (1 ml) was added dropwise, and the mixture was then stirred at room temperature for seven hours. The reaction mixture was separated by adding dichloromethane and ice water thereto, and the aqueous layer was then extracted with dichloromethane twice. The combined organic layers were washed with brine twice and then dried over anhydrous sodium sulfate. The drying agent was removed by filtration, then concentration under reduced pressure was carried out to give a crude product of the title compound.

LCMS: m/z 218 [M−H]$^−$

HPLC retention time: 0.54 min (analysis condition K)

Example 743

Compound n37

5-Chloro-4-[1-[(2-methylpropan-2-yl)oxycarbonyl]piperidin-4-yl]oxy-2-nitrobenzoic acid

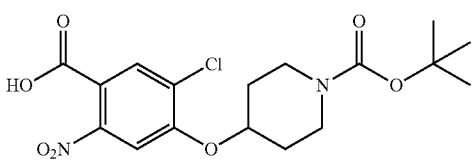 [SMILES: CC(C)(C)OC(=O)N1CCC(Oc2cc([N+](=O)[O-])c(C(=O)O)cc2Cl)CC1]

A solution of tert-butyl 4-hydroxypiperidine-1-carboxylate (138 mg, 0.683 mmol) in DMF (0.5 ml) was cooled to 0° C., sodium hydride (>60% oil, 27.3 mg, 0.683 mmol) was added, and the mixture was stirred at 0° C. for 10 minutes. 5-Chloro-4-fluoro-2-nitrobenzoic acid (Compound n36, 50.0 mg, 0.228 mmol) was added, and the mixture was warmed to room temperature and stirred for 30 minutes. Water was added to the reaction mixture, then extraction with ethyl acetate was carried out. The organic layer was washed with brine and then dried over anhydrous sodium sulfate. The drying agent was removed by filtration, then concentration under reduced pressure was carried out to give a crude product of the title compound.

LCMS: m/z 401 [M+H]$^+$

HPLC retention time: 0.83 min (analysis condition K)

Example 744

Compound n38

2-Amino-5-chloro-4-[1-[(2-methylpropan-2-yl)oxycarbonyl]piperidin-4-yl]oxybenzoic acid

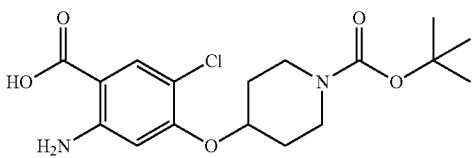

The title compound was synthesized from 5-chloro-4-[1-[(2-methylpropan-2-yl)oxycarbonyl]piperidin-4-yl]oxy-2-nitrobenzoic acid (Compound n37) under the same conditions as for Compound 30. However, the reaction was performed at a temperature of 80° C.

Example 745

Compound n39 tert-Butyl 4-[5-amino-2-chloro-4-[(5-chloro-2-ethyl-sulfonylphenyl)methylcarbamoyl]phenoxy]piperidine-1-carboxylate

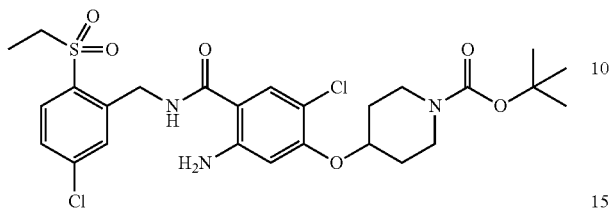

The title compound was synthesized from (5-chloro-2-ethylsulfonylphenyl)methanamine hydrochloride (Compound 3) under the same conditions as for Compound ff14. However, 2-amino-5-chloro-4-[1-[(2-methylpropan-2-yl)oxycarbonyl]piperidin-4-yl]oxybenzoic acid (Compound n38) was used in place of 2-amino-3-chloro-4-[[(3R)-3-[(2-methylpropan-2-yl)oxycarbonylamino]piperidin-1-yl]methyl]-5-(trifluoromethyl)benzoic acid (Compound ff2) as a carboxylic acid, HBTU was used in place of HATU as a condensing agent, and DCM was used in place of DMF as a solvent.

Example 746

Compound n40 tert-Butyl 4-[[6-chloro-3-[(5-chloro-2-ethylsulfonyl-phenyl)methyl]-2,4-dioxo-1H-quinazolin-7-yl]oxy]piperidine-1-carboxylate

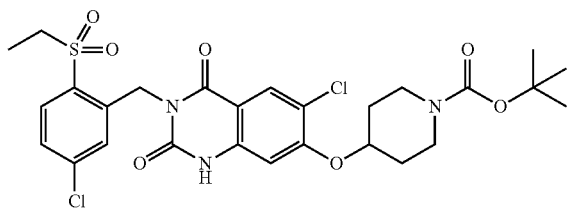 [SMILES: CCS(=O)(=O)c1ccc(Cl)cc1Cn1c(=O)[nH]c2cc(OC3CCN(C(=O)OC(C)(C)C)CC3)c(Cl)cc2c1=O]

The title compound was synthesized from tert-butyl 4-[5-amino-2-chloro-4-[(5-chloro-2-ethylsulfonylphenyl)methylcarbamoyl]phenoxy]piperidine-1-carboxylate (Compound n39) under the same conditions as for Compound A-4.

Example 747

Compound N-14

6-Chloro-3-[(5-chloro-2-ethylsulfonylphenyl)methyl]-7-piperidin-4-yloxy-1H-quinazoline-2,4-dione

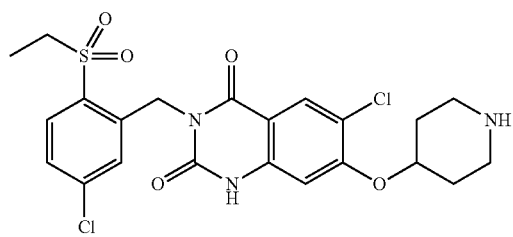 [SMILES: CCS(=O)(=O)c1ccc(Cl)cc1Cn1c(=O)[nH]c2cc(OC3CCNCC3)c(Cl)cc2c1=O]

The title compound was synthesized from tert-butyl 4-[[6-chloro-3-[(5-chloro-2-ethylsulfonylphenyl)methyl]-2,4-di-oxo-1H-quinazolin-7-yl]oxy]piperidine-1-carboxylate (Compound n40) under the same conditions as for Compound B-1.

LCMS: m/z 512 [M+H]$^+$
HPLC retention time: 0.49 min (analysis condition K)

Example 748

Amine 1 tert-Butyl N-methyl-N-[[(2R)-pyrrolidin-2-yl]methyl]carbamate

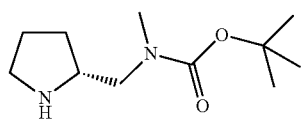

A solution of tert-butyl N-[[(2R)-pyrrolidin-2-yl]methyl]carbamate (302 mg, 1.46 mmol) and triethylamine (0.815 ml, 5.85 mmol) in DCM (3 mL) was cooled to 0° C., after which a solution of benzyl chloroformate (0.272 ml, 1.91 mmol) in DCM (1.5 ml) was added dropwise over five minutes, and the mixture was stirred at 0° C. for 2.5 hours. Water was added to the reaction mixture, followed by extraction with ethyl acetate. The organic layer was washed with a saturated aqueous solution of sodium bicarbonate, and then dried over anhydrous sodium sulfate. The drying agent was removed by filtration, followed by concentration under reduced pressure. The resultant residue was purified by silica gel column chromatography (ethyl acetate/hexane) to yield benzyl (2R)-2-[[(2-methylpropan-2-yl)oxycarbonylamino]methyl]pyrrolidine-1-carboxylate (410 mg, 81%) as a colorless solid.

LCMS: m/z 335 [M+H]$^+$
HPLC retention time: 0.83 min (analysis condition D)

A solution of benzyl (2R)-2-[[(2-methylpropan-2-yl)oxycarbonylamino]methyl]pyrrolidine-1-carboxylate (407 mg, 1.22 mmol) and methyl iodide (0.379 ml, 6.09 mmol) in DMF (2.4 ml) was cooled to 0° C., followed by addition of sodium hydride (>61% oil, 96.5 mg, 2.45 mmol), and it was stirred at room temperature for 16 hours. Water was added to the reaction mixture, followed by extraction with a mixed solvent of ethyl acetate and hexane. The organic layer was washed with saturated brine, and then dried over anhydrous sodium sulfate. The drying agent was removed by filtration, followed by concentration under reduced pressure. The resultant residue was purified by silica gel column chromatography (ethyl acetate/hexane) to yield benzyl (2R)-2-[[methyl-[(2-methylpropan-2-yl)oxycarbonyl]amino]methyl]pyrrolidine-1-carboxylate (414 mg, 97%) as a colorless oily substance.

LCMS: m/z 349 [M+H]$^+$
HPLC retention time: 0.90 min (analysis condition D)

10% palladium on carbon (43.5 mg) was added to a solution of benzyl (2R)-2-[[methyl-[(2-methylpropan-2-yl)oxycarbonyl]amino]methyl]pyrrolidine-1-carboxylate (410 mg, 1.18 mmol) in MeOH (4.1 ml) under argon atmosphere, and the mixture was stirred at room temperature for 15 hours under hydrogen atmosphere. The reaction mixture was filtered through celite, and the filtrate was then concentrated under reduced pressure to yield the title compound (253 mg, quant.) as a colorless oily substance.

1H-NMR (270 MHz, CDCl$_3$) δ: 2.73-3.51 (5H, m), 2.91 (3H, s), 1.26-1.99 (4H, m), 1.46 (9H, s).

Example 749

Amine 2 tert-Butyl N-methyl-N-[[(2S)-pyrrolidin-2-yl]methyl]carbamate

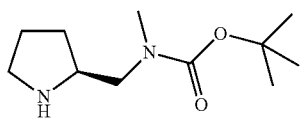

The title compound was synthesized from tert-butyl N-[[(2S)-pyrrolidin-2-yl]methyl]carbamate under the same conditions as for tert-butyl N-methyl-N-[[(2R)-pyrrolidin-2-yl]methyl]carbamate (Amine 1).

1H-NMR (270 MHz, CDCl$_3$) δ: 2.76-3.46 (5H, m), 2.91 (3H, s), 1.26-1.97 (4H, m), 1.46 (9H, s).

Example 750

Amine 3 tert-Butyl N-methyl-N-[[(3R)-pyrrolidin-3-yl]methyl]carbamate

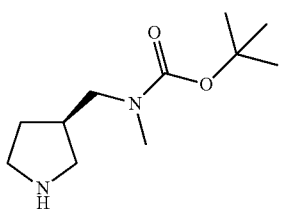

The title compound was synthesized from tert-butyl N-[[(3R)-pyrrolidin-3-yl]methyl]carbamate under the same conditions as for tert-butyl N-methyl-N-[[(2R)-pyrrolidin-2-yl]methyl]carbamate (Amine 1).

1H-NMR (400 MHz, CDCl$_3$) δ: 2.79-3.31 (5H, m), 2.87 (3H, s), 2.59-2.69 (1H, m), 2.31-2.49 (1H, m), 1.79-1.95 (1H, m), 1.34-1.53 (1H, m), 1.46 (9H, s).

Example 751

Amine 4 tert-Butyl N-methyl-N-[[(3S)-pyrrolidin-3-yl]methyl]carbamate

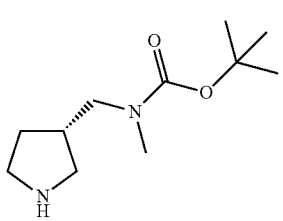

The title compound was synthesized from tert-butyl N-[[(3S)-pyrrolidin-3-yl]methyl]carbamate under the same conditions as for tert-butyl N-methyl-N-[[(2R)-pyrrolidin-2-yl]methyl]carbamate (Amine 1).

1H-NMR (400 MHz, CDCl$_3$) δ: 2.75-3.32 (5H, m), 2.87 (3H, s), 2.57-2.69 (1H, m), 2.32-2.46 (1H, m), 1.80-1.94 (1H, m), 1.35-1.55 (1H, m), 1.46 (9H, s).

Example 752

Amine 5 tert-Butyl N-methyl-N-[[(3S)-piperidin-3-yl]methyl]carbamate

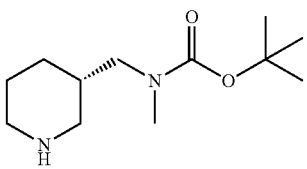 [SMILES: CN(C[C@H]1CCCNC1)C(=O)OC(C)(C)C]

The title compound was synthesized from tert-butyl N-[[(3S)-piperidin-3-yl]methyl]carbamate under the same conditions as for tert-butyl N-methyl-N-[[(2R)-pyrrolidin-2-yl]methyl]carbamate (Amine 1).

1H-NMR (400 MHz, CDCl$_3$) δ: 2.74-3.28 (4H, m), 2.85 (3H, s), 2.50-2.63 (1H, m), 2.23-2.41 (1H, m), 1.36-1.86 (4H, m), 1.45 (9H, s), 1.00-1.19 (1H, m).

Example 753

Amine 6 tert-Butyl N-methyl-N-[[(3R)-piperidin-3-yl]methyl]carbamate

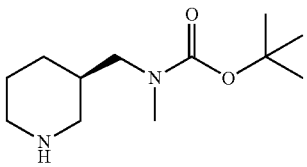 [SMILES: CN(C[C@@H]1CCCNC1)C(=O)OC(C)(C)C]

The title compound was synthesized from tert-butyl N-[[(3R)-piperidin-3-yl]methyl]carbamate under the same conditions as for tert-butyl N-methyl-N-[[(2R)-pyrrolidin-2-yl]methyl]carbamate (Amine 1).

1H-NMR (400 MHz, CDCl$_3$) δ: 2.67-3.31 (4H, m), 2.84 (3H, s), 2.48-2.64 (1H, m), 2.22-2.40 (1H, m), 1.31-1.92 (4H, m), 1.45 (9H, s), 0.97-1.20 (1H, m).

Example 754

Amine 7

4,4-Difluoro-1-pyrrolidin-3-ylpiperidine

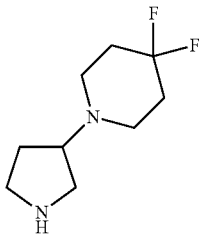 [SMILES: FC1(F)CCN(C2CCNC2)CC1]

4,4-Difluoro-1-pyrrolidin-3-ylpiperidine was synthesized from benzyl 3-oxopyrrolidine-1-carboxylate according to the method described in the patent (WO 2006134481).

Example 755

Amine 8

4-Fluoro-1-pyrrolidin-3-ylpiperidine

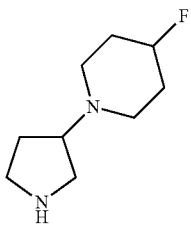 [SMILES: FC1CCN(C2CCNC2)CC1]

4-Fluoro-1-pyrrolidin-3-ylpiperidine was synthesized from benzyl 3-oxopyrrolidine-1-carboxylate according to the same method as for 4,4-difluoro-1-pyrrolidin-3-ylpiperidine (Amine 7).

Example 756

Amine 9

1-[(3R)-pyrrolidin-3-yl]pyrrolidin-2-one

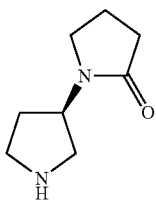 [SMILES: O=C1CCCN1[C@@H]1CCNC1]

1-[(3R)-Pyrrolidin-3-yl]pyrrolidin-2-one was synthesized from (3R)-1-benzylpyrrolidin-3-amine according to the method described in the patent (WO 2003051868).

Example 757

Amine 10

(3R)-3-Prop-2-enoxypyrrolidine

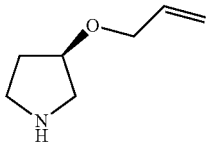

A solution of tert-butyl (3R)-3-hydroxypyrrolidine-1-carboxylate (195 mg, 1.04 mmol) in DMF (2 ml) was cooled to 0° C., sodium hydride (>50% oil, 75.0 mg, 1.56 mmol) was added, and the mixture was remained at 0° C. and stirred for 10 minutes. Allyl bromide (0.176 ml, 2.08 mmol) was added, and the mixture was stirred at room temperature for two hours. Water was added to the reaction mixture, then extraction with a mixed solvent of ethyl acetate and hexane was carried out. The organic layer was washed with brine twice and then dried over anhydrous sodium sulfate. The drying agent was removed by filtration, then concentration under reduced pressure was carried out. The resulting residue was purified by silica gel column chromatography (ethyl acetate/hexane) to give tert-butyl (3R)-3-prop-2-enoxypyrrolidine-1-carboxylate (230 mg, 97%) as a colorless oily substance.

1H-NMR (400 MHz, CDCl$_3$) δ: 5.83-5.98 (1H, m), 5.23-5.33 (1H, m), 5.14-5.22 (1H, m), 4.04-4.14 (1H, m), 3.93-4.03 (2H, m), 3.32-3.53 (4H, m), 1.87-2.07 (2H, m), 1.46 (9H, s).

tert-Butyl (3R)-3-prop-2-enoxypyrrolidine-1-carboxylate (230 mg, 1.01 mmol) was dissolved in a 4 N hydrochloric acid/1,4-dioxane solution, and the mixture was stirred at room temperature for one hour. The reaction mixture was concentrated under reduced pressure to give the hydrochloride of the title compound (173 mg, quant.) as a brown oily substance.

1H-NMR (400 MHz, DMSO-d$_6$) δ: 9.37 (1H, s), 9.16 (1H, s), 5.80-5.97 (1H, m), 5.22-5.37 (1H, m), 5.11-5.21 (1H, m), 4.14-4.28 (1H, m), 3.97 (2H, d, J=4.9 Hz), 3.04-3.32 (4H, m), 1.82-2.11 (2H, m).

Example 758

Amine 11

(2S)—N-Propan-2-ylpyrrolidine-2-carboxamide

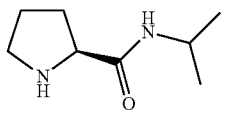

A solution of (2S)-1-phenylmethoxycarbonylpyrrolidine-2-carboxylic acid (200 mg, 0.802 mmol), HATU (458 mg, 1.21 mmol) and propan-2-amine (89.4 µl, 1.04 mmol) in DCM (4 ml) was cooled to 0° C., DIPEA (0.277 ml, 1.61 mmol) was added, and the mixture was stirred while gradually warming to room temperature for 2.5 hours. Water was added to the reaction mixture, then extraction with ethyl acetate was carried out. The organic layer was washed with brine and then dried over anhydrous sodium sulfate. The drying agent was removed by filtration, then concentration under reduced pressure was carried out. The resulting residue was purified by silica gel column chromatography (ethyl acetate/hexane) to give benzyl (2S)-2-(propan-2-ylcarbamoyl)pyrrolidine-1-carboxylate (233 mg, quant.) as a colorless solid.

LCMS: m/z 291 [M+H]+

HPLC retention time: 0.64 min (analysis condition D)

A solution of benzyl (2S)-2-(propan-2-ylcarbamoyl)pyrrolidine-1-carboxylate (233 mg, 0.802 mmol) in MeOH (16 ml) was allowed to pass through a continuous hydrogenation reactor (manufactured by Thalesnano Inc., H-cube) (10% palladium on carbon cartridge, flow rate: 1 ml/min, hydrogen pressure: 1 atm). The solution that has been allowed to pass through the reactor was concentrated under reduced pressure to give the title compound (117 mg, 93%) as a colorless solid.

1H-NMR (400 MHz, CDCl$_3$) δ: 7.30-7.54 (1H, m), 3.95-4.15 (1H, m), 3.64-3.79 (1H, m), 2.96-3.08 (1H, m), 2.85-2.95 (1H, m), 2.05-2.21 (1H, m), 1.83-1.97 (1H, m), 1.63-1.80 (2H, m), 1.01-1.26 (6H, m).

Example 759

Amine 12

(2S)-2-Methylpyrrolidine-2-carboxamide

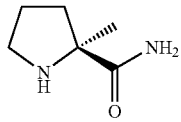

(2S)-2-Methylpyrrolidine-2-carboxamide was synthesized from (2S)-2-methylpyrrolidine-2-carboxylic acid according to the method described in the patent (WO 2011000855).

Example 760

Amine 13

(3S)—N-Methylpyrrolidine-3-carboxamide

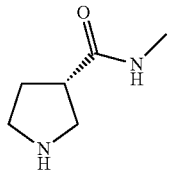

(3S)—N-Methylpyrrolidine-3-carboxamide was synthesized from (3S)-1-[(2-methylpropan-2-yl)oxycarbonyl]pyrrolidine-3-carboxylic acid according to the method described in the patent (WO 2011160020).

Example 761

Amine 14

(3S)—N,N-Dimethylpyrrolidine-3-carboxamide

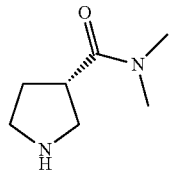

The title compound was synthesized from (3S)-1-[(2-methylpropan-2-yl)oxycarbonyl]pyrrolidine-3-carboxylic acid by the same method as for (3S)—N-methylpyrrolidine-3-carboxamide (Amine 13).

1H-NMR (400 MHz, CDCl$_3$) δ: 2.81-3.34 (11H, m), 1.86-2.15 (2H, m).

Example 762

Amine 15

(2R)—N-Methylpyrrolidine-2-carboxamide

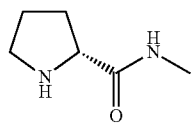

A solution of (2R)-1-phenylmethoxycarbonylpyrrolidine-2-carboxylic acid (300 mg, 1.20 mmol), methylamine hydrochloride (81.3 mg, 1.20 mmol), WSCDI (254 mg, 1.32 mmol) and HOBT (206 mg, 1.32 mmol) in DCM (12 ml) was cooled to 0° C., triethylamine (0.336 ml, 2.41 mmol) was added, and the mixture was stirred at room temperature for seven hours. Water was added to the reaction mixture, then extraction with ethyl acetate was carried out. The organic layer was washed with brine and then dried over anhydrous sodium sulfate. The drying agent was removed by filtration, then concentration under reduced pressure was carried out. The resulting residue was purified by silica gel column chromatography (ethyl acetate/hexane) to give benzyl (2R)-2-(methylcarbamoyl)pyrrolidine-1-carboxylate (317 mg, quant.) as a colorless oily substance.

LCMS: m/z 263 [M+H]+

HPLC retention time: 0.53 min (analysis condition D)

A solution of benzyl (2R)-2-(methylcarbamoyl)pyrrolidine-1-carboxylate (317 mg, 1.21 mmol) in MeOH (24 ml) was allowed to pass through a continuous hydrogenation reactor (manufactured by Thalesnano Inc., H-cube) (10% palladium on carbon cartridge, flow rate: 1 ml/min, hydrogen pressure: 1 atm). The solution that has been allowed to pass through the reactor was concentrated under reduced pressure to give a crude product of the title compound (172 mg) as a brown oily substance.

Example 763

Amine 16

(2R)—N,N-Dimethylpyrrolidine-2-carboxamide

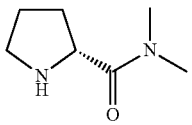

A solution of (2R)-1-phenylmethoxycarbonylpyrrolidine-2-carboxylic acid (300 mg, 1.20 mmol), dimethylamine hydrochloride (98.2 mg, 1.20 mmol), WSCDI (254 mg, 1.32 mmol) and HOBT (206 mg, 1.32 mmol) in DCM (12 ml) was cooled to 0° C., triethylamine (0.336 ml, 2.41 mmol) was added, and the mixture was stirred at room temperature for seven hours. Water was added to the reaction mixture, then extraction with ethyl acetate was carried out. The organic layer was washed with brine and then dried over anhydrous sodium sulfate. The drying agent was removed by filtration, then concentration under reduced pressure was carried out. The resulting residue was purified by silica gel column chromatography (ethyl acetate/hexane) to give benzyl (2R)-2-(dimethylcarbamoyl)pyrrolidine-1-carboxylate (331 mg, 99%) as a colorless oily substance.

LCMS: m/z 277 [M+H]$^+$

HPLC retention time: 0.58 min (analysis condition D)

A solution of benzyl (2R)-2-(dimethylcarbamoyl)pyrrolidine-1-carboxylate (331 mg, 1.20 mmol) in MeOH (24 ml) was allowed to pass through a continuous hydrogenation reactor (manufactured by Thalesnano Inc., H-cube) (10% palladium on carbon cartridge, flow rate: 1 ml/min, hydrogen pressure: 1 atm). The solution that has been allowed to pass through the reactor was concentrated under reduced pressure to give a crude product of the title compound (166 mg) as a brown oily substance.

Example 764

Amine 17

(2S)-Piperidine-2-carboxamide

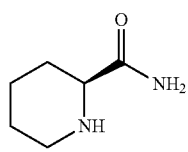

(2S)-Piperidine-2-carboxamide was synthesized from (2S)-piperidine-2-carboxylic acid according to the method described in the literature (Tetrahedron: Asymmetry, vol. 20, pp. 1759-1766, 2009).

Example 765

Amine 18

(2R)-Piperidine-2-carboxamide

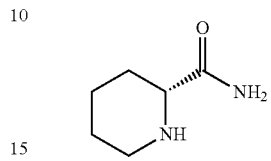

(2R)-Piperidine-2-carboxamide was synthesized from (2R)-piperidine-2-carboxylic acid according to the method described in the literature (Tetrahedron: Asymmetry, vol. 20, pp. 1759-1766, 2009).

Example 766

Amine 19

(3R)—N-(Methylsulfamoyl)pyrrolidin-3-amine

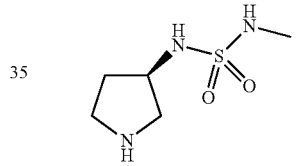

N-Methyl-2-oxo-1,3-oxazolidine-3-sulfonamide (580 mg, 3.22 mmol) was added to a solution of tert-butyl (3R)-3-aminopyrrolidine-1-carboxylate (200 mg, 1.07 mmol) and triethylamine (0.893 ml, 6.44 mmol) in acetonitrile (4.3 ml), and the mixture was stirred at 60° C. for 15 hours. Water was added to the reaction mixture, then extraction with ethyl acetate was carried out. The organic layer was washed with brine and then dried over anhydrous sodium sulfate. The drying agent was removed by filtration, then concentration under reduced pressure was carried out. The resulting residue was purified by silica gel column chromatography (ethyl acetate/hexane) to give tert-butyl (3R)-3-(methylsulfamoylamino)pyrrolidine-1-carboxylate (298 mg, quant.) as a colorless oily substance.

1H-NMR (400 MHz, CDCl$_3$) δ: 4.52-4.63 (1H, m), 4.28-4.40 (1H, m), 3.88-4.00 (1H, m), 3.54-3.69 (1H, m), 3.22-3.52 (3H, m), 2.70-2.76 (3H, m), 2.11-2.24 (1H, m), 1.84-2.02 (1H, m), 1.46 (9H, s).

TFA (2 ml) was added to a solution of tert-butyl (3R)-3-(methylsulfamoylamino)pyrrolidine-1-carboxylate (303 mg, 1.09 mmol) in DCM (3 ml), and the mixture was stirred at room temperature for one hour. The reaction mixture was concentrated under reduced pressure to give a crude product of the TFA salt of the title compound.

Example 767

Amine 20 tert-Butyl N-[2-[methyl-[(3R)-pyrrolidin-3-yl]amino]-2-oxoethyl]carbamate

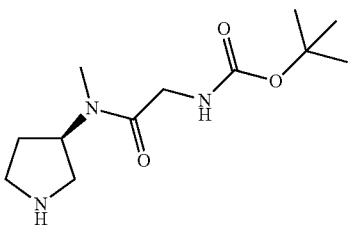 [SMILES: CN(C(=O)CNC(=O)OC(C)(C)C)[C@@H]1CCNC1]

A solution of (3R)-1-benzyl-N-methylpyrrolidin-3-amine (200 mg, 1.05 mmol), HATU (599 mg, 1.58 mmol) and 2-[(2-methylpropan-2-yl)oxycarbonylamino]acetic acid (239 mg, 1.37 mmol) in DCM (5.2 ml) was cooled to 0° C., DIPEA (0.357 ml, 2.10 mmol) was added, and the mixture was stirred at room temperature for three hours. Water was added to the reaction mixture, then extraction with ethyl acetate was carried out. The organic layer was washed with brine three times and then dried over anhydrous sodium sulfate. The drying agent was removed by filtration, then concentration under reduced pressure was carried out. The resulting residue was purified by amino silica gel column chromatography (ethyl acetate/hexane) to give tert-butyl N-[2-[[(3R)-1-benzylpyrrolidin-3-yl]-methylamino]-2-oxoethyl]carbamate (237 mg, 65%) as a colorless oily substance.

LCMS: m/z 348 [M+H]$^+$
HPLC retention time: 0.50 min (analysis condition E)

A solution of tert-butyl N-[2-[[(3R)-1-benzylpyrrolidin-3-yl]amino]-2-oxoethyl]carbamate (237 mg, 0.682 mmol) in MeOH (15 ml) was allowed to pass through a continuous hydrogenation reactor (manufactured by Thalesnano Inc., H-cube) (10% palladium on carbon cartridge, flow rate: 1 ml/min, hydrogen pressure: 1 atm). The solution that has been allowed to pass through the reactor was concentrated under reduced pressure to give the title compound (252 mg, 86%) as a brown oily substance.

1H-NMR (400 MHz, DMSO-d$_6$, 120° C.) δ: 5.97-6.11 (1H, m), 4.49-4.68 (1H, m), 3.79 (2H, d, J=5.1 Hz), 2.61-3.01 (7H, m), 1.81-1.96 (1H, m), 1.56-1.72 (1H, m), 1.39 (9H, s).

Example 768

Amine 21

Benzyl N-[2-[(3S)-piperidin-3-yl]oxoethyl]carbamate

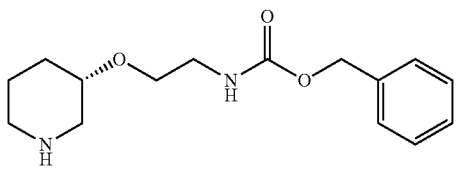 [SMILES: O=C(NCCO[C@H]1CCCNC1)OCc1ccccc1]

A solution of tert-butyl (3S)-3-hydroxypiperidine-1-carboxylate (100 mg, 0.497 mmol) in THF (0.5 ml) was cooled to 0° C., followed by addition of sodium hydride (>60% oil, 23.0 mg, 0.600 mmol), and it was stirred for 10 minutes. Sodium hydride (>60% oil, 24.0 mg, 0.626 mmol) and 2-bromoethanamine bromate (122 mg, 0.596 mmol) were added, and the mixture was stirred at room temperature for three days. Water was added to the reaction mixture, followed by extraction with ethyl acetate. The organic layer was washed with a saturated aqueous solution of sodium chloride, and then dried over anhydrous sodium sulfate. After the drying agent was removed by filtration, a crude product of tert-butyl (3S)-3-(2-aminoethoxy)piperidine-1-carboxylate (124 mg) was obtained as a yellow oily substance by concentration under reduced pressure.

Benzyl chloroformate (0.140 ml, 0.827 mmol) was added to a mixed solution of the crude product of tert-butyl (3S)-3-(2-aminoethoxy)piperidine-1-carboxylate (124 mg) and sodium bicarbonate (99.0 mg, 1.18 mmol) in ethanol/water (1/1, 2 ml), and it was stirred at room temperature for 16 hours. The reaction mixture was concentrated under reduced pressure, and water was added to the resultant residue, followed by extraction with ethyl acetate. The organic layer was washed with a saturated aqueous solution of sodium chloride, and then dried over anhydrous sodium sulfate. After the drying agent was removed by filtration, a crude product of tert-butyl (3S)-3-[2-(phenylmethoxycarbonylamino)ethoxy]piperidine-1-carboxylate (178 mg) was obtained as a yellow oily substance by concentration under reduced pressure.

A 4 N hydrochloric acid/ethyl acetate solution was added to the crude product of tert-butyl (3S)-3-[2-(phenylmethoxycarbonylamino)ethoxy]piperidine-1-carboxylate (178 mg), and it was stirred at room temperature for one hour. 1 N hydrochloric acid was added to the reaction mixture, followed by washing with ethyl acetate. The aqueous layer was made basic with a 1 N aqueous sodium hydroxide solution, followed by extraction with ethyl acetate three times. The combined organic layers were dried over anhydrous sodium sulfate. The drying agent was removed by filtration, and the title compound (23 mg, yield in three steps: 16%) was obtained as a yellow oily substance by concentration under reduced pressure.

1H-NMR (400 MHz, CDCl$_3$) δ: 7.27-7.40 (5H, m), 5.53-5.65 (1H, m), 5.10 (2H, s), 3.29-3.61 (4H, m), 2.65-3.05 (5H, m), 1.69-1.86 (2H, m), 1.51-1.63 (1H, m), 1.37-1.49 (1H, m).

Example 769

Amine 22 tert-Butyl N-[2-[tert-butyl(dimethyl)silyl]oxyethyl]-N-[(3S)-piperidin-3-yl]carbamate

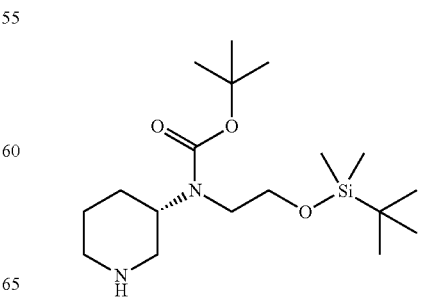

A solution of tert-butyl N-[(3S)-piperidin-3-yl]carbamate (100 mg, 0.499 mmol) and triethylamine (0.104 ml, 0.749 mmol) in DCM (2.5 ml) was cooled to 0° C., benzyl chloroformate (0.101 ml, 0.599 mmol) was added, and the mixture was stirred for one hour. Water was added to the reaction mixture, then extraction with ethyl acetate was carried out. The organic layer was washed with a saturated aqueous sodium chloride solution and then dried over anhydrous sodium sulfate. The drying agent was removed by filtration, then concentration under reduced pressure was carried out. The resulting residue was purified by silica gel column chromatography (ethyl acetate/hexane) to give benzyl (3S)-3-[(2-methylpropan-2-yl)oxycarbonylamino]piperidine-1-carboxylate (159 mg, 95%) as a colorless solid.

LCMS: m/z 335 [M+H]$^+$

HPLC retention time: 0.82 min (analysis condition K)

A solution of benzyl (3S)-3-[(2-methylpropan-2-yl)oxycarbonylamino]piperidine-1-carboxylate (99.5 mg, 0.298 mmol) in DMF (0.6 ml) was cooled to 0° C., sodium hydride (>60% oil, 17.9 mg, 0.448 mmol) was added, and the mixture was stirred for 15 minutes. 2-Bromoethoxy-tert-butyl-dimethylsilane (0.128 ml, 0.595 mmol) was added, and the mixture was stirred at room temperature for two hours. Water was added to the reaction mixture, then extraction with a mixed solvent of ethyl acetate and hexane was carried out. The organic layer was washed with a saturated aqueous sodium chloride solution three times and then dried over anhydrous sodium sulfate. The drying agent was removed by filtration, then concentration under reduced pressure was carried out. The resulting residue was purified by silica gel column chromatography (ethyl acetate/hexane) to give benzyl (3S)-3-[2-[tert-butyl(dimethyl)silyl]oxyethyl-[(2-methylpropan-2-yl)oxycarbonyl]amino]piperidine-1-carboxylate (89.0 mg, 61%) as a colorless oily substance.

LCMS: m/z 493 [M+H]$^+$

HPLC retention time: 1.24 min (analysis condition K)

10% palladium on carbon (19.0 mg) was added to a solution of benzyl (3S)-3-[2-[tert-butyl(dimethyl)silyl]oxyethyl-[(2-methylpropan-2-yl)oxycarbonyl]amino]piperidine-1-carboxylate (89.0 mg, 0.181 mmol) in MeOH (1 ml) under argon atmosphere, and the mixture was stirred at room temperature for 16 hours under hydrogen atmosphere. The reaction mixture was filtered through celite, and the filtrate was then concentrated under reduced pressure to give a rough product of the title compound (57 mg) as a yellow oily substance.

LCMS: m/z 359 [M+H]$^+$

Example 770

Amine 23 tert-Butyl N-methyl-N-[2-[(2-methylpropan-2-yl)oxycarbonyl-[(3S)-piperidin-3-yl]amino]ethyl]carbamate

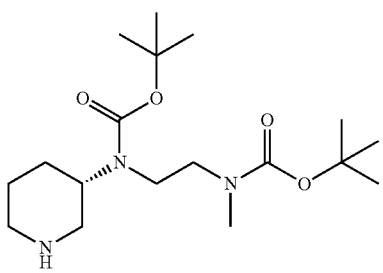 [SMILES: CN(CCN(C(=O)OC(C)(C)C)[C@H]1CCCNC1)C(=O)OC(C)(C)C]

TFA (4 ml) was added to a solution of benzyl (3S)-3-[(2-methylpropan-2-yl)oxycarbonylamino]piperidine-1-carboxylate (487 mg, 1.46 mmol) in DCM (6 ml), and the mixture was stirred at room temperature for one hour. The reaction mixture was concentrated under reduced pressure, and the resultant residue was dissolved in ethyl acetate and a saturated aqueous sodium bicarbonate solution. The separated organic layer was washed with a saturated aqueous sodium chloride solution, and dried over anhydrous sodium sulfate. After the drying agent was removed by filtration, a crude product of benzyl (3S)-3-aminopiperidine-1-carboxylate (501 mg) was obtained as a colorless oily substance by concentration under reduced pressure.

LCMS: m/z 235 [M+H]$^+$

HPLC retention time: 0.37 min (analysis condition K)

tert-Butyl N-methyl-N-(2-oxoethyl)carbamate was synthesized from tert-butyl N-(2-hydroxyethyl)-N-methylcarbamate by following the method described in the literature (Bioorganic and Medicinal Chemistry, vol. 12, pp. 5147-5160, 2004).

A solution of the crude product of benzyl (3S)-3-aminopiperidine-1-carboxylate (107 mg) and tert-butyl N-methyl-N-(2-oxoethyl)carbamate (59.3 mg, 0.343 mmol) in DCM (2.1 ml) was cooled to 0° C., followed by addition of sodium triacetoxyborohydride (145 mg, 0.685 mmol), and it was stirred at 0° C. After 30 minutes, tert-butyl N-methyl-N-(2-oxoethyl)carbamate (6.0 mg, 0.035 mmol) was added, and the mixture was stirred at 0° C. for 30 more minutes. Water was added to the reaction mixture, followed by extraction with ethyl acetate. The organic layer was washed with a saturated aqueous sodium chloride solution, and then dried over anhydrous sodium sulfate. After the drying agent was removed by filtration, a crude product of benzyl (3S)-3-[2-[methyl-[(2-methylpropan-2-yl)oxycarbonyl]amino]ethylamino]piperidine-1-carboxylate (169 mg) was obtained as a yellow oily substance by concentration under reduced pressure.

LCMS: m/z 392 [M+H]$^+$

HPLC retention time: 0.51 min (analysis condition K)

Boc$_2$O (188 mg, 0.863 mmol) was added to a solution of the crude product of benzyl (3S)-3-[2-[methyl-[(2-methylpropan-2-yl)oxycarbonyl]amino]ethylamino]piperidine-1-carboxylate (169 mg) and triethylamine (0.180 ml, 1.30 mmol) in THF (2.2 ml), and the mixture was stirred at room temperature for three hours. The reaction mixture was concentrated under reduced pressure, and the resultant residue was purified by silica gel column chromatography (ethyl acetate/hexane) to yield benzyl (3S)-3-[2-[methyl-[(2-methylpropan-2-yl)oxycarbonyl]amino]ethyl-[(2-methylpropan-2-yl)oxycarbonyl]amino]piperidine-1-carboxylate (139 mg, yield in two steps: 62%) as a yellow oily substance.

LCMS: m/z 492 [M+H]$^+$

HPLC retention time: 1.04 min (analysis condition K)

10% palladium on carbon (20.0 mg) was added to a solution of benzyl (3S)-3-[2-[methyl-[(2-methylpropan-2-yl)oxycarbonyl]amino]ethyl-[(2-methylpropan-2-yl)oxycarbonyl]amino]piperidine-1-carboxylate (112 mg, 0.228 mmol) in MeOH (2.2 ml) under argon atmosphere, and the mixture was stirred at room temperature for 16 hours under hydrogen atmosphere. The reaction mixture was filtered through celite, and a crude product of the title compound (91 mg) was obtained as a yellow oily substance by concentrating the filtrate under reduced pressure.

LCMS: m/z 358 [M+H]$^+$

Pharmacological Study
1. Measurement of DDR1 Binding Activity

DDR1 binding activity was measured using the LanthaScreen(Registered trademark) Eu Kinase Binding Assay (manufactured by Life Technologies Corporation). The test compound and the Alexa Fluor® 647-labeled Kinase Tracer 178 (manufactured by Life Technologies Corporation) were added to a mixture of DDR1 and the LanthaScreen(Registered trademark) Eu-anti-GST antibody. After one-hour reaction at room temperature, the fluorescence resonance energy transfer was measured. The 50% inhibitory concentration (IC50) was calculated from the inhibition rate relative to the test compound-free control.

2. Path-Hunter DDR1 Functional Assay

The human osteosarcoma cell line U2OS (manufactured by DiscoveRX Corporation) overexpressing DDR1 and SHC1 was suspended in a medium (MEM Eagle Medium manufactured by Life Technologies Corporation) supplemented with 10% fetal bovine serum and antibiotics (500 μg/mL geneticin (G418) manufactured by Life Technologies Corporation and 250 μg/mL hygromycin) to prepare a cell suspension at a concentration of 10000 cells/100 L. This cell suspension was added to a 96-well plate, and the plate was incubated at 37° C. in a 5% carbon dioxide incubator for one hour. The medium was then removed after the cells were confirmed to have adhered to the plate. The test compound was serially diluted with dimethyl sulfoxide, and added to 50 μL of the Cell Planting 16 Reagent (manufactured by DiscoveRX Corporation); and then the mixture was dispensed into the 96-well plate. After one-hour incubation at 37° C. in the 5% carbon dioxide incubator, 50 μL of 100 μg/mL collagen for tissue culture (Collagen Type I-C manufactured by Nitta Gelatin Inc.) was dispensed, and the plate was incubated at 37° C. in the 5% carbon dioxide incubator for 24 hours. The incubated plate was returned to room temperature, and 25 μL of the prepared Path-Hunter Detection Kit (manufactured by DiscoveRX Corporation) was dispensed into the plate. The plate was protected from light, and incubated at room temperature for two hours. Measurement was performed at 1 sec/well on a fluorescence plate reader. The 50% inhibitory concentration (IC50) of the test compound was calculated from the value obtained when the test compound was added, relative to the test compound-free control.

The results are provided in Tables 8 to 17.

TABLE 8

| Example | Compound No. | DDR1 binding activity IC50 (uM) | Path Hunter IC50 (uM) |
|---|---|---|---|
| 128 | B-2 | 0.021 | 0.45 |
| 178 | C-2 | 0.017 | 2.27 |
| 292 | F-1 | 0.043 | 0.68 |
| 293 | F-2 | 0.047 | 1.27 |
| 315 | F-15 | 0.020 | 0.33 |
| 317 | F-17 | 0.029 | 1.26 |
| 334 | F-34 | 0.037 | 0.64 |
| 351 | F-43 | 0.016 | 1.70 |
| 363 | F-54 | 0.015 | 0.37 |
| 364 | F-55 | 0.024 | 1.31 |
| 368 | F-59 | 0.030 | 1.10 |
| 370 | F-61 | 0.016 | 0.39 |
| 379 | F-70 | 0.016 | 0.15 |
| 388 | F-79 | 0.017 | 0.40 |
| 395 | F-86 | 0.042 | 1.45 |
| 396 | F-87 | 0.043 | 1.48 |
| 410 | F-101 | 0.017 | 0.080 |
| 417 | F-108 | 0.025 | 0.46 |
| 474 | G-1 | 0.045 | 5.52 |
| 482 | G-5 | 0.033 | 3.18 |
| 485 | G-8 | 0.030 | 3.44 |
| 487 | G-10 | 0.033 | 0.32 |
| 533 | H-5 | 0.019 | 1.20 |
| 534 | H-6 | 0.0098 | 0.41 |
| 540 | H-10 | 0.012 | 0.19 |
| 542 | H-12 | 0.042 | 0.55 |

TABLE 9

| Example | Compound No. | DDR1 binding activity IC50 (uM) |
|---|---|---|
| 58 | A-2 | 0.018 |
| 59 | A-3 | 0.070 |
| 61 | A-4 | 0.14 |
| 63 | A-5 | 0.12 |
| 66 | A-6 | 0.070 |
| 69 | A-7 | 0.11 |
| 71 | A-8 | 0.095 |
| 72 | A-9 | 0.10 |
| 76 | A-10 | 0.061 |
| 77 | A-11 | 0.049 |
| 79 | A-12 | 0.028 |
| 80 | A-13 | 0.032 |
| 83 | A-14 | 0.032 |
| 84 | A-15 | 0.033 |
| 86 | A-16 | 0.029 |
| 87 | A-17 | 0.027 |
| 91 | A-18 | 0.72 |
| 94 | A-19 | 0.10 |
| 96 | A-20 | 0.29 |
| 99 | A-21 | 1.53 |
| 101 | A-22 | 0.26 |
| 102 | A-23 | 0.046 |
| 104 | A-24 | 0.11 |
| 105 | A-25 | 0.24 |
| 106 | A-26 | 0.26 |
| 107 | A-27 | 0.17 |
| 112 | A-28 | 0.31 |
| 117 | A-29 | 10.66 |
| 122 | A-30 | 0.097 |
| 127 | B-1 | 0.016 |
| 129 | B-3 | 0.023 |
| 130 | B-4 | 0.030 |
| 131 | B-5 | 0.037 |
| 132 | B-6 | 0.052 |
| 133 | B-7 | 0.23 |
| 139 | B-8 | 0.046 |
| 140 | B-9 | 0.034 |
| 143 | B-10 | 0.10 |

TABLE 10

| Example | Compound No. | DDR1 binding activity IC50 (uM) |
|---|---|---|
| 148 | B-11 | 0.018 |
| 149 | B-12 | 0.027 |
| 151 | B-13 | 0.032 |
| 152 | B-14 | 0.0079 |
| 153 | B-15 | 0.011 |
| 154 | B-16 | 0.033 |
| 159 | B-17 | 0.015 |
| 160 | B-18 | 0.045 |
| 162 | B-19 | 0.020 |
| 163 | B-20 | 0.023 |
| 165 | B-21 | 2.42 |
| 166 | B-22 | 0.61 |
| 171 | B-23 | 0.35 |
| 177 | C-1 | 0.025 |
| 179 | C-3 | 0.052 |

TABLE 10-continued

| Example | Compound No. | DDR1 binding activity IC50 (uM) |
|---|---|---|
| 180 | C-4 | 0.082 |
| 181 | C-5 | 0.082 |
| 182 | C-6 | 0.36 |
| 183 | C-7 | 0.10 |
| 184 | C-8 | 0.20 |
| 187 | C-9 | 0.022 |
| 188 | C-10 | 0.020 |
| 189 | C-11 | 0.052 |
| 193 | C-12 | 0.043 |
| 196 | C-13 | 2.74 |
| 197 | C-14 | 0.17 |
| 204 | D-1 | 0.038 |
| 205 | D-2 | 0.037 |
| 212 | D-3 | 0.016 |
| 213 | D-4 | 0.035 |
| 219 | D-5 | 2.05 |
| 222 | D-6 | 2.43 |
| 228 | E-1 | 0.025 |
| 229 | E-2 | 0.016 |
| 230 | E-3 | 0.033 |
| 231 | E-4 | 0.058 |
| 237 | E-5 | 0.11 |
| 238 | E-6 | 0.012 |
| 239 | E-7 | 0.016 |

TABLE 11

| Example | Compound No. | DDR1 binding activity IC50 (uM) |
|---|---|---|
| 240 | E-8 | 0.047 |
| 241 | E-9 | 0.013 |
| 242 | E-10 | 0.015 |
| 249 | E-11 | 0.015 |
| 250 | E-12 | 0.012 |
| 254 | E-13 | 0.031 |
| 251 | E-14 | 0.025 |
| 252 | E-15 | 0.025 |
| 255 | E-16 | 0.043 |
| 253 | E-17 | 0.020 |
| 260 | E-18 | 0.022 |
| 261 | E-19 | 0.034 |
| 262 | E-20 | 0.15 |
| 263 | E-21 | 0.099 |
| 264 | E-22 | 0.086 |
| 265 | E-23 | 0.34 |
| 266 | E-24 | 0.25 |
| 267 | E-25 | 0.29 |
| 268 | E-26 | 0.84 |
| 275 | E-27 | 0.090 |
| 286 | E-28 | 1.12 |
| 287 | E-29 | 1.30 |
| 294 | F-3 | 0.22 |
| 295 | F-4 | 1.13 |
| 296 | F-5 | 0.35 |
| 297 | F-6 | 0.27 |
| 298 | F-7 | 0.23 |
| 299 | F-8 | 0.51 |
| 300 | F-9 | 0.19 |
| 301 | F-10 | 0.099 |
| 302 | F-11 | 2.52 |
| 305 | F-12 | 0.21 |
| 308 | F-13 | 0.030 |
| 309 | F-14 | 0.063 |
| 316 | F-16 | 0.019 |
| 318 | F-18 | 0.12 |
| 319 | F-19 | 0.035 |
| 320 | F-20 | 0.14 |
| 321 | F-21 | 0.080 |

TABLE 12

| Example | Compound No. | DDR1 binding activity IC50 (uM) |
|---|---|---|
| 322 | F-22 | 0.084 |
| 323 | F-23 | 0.043 |
| 324 | F-24 | 0.058 |
| 325 | F-25 | 0.098 |
| 326 | F-26 | 0.13 |
| 327 | F-27 | 0.018 |
| 328 | F-28 | 0.028 |
| 329 | F-29 | 0.13 |
| 330 | F-30 | 0.23 |
| 331 | F-31 | 0.053 |
| 332 | F-32 | 0.092 |
| 333 | F-33 | 0.054 |
| 335 | F-35 | 0.029 |
| 340 | F-36 | 0.086 |
| 342 | F-37 | 0.016 |
| 343 | F-38 | 0.11 |
| 344 | F-39 | 0.19 |
| 462 | F-40 | 0.048 |
| 348 | F-41 | 0.025 |
| 349 | F-42 | 0.034 |
| 353 | F-44 | 0.043 |
| 354 | F-45 | 0.35 |
| 355 | F-46 | 0.10 |
| 356 | F-47 | 0.018 |
| 357 | F-48 | 0.024 |
| 358 | F-49 | 0.067 |
| 359 | F-50 | 0.072 |
| 360 | F-51 | 0.14 |
| 361 | F-52 | 0.021 |
| 362 | F-53 | 0.44 |
| 365 | F-56 | 0.16 |
| 366 | F-57 | 0.20 |
| 367 | F-58 | 0.53 |
| 369 | F-60 | 0.14 |
| 371 | F-62 | 0.041 |
| 372 | F-63 | 0.054 |
| 373 | F-64 | 0.090 |
| 374 | F-65 | 0.079 |
| 375 | F-66 | 0.15 |

TABLE 13

| Example | Compound No. | DDR1 binding activity IC50 (uM) |
|---|---|---|
| 376 | F-67 | 0.075 |
| 377 | F-68 | 0.057 |
| 378 | F-69 | 3.22 |
| 380 | F-71 | 0.28 |
| 381 | F-72 | 0.020 |
| 382 | F-73 | 0.047 |
| 383 | F-74 | 0.073 |
| 384 | F-75 | 0.13 |
| 385 | F-76 | 0.98 |
| 386 | F-77 | 0.025 |
| 387 | F-78 | 1.80 |
| 389 | F-80 | 0.032 |
| 390 | F-81 | 0.26 |
| 391 | F-82 | 0.53 |
| 392 | F-83 | 4.65 |
| 393 | F-84 | 0.033 |
| 394 | F-85 | 0.26 |
| 397 | F-88 | 0.11 |
| 398 | F-89 | 0.097 |
| 399 | F-90 | 0.15 |
| 400 | F-91 | 0.022 |
| 401 | F-92 | 0.027 |
| 402 | F-93 | 0.14 |
| 403 | F-94 | 0.059 |
| 404 | F-95 | 0.98 |
| 405 | F-96 | 0.024 |
| 406 | F-97 | 0.029 |
| 407 | F-98 | 0.14 |
| 408 | F-99 | 0.15 |

TABLE 13-continued

| Example | Compound No. | DDR1 binding activity IC50 (uM) |
|---|---|---|
| 409 | F-100 | 1.00 |
| 411 | F-102 | 0.31 |
| 412 | F-103 | 0.022 |
| 413 | F-104 | 0.020 |
| 414 | F-105 | 0.12 |
| 415 | F-106 | 0.069 |
| 416 | F-107 | 0.83 |
| 418 | F-109 | 0.083 |
| 419 | F-110 | 0.041 |
| 420 | F-111 | 0.24 |

TABLE 14

| Example | Compound No. | DDR1 binding activity IC50 (uM) |
|---|---|---|
| 421 | F-112 | 0.076 |
| 422 | F-113 | 1.19 |
| 423 | F-114 | 0.049 |
| 424 | F-115 | 0.16 |
| 425 | F-116 | 0.14 |
| 426 | F-117 | 0.14 |
| 427 | F-118 | 0.10 |
| 428 | F-119 | 0.44 |
| 429 | F-120 | 0.11 |
| 430 | F-121 | 0.030 |
| 431 | F-122 | 0.021 |
| 432 | F-123 | 0.043 |
| 433 | F-124 | 0.046 |
| 435 | F-125 | 0.088 |
| 436 | F-126 | 0.21 |
| 437 | F-127 | 0.58 |
| 439 | F-128 | 0.036 |
| 440 | F-129 | 0.030 |
| 441 | F-130 | 0.082 |
| 442 | F-131 | 0.098 |
| 443 | F-132 | 0.069 |
| 444 | F-133 | 1.46 |
| 456 | F-134 | 0.15 |
| 445 | F-135 | 0.088 |
| 446 | F-136 | 0.32 |
| 447 | F-137 | 0.10 |
| 448 | F-138 | 0.64 |
| 449 | F-139 | 0.058 |
| 458 | F-140 | 0.11 |
| 450 | F-141 | 0.11 |
| 459 | F-142 | 0.84 |
| 460 | F-143 | 1.95 |
| 451 | F-144 | 0.088 |
| 452 | F-145 | 0.13 |
| 453 | F-146 | 0.41 |
| 454 | F-147 | 0.25 |
| 455 | F-148 | 0.084 |
| 465 | F-149 | 0.052 |
| 469 | F-150 | 0.24 |

TABLE 15

| Example | Compound No. | DDR1 binding activity IC50 (uM) |
|---|---|---|
| 475 | G-2 | 0.10 |
| 476 | G-3 | 0.11 |
| 477 | G-4 | 0.41 |
| 483 | G-6 | 0.034 |
| 484 | G-7 | 1.24 |
| 486 | G-9 | 0.27 |
| 488 | G-11 | 0.043 |
| 489 | G-12 | 0.12 |
| 490 | G-13 | 0.16 |
| 492 | G-14 | 0.053 |
| 493 | G-15 | 1.03 |

TABLE 15-continued

| Example | Compound No. | DDR1 binding activity IC50 (uM) |
|---|---|---|
| 494 | G-16 | 0.038 |
| 495 | G-17 | 0.049 |
| 496 | G-18 | 0.14 |
| 497 | G-19 | 0.27 |
| 498 | G-20 | 0.024 |
| 499 | G-21 | 3.96 |
| 500 | G-22 | 0.034 |
| 501 | G-23 | 0.076 |
| 502 | G-24 | 0.36 |
| 503 | G-25 | 0.33 |
| 504 | G-26 | 3.23 |
| 505 | G-27 | 0.042 |
| 506 | G-28 | 0.022 |
| 507 | G-29 | 0.047 |
| 508 | G-30 | 0.11 |
| 509 | G-31 | 0.081 |
| 510 | G-32 | 0.032 |
| 511 | G-33 | 0.017 |
| 512 | G-34 | 0.016 |
| 515 | G-35 | 0.15 |
| 517 | G-36 | 1.07 |
| 523 | H-1 | 0.069 |
| 524 | H-2 | 0.038 |
| 530 | H-3 | 0.026 |
| 531 | H-4 | 0.094 |
| 535 | H-7 | 0.014 |
| 536 | H-8 | 0.018 |
| 537 | H-9 | 0.065 |

TABLE 16

| Example | Compound No. | DDR1 binding activity IC50 (uM) |
|---|---|---|
| 541 | H-11 | 0.046 |
| 547 | H-13 | 0.12 |
| 548 | H-14 | 0.20 |
| 551 | H-15 | 0.018 |
| 553 | H-16 | 0.040 |
| 554 | H-17 | 0.090 |
| 555 | H-18 | 0.20 |
| 556 | H-19 | 0.085 |
| 566 | I-1 | 0.60 |
| 573 | I-2 | 0.16 |
| 574 | I-3 | 0.086 |
| 575 | I-4 | 0.23 |
| 576 | I-5 | 0.60 |
| 583 | I-6 | 0.069 |
| 584 | I-7 | 0.019 |
| 585 | I-8 | 0.053 |
| 586 | I-9 | 0.21 |
| 587 | I-10 | 0.37 |

TABLE 17

| Example | Compound No. | DDR1 binding activity IC50 (uM) |
|---|---|---|
| 52 | A-1 | 0.049 |
| 595 | FF-1 | 0.028 |
| 598 | FF-2 | 0.031 |
| 599 | FF-3 | 0.037 |
| 606 | FF-4 | 0.46 |
| 615 | FF-5 | 0.38 |
| 617 | FF-6 | 0.16 |
| 620 | FF-7 | 0.082 |
| 621 | FF-8 | 0.069 |
| 623 | FF-9 | 0.045 |
| 629 | J-1 | 0.033 |
| 632 | J-2 | 0.093 |
| 634 | J-3 | 0.032 |
| 635 | J-4 | 0.070 |

TABLE 17-continued

| Example | Compound No. | DDR1 binding activity IC50 (uM) |
|---|---|---|
| 635 | J-5 | 0.054 |
| 635 | J-6 | 0.38 |
| 636 | J-7 | 0.068 |
| 648 | K-1 | 0.10 |
| 658 | K-2 | 0.065 |
| 663 | K-3 | 0.026 |
| 672 | L-1 | 0.017 |
| 673 | L-2 | 0.066 |
| 674 | L-3 | 0.22 |
| 676 | L-4 | 2.43 |
| 677 | L-5 | 0.021 |
| 679 | L-6 | 0.043 |
| 680 | L-7 | 0.089 |
| 684 | M-1 | 0.54 |
| 685 | M-2 | 0.32 |
| 686 | M-3 | 2.89 |
| 701 | N-1 | 0.026 |
| 707 | N-2 | 0.092 |
| 715 | N-3 | 0.50 |
| 720 | N-6 | 25.9 |
| 722 | N-7 | 0.031 |
| 724 | N-8 | 0.044 |
| 725 | N-9 | 0.022 |
| 731 | N-10 | 10.1 |
| 739 | N-11 | 0.087 |
| 740 | N-12 | 10.3 |
| 741 | N-13 | 0.12 |
| 747 | N-14 | 0.59 |

3. Measurement of Antitumor Effect

The antitumor effect was measured for representative examples of the compounds of the present invention.

The antitumor effect was measured using cancer-bearing mice in which the human endometrial cancer cell line MFE-280 (manufactured by DSMZ) was subcutaneously transplanted to the flank of BALB/c nude mice (manufactured by Charles River Laboratories Japan, Inc.).

About $1 \times 10^7$ MFE-280 cells were subcutaneously transplanted to the flank of the purchased nude mice after a one-week quarantine period. The tumor size was measured with calipers, and the tumor volume was calculated (tumor volume=length×breadth$^2$/2 (mm$^3$)). The mice were subjected to the experiment when the tumor volume was about 200 mm$^3$.

The test compound was suspended in the administration solution, and 0.4 mL of the suspension was orally administered once daily. The antitumor effect was calculated as inhibition of tumor growth by comparing the tumor growth between the drug-treated group and the administration solution-administered control group on the 11th day after the start of administration.

Tumor volume growth inhibition (TGI)=(1−tumor volume growth in drug-treated group/tumor volume growth in control group)×100(%)

The results are shown in Table 18 and FIG. 1.

TABLE 18

| Compound No. | Antitumor effect | |
|---|---|---|
| | Dose (mg/kg) | TGI after 11 days (%) |
| F-1 | 200 | 61 |

4. Measurement of Inhibition of DDR1 Phosphorylation in Tumors

Inhibition of DDR1 by the test compound in MFE-280 tumors was measured using Western blotting.

Four hours after the final administration, tumors were homogenized and solubilized, subjected to SDS-PAGE, and then transferred to PVDF membrane. After blocking, the membrane was treated with an anti-phosphorylated Y796-DDR1 antibody (manufactured by Sigma-Aldrich Co. LLC.), an anti-DDR1 antibody (manufactured by Santa Cruz Biotechnology, Inc.), and an anti-actin antibody (manufactured by Santa Cruz Biotechnology, Inc.). After the primary antibodies were washed off, the membrane was treated with an HRP-labeled secondary antibody. After the secondary antibody was washed off, signals were detected by a chemiluminescence method using ECL Plus or ECL (manufactured by GE Healthcare).

Figure 2:
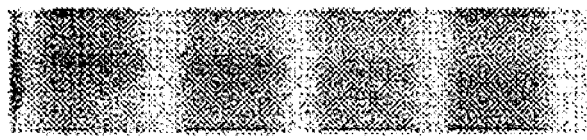
FIG. 2 shows a DDR1 phosphorylation inhibitory effect of Compound F-1 in tumors.
Figure 2:
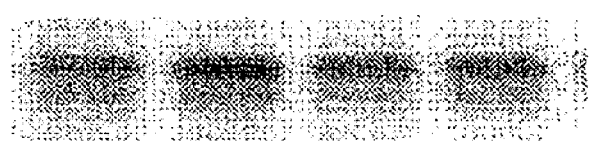
Figure 2:
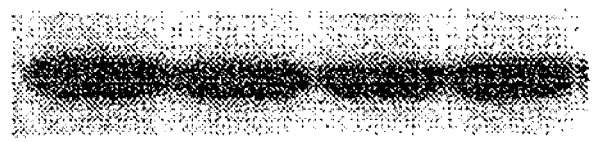

The results are shown in FIG. 2.

From these results, it was observed that the compounds of the present invention have a high DDR1 inhibitory activity and a high antitumor effect.

INDUSTRIAL APPLICABILITY

The present invention provides compounds having a DDR1 inhibitory effect. The present invention also provides pharmaceutical agents for prevention and/or treatment of cancer, prevention and/or treatment of cancer invasion and metastasis, and prevention and/or treatment of fibrosis and inflammation.

The invention claimed is:

1. A compound represented by general formula (I) below, or a pharmaceutically acceptable salt thereof:

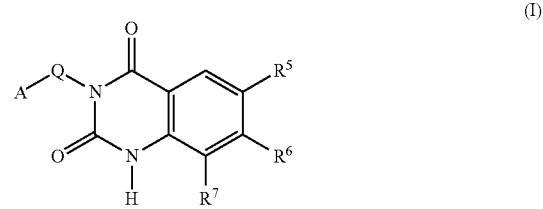

wherein
A represents formula (1) below:

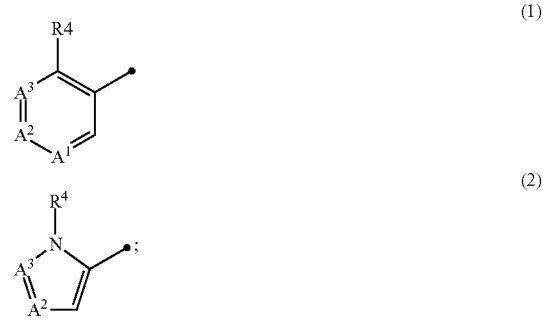

Q represents CH$_2$ or NH;
A$^1$ represents N or CR$^1$;
R$^1$ represents a hydrogen atom, C$_{1-3}$ alkyl group, C$_{1-3}$ alkoxy group, halogen atom, or cyano group, wherein the C$_{1-3}$ alkyl group or C$_{1-3}$ alkoxy group may be substituted with 1 to 5 halogen atoms,
wherein when A$^2$ and/or A$^3$ is N, R$^1$ may be an hydrogen atom;

$A^2$ represents N or $CR^2$;

$R^2$ represents a hydrogen atom, $C_{1-3}$ alkyl group, $C_{1-3}$ alkoxy group, or halogen atom;

$A^3$ represents N or $CR^3$;

$R^3$ represents a hydrogen atom, $C_{1-6}$ alkyl group, $C_{1-6}$ alkoxy group, or halogen atom;

$R^4$ represents a $C_{1-6}$ alkylsulfonyl group, $C_{1-6}$ alkylsulfanyl group, $C_{1-6}$ alkylsulfinyl group, $C_{3-8}$ cycloalkylsulfonyl group, $C_{3-8}$ cycloalkylsulfanyl group, $C_{3-8}$ cycloalkylsulfinyl group, $C_{6-10}$ arylsulfonyl group, $C_{6-10}$ arylsulfanyl group, or $C_{6-10}$ arylsulfinyl group;

$R^5$ represents a halogen atom, $C_{1-6}$ alkyl group, $C_{1-6}$ alkoxy group, $C_{2-6}$ alkenyl group, cyano group, nitro group, $C_{3-8}$ cycloalkyl group, 4- to 10-membered aromatic ring, 4- to 10-membered aromatic heterocycle, 3- to 12-membered heterocycle, or $C_{1-6}$ alkylsulfanyl group, wherein the $C_{1-6}$ alkyl group, $C_{1-6}$ alkoxy group, $C_{2-6}$ alkenyl group, or $C_{1-6}$ alkylsulfanyl group may be substituted with 1 to 5 halogen atoms;

$R^6$ represents a hydrogen atom, a $C_{1-6}$ alkyl group, $C_{2-6}$ alkenyl group, halogen atom, formyl group, [1,3]dioxolane, or a group represented by formula (i) below, wherein the $C_{1-6}$ alkyl group or $C_{2-6}$ alkenyl group may be substituted with 1 to 5 amino, hydroxyl, and/or $OSO_2CH_3$ groups,

   (i)

wherein in formula (i),

X represents $-(CH_2)_n-$, $-NH-$, or $-O-$;

Y represents a 4- to 10-membered aromatic ring, 3- to 12-membered heterocycle, or 4- to 10-membered aromatic heterocycle, wherein the 4- to 10-membered aromatic ring, 3- to 12-membered heterocycle, and 4- to 10-membered aromatic heterocycle may be substituted with 1 to 5 halogen atoms and/or $C_{1-3}$ alkyl groups;

Z represents a hydrogen atom, a $C_{1-6}$ alkyl group, a $C_{2-6}$ alkynyl group, a $C_{3-8}$ cycloalkyl group, $-(CH_2)_mNRaRb$, $-NHCO(CH_2)_mRc$, $-(CH_2)_mNHCORc$, $-NH(CH_2)_mCORc$, $-(CH_2)_mN(CH_3)CORc$, $-(CH_2)_mORd$, $-(CH_2)_mCORe$, $-(CH_2)_mCOORe$, $-(CH_2)_mNHSO_2Rf$, $-(CH_2)_mSO_2Rf$, $-(CH_2)_mCONRgRh$, a 4- to 10-membered aromatic ring, 4- to 10-membered aromatic heterocycle, or a 3- to 12-membered heterocycle, wherein the $C_{1-6}$ alkyl group may be substituted with 1 to 5 halogen atoms, hydroxyl groups, and/or cyano groups; and the 3- to 12-membered heterocycle and 4- to 10-membered aromatic heterocycle may be substituted with 1 to 5 halogen atoms, $C_{1-3}$ alkyl groups, and/or oxo groups;

n represents 0, 1, 2, or 3;

m represents 0, 1, 2, or 3;

Ra and Rb are identical or different, each representing a hydrogen atom, $C_{1-6}$ alkyl group, $C_{2-6}$ alkynyl group, 3- to 12-membered heterocycle, 4- to 10-membered aromatic heterocycle, or $-SO_2CH_3$, wherein the $C_{1-6}$ alkyl group may be substituted with 1 to 5 halogen atoms, amino groups, mono-$C_{1-6}$ alkylamino groups, di-$C_{1-6}$ alkylamino groups, hydroxyl groups, and/or cyano groups;

Rc represents a $C_{1-6}$ alkyl group, $C_{1-6}$ alkoxy group, $C_{3-8}$ cycloalkyl group, amino group, or 3- to 12-membered heterocycle, wherein the $C_{1-6}$ alkyl group may be substituted with 1 to 3 amino groups, mono-$C_{1-6}$ alkylamino groups, di-$C_{1-6}$ alkylamino groups, and/or 3- to 12-membered heterocycles;

Rd represents a hydrogen atom, $C_{1-6}$ alkyl group, $C_{2-3}$ alkenyl group, or $C_{2-6}$ alkynyl group, wherein the $C_{1-6}$ alkyl group may be substituted with 1 to 5 $C_{1-6}$ alkoxy groups and/or amino groups;

Re represents a hydrogen atom or $C_{1-6}$ alkyl group, wherein the $C_{1-6}$ alkyl group may be substituted with an amino group;

Rf represents a $C_{1-6}$ alkyl group, an amino group, a mono-$C_{1-6}$ alkylamino group, or a di-$C_{1-6}$ alkylamino group; and Rg and Rh are identical or different, each representing a hydrogen atom, $C_{1-6}$ alkyl group, or 3- to 12-membered heterocycle, wherein the $C_{1-6}$ alkyl group may be substituted with 1 to 3 amino groups, mono-$C_{1-6}$ alkylamino groups, and/or di-$C_{1-6}$ alkylamino groups; and $R^7$ represents a hydrogen atom, halogen atom, $C_{1-6}$ alkyl group, $C_{2-6}$ alkenyl group, $C_{1-6}$ alkoxy group, cyano group, or a group represented by formula (ii) below, wherein the $C_{1-6}$ alkyl group may be substituted with 1 to 5 halogen atoms:

   (ii)

wherein $X^2$ represents $-(CH_2)_p-$;

$Y^2$ represents a 3- to 12-membered heterocycle or 4- to 10-membered aromatic heterocycle;

$Z^2$ represents a hydrogen atom, $C_{1-6}$ alkyl group, $C_{2-6}$ alkenyl group, $C_{1-6}$ alkoxy group, $C_{3-7}$ cycloalkyl group, cyano group, or COORi;

p represents 0, 1, or 2; and

Ri represents a $C_{1-6}$ alkyl group.

2. The compound or pharmaceutically acceptable salt thereof according to claim 1, wherein A is formula (1) below:

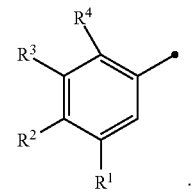   (1)

3. The compound or pharmaceutically acceptable salt thereof according to claim 1, wherein Q is $CH_2$.

4. The compound or pharmaceutically acceptable salt thereof according to claim 1, wherein $R^2$ is a hydrogen atom or $C_{1-3}$ alkyl group.

5. The compound or pharmaceutically acceptable salt thereof according to claim 1, wherein $R^3$ is a hydrogen atom, $C_{1-6}$ alkyl group, or halogen atom.

6. The compound or pharmaceutically acceptable salt thereof according to claim 1, wherein $R^4$ is a $C_{1-6}$ alkylsulfonyl group or $C_{1-6}$ alkylsulfanyl group.

7. The compound or pharmaceutically acceptable salt thereof according to claim 1, wherein $R^5$ represents a halogen atom, $C_{1-3}$ alkyl group, or $C_{1-3}$ alkoxy group, wherein the $C_{1-3}$ alkyl group or $C_{1-3}$ alkoxy group may be substituted with 1 to 5 halogen atoms.

8. The compound or pharmaceutically acceptable salt thereof according to claim 1, wherein $R^6$ represents a hydrogen atom or a group represented by formula (i) below:

   (i)

wherein X represents $CH_2$;

Y represents piperazine, pyrrolidine, piperidine, morpholine, 3,3-dimethylpiperazine, (R) or (S)-hexahydropyrrolo[1,2-a]pyrazine, 3-oxopiperazine, azetidine, pyridine, or 2-oxo-imidazolidine;

Z represents a hydrogen atom, a $C_{1-3}$ alkyl group, a $C_{4-6}$ cycloalkyl group, —$(CH_2)_m$NRaRb, —NHCO$(CH_2)_m$Rc, —$(CH_2)_m$NHCORc, —NH$(CH_2)_m$CORc, —$(CH_2)_m$N$(CH_3)$CORc, ORd, —CORe, —COORe, —NHSO$_2$Rf, —SO$_2$Rf, —$(CH_2)_m$CONRgRh, or piperazine, pyrrolidine, piperidine, tetrahydropyran, morpholine, or oxetane, wherein the piperazine, pyrrolidine, piperidine, tetrahydropyran, morpholine, or oxetane may be substituted with 1 to 5 halogen atoms, $C_{1-3}$ alkyl groups, and/or oxo groups;

m represents 0 or 1;

Ra and Rb are identical or different, each representing a hydrogen atom, a $C_{1-3}$ alkyl group, —$SO_2CH_3$, prop-2-ynyl, or oxetane, wherein the $C_{1-3}$ alkyl group may be substituted with 1 to 5 halogen atoms;

Rc represents a $C_{1-3}$ alkyl group, a $C_{1-4}$ alkoxy group, a $C_{4-6}$ cycloalkyl group, or an amino group, wherein the $C_{1-3}$ alkyl group may be substituted with 1 to 2 amino, mono-$C_{1-2}$ alkylamino, and/or di-$C_{1-2}$ alkylamino groups;

Rd represents a hydrogen atom, $C_{1-2}$ alkyl group, or $C_{2-3}$ alkenyl group, wherein the $C_{1-2}$alkyl group may be substituted with 1 to 2 $C_{1-2}$ alkoxy groups;

Re represents a hydrogen atom or $C_{1-4}$ alkyl group, wherein the $C_{1-4}$ alkyl group may be substituted with an amino group;

Rf represents a $C_{1-3}$ alkyl group, an amino group, a mono-$C_{1-3}$ alkylamino group, or a di-$C_{1-3}$ alkylamino group; and Rg and Rh are identical or different, each representing a hydrogen atom or $C_{1-3}$ alkyl group.

9. The compound or pharmaceutically acceptable salt thereof according to claim 1, wherein $R^7$ represents a $C_{1-6}$ alkyl group, $C_{2-6}$ alkenyl group, $C_{1-6}$ alkoxy group, cyano group or a group represented by formula (ii) below, wherein the $C_{1-6}$ alkyl group may be substituted with 1 to 5 halogen atoms:

$$\bullet-X^2-Y^2-Z^2 \qquad (ii)$$

wherein $X^2$ represents —$CH_2$—;

$Y^2$ represents piperazine;

$Z^2$ represents a hydrogen atom, a methyl group, or COORi; and

Ri represents a $C_{1-6}$ alkyl group.

10. A pharmaceutical comprising the compound or pharmaceutically acceptable salt thereof according to claim 1 as an active ingredient.

* * * * *

UNITED STATES PATENT AND TRADEMARK OFFICE
CERTIFICATE OF CORRECTION

PATENT NO. : 9,567,304 B2
APPLICATION NO. : 14/396498
DATED : February 14, 2017
INVENTOR(S) : Murata et al.

Page 1 of 2

It is certified that error appears in the above-identified patent and that said Letters Patent is hereby corrected as shown below:

In the Specification

Columns 17 to 18
Line 34 please add

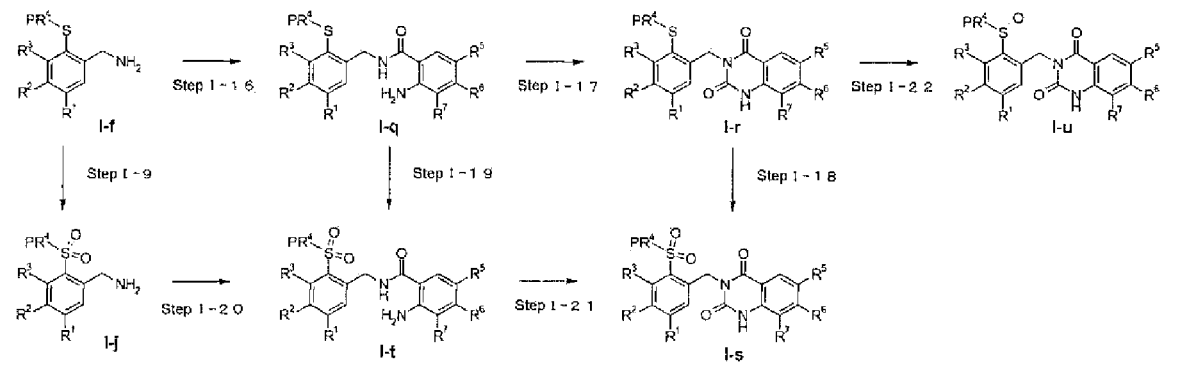

" "

under the current printed figure.

In the Claims

Column 400
Line 55 "A represents formula (1) below:

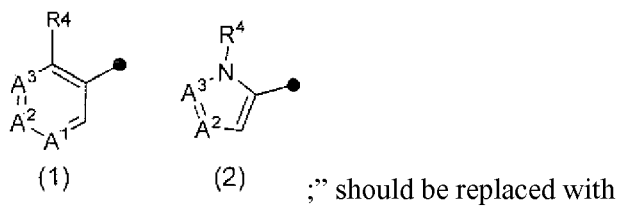

;" should be replaced with

Signed and Sealed this
Sixteenth Day of May, 2017

Michelle K. Lee
*Director of the United States Patent and Trademark Office*

--A represents formula (1) below:
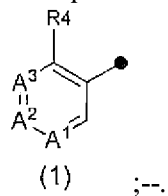
(1)    ;--.